United States Patent
Narine et al.

(10) Patent No.: US 9,497,970 B2
(45) Date of Patent: Nov. 22, 2016

(54) PESTICIDE COMPOUNDS

(71) Applicant: BASF SE, Ludwigshafen (DE)

(72) Inventors: Arun Narine, Mannheim (DE); Nina Gertrud Bandur, Ludwigshafen (DE); Joachim Dickhaut, Heidelberg (DE); Raffael Koller, Zurich (CH); Wolfgang Von Deyn, Neustadt (DE); Jean-Yves Wach, Mannheim (DE); Vincent Salgado, Durham, NC (US)

(73) Assignee: BASF SE, Ludwigshafen (DE)

( * ) Notice: Subject to any disclaimer, the term of this patent is extended or adjusted under 35 U.S.C. 154(b) by 0 days.

(21) Appl. No.: 14/903,887

(22) PCT Filed: Jul. 14, 2014

(86) PCT No.: PCT/EP2014/065034
§ 371 (c)(1),
(2) Date: Jan. 8, 2016

(87) PCT Pub. No.: WO2015/007682
PCT Pub. Date: Jan. 22, 2015

(65) Prior Publication Data
US 2016/0157491 A1   Jun. 9, 2016

Related U.S. Application Data

(60) Provisional application No. 61/846,105, filed on Jul. 15, 2013.

(51) Int. Cl.

| | | |
|---|---|---|
| C07D 235/02 | (2006.01) |
| C07D 401/12 | (2006.01) |
| C07D 417/12 | (2006.01) |
| C07D 491/04 | (2006.01) |
| C07D 495/04 | (2006.01) |
| A01N 43/50 | (2006.01) |
| A01N 47/30 | (2006.01) |
| A01N 43/56 | (2006.01) |
| A01N 43/647 | (2006.01) |
| A01N 43/78 | (2006.01) |
| A01N 43/80 | (2006.01) |
| A01N 43/86 | (2006.01) |
| A01N 47/20 | (2006.01) |
| A01N 47/36 | (2006.01) |
| A01N 47/48 | (2006.01) |

(Continued)

(52) U.S. Cl.
CPC ............. *A01N 47/30* (2013.01); *A01N 43/56* (2013.01); *A01N 43/647* (2013.01); *A01N 43/78* (2013.01); *A01N 43/80* (2013.01); *A01N 43/86* (2013.01); *A01N 47/20* (2013.01); *A01N 47/36* (2013.01); *A01N 47/48* (2013.01); *C07D 231/56* (2013.01); *C07D 235/02* (2013.01); *C07D 235/06* (2013.01); *C07D 249/22* (2013.01); *C07D 261/20* (2013.01); *C07D 275/04* (2013.01); *C07D 401/12* (2013.01); *C07D 417/12* (2013.01); *C07D 491/04* (2013.01); *C07D 495/04* (2013.01)

(58) Field of Classification Search
None
See application file for complete search history.

(56) References Cited

FOREIGN PATENT DOCUMENTS

| WO | WO 2009/102736 | 8/2009 |
| WO | WO 2011/017504 | 2/2011 |

OTHER PUBLICATIONS

International Search Report dated Sep. 30, 2014, prepared in International Application No. PCT/EP2014/065034.

(Continued)

*Primary Examiner* — Zinna Northington Davis
(74) *Attorney, Agent, or Firm* — Brinks Gilson & Lione

(57) ABSTRACT

The present invention relates to novel compounds of the formula I and the N-oxides, stereoisomers, tautomers and agriculturally or veterinarily acceptable salts thereof

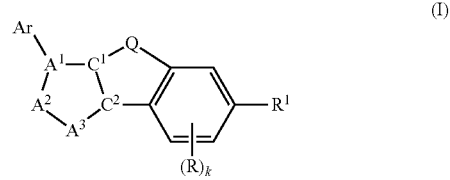

(I)

wherein $C^1$ is C or CH; $C^2$ is C or CH; $A^1$ is N or C; $A^2$ is N, $C(R^2)$, $N(R^3)$, O, S or $C(R^4,R^5)$; and $A^3$ is N, O, S, $N(R^6)$, $C(R^7)$ or $C(R^8,R^9)$; where one or two non-adjacent bonds in the 5-membered ring formed by $C^1$, $C^2$, $A^1$, $A^2$ and $A^3$ are double bonds, while the others are single bonds, provided that the bond between $A^1$ and $A^2$ or the bond between $A^1$ and $C^1$ or the bond between $A^2$ and $A^3$ or the bond between $C^1$ and $C^2$ or the bond between $A^3$ and $C^2$ is a double bond further provided that at least one of $A^1$, $A^2$ and $A^3$ is N, $N(R^3)$ or $N(R^6)$, and where Ar, $R^1$, $R^2$, $R^3$, $R^4$, $R^5$, $R^6$, $R^7$, $R^8$, $R^9$ and $(R)_k$ are as defined in the claims and in the description, which are useful for combating or controlling invertebrate pests, in particular arthropod pests and nematodes. The invention also relates to a method for controlling invertebrate pests by using these compounds and to plant propagation material and to an agricultural and a veterinary composition comprising said compounds.

28 Claims, No Drawings

(51) Int. Cl.
*C07D 231/56* (2006.01)
*C07D 235/06* (2006.01)
*C07D 249/22* (2006.01)
*C07D 261/20* (2006.01)
*C07D 275/04* (2006.01)

(56) References Cited

OTHER PUBLICATIONS

International Preliminary Report on Patentability dated Jan. 19, 2016, prepared in International Application No. PCT/EP2014/065034.

PESTICIDE COMPOUNDS

This application is a National Stage application of International Application No. PCT/EP2014/065034, filed Jul. 14, 2014, which claims the benefit of U.S. Provisional Application No. 61/846,105, filed Jul. 15, 2013.

The present invention relates to novel compounds which are useful for combating or controlling invertebrate pests, in particular arthropod pests and nematodes. The invention also relates to a method for controlling invertebrate pests by using these compounds and to plant propagation material and to an agricultural and a veterinary composition comprising said compounds.

Invertebrate pests and in particular arthropods and nematodes destroy growing and harvested crops and attack wooden dwelling and commercial structures, causing large economic loss to the food supply and to property. While a large number of pesticidal agents are known, due to the ability of target pests to develop resistance to said agents, there is an on-going need for new agents for combating invertebrate pests, in particular insects, arachnids and nematodes.

WO 2009/102736 describes linear triaryls having a rhamnose type radical which is bound to a terminal aryl group via a bivalent linker such as (thio)carbamate or iminoxy linker. Similar compounds are known from WO 2012/027521.

WO 2011/017504 describes linear triaryls having a methyliden(thio)carbazone motive that carries a (het)aryl or (het)arylalkyl radical.

WO 2011/017513 describe linear triaryls having a carbamate or thiocarbamate motive that carries a (het)arylalkyl radical.

US 2012/0202687 describes linear triaryls having a methylideniminoisothiourea motive that carries a (het)aryl or (het)arylalkyl radical.

It is an object of the present invention to provide compounds that have a good pesticidal activity, in particular insecticidal activity, and show a broad activity spectrum against a large number of different invertebrate pests, especially against difficult to control arthropod pests and/or nematodes.

It has been found that these objectives can be achieved by compounds of the formula I below, by their stereoisomers, their tautomers, their N-oxides and by their salts, in particular their agriculturally or veterinarily acceptable salts.

Therefore, in a first aspect, the invention relates to compounds of formula I

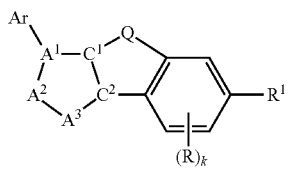
(I)

wherein
$C^1$ is C or CH
$C^2$ is C or CH
$A^1$ is N or C
$A^2$ is N, $C(R^2)$, $N(R^3)$, O, S or $C(R^4,R^5)$; and
$A^3$ is N, O, S, $N(R^6)$, $C(R^7)$ or $C(R^8,R^9)$;
  where one or two non-adjacent bonds in the 5-membered ring formed by $C^1$, $C^2$, $A^1$, $A^2$ and $A^3$ are double bonds, while the others are single bonds, provided that the bond between $A^1$ and $A^2$ or the bond between $A^1$ and $C^1$ or the bond between $A^2$ and $A^3$ or the bond between $C^1$ and $C^2$ or the bond between $A^3$ and $C^2$ is a double bond further provided that at least one of $A^1$, $A^2$ and $A^3$ is N, $N(R^3)$ or $N(R^6)$,
and where
$R^2$, $R^7$ independently of each other, are selected from the group consisting of hydrogen, halogen, $N_3$, OH, CN, $NO_2$, —SCN, —$SF_5$, $C_1$-$C_6$-alkyl, $C_1$-$C_6$-haloalkyl, $C_1$-$C_6$-alkoxy, $C_1$-$C_6$-haloalkoxy, $C_2$-$C_6$-alkenyl, tri-$C_1$-$C_6$-alkylsilyl, $C_2$-$C_6$-alkynyl, $C_1$-$C_6$-alkoxy-$C_1$-$C_4$-alkyl, $C_1$-$C_6$-alkoxy-$C_1$-$C_4$-alkoxy, $C_3$-$C_6$-cycloalkyl, $C_3$-$C_6$-cycloalkoxy, $C_3$-$C_6$-cycloalkyl-$C_1$-$C_4$-alkyl, $C_3$-$C_6$-cycloalkoxy-$C_1$-$C_4$-alkyl, where the alkyl, cycloalkyl, cycloalkoxy and alkoxy parts of the last 6 mentioned radicals are unsubstituted or partially or completely halogenated, C(O)—$OR^a$, $NR^bR^c$, $C_1$-$C_6$-alkylen-$NR^bR^c$, O—$C_1$-$C_6$-alkylen-$NR^bR^c$, $C_1$-$C_6$-alkylen-CN, NH—$C_1$-$C_6$-alkylen-$NR^bR^c$,
C(O)—$NR^bR^c$, C(O)—$R^d$, $SO_2NR^bR^c$ and S(=O)$_m R^e$;
$R^3$, $R^6$ independently of each other, are selected from the group consisting of hydrogen, $C_1$-$C_6$-alkyl, $C_1$-$C_6$-haloalkyl, $C_1$-$C_6$-alkoxy, $C_1$-$C_6$-haloalkoxy, $C_2$-$C_6$-alkenyl, $C_2$-$C_6$-alkynyl, $C_1$-$C_6$-alkoxy-$C_1$-$C_4$-alkyl, $C_1$-$C_6$-alkoxy-$C_1$-$C_4$-alkoxy, $C_3$-$C_6$-cycloalkyl, $C_3$-$C_6$-cycloalkoxy, $C_3$-$C_6$-cycloalkyl-$C_1$-$C_4$-alkyl, $C_3$-$C_6$-cycloalkoxy-$C_1$-$C_4$-alkyl, where the alkyl, cycloalkyl, cycloalkoxy and alkoxy parts of the last 6 mentioned radicals are unsubstituted or partially or completely halogenated, C(O)—$OR^a$, $NR^bR^c$, $C_1$-$C_6$-alkylen-$NR^bR^c$, O—$C_1$-$C_6$-alkylen-$NR^bR^c$, $C_1$-$C_6$-alkylen-CN, NH—$C_1$-$C_6$-alkylen-$NR^bR^c$, C(O)—$NR^bR^c$, C(O)—$R^d$, $SO_2NR^bR^c$, S(=O)$_m R^e$, phenyl and benzyl, where the phenyl ring in the last 2 radicals is unsubstituted or carry 1, 2, 3, 4 or 5 radicals $R^f$;
$R^4$, $R^5$ independently of each other, are selected from the group consisting of hydrogen, halogen, CN, $C_1$-$C_4$-alkyl, $C_1$-$C_4$-haloalkyl, $C_1$-$C_4$-alkoxy, $C_1$-$C_4$-haloalkoxy, $C_1$-$C_4$-alkylthio and $C_1$-$C_4$-haloalkylthio or $C(R^4,R^5)$ may be a carbonyl group or thiocarbonyl group;
$R^8$, $R^9$ independently of each other, are selected from the group consisting of hydrogen, halogen, CN, $C_1$-$C_4$-alkyl, $C_1$-$C_4$-haloalkyl, $C_1$-$C_4$-alkoxy, $C_1$-$C_4$-haloalkoxy, $C_1$-$C_4$-alkylthio and $C_1$-$C_4$-haloalkylthio or $C(R^8,R^9)$ may be a carbonyl group or thiocarbonyl group;
Ar is phenyl or 5- or 6-membered hetaryl, which are unsubstituted or carry 1, 2, 3 or 4 radicals $R^{Ar}$, which are identical or different, where
$R^{Ar}$ independently of each other, are selected from the group consisting of halogen, $N_3$, OH, CN, $NO_2$, —SCN, —$SF_5$, $C_1$-$C_6$-alkyl, $C_1$-$C_6$-haloalkyl, $C_1$-$C_6$-alkoxy, $C_1$-$C_6$-haloalkoxy, $C_2$-$C_6$-alkenyl, tri-$C_1$-$C_6$-alkylsilyl, $C_2$-$C_6$-alkynyl, $C_1$-$C_6$-alkoxy-$C_1$-$C_4$-alkyl, $C_1$-$C_6$-alkoxy-$C_1$-$C_4$-alkoxy, $C_3$-$C_6$-cycloalkyl, $C_3$-$C_6$-cycloalkoxy, $C_3$-$C_6$-cycloalkyl-$C_1$-$C_4$-alkyl, $C_3$-$C_6$-cycloalkoxy-$C_1$-$C_4$-alkyl, where the alkyl, cycloalkyl, cycloalkoxy and alkoxy parts of the last 6 mentioned radicals are unsubstituted or partially or completely halogenated, C(O)—$OR^a$, $NR^bR^c$, $C_1$-$C_6$-alkylen-$NR^bR^c$, O—$C_1$-$C_6$-alkylen-$NR^bR^c$, $C_1$-$C_6$-alkylen-CN, NH—$C_1$-$C_6$-alkylen-$NR^bR^c$, C(O)—$NR^bR^c$, C(O)—$R^d$, $SO_2NR^bR^c$ and S(=O)$_m R^e$, one radical may also be phenyl, phenoxy, phenylcarbonyl, phenylthio or benzyl, where the phenyl ring in the last 5 radicals is unsubstituted or carry 1, 2, 3, 4 or 5 radicals $R^f$;

Q is —O—, —S—, —S(=O)—, —S(=O)$_2$—, —C(R$^{Q2a}$R$^{Q2b}$)—, —N(R$^{Q1}$)—, —N(R$^{Q2}$)—C(=O)—, —O—C(=O)—, —C(R$^{Q3}$)=C(R$^{Q4}$)—, —C(R$^{Q3a}$R$^{Q3b}$)—C(R$^{Q4a}$R$^{Q4b}$)—, —C(R$^{Q3a}$R$^{Q3b}$)—C(=O)—, —O—C(R$^{Q4a}$R$^{Q4b}$)—, —S(=O)$_n$—C(R$^{Q4a}$R$^{Q4b}$)— or —N(R$^{Q2}$)—C(R$^{Q4a}$R$^{Q4b}$)—, where n is 0, 1 or 2;

R$^{Q1}$, R$^{Q2}$ independently of each other are selected from the group consisting of hydrogen, C$_1$-C$_6$-alkyl, C$_1$-C$_6$-haloalkyl, C$_1$-C$_6$-alkoxy, C$_1$-C$_6$-haloalkoxy, C$_2$-C$_6$-alkenyl, C$_2$-C$_6$-alkynyl, C$_1$-C$_6$-alkoxy-C$_1$-C$_4$-alkyl, C$_1$-C$_6$-alkoxy-C$_1$-C$_4$-alkoxy, C$_3$-C$_6$-cycloalkyl, C$_3$-C$_6$-cycloalkoxy, C$_3$-C$_6$-cycloalkyl-C$_1$-C$_4$-alkyl, C$_3$-C$_6$-cycloalkoxy-C$_1$-C$_4$-alkyl, where the alkyl, cycloalkyl, cycloalkoxy and alkoxy parts of the last 6 mentioned radicals are unsubstituted or partially or completely halogenated, C(O)—OR$^a$, NR$^b$R$^c$, C$_1$-C$_6$-alkylen-NR$^b$R$^c$, C$_1$-C$_6$-alkylen-CN, C(O)—NR$^b$R$^c$, C(O)—R$^d$, SO$_2$NR$^b$R$^c$, S(=O)$_m$R$^e$, phenyl and benzyl, where the phenyl ring in the last 2 radicals is unsubstituted or carry 1, 2, 3, 4 or 5 radicals R$^f$;

R$^{Q3}$, R$^{Q4}$ independently of each other, are selected from the group consisting of hydrogen, halogen, OH, CN, C$_1$-C$_4$-alkyl, C$_1$-C$_4$-haloalkyl, C$_1$-C$_4$-alkoxy, C$_1$-C$_4$-haloalkoxy, C(O)—OR$^a$, NR$^b$R$^c$, C$_1$-C$_6$-alkylen-NR$^b$R$^c$, O—C$_1$-C$_6$-alkylen-NR$^b$R$^c$, C$_1$-C$_6$-alkylen-CN, NH—C$_1$-C$_6$-alkylen-NR$^b$R$^c$, C(O)—NR$^b$R$^c$, C(O)—R$^d$, SO$_2$NR$^b$R$^c$ and S(=O)$_m$R$^e$;

R$^{Q2a}$, R$^{Q2b}$ independently of each other, are selected from the group consisting of hydrogen, halogen, CN, C$_1$-C$_4$-alkyl, C$_1$-C$_4$-haloalkyl, C$_1$-C$_4$-alkoxy, C$_1$-C$_4$-haloalkoxy, C$_1$-C$_4$-alkylthio and C$_1$-C$_4$-haloalkylthio or —C(R$^{Q2a}$R$^{Q2b}$)— is C=O or C=S;

R$^{Q3a}$, R$^{Q3b}$ independently of each other, are selected from the group consisting of hydrogen, halogen, CN, C$_1$-C$_4$-alkyl, C$_1$-C$_4$-haloalkyl, C$_1$-C$_4$-alkoxy, C$_1$-C$_4$-haloalkoxy, C$_1$-C$_4$-alkylthio and C$_1$-C$_4$-haloalkylthio;

R$^{Q4a}$, R$^{Q4b}$ independently of each other, are selected from the group consisting of hydrogen, halogen, CN, C$_1$-C$_4$-alkyl, C$_1$-C$_4$-haloalkyl, C$_1$-C$_4$-alkoxy, C$_1$-C$_4$-haloalkoxy, C$_1$-C$_4$-alkylthio and C$_1$-C$_4$-haloalkylthio;

R$^1$ is a moiety of the formula —X—Y—Z—R$^{11}$, where R$^{11}$ is selected from the group consisting of C$_1$-C$_6$-alkyl, C$_1$-C$_6$-haloalkyl, C$_2$-C$_6$-alkenyl, C$_2$-C$_6$-alkynyl, C$_1$-C$_6$-alkoxy-C$_1$-C$_4$-alkyl, C$_3$-C$_6$-cycloalkyl, C$_3$-C$_6$-cycloalkyl-C$_1$-C$_4$-alkyl, C$_3$-C$_6$-cycloalkoxy-C$_1$-C$_4$-alkyl, where the alkyl, cycloalkyl, cycloalkoxy and alkoxy parts of the last four mentioned radicals are unsubstituted or partially or completely halogenated, C$_1$-C$_6$-alkylen-NR$^b$R$^c$, C$_1$-C$_6$-alkylen-CN, C(O)—NR$^b$R$^c$, C(O)—R$^d$, aryl, arylcarbonyl, aryl-C$_1$-C$_4$-alkyl, aryloxy-C$_1$-C$_4$-alkyl, hetaryl, hetarylcarbonyl, hetaryl-C$_1$-C$_4$-alkyl and hetaryloxy-C$_1$-C$_4$-alkyl, where the aryl and hetaryl rings in the last 8 radicals are unsubstituted or carry 1, 2, 3, 4 or 5 radicals R$^g$ and where hetaryl is a 5- or 6-membered monocyclic hetaryl or a 8-, 9- or 10-membered bicyclic hetaryl;

X is a single bond, NR$^{x1}$, or a bivalent group —N(R$^{x2}$)—C(=O)—, where C=(O) is bound to Y, —N(R$^{x2}$)—C(=S)—, where C=(S) is bound to Y, or a bivalent group —C(R$^{x3}$)=N—, where the nitrogen is bound to Y, Y is a bivalent group —N(R$^{y1}$)—C(=O)—, —N(R$^{y2}$)—C(=S)—, —N=C((O)$_p$—R$^{y3}$)— or —N=C((S)$_p$—R$^{y3}$)—, where the nitrogen atom in the four groups is bound to X and where p is 0 or 1, Z is O, S or N—R$^z$, and where R$^{x1}$, R$^{x2}$ independently of each other, are selected from the group consisting of hydrogen, C$_1$-C$_6$-alkyl, C$_1$-C$_6$-haloalkyl, C$_2$-C$_6$-alkenyl, C$_2$-C$_6$-alkynyl, C$_1$-C$_6$-alkoxy-C$_1$-C$_4$-alkyl, C$_3$-C$_6$-cycloalkyl, C$_3$-C$_6$-cycloalkyl-C$_1$-C$_4$-alkyl, C$_3$-C$_6$-cycloalkoxy-C$_1$-C$_4$-alkyl, where the alkyl, cycloalkyl, cycloalkoxy and alkoxy parts of the last four mentioned radicals are unsubstituted or partially or completely halogenated, C(O)—OR$^a$, C$_1$-C$_6$-alkylen-NR$^b$R$^c$, C$_1$-C$_6$-alkylen-CN, C(O)—NR$^b$R$^c$, C(O)—R$^d$, SO$_2$NR$^b$R$^c$, S(=O)$_m$R$^e$, phenyl and benzyl, where the phenyl ring in the last 2 radicals is unsubstituted or carry 1, 2, 3, 4 or 5 radicals R$^f$;

R$^{x3}$ is selected from the group consisting of hydrogen, halogen, CN, C$_1$-C$_6$-alkyl, C$_1$-C$_6$-haloalkyl, C$_1$-C$_6$-alkoxy, C$_1$-C$_6$-haloalkoxy, C$_2$-C$_6$-alkenyl, tri-C$_1$-C$_6$-alkylsilyl, C$_2$-C$_6$-alkynyl, C$_1$-C$_6$-alkoxy-C$_1$-C$_4$-alkyl, C$_1$-C$_6$-alkoxy-C$_1$-C$_4$-alkoxy, C$_3$-C$_6$-cycloalkyl, C$_3$-C$_6$-cycloalkoxy, C$_3$-C$_6$-cycloalkyl-C$_1$-C$_4$-alkyl, C$_3$-C$_6$-cycloalkoxy-C$_1$-C$_4$-alkyl, where the alkyl, cycloalkyl, cycloalkoxy and alkoxy parts of the last 6 mentioned radicals are unsubstituted or partially or completely halogenated, C$_1$-C$_6$-alkylen-NR$^b$R$^c$, O—C$_1$-C$_6$-alkylen-NR$^b$R$^c$, C$_1$-C$_6$-alkylen-CN, NH—C$_1$-C$_6$-alkylen-NR$^b$R$^c$, C(O)—NR$^b$R$^c$, C(O)—R$^d$, phenyl, phenoxy, phenylcarbonyl, phenylthio and benzyl, where the phenyl ring in the last 5 radicals is unsubstituted or carry 1, 2, 3, 4 or 5 radicals R$^f$;

p is 0 or 1;

R$^{y1}$, R$^{y2}$ independently of each other, are selected from the group consisting of hydrogen, C$_1$-C$_6$-alkyl, C$_1$-C$_6$-haloalkyl, C$_2$-C$_6$-alkenyl, C$_2$-C$_6$-alkynyl, C$_1$-C$_6$-alkoxy-C$_1$-C$_4$-alkyl, C$_1$-C$_6$-alkoxy-C$_1$-C$_4$-alkoxy, C$_3$-C$_6$-cycloalkyl, C$_3$-C$_6$-cycloalkyl-C$_1$-C$_4$-alkyl, C$_3$-C$_6$-cycloalkoxy-C$_1$-C$_4$-alkyl, where the alkyl, cycloalkyl, cycloalkoxy and alkoxy parts of the last 4 mentioned radicals are unsubstituted or partially or completely halogenated, C(O)—OR$^a$, C$_1$-C$_6$-alkylen-NR$^b$R$^c$, C$_1$-C$_6$-alkylen-CN, C(O)—NR$^b$R$^c$, C(O)—R$^d$, SO$_2$NR$^b$R$^c$, S(=O)$_m$R$^e$, phenyl and benzyl, where the phenyl ring in the last 2 radicals is unsubstituted or carry 1, 2, 3, 4 or 5 radicals R$^f$;

R$^{y3}$ is selected from the group consisting of hydrogen, C$_1$-C$_6$-alkyl, C$_1$-C$_6$-haloalkyl, C$_1$-C$_6$-alkoxy, C$_1$-C$_6$-haloalkoxy, C$_2$-C$_6$-alkenyl, tri-C$_1$-C$_6$-alkylsilyl, C$_2$-C$_6$-alkynyl, C$_1$-C$_6$-alkoxy-C$_1$-C$_4$-alkyl, C$_3$-C$_6$-cycloalkyl, C$_3$-C$_6$-cycloalkyl-C$_1$-C$_4$-alkyl, C$_3$-C$_6$-cycloalkoxy-C$_1$-C$_4$-alkyl, where the alkyl, cycloalkyl, cycloalkoxy and alkoxy parts of the last four mentioned radicals are unsubstituted or partially or completely halogenated, C$_1$-C$_6$-alkylen-NR$^b$R$^c$, C$_1$-C$_6$-alkylen-CN, C(O)—NR$^b$R$^c$, C(O)—R$^d$, phenyl, phenylcarbonyl and benzyl, where the phenyl ring in the last 3 radicals is unsubstituted or carry 1, 2, 3, 4 or 5 radicals R$^f$;

R$^z$ is selected from the group consisting of hydrogen, C$_1$-C$_6$-alkyl, C$_1$-C$_6$-haloalkyl, C$_2$-C$_6$-alkenyl, C$_2$-C$_6$-alkynyl, C$_1$-C$_6$-alkoxy-C$_1$-C$_4$-alkyl, C$_3$-C$_6$-cycloalkyl, C$_3$-C$_6$-cycloalkyl-C$_1$-C$_4$-alkyl, C$_3$-C$_6$-cycloalkoxy-C$_1$-C$_4$-alkyl, where the alkyl, cycloalkyl, cycloalkoxy and alkoxy parts of the last 4 mentioned radicals are unsubstituted or partially or completely halogenated, C(O)—OR$^a$, C$_1$-C$_6$-alkylen-NR$^b$R$^c$, C$_1$-C$_6$-alkylen-CN, C(O)—NR$^b$R$^c$, C(O)—R$^d$, SO$_2$NR$^b$R$^c$, S(=O)$_m$R$^e$, phenyl and benzyl, where the phenyl ring in the last 2 radicals is unsubstituted or carry 1, 2, 3, 4 or 5 radicals R$^f$, or R$^z$ together with R$^{y3}$, if present, may also form a C$_2$-C$_6$-alkylene group, wherein a CH$_2$ moiety may be replaced by a carbonyl group and/or wherein 1 or 2 CH$_2$ moieties may be replaced by O or S and/or wherein the alkylene group may be substituted 1, 2, 3, 4, 5 or 6 radicals R$^{hh}$;

k is 0, 1, 2 or 3;

R is selected from the group consisting of halogen, N$_3$, OH, CN, NO$_2$, —SCN, —SF$_5$, C$_1$-C$_6$-alkyl, C$_1$-C$_6$-haloalkyl, C$_1$-C$_6$-alkoxy, C$_1$-C$_6$-haloalkoxy, C$_2$-C$_6$-alkenyl, tri-C$_1$-C$_6$-alkylsilyl, C$_2$-C$_6$-alkynyl, C$_1$-C$_6$-alkoxy-C$_1$-C$_4$-alkyl, C$_1$-C$_6$-alkoxy-C$_1$-C$_4$-alkoxy, C$_3$-C$_6$-cycloalkyl, C$_3$-C$_6$-cycloalkoxy, C$_3$-C$_6$-cycloalkyl-C$_1$-C$_4$-alkyl, C$_3$-C$_6$-cycloalkoxyx-C$_1$-C$_4$-alkyl, where the alkyl, cycloalkyl, cycloalkoxy and alkoxy parts of the last 6 mentioned radicals are unsubstituted or partially or completely halogenated, C(O)—OR$^a$, NR$^b$R$^c$, C$_1$-C$_6$-alkylen-NR$^b$R$^c$, O—C$_1$-C$_6$-alkylen-NR$^b$R$^c$, C$_1$-C$_6$-alkylen-CN, NH—C$_1$-C$_6$-alkylen-NR$^b$R$^c$, C(O)—NR$^b$R$^c$, C(O)—R$^d$, SO$_2$NR$^b$R$^c$ and S(=O)$_m$R$^e$, one radical may also be phenyl, phenoxy, phenylcarbonyl, phenylthio or benzyl, where the phenyl ring in the last 5 radicals is unsubstituted or carry 1, 2, 3, 4 or 5 radicals R$^f$;

it being possible for k=2 or 3 that R are identical or different;

and where each m is independently 0, 1 or 2;

each R$^a$ is selected from the group consisting of hydrogen, C$_1$-C$_6$-alkyl, C$_1$-C$_6$-haloalkyl, C$_2$-C$_6$-alkenyl, C$_2$-C$_6$-alkynyl, C$_1$-C$_6$-alkoxy-C$_1$-C$_4$-alkyl, C$_3$-C$_6$-cycloalkyl, C$_3$-C$_6$-cycloalkyl-C$_1$-C$_4$-alkyl, C$_3$-C$_6$-cycloalkoxy-C$_1$-C$_4$-alkyl, where the alkyl, cycloalkyl, cycloalkoxy and alkoxy parts of the last 4 mentioned radicals are unsubstituted or partially or completely halogenated, C$_1$-C$_6$-alkylen-NR$^b$R$^c$, C$_1$-C$_6$-alkylen-CN, phenyl and benzyl, where the phenyl ring in the last 2 radicals is unsubstituted or carry 1, 2, 3, 4 or 5 radicals R$^f$;

each R$^b$ is selected from the group consisting of hydrogen, C$_1$-C$_6$-alkyl, C$_1$-C$_6$-haloalkyl, C$_2$-C$_6$-alkenyl, C$_2$-C$_6$-alkynyl, C$_1$-C$_6$-alkoxy-C$_1$-C$_4$-alkyl, C$_3$-C$_6$-cycloalkyl, C$_3$-C$_6$-cycloalkyl-C$_1$-C$_4$-alkyl, C$_3$-C$_6$-cycloalkoxy-C$_1$-C$_4$-alkyl, where the alkyl, cycloalkyl, cycloalkoxy and alkoxy parts of the last 4 mentioned radicals are unsubstituted or partially or completely halogenated, C$_1$-C$_6$-alkylen-CN, phenyl and benzyl, where the phenyl ring in the last 2 radicals is unsubstituted or carry 1, 2, 3, 4 or 5 radicals R$^f$;

each R$^c$ is selected from the group consisting of hydrogen, C$_1$-C$_6$-alkyl, C$_1$-C$_6$-haloalkyl, C$_2$-C$_6$-alkenyl, C$_2$-C$_6$-alkynyl, C$_1$-C$_6$-alkoxy-C$_1$-C$_4$-alkyl, C$_3$-C$_6$-cycloalkyl, C$_3$-C$_6$-cycloalkyl-C$_1$-C$_4$-alkyl, C$_3$-C$_6$-cycloalkoxy-C$_1$-C$_4$-alkyl, where the alkyl, cycloalkyl, cycloalkoxy and alkoxy parts of the last 4 mentioned radicals are unsubstituted or partially or completely halogenated, C$_1$-C$_6$-alkylen-CN, phenyl and benzyl, where the phenyl ring in the last 2 radicals is unsubstituted or carry 1, 2, 3, 4 or 5 radicals R$^f$;

each moiety NR$^b$R$^c$ may also form an N-bound, saturated 5- to 8-membered heterocycle, which in addition to the nitrogen atom may have 1 or 2 further heteroatoms or heteroatom moieties selected from O, S(=O)$_m$ and N—R', where R' is hydrogen or C$_1$-C$_6$-alkyl and where the N-bound heterocycle is unsubstituted or carries 1, 2, 3, 4, 5 or 6 radicals selected from halogen, C$_1$-C$_4$-alkyl, C$_1$-C$_4$-haloalkyl, C$_1$-C$_4$-alkoxy and C$_1$-C$_4$-haloalkoxy;

each R$^d$ is selected from the group consisting of hydrogen, C$_1$-C$_6$-alkyl, C$_1$-C$_6$-haloalkyl, C$_2$-C$_6$-alkenyl, C$_2$-C$_6$-alkynyl, C$_1$-C$_6$-alkoxy-C$_1$-C$_4$-alkyl, C$_3$-C$_6$-cycloalkyl, C$_3$-C$_6$-cycloalkyl-C$_1$-C$_4$-alkyl, C$_3$-C$_6$-cycloalkoxy-C$_1$-C$_4$-alkyl, where the alkyl, cycloalkyl, cycloalkoxy and alkoxy parts of the last 4 mentioned radicals are unsubstituted or partially or completely halogenated, phenyl and benzyl, where the phenyl ring in the last 2 radicals is unsubstituted or carry 1, 2, 3, 4 or 5 radicals R$^f$;

each R$^e$ is selected from the group consisting of C$_1$-C$_6$-alkyl, C$_1$-C$_6$-haloalkyl, C$_3$-C$_6$-cycloalkyl, C$_3$-C$_6$-cycloalkyl-C$_1$-C$_4$-alkyl, where the alkyl and cycloalkyl parts of the last 2 mentioned radicals are unsubstituted or partially or completely halogenated, phenyl and benzyl, where the phenyl ring in the last 2 radicals is unsubstituted or carry 1, 2, 3, 4 or 5 radicals R$^f$;

each R$^f$ is selected from the group consisting of halogen, N$_3$, OH, CN, NO$_2$, —SCN, —SF$_5$, C$_1$-C$_6$-alkyl, C$_1$-C$_6$-haloalkyl, C$_1$-C$_6$-alkoxy, C$_1$-C$_6$-haloalkoxy, C$_2$-C$_6$-alkenyl, tri-C$_1$-C$_6$-alkylsilyl, C$_2$-C$_6$-alkynyl, C$_1$-C$_6$-alkoxy-C$_1$-C$_4$-alkyl, C$_1$-C$_6$-alkoxy-C$_1$-C$_4$-alkoxy, C$_3$-C$_6$-cycloalkyl, C$_3$-C$_6$-cycloalkoxy, C$_3$-C$_6$-cycloalkyl-C$_1$-C$_4$-alkyl, C$_3$-C$_6$-cycloalkoxyx-C$_1$-C$_4$-alkyl, where the alkyl, cycloalkyl, cycloalkoxy and alkoxy parts of the last 6 mentioned radicals are unsubstituted or partially or completely halogenated, C(O)—OR$^a$, NR$^b$R$^c$, C$_1$-C$_6$-alkylen-NR$^b$R$^c$, O—C$_1$-C$_6$-alkylen-NR$^b$R$^c$, C$_1$-C$_6$-alkylen-CN, NH—C$_1$-C$_6$-alkylen-NR$^b$R$^c$, C(O)—NR$^b$R$^c$, C(O)—R$^d$, SO$_2$NR$^b$R$^c$ and S(=O)$_m$R$^e$;

each R$^g$ is selected from the group consisting of halogen, N$_3$, OH, CN, NO$_2$, —SCN, —SF$_5$, C$_1$-C$_6$-alkyl, C$_1$-C$_6$-haloalkyl, C$_1$-C$_6$-alkoxy, C$_1$-C$_6$-haloalkoxy, C$_2$-C$_6$-alkenyl, tri-C$_1$-C$_6$-alkylsilyl, C$_2$-C$_6$-alkynyl, C$_1$-C$_6$-alkoxy-C$_1$-C$_4$-alkyl, C$_1$-C$_6$-alkoxy-C$_1$-C$_4$-alkoxy, C$_3$-C$_6$-cycloalkyl, C$_3$-C$_6$-cycloalkoxy, C$_3$-C$_6$-cycloalkyl-C$_1$-C$_4$-alkyl, C$_3$-C$_6$-cycloalkoxy-C$_1$-C$_4$-alkyl, where the alkyl, cycloalkyl, cycloalkoxy and alkoxy parts of the last 6 mentioned radicals are unsubstituted or partially or completely halogenated, C(O)—OR$^a$, NR$^b$R$^c$, C$_1$-C$_6$-alkylen-NR$^b$R$^c$, O—C$_1$-C$_6$-alkylen-NR$^b$R$^c$, C$_1$-C$_6$-alkylen-CN, NH—C$_1$-C$_6$-alkylen-NR$^b$R$^c$, C(O)—NR$^b$R$^c$, C(O)—R$^d$, SO$_2$NR$^b$R$^c$ and S(=O)$_m$R$^e$;

each R$^{hh}$ is selected from halogen, C$_1$-C$_6$-alkyl, C$_3$-C$_6$-cycloalkyl, or CN;

and the N-oxides, stereoisomers, tautomers and agriculturally or veterinarily acceptable salts thereof.

The present invention also relates to a compound of the formula INT and to the tautomers and salts thereof

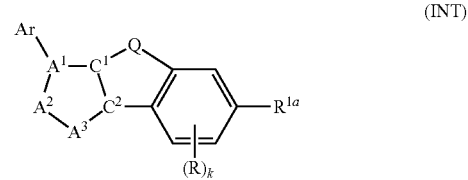

(INT)

where $R^{1a}$ is C(=O)$R^{3xa}$, CN, N($R^{X1a}$)H, halogen and where $R^{x1a}$ is selected from the group consisting of hydrogen, OH, $C_1$-$C_6$-alkyl, $C_1$-$C_6$-haloalkyl, $C_2$-$C_6$-alkenyl, $C_2$-$C_6$-alkynyl, $C_1$-$C_6$-alkoxy-$C_1$-$C_4$-alkyl, $C_3$-$C_6$-cycloalkyl, $C_3$-$C_6$-cycloalkyl-$C_1$-$C_4$-alkyl, $C_3$-$C_6$-cycloalkoxy-$C_1$-$C_4$-alkyl, where the alkyl, cycloalkyl, cycloalkoxy and alkoxy parts of the last four mentioned radicals are unsubstituted or partially or completely halogenated, $C_1$-$C_6$-alkylen-NR$^b$R$^c$, $C_1$-$C_6$-alkylen-CN, phenyl and benzyl, where the phenyl ring in the last 2 radicals is unsubstituted or carry 1, 2, 3, 4 or 5 radicals R$^f$; and where $R^{x1a}$ is in particular hydrogen, OH, or $C_1$-$C_6$-alkoxy such as methoxy, ethoxy, n-propoxy, isopropoxy or tert.-butoxy;

$R^{x3a}$ is selected from the group consisting of hydrogen, OH, $C_1$-$C_6$-alkyl, $C_1$-$C_6$-haloalkyl, $C_1$-$C_6$-alkoxy, $C_1$-$C_6$-haloalkoxy, $C_2$-$C_6$-alkenyl, tri-$C_1$-$C_6$-alkylsilyl, $C_2$-$C_6$-alkynyl, $C_1$-$C_6$-alkoxy-$C_1$-$C_4$-alkyl, $C_1$-$C_6$-alkoxy-$C_1$-$C_4$-alkoxy, $C_3$-$C_6$-cycloalkyl, $C_3$-$C_6$-cycloalkoxy, $C_3$-$C_6$-cycloalkoxy-$C_1$-$C_4$-alkyl, $C_3$-$C_6$-cycloalkyl-$C_1$-$C_4$-alkyl, where the alkyl, cycloalkyl, cycloalkoxy and alkoxy parts of the last 6 mentioned radicals are unsubstituted or partially or completely halogenated, $C_1$-$C_6$-alkylen-NR$^b$R$^c$, O—$C_1$-$C_6$-alkylen-NR$^b$R$^c$, $C_1$-$C_6$-alkylen-CN, phenyl, phenoxy, phenylcarbonyl, phenylthio and benzyl, where the phenyl ring in the last 5 radicals is unsubstituted or carry 1, 2, 3, 4 or 5 radicals R$^f$; and where $R^{x3a}$ is in particular hydrogen;

and where Ar, $A^1$, $A^2$, $A^3$, $C^1$, $C^2$, Q, k and R are as defined herein and the salts thereof.

The compounds of formula INT and their tautomers and salts are valuable intermediates in the preparation of the compounds of formula I.

Moreover, the present invention also relates to and includes the following aspects:

an agricultural composition comprising at least one compound of formula (I) or a stereoisomer, a tautomer, a N-oxide or an agriculturally acceptable salt thereof, and at least one liquid and/or solid carrier.

a veterinary composition comprising at least one compound of formula (I) or a stereoisomer, a tautomer, a N-oxide or a veterinarily acceptable salt thereof, and at least one liquid and/or solid carrier.

a method for combating or controlling invertebrate pests which method comprises treating the pests, their food supply, their habitat or their breeding ground or a cultivated plant, plant propagation materials (such as seed), soil, area, material or environment in which the pests are growing or may grow, or the materials, cultivated plants, plant propagation materials (such as seed), soils, surfaces or spaces to be protected from pest attack or infestation with a pesticidally effective amount of a compound selected from compounds of formula I, the N-oxides, stereoisomers, tautomers or salts thereof as defined herein.

a method for protecting growing plants from attack or infestation by invertebrate pests, which method comprises contacting a plant, or soil or water in which the plant is growing, with a pesticidally effective amount of at least one compound of formula (I) or a stereoisomer, a tautomer, a N-oxide or an agriculturally or veterinarily acceptable salt thereof, or a composition as defined herein.

a method for the protection of plant propagation material, especially seeds, from soil insects and of the seedlings' roots and shoots from soil and foliar insects comprising contacting the plant propagation material respectively seeds before sowing and/or after pre-germination with at least one compound of formula (I) or a stereoisomer, a tautomer, a N-oxide or an agriculturally or veterinarily acceptable salt thereof, or a composition as defined herein.

plant propagation material, in particular seed, comprising at least one compound of formula I, an N-oxide, a stereoisomer, a tautomer and/or an agriculturally acceptable salt thereof as defined herein.

use of a compound of formula (I) or a stereoisomer, a tautomer, a N-oxide or an agriculturally or veterinarily acceptable salt thereof, or a composition as defined herein for combating or controlling invertebrate pests of the group of insects, arachnids or nematodes.

use of a compound of formula (I) or a stereoisomer, a tautomer, a N-oxide or an agriculturally or veterinarily acceptable salt thereof, or a composition as defined herein for protecting growing plants from attack or infestation by invertebrate pests.

use of a compound of formula (I) or a stereoisomer, a tautomer, a N-oxide or a veterinarily acceptable salt thereof or a composition as defined herein for combating or controlling invertebrate parasites in and on animals.

a method for treating a non-human animal infested or infected by parasites or for preventing a non-human animal from getting infested or infected by parasites or for protecting a non-human animal against infestation or infection by parasites which comprises orally, topically or parenteraly administering or applying to the non-human animal a parasiticidally effective amount of a compound compound of formula (I) or a stereoisomer, a tautomer, a N-oxide or a veterinarily acceptable salt thereof or a composition as defined in claim herein.

a compound compound of formula (I) or a stereoisomer, a tautomer, a N-oxide or a veterinarily acceptable salt thereof for use as a medicament.

a compound compound of formula (I) or a stereoisomer, a tautomer, a N-oxide or a veterinarily acceptable salt thereof for use in the treatment, control, prevention or protection of animals against infestation or infection by parasites.

The term "tautomers" encompasses isomers, which are derived from the compounds of formula I by the shift of an H-atom involving at least one H-atom located at a nitrogen, oxygen or sulphur atom. Examples of tautomeric forms are keto-enol forms, imine-enamine forms, urea-isourea forms, thiourea-isothiourea forms, (thio)amide(thio)imidate forms etc.

The term "stereoisomers" encompasses both optical isomers, such as enantiomers or diastereomers, the latter existing due to more than one center of chirality in the molecule, as well as geometrical isomers (cis/trans isomers).

Depending on the substitution pattern, the compounds of the formula I may have one or more centers of chirality, in which case they are present as mixtures of enantiomers or diastereomers. One center of chirality is the carbon ring atom of the isothiazoline ring carrying radical $R^1$. The invention provides both the pure enantiomers or diastereomers and their mixtures and the use according to the invention of the pure enantiomers or diastereomers of the compound I or its mixtures. Suitable compounds of the formula I also include all possible geometrical stereoisomers (cis/trans isomers) and mixtures thereof.

The term N-oxides relates to a form of compounds I in which at least one nitrogen atom is present in oxidized form (as NO). To be more precise, it relates to any compound of the present invention which has at least one tertiary nitrogen atom that is oxidized to an N-oxide moiety. N-oxides of compounds I can in particular be prepared by oxidizing e.g. the ring nitrogen atom of an N-heterocycle, e.g. a pyridine or pyrimidine ring present in Ar or $R^{11}$, or an imino-nitrogen present in central tricyclic core, with a suitable oxidizing agent, such as peroxo carboxylic acids or other peroxides. The person skilled in the art knows if and in which positions compounds of the present invention may form N-oxides.

The compounds of the present invention may be amorphous or may exist in one or more different crystalline states (polymorphs) which may have a different macroscopic properties such as stability or show different biological properties such as activities. The present invention includes both amorphous and crystalline compounds of the formula I, mixtures of different crystalline states of the respective compound I, as well as amorphous or crystalline salts thereof.

Salts of the compounds of the formula I are preferably agriculturally and veterinarily acceptable salts. They can be formed in a customary method, e.g. by reacting the compound with an acid of the anion in question if the compound of formula I has a basic functionality or by reacting an acidic compound of formula I with a suitable base.

Suitable agriculturally acceptable salts are especially the salts of those cations or the acid addition salts of those acids whose cations and anions, respectively, do not have any adverse effect on the action of the compounds according to the present invention. Suitable cations are in particular the ions of the alkali metals, preferably lithium, sodium and potassium, of the alkaline earth metals, preferably calcium, magnesium and barium, and of the transition metals, preferably manganese, copper, zinc and iron, and also ammonium ($NH^{4+}$) and substituted ammonium in which one to four of the hydrogen atoms are replaced by $C_1$-$C_4$-alkyl, $C_1$-$C_4$-hydroxyalkyl, $C_1$-$C_4$-alkoxy, $C_1$-$C_4$-alkoxy-$C_1$-$C_4$-alkyl, hydroxy-$C_1$-$C_4$-alkoxy-$C_1$-$C_4$-alkyl, phenyl or benzyl. Examples of substituted ammonium ions comprise methylammonium, isopropylammonium, dimethylammonium, diisopropylammonium, trimethylammonium, tetramethylammonium, tetraethylammonium, tetrabutylammonium, 2-hydroxyethylammonium, 2-(2-hydroxyethoxy) ethylammonium, bis(2-hydroxyethyl)ammonium, benzyltrimethylammonium and benzyl-triethylammonium, furthermore phosphonium ions, sulfonium ions, preferably tri($C_1$-$C_4$-alkyl)sulfonium, and sulfoxonium ions, preferably tri($C_1$-$C_4$-alkyl)sulfoxonium.

Anions of useful acid addition salts are primarily chloride, bromide, fluoride, hydrogen sulfate, sulfate, dihydrogen phosphate, hydrogen phosphate, phosphate, nitrate, hydrogen carbonate, carbonate, hexafluorosilicate, hexafluorophosphate, benzoate, and the anions of $C_1$-$C_4$-alkanoic acids, preferably formate, acetate, propionate and butyrate. They can be formed by reacting a compound of formulae I with an acid of the corresponding anion, preferably of hydrochloric acid, hydrobromic acid, sulfuric acid, phosphoric acid or nitric acid.

By the term "veterinarily acceptable salts" is meant salts of those cations or anions which are known and accepted in the art for the formation of salts for veterinary use. Suitable acid addition salts, e.g. formed by compounds of formula I containing a basic nitrogen atom, e.g. an amino group, include salts with inorganic acids, for example hydrochlorides, sulphates, phosphates, and nitrates and salts of organic acids for example acetic acid, maleic acid, dimaleic acid, fumaric acid, difumaric acid, methane sulfenic acid, methane sulfonic acid, and succinic acid.

The term "invertebrate pest" as used herein encompasses animal populations, such as insects, arachnids and nematodes, which may attack plants, thereby causing substantial damage to the plants attacked, as well as ectoparasites which may infest animals, in particular warm blooded animals such as e.g. mammals or birds, or other higher animals such as reptiles, amphibians or fish, thereby causing substantial damage to the animals infested.

The term "plant propagation material" is to be understood to denote all the generative parts of the plant such as seeds and vegetative plant material such as cuttings and tubers (e.g. potatoes), which can be used for the multiplication of the plant. This includes seeds, roots, fruits, tubers, bulbs, rhizomes, shoots, sprouts and other parts of plants, including seedlings and young plants, which are to be transplanted after germination or after emergence from soil. The plant propagation materials may be treated prophylactically with a plant protection compound either at or before planting or transplanting. Said young plants may also be protected before transplantation by a total or partial treatment by immersion or pouring.

The term "plants" comprises any types of plants including "non-cultivated plants" and in particular "cultivated plants".

The term "non-cultivated plants" refers to any wild type species or related species or related genera of a cultivated plant.

The term "cultivated plants" is to be understood as including plants which have been modified by breeding, mutagenesis or genetic engineering including but not limiting to agricultural biotech products on the market or in development (cf. http://www.bio.org/speeches/pubs/er/agri_products.asp). Genetically modified plants are plants, which genetic material has been so modified by the use of recombinant DNA techniques that under natural circumstances cannot readily be obtained by cross breeding, mutations or natural recombination. Typically, one or more genes have been integrated into the genetic material of a genetically modified plant in order to improve certain properties of the plant. Such genetic modifications also include but are not limited to targeted post-translational modification of protein(s), oligo- or polypeptides e.g. by glycosylation or polymer additions such as prenylated, acetylated or farnesylated moieties or PEG moieties.

Plants that have been modified by breeding, mutagenesis or genetic engineering, e.g. have been rendered tolerant to applications of specific classes of herbicides, such as auxin herbicides such as dicamba or 2,4-D; bleacher herbicides such as hydroxylphenylpyruvate dioxygenase (HPPD) inhibitors or phytoene desaturase (PDS) inhibitors; acetolactate synthase (ALS) inhibitors such as sulfonyl ureas or imidazolinones; enolpyruvylshikimate-3-phosphate synthase (EPSPS) inhibitors, such as glyphosate; glutamine synthetase (GS) inhibitors such as glufosinate; protoporphyrinogen-IX oxidase inhibitors; lipid biosynthesis inhibitors such as acetyl CoA carboxylase (ACCase) inhibitors; or oxynil (i.e. bromoxynil or ioxynil) herbicides as a result of conventional methods of breeding or genetic engineering. Furthermore, plants have been made resistant to multiple classes of herbicides through multiple genetic modifications, such as resistance to both glyphosate and glufosinate or to both glyphosate and a herbicide from another class such as ALS inhibitors, HPPD inhibitors, auxin herbicides, or ACCase inhibitors. These herbicide resistance technologies are e.g. described in Pest Managem. Sci. 61, 2005, 246; 61, 2005, 258; 61, 2005, 277; 61, 2005, 269; 61, 2005, 286; 64, 2008, 326; 64, 2008, 332; Weed Sci. 57, 2009, 108; Austral. J. Agricult. Res. 58, 2007, 708; Science 316, 2007, 1185; and references quoted therein. Several cultivated plants have been rendered tolerant to herbicides by conventional methods of breeding (mutagenesis), e.g. Clearfield® summer rape (Canola, BASF SE, Germany) being tolerant to imidazolinones, e.g. imazamox, or ExpressSun® sunflowers (DuPont, USA) being tolerant to sulfonyl ureas, e. g. tribenuron. Genetic engineering methods have been used to render cultivated plants such as soybean, cotton, corn, beets and rape, tolerant to herbicides such as glyphosate and glufosinate, some of which are commercially available under the trade names RoundupReady® (glyphosate-tolerant, Monsanto, U.S.A.), Cultivance® (imidazolinone tolerant, BASF SE, Germany) and LibertyLink® (glufosinate-tolerant, Bayer CropScience, Germany).

Furthermore, plants are also covered that are by the use of recombinant DNA techniques capable to synthesize one or more insecticidal proteins, especially those known from the bacterial genus *Bacillus*, particularly from *Bacillus thuringiensis*, such as δ-endotoxins, e. g. CryIA(b), CryIA(c), CryIF, CryIF(a2), CryIIA(b), CryIIIA, CryIIIB(b1) or Cry9c; vegetative insecticidal proteins (VIP), e. g. VIP1, VIP2, VIP3 or VIP3A; insecticidal proteins of bacteria colonizing nematodes, e. g. *Photorhabdus* spp. or *Xenorhabdus* spp.; toxins produced by animals, such as scorpion toxins, arachnid toxins, wasp toxins, or other insect-specific neurotoxins; toxins produced by fungi, such Streptomycetes toxins, plant lectins, such as pea or barley lectins; agglutinins; proteinase inhibitors, such as trypsin inhibitors, serine protease inhibitors, patatin, cystatin or papain inhibitors; ribosome-inactivating proteins (RIP), such as ricin, maize-RIP, abrin, luffin, saporin or bryodin; steroid metabolism enzymes, such as 3-hydroxysteroid oxidase, ecdysteroid-IDP-glycosyl-transferase, cholesterol oxidases, ecdysone inhibitors or HMG-CoA-reductase; ion channel blockers, such as blockers of sodium or calcium channels; juvenile hormone esterase; diuretic hormone receptors (helicokinin receptors); stilben synthase, bibenzyl synthase, chitinases or glucanases. In the context of the present invention these insecticidal proteins or toxins are to be understood expressly also as pre-toxins, hybrid proteins, truncated or otherwise modified proteins. Hybrid proteins are characterized by a new combination of protein domains, (see, e. g. WO 02/015701). Further examples of such toxins or genetically modified plants capable of synthesizing such toxins are disclosed, e.g., in EP-A 374 753, WO 93/007278, WO 95/34656, EP-A 427 529, EP-A 451 878, WO 03/18810 und WO 03/52073. The methods for producing such genetically modified plants are generally known to the person skilled in the art and are described, e. g. in the publications mentioned above. These insecticidal proteins contained in the genetically modified plants impart to the plants producing these proteins tolerance to harmful pests from all taxonomic groups of athropods, especially to beetles (Coeloptera), two-winged insects (Diptera), and moths (Lepidoptera) and to nematodes (Nematoda). Genetically modified plants capable to synthesize one or more insecticidal proteins are, e.g., described in the publications mentioned above, and some of which are commercially available such as YieldGard® (corn cultivars producing the Cry1Ab toxin), YieldGard® Plus (corn cultivars producing Cry1Ab and Cry3Bb1 toxins), Starlink® (corn cultivars producing the Cry9c toxin), Herculex® RW (corn cultivars producing Cry34Ab1, Cry35Ab1 and the enzyme Phosphinothricin-N-Acetyltransferase [PAT]); NuCOTN® 33B (cotton cultivars producing the Cry1Ac toxin), Bollgard® I (cotton cultivars producing the Cry1Ac toxin), Bollgard® II (cotton cultivars producing Cry1Ac and Cry2Ab2 toxins); VIPCOT® (cotton cultivars producing a VIP-toxin); NewLeaf® (potato cultivars producing the Cry3A toxin); BtXtra®, NatureGard®, KnockOut®, BiteGard®, Protecta®, Bt11 (e. g. Agrisure® CB) and Bt176 from Syngenta Seeds SAS, France, (corn cultivars producing the Cry1Ab toxin and PAT enyzme), MIR604 from Syngenta Seeds SAS, France (corn cultivars producing a modified version of the Cry3A toxin, c.f. WO 03/018810), MON 863 from Monsanto Europe S.A., Belgium (corn cultivars producing the Cry3Bb1 toxin), IPC 531 from Monsanto Europe S.A., Belgium (cotton cultivars producing a modified version of the Cry1Ac toxin) and 1507 from Pioneer Overseas Corporation, Belgium (corn cultivars producing the Cry1F toxin and PAT enzyme).

Furthermore, plants are also covered that are by the use of recombinant DNA techniques capable to synthesize one or more proteins to increase the resistance or tolerance of those plants to bacterial, viral or fungal pathogens. Examples of such proteins are the so-called "pathogenesis-related proteins" (PR proteins, see, e. g. EP-A 392 225), plant disease resistance genes (e. g. potato cultivars, which express resistance genes acting against *Phytophthora infestans* derived from the mexican wild potato *Solanum bulbocastanum*) or T4-lysozym (e. g. potato cultivars capable of synthesizing these proteins with increased resistance against bacteria such as *Erwinia amylvora*). The methods for producing such genetically modified plants are generally known to the person skilled in the art and are described, e. g. in the publications mentioned above.

Furthermore, plants are also covered that are by the use of recombinant DNA techniques capable to synthesize one or more proteins to increase the productivity (e. g. bio mass production, grain yield, starch content, oil content or protein content), tolerance to drought, salinity or other growth-limiting environmental factors or tolerance to pests and fungal, bacterial or viral pathogens of those plants.

Furthermore, plants are also covered that contain by the use of recombinant DNA techniques a modified amount of substances of content or new substances of content, specifically to improve human or animal nutrition, e. g. oil crops that produce health-promoting long-chain omega-3 fatty acids or unsaturated omega-9 fatty acids (e. g. Nexera® rape, DOW Agro Sciences, Canada).

Furthermore, plants are also covered that contain by the use of recombinant DNA techniques a modified amount of substances of content or new substances of content, specifically to improve raw material production, e. g. potatoes that produce increased amounts of amylopectin (e. g. Amflora® potato, BASF SE, Germany).

The organic moieties mentioned in the above definitions of the variables are—like the term halogen—collective terms for individual listings of the individual group members. The prefix $C_n$-$C_m$ indicates in each case the possible number of carbon atoms in the group.

The term halogen denotes in each case fluorine, bromine, chlorine or iodine, in particular fluorine, chlorine or bromine.

The term "partially or fully halogenated" will be taken to mean that 1 or more, e.g. 1, 2, 3, 4 or 5 or all of the hydrogen atoms of a given radical have been replaced by a halogen atom, in particular by fluorine or chlorine. A partially or fully halogenated radical is termed below also "halo-radical". For example, partially or fully halogenated alkyl is also termed haloalkyl, partially or fully halogenated cycloalkyl is also termed halocycloalkyl, partially or fully halogenated alkylenyl is also termed haloalkenyl, partially or fully halogenated alkylynyl is also termed haloalkynyl, partially or fully halogenated cycloalkylalkyl is also termed halocycloalkylalkyl.

The term "alkyl" as used herein and in the alkyl moieties of alkoxy, alkylthio, and the like refers to saturated straight-chain or branched hydrocarbon radicals having 1 to 2 ("$C_1$-$C_2$-alkyl"), 1 to 3 ("$C_1$-$C_3$-alkyl"), 1 to 4 ("$C_1$-$C_4$-alkyl") or 1 to 6 ("$C_1$-$C_6$-alkyl") carbon atoms. $C_1$-$C_2$-Alkyl is methyl or ethyl. $C_1$-$C_3$-Alkyl is additionally propyl and isopropyl. $C_1$-$C_4$-Alkyl is additionally butyl, 1-methylpropyl(sec-butyl), 2-methylpropyl(isobutyl) or 1,1-dimethylethyl(tert-butyl). $C_1$-$C_6$-Alkyl is additionally also, for example, pentyl, 1-methylbutyl, 2-methylbutyl, 3-methylbutyl, 2,2-dimethylpropyl, 1-ethylpropyl, 1,1-dimethylpropyl, 1,2-dimethylpropyl, hexyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl, or 1-ethyl-2-methylpropyl.

The term "haloalkyl" as used herein, which is also expressed as "alkyl which is partially or fully halogenated", refers to straight-chain or branched alkyl groups having 1 to 2 ("$C_1$-$C_2$-haloalkyl"), 1 to 3 ("$C_1$-$C_3$-haloalkyl"), 1 to 4 ("$C_1$-$C_4$-haloalkyl") or 1 to 6 ("$C_1$-$C_6$-haloalkyl") carbon atoms (as mentioned above), where some or all of the hydrogen atoms in these groups are replaced by halogen atoms as mentioned above: in particular $C_1$-$C_2$-haloalkyl, such as chloromethyl, bromomethyl, dichloromethyl, trichloromethyl, fluoromethyl, difluoromethyl, trifluoromethyl, chlorofluoromethyl, dichlorofluoromethyl, chlorodifluoromethyl, 1-chloroethyl, 1-bromoethyl, 1-fluoroethyl, 2-fluoroethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl or pentafluoroethyl. $C_1$-$C_3$-haloalkyl is additionally, for example, 1-fluoropropyl, 2-fluoropropyl, 3-fluoropropyl, 1,1-difluoropropyl, 2,2-difluoropropyl, 1,2-difluoropropyl, 3,3-difluoropropyl, 3,3,3-trifluoropropyl, heptafluoropropyl, 1,1,1-trifluoroprop-2-yl, 3-chloropropyl and the like. Examples for $C_1$-$C_4$-haloalkyl are, apart those mentioned for $C_1$-$C_3$-haloalkyl, 4-chlorobutyl and the like.

"Halomethyl" is methyl in which 1, 2 or 3 of the hydrogen atoms are replaced by halogen atoms. Examples are bromomethyl, chloromethyl, fluoromethyl, dichloromethyl, trichloromethyl, difluoromethyl, trifluoromethyl, chlorofluoromethyl, dichlorofluoromethyl, chlorodifluoromethyl and the like.

The term "alkylene" (or alkanediyl) as used herein in each case denotes an alkyl radical as defined above, wherein one hydrogen atom at any position of the carbon backbone is replaced by one further binding site, thus forming a bivalent moiety. Alkylene has preferably 1 to 6 carbon atoms ($C_1$-$C_6$-alkylene), 2 to 6 carbon atoms ($C_2$-$C_6$-alkylene), in particular 1 to 4 carbon atoms ($C_1$-$C_4$-alkylene) or 2 to 4 carbon atoms ($C_2$-$C_4$-alkylene). Examples of alkylene are methylene (CH2), 1,1-ethandiyl, 1,2-ethandiyl, 1,3-propandiyl, 1,2-propandiyl, 2,2-propandiyl, 1,4-butandiyl, 1,2-butandiyl, 1,3-butandiyl, 2,3-butandiyl, 2,2-butandiyl, 1,5-pentandiyl, 2,2-dimethylpropan-1,3-diyl, 1,3-dimethyl-1,3-propandiyl, 1,6-hexandiyl etc.

The term "alkenyl" as used herein refers to monounsaturated straight-chain or branched hydrocarbon radicals having 2 to 3 ("$C_2$-$C_3$-alkenyl"), 2 to 4 ("$C_2$-$C_4$-alkenyl") or 2 to 6 ("$C_2$-$C_6$-alkenyl) carbon atoms and a double bond in any position, for example $C_2$-$C_3$-alkenyl, such as ethenyl, 1-propenyl, 2-propenyl or 1-methylethenyl; $C_2$-$C_4$-alkenyl, such as ethenyl, 1-propenyl, 2-propenyl, 1-methylethenyl, 1-butenyl, 2-butenyl, 3-butenyl, 1-methyl-1-propenyl, 2-methyl-1-propenyl, 1-methyl-2-propenyl or 2-methyl-2-propenyl; $C_2$-$C_6$-alkenyl, such as ethenyl, 1-propenyl, 2-propenyl, 1-methylethenyl, 1-butenyl, 2-butenyl, 3-butenyl, 1-methyl-1-propenyl, 2-methyl-1-propenyl, 1-methyl-2-propenyl, 2-methyl-2-propenyl, 1-pentenyl, 2-pentenyl, 3-pentenyl, 4-pentenyl, 1-methyl-1-butenyl, 2-methyl-1-butenyl, 3-methyl-1-butenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-1-propenyl, 1,2-dimethyl-2-propenyl, 1-ethyl-1-propenyl, 1-ethyl-2-propenyl, 1-hexenyl, 2-hexenyl, 3-hexenyl, 4-hexenyl, 5-hexenyl, 1-methyl-1-pentenyl, 2-methyl-1-pentenyl, 3-methyl-1-pentenyl, 4-methyl-1-pentenyl, 1-methyl-2-pentenyl, 2-methyl-2-pentenyl, 3-methyl-2-pentenyl, 4-methyl-2-pentenyl, 1-methyl-3-pentenyl, 2-methyl-3-pentenyl, 3-methyl-3-pentenyl, 4-methyl-3-pentenyl, 1-methyl-4-pentenyl, 2-methyl-4-pentenyl, 3-methyl-4-pentenyl, 4-methyl-4-pentenyl, 1,1-dimethyl-2-butenyl, 1,1-dimethyl-3-butenyl, 1,2-dimethyl-1-butenyl, 1,2-dimethyl-2-butenyl, 1,2-dimethyl-3-butenyl, 1,3-dimethyl-1-butenyl, 1,3-dimethyl-2-butenyl, 1,3-dimethyl-3-butenyl, 2,2-dimethyl-3-butenyl, 2,3-dimethyl-1-butenyl, 2,3-dimethyl-2-butenyl, 2,3-dimethyl-3-butenyl, 3,3-dimethyl-1-butenyl, 3,3-dimethyl-2-butenyl, 1-ethyl-1-butenyl, 1-ethyl-2-butenyl, 1-ethyl-3-butenyl, 2-ethyl-1-butenyl, 2-ethyl-2-butenyl, 2-ethyl-3-butenyl, 1,1,2-trimethyl-2-propenyl, 1-ethyl-1-methyl-2-propenyl, 1-ethyl-2-methyl-1-propenyl, 1-ethyl-2-methyl-2-propenyl and the like.

The term "haloalkenyl" as used herein, which is also expressed as "alkenyl which is partially or fully halogenated", refers to unsaturated straight-chain or branched hydrocarbon radicals having 2 to 3 ("$C_2$-$C_3$-haloalkenyl"), 2 to 4 ("$C_2$-$C_4$-haloalkenyl") or 2 to 6 ("$C_2$-$C_6$-haloalkenyl") carbon atoms and a double bond in any position (as mentioned above), where some or all of the hydrogen atoms in these groups are replaced by halogen atoms as mentioned above, in particular fluorine, chlorine and bromine, for example chlorovinyl, chloroallyl and the like.

The term "alkynyl" as used herein refers to straight-chain or branched hydrocarbon groups having 2 to 3 ("$C_2$-$C_3$-alkynyl"), 2 to 4 ("$C_2$-$C_4$-alkynyl") or 2 to 6 ("$C_2$-$C_6$-alkynyl") carbon atoms and one or two triple bonds in any position, for example $C_2$-$C_3$-alkynyl, such as ethynyl, 1-propynyl or 2-propynyl; $C_2$-$C_4$-alkynyl, such as ethynyl, 1-propynyl, 2-propynyl, 1-butynyl, 2-butynyl, 3-butynyl, 1-methyl-2-propynyl and the like, $C_2$-$C_6$-alkynyl, such as ethynyl, 1-propynyl, 2-propynyl, 1-butynyl, 2-butynyl, 3-butynyl, 1-methyl-2-propynyl, 1-pentynyl, 2-pentynyl, 3-pentynyl, 4-pentynyl, 1-methyl-2-butynyl, 1-methyl-3-butynyl, 2-methyl-3-butynyl, 3-methyl-1-butynyl, 1,1-dimethyl-2-propynyl, 1-ethyl-2-propynyl, 1-hexynyl, 2-hexynyl, 3-hexynyl, 4-hexynyl, 5-hexynyl, 1-methyl-2-pentynyl, 1-methyl-3-pentynyl, 1-methyl-4-pentynyl, 2-methyl-3-pentynyl, 2-methyl-4-pentynyl, 3-methyl-1-pentynyl, 3-methyl-4-pentynyl, 4-methyl-1-pentynyl, 4-methyl-2-pentynyl, 1,1-dimethyl-2-butynyl, 1,1-dimethyl-3-butynyl, 1,2-dimethyl-3-butynyl, 2,2-dimethyl-3-butynyl, 3,3-dimethyl-1-butynyl, 1-ethyl-2-butynyl, 1-ethyl-3-butynyl, 2-ethyl-3-butynyl, 1-ethyl-1-methyl-2-propynyl and the like;

The term "haloalkynyl" as used herein, which is also expressed as "alkynyl which is partially or fully halogenated", refers to unsaturated straight-chain or branched hydrocarbon radicals having 2 to 3 ("$C_2$-$C_3$-haloalkynyl"), 2 to 4 ("$C_2$-$C_4$-haloalkynyl"), 3 to 4 ("$C_3$-$C_4$-haloalkynyl") or 2 to 6 ("$C_2$-$C_6$-haloalkynyl") carbon atoms and one or two triple bonds in any position (as mentioned above), where some or all of the hydrogen atoms in these groups are replaced by halogen atoms as mentioned above, in particular fluorine, chlorine and bromine;

The term "cycloalkyl" as used herein refers to mono- or bi- or polycyclic saturated hydrocarbon radicals having in particular 3 to 6 ("$C_3$-$C_6$-cycloalkyl") or 3 to 5 ("$C_3$-$C_5$-cycloalkyl") or 3 to 4 ("$C_3$-$C_4$-cycloalkyl") carbon atoms. Examples of monocyclic radicals having 3 to 4 carbon atoms comprise cyclopropyl and cyclobutyl. Examples of monocyclic radicals having 3 to 5 carbon atoms comprise cyclopropyl, cyclobutyl and cyclopentyl. Examples of monocyclic radicals having 3 to 6 carbon atoms comprise cyclopropyl, cyclobutyl, cyclopentyl and cyclohexyl. Examples of monocyclic radicals having 3 to 8 carbon atoms comprise cyclopropyl, cyclobutyl, cyclopentyl, cyclohexyl, cycloheptyl and cyclooctyl. Examples of bicyclic radicals having 7 or 8 carbon atoms comprise bicyclo[2.2.1]heptyl, bicyclo[3.1.1]heptyl, bicyclo[2.2.2]octyl and bicyclo[3.2.1]octyl. Preferably, the term cycloalkyl denotes a monocyclic saturated hydrocarbon radical.

The term "cycloalkoxy" as used herein refers to a cycloalkyl radical, in particular a monocyclic cycloalkyl radical, as defined above having in particular 3 to 6 ("$C_3$-$C_6$-cycloalkoxy") or 3 to 5 ("$C_3$-$C_5$-cycloalkoxy") or 3 to 4 ("$C_3$-$C_4$-cycloalksoxy") carbon atoms, which is bound via an oxygen atom to the remainder of the molecule.

The term "halocycloalkyl" as used herein, which is also expressed as "cycloalkyl which is partially or fully halogenated", refers to mono- or bi- or polycyclic saturated hydrocarbon groups having preferably 3 to 6 ("$C_3$-$C_6$-halocycloalkyl") or 3 to 5 ("$C_3$-$C_5$-halocycloalkyl") or 3 to 4 ("$C_3$-$C_4$-halocycloalkyl") carbon ring members (as mentioned above) in which some or all of the hydrogen atoms are replaced by halogen atoms as mentioned above, in particular fluorine, chlorine and bromine.

The term "cycloalkyl-$C_1$-$C_4$-alkyl" refers to a $C_3$-$C_8$-cycloalkyl group ("$C_3$-$C_8$-cycloalkyl-$C_1$-$C_4$-alkyl"), preferably a $C_3$-$C_6$-cycloalkyl group ("$C_3$-$C_6$-cycloalkyl-$C_1$-$C_4$-alkyl"), more preferably a $C_3$-$C_4$-cycloalkyl group ("$C_3$-$C_4$-cycloalkyl-$C_1$-$C_4$-alkyl") as defined above (preferably a monocyclic cycloalkyl group) which is bound to the remainder of the molecule via a $C_1$-$C_4$-alkyl group, as defined above. Examples for $C_3$-$C_4$-cycloalkyl-$C_1$-$C_4$-alkyl are cyclopropylmethyl, cyclopropylethyl, cyclopropylpropyl, cyclobutylmethyl, cyclobutylethyl and cyclobutylpropyl, Examples for $C_3$-$C_6$-cycloalkyl-$C_1$-$C_4$-alkyl, apart those mentioned for $C_3$-$C_4$-cycloalkyl-$C_1$-$C_4$-alkyl, are cyclopentylmethyl, cyclopentylethyl, cyclopentylpropyl, cyclohexylmethyl, cyclohexylethyl and cyclohexylpropyl.

The term "$C_3$-$C_6$-halocycloalkyl-$C_1$-$C_4$-alkyl" refers to a $C_3$-$C_8$-halocycloalkyl group as defined above which is bound to the remainder of the molecule via a $C_1$-$C_4$-alkyl group, as defined above.

The term "$C_3$-$C_6$-cycloalkxoy-$C_1$-$C_4$-alkyl" refers to a $C_3$-$C_6$-cycloalkoxy group ("$C_3$-$C_8$-cycloalkoxy-$C_1$-$C_4$-alkyl"), as defined above (preferably a monocyclic cycloalkoxy group) which is bound to the remainder of the molecule via a $C_1$-$C_4$-alkyl group, as defined above. Examples for $C_3$-$C_4$-cycloalkoxy-$C_1$-$C_4$-alkyl are cyclopropyloxymethyl, cyclopropyloxyethyl, cyclopropyloxypropyl, cyclobutyloxymethyl, 1-cyclobutyloxyethyl and 2-cyclobutyloxypropyl, Examples for $C_3$-$C_6$-cycloalkoxy-$C_1$-$C_4$-alkyl, apart those mentioned for $C_3$-$C_4$-cycloalkoxy-$C_1$-$C_4$-alkyl, are cyclopentyloxymethyl, cyclopentyloxyethyl, cyclopentyloxypropyl, cyclohexyloxymethyl, cyclohexyloxyethyl and cyclohexyloxypropyl.

The term "$C_1$-$C_2$-alkoxy" is a $C_1$-$C_2$-alkyl group, as defined above, attached via an oxygen atom. The term "$C_1$-$C_3$-alkoxy" is a $C_1$-$C_3$-alkyl group, as defined above, attached via an oxygen atom. The term "$C_1$-$C_4$-alkoxy" is a $C_1$-$C_4$-alkyl group, as defined above, attached via an oxygen atom. The term "$C_1$-$C_6$-alkoxy" is a $C_1$-$C_6$-alkyl group, as defined above, attached via an oxygen atom. The term "$C_1$-$C_{10}$-alkoxy" is a $C_1$-$C_{10}$-alkyl group, as defined above, attached via an oxygen atom. $C_1$-$C_2$-Alkoxy is methoxy or ethoxy. $C_1$-$C_3$-Alkoxy is additionally, for example, n-propoxy and 1-methylethoxy(isopropoxy). $C_1$-$C_4$-Alkoxy is additionally, for example, butoxy, 1-methylpropoxy (secbutoxy), 2-methylpropoxy(isobutoxy) or 1,1-dimethylethoxy(tert-butoxy). $C_1$-$C_6$-Alkoxy is additionally, for example, pentoxy, 1-methylbutoxy, 2-methylbutoxy, 3-methylbutoxy, 1,1-dimethylpropoxy, 1,2-dimethylpropoxy, 2,2-dimethylpropoxy, 1-ethylpropoxy, hexoxy, 1-methylpentoxy, 2-methylpentoxy, 3-methylpentoxy, 4-methylpentoxy, 1,1-dimethylbutoxy, 1,2-dimethylbutoxy, 1,3-dimethylbutoxy, 2,2-dimethylbutoxy, 2,3-dimethylbutoxy, 3,3-dimethylbutoxy, 1-ethylbutoxy, 2-ethylbutoxy, 1,1,2-trimethylpropoxy, 1,2,2-trimethylpropoxy, 1-ethyl-1-methylpropoxy or 1-ethyl-2-methylpropoxy. $C_1$-$C_8$-Alkoxy is additionally, for example, heptyloxy, octyloxy, 2-ethylhexyloxy and positional isomers thereof. $C_1$-$C_{10}$-Alkoxy is additionally, for example, nonyloxy, decyloxy and positional isomers thereof.

The term "$C_1$-$C_2$-haloalkoxy" is a $C_1$-$C_2$-haloalkyl group, as defined above, attached via an oxygen atom. The term "$C_1$-$C_3$-haloalkoxy" is a $C_1$-$C_3$-haloalkyl group, as defined above, attached via an oxygen atom. The term "$C_1$-$C_4$-haloalkoxy" is a $C_1$-$C_4$-haloalkyl group, as defined above, attached via an oxygen atom. The term "$C_1$-$C_6$-haloalkoxy" is a $C_1$-$C_6$-haloalkyl group, as defined above, attached via an oxygen atom. The term "$C_1$-$C_{10}$-haloalkoxy" is a $C_1$-$C_{10}$-haloalkyl group, as defined above, attached via an oxygen atom. $C_1$-$C_2$-Haloalkoxy is, for example, $OCH_2F$, $OCHF_2$, $OCF_3$, $OCH_2Cl$, $OCHCl_2$, $OCCl_3$, chlorofluoromethoxy, dichlorofluoromethoxy, chlorodifluoromethoxy, 2-fluoroethoxy, 2-chloroethoxy, 2-bromoethoxy, 2-iodoethoxy, 2,2-difluoroethoxy, 2,2,2-trifluoroethoxy, 2-chloro-2-fluoroethoxy, 2-chloro-2,2-difluoroethoxy, 2,2-dichloro-2-fluoroethoxy, 2,2,2-trichloroethoxy or $OC_2F_5$. $C_1$-$C_3$-Haloalkoxy is additionally, for example, 2-fluoropropoxy, 3-fluoropropoxy, 2,2-difluoropropoxy, 2,3-difluoropropoxy, 2-chloropropoxy, 3-chloropropoxy, 2,3-dichloropropoxy, 2-bromopropoxy, 3-bromopropoxy, 3,3,3-trifluoropropoxy, 3,3,3-trichloropropoxy, $OCH_2$—$C_2F_5$, $OCF_2$—$C_2F_5$, 1-($CH_2F$)-2-fluoroethoxy, 1-($CH_2Cl$)-2-chloroethoxy or 1-($CH_2Br$)-2-bromoethoxy. $C_1$-$C_4$-Haloalkoxy is additionally, for example, 4-fluorobutoxy, 4-chlorobutoxy, 4-bromobutoxy or nonafluorobutoxy. $C_1$-$C_6$-Haloalkoxy is additionally, for example, 5-fluoropentoxy, 5-chloropentoxy, 5-brompentoxy, 5-iodopentoxy, undecafluoropentoxy, 6-fluorohexoxy, 6-chlorohexoxy, 6-bromohexoxy, 6-iodohexoxy or dodecafluorohexoxy.

The term "$C_1$-$C_3$-alkoxy-$C_1$-$C_3$-alkyl" as used herein, refers to a straight-chain or branched alkyl group having 1 to 3 carbon atoms, as defined above, where one hydrogen atom is replaced by a $C_1$-$C_3$-alkoxy group, as defined above. The term "$C_1$-$C_4$-alkoxy-$C_1$-$C_4$-alkyl" as used herein, refers to a straight-chain or branched alkyl group having 1 to 4 carbon atoms, as defined above, where one hydrogen atom is replaced by a $C_1$-$C_4$-alkoxy group, as defined above. The term "$C_1$-$C_6$-alkoxy-$C_1$-$C_4$-alkyl" as used herein, refers to a straight-chain or branched alkyl group having 1 to 4 carbon atoms, as defined above, where one hydrogen atom is replaced by a $C_1$-$C_6$-alkoxy group, as defined above. Examples are methoxymethyl, ethoxymethyl, propoxymethyl, isopropoxymethyl, n-butoxymethyl, sec-butoxymethyl, isobutoxymethyl, tert-butoxymethyl, 1-methoxyethyl, 1-ethoxyethyl, 1-propoxyethyl, 1-isopropoxyethyl, 1-n-butoxyethyl, 1-sec-butoxyethyl, 1-isobutoxyethyl, 1-tert-butoxyethyl, 2-methoxyethyl, 2-ethoxyethyl, 2-propoxyethyl, 2-isopropoxyethyl, 2-n-butoxyethyl, 2-sec-butoxyethyl, 2-isobutoxyethyl, 2-tert-butoxyethyl, 1-methoxypropyl, 1-ethoxypropyl, 1-propoxypropyl, 1-isopropoxypropyl, 1-n-butoxypropyl, 1-sec-butoxypropyl, 1-isobutoxypropyl, 1-tert-butoxypropyl, 2-methoxypropyl, 2-ethoxypropyl, 2-propoxypropyl, 2-isopropoxypropyl, 2-n-butoxypropyl, 2-sec-butoxypropyl, 2-isobutoxypropyl, 2-tert-butoxypropyl, 3-methoxypropyl, 3-ethoxypropyl, 3-propoxypropyl, 3-isopropoxypropyl, 3-n-butoxypropyl, 3-sec-butoxypropyl, 3-isobutoxypropyl, 3-tert-butoxypropyl and the like.

The term "$C_1$-$C_4$-alkoxy-methyl" as used herein, refers to methyl in which one hydrogen atom is replaced by a $C_1$-$C_4$-alkoxy group, as defined above. The term "$C_1$-$C_6$-alkoxy-methyl" as used herein, refers to methyl in which one hydrogen atom is replaced by a $C_1$-$C_6$-alkoxy group, as defined above. Examples are methoxymethyl, ethoxymethyl, propoxymethyl, isopropoxymethyl, n-butoxymethyl, sec-butoxymethyl, isobutoxymethyl, tert-butoxymethyl, pentyloxymethyl, hexyloxymethyl and the like.

The term "alkoxyalkoxy" as used herein refers to an alkoxyalkyl radical, in particular a $C_1$-$C_6$-alkoxy-$C_1$-$C_4$-alkyl radical, as defined above, which is bound via an oxygen atom to the remainder of the molecule. Examples thereof are $OCH_2$—$OCH_3$, $OCH_2$—$OC_2H_5$, n-propoxymethoxy, $OCH_2$—$OCH(CH_3)_2$, n-butoxymethoxy, (1-methylpropoxy)methoxy, (2-methylpropoxy)methoxy, $OCH_2$—$OC(CH_3)_3$, 2-(methoxy)ethoxy, 2-(ethoxy)ethoxy, 2-(n-propoxy)ethoxy, 2-(1-methylethoxy)ethoxy, 2-(n-butoxy)ethoxy, 2-(1-methylpropoxy)ethoxy, 2-(2-methylpropoxy)ethoxy, 2-(1,1-dimethylethoxy)ethoxy, etc.

$C_1$-$C_6$-Haloalkoxy-$C_1$-$C_6$-alkyl is a straight-chain or branched alkyl group having from 1 to 6, especially 1 to 4 carbon atoms (=$C_1$-$C_6$-haloalkoxy-$C_1$-$C_4$-alkyl), wherein one of the hydrogen atoms is replaced by a $C_1$-$C_6$-alkoxy group and wherein at least one, e.g. 1, 2, 3, 4 or all of the remaining hydrogen atoms (either in the alkoxy moiety or in the alkyl moiety or in both) are replaced by halogen atoms. $C_1$-$C_4$-Haloalkoxy-$C_1$-$C_4$-alkyl is a straight-chain or branched alkyl group having from 1 to 4 carbon atoms, wherein one of the hydrogen atoms is replaced by a $C_1$-$C_4$-alkoxy group and wherein at least one, e.g. 1, 2, 3, 4 or all of the remaining hydrogen atoms (either in the alkoxy moiety or in the alkyl moiety or in both) are replaced by halogen atoms. Examples are difluoromethoxymethyl ($CHF_2OCH_2$), trifluoromethoxymethyl, 1-difluoromethoxyethyl, 1-trifluoromethoxyethyl, 2-difluoromethoxyethyl, 2-trifluoromethoxyethyl, difluoromethoxy-methyl ($CH_3OCF_2$), 1,1-difluoro-2-methoxyethyl, 2,2-difluoro-2-methoxyethyl and the like.

The term "$C_1$-$C_2$-alkylthio" is a $C_1$-$C_2$-alkyl group, as defined above, attached via a sulfur atom. The term "$C_1$-$C_3$-alkylthio" is a $C_1$-$C_3$-alkyl group, as defined above, attached via a sulfur atom. The term "$C_1$-$C_4$-alkylthio" is a $C_1$-$C_4$-alkyl group, as defined above, attached via a sulfur atom. The term "$C_1$-$C_6$-alkylthio" is a $C_1$-$C_6$-alkyl group, as defined above, attached via a sulfur atom. The term "$C_1$-$C_{10}$-alkylthio" is a $C_1$-$C_{10}$-alkyl group, as defined above, attached via a sulfur atom. $C_1$-$C_2$-Alkylthio is methylthio or ethylthio. $C_1$-$C_3$-Alkylthio is additionally, for example, n-propylthio or 1-methylethylthio(isopropylthio). $C_1$-$C_4$-Alkylthio is additionally, for example, butylthio, 1-methylpropylthio(sec-butylthio), 2-methylpropylthio(isobutylthio) or 1,1-dimethylethylthio(tert-butylthio). $C_1$-$C_6$-Alkylthio is additionally, for example, pentylthio, 1-methylbutylthio, 2-methylbutylthio, 3-methylbutylthio, 1,1-dimethylpropylthio, 1,2-dimethylpropylthio, 2,2-dimethylpropylthio, 1-ethylpropylthio, hexylthio, 1-methylpentylthio, 2-methylpentylthio, 3-methylpentylthio, 4-methylpentylthio, 1,1-dimethylbutylthio, 1,2-dimethylbutylthio, 1,3-dimethylbutylthio, 2,2-dimethylbutylthio, 2,3-dimethylbutylthio, 3,3-dimethylbutylthio, 1-ethylbutylthio, 2-ethylbutylthio, 1,1,2-trimethylpropylthio, 1,2,2-trimethylpropylthio, 1-ethyl-1-methylpropylthio or 1-ethyl-2-methylpropylthio. $C_1$-$C_8$-Alkylthio is additionally, for example, heptylthio, octylthio, 2-ethylhexylthio and positional isomers thereof. $C_1$-$C_{10}$-Alkylthio is additionally, for example, nonylthio, decylthio and positional isomers thereof.

The term "$C_1$-$C_2$-haloalkylthio" is a $C_1$-$C_2$-haloalkyl group, as defined above, attached via a sulfur atom. The term "$C_1$-$C_3$-haloalkylthio" is a $C_1$-$C_3$-haloalkyl group, as defined above, attached via a sulfur atom. The term "$C_1$-$C_4$-haloalkylthio" is a $C_1$-$C_4$-haloalkyl group, as defined above, attached via a sulfur atom. The term "$C_1$-$C_6$-haloalkylthio" is a $C_1$-$C_6$-haloalkyl group, as defined above, attached via a sulfur atom. The term "$C_1$-$C_{10}$-haloalkylthio" is a $C_1$-$C_{10}$-haloalkyl group, as defined above, attached via a sulfur atom. $C_1$-$C_2$-Haloalkylthio is, for example, $SCH_2F$, $SCHF_2$, $SCF_3$, $SCH_2Cl$, $SCHCl_2$, $SCCl_3$, chlorofluoromethylthio, dichlorofluoromethylthio, chlorodifluoromethylthio, 2-fluoroethylthio, 2-chloroethylthio, 2-bromoethylthio, 2-iodoethylthio, 2,2-difluoroethylthio, 2,2,2-trifluoroethylthio, 2-chloro-2-fluoroethylthio, 2-chloro-2,2-difluoroethylthio, 2,2-dichloro-2-fluoroethylthio, 2,2,2-trichloroethylthio or $SC_2F_5$. $C_1$-$C_3$-Haloalkylthio is additionally, for example, 2-fluoropropylthio, 3-fluoropropylthio, 2,2-difluoropropylthio, 2,3-difluoropropylthio, 2-chloropropylthio, 3-chloropropylthio, 2,3-dichloropropylthio, 2-bromopropylthio, 3-bromopropylthio, 3,3,3-trifluoropropylthio, 3,3,3-trichloropropylthio, $SCH_2$—$C_2F_5$, $SCF_2$—$C_2F_5$, 1-($CH_2F$)-2-fluoroethylthio, 1-($CH_2Cl$)-2-chloroethylthio or 1-($CH_2Br$)-2-bromoethylthio. $C_1$-$C_4$-Haloalkylthio is additionally, for example, 4-fluorobutylthio, 4-chlorobutylthio, 4-bromobutylthio or nonafluorobutylthio. $C_1$-$C_6$-Haloalkylthio is additionally, for example, 5-fluoropentylthio, 5-chloropentylthio, 5-brompentylthio, 5-iodopentylthio, undecafluoropentylthio, 6-fluorohexylthio, 6-chlorohexylthio, 6-bromohexylthio, 6-iodohexylthio or dodecafluorohexylthio.

The substituent "oxo" replaces a $CH_2$ group by a $C(=O)$ group.

The term "aryl" relates to phenyl and bi- or polycyclic carbocycles having at least one fused phenylene ring, which is bound to the remainder of the molecule. Examples of bi- or polycyclic carbocycles having at least one phenylene ring include naphthyl, tetrahydronaphthyl, indanyl, indenyl, anthracenyl, fluorenyl etc.

The term "aryl-$C_1$-$C_4$-alkyl" relates to $C_1$-$C_4$-alkyl, as defined above, wherein one hydrogen atom has been replaced by an aryl radical, in particular a phenyl radical. Particular examples of aryl-$C_1$-$C_4$-alkyl include benzyl, 1-phenethyl, 2-phenetyl, 1-phenylpropyl, 2-phenylpropyl, 3-phenyl-1-propyl and 2-phenyl-2-propyl.

The term "aryloxy-$C_1$-$C_4$-alkyl" relates to $C_1$-$C_4$-alkyl, as defined above, wherein one hydrogen atom has been replaced by an aryloxy radical, in particular a phenoxy radical. Particular examples of aryloxy-$C_1$-$C_4$-alkyl include phenoxymethyl, 1-phenoxyethyl, 2-phenoxyetyl, 1-phenoxypropyl, 2-phenoxypropyl, 3-phenoxy-1-propyl and 2-phenoxy-2-propyl.

The term "aryl-$C_1$-$C_4$-carbonyl" relates to aryl as defined above, in particular a phenyl radical, which is bound by a carbonyl group to the remainder of the molecule. Particular examples of arylcarbonyl include benzoyl, 1-naphthoyl and 2-naphthoyl.

The term hetaryl relates to aromatic heterocycles having either 5 or 6 ring atoms (5- or 6-membered hetaryl) and being monocyclic or 8, 9 or 10 ring atoms and bing bicyclic. Hetaryl will generally have at least one ring atom selected from O, S and N, which in case of N may be an imino-nitrogen or an amino-nitrogen, which carries hydrogen or a radical different from hydrogen. Hetaryl may have 1, 2, 3 or 4 further nitrogen atoms as ring members, which are imino nitrogens. Examples of 5- or 6-membered hetaryl include 2-furyl, 3-furyl, 2-thienyl, 3-thienyl, 1-pyrrolyl, 2-pyrrolyl, 3-pyrrolyl, 1-pyrazolyl, 3-pyrazolyl, 4-pyrazolyl, 5-pyrazolyl, 2-oxazolyl, 4-oxazolyl, 5-oxazolyl, 2-thiazolyl, 4-thiazolyl, 5-thiazolyl, 1-imidazolyl, 2-imidazolyl, 4-imidazolyl, 1,3,4-triazol-1-yl, 1,3,4-triazol-2-yl, 1,3,4-oxadiazolyl-2-yl, 1,3,4-thiadiazol-2-yl, 2-pyridinyl, 3-pyridinyl, 4-pyridinyl, 3-pyridazinyl, 4-pyridazinyl, 2-pyrimidinyl, 4-pyrimidinyl, 5-pyrimidinyl, 2-pyrazinyl and 1,3,5-triazin-2-yl. Examples of 8-, 9- or 10-membered hetaryl include, for example, quinolinyl, isoquinolinyl, cinnolinyl, indolyl, indolizynyl, isoindolyl, indazolyl, benzofuryl, benzothienyl, benzo[b]thiazolyl, benzoxazolyl, benzthiazolyl, benzimidazolyl, imidazo[1,2-a]pyridine-2-yl, thieno[3,2-b]pyridine-5-yl, imidazo-[2,1-b]-thiazol-6-yl and 1,2,4-triazolo[1,5-a]pyridine-2-yl.

Examples of N-bound 5-, 6-, 7 or 8-membered saturated heterocycles include: pyrrolidin-1-yl, pyrazolidin-1-yl, imidazolidin-1-yl, oxazolidin-3-yl, isoxazolidin-2-yl, thiazolidin-3-yl, isothiazolidin-2-yl, piperidin-1-yl, piperazin-1-yl, morpholin-4-yl, thiomorpholin-4-yl, 1-oxothiomorpholin-4-yl, 1,1-dioxothiomorpholin-4-yl, azepan-1-yl and the like.

The term "hetaryl-$C_1$-$C_4$-alkyl" relates to $C_1$-$C_4$-alkyl, as defined above, wherein one hydrogen atom has been replaced by a hetaryl radical, in particular a pyridyl radical. Particular examples of hetaryl-$C_1$-$C_4$-alkyl include 2-pyridylmethyl, 3-pyridylmethyl, 4-pyridylmethyl, 1-(2-pyridyl)ethyl, 2-(2-pyridyl)ethyl, 1-(3-pyridyl)ethyl, 2-(3-pyridyl)ethyl, 1-(4-pyridyl)ethyl, 2-(4-pyridyl)ethyl etc.

The term "hetaryloxy-$C_1$-$C_4$-alkyl" relates to $C_1$-$C_4$-alkyl, as defined above, wherein one hydrogen atom has been replaced by an hetaryloxy radical, in particular a pyridyloxy radical. Particular examples of hetaryloxy-$C_1$-$C_4$-alkyl include 2-pyridyloxymethyl, 3-pyridyloxymethyl, 4-pyridyloxymethyl, 1-(2-pyridyloxy)ethyl, 2-(2-pyridyloxy)ethyl, 1-(3-pyridyloxy)ethyl, 2-(3-pyridyloxy)ethyl, 1-(4-pyridyloxy)ethyl, 2-(4-pyridyloxy)ethyl etc.

The term "hetaryl-$C_1$-$C_4$-carbonyl" relates to hetaryl as defined above, in particular a C-bound hetaryl radical, e.g. 2-, 3- or 4-pyridyl, 2- or 3-thienyl, 2- or 3-furyl, 1-, 2- or 3-pyrrolyl, 2- or 4-pyrimidinyl, pyridazinyl, 1-, 3- or 4-pyrazolyl, 1-, 2- or 4-imidazolyl radical, which is bound by a carbonyl group to the remainder of the molecule.

A first particular group of embodiments of the present invention relates to compounds of the formula Ia, including their N-oxides, stereoisomers, tautomers and their agriculturally or veterinarily acceptable salts:

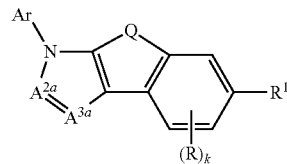

(Ia)

wherein:
$A^{2a}$ is N or $C(R^2)$; and
$A^{3a}$ is N or $C(R^7)$;
and wherein k, Ar, Q, $R^1$, $R^2$ and $R^7$ are as defined herein.

In a particular group of embodiments of the compounds of formula Ia, $A^{2a}$ is N and $A^{3a}$ is $C(R^7)$.

In another particular group of embodiments of the compounds of formula Ia, $A^{2a}$ is $C(R^2)$ and $A^{3a}$ is N.

In a further particular group of embodiments of the compounds of formula Ia, $A^{2a}$ and $A^{3a}$ are both N.

A second particular group of embodiments of the present invention relates to compounds of the formula Ib, including their N-oxides, stereoisomers, tautomers and their agriculturally or veterinarily acceptable salts:

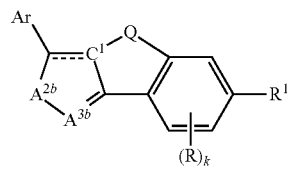

(Ib)

wherein:
$C^1$ is CH or C, provided that ---- indicates a single bond, if $C^1$ is CH or a double bond, if $C^1$ is C,
$A^{2b}$ is $N(R^3)$, O or S; and
$A^{3b}$ is N or $C(R^7)$;
provided that one or both of $A^{2b}$ and $A^{3b}$ are N or $N(R^3)$, respectively;
and wherein k, Ar, Q, $R^1$, $R^3$ and $R^7$ are as defined herein.

In a particular group of embodiments of the compounds of formula Ib, $C^1$ is C, $A^{2b}$ is O and $A^{3b}$ is $C(R^7)$.

In another particular group of embodiments of the compounds of formula Ib, $C^1$ is C, $A^{2b}$ is S and $A^{3b}$ is $C(R^7)$.

In a further particular group of embodiments of the compounds of formula Ib, $C^1$ is C, $A^{2b}$ is $N(R^3)$ and $A^{3b}$ is $C(R^7)$.

In yet a further particular group of embodiments of the compounds of formula Ib, $C^1$ is C, $A^{2b}$ is O and $A^{3b}$ is N.

In yet a further particular group of embodiments of the compounds of formula Ib, $C^1$ is CH, $A^{2b}$ is O and $A^{3b}$ is N.

In yet a further particular group of embodiments of the compounds of formula Ib, $C^1$ is C, $A^{2b}$ is $N(R^3)$ and $A^{3b}$ is N.

In yet a further particular group of embodiments of the compounds of formula Ib, $C^1$ is CH, $A^{2b}$ is $N(R^3)$ and $A^{3b}$ is N.

In yet a further particular group of embodiments of the compounds of formula Ib, $C^1$ is C, $A^{2b}$ is S and $A^{3b}$ is N.

In yet a further particular group of embodiments of the compounds of formula Ib, $C^1$ is CH, $A^{2b}$ is S and $A^{3b}$ is N.

A third particular group of embodiments of the present invention relates to compounds of the formula Ic, including their N-oxides, stereoisomers, tautomers and their agriculturally or veterinarily acceptable salts:

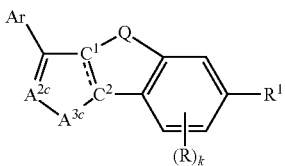

(Ic)

wherein
$C^1$ and $C^2$ are both CH or both C provided that ---- indicates a single bond, if $C^1$ and $C^2$ are CH, or a double bond, if $C^1$ and $C^2$ are C,
$A^{2c}$ is N or $C(R^2)$; and
$A^{3c}$ is O, S, $N(R^6)$ or $C(R^8,R^9)$;
and wherein k, Ar, Q, $R^1$, $R^2$, $R^6$, $R^8$ and $R^9$ are as defined herein.

In a particular group of embodiments of the compounds of formula Ic, $C^1$ and $C^2$ are CH, $A^{2c}$ is N and $A^{3c}$ is $C(R^8,R^9)$.

In another particular group of embodiments of the compounds of formula Ic, C and $C^2$ are CH, $A^{2c}$ is N and $A^{3c}$ is O.

In a further particular group of embodiments of the compounds of formula Ic, $C^1$ and $C^2$ are CH, $A^{2c}$ is N and $A^{3c}$ is S.

In yet a further particular group of embodiments of the compounds of formula Ic, $C^1$ and $C^2$ are CH, $A^{2c}$ is N and $A^{3c}$ is $N(R^6)$.

In yet a further particular group of embodiments of the compounds of formula Ic, $C^1$ and $C^2$ are C, $A^{2c}$ is N and $A^{3c}$ is O.

In yet a further particular group of embodiments of the compounds of formula Ic, $C^1$ and $C^2$ are C, $A^{2c}$ is N and $A^{3c}$ is S.

In yet a further particular group of embodiments of the compounds of formula Ic, $C^1$ and $C^2$ are C, $A^{2c}$ is N and $A^{3c}$ is $N(R^6)$.

A fourth particular group of embodiments of the present invention relates to compounds of the formula Id, including their N-oxides, stereoisomers, tautomers and their agriculturally or veterinarily acceptable salts:

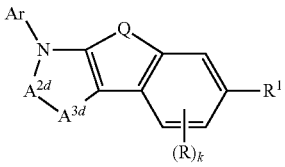

(Id)

where in formula Id
$A^{2d}$ is $N(R^3)$, O, S or $C(R^4,R^5)$; and
$A^{3d}$ is O, S, $N(R^6)$ or $C(R^8,R^9)$;
provided that at least one of $A^{2d}$ and $A^{3d}$ is different from O and S and that the bond between $A^{2d}$ and $A^{3d}$ is a single bond;
and wherein k, Ar, Q, $R^1$, $R^3$, $R^4$, $R^5$, $R^6$, $R^8$ and $R^9$ are as defined herein.

In a particular group of embodiments of the compounds of formula Id, $A^{2d}$ is $C(R^4,R^5)$, in particular $CH_2$, C=O or C=S and $A^{3d}$ is O.

In another particular group of embodiments of the compounds of formula Id, $A^{2d}$ is $C(R^4,R^5)$, in particular $CH_2$, C=O or C=S and $A^{3d}$ is S.

In a further particular group of embodiments of the compounds of formula Id, $A^{2d}$ is $C(R^4,R^5)$, in particular $CH_2$, C=O or C=S and $A^{3d}$ is $N(R^6)$.

Irrespectively of their occurrence, in particular in context with formulae Ia, Ib, Ic and Id, but also in context with formula INT the variables $R^2$, $R^3$, $R^4$, $R^5$, $R^6$, $R^7$, $R^8$ and $R^9$ have in particular the following meanings:

$R^2$ is in particular hydrogen, halogen, such as fluorine or chlorine, $C_1$-$C_4$-alkyl, such as methyl, ethyl, n-propyl or isopropyl, $C_1$-$C_4$-haloalkyl, such as fluoromethyl, difluoromethyl or trifluoromethyl, $C_1$-$C_4$-alkoxy, such as methoxy or ethoxy, or $C_1$-$C_4$-haloalkoxy, such as fluoromethoxy, difluoromethoxy or trifluoromethoxy, especially hydrogen.

$R^3$ is in particular $C_1$-$C_4$-alkyl, such as methyl, ethyl, n-propyl or isopropyl, $C_3$-$C_6$-cycloalkyl such as cyclopropyl, cyclobutyl, or cyclohexyl, $C_3$-$C_6$-cycloalkymethyl, such as cyclopropylmethyl, cyclobutylmethyl or cyclopentylmethyl, or benzyl, and especially $C_1$-$C_4$-alkyl.

$R^4$, $R^5$ independently of each other are in particular hydrogen, halogen, such as fluorine or chlorine, $C_1$-$C_4$-alkyl, such as methyl, ethyl, n-propyl or isopropyl, $C_1$-$C_4$-haloalkyl, such as fluoromethyl, difluoromethyl or trifluoromethyl, $C_1$-$C_4$-alkoxy, such as methoxy or ethoxy, or $C_1$-$C_4$-haloalkoxy, such as fluoromethoxy, difluoromethoxy or trifluoromethoxy, or $C(R^4,R^5)$ forms a carbonyl (C=O) or thiocarbonyl (C=S), especially $R^4$, $R^5$ are hydrogen or $C(R^4,R^5)$ forms a carbonyl (C=O) or thiocarbonyl (C=S).

$R^6$ is in particular $C_1$-$C_4$-alkyl, such as methyl, ethyl, n-propyl or isopropyl, $C_3$-$C_6$-cycloalkyl such as cyclopropyl, cyclobutyl, or cyclohexyl, $C_3$-$C_6$-cycloalkymethyl, such as cyclopropylmethyl, cyclobutylmethyl or cyclopentylmethyl, or benzyl, and especially $C_1$-$C_4$-alkyl.

$R^7$ is in particular hydrogen, halogen, such as fluorine or chlorine, $C_1$-$C_4$-alkyl, such as methyl, ethyl, n-propyl or isopropyl, $C_1$-$C_4$-haloalkyl, such as fluoromethyl, difluoromethyl or trifluoromethyl, $C_1$-$C_4$-alkoxy, such as methoxy or ethoxy, or $C_1$-$C_4$-haloalkoxy, such as fluoromethoxy, difluoromethoxy or trifluoromethoxy, especially hydrogen.

$R^8$, $R^9$ independently of each other are in particular hydrogen, halogen, such as fluorine or chlorine, $C_1$-$C_4$-alkyl, such as methyl, ethyl, n-propyl or isopropyl, $C_1$-$C_4$-haloalkyl, such as fluoromethyl, difluoromethyl or trifluoromethyl, $C_1$-$C_4$-alkoxy, such as methoxy or ethoxy, or $C_1$-$C_4$-haloalkoxy, such as fluoromethoxy, difluoromethoxy or trifluoromethoxy, or $C(R^8,R^9)$ forms a carbonyl (C=O) or thiocarbonyl (C=S), especially $R^8$, $R^9$ are hydrogen or $C(R^8,R^9)$ forms a carbonyl (C=O) or thiocarbonyl (C=S).

Particular groups of embodiments relate to compounds of the formulae I, INT, Ia, Ib, Ic and Id, including their N-oxides, stereoisomers, tautomers and their agriculturally or veterinarily acceptable salts, wherein Q is —O—, —S—, —C($R^{Q2a}R^{Q2b}$)—, —N($R^{Q2}$)—C(=O)—, —C($R^{Q3}$)=C($R^{Q4}$)—, —C($R^{Q3a}R^{Q3b}$)—C($R^{Q4a}R^{Q4b}$)—, —O—C($R^{Q4a}R^{Q4b}$)—, —S(=O)$_n$—C($R^{Q4a}R^{Q4b}$)— or —N($R^{Q2}$)—C($R^{Q4a}R^{Q4b}$)—, where $R^{Q2}$, $R^{Q3}$, $R^{Q3a}$, $R^{Q3b}$, $R^{Q4}$, $R^{Q4a}$ and $R^{Q4b}$ are as defined herein and where, $R^{Q2}$ is in particular hydrogen, $C_1$-$C_4$-alkyl, such as methyl, ethyl, n-propyl or isopropyl, $C_3$-$C_6$-cycloalkyl such as cyclopropyl, cyclobutyl, or cyclohexyl, $C_3$-$C_6$-cycloalkymethyl, such as cyclopropylmethyl, cyclobutylmethyl or cyclopentylmethyl, or benzyl, and especially hydrogen or methyl;

$R^{Q3}$ is in particular hydrogen, chlorine, fluorine, $C_1$-$C_4$-alkyl, such as methyl or ethyl, or $C_1$-$C_4$-haloalkyl, such as fluoromethyl, difluoromethyl or trifluoromethyl, and especially hydrogen;

$R^{Q4}$ is in particular hydrogen, chlorine, fluorine, $C_1$-$C_4$-alkyl, such as methyl or ethyl, or $C_1$-$C_4$-haloalkyl, such as fluoromethyl, difluoromethyl or trifluoromethyl, and especially hydrogen;

$R^{Q2a}$ is in particular hydrogen, $C_1$-$C_4$-alkyl, such as methyl or ethyl, or $C_1$-$C_4$-haloalkyl, such as fluoromethyl, difluoromethyl or trifluoromethyl, and especially hydrogen;

$R^{Q2b}$ is in particular hydrogen, $C_1$-$C_4$-alkyl, such as methyl or ethyl, or $C_1$-$C_4$-haloalkyl, such as fluoromethyl, difluoromethyl or trifluoromethyl, and especially hydrogen;

$R^{Q3a}$ is in particular hydrogen, $C_1$-$C_4$-alkyl, such as methyl or ethyl, or $C_1$-$C_4$-haloalkyl, such as fluoromethyl, difluoromethyl or trifluoromethyl, and especially hydrogen;

$R^{Q3b}$ is in particular hydrogen, $C_1$-$C_4$-alkyl, such as methyl or ethyl, or $C_1$-$C_4$-haloalkyl, such as fluoromethyl, difluoromethyl or trifluoromethyl, and especially hydrogen;

$R^{Q4a}$ is in particular hydrogen, $C_1$-$C_4$-alkyl, such as methyl or ethyl, or $C_1$-$C_4$-haloalkyl, such as fluoromethyl, difluoromethyl or trifluoromethyl, and especially hydrogen;

$R^{Q4b}$ is in particular hydrogen, $C_1$-$C_4$-alkyl, such as methyl or ethyl, or $C_1$-$C_4$-haloalkyl, such as fluoromethyl, difluoromethyl or trifluoromethyl, and especially hydrogen.

Particular groups of embodiments relate to compounds of the formulae I, INT, Ia, Ib, Ic and Id, including their N-oxides, stereoisomers, tautomers and their agriculturally or veterinarily acceptable salts, wherein Q is —O—, —S—, —C($R^{Q2a}R^{Q2b}$)—, —C($R^{Q3}$)=C($R^{Q4}$)—, —C($R^{Q3a}R^{Q3b}$)—C($R^{Q4a}R^{Q4b}$)—, —O—C($R^{Q4a}R^{Q4b}$)— or —S(=O)$_n$—C($R^{Q4a}R^{Q4b}$)—, where $R^{Q2}$, $R^{Q3}$, $R^{Q2a}$, $R^{Q2b}$, $R^{Q3a}$, $R^{Q3b}$, $R^{Q4}$, $R^{Q4a}$ and $R^{Q4b}$ are as defined herein and where, $R^{Q3}$ is in particular hydrogen, chlorine, fluorine, $C_1$-$C_4$-alkyl, such as methyl or ethyl, or $C_1$-$C_4$-haloalkyl, such as fluoromethyl, difluoromethyl or trifluoromethyl, and especially hydrogen;

$R^{Q4}$ is in particular hydrogen, chlorine, fluorine, $C_1$-$C_4$-alkyl, such as methyl or ethyl, or $C_1$-$C_4$-haloalkyl, such as fluoromethyl, difluoromethyl or trifluoromethyl, and especially hydrogen;

$R^{Q2a}$ is in particular hydrogen, $C_1$-$C_4$-alkyl, such as methyl or ethyl, or $C_1$-$C_4$-haloalkyl, such as fluoromethyl, difluoromethyl or trifluoromethyl, and especially hydrogen;

$R^{Q2b}$ is in particular hydrogen, $C_1$-$C_4$-alkyl, such as methyl or ethyl, or $C_1$-$C_4$-haloalkyl, such as fluoromethyl, difluoromethyl or trifluoromethyl, and especially hydrogen;

$R^{Q3a}$ is in particular hydrogen, $C_1$-$C_4$-alkyl, such as methyl or ethyl, or $C_1$-$C_4$-haloalkyl, such as fluoromethyl, difluoromethyl or trifluoromethyl, and especially hydrogen;

$R^{Q3b}$ is in particular hydrogen, $C_1$-$C_4$-alkyl, such as methyl or ethyl, or $C_1$-$C_4$-haloalkyl, such as fluoromethyl, difluoromethyl or trifluoromethyl, and especially hydrogen;

$R^{Q4a}$ is in particular hydrogen, $C_1$-$C_4$-alkyl, such as methyl or ethyl, or $C_1$-$C_4$-haloalkyl, such as fluoromethyl, difluoromethyl or trifluoromethyl, and especially hydrogen;

$R^{Q4b}$ is in particular hydrogen, $C_1$-$C_4$-alkyl, such as methyl or ethyl, or $C_1$-$C_4$-haloalkyl, such as fluoromethyl, difluoromethyl or trifluoromethyl, and especially hydrogen.

Particular preferred groups of embodiments relate to compounds of the formulae I, INT, Ia, Ib, Ic and Id, including their N-oxides, stereoisomers, tautomers and their agriculturally or veterinarily acceptable salts, wherein Q is selected from the group consisting of O, S, —CH$_2$—, —CH=CH—, —CH$_2$CH$_2$—, O—CH$_2$, —S(=O)—CH$_2$—, —N($R^{Q2}$)—C(=O)— and —N($R^{Q2}$)—CH$_2$—, where $R^{Q2}$ is as defined herein.

Especially preferred groups of embodiments relate to compounds of the formulae I, Ia, Ib, Ic and Id, including their N-oxides, stereoisomers, tautomers and their agriculturally or veterinarily acceptable salts, wherein Q is selected from the group consisting of O, S, —CH$_2$—, —CH=CH—, —CH$_2$CH$_2$—, O—CH$_2$, —S(=O)—CH$_2$—, —N(R')—C(=O)— and —N(R')—CH$_2$—, wherein R' is hydrogen or methyl.

A particular group of embodiments relates to the compounds of formulae Ia.1 to Ia.56 as described below, to their N-oxides, their stereoisomers, their tautomers and to the agriculturally or veterinarily acceptable salt thereof. In formulae Ia.1 to Ia.56 Ar, $R^1$ and $R^{Q2}$ are as defined above and hereinafter and $R^{Q2}$ is in particular hydrogen, $C_1$-$C_4$-alkyl, such as methyl, ethyl, n-propyl or isopropyl, $C_3$-$C_6$-cycloalkyl such as cyclopropyl, cyclobutyl, or cyclohexyl, $C_3$-$C_6$-cycloalkymethyl, such as cyclopropylmethyl, cyclobutylmethyl or cyclopentylmethyl, or benzyl, especially hydrogen or methyl.

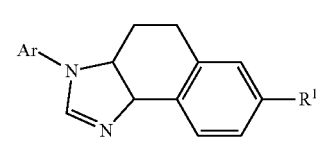

Ia.1

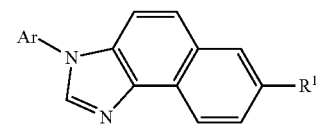

Ia.2

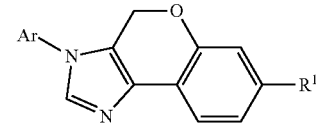

Ia.3

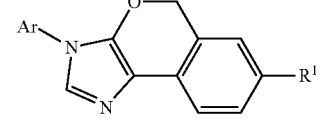

Ia.4

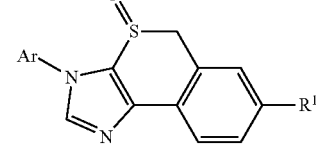

Ia.5

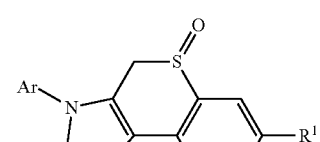

Ia.6

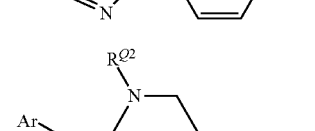

Ia.7

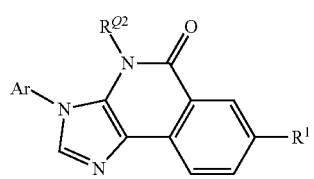
Ia.8
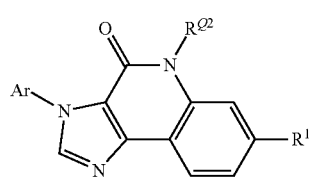
Ia.9
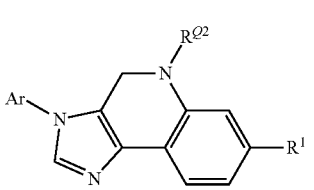
Ia.10
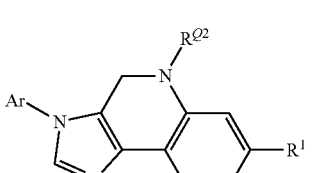
Ia.11
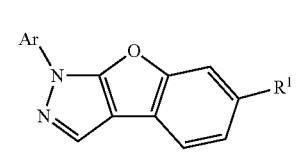
Ia.12
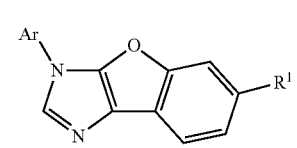
Ia.13
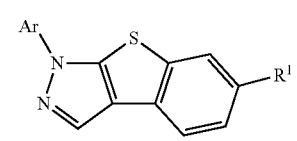
Ia.14
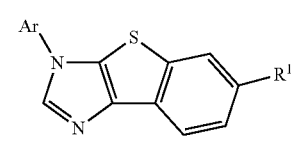
Ia.15
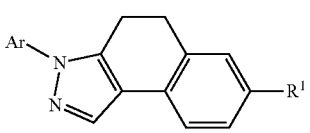
Ia.16
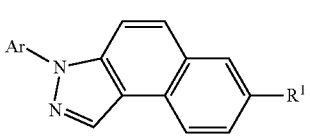
Ia.17
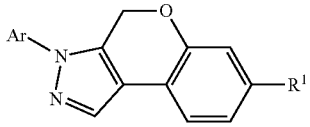
Ia.18
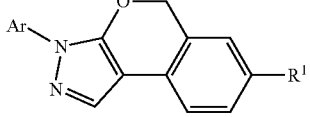
Ia.19
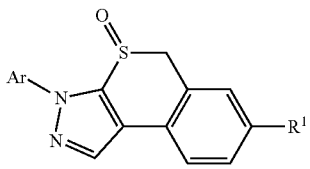
Ia.20
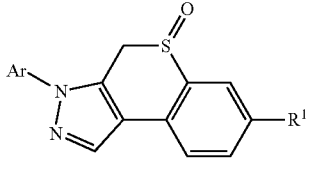
Ia.21
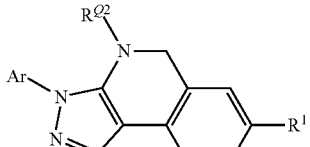
Ia.22
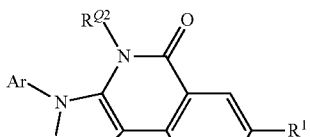
Ia.23
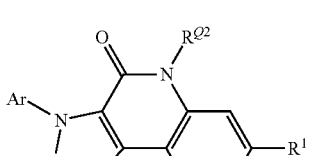
Ia.24
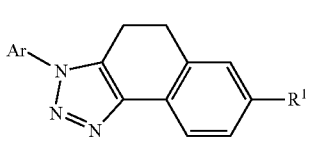
Ia.25
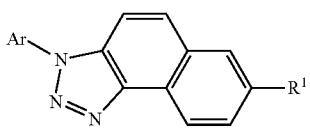
Ia.26
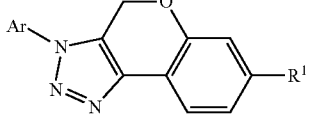
Ia.27

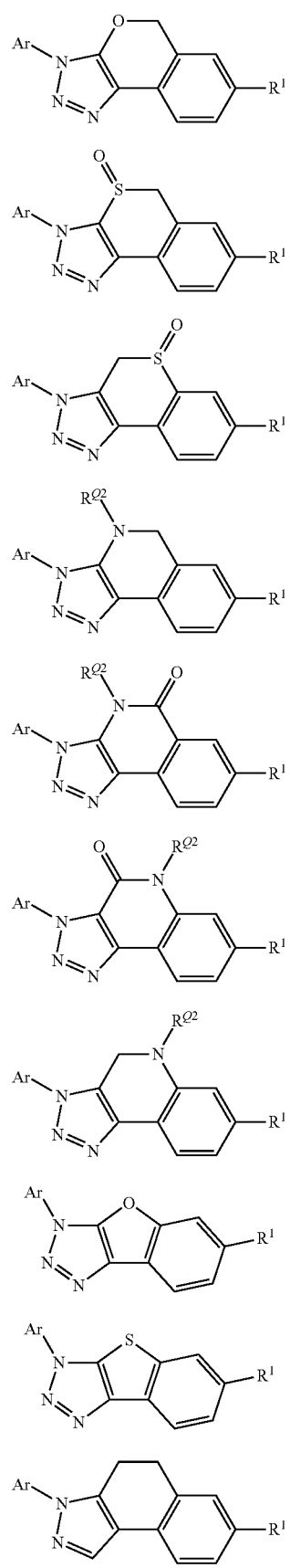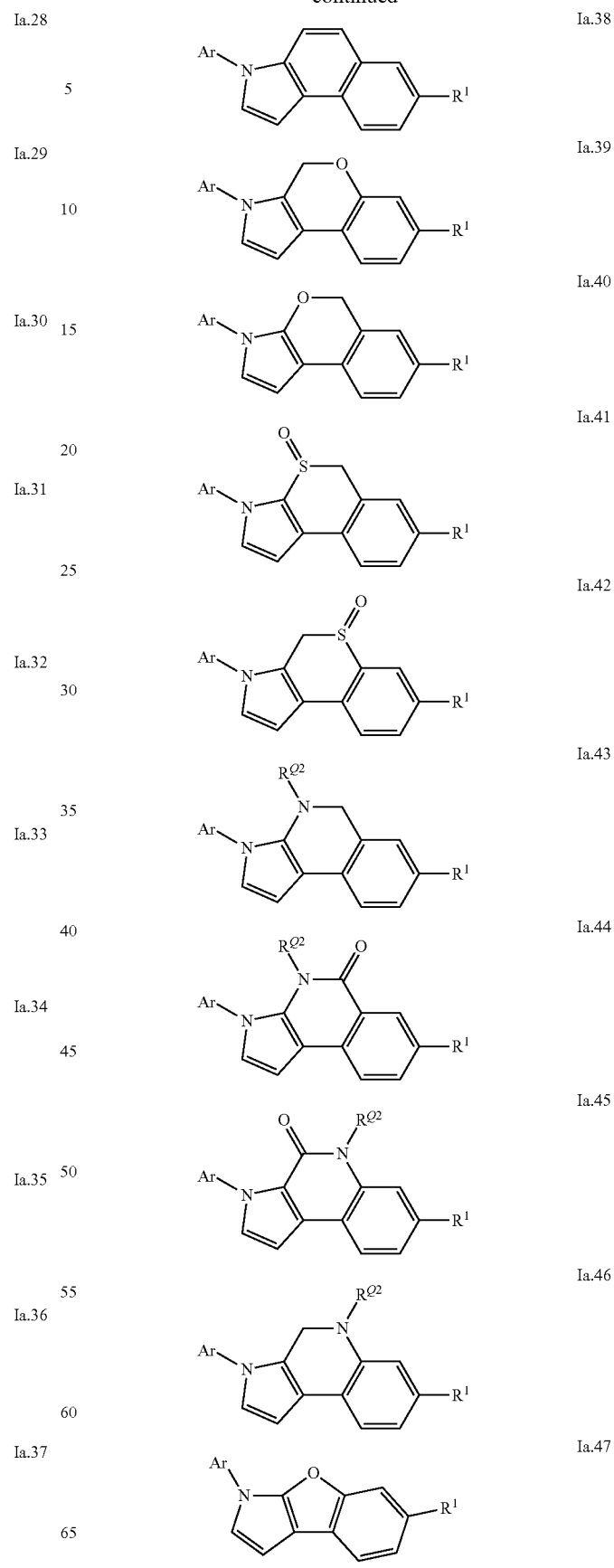

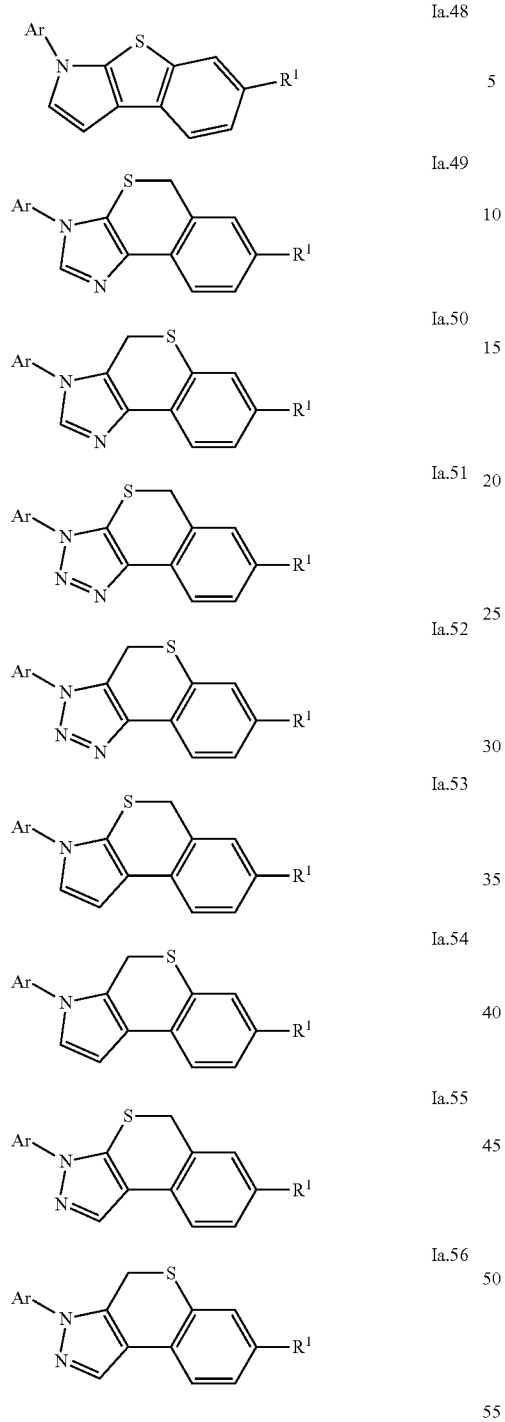

A further particular group of embodiments relates to the compounds of formulae Ib.1 to Ib.18 as described below, to their N-oxides, their stereoisomers, their tautomers and to the agriculturally or veterinarily acceptable salt thereof. In formulae Ib.1 to Ib.14 Ar, $R^1$ and $R^3$ are as defined above and hereinafter and $R^3$ is in particular $C_1$-$C_4$-alkyl, such as methyl, ethyl, n-propyl or isopropyl, $C_3$-$C_6$-cycloalkyl such as cyclopropyl, cyclobutyl, or cyclohexyl, $C_3$-$C_6$-cycloalkymethyl, such as cyclopropylmethyl, cyclobutylmethyl or cyclopentylmethyl, or benzyl, especially $C_1$-$C_4$-alkyl.

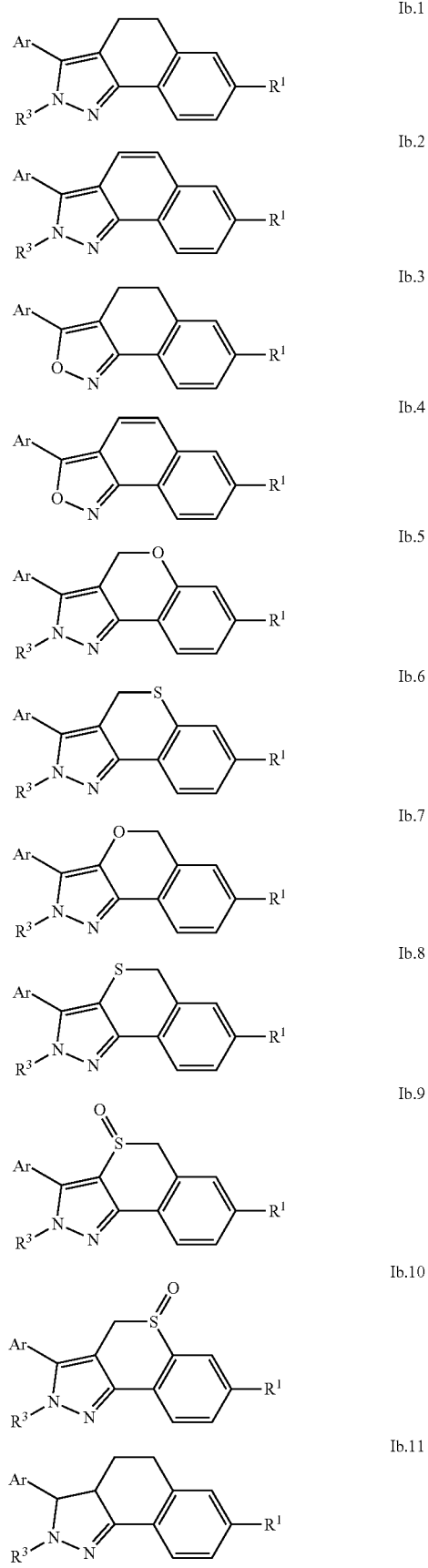

A further particular group of embodiments relates to the compounds of formulae Ic.1 to Ic.62 as described below, to their N-oxides, their stereoisomers, their tautomers and to the agriculturally or veterinarily acceptable salt thereof. In formulae Ic.1 to Ic.62 Ar, $R^1$, $R^6$ and $R^{Q2}$ are as defined above and hereinafter. $R^{Q2}$ is in particular hydrogen, $C_1$-$C_4$-alkyl, such as methyl, ethyl, n-propyl or isopropyl, $C_3$-$C_6$-cycloalkyl such as cyclopropyl, cyclobutyl, or cyclohexyl, $C_3$-$C_6$-cycloalkymethyl, such as cyclopropylmethyl, cyclobutylmethyl or cyclopentylmethyl, or benzyl, especially hydrogen or methyl. $R^6$ is in particular $C_1$-$C_4$-alkyl, such as methyl, ethyl, n-propyl or isopropyl, $C_3$-$C_6$-cycloalkyl such as cyclopropyl, cyclobutyl, or cyclohexyl, $C_3$-$C_6$-cycloalkymethyl, such as cyclopropylmethyl, cyclobutylmethyl or cyclopentylmethyl, or benzyl, especially $C_1$-$C_4$-alkyl.

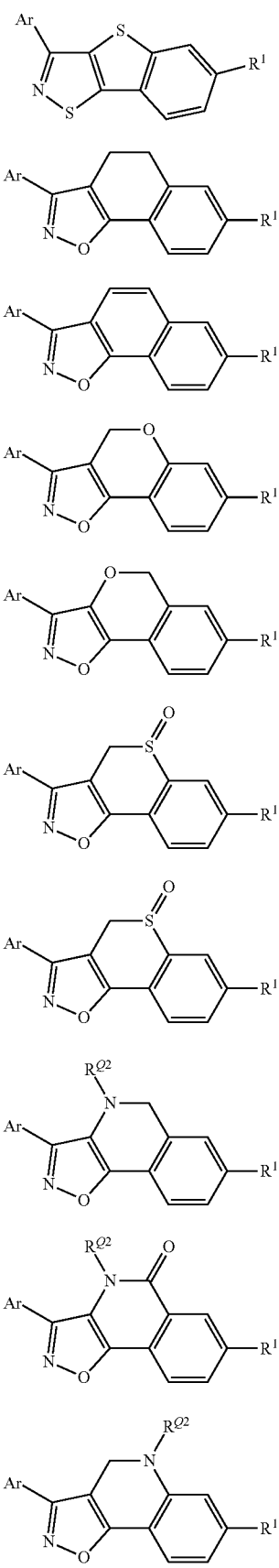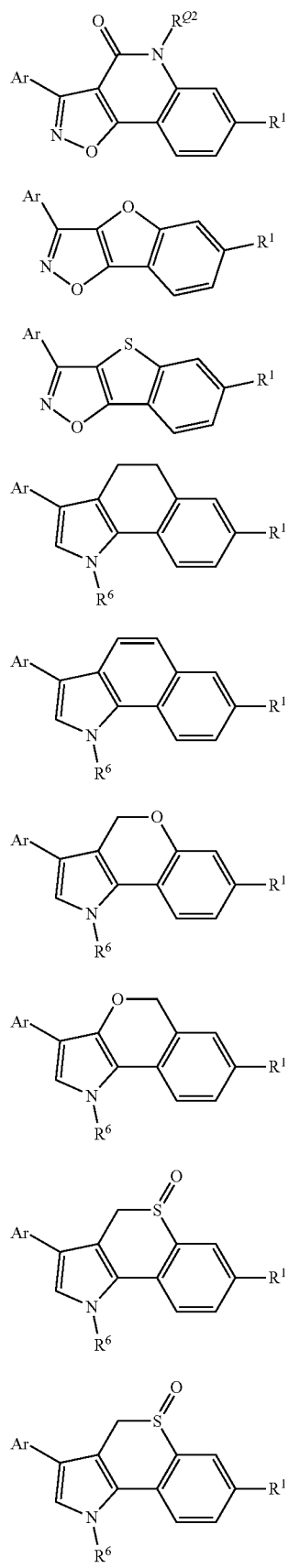

-continued
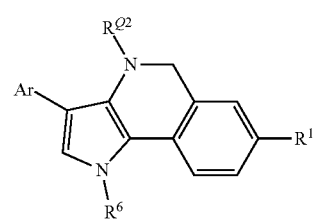
Ic.31
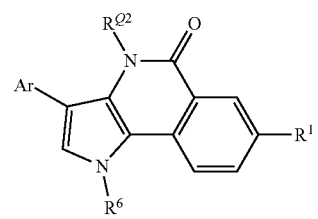
Ic.32
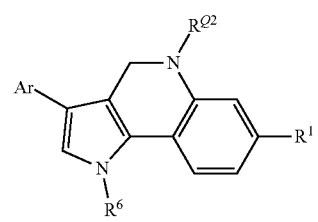
Ic.33
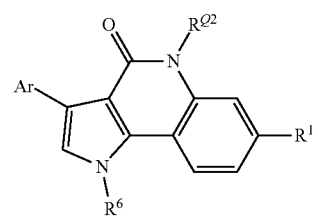
Ic.34
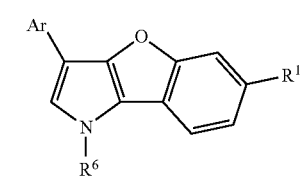
Ic.35
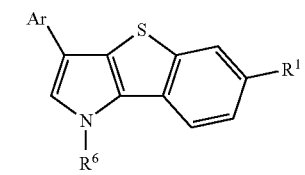
Ic.36
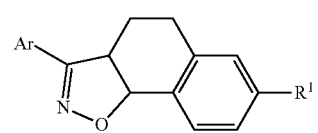
Ic.37
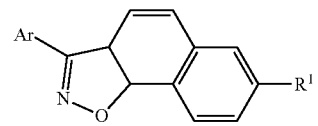
Ic.38
-continued
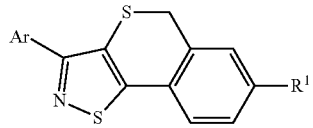
Ic.39
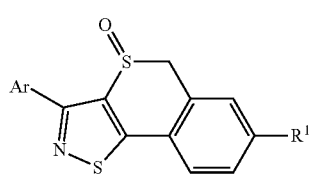
Ic.40
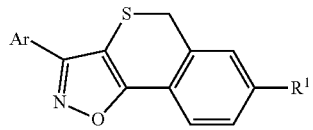
Ic.41
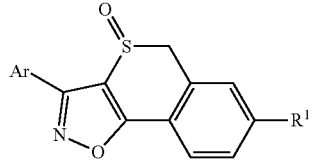
Ic.42
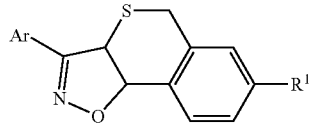
Ic.43
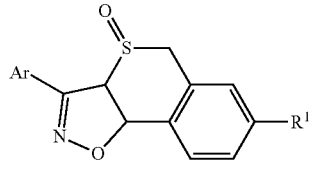
Ic.44
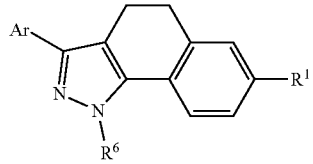
Ic.45
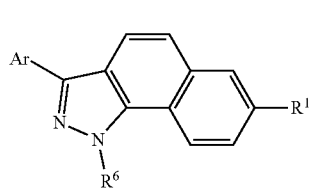
Ic.46
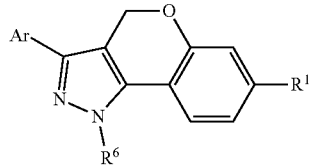
Ic.47

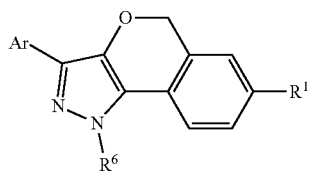 Ic.48

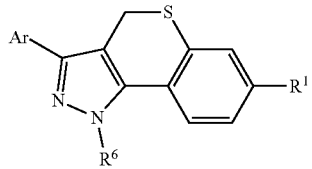 Ic.49

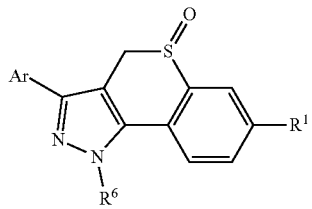 Ic.50

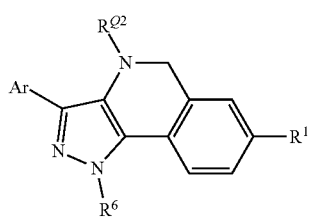 Ic.51

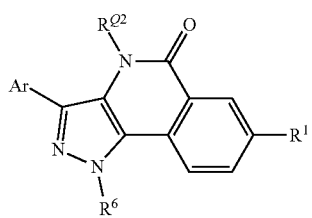 Ic.52

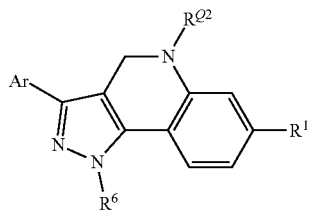 Ic.53

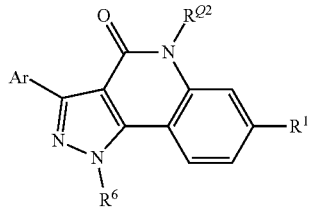 Ic.54

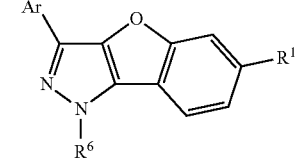 Ic.55

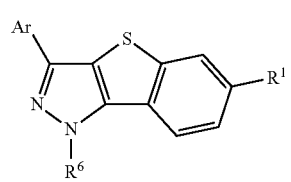 Ic.56

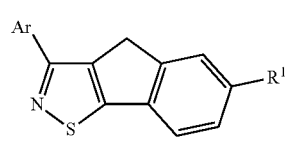 Ic.57

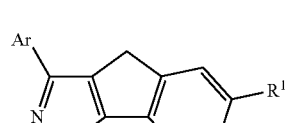 Ic.58

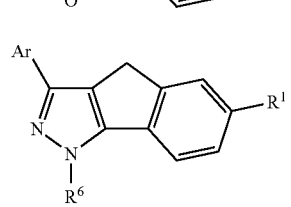 Ic.59

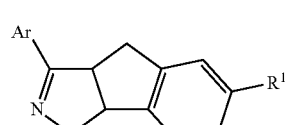 Ic.60

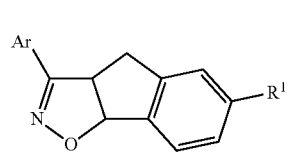 Ic.61

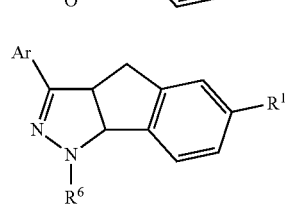 Ic.62

A further particular group of embodiments relates to the compounds of formulae Id.1 to Id.4 as described below, to their N-oxides, their stereoisomers, their tautomers and to the agriculturally or veterinarily acceptable salt thereof. In formulae Id.1 to Id.4 Ar, $R^1$ and $R^6$ are as defined above and hereinafter. $R^6$ is in particular $C_1$-$C_4$-alkyl, such as methyl, ethyl, n-propyl or isopropyl, $C_3$-$C_6$-cycloalkyl such as cyclopropyl, cyclobutyl, or cyclohexyl, $C_3$-$C_6$-cycloalkymethyl, such as cyclopropylmethyl, cyclobutylmethyl or cyclopentylmethyl, or benzyl, especially $C_1$-$C_4$-alkyl.

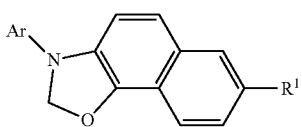 Id.1

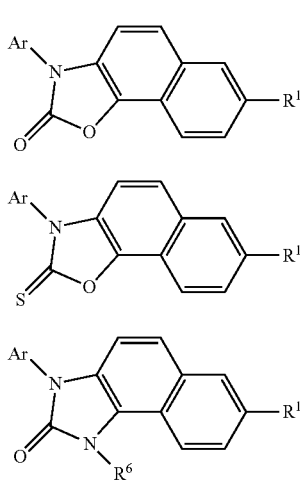

Amongst formulae Ia.1 to Ia.56 particular preference is given to the following formulae Ia.1, Ia.2, Ia.3, Ia.4, Ia.5, Ia.6, Ia.25, Ia.26, Ia.27, Ia.28, Ia.29, Ia.30, Ia.49 and Ia.50.

Amongst formulae Ib.1 to Ib.18 particular preference is given to the following formulae: Ib.1, Ib.2, Ib.3, Ib.4, Ib.12, Ib.15, Ib.17 and Ib.18.

Amongst formulae Ic.1 to Ic.62 particular preference is given to the following formulae: Ic.1, Ic.2, Ic.13, Ic.14, Ic.45, Ic.46, Ic.57, Ic.58 and Ic.59

Amongst formulae Id.1 to Id.4, particular preference is given to the following formulae: Id.2 and Id.3

In formula I as well as in formulae INT, Ia, Ia.1 to Ia.56, Ib, Ib.1 to Ib.18, Ic, Ic.1 to Ic.62, I.d and Id.1 to Id.4 Ar is in particular selected from the group consisting of phenyl and pyridyl, which are unsubstituted or carry 1, 2 or 3 radicals $R^{Ar}$. $R^{Ar}$ is in particular selected from the group consisting of halogen, such as fluorine, chlorine or bromine, OH, CN, $NO_2$, SCN, $C_1$-$C_6$-alkyl, in particular $C_1$-$C_3$-alkyl such as methyl, ethyl, n-propyl or isopropyl, $C_1$-$C_6$-haloalkyl, in particular fluorinated $C_1$-$C_3$-alkyl such as $CH_2F$, $CHF_2$, $CF_3$, $CH_2CF_3$, $CF_2CHF_2$, $C_2F_5$, $CH_2CH_2CF_3$, $CH_2CF_2CHF_2$, or $CH_2CF_2CF_3$, $C_1$-$C_6$-alkoxy, in particular $C_1$-$C_3$-alkoxy such as methoxy, ethoxy, n-propyloxy or isopropyloxy, $C_1$-$C_6$-haloalkoxy, in particular fluorinated $C_1$-$C_3$-alkoxy such as $OCH_2F$, $OCHF_2$, $OCF_3$, $OCH_2CF_3$, $OCF_2CHF_2$, $OC_2F_5$, $OCH_2CH_2CF_3$, $OCH_2CF_2CHF_2$, or $OCH_2CF_2CF_3$, and S—$R^e$, where $R^e$ is $C_1$-$C_6$-alkyl, in particular $C_1$-$C_3$-alkyl such as methyl, ethyl, n-propyl or isopropyl, or $C_1$-$C_6$-haloalkyl, in particular fluorinated $C_1$-$C_3$-alkyl such as $CH_2F$, $CHF_2$, $CF_3$, $CH_2CF_3$, $CF_2CHF_2$, $C_2F_5$, $CH_2CH_2CF_3$, $CH_2CF_2CHF_2$ or $CH_2CF_2CF_3$.

In formula I as well as in formulae Ia, Ia.1 to Ia.56, Ib, Ib.1 to Ib.18, Ic, Ic.1 to Ic.62, I.d and Id.1 to Id.4 Ar is especially selected from the group consisting of phenyl, which carries one radical $R^{Ar}$ in the 4-position, and 3-pyridyl, which carries one radical $R^{Ar}$ in the 6-position and where phenyl and 3-pyridyl may carry 1 or 2 further radicals $R^{Ar}$. In this context, $R^{Ar}$ is in particular selected from the group consisting of halogen, such as fluorine, chlorine or bromine, $C_1$-$C_6$-alkyl, in particular $C_1$-$C_3$-alkyl such as methyl, ethyl, n-propyl or isopropyl, $C_1$-$C_6$-haloalkyl, in particular fluorinated $C_1$-$C_3$-alkyl such as $CH_2F$, $CHF_2$, $CF_3$, $CH_2CF_3$, $CF_2CHF_2$, $C_2F_5$, $CH_2CH_2CF_3$, $CH_2CF_2CHF_2$, or $CH_2CF_2CF_3$, $C_1$-$C_6$-alkoxy, in particular $C_1$-$C_3$-alkoxy such as methoxy, ethoxy, n-propyloxy or isopropyloxy, $C_1$-$C_6$-haloalkoxy, in particular fluorinated $C_1$-$C_3$-alkoxy such as $OCH_2F$, $OCHF_2$, $OCF_3$, $OCH_2CF_3$, $OCF_2CHF_2$, $OC_2F_5$, $OCH_2CH_2CF_3$, $OCH_2CF_2CHF_2$, or $OCH_2CF_2CF_3$, and S—$R^e$, where $R^e$ is $C_1$-$C_6$-alkyl, in particular $C_1$-$C_3$-alkyl such as methyl, ethyl, n-propyl or isopropyl, or $C_1$-$C_6$-haloalkyl, in particular fluorinated $C_1$-$C_3$-alkyl such as $CH_2F$, $CHF_2$, $CF_3$, $CH_2CF_3$, $CF_2CHF_2$, $C_2F_5$, $CH_2CH_2CF_3$, $CH_2CF_2CHF_2$ or $CH_2CF_2CF_3$. In this context, the radical $R^{Ar}$ in the 4-position of phenyl is preferably selected from the group consisting of $C_1$-$C_4$-haloalkyl, especially fluorinated $C_1$-$C_3$-alkyl such as $CH_2F$, $CHF_2$, $CF_3$, $CH_2CF_3$, $CF_2CHF_2$, $C_2F_5$, $CH_2CH_2CF_3$, $CH_2CF_2CHF_2$, or $CH_2CF_2CF_3$; $C_1$-$C_4$-haloalkoxy, especially fluorinated $C_1$-$C_3$-alkoxy such as $OCH_2F$, $OCHF_2$, $OCF_3$, $OCH_2CF_3$, $OCF_2CHF_2$, $OC_2F_5$, $OCH_2CH_2CF_3$, $OCH_2CF_2CHF_2$, or $OCH_2CF_2CF_3$, and S—$R^e$, where $R^e$ is $C_1$-$C_4$-haloalkyl, especially fluorinated $C_1$-$C_3$-alkyl such as $CH_2F$, $CHF_2$, $CF_3$, $CH_2CF_3$, $CF_2CHF_2$, $C_2F_5$, $CH_2CH_2CF_3$, $CH_2CF_2CHF_2$, or $CH_2CF_2CF_3$. In this context, the radical $R^A$ in the 6-position of 3-pyridyl is preferably selected from the group consisting of $C_1$-$C_4$-haloalkyl, especially fluorinated $C_1$-$C_3$-alkyl such as $CH_2F$, $CHF_2$, $CF_3$, $CH_2CF_3$, $CF_2CHF_2$, $C_2F_5$, $CH_2CH_2CF_3$, $CH_2CF_2CHF_2$, or $CH_2CF_2CF_3$; $C_1$-$C_4$-haloalkoxy, especially fluorinated $C_1$-$C_3$-alkoxy such as $OCH_2F$, $OCHF_2$, $OCF_3$, $OCH_2CF_3$, $OCF_2CHF_2$, $OC_2F_5$, $OCH_2CH_2CF_3$, $OCH_2CF_2CHF_2$, or $OCH_2CF_2CF_3$, and S—$R^e$, where $R^e$ is $C_1$-$C_4$-haloalky, especially fluorinated $C_1$-$C_3$-alkyl such as $CH_2F$, $CHF_2$, $CF_3$, $CH_2CF_3$, $CF_2CHF_2$, $C_2F_5$, $CH_2CH_2CF_3$, $CH_2CF_2CHF_2$, or $CH_2CF_2CF_3$. The further 1 or 2 radicals $R^{Ar}$, if present, are preferably selected from the group consisting of halogen, such as fluorine, chlorine or bromine, $C_1$-$C_3$-alkyl such as methyl, ethyl, n-propyl or isopropyl, fluorinated $C_1$-$C_3$-alkyl such as $CH_2F$, $CHF_2$, $CF_3$, $CH_2CF_3$, $CF_2CHF_2$, $C_2F_5$, $CH_2CH_2CF_3$, $CH_2CF_2CHF_2$, or $CH_2CF_2CF_3$, $C_1$-$C_3$-alkoxy such as methoxy, ethoxy, n-propyloxy or isopropyloxy, and fluorinated $C_1$-$C_3$-alkoxy such as $OCH_2F$, $OCHF_2$, $OCF_3$, $OCH_2CF_3$, $OCF_2CHF_2$, $OC_2F_5$, $OCH_2CH_2CF_3$, $OCH_2CF_2CHF_2$, or $OCH_2CF_2CF_3$, Examples of particularly preferred radicals Ar are the radicals Ar-1 to Ar-8 summarized in Table A below.

TABLE A

| | Examples of radicals Ar |
|---|---|
| Ar-1 | 4-trifluoromethylphenyl |
| Ar-2 | 4-trifluoromethoxyphenyl |
| Ar-3 | 4-(pentafluoroethoxy)phenyl |
| Ar-4 | 4-(trifluoromethylthio)phenyl |
| Ar-5 | 6-trifluoro-3-pyridyl |
| Ar-6 | 6-trifluoromethoxy-3-pyridyl |
| Ar-7 | 6-(pentafluoroethoxy)-3-pyridyl |
| Ar-8 | 6-(trifluoromethylthio)3-pyridyl |

In formula I as well as in formulae Ia, Ia.1 to Ia.56, Ib, Ib.1 to Ib.18, Ic, Ic.1 to Ic.62, I.d and Id.1 to Id.4, the radical $R^1$ is in particular a radical of one of the following formulae $R^1$-a to $R^1$-v:

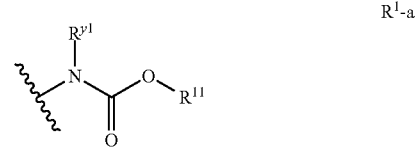

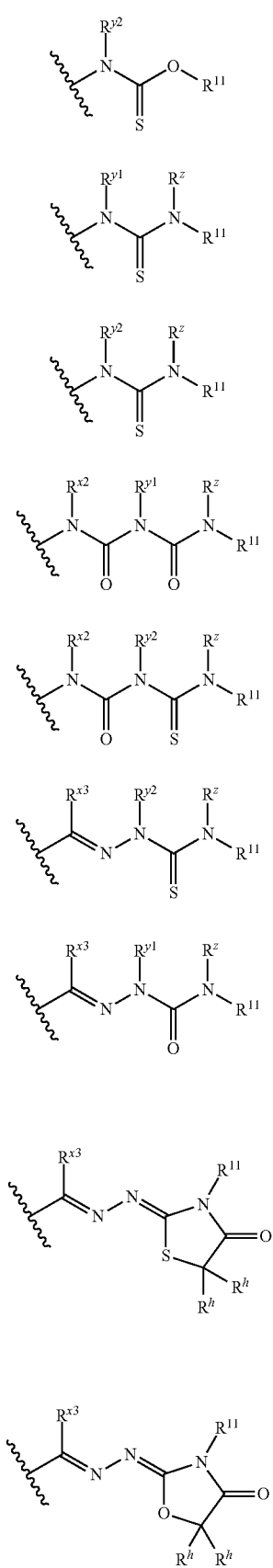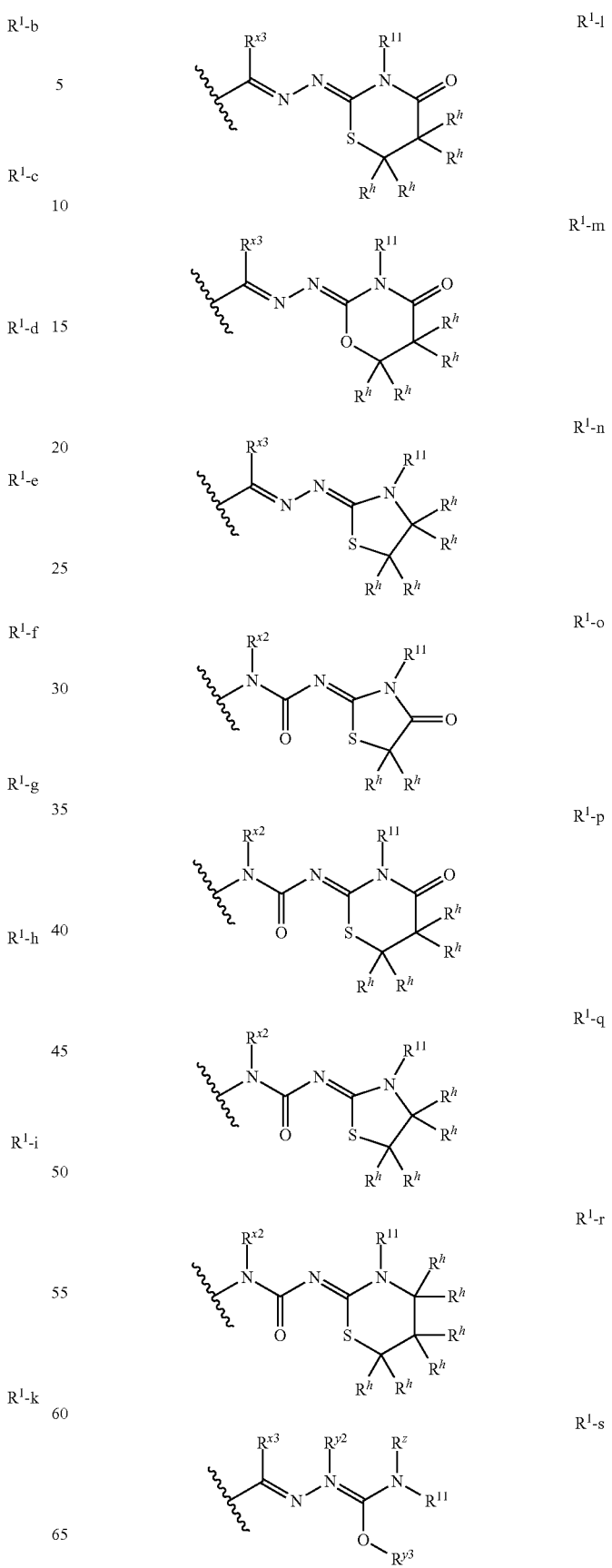

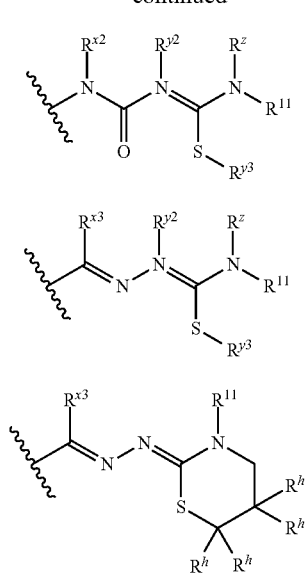

wherein $R^{11}$, $R^{x2}$, $R^{x3}$, $R^{y1}$, $R^{y2}$, $R^{y3}$ and $R^z$ are as defined herein and in particular hydrogen and $R^h$ is hydrogen or has one of the meanings given for $R^{hh}$.

Amongst formulae $R^1$-a to $R^1$-v, particular preference is given to the following groups: $R^1$-a, $R^1$-g, $R^1$-i, $R^1$-l, $R^1$-n, $R^1$-o, $R^1$-p, $R^1$-q and $R^1$-r.

Irrespectively of their occurrence, i.e. either in the variables X, Y and Z as well as in context with formulae $R^{1a}$ to $R^{1v}$ the variables $R^h$, $R^{hh}$, $R^{x1}$, $R^{x2}$, $R^{x3}$, $R^{y1}$, $R^{y2}$, $R^{y3}$ and $R^z$ preferably have one of the following meanings:

$R^{x1}$, $R^{x2}$ independently of each other, are selected from the group consisting of hydrogen, $C_1$-$C_6$-alkyl, $C_1$-$C_6$-haloalkyl, $C_1$-$C_6$-alkoxy-$C_1$-$C_4$-alkyl, $C_3$-$C_6$-cycloalkyl, $C_3$-$C_6$-cycloalkyl-$C_1$-$C_4$-alkyl, $C_3$-$C_6$-cycloalkoxy-$C_1$-$C_4$-alkyl, where the alkyl, cycloalkyl, cycloalkoxy and alkoxy parts of the last four mentioned radicals are unsubstituted or partially or completely halogenated, phenyl and benzyl, where the phenyl ring in the last 2 radicals is unsubstituted or carry 1, 2 or 3 radicals $R^f$;

$R^{x3}$ is selected from the group consisting of hydrogen, $C_1$-$C_6$-alkyl, $C_1$-$C_6$-haloalkyl, $C_1$-$C_6$-alkoxy-$C_1$-$C_4$-alkyl, $C_3$-$C_6$-cycloalkyl, $C_3$-$C_6$-cycloalkyl-$C_1$-$C_4$-alkyl, where the alkyl, cycloalkyl and alkoxy parts of the last 3 mentioned radicals are unsubstituted or partially or completely halogenated, and phenyl, where the phenyl ring is unsubstituted or carries 1, 2 or 3 radicals $R^f$;

$R^{y1}$, $R^{y2}$ independently of each other, are selected from the group consisting of hydrogen, $C_1$-$C_6$-alkyl, $C_1$-$C_6$-haloalkyl, $C_1$-$C_6$-alkoxy-$C_1$-$C_4$-alkyl, $C_3$-$C_6$-cycloalkyl, $C_3$-$C_6$-cycloalkyl-$C_1$-$C_4$-alkyl, $C_3$-$C_6$-cycloalkoxy-$C_1$-$C_4$-alkyl, where the alkyl, cycloalkyl, cycloalkoxy and alkoxy parts of the last four mentioned radicals are unsubstituted or partially or completely halogenated, phenyl and benzyl, where the phenyl ring in the last 2 radicals is unsubstituted or carry 1, 2 or 3 radicals $R^f$;

$R^{y3}$ is selected from the group consisting of hydrogen, $C_1$-$C_6$-alkyl, $C_1$-$C_6$-haloalkyl, $C_1$-$C_6$-alkoxy-$C_1$-$C_4$-alkyl, $C_3$-$C_6$-cycloalkyl, $C_3$-$C_6$-cycloalkyl-$C_1$-$C_4$-alkyl, $C_3$-$C_6$-cycloalkoxy-$C_1$-$C_4$-alkyl, where the alkyl, cycloalkyl, cycloalkoxy and alkoxy parts of the last four mentioned radicals are unsubstituted or partially or completely halogenated, phenyl and benzyl, where the phenyl ring in the last 2 radicals is unsubstituted or carry 1, 2 or 3 radicals $R^f$;

$R^z$ is selected from the group consisting of hydrogen, $C_1$-$C_6$-alkyl, $C_1$-$C_6$-haloalkyl, $C_1$-$C_6$-alkoxy-$C_1$-$C_4$-alkyl, $C_3$-$C_6$-cycloalkyl, $C_3$-$C_6$-cycloalkyl-$C_1$-$C_4$-alkyl, $C_3$-$C_6$-cycloalkoxy-$C_1$-$C_4$-alkyl, where the alkyl, cycloalkyl, cycloalkoxy and alkoxy parts of the last four mentioned radicals are unsubstituted or partially or completely halogenated, phenyl and benzyl, where the phenyl ring in the last 2 radicals is unsubstituted or carry 1, 2 or 3 radicals $R^f$; or $R^z$ together with $R^{y3}$, if present, may also form a $C_3$-$C_4$-alkylene group, wherein a $CH_2$ moiety may be replaced by a carbonyl group and/or wherein the alkylene group may be substituted 1, 2, 3 or 4 radicals $R^{hh}$ which are preferably $C_1$-$C_3$-alkyl such as methyl, ethyl or n-propyl;

$R^{hh}$ is selected from the group consisting of halogen, such as chlorine or fluorine, and $C_1$-$C_4$-alkyl such as methyl, ethyl, n-propyl or isopropyl;

$R^h$ is selected from the group consisting of hydrogen, halogen, such as chlorine or fluorine, and $C_1$-$C_4$-alkyl such as methyl, ethyl, n-propyl or isopropyl, with particular preference given to $R^h$=hydrogen;

Irrespectively of their occurrence, i.e. either in the variables X, Y and Z as well as in context with formulae $R^{1a}$ to $R^{1v}$ the variables $R^h$, $R^{x1}$, $R^{x2}$, $R^{x3}$, $R^{y1}$, $R^{y2}$, $R^{y3}$ and $R^z$ especially have one of the following meanings:

$R^{x1}$, $R^{x2}$ independently of each other, are selected from the group consisting of hydrogen and $C_1$-$C_4$-alkyl such as methyl, ethyl, n-propyl or isopropyl;

$R^{x3}$ is selected from the group consisting of hydrogen and $C_1$-$C_4$-alkyl such as methyl, ethyl, n-propyl or isopropyl;

$R^{y1}$, $R^{y2}$ independently of each other, are selected from the group consisting of hydrogen and $C_1$-$C_4$-alkyl such as methyl, ethyl, n-propyl or isopropyl;

$R^{y3}$ is selected from the group consisting of hydrogen and $C_1$-$C_4$-alkyl such as methyl, ethyl, n-propyl or isopropyl;

$R^z$ is selected from the group consisting of hydrogen and $C_1$-$C_4$-alkyl such as methyl, ethyl, n-propyl or isopropyl; or $R^z$ together with $R^{y3}$, if present, may also form —$CH_2CH_2$—, —$CH_2CH_2CH_2$—, —$CH_2$—$C(O)$—, —$CH_2CH_2C(O)$—, —$CH_2$—$C(S)$—, or —$CH_2CH_2C(S)$—;

$R^h$ is selected from the group consisting of hydrogen, halogen, such as chlorine or fluorine, and $C_1$-$C_4$-alkyl such as methyl, ethyl, n-propyl or isopropyl, with particular preference given to $R^h$=hydrogen;

A particular group of embodiments relates to compounds of the formulae I, Ia, Ia.1 to Ia.55, Ib, Ib.1 to Ib.18, Ic, Ic.1 to Ic.62, I.d and Id.1 to Id.4, where —X—Y—Z— is selected from the bivalent radicals XYZ-a to XYZ-w, where the left hand bond is attached to the tricyclic core while the right hand bond is attached to $R^{11}$:

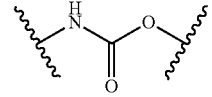

XYZ-a

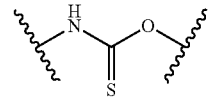

XYZ-b

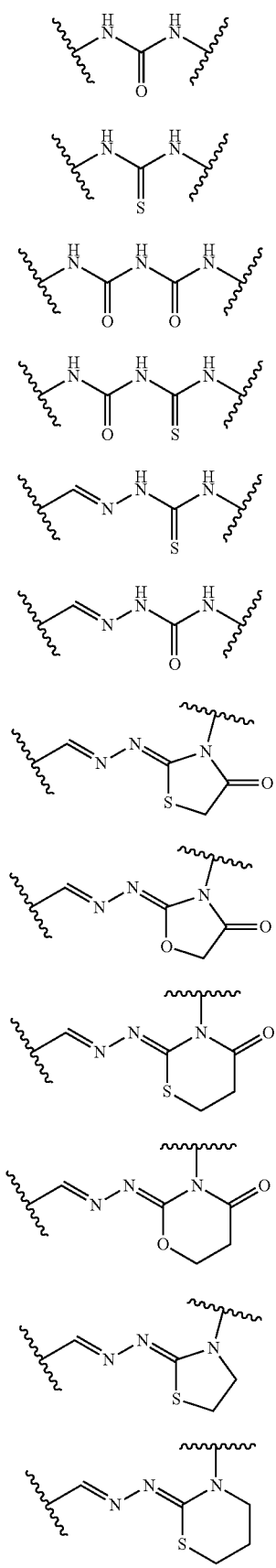
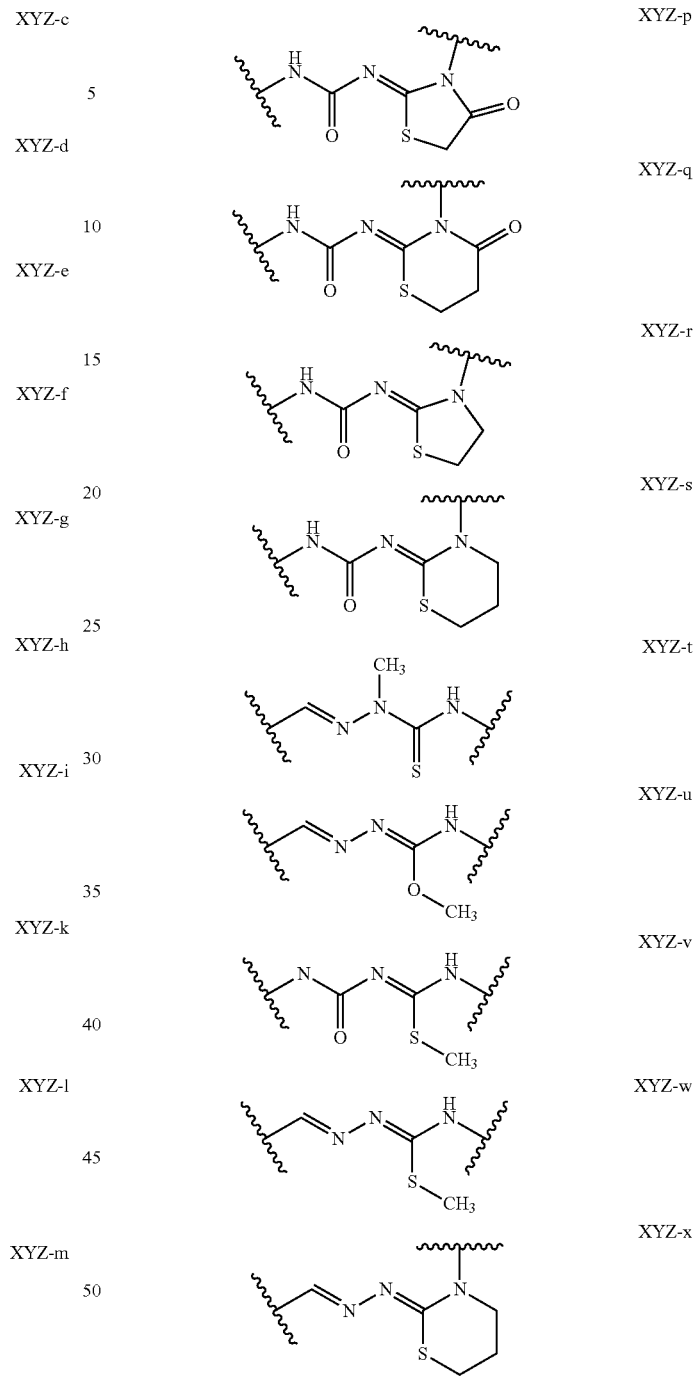

Amongst formulae XYZ-a to XYZ-x, particular preference is given to the following groups: XYZ-a, XYZ-g, XYZ-i, XYZ-l, XYZ-n, XYZ-o, XYZ-p, XYZ-q, XYZ-v and XYZ-w.

In formula I as well as in formulae Ia, Ia.1 to Ia.56, Ib, Ib.1 to Ib.18, Ic, Ic.1 to Ic.62, I.d and Id.1 to Id.4 $R^{11}$ is in particular aryl, aryl-$C_1$-$C_4$-alkyl, hetaryl, or hetaryl-$C_1$-$C_4$-alkyl, where the aryl and hetaryl rings in the last 4 radicals are unsubstituted or carry 1, 2, 3, 4 or 5 radicals $R^g$ and where hetaryl in hetaryl or hetaryl-$C_1$-$C_4$-alkyl, is preferably a 5- or 6-membered monocyclic hetaryl such as pyridyl, pyrimidinyl, pyridazinyl, pyrrolyl, pyrazolyl, imidazolyl, oxazolyl, thiazolyl, isoxazolyl or isothiazolyl which 5- or 6-membered hetaryl is unsubstituted or carries 1, 2 or 3 radicals $R^g$.

In formula I as well as in formulae Ia, Ia.1 to Ia.56, Ib, Ib.1 to Ib.18, Ic, Ic.1 to Ic.62, I.d and Id.1 to Id.4 $R^{11}$ is in especially phenyl, benzyl, 1-phenylethyl, pyridyl, pyridylmethyl and 1-(pyridyl)ethyl, where phenyl and pyridyl in the last 6 radicals may be unsubstituted or preferably carry 1, 2 or 3 radicals $R^g$.

In context of $R^{11}$, the radicals $R^g$ are independently of each other selected from the group consisting of halogen, such as fluorine, chlorine or bromine, $C_1$-$C_6$-alkyl, in particular $C_1$-$C_3$-alkyl such as methyl, ethyl, n-propyl or isopropyl, $C_1$-$C_6$-haloalkyl, in particular fluorinated $C_1$-$C_3$-alkyl such as $CH_2F$, $CHF_2$, $CF_3$, $CH_2CF_3$, $CF_2CHF_2$, $C_2F_5$, $CH_2CH_2CF_3$, $CH_2CF_2CHF_2$, or $CH_2CF_2CF_3$, $C_1$-$C_6$-alkoxy, in particular $C_1$-$C_3$-alkoxy such as methoxy, ethoxy, n-propyloxy or isopropyloxy, $C_1$-$C_6$-haloalkoxy, in particular fluorinated $C_1$-$C_3$-alkoxy such as $OCH_2F$, $OCHF_2$, $OCF_3$, $OCH_2CF_3$, $OCF_2CHF_2$, $OC_2F_5$, $OCH_2CH_2CF_3$, $OCH_2CF_2CHF_2$, or $OCH_2CF_2CF_3$, and S—$R^e$, where $R^e$ is $C_1$-$C_6$-alkyl, in particular $C_1$-$C_3$-alkyl such as methyl, ethyl, n-propyl or isopropyl, or $C_1$-$C_6$-haloalkyl, in particular fluorinated $C_1$-$C_3$-alkyl such as $CH_2F$, $CHF_2$, $CF_3$, $CH_2CF_3$, $CF_2CHF_2$, $C_2F_5$, $CH_2CH_2CF_3$, $CH_2CF_2CHF_2$ or $CH_2CF_2CF_3$. If two or more radicals $R^g$ are present on $R^{11}$, it is possible that the radicals $R^g$ are identical or different.

Examples of particularly preferred radicals $R^{11}$ are the radicals $R^{11}$-1 to $R^{11}$-28 summarized in Table B below.

TABLE B

Examples of radicals $R^{11}$

| | |
|---|---|
| $R^{11}$-1 | 2-isopropylphenyl |
| $R^{11}$-2 | 2-trifluoromethyphenyl |
| $R^{11}$-3 | 2-ethylphenyl |
| $R^{11}$-4 | 2-methoxyphenyl |
| $R^{11}$-5 | 2,4-dichlorophenyl |
| $R^{11}$-6 | 2,5-dimethylphenyl |
| $R^{11}$-7 | 2,5-dichlorophenyl |
| $R^{11}$-8 | 2,6-dichlorophenyl |
| $R^{11}$-9 | 2,6-difluorophenyl |
| $R^{11}$-10 | 2,6-dimethylphenyl |
| $R^{11}$-11 | 2,4,6-trifluorophenyl |
| $R^{11}$-12 | 2,4,6-trichlorophenyl |
| $R^{11}$-13 | 2,4,6-trimethylphenyl |
| $R^{11}$-14 | 2-methyl-4-chlorophenyl |
| $R^{11}$-15 | 2-methyl-5-chlorophenyl |
| $R^{11}$-16 | 2-chloro-5-trifluoromethylphenyl |
| $R^{11}$-17 | 2,6-dimethyl-4-bromophenyl |
| $R^{11}$-18 | 1-(5-chloro-2-pyridyl)ethyl |
| $R^{11}$-19 | 1-(5-fluoro-2-pyridyl)ethyl |
| $R^{11}$-20 | 1-(5-methoxy-2-pyridyl)ethyl |
| $R^{11}$-21 | 1-(6-chloro-2-pyridyl)ethyl |
| $R^{11}$-22 | 1-naphthyl |
| $R^{11}$-23 | 2-chlorophenyl |
| $R^{11}$-24 | 2-fluorophenyl |
| $R^{11}$-25 | 2-methylphenyl |
| $R^{11}$-26 | 2,4-difluorophenyl |
| $R^{11}$-27 | 2,4-dimethylphenyl |
| $R^{11}$-28 | 2-methyl-5-methoxyphenyl |

In formulae I, Ia, Ib, Ic and Id, the variable k is preferably 0. If k is 1, 2 or 3, the variable R is preferably selected from the group consisting of halogen such as fluorine, chlorine or bromine, CN, $NO_2$, SCN, $C_1$-$C_6$-alkyl, in particular $C_1$-$C_3$-alkyl such as methyl, ethyl, n-propyl or isopropyl, $C_1$-$C_6$-haloalkyl, in particular fluorinated $C_1$-$C_3$-alkyl such as $CH_2F$, $CHF_2$, $CF_3$, $CH_2CF_3$, $CF_2CHF_2$, $C_2F_5$, $CH_2CH_2CF_3$, $CH_2CF_2CHF_2$, or $CH_2CF_2CF_3$, $C_1$-$C_6$-alkoxy, in particular $C_1$-$C_3$-alkoxy such as methoxy, ethoxy, n-propyloxy or isopropyloxy, $C_1$-$C_6$-haloalkoxy, in particular fluorinated $C_1$-$C_3$-alkoxy such as $OCH_2F$, $OCHF_2$, $OCF_3$, $OCH_2CF_3$, $OCF_2CHF_2$, $OC_2F_5$, $OCH_2CH_2CF_3$, $OCH_2CF_2CHF_2$, or $OCH_2CF_2CF_3$, and S—$R^e$, where $R^e$ is $C_1$-$C_6$-alkyl, in particular $C_1$-$C_3$-alkyl such as methyl, ethyl, n-propyl or isopropyl, or $C_1$-$C_6$-haloalkyl, in particular fluorinated $C_1$-$C_3$-alkyl such as $CH_2F$, $CHF_2$, $CF_3$, $CH_2CF_3$, $CF_2CHF_2$, $C_2F_5$, $CH_2CH_2CF_3$, $CH_2CF_2CHF_2$ or $CH_2CF_2CF_3$. For k=2 or 3 it will be possible that the radicals R are identical or different.

Apart from that, the variables $R^a$, $R^b$, $R^c$, $R^d$, $R^e$, $R^f$ and $R^g$ independently of each other, preferably have one of the following meanings:

Preferably, each $R^a$ is independently selected from the group consisting of $C_1$-$C_6$-alkyl, $C_1$-$C_6$-haloalkyl, $C_3$-$C_8$-cycloalkyl, $C_3$-$C_8$-halocycloalkyl, benzyl and phenyl, where the phenyl ring in the last two radicals is unsubstituted or may be substituted by 1, 2 or 3 radicals $R^f$.

Preferably, $R^c$ and $R^d$ are, independently of each other and independently of their occurrence, selected from the group consisting of hydrogen, $C_1$-$C_4$-alkyl, $C_1$-$C_4$-haloalkyl, $C_3$-$C_6$-cycloalkyl-$CH_2$, $C_3$-$C_6$-cycloalkyl, benzyl and phenyl, where the phenyl ring in the last two radicals is unsubstituted or may be substituted by 1, 2 or 3 radicals $R^f$; or $R^b$ and $R^c$ together with the nitrogen atom to which they are bound may form a saturated 5-, 6- or 7-membered saturated N-bound heterocycle, which may contain 1 or 2 further heteroatoms selected from N, O and S as ring members, where the heterocyclic ring may carry 1, 2, 3 or 4 substituents selected from $C_1$-$C_4$-alkyl, examples including 1-pyrrolidinyl, 1-piperidinyl, 1-piperazinyl, 4-methyl-1-piperazinyl, 4-morpholinyl and 4-thiomorpholinyl.

Preferably, each $R^d$ is independently selected from the group consisting of $C_1$-$C_4$-alkyl, $C_1$-$C_4$-haloalkyl, $C_3$-$C_8$-cycloalkyl, benzyl and phenyl, where the phenyl ring in the last two radicals is unsubstituted or may be substituted by 1, 2 or 3 radicals $R^f$.

Preferably, each $R^e$ is independently selected from the group consisting of $C_1$-$C_4$-alkyl, $C_1$-$C_4$-haloalkyl, $C_3$-$C_8$-cycloalkyl, benzyl and phenyl, where the phenyl ring in the last two radicals is unsubstituted or may be substituted by 1, 2 or 3 radicals $R^f$.

Preferably each $R^f$ is independently selected from the group consisting of halogen, in particular fluorine, chlorine or bromine, $C_1$-$C_4$-alkyl, $C_1$-$C_4$-haloalkyl, $C_1$-$C_4$-alkoxycarbonyl, cyano, $C_1$-$C_4$-alkoxy and $C_1$-$C_4$-haloalkoxy, especially from the group consisting of halogen, in particular fluorine, chlorine or bromine, methyl, halomethyl, e.g. trifluoromethyl, difluoromethyl or bromodifluoromethyl, cyano, methoxy and halo-methoxy, e.g. trifluoromethoxy, difluoromethoxy or fluoromethoxy. If two or more radicals $R^f$ are present, it is possible that the radicals $R^f$ are identical or different.

$R^g$ are independently of each other selected from the group consisting of halogen, such as fluorine, chlorine or bromine, $C_1$-$C_6$-alkyl, in particular $C_1$-$C_3$-alkyl such as methyl, ethyl, n-propyl or isopropyl, $C_1$-$C_6$-haloalkyl, in particular fluorinated $C_1$-$C_3$-alkyl such as $CH_2F$, $CHF_2$, $CF_3$, $CH_2CF_3$, $CF_2CHF_2$, $C_2F_5$, $CH_2CH_2CF_3$, $CH_2CF_2CHF_2$, or $CH_2CF_2CF_3$, $C_1$-$C_6$-alkoxy, in particular $C_1$-$C_3$-alkoxy such as methoxy, ethoxy, n-propyloxy or isopropyloxy, $C_1$-$C_6$-haloalkoxy, in particular fluorinated $C_1$-$C_3$-alkoxy such as $OCH_2F$, $OCHF_2$, $OCF_3$, $OCH_2CF_3$, $OCF_2CHF_2$, $OC_2F_5$, $OCH_2CH_2CF_3$, $OCH_2CF_2CHF_2$, or $OCH_2CF_2CF_3$, and S—$R^e$, where $R^e$ is $C_1$-$C_6$-alkyl, in particular $C_1$-$C_3$-alkyl such as methyl, ethyl, n-propyl or isopropyl, or $C_1$-$C_6$- haloalkyl, in particular fluorinated $C_1$-$C_3$-alkyl such as $CH_2F$, $CHF_2$, $CF_3$, $CH_2CF_3$, $CF_2CHF_2$, $C_2F_5$, $CH_2CH_2CF_3$, $CH_2CF_2CHF_2$ or $CH_2CF_2CF_3$. If two or more radicals $R^g$ are present, it is possible that the radicals $R^g$ are identical or different.

Examples of compounds of the present invention are given in the tables 1 to 164 below:

Table 1: Compounds of the formula Ia.1, their stereoisomers, their tautomers and the agriculturally or veterinarily acceptable salts, wherein $R^1$ is a radical —XYZ—$R^{11}$, where Ar, —XYZ— and $R^{11}$ are as defined in the rows of table C.

Table 2: Compounds of the formula Ia.2, their stereoisomers, their tautomers and the agriculturally or veterinarily acceptable salts, wherein $R^1$ is a radical —XYZ—$R^{11}$, where Ar, —XYZ— and $R^{11}$ are as defined in the rows of table C.

Table 3: Compounds of the formula Ia.3, their stereoisomers, their tautomers and the agriculturally or veterinarily acceptable salts, wherein $R^1$ is a radical —XYZ—$R^{11}$, where Ar, —XYZ— and $R^{11}$ are as defined in the rows of table C.

Table 4: Compounds of the formula Ia.4, their stereoisomers, their tautomers and the agriculturally or veterinarily acceptable salts, wherein $R^1$ is a radical —XYZ—$R^{11}$, where Ar, —XYZ— and $R^{11}$ are as defined in the rows of table C.

Table 5: Compounds of the formula Ia.5, their stereoisomers, their tautomers and the agriculturally or veterinarily acceptable salts, wherein $R^1$ is a radical —XYZ—$R^{11}$, where Ar, —XYZ— and $R^{11}$ are as defined in the rows of table C.

Table 6: Compounds of the formula Ia.6, their stereoisomers, their tautomers and the agriculturally or veterinarily acceptable salts, wherein $R^1$ is a radical —XYZ—$R^{11}$, where Ar, —XYZ— and $R^{11}$ are as defined in the rows of table C.

Table 7: Compounds of the formula Ia.7, their stereoisomers, their tautomers and the agriculturally or veterinarily acceptable salts, wherein $R^1$ is a radical —XYZ—$R^{11}$, where Ar, —XYZ— and $R^{11}$ are as defined in the rows of table C.

Table 8: Compounds of the formula Ia.8, their stereoisomers, their tautomers and the agriculturally or veterinarily acceptable salts, wherein $R^1$ is a radical —XYZ—$R^{11}$, where Ar, —XYZ— and $R^{11}$ are as defined in the rows of table C.

Table 9: Compounds of the formula Ia.9, their stereoisomers, their tautomers and the agriculturally or veterinarily acceptable salts, wherein $R^1$ is a radical —XYZ—$R^{11}$, where Ar, —XYZ— and $R^{11}$ are as defined in the rows of table C.

Table 10: Compounds of the formula Ia.10, their stereoisomers, their tautomers and the agriculturally or veterinarily acceptable salts, wherein $R^1$ is a radical —XYZ—$R^{11}$, where Ar, —XYZ— and $R^{11}$ are as defined in the rows of table C.

Table 11: Compounds of the formula Ia.11, their stereoisomers, their tautomers and the agriculturally or veterinarily acceptable salts, wherein $R^1$ is a radical —XYZ—$R^{11}$, where Ar, —XYZ— and $R^{11}$ are as defined in the rows of table C.

Table 12: Compounds of the formula Ia.12, their stereoisomers, their tautomers and the agriculturally or veterinarily acceptable salts, wherein $R^1$ is a radical —XYZ—$R^{11}$, where Ar, —XYZ— and $R^{11}$ are as defined in the rows of table C.

Table 13: Compounds of the formula Ia.13, their stereoisomers, their tautomers and the agriculturally or veterinarily acceptable salts, wherein $R^1$ is a radical —XYZ—$R^{11}$, where Ar, —XYZ— and $R^{11}$ are as defined in the rows of table C.

Table 14: Compounds of the formula Ia.14, their stereoisomers, their tautomers and the agriculturally or veterinarily acceptable salts, wherein $R^1$ is a radical —XYZ—$R^{11}$, where Ar, —XYZ— and $R^{11}$ are as defined in the rows of table C.

Table 15: Compounds of the formula Ia.15, their stereoisomers, their tautomers and the agriculturally or veterinarily acceptable salts, wherein $R^1$ is a radical —XYZ—$R^{11}$, where Ar, —XYZ— and $R^{11}$ are as defined in the rows of table C.

Table 16: Compounds of the formula Ia.16, their stereoisomers, their tautomers and the agriculturally or veterinarily acceptable salts, wherein $R^1$ is a radical —XYZ—$R^{11}$, where Ar, —XYZ— and $R^{11}$ are as defined in the rows of table C.

Table 17: Compounds of the formula Ia.17, their stereoisomers, their tautomers and the agriculturally or veterinarily acceptable salts, wherein $R^1$ is a radical —XYZ—$R^{11}$, where Ar, —XYZ— and $R^{11}$ are as defined in the rows of table C.

Table 18: Compounds of the formula Ia.18, their stereoisomers, their tautomers and the agriculturally or veterinarily acceptable salts, wherein $R^1$ is a radical —XYZ—$R^{11}$, where Ar, —XYZ— and $R^{11}$ are as defined in the rows of table C.

Table 19: Compounds of the formula Ia.19, their stereoisomers, their tautomers and the agriculturally or veterinarily acceptable salts, wherein $R^1$ is a radical —XYZ—$R^{11}$, where Ar, —XYZ— and $R^{11}$ are as defined in the rows of table C.

Table 20: Compounds of the formula Ia.20, their stereoisomers, their tautomers and the agriculturally or veterinarily acceptable salts, wherein $R^1$ is a radical —XYZ—$R^{11}$, where Ar, —XYZ— and $R^{11}$ are as defined in the rows of table C.

Table 21: Compounds of the formula Ia.21, their stereoisomers, their tautomers and the agriculturally or veterinarily acceptable salts, wherein $R^1$ is a radical —XYZ—$R^{11}$, where Ar, —XYZ— and $R^{11}$ are as defined in the rows of table C.

Table 22: Compounds of the formula Ia.22, their stereoisomers, their tautomers and the agriculturally or veterinarily acceptable salts, wherein $R^1$ is a radical —XYZ—$R^{11}$, where Ar, —XYZ— and $R^{11}$ are as defined in the rows of table C.

Table 23: Compounds of the formula Ia.23, their stereoisomers, their tautomers and the agriculturally or veterinarily acceptable salts, wherein $R^1$ is a radical —XYZ—$R^{11}$, where Ar, —XYZ— and $R^{11}$ are as defined in the rows of table C.

Table 24: Compounds of the formula Ia.24, their stereoisomers, their tautomers and the agriculturally or veterinarily acceptable salts, wherein $R^1$ is a radical —XYZ—$R^{11}$, where Ar, —XYZ— and $R^{11}$ are as defined in the rows of table C.

Table 25: Compounds of the formula Ia.25, their stereoisomers, their tautomers and the agriculturally or veterinarily acceptable salts, wherein $R^1$ is a radical —XYZ—$R^{11}$, where Ar, —XYZ— and $R^{11}$ are as defined in the rows of table C.

Table 26: Compounds of the formula Ia.26, their stereoisomers, their tautomers and the agriculturally or veterinarily acceptable salts, wherein $R^1$ is a radical —XYZ—$R^{11}$, where Ar, —XYZ— and $R^{11}$ are as defined in the rows of table C.

Table 27: Compounds of the formula Ia.27, their stereoisomers, their tautomers and the agriculturally or veterinarily acceptable salts, wherein $R^1$ is a radical —XYZ—$R^{11}$, where Ar, —XYZ— and $R^{11}$ are as defined in the rows of table C.

Table 28: Compounds of the formula Ia.28, their stereoisomers, their tautomers and the agriculturally or veterinarily acceptable salts, wherein $R^1$ is a radical —XYZ—$R^{11}$, where Ar, —XYZ— and $R^{11}$ are as defined in the rows of table C.

Table 29: Compounds of the formula Ia.29, their stereoisomers, their tautomers and the agriculturally or veterinarily acceptable salts, wherein $R^1$ is a radical —XYZ—$R^{11}$, where Ar, —XYZ— and $R^{11}$ are as defined in the rows of table C.

Table 30: Compounds of the formula Ia.30, their stereoisomers, their tautomers and the agriculturally or veterinarily acceptable salts, wherein $R^1$ is a radical —XYZ—$R^{11}$, where Ar, —XYZ— and $R^{11}$ are as defined in the rows of table C.

Table 31: Compounds of the formula Ia.31, their stereoisomers, their tautomers and the agriculturally or veterinarily acceptable salts, wherein $Q^2$ is hydrogen, $R^1$ is a radical —XYZ—$R^{11}$, where Ar, —XYZ— and $R^{11}$ are as defined in the rows of table C.

Table 32: Compounds of the formula Ia.32, their stereoisomers, their tautomers and the agriculturally or veterinarily acceptable salts, wherein $Q^2$ is hydrogen, $R^1$ is a radical —XYZ—$R^{11}$, where Ar, —XYZ— and $R^{11}$ are as defined in the rows of table C.

Table 33: Compounds of the formula Ia.33, their stereoisomers, their tautomers and the agriculturally or veterinarily acceptable salts, wherein $Q^2$ is hydrogen, $R^1$ is a radical —XYZ—$R^{11}$, where Ar, —XYZ— and $R^{11}$ are as defined in the rows of table C.

Table 34: Compounds of the formula Ia.34, their stereoisomers, their tautomers and the agriculturally or veterinarily acceptable salts, wherein $Q^2$ is hydrogen, $R^1$ is a radical —XYZ—$R^{11}$, where Ar, —XYZ— and $R^{11}$ are as defined in the rows of table C.

Table 35: Compounds of the formula Ia.31, their stereoisomers, their tautomers and the agriculturally or veterinarily acceptable salts, wherein $Q^2$ is methyl, $R^1$ is a radical —XYZ—$R^{11}$, where Ar, —XYZ— and $R^{11}$ are as defined in the rows of table C.

Table 36: Compounds of the formula Ia.32, their stereoisomers, their tautomers and the agriculturally or veterinarily acceptable salts, wherein $Q^2$ is methyl, $R^1$ is a radical —XYZ—$R^{11}$, where Ar, —XYZ— and $R^{11}$ are as defined in the rows of table C.

Table 37: Compounds of the formula Ia.33, their stereoisomers, their tautomers and the agriculturally or veterinarily acceptable salts, wherein $Q^2$ is methyl, $R^1$ is a radical —XYZ—$R^{11}$, where Ar, —XYZ— and $R^{11}$ are as defined in the rows of table C.

Table 38: Compounds of the formula Ia.34, their stereoisomers, their tautomers and the agriculturally or veterinarily acceptable salts, wherein $Q^2$ is methyl, $R^1$ is a radical —XYZ—$R^{11}$, where Ar, —XYZ— and $R^{11}$ are as defined in the rows of table C.

Table 39: Compounds of the formula Ia.35, their stereoisomers, their tautomers and the agriculturally or veterinarily acceptable salts, wherein $R^1$ is a radical —XYZ—$R^{11}$, where Ar, —XYZ— and $R^{11}$ are as defined in the rows of table C.

Table 40: Compounds of the formula Ia.36, their stereoisomers, their tautomers and the agriculturally or veterinarily acceptable salts, wherein $R^1$ is a radical —XYZ—$R^{11}$, where Ar, —XYZ— and $R^{11}$ are as defined in the rows of table C.

Table 41: Compounds of the formula Ia.37, their stereoisomers, their tautomers and the agriculturally or veterinarily acceptable salts, wherein $R^1$ is a radical —XYZ—$R^{11}$, where Ar, —XYZ— and $R^{11}$ are as defined in the rows of table C.

Table 42: Compounds of the formula Ia.38, their stereoisomers, their tautomers and the agriculturally or veterinarily acceptable salts, wherein $R^1$ is a radical —XYZ—$R^{11}$, where Ar, —XYZ— and $R^{11}$ are as defined in the rows of table C.

Table 43: Compounds of the formula Ia.39, their stereoisomers, their tautomers and the agriculturally or veterinarily acceptable salts, wherein $R^1$ is a radical —XYZ—$R^{11}$, where Ar, —XYZ— and $R^{11}$ are as defined in the rows of table C.

Table 44: Compounds of the formula Ia.40, their stereoisomers, their tautomers and the agriculturally or veterinarily acceptable salts, wherein $R^1$ is a radical —XYZ—$R^{11}$, where Ar, —XYZ— and $R^{11}$ are as defined in the rows of table C.

Table 45: Compounds of the formula Ia.41, their stereoisomers, their tautomers and the agriculturally or veterinarily acceptable salts, wherein $R^1$ is a radical —XYZ—$R^{11}$, where Ar, —XYZ— and $R^{11}$ are as defined in the rows of table C.

Table 46: Compounds of the formula Ia.42, their stereoisomers, their tautomers and the agriculturally or veterinarily acceptable salts, wherein $R^1$ is a radical —XYZ—$R^{11}$, where Ar, —XYZ— and $R^{11}$ are as defined in the rows of table C.

Table 47: Compounds of the formula Ia.43, their stereoisomers, their tautomers and the agriculturally or veterinarily acceptable salts, wherein $Q^2$ is hydrogen, $R^1$ is a radical —XYZ—$R^{11}$, where Ar, —XYZ— and $R^{11}$ are as defined in the rows of table C.

Table 48: Compounds of the formula Ia.44, their stereoisomers, their tautomers and the agriculturally or veterinarily acceptable salts, wherein $Q^2$ is hydrogen, $R^1$ is a radical —XYZ—$R^{11}$, where Ar, —XYZ— and $R^{11}$ are as defined in the rows of table C.

Table 49: Compounds of the formula Ia.45, their stereoisomers, their tautomers and the agriculturally or veterinarily acceptable salts, wherein $Q^2$ is hydrogen, $R^1$ is a radical —XYZ—$R^{11}$, where Ar, —XYZ— and $R^{11}$ are as defined in the rows of table C.

Table 50: Compounds of the formula Ia.46, their stereoisomers, their tautomers and the agriculturally or veterinarily acceptable salts, wherein $Q^2$ is hydrogen, $R^1$ is a radical —XYZ—$R^{11}$, where Ar, —XYZ— and $R^{11}$ are as defined in the rows of table C.

Table 51: Compounds of the formula Ia.43, their stereoisomers, their tautomers and the agriculturally or veterinarily acceptable salts, wherein $Q^2$ is methyl, $R^1$ is a radical —XYZ—$R^{11}$, where Ar, —XYZ— and $R^{11}$ are as defined in the rows of table C.

Table 52: Compounds of the formula Ia.44, their stereoisomers, their tautomers and the agriculturally or veterinarily acceptable salts, wherein $Q^2$ is methyl, $R^1$ is a radical —XYZ—$R^{11}$, where Ar, —XYZ— and $R^{11}$ are as defined in the rows of table C.

Table 53: Compounds of the formula Ia.45, their stereoisomers, their tautomers and the agriculturally or veterinarily acceptable salts, wherein $Q^2$ is methyl, $R^1$ is a radical —XYZ—$R^{11}$, where Ar, —XYZ— and $R^{11}$ are as defined in the rows of table C.

Table 54: Compounds of the formula Ia.46, their stereoisomers, their tautomers and the agriculturally or veterinarily acceptable salts, wherein $Q^2$ is methyl, $R^1$ is a radical —XYZ—$R^{11}$, where Ar, —XYZ— and $R^{11}$ are as defined in the rows of table C.

Table 55: Compounds of the formula Ia.47, their stereoisomers, their tautomers and the agriculturally or veterinarily acceptable salts, wherein $R^1$ is a radical —XYZ—$R^{11}$, where Ar, —XYZ— and $R^{11}$ are as defined in the rows of table C.

Table 56: Compounds of the formula Ia.48, their stereoisomers, their tautomers and the agriculturally or veterinarily acceptable salts, wherein $R^1$ is a radical —XYZ—$R^{11}$, where Ar, —XYZ— and $R^{11}$ are as defined in the rows of table C.

Table 57: Compounds of the formula Ia.49, their stereoisomers, their tautomers and the agriculturally or veterinarily acceptable salts, wherein $R^1$ is a radical —XYZ—$R^{11}$, where Ar, —XYZ— and $R^{11}$ are as defined in the rows of table C.

Table 58: Compounds of the formula Ia.50, their stereoisomers, their tautomers and the agriculturally or veterinarily acceptable salts, wherein $R^1$ is a radical —XYZ—$R^{11}$, where Ar, —XYZ— and $R^{11}$ are as defined in the rows of table C.

Table 59: Compounds of the formula Ia.51, their stereoisomers, their tautomers and the agriculturally or veterinarily acceptable salts, wherein $R^1$ is a radical —XYZ—$R^{11}$, where Ar, —XYZ— and $R^{11}$ are as defined in the rows of table C.

Table 60: Compounds of the formula Ia.52, their stereoisomers, their tautomers and the agriculturally or veterinarily acceptable salts, wherein $R^1$ is a radical —XYZ—$R^{11}$, where Ar, —XYZ— and $R^{11}$ are as defined in the rows of table C.

Table 61: Compounds of the formula Ia.53, their stereoisomers, their tautomers and the agriculturally or veterinarily acceptable salts, wherein $R^1$ is a radical —XYZ—$R^{11}$, where Ar, —XYZ— and $R^{11}$ are as defined in the rows of table C.

Table 62: Compounds of the formula Ia.54, their stereoisomers, their tautomers and the agriculturally or veterinarily acceptable salts, wherein $R^1$ is a radical —XYZ—$R^{11}$, where Ar, —XYZ— and $R^{11}$ are as defined in the rows of table C.

Table 63: Compounds of the formula Ia.55, their stereoisomers, their tautomers and the agriculturally or veterinarily acceptable salts, wherein $R^1$ is a radical —XYZ—$R^{11}$, where Ar, —XYZ— and $R^{11}$ are as defined in the rows of table C.

Table 64: Compounds of the formula Ia.56, their stereoisomers, their tautomers and the agriculturally or veterinarily acceptable salts, wherein $R^1$ is a radical —XYZ—$R^{11}$, where Ar, —XYZ— and $R^{11}$ are as defined in the rows of table C.

Table 65: Compounds of the formula Ib.1, their stereoisomers, their tautomers and the agriculturally or veterinarily acceptable salts, wherein $R^3$ is methyl, $R^1$ is a radical —XYZ—$R^{11}$, where Ar, —XYZ— and $R^{11}$ are as defined in the rows of table C.

Table 66: Compounds of the formula Ib.2, their stereoisomers, their tautomers and the agriculturally or veterinarily acceptable salts, wherein $R^3$ is methyl, $R^1$ is a radical —XYZ—$R^{11}$, where Ar, —XYZ— and $R^{11}$ are as defined in the rows of table C.

Table 67: Compounds of the formula Ib.3, their stereoisomers, their tautomers and the agriculturally or veterinarily acceptable salts, wherein $R^1$ is a radical —XYZ—$R^{11}$, where Ar, —XYZ— and $R^{11}$ are as defined in the rows of table C.

Table 68: Compounds of the formula Ib.4, their stereoisomers, their tautomers and the agriculturally or veterinarily acceptable salts, wherein $R^1$ is a radical —XYZ—$R^{11}$, where Ar, —XYZ— and $R^{11}$ are as defined in the rows of table C.

Table 69: Compounds of the formula Ib.5, their stereoisomers, their tautomers and the agriculturally or veterinarily acceptable salts, wherein $R^3$ is methyl, $R^1$ is a radical —XYZ—$R^{11}$, where Ar, —XYZ— and $R^{11}$ are as defined in the rows of table C.

Table 70: Compounds of the formula Ib.6, their stereoisomers, their tautomers and the agriculturally or veterinarily acceptable salts, wherein $R^3$ is methyl, $R^1$ is a radical —XYZ—$R^{11}$, where Ar, —XYZ— and $R^{11}$ are as defined in the rows of table C.

Table 71: Compounds of the formula Ib.7, their stereoisomers, their tautomers and the agriculturally or veterinarily acceptable salts, wherein $R^3$ is methyl, $R^1$ is a radical —XYZ—$R^{11}$, where Ar, —XYZ— and $R^{11}$ are as defined in the rows of table C.

Table 72: Compounds of the formula Ib.8, their stereoisomers, their tautomers and the agriculturally or veterinarily acceptable salts, wherein $R^3$ is methyl, $R^1$ is a radical —XYZ—$R^{11}$, where Ar, —XYZ— and $R^{11}$ are as defined in the rows of table C.

Table 73: Compounds of the formula Ib.9, their stereoisomers, their tautomers and the agriculturally or veterinarily acceptable salts, wherein $R^3$ is methyl, $R^1$ is a radical —XYZ—$R^{11}$, where Ar, —XYZ— and $R^{11}$ are as defined in the rows of table C.

Table 74: Compounds of the formula Ib.10, their stereoisomers, their tautomers and the agriculturally or veterinarily acceptable salts, wherein $R^3$ is methyl, $R^1$ is a radical —XYZ—$R^{11}$, where Ar, —XYZ— and $R^{11}$ are as defined in the rows of table C.

Table 75: Compounds of the formula Ib.11, their stereoisomers, their tautomers and the agriculturally or veterinarily acceptable salts, wherein $R^3$ is methyl, $R^1$ is a radical —XYZ—$R^{11}$, where Ar, —XYZ— and $R^{11}$ are as defined in the rows of table C.

Table 76: Compounds of the formula Ib.12, their stereoisomers, their tautomers and the agriculturally or veterinarily acceptable salts, wherein $R^3$ is methyl, $R^1$ is a radical —XYZ—$R^{11}$, where Ar, —XYZ— and $R^{11}$ are as defined in the rows of table C.

Table 77: Compounds of the formula Ib.13, their stereoisomers, their tautomers and the agriculturally or veterinarily acceptable salts, wherein $R^3$ is methyl, $R^1$ is a radical —XYZ—$R^{11}$, where Ar, —XYZ— and $R^{11}$ are as defined in the rows of table C.

Table 78: Compounds of the formula Ib.14, their stereoisomers, their tautomers and the agriculturally or veterinarily acceptable salts, wherein $R^1$ is a radical —XYZ—$R^{11}$, where Ar, —XYZ— and $R^{11}$ are as defined in the rows of table C.

Table 79: Compounds of the formula Ib.15, their stereoisomers, their tautomers and the agriculturally or veterinarily acceptable salts, wherein $R^1$ is a radical —XYZ—$R^{11}$, where Ar, —XYZ— and $R^{11}$ are as defined in the rows of table C.

Table 80: Compounds of the formula Ib.16, their stereoisomers, their tautomers and the agriculturally or veterinarily acceptable salts, wherein $R^1$ is a radical —XYZ—$R^{11}$, where Ar, —XYZ— and $R^{11}$ are as defined in the rows of table C.

Table 81: Compounds of the formula Ib.17, their stereoisomers, their tautomers and the agriculturally or veterinarily acceptable salts, wherein $R^1$ is a radical —XYZ—$R^{11}$, where Ar, —XYZ— and $R^{11}$ are as defined in the rows of table C.

Table 82: Compounds of the formula Ib.18, their stereoisomers, their tautomers and the agriculturally or veterinarily acceptable salts, wherein $R^1$ is a radical —XYZ—$R^{11}$, where Ar, —XYZ— and $R^{11}$ are as defined in the rows of table C.

Table 83: Compounds of the formula Ic.1, their stereoisomers, their tautomers and the agriculturally or veterinarily acceptable salts, wherein $R^1$ is a radical —XYZ—$R^{11}$, where Ar, —XYZ— and $R^{11}$ are as defined in the rows of table C.

Table 84: Compounds of the formula Ic.2, their stereoisomers, their tautomers and the agriculturally or veterinarily acceptable salts, wherein $R^1$ is a radical —XYZ—$R^{11}$, where Ar, —XYZ— and $R^{11}$ are as defined in the rows of table C.

Table 85: Compounds of the formula Ic.3, their stereoisomers, their tautomers and the agriculturally or veterinarily acceptable salts, wherein $R^1$ is a radical —XYZ—$R^{11}$, where Ar, —XYZ— and $R^{11}$ are as defined in the rows of table C.

Table 86: Compounds of the formula Ic.4, their stereoisomers, their tautomers and the agriculturally or veterinarily acceptable salts, wherein $R^1$ is a radical —XYZ—$R^{11}$, where Ar, —XYZ— and $R^{11}$ are as defined in the rows of table C.

Table 87: Compounds of the formula Ic.5, their stereoisomers, their tautomers and the agriculturally or veterinarily acceptable salts, wherein $R^1$ is a radical —XYZ—$R^{11}$, where Ar, —XYZ— and $R^{11}$ are as defined in the rows of table C.

Table 88: Compounds of the formula Ic.6, their stereoisomers, their tautomers and the agriculturally or veterinarily acceptable salts, wherein $R^1$ is a radical —XYZ—$R^{11}$, where Ar, —XYZ— and $R^{11}$ are as defined in the rows of table C.

Table 89: Compounds of the formula Ic.7, their stereoisomers, their tautomers and the agriculturally or veterinarily acceptable salts, wherein $Q^2$ is hydrogen, $R^1$ is a radical —XYZ—$R^{11}$, where Ar, —XYZ— and $R^{11}$ are as defined in the rows of table C.

Table 90: Compounds of the formula Ic.8, their stereoisomers, their tautomers and the agriculturally or veterinarily acceptable salts, wherein $Q^2$ is hydrogen, $R^1$ is a radical —XYZ—$R^{11}$, where Ar, —XYZ— and $R^{11}$ are as defined in the rows of table C.

Table 91: Compounds of the formula Ic.9, their stereoisomers, their tautomers and the agriculturally or veterinarily acceptable salts, wherein $Q^2$ is hydrogen, $R^1$ is a radical —XYZ—$R^{11}$, where Ar, —XYZ— and $R^{11}$ are as defined in the rows of table C.

Table 92: Compounds of the formula Ic.10, their stereoisomers, their tautomers and the agriculturally or veterinarily acceptable salts, wherein $Q^2$ is hydrogen, $R^1$ is a radical —XYZ—$R^{11}$, where Ar, —XYZ— and $R^{11}$ are as defined in the rows of table C.

Table 93: Compounds of the formula Ic.7, their stereoisomers, their tautomers and the agriculturally or veterinarily acceptable salts, wherein $Q^2$ is methyl, $R^1$ is a radical —XYZ—$R^{11}$, where Ar, —XYZ— and $R^{11}$ are as defined in the rows of table C.

Table 94: Compounds of the formula Ic.8, their stereoisomers, their tautomers and the agriculturally or veterinarily acceptable salts, wherein $Q^2$ is methyl, $R^1$ is a radical —XYZ—$R^{11}$, where Ar, —XYZ— and $R^{11}$ are as defined in the rows of table C.

Table 95: Compounds of the formula Ic.9, their stereoisomers, their tautomers and the agriculturally or veterinarily acceptable salts, wherein $Q^2$ is methyl, $R^1$ is a radical —XYZ—$R^{11}$, where Ar, —XYZ— and $R^{11}$ are as defined in the rows of table C.

Table 96: Compounds of the formula Ic.10, their stereoisomers, their tautomers and the agriculturally or veterinarily acceptable salts, wherein $Q^2$ is methyl, $R^1$ is a radical —XYZ—$R^{11}$, where Ar, —XYZ— and $R^{11}$ are as defined in the rows of table C.

Table 97: Compounds of the formula Ic.11, their stereoisomers, their tautomers and the agriculturally or veterinarily acceptable salts, wherein $R^1$ is a radical —XYZ—$R^{11}$, where Ar, —XYZ— and $R^{11}$ are as defined in the rows of table C.

Table 98: Compounds of the formula Ic.12, their stereoisomers, their tautomers and the agriculturally or veterinarily acceptable salts, wherein $R^1$ is a radical —XYZ—$R^{11}$, where Ar, —XYZ— and $R^{11}$ are as defined in the rows of table C.

Table 99: Compounds of the formula Ic.13, their stereoisomers, their tautomers and the agriculturally or veterinarily acceptable salts, wherein $R^1$ is a radical —XYZ—$R^{11}$, where Ar, —XYZ— and $R^{11}$ are as defined in the rows of table C.

Table 100: Compounds of the formula Ic.14, their stereoisomers, their tautomers and the agriculturally or veterinarily acceptable salts, wherein $R^1$ is a radical —XYZ—$R^{11}$, where Ar, —XYZ— and $R^{11}$ are as defined in the rows of table C.

Table 101: Compounds of the formula Ic.15, their stereoisomers, their tautomers and the agriculturally or veterinarily acceptable salts, wherein $R^1$ is a radical —XYZ—$R^{11}$, where Ar, —XYZ— and $R^{11}$ are as defined in the rows of table C.

Table 102: Compounds of the formula Ic.16, their stereoisomers, their tautomers and the agriculturally or veterinarily acceptable salts, wherein $R^1$ is a radical —XYZ—$R^{11}$, where Ar, —XYZ— and $R^{11}$ are as defined in the rows of table C.

Table 103: Compounds of the formula Ic.17, their stereoisomers, their tautomers and the agriculturally or veterinarily acceptable salts, wherein $R^1$ is a radical —XYZ—$R^{11}$, where Ar, —XYZ— and $R^{11}$ are as defined in the rows of table C.

Table 104: Compounds of the formula Ic.18, their stereoisomers, their tautomers and the agriculturally or veterinarily acceptable salts, wherein $R^1$ is a radical —XYZ—$R^{11}$, where Ar, —XYZ— and $R^{11}$ are as defined in the rows of table C.

Table 105: Compounds of the formula Ic.19, their stereoisomers, their tautomers and the agriculturally or veterinarily acceptable salts, wherein $Q^2$ is hydrogen, $R^1$ is a radical —XYZ—$R^{11}$, where Ar, —XYZ— and $R^{11}$ are as defined in the rows of table C.

Table 106: Compounds of the formula Ic.20, their stereoisomers, their tautomers and the agriculturally or veterinarily acceptable salts, wherein $Q^2$ is hydrogen, $R^1$ is a radical —XYZ—$R^{11}$, where Ar, —XYZ— and $R^{11}$ are as defined in the rows of table C.

Table 107: Compounds of the formula Ic.21, their stereoisomers, their tautomers and the agriculturally or veterinarily acceptable salts, wherein $Q^2$ is hydrogen, $R^1$ is a radical —XYZ—$R^{11}$, where Ar, —XYZ— and $R^{11}$ are as defined in the rows of table C.

Table 108: Compounds of the formula Ic.22, their stereoisomers, their tautomers and the agriculturally or veterinarily acceptable salts, wherein $Q^2$ is hydrogen, $R^1$ is a radical —XYZ—$R^{11}$, where Ar, —XYZ— and $R^{11}$ are as defined in the rows of table C.

Table 109: Compounds of the formula Ic.19, their stereoisomers, their tautomers and the agriculturally or veterinarily acceptable salts, wherein $Q^2$ is methyl, $R^1$ is a radical —XYZ—$R^{11}$, where Ar, —XYZ— and $R^{11}$ are as defined in the rows of table C.

Table 110: Compounds of the formula Ic.20, their stereoisomers, their tautomers and the agriculturally or veterinarily acceptable salts, wherein $Q^2$ is methyl, $R^1$ is a radical —XYZ—$R^{11}$, where Ar, —XYZ— and $R^{11}$ are as defined in the rows of table C.

Table 111: Compounds of the formula Ic.21, their stereoisomers, their tautomers and the agriculturally or veterinarily acceptable salts, wherein $Q^2$ is methyl, $R^1$ is a radical —XYZ—$R^{11}$, where Ar, —XYZ— and $R^{11}$ are as defined in the rows of table C.

Table 112: Compounds of the formula Ic.22, their stereoisomers, their tautomers and the agriculturally or veterinarily acceptable salts, wherein $Q^2$ is methyl, $R^1$ is a radical —XYZ—$R^{11}$, where Ar, —XYZ— and $R^{11}$ are as defined in the rows of table C.

Table 113: Compounds of the formula Ic.23, their stereoisomers, their tautomers and the agriculturally or veterinarily acceptable salts, wherein $R^1$ is a radical —XYZ—$R^{11}$, where Ar, —XYZ— and $R^{11}$ are as defined in the rows of table C.

Table 114: Compounds of the formula Ic.24, their stereoisomers, their tautomers and the agriculturally or veterinarily acceptable salts, wherein $R^1$ is a radical —XYZ—$R^{11}$, where Ar, —XYZ— and $R^{11}$ are as defined in the rows of table C.

Table 115: Compounds of the formula Ic.25, their stereoisomers, their tautomers and the agriculturally or veterinarily acceptable salts, wherein $R^6$ is methyl, $R^1$ is a radical —XYZ—$R^{11}$, where Ar, —XYZ— and $R^{11}$ are as defined in the rows of table C.

Table 116: Compounds of the formula Ic.26, their stereoisomers, their tautomers and the agriculturally or veterinarily acceptable salts, wherein $R^6$ is methyl, $R^1$ is a radical —XYZ—$R^{11}$, where Ar, —XYZ— and $R^{11}$ are as defined in the rows of table C.

Table 117: Compounds of the formula Ic.27, their stereoisomers, their tautomers and the agriculturally or veterinarily acceptable salts, wherein $R^6$ is methyl, $R^1$ is a radical —XYZ—$R^{11}$, where Ar, —XYZ— and $R^{11}$ are as defined in the rows of table C.

Table 118: Compounds of the formula Ic.28, their stereoisomers, their tautomers and the agriculturally or veterinarily acceptable salts, wherein $R^6$ is methyl, $R^1$ is a radical —XYZ—$R^{11}$, where Ar, —XYZ— and $R^{11}$ are as defined in the rows of table C.

Table 119: Compounds of the formula Ic.29, their stereoisomers, their tautomers and the agriculturally or veterinarily acceptable salts, wherein $R^6$ is methyl, $R^1$ is a radical —XYZ—$R^{11}$, where Ar, —XYZ— and $R^{11}$ are as defined in the rows of table C.

Table 120: Compounds of the formula Ic.30, their stereoisomers, their tautomers and the agriculturally or veterinarily acceptable salts, wherein $R^6$ is methyl, $R^1$ is a radical —XYZ—$R^{11}$, where Ar, —XYZ— and $R^{11}$ are as defined in the rows of table C.

Table 121: Compounds of the formula Ic.31, their stereoisomers, their tautomers and the agriculturally or veterinarily acceptable salts, wherein $R^6$ is methyl, $Q^2$ is hydrogen, $R^1$ is a radical —XYZ—$R^{11}$, where Ar, —XYZ— and $R^{11}$ are as defined in the rows of table C.

Table 122: Compounds of the formula Ic.32, their stereoisomers, their tautomers and the agriculturally or veterinarily acceptable salts, wherein $R^6$ is methyl, $Q^2$ is hydrogen, $R^1$ is a radical —XYZ—$R^{11}$, where Ar, —XYZ— and $R^{11}$ are as defined in the rows of table C.

Table 123: Compounds of the formula Ic.33, their stereoisomers, their tautomers and the agriculturally or veterinarily acceptable salts, wherein $R^6$ is methyl, $Q^2$ is hydrogen, $R^1$ is a radical —XYZ—$R^{11}$, where Ar, —XYZ— and $R^{11}$ are as defined in the rows of table C.

Table 124: Compounds of the formula Ic.34, their stereoisomers, their tautomers and the agriculturally or veterinarily acceptable salts, wherein $R^6$ is methyl, $Q^2$ is hydrogen, $R^1$ is a radical —XYZ—$R^{11}$, where Ar, —XYZ— and $R^{11}$ are as defined in the rows of table C.

Table 125: Compounds of the formula Ic.31, their stereoisomers, their tautomers and the agriculturally or veterinarily acceptable salts, wherein $R^6$ is methyl, $Q^2$ is methyl, $R^1$ is a radical —XYZ—$R^{11}$, where Ar, —XYZ— and $R^{11}$ are as defined in the rows of table C.

Table 126: Compounds of the formula Ic.32, their stereoisomers, their tautomers and the agriculturally or veterinarily acceptable salts, wherein $R^6$ is methyl, $Q^2$ is methyl, $R^1$ is a radical —XYZ—$R^{11}$, where Ar, —XYZ— and $R^{11}$ are as defined in the rows of table C.

Table 127: Compounds of the formula Ic.33, their stereoisomers, their tautomers and the agriculturally or veterinarily acceptable salts, wherein $R^6$ is methyl, $Q^2$ is methyl, $R^1$ is a radical —XYZ—$R^{11}$, where Ar, —XYZ— and $R^{11}$ are as defined in the rows of table C.

Table 128: Compounds of the formula Ic.34, their stereoisomers, their tautomers and the agriculturally or veterinarily acceptable salts, wherein $R^6$ is methyl, $Q^2$ is methyl, $R^1$ is a radical —XYZ—$R^{11}$, where Ar, —XYZ— and $R^{11}$ are as defined in the rows of table C.

Table 129: Compounds of the formula Ic.35, their stereoisomers, their tautomers and the agriculturally or veterinarily acceptable salts, wherein $R^1$ is a radical —XYZ—$R^{11}$, where Ar, —XYZ— and $R^{11}$ are as defined in the rows of table C.

Table 130: Compounds of the formula Ic.36, their stereoisomers, their tautomers and the agriculturally or veterinarily acceptable salts, wherein $R^1$ is a radical —XYZ—$R^{11}$, where Ar, —XYZ— and $R^{11}$ are as defined in the rows of table C.

Table 131: Compounds of the formula Ic.37, their stereoisomers, their tautomers and the agriculturally or veterinarily acceptable salts, wherein $R^1$ is a radical —XYZ—$R^{11}$, where Ar, —XYZ— and $R^{11}$ are as defined in the rows of table C.

Table 132: Compounds of the formula Ic.38, their stereoisomers, their tautomers and the agriculturally or veterinarily acceptable salts, wherein $R^1$ is a radical —XYZ—$R^{11}$, where Ar, —XYZ— and $R^{11}$ are as defined in the rows of table C.

Table 133: Compounds of the formula Ic.39, their stereoisomers, their tautomers and the agriculturally or veterinarily acceptable salts, wherein $R^1$ is a radical —XYZ—$R^{11}$, where Ar, —XYZ— and $R^{11}$ are as defined in the rows of table C.

Table 134: Compounds of the formula Ic.40, their stereoisomers, their tautomers and the agriculturally or veterinarily acceptable salts, wherein $R^1$ is a radical —XYZ—$R^{11}$, where Ar, —XYZ— and $R^{11}$ are as defined in the rows of table C.

Table 135: Compounds of the formula Ic.41, their stereoisomers, their tautomers and the agriculturally or veterinarily acceptable salts, wherein $R^1$ is a radical —XYZ—$R^{11}$, where Ar, —XYZ— and $R^{11}$ are as defined in the rows of table C.

Table 136: Compounds of the formula Ic.42, their stereoisomers, their tautomers and the agriculturally or veterinarily acceptable salts, wherein $R^1$ is a radical —XYZ—$R^{11}$, where Ar, —XYZ— and $R^{11}$ are as defined in the rows of table C.

Table 137: Compounds of the formula Ic.43, their stereoisomers, their tautomers and the agriculturally or veterinarily acceptable salts, wherein $R^1$ is a radical —XYZ—$R^{11}$, where Ar, —XYZ— and $R^{11}$ are as defined in the rows of table C.

Table 138: Compounds of the formula Ic.44, their stereoisomers, their tautomers and the agriculturally or veterinarily acceptable salts, wherein $R^1$ is a radical —XYZ—$R^{11}$, where Ar, —XYZ— and $R^{11}$ are as defined in the rows of table C.

Table 139: Compounds of the formula Ic.45, their stereoisomers, their tautomers and the agriculturally or veterinarily acceptable salts, wherein $R^6$ is methyl, $R^1$ is a radical —XYZ—$R^{11}$, where Ar, —XYZ— and $R^{11}$ are as defined in the rows of table C.

Table 140: Compounds of the formula Ic.46, their stereoisomers, their tautomers and the agriculturally or veterinarily acceptable salts, wherein $R^6$ is methyl, $R^1$ is a radical —XYZ—$R^{11}$, where Ar, —XYZ— and $R^{11}$ are as defined in the rows of table C.

Table 141: Compounds of the formula Ic.47, their stereoisomers, their tautomers and the agriculturally or veterinarily acceptable salts, wherein $R^6$ is methyl, $R^1$ is a radical —XYZ—$R^{11}$, where Ar, —XYZ— and $R^{11}$ are as defined in the rows of table C.

Table 142: Compounds of the formula Ic.48, their stereoisomers, their tautomers and the agriculturally or veterinarily acceptable salts, wherein $R^6$ is methyl, $R^1$ is a radical —XYZ—$R^{11}$, where Ar, —XYZ— and $R^{11}$ are as defined in the rows of table C.

Table 143: Compounds of the formula Ic.49, their stereoisomers, their tautomers and the agriculturally or veterinarily acceptable salts, wherein $R^6$ is methyl, $R^1$ is a radical —XYZ—$R^{11}$, where Ar, —XYZ— and $R^{11}$ are as defined in the rows of table C.

Table 144: Compounds of the formula Ic.50, their stereoisomers, their tautomers and the agriculturally or veterinarily acceptable salts, wherein $R^6$ is methyl, $R^1$ is a radical —XYZ—$R^{11}$, where Ar, —XYZ— and $R^{11}$ are as defined in the rows of table C.

Table 145: Compounds of the formula Ic.51, their stereoisomers, their tautomers and the agriculturally or veterinarily acceptable salts, wherein $R^6$ is methyl, $Q^2$ is hydrogen, $R^1$ is a radical —XYZ—$R^{11}$, where Ar, —XYZ— and $R^{11}$ are as defined in the rows of table C.

Table 146: Compounds of the formula Ic.52, their stereoisomers, their tautomers and the agriculturally or veterinarily acceptable salts, wherein $R^6$ is methyl, $Q^2$ is hydrogen, $R^1$ is a radical —XYZ—$R^{11}$, where Ar, —XYZ— and $R^{11}$ are as defined in the rows of table C.

Table 147: Compounds of the formula Ic.53, their stereoisomers, their tautomers and the agriculturally or veterinarily acceptable salts, wherein $R^6$ is methyl, $Q^2$ is hydrogen, $R^1$ is a radical —XYZ—$R^{11}$, where Ar, —XYZ— and $R^{11}$ are as defined in the rows of table C.

Table 148: Compounds of the formula Ic.54, their stereoisomers, their tautomers and the agriculturally or veterinarily acceptable salts, wherein $R^6$ is methyl, $Q^2$ is hydrogen, $R^1$ is a radical —XYZ—$R^{11}$, where Ar, —XYZ— and $R^{11}$ are as defined in the rows of table C.

Table 149: Compounds of the formula Ic.51, their stereoisomers, their tautomers and the agriculturally or veterinarily acceptable salts, wherein $R^6$ is methyl, $Q^2$ is methyl, $R^1$ is a radical —XYZ—$R^{11}$, where Ar, —XYZ— and $R^{11}$ are as defined in the rows of table C.

Table 150: Compounds of the formula Ic.52, their stereoisomers, their tautomers and the agriculturally or veterinarily acceptable salts, wherein $R^6$ is methyl, $Q^2$ is methyl, $R^1$ is a radical —XYZ—$R^{11}$, where Ar, —XYZ— and $R^{11}$ are as defined in the rows of table C.

Table 151: Compounds of the formula Ic.53, their stereoisomers, their tautomers and the agriculturally or veterinarily acceptable salts, wherein $R^6$ is methyl, $Q^2$ is methyl, $R^1$ is a radical —XYZ—$R^{11}$, where Ar, —XYZ— and $R^{11}$ are as defined in the rows of table C.

Table 152: Compounds of the formula Ic.54, their stereoisomers, their tautomers and the agriculturally or veterinarily acceptable salts, wherein $R^6$ is methyl, $Q^2$ is methyl, $R^1$ is a radical —XYZ—$R^{11}$, where Ar, —XYZ— and $R^{11}$ are as defined in the rows of table C.

Table 153: Compounds of the formula Ic.55, their stereoisomers, their tautomers and the agriculturally or veterinarily acceptable salts, wherein $R^6$ is methyl, $R^1$ is a radical —XYZ—$R^{11}$, where Ar, —XYZ— and $R^{11}$ are as defined in the rows of table C.

Table 154: Compounds of the formula Ic.56, their stereoisomers, their tautomers and the agriculturally or veterinarily acceptable salts, wherein $R^6$ is methyl, $R^1$ is a radical —XYZ—$R^{11}$, where Ar, —XYZ— and $R^{11}$ are as defined in the rows of table C.

Table 155: Compounds of the formula Ic.57, their stereoisomers, their tautomers and the agriculturally or veterinarily acceptable salts, wherein $R^1$ is a radical —XYZ—$R^{11}$, where Ar, —XYZ— and $R^{11}$ are as defined in the rows of table C.

Table 156: Compounds of the formula Ic.58, their stereoisomers, their tautomers and the agriculturally or veterinarily acceptable salts, wherein $R^1$ is a radical —XYZ—$R^{11}$, where Ar, —XYZ— and $R^{11}$ are as defined in the rows of table C.

Table 157: Compounds of the formula Ic.59, their stereoisomers, their tautomers and the agriculturally or veterinarily acceptable salts, wherein $R^6$ is methyl, $R^1$ is a radical —XYZ—R$^{11}$, where Ar, —XYZ— and R$^{11}$ are as defined in the rows of table C.

Table 158: Compounds of the formula Ic.60, their stereoisomers, their tautomers and the agriculturally or veterinarily acceptable salts, wherein R$^1$ is a radical —XYZ—R$^{11}$, where Ar, —XYZ— and R$^{11}$ are as defined in the rows of table C.

Table 159: Compounds of the formula Ic.61, their stereoisomers, their tautomers and the agriculturally or veterinarily acceptable salts, wherein R$^1$ is a radical —XYZ—R$^{11}$, where Ar, —XYZ— and R$^{11}$ are as defined in the rows of table C.

Table 160: Compounds of the formula Ic.62, their stereoisomers, their tautomers and the agriculturally or veterinarily acceptable salts, wherein R$^6$ is methyl, R$^1$ is a radical —XYZ—R$^{11}$, where Ar, —XYZ— and R$^{11}$ are as defined in the rows of table C.

Table 161: Compounds of the formula Id.1, their stereoisomers, their tautomers and the agriculturally or veterinarily acceptable salts, wherein R$^1$ is a radical —XYZ—R$^{11}$, where Ar, —XYZ— and R$^{11}$ are as defined in the rows of table C.

Table 162: Compounds of the formula Id.2, their stereoisomers, their tautomers and the agriculturally or veterinarily acceptable salts, wherein R$^1$ is a radical —XYZ—R$^{11}$, where Ar, —XYZ— and R$^{11}$ are as defined in the rows of table C.

Table 163: Compounds of the formula Id.3, their stereoisomers, their tautomers and the agriculturally or veterinarily acceptable salts, wherein R$^1$ is a radical —XYZ—R$^{11}$, where Ar, —XYZ— and R$^{11}$ are as defined in the rows of table C.

Table 164: Compounds of the formula Id.4, their stereoisomers, their tautomers and the agriculturally or veterinarily acceptable salts, wherein R$^6$ is methyl, R$^1$ is a radical —XYZ—R$^{11}$, where Ar, —XYZ— and R$^{11}$ are as defined in the rows of table C.

TABLE C

|    | Ar   | -X-Y-Z- | R$^{11}$     |
|----|------|---------|--------------|
| 1. | Ar-1 | XYZ-a   | R$^{11}$-1   |
| 2. | Ar-1 | XYZ-a   | R$^{11}$-2   |
| 3. | Ar-1 | XYZ-a   | R$^{11}$-3   |
| 4. | Ar-1 | XYZ-a   | R$^{11}$-4   |
| 5. | Ar-1 | XYZ-a   | R$^{11}$-5   |
| 6. | Ar-1 | XYZ-a   | R$^{11}$-6   |
| 7. | Ar-1 | XYZ-a   | R$^{11}$-7   |
| 8. | Ar-1 | XYZ-a   | R$^{11}$-8   |
| 9. | Ar-1 | XYZ-a   | R$^{11}$-9   |
| 10. | Ar-1 | XYZ-a  | R$^{11}$-10  |
| 11. | Ar-1 | XYZ-a  | R$^{11}$-11  |
| 12. | Ar-1 | XYZ-a  | R$^{11}$-12  |
| 13. | Ar-1 | XYZ-a  | R$^{11}$-13  |
| 14. | Ar-1 | XYZ-a  | R$^{11}$-14  |
| 15. | Ar-1 | XYZ-a  | R$^{11}$-15  |
| 16. | Ar-1 | XYZ-a  | R$^{11}$-16  |
| 17. | Ar-1 | XYZ-a  | R$^{11}$-17  |
| 18. | Ar-1 | XYZ-a  | R$^{11}$-18  |
| 19. | Ar-1 | XYZ-a  | R$^{11}$-19  |
| 20. | Ar-1 | XYZ-a  | R$^{11}$-20  |
| 21. | Ar-1 | XYZ-a  | R$^{11}$-21  |
| 22. | Ar-1 | XYZ-b  | R$^{11}$-1   |
| 23. | Ar-1 | XYZ-b  | R$^{11}$-2   |
| 24. | Ar-1 | XYZ-b  | R$^{11}$-3   |
| 25. | Ar-1 | XYZ-b  | R$^{11}$-4   |
| 26. | Ar-1 | XYZ-b  | R$^{11}$-5   |
| 27. | Ar-1 | XYZ-b  | R$^{11}$-6   |
| 28. | Ar-1 | XYZ-b  | R$^{11}$-7   |
| 29. | Ar-1 | XYZ-b  | R$^{11}$-8   |
| 30. | Ar-1 | XYZ-b  | R$^{11}$-9   |
| 31. | Ar-1 | XYZ-b  | R$^{11}$-10  |
| 32. | Ar-1 | XYZ-b  | R$^{11}$-11  |
| 33. | Ar-1 | XYZ-b  | R$^{11}$-12  |
| 34. | Ar-1 | XYZ-b  | R$^{11}$-13  |
| 35. | Ar-1 | XYZ-b  | R$^{11}$-14  |
| 36. | Ar-1 | XYZ-b  | R$^{11}$-15  |
| 37. | Ar-1 | XYZ-b  | R$^{11}$-16  |
| 38. | Ar-1 | XYZ-b  | R$^{11}$-17  |
| 39. | Ar-1 | XYZ-b  | R$^{11}$-18  |
| 40. | Ar-1 | XYZ-b  | R$^{11}$-19  |
| 41. | Ar-1 | XYZ-b  | R$^{11}$-20  |
| 42. | Ar-1 | XYZ-b  | R$^{11}$-21  |
| 43. | Ar-1 | XYZ-c  | R$^{11}$-1   |
| 44. | Ar-1 | XYZ-c  | R$^{11}$-2   |
| 45. | Ar-1 | XYZ-c  | R$^{11}$-3   |
| 46. | Ar-1 | XYZ-c  | R$^{11}$-4   |
| 47. | Ar-1 | XYZ-c  | R$^{11}$-5   |
| 48. | Ar-1 | XYZ-c  | R$^{11}$-6   |
| 49. | Ar-1 | XYZ-c  | R$^{11}$-7   |
| 50. | Ar-1 | XYZ-c  | R$^{11}$-8   |
| 51. | Ar-1 | XYZ-c  | R$^{11}$-9   |
| 52. | Ar-1 | XYZ-c  | R$^{11}$-10  |
| 53. | Ar-1 | XYZ-c  | R$^{11}$-11  |
| 54. | Ar-1 | XYZ-c  | R$^{11}$-12  |
| 55. | Ar-1 | XYZ-c  | R$^{11}$-13  |
| 56. | Ar-1 | XYZ-c  | R$^{11}$-14  |
| 57. | Ar-1 | XYZ-c  | R$^{11}$-15  |
| 58. | Ar-1 | XYZ-c  | R$^{11}$-16  |
| 59. | Ar-1 | XYZ-c  | R$^{11}$-17  |
| 60. | Ar-1 | XYZ-c  | R$^{11}$-18  |
| 61. | Ar-1 | XYZ-c  | R$^{11}$-19  |
| 62. | Ar-1 | XYZ-c  | R$^{11}$-20  |
| 63. | Ar-1 | XYZ-c  | R$^{11}$-21  |
| 64. | Ar-1 | XYZ-d  | R$^{11}$-1   |
| 65. | Ar-1 | XYZ-d  | R$^{11}$-2   |
| 66. | Ar-1 | XYZ-d  | R$^{11}$-3   |
| 67. | Ar-1 | XYZ-d  | R$^{11}$-4   |
| 68. | Ar-1 | XYZ-d  | R$^{11}$-5   |
| 69. | Ar-1 | XYZ-d  | R$^{11}$-6   |
| 70. | Ar-1 | XYZ-d  | R$^{11}$-7   |
| 71. | Ar-1 | XYZ-d  | R$^{11}$-8   |
| 72. | Ar-1 | XYZ-d  | R$^{11}$-9   |
| 73. | Ar-1 | XYZ-d  | R$^{11}$-10  |
| 74. | Ar-1 | XYZ-d  | R$^{11}$-11  |
| 75. | Ar-1 | XYZ-d  | R$^{11}$-12  |
| 76. | Ar-1 | XYZ-d  | R$^{11}$-13  |
| 77. | Ar-1 | XYZ-d  | R$^{11}$-14  |
| 78. | Ar-1 | XYZ-d  | R$^{11}$-15  |
| 79. | Ar-1 | XYZ-d  | R$^{11}$-16  |
| 80. | Ar-1 | XYZ-d  | R$^{11}$-17  |
| 81. | Ar-1 | XYZ-d  | R$^{11}$-18  |
| 82. | Ar-1 | XYZ-d  | R$^{11}$-19  |
| 83. | Ar-1 | XYZ-d  | R$^{11}$-20  |
| 84. | Ar-1 | XYZ-d  | R$^{11}$-21  |
| 85. | Ar-1 | XYZ-e  | R$^{11}$-1   |
| 86. | Ar-1 | XYZ-e  | R$^{11}$-2   |
| 87. | Ar-1 | XYZ-e  | R$^{11}$-3   |
| 88. | Ar-1 | XYZ-e  | R$^{11}$-4   |
| 89. | Ar-1 | XYZ-e  | R$^{11}$-5   |
| 90. | Ar-1 | XYZ-e  | R$^{11}$-6   |
| 91. | Ar-1 | XYZ-e  | R$^{11}$-7   |
| 92. | Ar-1 | XYZ-e  | R$^{11}$-8   |
| 93. | Ar-1 | XYZ-e  | R$^{11}$-9   |
| 94. | Ar-1 | XYZ-e  | R$^{11}$-10  |
| 95. | Ar-1 | XYZ-e  | R$^{11}$-11  |
| 96. | Ar-1 | XYZ-e  | R$^{11}$-12  |
| 97. | Ar-1 | XYZ-e  | R$^{11}$-13  |
| 98. | Ar-1 | XYZ-e  | R$^{11}$-14  |
| 99. | Ar-1 | XYZ-e  | R$^{11}$-15  |
| 100. | Ar-1 | XYZ-e | R$^{11}$-16  |
| 101. | Ar-1 | XYZ-e | R$^{11}$-17  |
| 102. | Ar-1 | XYZ-e | R$^{11}$-18  |
| 103. | Ar-1 | XYZ-e | R$^{11}$-19  |
| 104. | Ar-1 | XYZ-e | R$^{11}$-20  |
| 105. | Ar-1 | XYZ-e | R$^{11}$-21  |
| 106. | Ar-1 | XYZ-f | R$^{11}$-1   |
| 107. | Ar-1 | XYZ-f | R$^{11}$-2   |
| 108. | Ar-1 | XYZ-f | R$^{11}$-3   |

TABLE C-continued

|  | Ar | -X-Y-Z- | $R^{11}$ |
|---|---|---|---|
| 109. | Ar-1 | XYZ-f | $R^{11}$-4 |
| 110. | Ar-1 | XYZ-f | $R^{11}$-5 |
| 111. | Ar-1 | XYZ-f | $R^{11}$-6 |
| 112. | Ar-1 | XYZ-f | $R^{11}$-7 |
| 113. | Ar-1 | XYZ-f | $R^{11}$-8 |
| 114. | Ar-1 | XYZ-f | $R^{11}$-9 |
| 115. | Ar-1 | XYZ-f | $R^{11}$-10 |
| 116. | Ar-1 | XYZ-f | $R^{11}$-11 |
| 117. | Ar-1 | XYZ-f | $R^{11}$-12 |
| 118. | Ar-1 | XYZ-f | $R^{11}$-13 |
| 119. | Ar-1 | XYZ-f | $R^{11}$-14 |
| 120. | Ar-1 | XYZ-f | $R^{11}$-15 |
| 121. | Ar-1 | XYZ-f | $R^{11}$-16 |
| 122. | Ar-1 | XYZ-f | $R^{11}$-17 |
| 123. | Ar-1 | XYZ-f | $R^{11}$-18 |
| 124. | Ar-1 | XYZ-f | $R^{11}$-19 |
| 125. | Ar-1 | XYZ-f | $R^{11}$-20 |
| 126. | Ar-1 | XYZ-f | $R^{11}$-21 |
| 127. | Ar-1 | XYZ-g | $R^{11}$-1 |
| 128. | Ar-1 | XYZ-g | $R^{11}$-2 |
| 129. | Ar-1 | XYZ-g | $R^{11}$-3 |
| 130. | Ar-1 | XYZ-g | $R^{11}$-4 |
| 131. | Ar-1 | XYZ-g | $R^{11}$-5 |
| 132. | Ar-1 | XYZ-g | $R^{11}$-6 |
| 133. | Ar-1 | XYZ-g | $R^{11}$-7 |
| 134. | Ar-1 | XYZ-g | $R^{11}$-8 |
| 135. | Ar-1 | XYZ-g | $R^{11}$-9 |
| 136. | Ar-1 | XYZ-g | $R^{11}$-10 |
| 137. | Ar-1 | XYZ-g | $R^{11}$-11 |
| 138. | Ar-1 | XYZ-g | $R^{11}$-12 |
| 139. | Ar-1 | XYZ-g | $R^{11}$-13 |
| 140. | Ar-1 | XYZ-g | $R^{11}$-14 |
| 141. | Ar-1 | XYZ-g | $R^{11}$-15 |
| 142. | Ar-1 | XYZ-g | $R^{11}$-16 |
| 143. | Ar-1 | XYZ-g | $R^{11}$-17 |
| 144. | Ar-1 | XYZ-g | $R^{11}$-18 |
| 145. | Ar-1 | XYZ-g | $R^{11}$-19 |
| 146. | Ar-1 | XYZ-g | $R^{11}$-20 |
| 147. | Ar-1 | XYZ-g | $R^{11}$-21 |
| 148. | Ar-1 | XYZ-h | $R^{11}$-1 |
| 149. | Ar-1 | XYZ-h | $R^{11}$-2 |
| 150. | Ar-1 | XYZ-h | $R^{11}$-3 |
| 151. | Ar-1 | XYZ-h | $R^{11}$-4 |
| 152. | Ar-1 | XYZ-h | $R^{11}$-5 |
| 153. | Ar-1 | XYZ-h | $R^{11}$-6 |
| 154. | Ar-1 | XYZ-h | $R^{11}$-7 |
| 155. | Ar-1 | XYZ-h | $R^{11}$-8 |
| 156. | Ar-1 | XYZ-h | $R^{11}$-9 |
| 157. | Ar-1 | XYZ-h | $R^{11}$-10 |
| 158. | Ar-1 | XYZ-h | $R^{11}$-11 |
| 159. | Ar-1 | XYZ-h | $R^{11}$-12 |
| 160. | Ar-1 | XYZ-h | $R^{11}$-13 |
| 161. | Ar-1 | XYZ-h | $R^{11}$-14 |
| 162. | Ar-1 | XYZ-h | $R^{11}$-15 |
| 163. | Ar-1 | XYZ-h | $R^{11}$-16 |
| 164. | Ar-1 | XYZ-h | $R^{11}$-17 |
| 165. | Ar-1 | XYZ-h | $R^{11}$-18 |
| 166. | Ar-1 | XYZ-h | $R^{11}$-19 |
| 167. | Ar-1 | XYZ-h | $R^{11}$-20 |
| 168. | Ar-1 | XYZ-h | $R^{11}$-21 |
| 169. | Ar-1 | XYZ-i | $R^{11}$-1 |
| 170. | Ar-1 | XYZ-i | $R^{11}$-2 |
| 171. | Ar-1 | XYZ-i | $R^{11}$-3 |
| 172. | Ar-1 | XYZ-i | $R^{11}$-4 |
| 173. | Ar-1 | XYZ-i | $R^{11}$-5 |
| 174. | Ar-1 | XYZ-i | $R^{11}$-6 |
| 175. | Ar-1 | XYZ-i | $R^{11}$-7 |
| 176. | Ar-1 | XYZ-i | $R^{11}$-8 |
| 177. | Ar-1 | XYZ-i | $R^{11}$-9 |
| 178. | Ar-1 | XYZ-i | $R^{11}$-10 |
| 179. | Ar-1 | XYZ-i | $R^{11}$-11 |
| 180. | Ar-1 | XYZ-i | $R^{11}$-12 |
| 181. | Ar-1 | XYZ-i | $R^{11}$-13 |
| 182. | Ar-1 | XYZ-i | $R^{11}$-14 |
| 183. | Ar-1 | XYZ-i | $R^{11}$-15 |
| 184. | Ar-1 | XYZ-i | $R^{11}$-16 |
| 185. | Ar-1 | XYZ-i | $R^{11}$-17 |
| 186. | Ar-1 | XYZ-i | $R^{11}$-18 |
| 187. | Ar-1 | XYZ-i | $R^{11}$-19 |
| 188. | Ar-1 | XYZ-i | $R^{11}$-20 |
| 189. | Ar-1 | XYZ-i | $R^{11}$-21 |
| 190. | Ar-1 | XYZ-k | $R^{11}$-1 |
| 191. | Ar-1 | XYZ-k | $R^{11}$-2 |
| 192. | Ar-1 | XYZ-k | $R^{11}$-3 |
| 193. | Ar-1 | XYZ-k | $R^{11}$-4 |
| 194. | Ar-1 | XYZ-k | $R^{11}$-5 |
| 195. | Ar-1 | XYZ-k | $R^{11}$-6 |
| 196. | Ar-1 | XYZ-k | $R^{11}$-7 |
| 197. | Ar-1 | XYZ-k | $R^{11}$-8 |
| 198. | Ar-1 | XYZ-k | $R^{11}$-9 |
| 199. | Ar-1 | XYZ-k | $R^{11}$-10 |
| 200. | Ar-1 | XYZ-k | $R^{11}$-11 |
| 201. | Ar-1 | XYZ-k | $R^{11}$-12 |
| 202. | Ar-1 | XYZ-k | $R^{11}$-13 |
| 203. | Ar-1 | XYZ-k | $R^{11}$-14 |
| 204. | Ar-1 | XYZ-k | $R^{11}$-15 |
| 205. | Ar-1 | XYZ-k | $R^{11}$-16 |
| 206. | Ar-1 | XYZ-k | $R^{11}$-17 |
| 207. | Ar-1 | XYZ-k | $R^{11}$-18 |
| 208. | Ar-1 | XYZ-k | $R^{11}$-19 |
| 209. | Ar-1 | XYZ-k | $R^{11}$-20 |
| 210. | Ar-1 | XYZ-k | $R^{11}$-21 |
| 211. | Ar-1 | XYZ-l | $R^{11}$-1 |
| 212. | Ar-1 | XYZ-l | $R^{11}$-2 |
| 213. | Ar-1 | XYZ-l | $R^{11}$-3 |
| 214. | Ar-1 | XYZ-l | $R^{11}$-4 |
| 215. | Ar-1 | XYZ-l | $R^{11}$-5 |
| 216. | Ar-1 | XYZ-l | $R^{11}$-6 |
| 217. | Ar-1 | XYZ-l | $R^{11}$-7 |
| 218. | Ar-1 | XYZ-l | $R^{11}$-8 |
| 219. | Ar-1 | XYZ-l | $R^{11}$-9 |
| 220. | Ar-1 | XYZ-l | $R^{11}$-10 |
| 221. | Ar-1 | XYZ-l | $R^{11}$-11 |
| 222. | Ar-1 | XYZ-l | $R^{11}$-12 |
| 223. | Ar-1 | XYZ-l | $R^{11}$-13 |
| 224. | Ar-1 | XYZ-l | $R^{11}$-14 |
| 225. | Ar-1 | XYZ-l | $R^{11}$-15 |
| 226. | Ar-1 | XYZ-l | $R^{11}$-16 |
| 227. | Ar-1 | XYZ-l | $R^{11}$-17 |
| 228. | Ar-1 | XYZ-l | $R^{11}$-18 |
| 229. | Ar-1 | XYZ-l | $R^{11}$-19 |
| 230. | Ar-1 | XYZ-l | $R^{11}$-20 |
| 231. | Ar-1 | XYZ-l | $R^{11}$-21 |
| 232. | Ar-1 | XYZ-m | $R^{11}$-1 |
| 233. | Ar-1 | XYZ-m | $R^{11}$-2 |
| 234. | Ar-1 | XYZ-m | $R^{11}$-3 |
| 235. | Ar-1 | XYZ-m | $R^{11}$-4 |
| 236. | Ar-1 | XYZ-m | $R^{11}$-5 |
| 237. | Ar-1 | XYZ-m | $R^{11}$-6 |
| 238. | Ar-1 | XYZ-m | $R^{11}$-7 |
| 239. | Ar-1 | XYZ-m | $R^{11}$-8 |
| 240. | Ar-1 | XYZ-m | $R^{11}$-9 |
| 241. | Ar-1 | XYZ-m | $R^{11}$-10 |
| 242. | Ar-1 | XYZ-m | $R^{11}$-11 |
| 243. | Ar-1 | XYZ-m | $R^{11}$-12 |
| 244. | Ar-1 | XYZ-m | $R^{11}$-13 |
| 245. | Ar-1 | XYZ-m | $R^{11}$-14 |
| 246. | Ar-1 | XYZ-m | $R^{11}$-15 |
| 247. | Ar-1 | XYZ-m | $R^{11}$-16 |
| 248. | Ar-1 | XYZ-m | $R^{11}$-17 |
| 249. | Ar-1 | XYZ-m | $R^{11}$-18 |
| 250. | Ar-1 | XYZ-m | $R^{11}$-19 |
| 251. | Ar-1 | XYZ-m | $R^{11}$-20 |
| 252. | Ar-1 | XYZ-m | $R^{11}$-21 |
| 253. | Ar-1 | XYZ-n | $R^{11}$-1 |
| 254. | Ar-1 | XYZ-n | $R^{11}$-2 |
| 255. | Ar-1 | XYZ-n | $R^{11}$-3 |
| 256. | Ar-1 | XYZ-n | $R^{11}$-4 |
| 257. | Ar-1 | XYZ-n | $R^{11}$-5 |
| 258. | Ar-1 | XYZ-n | $R^{11}$-6 |
| 259. | Ar-1 | XYZ-n | $R^{11}$-7 |
| 260. | Ar-1 | XYZ-n | $R^{11}$-8 |
| 261. | Ar-1 | XYZ-n | $R^{11}$-9 |
| 262. | Ar-1 | XYZ-n | $R^{11}$-10 |
| 263. | Ar-1 | XYZ-n | $R^{11}$-11 |
| 264. | Ar-1 | XYZ-n | $R^{11}$-12 |

TABLE C-continued

| | Ar | -X-Y-Z- | $R^{11}$ |
|---|---|---|---|
| 265. | Ar-1 | XYZ-n | $R^{11}$-13 |
| 266. | Ar-1 | XYZ-n | $R^{11}$-14 |
| 267. | Ar-1 | XYZ-n | $R^{11}$-15 |
| 268. | Ar-1 | XYZ-n | $R^{11}$-16 |
| 269. | Ar-1 | XYZ-n | $R^{11}$-17 |
| 270. | Ar-1 | XYZ-n | $R^{11}$-18 |
| 271. | Ar-1 | XYZ-n | $R^{11}$-19 |
| 272. | Ar-1 | XYZ-n | $R^{11}$-20 |
| 273. | Ar-1 | XYZ-n | $R^{11}$-21 |
| 274. | Ar-1 | XYZ-o | $R^{11}$-1 |
| 275. | Ar-1 | XYZ-o | $R^{11}$-2 |
| 276. | Ar-1 | XYZ-o | $R^{11}$-3 |
| 277. | Ar-1 | XYZ-o | $R^{11}$-4 |
| 278. | Ar-1 | XYZ-o | $R^{11}$-5 |
| 279. | Ar-1 | XYZ-o | $R^{11}$-6 |
| 280. | Ar-1 | XYZ-o | $R^{11}$-7 |
| 281. | Ar-1 | XYZ-o | $R^{11}$-8 |
| 282. | Ar-1 | XYZ-o | $R^{11}$-9 |
| 283. | Ar-1 | XYZ-o | $R^{11}$-10 |
| 284. | Ar-1 | XYZ-o | $R^{11}$-11 |
| 285. | Ar-1 | XYZ-o | $R^{11}$-12 |
| 286. | Ar-1 | XYZ-o | $R^{11}$-13 |
| 287. | Ar-1 | XYZ-o | $R^{11}$-14 |
| 288. | Ar-1 | XYZ-o | $R^{11}$-15 |
| 289. | Ar-1 | XYZ-o | $R^{11}$-16 |
| 290. | Ar-1 | XYZ-o | $R^{11}$-17 |
| 291. | Ar-1 | XYZ-o | $R^{11}$-18 |
| 292. | Ar-1 | XYZ-o | $R^{11}$-19 |
| 293. | Ar-1 | XYZ-o | $R^{11}$-20 |
| 294. | Ar-1 | XYZ-o | $R^{11}$-21 |
| 295. | Ar-1 | XYZ-p | $R^{11}$-1 |
| 296. | Ar-1 | XYZ-p | $R^{11}$-2 |
| 297. | Ar-1 | XYZ-p | $R^{11}$-3 |
| 298. | Ar-1 | XYZ-p | $R^{11}$-4 |
| 299. | Ar-1 | XYZ-p | $R^{11}$-5 |
| 300. | Ar-1 | XYZ-p | $R^{11}$-6 |
| 301. | Ar-1 | XYZ-p | $R^{11}$-7 |
| 302. | Ar-1 | XYZ-p | $R^{11}$-8 |
| 303. | Ar-1 | XYZ-p | $R^{11}$-9 |
| 304. | Ar-1 | XYZ-p | $R^{11}$-10 |
| 305. | Ar-1 | XYZ-p | $R^{11}$-11 |
| 306. | Ar-1 | XYZ-p | $R^{11}$-12 |
| 307. | Ar-1 | XYZ-p | $R^{11}$-13 |
| 308. | Ar-1 | XYZ-p | $R^{11}$-14 |
| 309. | Ar-1 | XYZ-p | $R^{11}$-15 |
| 310. | Ar-1 | XYZ-p | $R^{11}$-16 |
| 311. | Ar-1 | XYZ-p | $R^{11}$-17 |
| 312. | Ar-1 | XYZ-p | $R^{11}$-18 |
| 313. | Ar-1 | XYZ-p | $R^{11}$-19 |
| 314. | Ar-1 | XYZ-p | $R^{11}$-20 |
| 315. | Ar-1 | XYZ-p | $R^{11}$-21 |
| 316. | Ar-1 | XYZ-q | $R^{11}$-1 |
| 317. | Ar-1 | XYZ-q | $R^{11}$-2 |
| 318. | Ar-1 | XYZ-q | $R^{11}$-3 |
| 319. | Ar-1 | XYZ-q | $R^{11}$-4 |
| 320. | Ar-1 | XYZ-q | $R^{11}$-5 |
| 321. | Ar-1 | XYZ-q | $R^{11}$-6 |
| 322. | Ar-1 | XYZ-q | $R^{11}$-7 |
| 323. | Ar-1 | XYZ-q | $R^{11}$-8 |
| 324. | Ar-1 | XYZ-q | $R^{11}$-9 |
| 325. | Ar-1 | XYZ-q | $R^{11}$-10 |
| 326. | Ar-1 | XYZ-q | $R^{11}$-11 |
| 327. | Ar-1 | XYZ-q | $R^{11}$-12 |
| 328. | Ar-1 | XYZ-q | $R^{11}$-13 |
| 329. | Ar-1 | XYZ-q | $R^{11}$-14 |
| 330. | Ar-1 | XYZ-q | $R^{11}$-15 |
| 331. | Ar-1 | XYZ-q | $R^{11}$-16 |
| 332. | Ar-1 | XYZ-q | $R^{11}$-17 |
| 333. | Ar-1 | XYZ-q | $R^{11}$-18 |
| 334. | Ar-1 | XYZ-q | $R^{11}$-19 |
| 335. | Ar-1 | XYZ-q | $R^{11}$-20 |
| 336. | Ar-1 | XYZ-q | $R^{11}$-21 |
| 337. | Ar-1 | XYZ-r | $R^{11}$-1 |
| 338. | Ar-1 | XYZ-r | $R^{11}$-2 |
| 339. | Ar-1 | XYZ-r | $R^{11}$-3 |
| 340. | Ar-1 | XYZ-r | $R^{11}$-4 |
| 341. | Ar-1 | XYZ-r | $R^{11}$-5 |
| 342. | Ar-1 | XYZ-r | $R^{11}$-6 |
| 343. | Ar-1 | XYZ-r | $R^{11}$-7 |
| 344. | Ar-1 | XYZ-r | $R^{11}$-8 |
| 345. | Ar-1 | XYZ-r | $R^{11}$-9 |
| 346. | Ar-1 | XYZ-r | $R^{11}$-10 |
| 347. | Ar-1 | XYZ-r | $R^{11}$-11 |
| 348. | Ar-1 | XYZ-r | $R^{11}$-12 |
| 349. | Ar-1 | XYZ-r | $R^{11}$-13 |
| 350. | Ar-1 | XYZ-r | $R^{11}$-14 |
| 351. | Ar-1 | XYZ-r | $R^{11}$-15 |
| 352. | Ar-1 | XYZ-r | $R^{11}$-16 |
| 353. | Ar-1 | XYZ-r | $R^{11}$-17 |
| 354. | Ar-1 | XYZ-r | $R^{11}$-18 |
| 355. | Ar-1 | XYZ-r | $R^{11}$-19 |
| 356. | Ar-1 | XYZ-r | $R^{11}$-20 |
| 357. | Ar-1 | XYZ-r | $R^{11}$-21 |
| 358. | Ar-1 | XYZ-s | $R^{11}$-1 |
| 359. | Ar-1 | XYZ-s | $R^{11}$-2 |
| 360. | Ar-1 | XYZ-s | $R^{11}$-3 |
| 361. | Ar-1 | XYZ-s | $R^{11}$-4 |
| 362. | Ar-1 | XYZ-s | $R^{11}$-5 |
| 363. | Ar-1 | XYZ-s | $R^{11}$-6 |
| 364. | Ar-1 | XYZ-s | $R^{11}$-7 |
| 365. | Ar-1 | XYZ-s | $R^{11}$-8 |
| 366. | Ar-1 | XYZ-s | $R^{11}$-9 |
| 367. | Ar-1 | XYZ-s | $R^{11}$-10 |
| 368. | Ar-1 | XYZ-s | $R^{11}$-11 |
| 369. | Ar-1 | XYZ-s | $R^{11}$-12 |
| 370. | Ar-1 | XYZ-s | $R^{11}$-13 |
| 371. | Ar-1 | XYZ-s | $R^{11}$-14 |
| 372. | Ar-1 | XYZ-s | $R^{11}$-15 |
| 373. | Ar-1 | XYZ-s | $R^{11}$-16 |
| 374. | Ar-1 | XYZ-s | $R^{11}$-17 |
| 375. | Ar-1 | XYZ-s | $R^{11}$-18 |
| 376. | Ar-1 | XYZ-s | $R^{11}$-19 |
| 377. | Ar-1 | XYZ-s | $R^{11}$-20 |
| 378. | Ar-1 | XYZ-s | $R^{11}$-21 |
| 379. | Ar-1 | XYZ-t | $R^{11}$-1 |
| 380. | Ar-1 | XYZ-t | $R^{11}$-2 |
| 381. | Ar-1 | XYZ-t | $R^{11}$-3 |
| 382. | Ar-1 | XYZ-t | $R^{11}$-4 |
| 383. | Ar-1 | XYZ-t | $R^{11}$-5 |
| 384. | Ar-1 | XYZ-t | $R^{11}$-6 |
| 385. | Ar-1 | XYZ-t | $R^{11}$-7 |
| 386. | Ar-1 | XYZ-t | $R^{11}$-8 |
| 387. | Ar-1 | XYZ-t | $R^{11}$-9 |
| 388. | Ar-1 | XYZ-t | $R^{11}$-10 |
| 389. | Ar-1 | XYZ-t | $R^{11}$-11 |
| 390. | Ar-1 | XYZ-t | $R^{11}$-12 |
| 391. | Ar-1 | XYZ-t | $R^{11}$-13 |
| 392. | Ar-1 | XYZ-t | $R^{11}$-14 |
| 393. | Ar-1 | XYZ-t | $R^{11}$-15 |
| 394. | Ar-1 | XYZ-t | $R^{11}$-16 |
| 395. | Ar-1 | XYZ-t | $R^{11}$-17 |
| 396. | Ar-1 | XYZ-t | $R^{11}$-18 |
| 397. | Ar-1 | XYZ-t | $R^{11}$-19 |
| 398. | Ar-1 | XYZ-t | $R^{11}$-20 |
| 399. | Ar-1 | XYZ-t | $R^{11}$-21 |
| 400. | Ar-1 | XYZ-u | $R^{11}$-1 |
| 401. | Ar-1 | XYZ-u | $R^{11}$-2 |
| 402. | Ar-1 | XYZ-u | $R^{11}$-3 |
| 403. | Ar-1 | XYZ-u | $R^{11}$-4 |
| 404. | Ar-1 | XYZ-u | $R^{11}$-5 |
| 405. | Ar-1 | XYZ-u | $R^{11}$-6 |
| 406. | Ar-1 | XYZ-u | $R^{11}$-7 |
| 407. | Ar-1 | XYZ-u | $R^{11}$-8 |
| 408. | Ar-1 | XYZ-u | $R^{11}$-9 |
| 409. | Ar-1 | XYZ-u | $R^{11}$-10 |
| 410. | Ar-1 | XYZ-u | $R^{11}$-11 |
| 411. | Ar-1 | XYZ-u | $R^{11}$-12 |
| 412. | Ar-1 | XYZ-u | $R^{11}$-13 |
| 413. | Ar-1 | XYZ-u | $R^{11}$-14 |
| 414. | Ar-1 | XYZ-u | $R^{11}$-15 |
| 415. | Ar-1 | XYZ-u | $R^{11}$-16 |
| 416. | Ar-1 | XYZ-u | $R^{11}$-17 |
| 417. | Ar-1 | XYZ-u | $R^{11}$-18 |
| 418. | Ar-1 | XYZ-u | $R^{11}$-19 |
| 419. | Ar-1 | XYZ-u | $R^{11}$-20 |
| 420. | Ar-1 | XYZ-u | $R^{11}$-21 |

TABLE C-continued

| | Ar | -X-Y-Z- | $R^{11}$ |
|---|---|---|---|
| 421. | Ar-1 | XYZ-v | $R^{11}$-1 |
| 422. | Ar-1 | XYZ-v | $R^{11}$-2 |
| 423. | Ar-1 | XYZ-v | $R^{11}$-3 |
| 424. | Ar-1 | XYZ-v | $R^{11}$-4 |
| 425. | Ar-1 | XYZ-v | $R^{11}$-5 |
| 426. | Ar-1 | XYZ-v | $R^{11}$-6 |
| 427. | Ar-1 | XYZ-v | $R^{11}$-7 |
| 428. | Ar-1 | XYZ-v | $R^{11}$-8 |
| 429. | Ar-1 | XYZ-v | $R^{11}$-9 |
| 430. | Ar-1 | XYZ-v | $R^{11}$-10 |
| 431. | Ar-1 | XYZ-v | $R^{11}$-11 |
| 432. | Ar-1 | XYZ-v | $R^{11}$-12 |
| 433. | Ar-1 | XYZ-v | $R^{11}$-13 |
| 434. | Ar-1 | XYZ-v | $R^{11}$-14 |
| 435. | Ar-1 | XYZ-v | $R^{11}$-15 |
| 436. | Ar-1 | XYZ-v | $R^{11}$-16 |
| 437. | Ar-1 | XYZ-v | $R^{11}$-17 |
| 438. | Ar-1 | XYZ-v | $R^{11}$-18 |
| 439. | Ar-1 | XYZ-v | $R^{11}$-19 |
| 440. | Ar-1 | XYZ-v | $R^{11}$-20 |
| 441. | Ar-1 | XYZ-v | $R^{11}$-21 |
| 442. | Ar-1 | XYZ-w | $R^{11}$-1 |
| 443. | Ar-1 | XYZ-w | $R^{11}$-2 |
| 444. | Ar-1 | XYZ-w | $R^{11}$-3 |
| 445. | Ar-1 | XYZ-w | $R^{11}$-4 |
| 446. | Ar-1 | XYZ-w | $R^{11}$-5 |
| 447. | Ar-1 | XYZ-w | $R^{11}$-6 |
| 448. | Ar-1 | XYZ-w | $R^{11}$-7 |
| 449. | Ar-1 | XYZ-w | $R^{11}$-8 |
| 450. | Ar-1 | XYZ-w | $R^{11}$-9 |
| 451. | Ar-1 | XYZ-w | $R^{11}$-10 |
| 452. | Ar-1 | XYZ-w | $R^{11}$-11 |
| 453. | Ar-1 | XYZ-w | $R^{11}$-12 |
| 454. | Ar-1 | XYZ-w | $R^{11}$-13 |
| 455. | Ar-1 | XYZ-w | $R^{11}$-14 |
| 456. | Ar-1 | XYZ-w | $R^{11}$-15 |
| 457. | Ar-1 | XYZ-w | $R^{11}$-16 |
| 458. | Ar-1 | XYZ-w | $R^{11}$-17 |
| 459. | Ar-1 | XYZ-w | $R^{11}$-18 |
| 460. | Ar-1 | XYZ-w | $R^{11}$-19 |
| 461. | Ar-1 | XYZ-w | $R^{11}$-20 |
| 462. | Ar-1 | XYZ-w | $R^{11}$-21 |
| 463. | Ar-2 | XYZ-a | $R^{11}$-1 |
| 464. | Ar-2 | XYZ-a | $R^{11}$-2 |
| 465. | Ar-2 | XYZ-a | $R^{11}$-3 |
| 466. | Ar-2 | XYZ-a | $R^{11}$-4 |
| 467. | Ar-2 | XYZ-a | $R^{11}$-5 |
| 468. | Ar-2 | XYZ-a | $R^{11}$-6 |
| 469. | Ar-2 | XYZ-a | $R^{11}$-7 |
| 470. | Ar-2 | XYZ-a | $R^{11}$-8 |
| 471. | Ar-2 | XYZ-a | $R^{11}$-9 |
| 472. | Ar-2 | XYZ-a | $R^{11}$-10 |
| 473. | Ar-2 | XYZ-a | $R^{11}$-11 |
| 474. | Ar-2 | XYZ-a | $R^{11}$-12 |
| 475. | Ar-2 | XYZ-a | $R^{11}$-13 |
| 476. | Ar-2 | XYZ-a | $R^{11}$-14 |
| 477. | Ar-2 | XYZ-a | $R^{11}$-15 |
| 478. | Ar-2 | XYZ-a | $R^{11}$-16 |
| 479. | Ar-2 | XYZ-a | $R^{11}$-17 |
| 480. | Ar-2 | XYZ-a | $R^{11}$-18 |
| 481. | Ar-2 | XYZ-a | $R^{11}$-19 |
| 482. | Ar-2 | XYZ-a | $R^{11}$-20 |
| 483. | Ar-2 | XYZ-a | $R^{11}$-21 |
| 484. | Ar-2 | XYZ-b | $R^{11}$-1 |
| 485. | Ar-2 | XYZ-b | $R^{11}$-2 |
| 486. | Ar-2 | XYZ-b | $R^{11}$-3 |
| 487. | Ar-2 | XYZ-b | $R^{11}$-4 |
| 488. | Ar-2 | XYZ-b | $R^{11}$-5 |
| 489. | Ar-2 | XYZ-b | $R^{11}$-6 |
| 490. | Ar-2 | XYZ-b | $R^{11}$-7 |
| 491. | Ar-2 | XYZ-b | $R^{11}$-8 |
| 492. | Ar-2 | XYZ-b | $R^{11}$-9 |
| 493. | Ar-2 | XYZ-b | $R^{11}$-10 |
| 494. | Ar-2 | XYZ-b | $R^{11}$-11 |
| 495. | Ar-2 | XYZ-b | $R^{11}$-12 |
| 496. | Ar-2 | XYZ-b | $R^{11}$-13 |
| 497. | Ar-2 | XYZ-b | $R^{11}$-14 |
| 498. | Ar-2 | XYZ-b | $R^{11}$-15 |
| 499. | Ar-2 | XYZ-b | $R^{11}$-16 |
| 500. | Ar-2 | XYZ-b | $R^{11}$-17 |
| 501. | Ar-2 | XYZ-b | $R^{11}$-18 |
| 502. | Ar-2 | XYZ-b | $R^{11}$-19 |
| 503. | Ar-2 | XYZ-b | $R^{11}$-20 |
| 504. | Ar-2 | XYZ-b | $R^{11}$-21 |
| 505. | Ar-2 | XYZ-c | $R^{11}$-1 |
| 506. | Ar-2 | XYZ-c | $R^{11}$-2 |
| 507. | Ar-2 | XYZ-c | $R^{11}$-3 |
| 508. | Ar-2 | XYZ-c | $R^{11}$-4 |
| 509. | Ar-2 | XYZ-c | $R^{11}$-5 |
| 510. | Ar-2 | XYZ-c | $R^{11}$-6 |
| 511. | Ar-2 | XYZ-c | $R^{11}$-7 |
| 512. | Ar-2 | XYZ-c | $R^{11}$-8 |
| 513. | Ar-2 | XYZ-c | $R^{11}$-9 |
| 514. | Ar-2 | XYZ-c | $R^{11}$-10 |
| 515. | Ar-2 | XYZ-c | $R^{11}$-11 |
| 516. | Ar-2 | XYZ-c | $R^{11}$-12 |
| 517. | Ar-2 | XYZ-c | $R^{11}$-13 |
| 518. | Ar-2 | XYZ-c | $R^{11}$-14 |
| 519. | Ar-2 | XYZ-c | $R^{11}$-15 |
| 520. | Ar-2 | XYZ-c | $R^{11}$-16 |
| 521. | Ar-2 | XYZ-c | $R^{11}$-17 |
| 522. | Ar-2 | XYZ-c | $R^{11}$-18 |
| 523. | Ar-2 | XYZ-c | $R^{11}$-19 |
| 524. | Ar-2 | XYZ-c | $R^{11}$-20 |
| 525. | Ar-2 | XYZ-c | $R^{11}$-21 |
| 526. | Ar-2 | XYZ-d | $R^{11}$-1 |
| 527. | Ar-2 | XYZ-d | $R^{11}$-2 |
| 528. | Ar-2 | XYZ-d | $R^{11}$-3 |
| 529. | Ar-2 | XYZ-d | $R^{11}$-4 |
| 530. | Ar-2 | XYZ-d | $R^{11}$-5 |
| 531. | Ar-2 | XYZ-d | $R^{11}$-6 |
| 532. | Ar-2 | XYZ-d | $R^{11}$-7 |
| 533. | Ar-2 | XYZ-d | $R^{11}$-8 |
| 534. | Ar-2 | XYZ-d | $R^{11}$-9 |
| 535. | Ar-2 | XYZ-d | $R^{11}$-10 |
| 536. | Ar-2 | XYZ-d | $R^{11}$-11 |
| 537. | Ar-2 | XYZ-d | $R^{11}$-12 |
| 538. | Ar-2 | XYZ-d | $R^{11}$-13 |
| 539. | Ar-2 | XYZ-d | $R^{11}$-14 |
| 540. | Ar-2 | XYZ-d | $R^{11}$-15 |
| 541. | Ar-2 | XYZ-d | $R^{11}$-16 |
| 542. | Ar-2 | XYZ-d | $R^{11}$-17 |
| 543. | Ar-2 | XYZ-d | $R^{11}$-18 |
| 544. | Ar-2 | XYZ-d | $R^{11}$-19 |
| 545. | Ar-2 | XYZ-d | $R^{11}$-20 |
| 546. | Ar-2 | XYZ-d | $R^{11}$-21 |
| 547. | Ar-2 | XYZ-e | $R^{11}$-1 |
| 548. | Ar-2 | XYZ-e | $R^{11}$-2 |
| 549. | Ar-2 | XYZ-e | $R^{11}$-3 |
| 550. | Ar-2 | XYZ-e | $R^{11}$-4 |
| 551. | Ar-2 | XYZ-e | $R^{11}$-5 |
| 552. | Ar-2 | XYZ-e | $R^{11}$-6 |
| 553. | Ar-2 | XYZ-e | $R^{11}$-7 |
| 554. | Ar-2 | XYZ-e | $R^{11}$-8 |
| 555. | Ar-2 | XYZ-e | $R^{11}$-9 |
| 556. | Ar-2 | XYZ-e | $R^{11}$-10 |
| 557. | Ar-2 | XYZ-e | $R^{11}$-11 |
| 558. | Ar-2 | XYZ-e | $R^{11}$-12 |
| 559. | Ar-2 | XYZ-e | $R^{11}$-13 |
| 560. | Ar-2 | XYZ-e | $R^{11}$-14 |
| 561. | Ar-2 | XYZ-e | $R^{11}$-15 |
| 562. | Ar-2 | XYZ-e | $R^{11}$-16 |
| 563. | Ar-2 | XYZ-e | $R^{11}$-17 |
| 564. | Ar-2 | XYZ-e | $R^{11}$-18 |
| 565. | Ar-2 | XYZ-e | $R^{11}$-19 |
| 566. | Ar-2 | XYZ-e | $R^{11}$-20 |
| 567. | Ar-2 | XYZ-e | $R^{11}$-21 |
| 568. | Ar-2 | XYZ-f | $R^{11}$-1 |
| 569. | Ar-2 | XYZ-f | $R^{11}$-2 |
| 570. | Ar-2 | XYZ-f | $R^{11}$-3 |
| 571. | Ar-2 | XYZ-f | $R^{11}$-4 |
| 572. | Ar-2 | XYZ-f | $R^{11}$-5 |
| 573. | Ar-2 | XYZ-f | $R^{11}$-6 |
| 574. | Ar-2 | XYZ-f | $R^{11}$-7 |
| 575. | Ar-2 | XYZ-f | $R^{11}$-8 |
| 576. | Ar-2 | XYZ-f | $R^{11}$-9 |

TABLE C-continued

|  | Ar | -X-Y-Z- | R$^{11}$ |
|---|---|---|---|
| 577. | Ar-2 | XYZ-f | R$^{11}$-10 |
| 578. | Ar-2 | XYZ-f | R$^{11}$-11 |
| 579. | Ar-2 | XYZ-f | R$^{11}$-12 |
| 580. | Ar-2 | XYZ-f | R$^{11}$-13 |
| 581. | Ar-2 | XYZ-f | R$^{11}$-14 |
| 582. | Ar-2 | XYZ-f | R$^{11}$-15 |
| 583. | Ar-2 | XYZ-f | R$^{11}$-16 |
| 584. | Ar-2 | XYZ-f | R$^{11}$-17 |
| 585. | Ar-2 | XYZ-f | R$^{11}$-18 |
| 586. | Ar-2 | XYZ-f | R$^{11}$-19 |
| 587. | Ar-2 | XYZ-f | R$^{11}$-20 |
| 588. | Ar-2 | XYZ-f | R$^{11}$-21 |
| 589. | Ar-2 | XYZ-g | R$^{11}$-1 |
| 590. | Ar-2 | XYZ-g | R$^{11}$-2 |
| 591. | Ar-2 | XYZ-g | R$^{11}$-3 |
| 592. | Ar-2 | XYZ-g | R$^{11}$-4 |
| 593. | Ar-2 | XYZ-g | R$^{11}$-5 |
| 594. | Ar-2 | XYZ-g | R$^{11}$-6 |
| 595. | Ar-2 | XYZ-g | R$^{11}$-7 |
| 596. | Ar-2 | XYZ-g | R$^{11}$-8 |
| 597. | Ar-2 | XYZ-g | R$^{11}$-9 |
| 598. | Ar-2 | XYZ-g | R$^{11}$-10 |
| 599. | Ar-2 | XYZ-g | R$^{11}$-11 |
| 600. | Ar-2 | XYZ-g | R$^{11}$-12 |
| 601. | Ar-2 | XYZ-g | R$^{11}$-13 |
| 602. | Ar-2 | XYZ-g | R$^{11}$-14 |
| 603. | Ar-2 | XYZ-g | R$^{11}$-15 |
| 604. | Ar-2 | XYZ-g | R$^{11}$-16 |
| 605. | Ar-2 | XYZ-g | R$^{11}$-17 |
| 606. | Ar-2 | XYZ-g | R$^{11}$-18 |
| 607. | Ar-2 | XYZ-g | R$^{11}$-19 |
| 608. | Ar-2 | XYZ-g | R$^{11}$-20 |
| 609. | Ar-2 | XYZ-g | R$^{11}$-21 |
| 610. | Ar-2 | XYZ-h | R$^{11}$-1 |
| 611. | Ar-2 | XYZ-h | R$^{11}$-2 |
| 612. | Ar-2 | XYZ-h | R$^{11}$-3 |
| 613. | Ar-2 | XYZ-h | R$^{11}$-4 |
| 614. | Ar-2 | XYZ-h | R$^{11}$-5 |
| 615. | Ar-2 | XYZ-h | R$^{11}$-6 |
| 616. | Ar-2 | XYZ-h | R$^{11}$-7 |
| 617. | Ar-2 | XYZ-h | R$^{11}$-8 |
| 618. | Ar-2 | XYZ-h | R$^{11}$-9 |
| 619. | Ar-2 | XYZ-h | R$^{11}$-10 |
| 620. | Ar-2 | XYZ-h | R$^{11}$-11 |
| 621. | Ar-2 | XYZ-h | R$^{11}$-12 |
| 622. | Ar-2 | XYZ-h | R$^{11}$-13 |
| 623. | Ar-2 | XYZ-h | R$^{11}$-14 |
| 624. | Ar-2 | XYZ-h | R$^{11}$-15 |
| 625. | Ar-2 | XYZ-h | R$^{11}$-16 |
| 626. | Ar-2 | XYZ-h | R$^{11}$-17 |
| 627. | Ar-2 | XYZ-h | R$^{11}$-18 |
| 628. | Ar-2 | XYZ-h | R$^{11}$-19 |
| 629. | Ar-2 | XYZ-h | R$^{11}$-20 |
| 630. | Ar-2 | XYZ-h | R$^{11}$-21 |
| 631. | Ar-2 | XYZ-i | R$^{11}$-1 |
| 632. | Ar-2 | XYZ-i | R$^{11}$-2 |
| 633. | Ar-2 | XYZ-i | R$^{11}$-3 |
| 634. | Ar-2 | XYZ-i | R$^{11}$-4 |
| 635. | Ar-2 | XYZ-i | R$^{11}$-5 |
| 636. | Ar-2 | XYZ-i | R$^{11}$-6 |
| 637. | Ar-2 | XYZ-i | R$^{11}$-7 |
| 638. | Ar-2 | XYZ-i | R$^{11}$-8 |
| 639. | Ar-2 | XYZ-i | R$^{11}$-9 |
| 640. | Ar-2 | XYZ-i | R$^{11}$-10 |
| 641. | Ar-2 | XYZ-i | R$^{11}$-11 |
| 642. | Ar-2 | XYZ-i | R$^{11}$-12 |
| 643. | Ar-2 | XYZ-i | R$^{11}$-13 |
| 644. | Ar-2 | XYZ-i | R$^{11}$-14 |
| 645. | Ar-2 | XYZ-i | R$^{11}$-15 |
| 646. | Ar-2 | XYZ-i | R$^{11}$-16 |
| 647. | Ar-2 | XYZ-i | R$^{11}$-17 |
| 648. | Ar-2 | XYZ-i | R$^{11}$-18 |
| 649. | Ar-2 | XYZ-i | R$^{11}$-19 |
| 650. | Ar-2 | XYZ-i | R$^{11}$-20 |
| 651. | Ar-2 | XYZ-i | R$^{11}$-21 |
| 652. | Ar-2 | XYZ-k | R$^{11}$-1 |
| 653. | Ar-2 | XYZ-k | R$^{11}$-2 |
| 654. | Ar-2 | XYZ-k | R$^{11}$-3 |
| 655. | Ar-2 | XYZ-k | R$^{11}$-4 |
| 656. | Ar-2 | XYZ-k | R$^{11}$-5 |
| 657. | Ar-2 | XYZ-k | R$^{11}$-6 |
| 658. | Ar-2 | XYZ-k | R$^{11}$-7 |
| 659. | Ar-2 | XYZ-k | R$^{11}$-8 |
| 660. | Ar-2 | XYZ-k | R$^{11}$-9 |
| 661. | Ar-2 | XYZ-k | R$^{11}$-10 |
| 662. | Ar-2 | XYZ-k | R$^{11}$-11 |
| 663. | Ar-2 | XYZ-k | R$^{11}$-12 |
| 664. | Ar-2 | XYZ-k | R$^{11}$-13 |
| 665. | Ar-2 | XYZ-k | R$^{11}$-14 |
| 666. | Ar-2 | XYZ-k | R$^{11}$-15 |
| 667. | Ar-2 | XYZ-k | R$^{11}$-16 |
| 668. | Ar-2 | XYZ-k | R$^{11}$-17 |
| 669. | Ar-2 | XYZ-k | R$^{11}$-18 |
| 670. | Ar-2 | XYZ-k | R$^{11}$-19 |
| 671. | Ar-2 | XYZ-k | R$^{11}$-20 |
| 672. | Ar-2 | XYZ-k | R$^{11}$-21 |
| 673. | Ar-2 | XYZ-l | R$^{11}$-1 |
| 674. | Ar-2 | XYZ-l | R$^{11}$-2 |
| 675. | Ar-2 | XYZ-l | R$^{11}$-3 |
| 676. | Ar-2 | XYZ-l | R$^{11}$-4 |
| 677. | Ar-2 | XYZ-l | R$^{11}$-5 |
| 678. | Ar-2 | XYZ-l | R$^{11}$-6 |
| 679. | Ar-2 | XYZ-l | R$^{11}$-7 |
| 680. | Ar-2 | XYZ-l | R$^{11}$-8 |
| 681. | Ar-2 | XYZ-l | R$^{11}$-9 |
| 682. | Ar-2 | XYZ-l | R$^{11}$-10 |
| 683. | Ar-2 | XYZ-l | R$^{11}$-11 |
| 684. | Ar-2 | XYZ-l | R$^{11}$-12 |
| 685. | Ar-2 | XYZ-l | R$^{11}$-13 |
| 686. | Ar-2 | XYZ-l | R$^{11}$-14 |
| 687. | Ar-2 | XYZ-l | R$^{11}$-15 |
| 688. | Ar-2 | XYZ-l | R$^{11}$-16 |
| 689. | Ar-2 | XYZ-l | R$^{11}$-17 |
| 690. | Ar-2 | XYZ-l | R$^{11}$-18 |
| 691. | Ar-2 | XYZ-l | R$^{11}$-19 |
| 692. | Ar-2 | XYZ-l | R$^{11}$-20 |
| 693. | Ar-2 | XYZ-l | R$^{11}$-21 |
| 694. | Ar-2 | XYZ-m | R$^{11}$-1 |
| 695. | Ar-2 | XYZ-m | R$^{11}$-2 |
| 696. | Ar-2 | XYZ-m | R$^{11}$-3 |
| 697. | Ar-2 | XYZ-m | R$^{11}$-4 |
| 698. | Ar-2 | XYZ-m | R$^{11}$-5 |
| 699. | Ar-2 | XYZ-m | R$^{11}$-6 |
| 700. | Ar-2 | XYZ-m | R$^{11}$-7 |
| 701. | Ar-2 | XYZ-m | R$^{11}$-8 |
| 702. | Ar-2 | XYZ-m | R$^{11}$-9 |
| 703. | Ar-2 | XYZ-m | R$^{11}$-10 |
| 704. | Ar-2 | XYZ-m | R$^{11}$-11 |
| 705. | Ar-2 | XYZ-m | R$^{11}$-12 |
| 706. | Ar-2 | XYZ-m | R$^{11}$-13 |
| 707. | Ar-2 | XYZ-m | R$^{11}$-14 |
| 708. | Ar-2 | XYZ-m | R$^{11}$-15 |
| 709. | Ar-2 | XYZ-m | R$^{11}$-16 |
| 710. | Ar-2 | XYZ-m | R$^{11}$-17 |
| 711. | Ar-2 | XYZ-m | R$^{11}$-18 |
| 712. | Ar-2 | XYZ-m | R$^{11}$-19 |
| 713. | Ar-2 | XYZ-m | R$^{11}$-20 |
| 714. | Ar-2 | XYZ-m | R$^{11}$-21 |
| 715. | Ar-2 | XYZ-n | R$^{11}$-1 |
| 716. | Ar-2 | XYZ-n | R$^{11}$-2 |
| 717. | Ar-2 | XYZ-n | R$^{11}$-3 |
| 718. | Ar-2 | XYZ-n | R$^{11}$-4 |
| 719. | Ar-2 | XYZ-n | R$^{11}$-5 |
| 720. | Ar-2 | XYZ-n | R$^{11}$-6 |
| 721. | Ar-2 | XYZ-n | R$^{11}$-7 |
| 722. | Ar-2 | XYZ-n | R$^{11}$-8 |
| 723. | Ar-2 | XYZ-n | R$^{11}$-9 |
| 724. | Ar-2 | XYZ-n | R$^{11}$-10 |
| 725. | Ar-2 | XYZ-n | R$^{11}$-11 |
| 726. | Ar-2 | XYZ-n | R$^{11}$-12 |
| 727. | Ar-2 | XYZ-n | R$^{11}$-13 |
| 728. | Ar-2 | XYZ-n | R$^{11}$-14 |
| 729. | Ar-2 | XYZ-n | R$^{11}$-15 |
| 730. | Ar-2 | XYZ-n | R$^{11}$-16 |
| 731. | Ar-2 | XYZ-n | R$^{11}$-17 |
| 732. | Ar-2 | XYZ-n | R$^{11}$-18 |

TABLE C-continued

|  | Ar | -X-Y-Z- | R[11] |
|---|---|---|---|
| 733. | Ar-2 | XYZ-n | R[11]-19 |
| 734. | Ar-2 | XYZ-n | R[11]-20 |
| 735. | Ar-2 | XYZ-n | R[11]-21 |
| 736. | Ar-2 | XYZ-o | R[11]-1 |
| 737. | Ar-2 | XYZ-o | R[11]-2 |
| 738. | Ar-2 | XYZ-o | R[11]-3 |
| 739. | Ar-2 | XYZ-o | R[11]-4 |
| 740. | Ar-2 | XYZ-o | R[11]-5 |
| 741. | Ar-2 | XYZ-o | R[11]-6 |
| 742. | Ar-2 | XYZ-o | R[11]-7 |
| 743. | Ar-2 | XYZ-o | R[11]-8 |
| 744. | Ar-2 | XYZ-o | R[11]-9 |
| 745. | Ar-2 | XYZ-o | R[11]-10 |
| 746. | Ar-2 | XYZ-o | R[11]-11 |
| 747. | Ar-2 | XYZ-o | R[11]-12 |
| 748. | Ar-2 | XYZ-o | R[11]-13 |
| 749. | Ar-2 | XYZ-o | R[11]-14 |
| 750. | Ar-2 | XYZ-o | R[11]-15 |
| 751. | Ar-2 | XYZ-o | R[11]-16 |
| 752. | Ar-2 | XYZ-o | R[11]-17 |
| 753. | Ar-2 | XYZ-o | R[11]-18 |
| 754. | Ar-2 | XYZ-o | R[11]-19 |
| 755. | Ar-2 | XYZ-o | R[11]-20 |
| 756. | Ar-2 | XYZ-o | R[11]-21 |
| 757. | Ar-2 | XYZ-p | R[11]-1 |
| 758. | Ar-2 | XYZ-p | R[11]-2 |
| 759. | Ar-2 | XYZ-p | R[11]-3 |
| 760. | Ar-2 | XYZ-p | R[11]-4 |
| 761. | Ar-2 | XYZ-p | R[11]-5 |
| 762. | Ar-2 | XYZ-p | R[11]-6 |
| 763. | Ar-2 | XYZ-p | R[11]-7 |
| 764. | Ar-2 | XYZ-p | R[11]-8 |
| 765. | Ar-2 | XYZ-p | R[11]-9 |
| 766. | Ar-2 | XYZ-p | R[11]-10 |
| 767. | Ar-2 | XYZ-p | R[11]-11 |
| 768. | Ar-2 | XYZ-p | R[11]-12 |
| 769. | Ar-2 | XYZ-p | R[11]-13 |
| 770. | Ar-2 | XYZ-p | R[11]-14 |
| 771. | Ar-2 | XYZ-p | R[11]-15 |
| 772. | Ar-2 | XYZ-p | R[11]-16 |
| 773. | Ar-2 | XYZ-p | R[11]-17 |
| 774. | Ar-2 | XYZ-p | R[11]-18 |
| 775. | Ar-2 | XYZ-p | R[11]-19 |
| 776. | Ar-2 | XYZ-p | R[11]-20 |
| 777. | Ar-2 | XYZ-p | R[11]-21 |
| 778. | Ar-2 | XYZ-q | R[11]-1 |
| 779. | Ar-2 | XYZ-q | R[11]-2 |
| 780. | Ar-2 | XYZ-q | R[11]-3 |
| 781. | Ar-2 | XYZ-q | R[11]-4 |
| 782. | Ar-2 | XYZ-q | R[11]-5 |
| 783. | Ar-2 | XYZ-q | R[11]-6 |
| 784. | Ar-2 | XYZ-q | R[11]-7 |
| 785. | Ar-2 | XYZ-q | R[11]-8 |
| 786. | Ar-2 | XYZ-q | R[11]-9 |
| 787. | Ar-2 | XYZ-q | R[11]-10 |
| 788. | Ar-2 | XYZ-q | R[11]-11 |
| 789. | Ar-2 | XYZ-q | R[11]-12 |
| 790. | Ar-2 | XYZ-q | R[11]-13 |
| 791. | Ar-2 | XYZ-q | R[11]-14 |
| 792. | Ar-2 | XYZ-q | R[11]-15 |
| 793. | Ar-2 | XYZ-q | R[11]-16 |
| 794. | Ar-2 | XYZ-q | R[11]-17 |
| 795. | Ar-2 | XYZ-q | R[11]-18 |
| 796. | Ar-2 | XYZ-q | R[11]-19 |
| 797. | Ar-2 | XYZ-q | R[11]-20 |
| 798. | Ar-2 | XYZ-q | R[11]-21 |
| 799. | Ar-2 | XYZ-r | R[11]-1 |
| 800. | Ar-2 | XYZ-r | R[11]-2 |
| 801. | Ar-2 | XYZ-r | R[11]-3 |
| 802. | Ar-2 | XYZ-r | R[11]-4 |
| 803. | Ar-2 | XYZ-r | R[11]-5 |
| 804. | Ar-2 | XYZ-r | R[11]-6 |
| 805. | Ar-2 | XYZ-r | R[11]-7 |
| 806. | Ar-2 | XYZ-r | R[11]-8 |
| 807. | Ar-2 | XYZ-r | R[11]-9 |
| 808. | Ar-2 | XYZ-r | R[11]-10 |
| 809. | Ar-2 | XYZ-r | R[11]-11 |
| 810. | Ar-2 | XYZ-r | R[11]-12 |
| 811. | Ar-2 | XYZ-r | R[11]-13 |
| 812. | Ar-2 | XYZ-r | R[11]-14 |
| 813. | Ar-2 | XYZ-r | R[11]-15 |
| 814. | Ar-2 | XYZ-r | R[11]-16 |
| 815. | Ar-2 | XYZ-r | R[11]-17 |
| 816. | Ar-2 | XYZ-r | R[11]-18 |
| 817. | Ar-2 | XYZ-r | R[11]-19 |
| 818. | Ar-2 | XYZ-r | R[11]-20 |
| 819. | Ar-2 | XYZ-r | R[11]-21 |
| 820. | Ar-2 | XYZ-s | R[11]-1 |
| 821. | Ar-2 | XYZ-s | R[11]-2 |
| 822. | Ar-2 | XYZ-s | R[11]-3 |
| 823. | Ar-2 | XYZ-s | R[11]-4 |
| 824. | Ar-2 | XYZ-s | R[11]-5 |
| 825. | Ar-2 | XYZ-s | R[11]-6 |
| 826. | Ar-2 | XYZ-s | R[11]-7 |
| 827. | Ar-2 | XYZ-s | R[11]-8 |
| 828. | Ar-2 | XYZ-s | R[11]-9 |
| 829. | Ar-2 | XYZ-s | R[11]-10 |
| 830. | Ar-2 | XYZ-s | R[11]-11 |
| 831. | Ar-2 | XYZ-s | R[11]-12 |
| 832. | Ar-2 | XYZ-s | R[11]-13 |
| 833. | Ar-2 | XYZ-s | R[11]-14 |
| 834. | Ar-2 | XYZ-s | R[11]-15 |
| 835. | Ar-2 | XYZ-s | R[11]-16 |
| 836. | Ar-2 | XYZ-s | R[11]-17 |
| 837. | Ar-2 | XYZ-s | R[11]-18 |
| 838. | Ar-2 | XYZ-s | R[11]-19 |
| 839. | Ar-2 | XYZ-s | R[11]-20 |
| 840. | Ar-2 | XYZ-s | R[11]-21 |
| 841. | Ar-2 | XYZ-t | R[11]-1 |
| 842. | Ar-2 | XYZ-t | R[11]-2 |
| 843. | Ar-2 | XYZ-t | R[11]-3 |
| 844. | Ar-2 | XYZ-t | R[11]-4 |
| 845. | Ar-2 | XYZ-t | R[11]-5 |
| 846. | Ar-2 | XYZ-t | R[11]-6 |
| 847. | Ar-2 | XYZ-t | R[11]-7 |
| 848. | Ar-2 | XYZ-t | R[11]-8 |
| 849. | Ar-2 | XYZ-t | R[11]-9 |
| 850. | Ar-2 | XYZ-t | R[11]-10 |
| 851. | Ar-2 | XYZ-t | R[11]-11 |
| 852. | Ar-2 | XYZ-t | R[11]-12 |
| 853. | Ar-2 | XYZ-t | R[11]-13 |
| 854. | Ar-2 | XYZ-t | R[11]-14 |
| 855. | Ar-2 | XYZ-t | R[11]-15 |
| 856. | Ar-2 | XYZ-t | R[11]-16 |
| 857. | Ar-2 | XYZ-t | R[11]-17 |
| 858. | Ar-2 | XYZ-t | R[11]-18 |
| 859. | Ar-2 | XYZ-t | R[11]-19 |
| 860. | Ar-2 | XYZ-t | R[11]-20 |
| 861. | Ar-2 | XYZ-t | R[11]-21 |
| 862. | Ar-2 | XYZ-u | R[11]-1 |
| 863. | Ar-2 | XYZ-u | R[11]-2 |
| 864. | Ar-2 | XYZ-u | R[11]-3 |
| 865. | Ar-2 | XYZ-u | R[11]-4 |
| 866. | Ar-2 | XYZ-u | R[11]-5 |
| 867. | Ar-2 | XYZ-u | R[11]-6 |
| 868. | Ar-2 | XYZ-u | R[11]-7 |
| 869. | Ar-2 | XYZ-u | R[11]-8 |
| 870. | Ar-2 | XYZ-u | R[11]-9 |
| 871. | Ar-2 | XYZ-u | R[11]-10 |
| 872. | Ar-2 | XYZ-u | R[11]-11 |
| 873. | Ar-2 | XYZ-u | R[11]-12 |
| 874. | Ar-2 | XYZ-u | R[11]-13 |
| 875. | Ar-2 | XYZ-u | R[11]-14 |
| 876. | Ar-2 | XYZ-u | R[11]-15 |
| 877. | Ar-2 | XYZ-u | R[11]-16 |
| 878. | Ar-2 | XYZ-u | R[11]-17 |
| 879. | Ar-2 | XYZ-u | R[11]-18 |
| 880. | Ar-2 | XYZ-u | R[11]-19 |
| 881. | Ar-2 | XYZ-u | R[11]-20 |
| 882. | Ar-2 | XYZ-u | R[11]-21 |
| 883. | Ar-2 | XYZ-v | R[11]-1 |
| 884. | Ar-2 | XYZ-v | R[11]-2 |
| 885. | Ar-2 | XYZ-v | R[11]-3 |
| 886. | Ar-2 | XYZ-v | R[11]-4 |
| 887. | Ar-2 | XYZ-v | R[11]-5 |
| 888. | Ar-2 | XYZ-v | R[11]-6 |

TABLE C-continued

|  | Ar | -X-Y-Z- | $R^{11}$ |
|---|---|---|---|
| 889. | Ar-2 | XYZ-v | $R^{11}$-7 |
| 890. | Ar-2 | XYZ-v | $R^{11}$-8 |
| 891. | Ar-2 | XYZ-v | $R^{11}$-9 |
| 892. | Ar-2 | XYZ-v | $R^{11}$-10 |
| 893. | Ar-2 | XYZ-v | $R^{11}$-11 |
| 894. | Ar-2 | XYZ-v | $R^{11}$-12 |
| 895. | Ar-2 | XYZ-v | $R^{11}$-13 |
| 896. | Ar-2 | XYZ-v | $R^{11}$-14 |
| 897. | Ar-2 | XYZ-v | $R^{11}$-15 |
| 898. | Ar-2 | XYZ-v | $R^{11}$-16 |
| 899. | Ar-2 | XYZ-v | $R^{11}$-17 |
| 900. | Ar-2 | XYZ-v | $R^{11}$-18 |
| 901. | Ar-2 | XYZ-v | $R^{11}$-19 |
| 902. | Ar-2 | XYZ-v | $R^{11}$-20 |
| 903. | Ar-2 | XYZ-v | $R^{11}$-21 |
| 904. | Ar-2 | XYZ-w | $R^{11}$-1 |
| 905. | Ar-2 | XYZ-w | $R^{11}$-2 |
| 906. | Ar-2 | XYZ-w | $R^{11}$-3 |
| 907. | Ar-2 | XYZ-w | $R^{11}$-4 |
| 908. | Ar-2 | XYZ-w | $R^{11}$-5 |
| 909. | Ar-2 | XYZ-w | $R^{11}$-6 |
| 910. | Ar-2 | XYZ-w | $R^{11}$-7 |
| 911. | Ar-2 | XYZ-w | $R^{11}$-8 |
| 912. | Ar-2 | XYZ-w | $R^{11}$-9 |
| 913. | Ar-2 | XYZ-w | $R^{11}$-10 |
| 914. | Ar-2 | XYZ-w | $R^{11}$-11 |
| 915. | Ar-2 | XYZ-w | $R^{11}$-12 |
| 916. | Ar-2 | XYZ-w | $R^{11}$-13 |
| 917. | Ar-2 | XYZ-w | $R^{11}$-14 |
| 918. | Ar-2 | XYZ-w | $R^{11}$-15 |
| 919. | Ar-2 | XYZ-w | $R^{11}$-16 |
| 920. | Ar-2 | XYZ-w | $R^{11}$-17 |
| 921. | Ar-2 | XYZ-w | $R^{11}$-18 |
| 922. | Ar-2 | XYZ-w | $R^{11}$-19 |
| 923. | Ar-2 | XYZ-w | $R^{11}$-20 |
| 924. | Ar-2 | XYZ-w | $R^{11}$-21 |
| 925. | Ar-3 | XYZ-a | $R^{11}$-1 |
| 926. | Ar-3 | XYZ-a | $R^{11}$-2 |
| 927. | Ar-3 | XYZ-a | $R^{11}$-3 |
| 928. | Ar-3 | XYZ-a | $R^{11}$-4 |
| 929. | Ar-3 | XYZ-a | $R^{11}$-5 |
| 930. | Ar-3 | XYZ-a | $R^{11}$-6 |
| 931. | Ar-3 | XYZ-a | $R^{11}$-7 |
| 932. | Ar-3 | XYZ-a | $R^{11}$-8 |
| 933. | Ar-3 | XYZ-a | $R^{11}$-9 |
| 934. | Ar-3 | XYZ-a | $R^{11}$-10 |
| 935. | Ar-3 | XYZ-a | $R^{11}$-11 |
| 936. | Ar-3 | XYZ-a | $R^{11}$-12 |
| 937. | Ar-3 | XYZ-a | $R^{11}$-13 |
| 938. | Ar-3 | XYZ-a | $R^{11}$-14 |
| 939. | Ar-3 | XYZ-a | $R^{11}$-15 |
| 940. | Ar-3 | XYZ-a | $R^{11}$-16 |
| 941. | Ar-3 | XYZ-a | $R^{11}$-17 |
| 942. | Ar-3 | XYZ-a | $R^{11}$-18 |
| 943. | Ar-3 | XYZ-a | $R^{11}$-19 |
| 944. | Ar-3 | XYZ-a | $R^{11}$-20 |
| 945. | Ar-3 | XYZ-a | $R^{11}$-21 |
| 946. | Ar-3 | XYZ-b | $R^{11}$-1 |
| 947. | Ar-3 | XYZ-b | $R^{11}$-2 |
| 948. | Ar-3 | XYZ-b | $R^{11}$-3 |
| 949. | Ar-3 | XYZ-b | $R^{11}$-4 |
| 950. | Ar-3 | XYZ-b | $R^{11}$-5 |
| 951. | Ar-3 | XYZ-b | $R^{11}$-6 |
| 952. | Ar-3 | XYZ-b | $R^{11}$-7 |
| 953. | Ar-3 | XYZ-b | $R^{11}$-8 |
| 954. | Ar-3 | XYZ-b | $R^{11}$-9 |
| 955. | Ar-3 | XYZ-b | $R^{11}$-10 |
| 956. | Ar-3 | XYZ-b | $R^{11}$-11 |
| 957. | Ar-3 | XYZ-b | $R^{11}$-12 |
| 958. | Ar-3 | XYZ-b | $R^{11}$-13 |
| 959. | Ar-3 | XYZ-b | $R^{11}$-14 |
| 960. | Ar-3 | XYZ-b | $R^{11}$-15 |
| 961. | Ar-3 | XYZ-b | $R^{11}$-16 |
| 962. | Ar-3 | XYZ-b | $R^{11}$-17 |
| 963. | Ar-3 | XYZ-b | $R^{11}$-18 |
| 964. | Ar-3 | XYZ-b | $R^{11}$-19 |
| 965. | Ar-3 | XYZ-b | $R^{11}$-20 |
| 966. | Ar-3 | XYZ-b | $R^{11}$-21 |
| 967. | Ar-3 | XYZ-c | $R^{11}$-1 |
| 968. | Ar-3 | XYZ-c | $R^{11}$-2 |
| 969. | Ar-3 | XYZ-c | $R^{11}$-3 |
| 970. | Ar-3 | XYZ-c | $R^{11}$-4 |
| 971. | Ar-3 | XYZ-c | $R^{11}$-5 |
| 972. | Ar-3 | XYZ-c | $R^{11}$-6 |
| 973. | Ar-3 | XYZ-c | $R^{11}$-7 |
| 974. | Ar-3 | XYZ-c | $R^{11}$-8 |
| 975. | Ar-3 | XYZ-c | $R^{11}$-9 |
| 976. | Ar-3 | XYZ-c | $R^{11}$-10 |
| 977. | Ar-3 | XYZ-c | $R^{11}$-11 |
| 978. | Ar-3 | XYZ-c | $R^{11}$-12 |
| 979. | Ar-3 | XYZ-c | $R^{11}$-13 |
| 980. | Ar-3 | XYZ-c | $R^{11}$-14 |
| 981. | Ar-3 | XYZ-c | $R^{11}$-15 |
| 982. | Ar-3 | XYZ-c | $R^{11}$-16 |
| 983. | Ar-3 | XYZ-c | $R^{11}$-17 |
| 984. | Ar-3 | XYZ-c | $R^{11}$-18 |
| 985. | Ar-3 | XYZ-c | $R^{11}$-19 |
| 986. | Ar-3 | XYZ-c | $R^{11}$-20 |
| 987. | Ar-3 | XYZ-c | $R^{11}$-21 |
| 988. | Ar-3 | XYZ-d | $R^{11}$-1 |
| 989. | Ar-3 | XYZ-d | $R^{11}$-2 |
| 990. | Ar-3 | XYZ-d | $R^{11}$-3 |
| 991. | Ar-3 | XYZ-d | $R^{11}$-4 |
| 992. | Ar-3 | XYZ-d | $R^{11}$-5 |
| 993. | Ar-3 | XYZ-d | $R^{11}$-6 |
| 994. | Ar-3 | XYZ-d | $R^{11}$-7 |
| 995. | Ar-3 | XYZ-d | $R^{11}$-8 |
| 996. | Ar-3 | XYZ-d | $R^{11}$-9 |
| 997. | Ar-3 | XYZ-d | $R^{11}$-10 |
| 998. | Ar-3 | XYZ-d | $R^{11}$-11 |
| 999. | Ar-3 | XYZ-d | $R^{11}$-12 |
| 1000. | Ar-3 | XYZ-d | $R^{11}$-13 |
| 1001. | Ar-3 | XYZ-d | $R^{11}$-14 |
| 1002. | Ar-3 | XYZ-d | $R^{11}$-15 |
| 1003. | Ar-3 | XYZ-d | $R^{11}$-16 |
| 1004. | Ar-3 | XYZ-d | $R^{11}$-17 |
| 1005. | Ar-3 | XYZ-d | $R^{11}$-18 |
| 1006. | Ar-3 | XYZ-d | $R^{11}$-19 |
| 1007. | Ar-3 | XYZ-d | $R^{11}$-20 |
| 1008. | Ar-3 | XYZ-d | $R^{11}$-21 |
| 1009. | Ar-3 | XYZ-e | $R^{11}$-1 |
| 1010. | Ar-3 | XYZ-e | $R^{11}$-2 |
| 1011. | Ar-3 | XYZ-e | $R^{11}$-3 |
| 1012. | Ar-3 | XYZ-e | $R^{11}$-4 |
| 1013. | Ar-3 | XYZ-e | $R^{11}$-5 |
| 1014. | Ar-3 | XYZ-e | $R^{11}$-6 |
| 1015. | Ar-3 | XYZ-e | $R^{11}$-7 |
| 1016. | Ar-3 | XYZ-e | $R^{11}$-8 |
| 1017. | Ar-3 | XYZ-e | $R^{11}$-9 |
| 1018. | Ar-3 | XYZ-e | $R^{11}$-10 |
| 1019. | Ar-3 | XYZ-e | $R^{11}$-11 |
| 1020. | Ar-3 | XYZ-e | $R^{11}$-12 |
| 1021. | Ar-3 | XYZ-e | $R^{11}$-13 |
| 1022. | Ar-3 | XYZ-e | $R^{11}$-14 |
| 1023. | Ar-3 | XYZ-e | $R^{11}$-15 |
| 1024. | Ar-3 | XYZ-e | $R^{11}$-16 |
| 1025. | Ar-3 | XYZ-e | $R^{11}$-17 |
| 1026. | Ar-3 | XYZ-e | $R^{11}$-18 |
| 1027. | Ar-3 | XYZ-e | $R^{11}$-19 |
| 1028. | Ar-3 | XYZ-e | $R^{11}$-20 |
| 1029. | Ar-3 | XYZ-e | $R^{11}$-21 |
| 1030. | Ar-3 | XYZ-f | $R^{11}$-1 |
| 1031. | Ar-3 | XYZ-f | $R^{11}$-2 |
| 1032. | Ar-3 | XYZ-f | $R^{11}$-3 |
| 1033. | Ar-3 | XYZ-f | $R^{11}$-4 |
| 1034. | Ar-3 | XYZ-f | $R^{11}$-5 |
| 1035. | Ar-3 | XYZ-f | $R^{11}$-6 |
| 1036. | Ar-3 | XYZ-f | $R^{11}$-7 |
| 1037. | Ar-3 | XYZ-f | $R^{11}$-8 |
| 1038. | Ar-3 | XYZ-f | $R^{11}$-9 |
| 1039. | Ar-3 | XYZ-f | $R^{11}$-10 |
| 1040. | Ar-3 | XYZ-f | $R^{11}$-11 |
| 1041. | Ar-3 | XYZ-f | $R^{11}$-12 |
| 1042. | Ar-3 | XYZ-f | $R^{11}$-13 |
| 1043. | Ar-3 | XYZ-f | $R^{11}$-14 |
| 1044. | Ar-3 | XYZ-f | $R^{11}$-15 |

TABLE C-continued

| | Ar | -X-Y-Z- | $R^{11}$ |
|---|---|---|---|
| 1045. | Ar-3 | XYZ-f | $R^{11}$-16 |
| 1046. | Ar-3 | XYZ-f | $R^{11}$-17 |
| 1047. | Ar-3 | XYZ-f | $R^{11}$-18 |
| 1048. | Ar-3 | XYZ-f | $R^{11}$-19 |
| 1049. | Ar-3 | XYZ-f | $R^{11}$-20 |
| 1050. | Ar-3 | XYZ-f | $R^{11}$-21 |
| 1051. | Ar-3 | XYZ-g | $R^{11}$-1 |
| 1052. | Ar-3 | XYZ-g | $R^{11}$-2 |
| 1053. | Ar-3 | XYZ-g | $R^{11}$-3 |
| 1054. | Ar-3 | XYZ-g | $R^{11}$-4 |
| 1055. | Ar-3 | XYZ-g | $R^{11}$-5 |
| 1056. | Ar-3 | XYZ-g | $R^{11}$-6 |
| 1057. | Ar-3 | XYZ-g | $R^{11}$-7 |
| 1058. | Ar-3 | XYZ-g | $R^{11}$-8 |
| 1059. | Ar-3 | XYZ-g | $R^{11}$-9 |
| 1060. | Ar-3 | XYZ-g | $R^{11}$-10 |
| 1061. | Ar-3 | XYZ-g | $R^{11}$-11 |
| 1062. | Ar-3 | XYZ-g | $R^{11}$-12 |
| 1063. | Ar-3 | XYZ-g | $R^{11}$-13 |
| 1064. | Ar-3 | XYZ-g | $R^{11}$-14 |
| 1065. | Ar-3 | XYZ-g | $R^{11}$-15 |
| 1066. | Ar-3 | XYZ-g | $R^{11}$-16 |
| 1067. | Ar-3 | XYZ-g | $R^{11}$-17 |
| 1068. | Ar-3 | XYZ-g | $R^{11}$-18 |
| 1069. | Ar-3 | XYZ-g | $R^{11}$-19 |
| 1070. | Ar-3 | XYZ-g | $R^{11}$-20 |
| 1071. | Ar-3 | XYZ-g | $R^{11}$-21 |
| 1072. | Ar-3 | XYZ-h | $R^{11}$-1 |
| 1073. | Ar-3 | XYZ-h | $R^{11}$-2 |
| 1074. | Ar-3 | XYZ-h | $R^{11}$-3 |
| 1075. | Ar-3 | XYZ-h | $R^{11}$-4 |
| 1076. | Ar-3 | XYZ-h | $R^{11}$-5 |
| 1077. | Ar-3 | XYZ-h | $R^{11}$-6 |
| 1078. | Ar-3 | XYZ-h | $R^{11}$-7 |
| 1079. | Ar-3 | XYZ-h | $R^{11}$-8 |
| 1080. | Ar-3 | XYZ-h | $R^{11}$-9 |
| 1081. | Ar-3 | XYZ-h | $R^{11}$-10 |
| 1082. | Ar-3 | XYZ-h | $R^{11}$-11 |
| 1083. | Ar-3 | XYZ-h | $R^{11}$-12 |
| 1084. | Ar-3 | XYZ-h | $R^{11}$-13 |
| 1085. | Ar-3 | XYZ-h | $R^{11}$-14 |
| 1086. | Ar-3 | XYZ-h | $R^{11}$-15 |
| 1087. | Ar-3 | XYZ-h | $R^{11}$-16 |
| 1088. | Ar-3 | XYZ-h | $R^{11}$-17 |
| 1089. | Ar-3 | XYZ-h | $R^{11}$-18 |
| 1090. | Ar-3 | XYZ-h | $R^{11}$-19 |
| 1091. | Ar-3 | XYZ-h | $R^{11}$-20 |
| 1092. | Ar-3 | XYZ-h | $R^{11}$-21 |
| 1093. | Ar-3 | XYZ-i | $R^{11}$-1 |
| 1094. | Ar-3 | XYZ-i | $R^{11}$-2 |
| 1095. | Ar-3 | XYZ-i | $R^{11}$-3 |
| 1096. | Ar-3 | XYZ-i | $R^{11}$-4 |
| 1097. | Ar-3 | XYZ-i | $R^{11}$-5 |
| 1098. | Ar-3 | XYZ-i | $R^{11}$-6 |
| 1099. | Ar-3 | XYZ-i | $R^{11}$-7 |
| 1100. | Ar-3 | XYZ-i | $R^{11}$-8 |
| 1101. | Ar-3 | XYZ-i | $R^{11}$-9 |
| 1102. | Ar-3 | XYZ-i | $R^{11}$-10 |
| 1103. | Ar-3 | XYZ-i | $R^{11}$-11 |
| 1104. | Ar-3 | XYZ-i | $R^{11}$-12 |
| 1105. | Ar-3 | XYZ-i | $R^{11}$-13 |
| 1106. | Ar-3 | XYZ-i | $R^{11}$-14 |
| 1107. | Ar-3 | XYZ-i | $R^{11}$-15 |
| 1108. | Ar-3 | XYZ-i | $R^{11}$-16 |
| 1109. | Ar-3 | XYZ-i | $R^{11}$-17 |
| 1110. | Ar-3 | XYZ-i | $R^{11}$-18 |
| 1111. | Ar-3 | XYZ-i | $R^{11}$-19 |
| 1112. | Ar-3 | XYZ-i | $R^{11}$-20 |
| 1113. | Ar-3 | XYZ-i | $R^{11}$-21 |
| 1114. | Ar-3 | XYZ-k | $R^{11}$-1 |
| 1115. | Ar-3 | XYZ-k | $R^{11}$-2 |
| 1116. | Ar-3 | XYZ-k | $R^{11}$-3 |
| 1117. | Ar-3 | XYZ-k | $R^{11}$-4 |
| 1118. | Ar-3 | XYZ-k | $R^{11}$-5 |
| 1119. | Ar-3 | XYZ-k | $R^{11}$-6 |
| 1120. | Ar-3 | XYZ-k | $R^{11}$-7 |
| 1121. | Ar-3 | XYZ-k | $R^{11}$-8 |
| 1122. | Ar-3 | XYZ-k | $R^{11}$-9 |
| 1123. | Ar-3 | XYZ-k | $R^{11}$-10 |
| 1124. | Ar-3 | XYZ-k | $R^{11}$-11 |
| 1125. | Ar-3 | XYZ-k | $R^{11}$-12 |
| 1126. | Ar-3 | XYZ-k | $R^{11}$-13 |
| 1127. | Ar-3 | XYZ-k | $R^{11}$-14 |
| 1128. | Ar-3 | XYZ-k | $R^{11}$-15 |
| 1129. | Ar-3 | XYZ-k | $R^{11}$-16 |
| 1130. | Ar-3 | XYZ-k | $R^{11}$-17 |
| 1131. | Ar-3 | XYZ-k | $R^{11}$-18 |
| 1132. | Ar-3 | XYZ-k | $R^{11}$-19 |
| 1133. | Ar-3 | XYZ-k | $R^{11}$-20 |
| 1134. | Ar-3 | XYZ-k | $R^{11}$-21 |
| 1135. | Ar-3 | XYZ-l | $R^{11}$-1 |
| 1136. | Ar-3 | XYZ-l | $R^{11}$-2 |
| 1137. | Ar-3 | XYZ-l | $R^{11}$-3 |
| 1138. | Ar-3 | XYZ-l | $R^{11}$-4 |
| 1139. | Ar-3 | XYZ-l | $R^{11}$-5 |
| 1140. | Ar-3 | XYZ-l | $R^{11}$-6 |
| 1141. | Ar-3 | XYZ-l | $R^{11}$-7 |
| 1142. | Ar-3 | XYZ-l | $R^{11}$-8 |
| 1143. | Ar-3 | XYZ-l | $R^{11}$-9 |
| 1144. | Ar-3 | XYZ-l | $R^{11}$-10 |
| 1145. | Ar-3 | XYZ-l | $R^{11}$-11 |
| 1146. | Ar-3 | XYZ-l | $R^{11}$-12 |
| 1147. | Ar-3 | XYZ-l | $R^{11}$-13 |
| 1148. | Ar-3 | XYZ-l | $R^{11}$-14 |
| 1149. | Ar-3 | XYZ-l | $R^{11}$-15 |
| 1150. | Ar-3 | XYZ-l | $R^{11}$-16 |
| 1151. | Ar-3 | XYZ-l | $R^{11}$-17 |
| 1152. | Ar-3 | XYZ-l | $R^{11}$-18 |
| 1153. | Ar-3 | XYZ-l | $R^{11}$-19 |
| 1154. | Ar-3 | XYZ-l | $R^{11}$-20 |
| 1155. | Ar-3 | XYZ-l | $R^{11}$-21 |
| 1156. | Ar-3 | XYZ-m | $R^{11}$-1 |
| 1157. | Ar-3 | XYZ-m | $R^{11}$-2 |
| 1158. | Ar-3 | XYZ-m | $R^{11}$-3 |
| 1159. | Ar-3 | XYZ-m | $R^{11}$-4 |
| 1160. | Ar-3 | XYZ-m | $R^{11}$-5 |
| 1161. | Ar-3 | XYZ-m | $R^{11}$-6 |
| 1162. | Ar-3 | XYZ-m | $R^{11}$-7 |
| 1163. | Ar-3 | XYZ-m | $R^{11}$-8 |
| 1164. | Ar-3 | XYZ-m | $R^{11}$-9 |
| 1165. | Ar-3 | XYZ-m | $R^{11}$-10 |
| 1166. | Ar-3 | XYZ-m | $R^{11}$-11 |
| 1167. | Ar-3 | XYZ-m | $R^{11}$-12 |
| 1168. | Ar-3 | XYZ-m | $R^{11}$-13 |
| 1169. | Ar-3 | XYZ-m | $R^{11}$-14 |
| 1170. | Ar-3 | XYZ-m | $R^{11}$-15 |
| 1171. | Ar-3 | XYZ-m | $R^{11}$-16 |
| 1172. | Ar-3 | XYZ-m | $R^{11}$-17 |
| 1173. | Ar-3 | XYZ-m | $R^{11}$-18 |
| 1174. | Ar-3 | XYZ-m | $R^{11}$-19 |
| 1175. | Ar-3 | XYZ-m | $R^{11}$-20 |
| 1176. | Ar-3 | XYZ-m | $R^{11}$-21 |
| 1177. | Ar-3 | XYZ-n | $R^{11}$-1 |
| 1178. | Ar-3 | XYZ-n | $R^{11}$-2 |
| 1179. | Ar-3 | XYZ-n | $R^{11}$-3 |
| 1180. | Ar-3 | XYZ-n | $R^{11}$-4 |
| 1181. | Ar-3 | XYZ-n | $R^{11}$-5 |
| 1182. | Ar-3 | XYZ-n | $R^{11}$-6 |
| 1183. | Ar-3 | XYZ-n | $R^{11}$-7 |
| 1184. | Ar-3 | XYZ-n | $R^{11}$-8 |
| 1185. | Ar-3 | XYZ-n | $R^{11}$-9 |
| 1186. | Ar-3 | XYZ-n | $R^{11}$-10 |
| 1187. | Ar-3 | XYZ-n | $R^{11}$-11 |
| 1188. | Ar-3 | XYZ-n | $R^{11}$-12 |
| 1189. | Ar-3 | XYZ-n | $R^{11}$-13 |
| 1190. | Ar-3 | XYZ-n | $R^{11}$-14 |
| 1191. | Ar-3 | XYZ-n | $R^{11}$-15 |
| 1192. | Ar-3 | XYZ-n | $R^{11}$-16 |
| 1193. | Ar-3 | XYZ-n | $R^{11}$-17 |
| 1194. | Ar-3 | XYZ-n | $R^{11}$-18 |
| 1195. | Ar-3 | XYZ-n | $R^{11}$-19 |
| 1196. | Ar-3 | XYZ-n | $R^{11}$-20 |
| 1197. | Ar-3 | XYZ-n | $R^{11}$-21 |
| 1198. | Ar-3 | XYZ-o | $R^{11}$-1 |
| 1199. | Ar-3 | XYZ-o | $R^{11}$-2 |
| 1200. | Ar-3 | XYZ-o | $R^{11}$-3 |

TABLE C-continued

|  | Ar | -X-Y-Z- | R¹¹ |
|---|---|---|---|
| 1201. | Ar-3 | XYZ-o | R¹¹-4 |
| 1202. | Ar-3 | XYZ-o | R¹¹-5 |
| 1203. | Ar-3 | XYZ-o | R¹¹-6 |
| 1204. | Ar-3 | XYZ-o | R¹¹-7 |
| 1205. | Ar-3 | XYZ-o | R¹¹-8 |
| 1206. | Ar-3 | XYZ-o | R¹¹-9 |
| 1207. | Ar-3 | XYZ-o | R¹¹-10 |
| 1208. | Ar-3 | XYZ-o | R¹¹-11 |
| 1209. | Ar-3 | XYZ-o | R¹¹-12 |
| 1210. | Ar-3 | XYZ-o | R¹¹-13 |
| 1211. | Ar-3 | XYZ-o | R¹¹-14 |
| 1212. | Ar-3 | XYZ-o | R¹¹-15 |
| 1213. | Ar-3 | XYZ-o | R¹¹-16 |
| 1214. | Ar-3 | XYZ-o | R¹¹-17 |
| 1215. | Ar-3 | XYZ-o | R¹¹-18 |
| 1216. | Ar-3 | XYZ-o | R¹¹-19 |
| 1217. | Ar-3 | XYZ-o | R¹¹-20 |
| 1218. | Ar-3 | XYZ-o | R¹¹-21 |
| 1219. | Ar-3 | XYZ-p | R¹¹-1 |
| 1220. | Ar-3 | XYZ-p | R¹¹-2 |
| 1221. | Ar-3 | XYZ-p | R¹¹-3 |
| 1222. | Ar-3 | XYZ-p | R¹¹-4 |
| 1223. | Ar-3 | XYZ-p | R¹¹-5 |
| 1224. | Ar-3 | XYZ-p | R¹¹-6 |
| 1225. | Ar-3 | XYZ-p | R¹¹-7 |
| 1226. | Ar-3 | XYZ-p | R¹¹-8 |
| 1227. | Ar-3 | XYZ-p | R¹¹-9 |
| 1228. | Ar-3 | XYZ-p | R¹¹-10 |
| 1229. | Ar-3 | XYZ-p | R¹¹-11 |
| 1230. | Ar-3 | XYZ-p | R¹¹-12 |
| 1231. | Ar-3 | XYZ-p | R¹¹-13 |
| 1232. | Ar-3 | XYZ-p | R¹¹-14 |
| 1233. | Ar-3 | XYZ-p | R¹¹-15 |
| 1234. | Ar-3 | XYZ-p | R¹¹-16 |
| 1235. | Ar-3 | XYZ-p | R¹¹-17 |
| 1236. | Ar-3 | XYZ-p | R¹¹-18 |
| 1237. | Ar-3 | XYZ-p | R¹¹-19 |
| 1238. | Ar-3 | XYZ-p | R¹¹-20 |
| 1239. | Ar-3 | XYZ-p | R¹¹-21 |
| 1240. | Ar-3 | XYZ-q | R¹¹-1 |
| 1241. | Ar-3 | XYZ-q | R¹¹-2 |
| 1242. | Ar-3 | XYZ-q | R¹¹-3 |
| 1243. | Ar-3 | XYZ-q | R¹¹-4 |
| 1244. | Ar-3 | XYZ-q | R¹¹-5 |
| 1245. | Ar-3 | XYZ-q | R¹¹-6 |
| 1246. | Ar-3 | XYZ-q | R¹¹-7 |
| 1247. | Ar-3 | XYZ-q | R¹¹-8 |
| 1248. | Ar-3 | XYZ-q | R¹¹-9 |
| 1249. | Ar-3 | XYZ-q | R¹¹-10 |
| 1250. | Ar-3 | XYZ-q | R¹¹-11 |
| 1251. | Ar-3 | XYZ-q | R¹¹-12 |
| 1252. | Ar-3 | XYZ-q | R¹¹-13 |
| 1253. | Ar-3 | XYZ-q | R¹¹-14 |
| 1254. | Ar-3 | XYZ-q | R¹¹-15 |
| 1255. | Ar-3 | XYZ-q | R¹¹-16 |
| 1256. | Ar-3 | XYZ-q | R¹¹-17 |
| 1257. | Ar-3 | XYZ-q | R¹¹-18 |
| 1258. | Ar-3 | XYZ-q | R¹¹-19 |
| 1259. | Ar-3 | XYZ-q | R¹¹-20 |
| 1260. | Ar-3 | XYZ-q | R¹¹-21 |
| 1261. | Ar-3 | XYZ-r | R¹¹-1 |
| 1262. | Ar-3 | XYZ-r | R¹¹-2 |
| 1263. | Ar-3 | XYZ-r | R¹¹-3 |
| 1264. | Ar-3 | XYZ-r | R¹¹-4 |
| 1265. | Ar-3 | XYZ-r | R¹¹-5 |
| 1266. | Ar-3 | XYZ-r | R¹¹-6 |
| 1267. | Ar-3 | XYZ-r | R¹¹-7 |
| 1268. | Ar-3 | XYZ-r | R¹¹-8 |
| 1269. | Ar-3 | XYZ-r | R¹¹-9 |
| 1270. | Ar-3 | XYZ-r | R¹¹-10 |
| 1271. | Ar-3 | XYZ-r | R¹¹-11 |
| 1272. | Ar-3 | XYZ-r | R¹¹-12 |
| 1273. | Ar-3 | XYZ-r | R¹¹-13 |
| 1274. | Ar-3 | XYZ-r | R¹¹-14 |
| 1275. | Ar-3 | XYZ-r | R¹¹-15 |
| 1276. | Ar-3 | XYZ-r | R¹¹-16 |
| 1277. | Ar-3 | XYZ-r | R¹¹-17 |
| 1278. | Ar-3 | XYZ-r | R¹¹-18 |
| 1279. | Ar-3 | XYZ-r | R¹¹-19 |
| 1280. | Ar-3 | XYZ-r | R¹¹-20 |
| 1281. | Ar-3 | XYZ-r | R¹¹-21 |
| 1282. | Ar-3 | XYZ-s | R¹¹-1 |
| 1283. | Ar-3 | XYZ-s | R¹¹-2 |
| 1284. | Ar-3 | XYZ-s | R¹¹-3 |
| 1285. | Ar-3 | XYZ-s | R¹¹-4 |
| 1286. | Ar-3 | XYZ-s | R¹¹-5 |
| 1287. | Ar-3 | XYZ-s | R¹¹-6 |
| 1288. | Ar-3 | XYZ-s | R¹¹-7 |
| 1289. | Ar-3 | XYZ-s | R¹¹-8 |
| 1290. | Ar-3 | XYZ-s | R¹¹-9 |
| 1291. | Ar-3 | XYZ-s | R¹¹-10 |
| 1292. | Ar-3 | XYZ-s | R¹¹-11 |
| 1293. | Ar-3 | XYZ-s | R¹¹-12 |
| 1294. | Ar-3 | XYZ-s | R¹¹-13 |
| 1295. | Ar-3 | XYZ-s | R¹¹-14 |
| 1296. | Ar-3 | XYZ-s | R¹¹-15 |
| 1297. | Ar-3 | XYZ-s | R¹¹-16 |
| 1298. | Ar-3 | XYZ-s | R¹¹-17 |
| 1299. | Ar-3 | XYZ-s | R¹¹-18 |
| 1300. | Ar-3 | XYZ-s | R¹¹-19 |
| 1301. | Ar-3 | XYZ-s | R¹¹-20 |
| 1302. | Ar-3 | XYZ-s | R¹¹-21 |
| 1303. | Ar-3 | XYZ-t | R¹¹-1 |
| 1304. | Ar-3 | XYZ-t | R¹¹-2 |
| 1305. | Ar-3 | XYZ-t | R¹¹-3 |
| 1306. | Ar-3 | XYZ-t | R¹¹-4 |
| 1307. | Ar-3 | XYZ-t | R¹¹-5 |
| 1308. | Ar-3 | XYZ-t | R¹¹-6 |
| 1309. | Ar-3 | XYZ-t | R¹¹-7 |
| 1310. | Ar-3 | XYZ-t | R¹¹-8 |
| 1311. | Ar-3 | XYZ-t | R¹¹-9 |
| 1312. | Ar-3 | XYZ-t | R¹¹-10 |
| 1313. | Ar-3 | XYZ-t | R¹¹-11 |
| 1314. | Ar-3 | XYZ-t | R¹¹-12 |
| 1315. | Ar-3 | XYZ-t | R¹¹-13 |
| 1316. | Ar-3 | XYZ-t | R¹¹-14 |
| 1317. | Ar-3 | XYZ-t | R¹¹-15 |
| 1318. | Ar-3 | XYZ-t | R¹¹-16 |
| 1319. | Ar-3 | XYZ-t | R¹¹-17 |
| 1320. | Ar-3 | XYZ-t | R¹¹-18 |
| 1321. | Ar-3 | XYZ-t | R¹¹-19 |
| 1322. | Ar-3 | XYZ-t | R¹¹-20 |
| 1323. | Ar-3 | XYZ-t | R¹¹-21 |
| 1324. | Ar-3 | XYZ-u | R¹¹-1 |
| 1325. | Ar-3 | XYZ-u | R¹¹-2 |
| 1326. | Ar-3 | XYZ-u | R¹¹-3 |
| 1327. | Ar-3 | XYZ-u | R¹¹-4 |
| 1328. | Ar-3 | XYZ-u | R¹¹-5 |
| 1329. | Ar-3 | XYZ-u | R¹¹-6 |
| 1330. | Ar-3 | XYZ-u | R¹¹-7 |
| 1331. | Ar-3 | XYZ-u | R¹¹-8 |
| 1332. | Ar-3 | XYZ-u | R¹¹-9 |
| 1333. | Ar-3 | XYZ-u | R¹¹-10 |
| 1334. | Ar-3 | XYZ-u | R¹¹-11 |
| 1335. | Ar-3 | XYZ-u | R¹¹-12 |
| 1336. | Ar-3 | XYZ-u | R¹¹-13 |
| 1337. | Ar-3 | XYZ-u | R¹¹-14 |
| 1338. | Ar-3 | XYZ-u | R¹¹-15 |
| 1339. | Ar-3 | XYZ-u | R¹¹-16 |
| 1340. | Ar-3 | XYZ-u | R¹¹-17 |
| 1341. | Ar-3 | XYZ-u | R¹¹-18 |
| 1342. | Ar-3 | XYZ-u | R¹¹-19 |
| 1343. | Ar-3 | XYZ-u | R¹¹-20 |
| 1344. | Ar-3 | XYZ-u | R¹¹-21 |
| 1345. | Ar-3 | XYZ-v | R¹¹-1 |
| 1346. | Ar-3 | XYZ-v | R¹¹-2 |
| 1347. | Ar-3 | XYZ-v | R¹¹-3 |
| 1348. | Ar-3 | XYZ-v | R¹¹-4 |
| 1349. | Ar-3 | XYZ-v | R¹¹-5 |
| 1350. | Ar-3 | XYZ-v | R¹¹-6 |
| 1351. | Ar-3 | XYZ-v | R¹¹-7 |
| 1352. | Ar-3 | XYZ-v | R¹¹-8 |
| 1353. | Ar-3 | XYZ-v | R¹¹-9 |
| 1354. | Ar-3 | XYZ-v | R¹¹-10 |
| 1355. | Ar-3 | XYZ-v | R¹¹-11 |
| 1356. | Ar-3 | XYZ-v | R¹¹-12 |

TABLE C-continued

|  | Ar | -X-Y-Z- | $R^{11}$ |
|---|---|---|---|
| 1357. | Ar-3 | XYZ-v | $R^{11}$-13 |
| 1358. | Ar-3 | XYZ-v | $R^{11}$-14 |
| 1359. | Ar-3 | XYZ-v | $R^{11}$-15 |
| 1360. | Ar-3 | XYZ-v | $R^{11}$-16 |
| 1361. | Ar-3 | XYZ-v | $R^{11}$-17 |
| 1362. | Ar-3 | XYZ-v | $R^{11}$-18 |
| 1363. | Ar-3 | XYZ-v | $R^{11}$-19 |
| 1364. | Ar-3 | XYZ-v | $R^{11}$-20 |
| 1365. | Ar-3 | XYZ-v | $R^{11}$-21 |
| 1366. | Ar-3 | XYZ-w | $R^{11}$-1 |
| 1367. | Ar-3 | XYZ-w | $R^{11}$-2 |
| 1368. | Ar-3 | XYZ-w | $R^{11}$-3 |
| 1369. | Ar-3 | XYZ-w | $R^{11}$-4 |
| 1370. | Ar-3 | XYZ-w | $R^{11}$-5 |
| 1371. | Ar-3 | XYZ-w | $R^{11}$-6 |
| 1372. | Ar-3 | XYZ-w | $R^{11}$-7 |
| 1373. | Ar-3 | XYZ-w | $R^{11}$-8 |
| 1374. | Ar-3 | XYZ-w | $R^{11}$-9 |
| 1375. | Ar-3 | XYZ-w | $R^{11}$-10 |
| 1376. | Ar-3 | XYZ-w | $R^{11}$-11 |
| 1377. | Ar-3 | XYZ-w | $R^{11}$-12 |
| 1378. | Ar-3 | XYZ-w | $R^{11}$-13 |
| 1379. | Ar-3 | XYZ-w | $R^{11}$-14 |
| 1380. | Ar-3 | XYZ-w | $R^{11}$-15 |
| 1381. | Ar-3 | XYZ-w | $R^{11}$-16 |
| 1382. | Ar-3 | XYZ-w | $R^{11}$-17 |
| 1383. | Ar-3 | XYZ-w | $R^{11}$-18 |
| 1384. | Ar-3 | XYZ-w | $R^{11}$-19 |
| 1385. | Ar-3 | XYZ-w | $R^{11}$-20 |
| 1386. | Ar-3 | XYZ-w | $R^{11}$-21 |
| 1387. | Ar-4 | XYZ-a | $R^{11}$-1 |
| 1388. | Ar-4 | XYZ-a | $R^{11}$-2 |
| 1389. | Ar-4 | XYZ-a | $R^{11}$-3 |
| 1390. | Ar-4 | XYZ-a | $R^{11}$-4 |
| 1391. | Ar-4 | XYZ-a | $R^{11}$-5 |
| 1392. | Ar-4 | XYZ-a | $R^{11}$-6 |
| 1393. | Ar-4 | XYZ-a | $R^{11}$-7 |
| 1394. | Ar-4 | XYZ-a | $R^{11}$-8 |
| 1395. | Ar-4 | XYZ-a | $R^{11}$-9 |
| 1396. | Ar-4 | XYZ-a | $R^{11}$-10 |
| 1397. | Ar-4 | XYZ-a | $R^{11}$-11 |
| 1398. | Ar-4 | XYZ-a | $R^{11}$-12 |
| 1399. | Ar-4 | XYZ-a | $R^{11}$-13 |
| 1400. | Ar-4 | XYZ-a | $R^{11}$-14 |
| 1401. | Ar-4 | XYZ-a | $R^{11}$-15 |
| 1402. | Ar-4 | XYZ-a | $R^{11}$-16 |
| 1403. | Ar-4 | XYZ-a | $R^{11}$-17 |
| 1404. | Ar-4 | XYZ-a | $R^{11}$-18 |
| 1405. | Ar-4 | XYZ-a | $R^{11}$-19 |
| 1406. | Ar-4 | XYZ-a | $R^{11}$-20 |
| 1407. | Ar-4 | XYZ-a | $R^{11}$-21 |
| 1408. | Ar-4 | XYZ-b | $R^{11}$-1 |
| 1409. | Ar-4 | XYZ-b | $R^{11}$-2 |
| 1410. | Ar-4 | XYZ-b | $R^{11}$-3 |
| 1411. | Ar-4 | XYZ-b | $R^{11}$-4 |
| 1412. | Ar-4 | XYZ-b | $R^{11}$-5 |
| 1413. | Ar-4 | XYZ-b | $R^{11}$-6 |
| 1414. | Ar-4 | XYZ-b | $R^{11}$-7 |
| 1415. | Ar-4 | XYZ-b | $R^{11}$-8 |
| 1416. | Ar-4 | XYZ-b | $R^{11}$-9 |
| 1417. | Ar-4 | XYZ-b | $R^{11}$-10 |
| 1418. | Ar-4 | XYZ-b | $R^{11}$-11 |
| 1419. | Ar-4 | XYZ-b | $R^{11}$-12 |
| 1420. | Ar-4 | XYZ-b | $R^{11}$-13 |
| 1421. | Ar-4 | XYZ-b | $R^{11}$-14 |
| 1422. | Ar-4 | XYZ-b | $R^{11}$-15 |
| 1423. | Ar-4 | XYZ-b | $R^{11}$-16 |
| 1424. | Ar-4 | XYZ-b | $R^{11}$-17 |
| 1425. | Ar-4 | XYZ-b | $R^{11}$-18 |
| 1426. | Ar-4 | XYZ-b | $R^{11}$-19 |
| 1427. | Ar-4 | XYZ-b | $R^{11}$-20 |
| 1428. | Ar-4 | XYZ-b | $R^{11}$-21 |
| 1429. | Ar-4 | XYZ-c | $R^{11}$-1 |
| 1430. | Ar-4 | XYZ-c | $R^{11}$-2 |
| 1431. | Ar-4 | XYZ-c | $R^{11}$-3 |
| 1432. | Ar-4 | XYZ-c | $R^{11}$-4 |
| 1433. | Ar-4 | XYZ-c | $R^{11}$-5 |
| 1434. | Ar-4 | XYZ-c | $R^{11}$-6 |
| 1435. | Ar-4 | XYZ-c | $R^{11}$-7 |
| 1436. | Ar-4 | XYZ-c | $R^{11}$-8 |
| 1437. | Ar-4 | XYZ-c | $R^{11}$-9 |
| 1438. | Ar-4 | XYZ-c | $R^{11}$-10 |
| 1439. | Ar-4 | XYZ-c | $R^{11}$-11 |
| 1440. | Ar-4 | XYZ-c | $R^{11}$-12 |
| 1441. | Ar-4 | XYZ-c | $R^{11}$-13 |
| 1442. | Ar-4 | XYZ-c | $R^{11}$-14 |
| 1443. | Ar-4 | XYZ-c | $R^{11}$-15 |
| 1444. | Ar-4 | XYZ-c | $R^{11}$-16 |
| 1445. | Ar-4 | XYZ-c | $R^{11}$-17 |
| 1446. | Ar-4 | XYZ-c | $R^{11}$-18 |
| 1447. | Ar-4 | XYZ-c | $R^{11}$-19 |
| 1448. | Ar-4 | XYZ-c | $R^{11}$-20 |
| 1449. | Ar-4 | XYZ-c | $R^{11}$-21 |
| 1450. | Ar-4 | XYZ-d | $R^{11}$-1 |
| 1451. | Ar-4 | XYZ-d | $R^{11}$-2 |
| 1452. | Ar-4 | XYZ-d | $R^{11}$-3 |
| 1453. | Ar-4 | XYZ-d | $R^{11}$-4 |
| 1454. | Ar-4 | XYZ-d | $R^{11}$-5 |
| 1455. | Ar-4 | XYZ-d | $R^{11}$-6 |
| 1456. | Ar-4 | XYZ-d | $R^{11}$-7 |
| 1457. | Ar-4 | XYZ-d | $R^{11}$-8 |
| 1458. | Ar-4 | XYZ-d | $R^{11}$-9 |
| 1459. | Ar-4 | XYZ-d | $R^{11}$-10 |
| 1460. | Ar-4 | XYZ-d | $R^{11}$-11 |
| 1461. | Ar-4 | XYZ-d | $R^{11}$-12 |
| 1462. | Ar-4 | XYZ-d | $R^{11}$-13 |
| 1463. | Ar-4 | XYZ-d | $R^{11}$-14 |
| 1464. | Ar-4 | XYZ-d | $R^{11}$-15 |
| 1465. | Ar-4 | XYZ-d | $R^{11}$-16 |
| 1466. | Ar-4 | XYZ-d | $R^{11}$-17 |
| 1467. | Ar-4 | XYZ-d | $R^{11}$-18 |
| 1468. | Ar-4 | XYZ-d | $R^{11}$-19 |
| 1469. | Ar-4 | XYZ-d | $R^{11}$-20 |
| 1470. | Ar-4 | XYZ-d | $R^{11}$-21 |
| 1471. | Ar-4 | XYZ-e | $R^{11}$-1 |
| 1472. | Ar-4 | XYZ-e | $R^{11}$-2 |
| 1473. | Ar-4 | XYZ-e | $R^{11}$-3 |
| 1474. | Ar-4 | XYZ-e | $R^{11}$-4 |
| 1475. | Ar-4 | XYZ-e | $R^{11}$-5 |
| 1476. | Ar-4 | XYZ-e | $R^{11}$-6 |
| 1477. | Ar-4 | XYZ-e | $R^{11}$-7 |
| 1478. | Ar-4 | XYZ-e | $R^{11}$-8 |
| 1479. | Ar-4 | XYZ-e | $R^{11}$-9 |
| 1480. | Ar-4 | XYZ-e | $R^{11}$-10 |
| 1481. | Ar-4 | XYZ-e | $R^{11}$-11 |
| 1482. | Ar-4 | XYZ-e | $R^{11}$-12 |
| 1483. | Ar-4 | XYZ-e | $R^{11}$-13 |
| 1484. | Ar-4 | XYZ-e | $R^{11}$-14 |
| 1485. | Ar-4 | XYZ-e | $R^{11}$-15 |
| 1486. | Ar-4 | XYZ-e | $R^{11}$-16 |
| 1487. | Ar-4 | XYZ-e | $R^{11}$-17 |
| 1488. | Ar-4 | XYZ-e | $R^{11}$-18 |
| 1489. | Ar-4 | XYZ-e | $R^{11}$-19 |
| 1490. | Ar-4 | XYZ-e | $R^{11}$-20 |
| 1491. | Ar-4 | XYZ-e | $R^{11}$-21 |
| 1492. | Ar-4 | XYZ-f | $R^{11}$-1 |
| 1493. | Ar-4 | XYZ-f | $R^{11}$-2 |
| 1494. | Ar-4 | XYZ-f | $R^{11}$-3 |
| 1495. | Ar-4 | XYZ-f | $R^{11}$-4 |
| 1496. | Ar-4 | XYZ-f | $R^{11}$-5 |
| 1497. | Ar-4 | XYZ-f | $R^{11}$-6 |
| 1498. | Ar-4 | XYZ-f | $R^{11}$-7 |
| 1499. | Ar-4 | XYZ-f | $R^{11}$-8 |
| 1500. | Ar-4 | XYZ-f | $R^{11}$-9 |
| 1501. | Ar-4 | XYZ-f | $R^{11}$-10 |
| 1502. | Ar-4 | XYZ-f | $R^{11}$-11 |
| 1503. | Ar-4 | XYZ-f | $R^{11}$-12 |
| 1504. | Ar-4 | XYZ-f | $R^{11}$-13 |
| 1505. | Ar-4 | XYZ-f | $R^{11}$-14 |
| 1506. | Ar-4 | XYZ-f | $R^{11}$-15 |
| 1507. | Ar-4 | XYZ-f | $R^{11}$-16 |
| 1508. | Ar-4 | XYZ-f | $R^{11}$-17 |
| 1509. | Ar-4 | XYZ-f | $R^{11}$-18 |
| 1510. | Ar-4 | XYZ-f | $R^{11}$-19 |
| 1511. | Ar-4 | XYZ-f | $R^{11}$-20 |
| 1512. | Ar-4 | XYZ-f | $R^{11}$-21 |

TABLE C-continued

|  | Ar | -X-Y-Z- | $R^{11}$ |
|---|---|---|---|
| 1513. | Ar-4 | XYZ-g | $R^{11}$-1 |
| 1514. | Ar-4 | XYZ-g | $R^{11}$-2 |
| 1515. | Ar-4 | XYZ-g | $R^{11}$-3 |
| 1516. | Ar-4 | XYZ-g | $R^{11}$-4 |
| 1517. | Ar-4 | XYZ-g | $R^{11}$-5 |
| 1518. | Ar-4 | XYZ-g | $R^{11}$-6 |
| 1519. | Ar-4 | XYZ-g | $R^{11}$-7 |
| 1520. | Ar-4 | XYZ-g | $R^{11}$-8 |
| 1521. | Ar-4 | XYZ-g | $R^{11}$-9 |
| 1522. | Ar-4 | XYZ-g | $R^{11}$-10 |
| 1523. | Ar-4 | XYZ-g | $R^{11}$-11 |
| 1524. | Ar-4 | XYZ-g | $R^{11}$-12 |
| 1525. | Ar-4 | XYZ-g | $R^{11}$-13 |
| 1526. | Ar-4 | XYZ-g | $R^{11}$-14 |
| 1527. | Ar-4 | XYZ-g | $R^{11}$-15 |
| 1528. | Ar-4 | XYZ-g | $R^{11}$-16 |
| 1529. | Ar-4 | XYZ-g | $R^{11}$-17 |
| 1530. | Ar-4 | XYZ-g | $R^{11}$-18 |
| 1531. | Ar-4 | XYZ-g | $R^{11}$-19 |
| 1532. | Ar-4 | XYZ-g | $R^{11}$-20 |
| 1533. | Ar-4 | XYZ-g | $R^{11}$-21 |
| 1534. | Ar-4 | XYZ-h | $R^{11}$-1 |
| 1535. | Ar-4 | XYZ-h | $R^{11}$-2 |
| 1536. | Ar-4 | XYZ-h | $R^{11}$-3 |
| 1537. | Ar-4 | XYZ-h | $R^{11}$-4 |
| 1538. | Ar-4 | XYZ-h | $R^{11}$-5 |
| 1539. | Ar-4 | XYZ-h | $R^{11}$-6 |
| 1540. | Ar-4 | XYZ-h | $R^{11}$-7 |
| 1541. | Ar-4 | XYZ-h | $R^{11}$-8 |
| 1542. | Ar-4 | XYZ-h | $R^{11}$-9 |
| 1543. | Ar-4 | XYZ-h | $R^{11}$-10 |
| 1544. | Ar-4 | XYZ-h | $R^{11}$-11 |
| 1545. | Ar-4 | XYZ-h | $R^{11}$-12 |
| 1546. | Ar-4 | XYZ-h | $R^{11}$-13 |
| 1547. | Ar-4 | XYZ-h | $R^{11}$-14 |
| 1548. | Ar-4 | XYZ-h | $R^{11}$-15 |
| 1549. | Ar-4 | XYZ-h | $R^{11}$-16 |
| 1550. | Ar-4 | XYZ-h | $R^{11}$-17 |
| 1551. | Ar-4 | XYZ-h | $R^{11}$-18 |
| 1552. | Ar-4 | XYZ-h | $R^{11}$-19 |
| 1553. | Ar-4 | XYZ-h | $R^{11}$-20 |
| 1554. | Ar-4 | XYZ-h | $R^{11}$-21 |
| 1555. | Ar-4 | XYZ-i | $R^{11}$-1 |
| 1556. | Ar-4 | XYZ-i | $R^{11}$-2 |
| 1557. | Ar-4 | XYZ-i | $R^{11}$-3 |
| 1558. | Ar-4 | XYZ-i | $R^{11}$-4 |
| 1559. | Ar-4 | XYZ-i | $R^{11}$-5 |
| 1560. | Ar-4 | XYZ-i | $R^{11}$-6 |
| 1561. | Ar-4 | XYZ-i | $R^{11}$-7 |
| 1562. | Ar-4 | XYZ-i | $R^{11}$-8 |
| 1563. | Ar-4 | XYZ-i | $R^{11}$-9 |
| 1564. | Ar-4 | XYZ-i | $R^{11}$-10 |
| 1565. | Ar-4 | XYZ-i | $R^{11}$-11 |
| 1566. | Ar-4 | XYZ-i | $R^{11}$-12 |
| 1567. | Ar-4 | XYZ-i | $R^{11}$-13 |
| 1568. | Ar-4 | XYZ-i | $R^{11}$-14 |
| 1569. | Ar-4 | XYZ-i | $R^{11}$-15 |
| 1570. | Ar-4 | XYZ-i | $R^{11}$-16 |
| 1571. | Ar-4 | XYZ-i | $R^{11}$-17 |
| 1572. | Ar-4 | XYZ-i | $R^{11}$-18 |
| 1573. | Ar-4 | XYZ-i | $R^{11}$-19 |
| 1574. | Ar-4 | XYZ-i | $R^{11}$-20 |
| 1575. | Ar-4 | XYZ-i | $R^{11}$-21 |
| 1576. | Ar-4 | XYZ-k | $R^{11}$-1 |
| 1577. | Ar-4 | XYZ-k | $R^{11}$-2 |
| 1578. | Ar-4 | XYZ-k | $R^{11}$-3 |
| 1579. | Ar-4 | XYZ-k | $R^{11}$-4 |
| 1580. | Ar-4 | XYZ-k | $R^{11}$-5 |
| 1581. | Ar-4 | XYZ-k | $R^{11}$-6 |
| 1582. | Ar-4 | XYZ-k | $R^{11}$-7 |
| 1583. | Ar-4 | XYZ-k | $R^{11}$-8 |
| 1584. | Ar-4 | XYZ-k | $R^{11}$-9 |
| 1585. | Ar-4 | XYZ-k | $R^{11}$-10 |
| 1586. | Ar-4 | XYZ-k | $R^{11}$-11 |
| 1587. | Ar-4 | XYZ-k | $R^{11}$-12 |
| 1588. | Ar-4 | XYZ-k | $R^{11}$-13 |
| 1589. | Ar-4 | XYZ-k | $R^{11}$-14 |
| 1590. | Ar-4 | XYZ-k | $R^{11}$-15 |
| 1591. | Ar-4 | XYZ-k | $R^{11}$-16 |
| 1592. | Ar-4 | XYZ-k | $R^{11}$-17 |
| 1593. | Ar-4 | XYZ-k | $R^{11}$-18 |
| 1594. | Ar-4 | XYZ-k | $R^{11}$-19 |
| 1595. | Ar-4 | XYZ-k | $R^{11}$-20 |
| 1596. | Ar-4 | XYZ-k | $R^{11}$-21 |
| 1597. | Ar-4 | XYZ-l | $R^{11}$-1 |
| 1598. | Ar-4 | XYZ-l | $R^{11}$-2 |
| 1599. | Ar-4 | XYZ-l | $R^{11}$-3 |
| 1600. | Ar-4 | XYZ-l | $R^{11}$-4 |
| 1601. | Ar-4 | XYZ-l | $R^{11}$-5 |
| 1602. | Ar-4 | XYZ-l | $R^{11}$-6 |
| 1603. | Ar-4 | XYZ-l | $R^{11}$-7 |
| 1604. | Ar-4 | XYZ-l | $R^{11}$-8 |
| 1605. | Ar-4 | XYZ-l | $R^{11}$-9 |
| 1606. | Ar-4 | XYZ-l | $R^{11}$-10 |
| 1607. | Ar-4 | XYZ-l | $R^{11}$-11 |
| 1608. | Ar-4 | XYZ-l | $R^{11}$-12 |
| 1609. | Ar-4 | XYZ-l | $R^{11}$-13 |
| 1610. | Ar-4 | XYZ-l | $R^{11}$-14 |
| 1611. | Ar-4 | XYZ-l | $R^{11}$-15 |
| 1612. | Ar-4 | XYZ-l | $R^{11}$-16 |
| 1613. | Ar-4 | XYZ-l | $R^{11}$-17 |
| 1614. | Ar-4 | XYZ-l | $R^{11}$-18 |
| 1615. | Ar-4 | XYZ-l | $R^{11}$-19 |
| 1616. | Ar-4 | XYZ-l | $R^{11}$-20 |
| 1617. | Ar-4 | XYZ-l | $R^{11}$-21 |
| 1618. | Ar-4 | XYZ-m | $R^{11}$-1 |
| 1619. | Ar-4 | XYZ-m | $R^{11}$-2 |
| 1620. | Ar-4 | XYZ-m | $R^{11}$-3 |
| 1621. | Ar-4 | XYZ-m | $R^{11}$-4 |
| 1622. | Ar-4 | XYZ-m | $R^{11}$-5 |
| 1623. | Ar-4 | XYZ-m | $R^{11}$-6 |
| 1624. | Ar-4 | XYZ-m | $R^{11}$-7 |
| 1625. | Ar-4 | XYZ-m | $R^{11}$-8 |
| 1626. | Ar-4 | XYZ-m | $R^{11}$-9 |
| 1627. | Ar-4 | XYZ-m | $R^{11}$-10 |
| 1628. | Ar-4 | XYZ-m | $R^{11}$-11 |
| 1629. | Ar-4 | XYZ-m | $R^{11}$-12 |
| 1630. | Ar-4 | XYZ-m | $R^{11}$-13 |
| 1631. | Ar-4 | XYZ-m | $R^{11}$-14 |
| 1632. | Ar-4 | XYZ-m | $R^{11}$-15 |
| 1633. | Ar-4 | XYZ-m | $R^{11}$-16 |
| 1634. | Ar-4 | XYZ-m | $R^{11}$-17 |
| 1635. | Ar-4 | XYZ-m | $R^{11}$-18 |
| 1636. | Ar-4 | XYZ-m | $R^{11}$-19 |
| 1637. | Ar-4 | XYZ-m | $R^{11}$-20 |
| 1638. | Ar-4 | XYZ-m | $R^{11}$-21 |
| 1639. | Ar-4 | XYZ-n | $R^{11}$-1 |
| 1640. | Ar-4 | XYZ-n | $R^{11}$-2 |
| 1641. | Ar-4 | XYZ-n | $R^{11}$-3 |
| 1642. | Ar-4 | XYZ-n | $R^{11}$-4 |
| 1643. | Ar-4 | XYZ-n | $R^{11}$-5 |
| 1644. | Ar-4 | XYZ-n | $R^{11}$-6 |
| 1645. | Ar-4 | XYZ-n | $R^{11}$-7 |
| 1646. | Ar-4 | XYZ-n | $R^{11}$-8 |
| 1647. | Ar-4 | XYZ-n | $R^{11}$-9 |
| 1648. | Ar-4 | XYZ-n | $R^{11}$-10 |
| 1649. | Ar-4 | XYZ-n | $R^{11}$-11 |
| 1650. | Ar-4 | XYZ-n | $R^{11}$-12 |
| 1651. | Ar-4 | XYZ-n | $R^{11}$-13 |
| 1652. | Ar-4 | XYZ-n | $R^{11}$-14 |
| 1653. | Ar-4 | XYZ-n | $R^{11}$-15 |
| 1654. | Ar-4 | XYZ-n | $R^{11}$-16 |
| 1655. | Ar-4 | XYZ-n | $R^{11}$-17 |
| 1656. | Ar-4 | XYZ-n | $R^{11}$-18 |
| 1657. | Ar-4 | XYZ-n | $R^{11}$-19 |
| 1658. | Ar-4 | XYZ-n | $R^{11}$-20 |
| 1659. | Ar-4 | XYZ-n | $R^{11}$-21 |
| 1660. | Ar-4 | XYZ-o | $R^{11}$-1 |
| 1661. | Ar-4 | XYZ-o | $R^{11}$-2 |
| 1662. | Ar-4 | XYZ-o | $R^{11}$-3 |
| 1663. | Ar-4 | XYZ-o | $R^{11}$-4 |
| 1664. | Ar-4 | XYZ-o | $R^{11}$-5 |
| 1665. | Ar-4 | XYZ-o | $R^{11}$-6 |
| 1666. | Ar-4 | XYZ-o | $R^{11}$-7 |
| 1667. | Ar-4 | XYZ-o | $R^{11}$-8 |
| 1668. | Ar-4 | XYZ-o | $R^{11}$-9 |

TABLE C-continued

|  | Ar | -X-Y-Z- | R^11 |
|---|---|---|---|
| 1669. | Ar-4 | XYZ-o | R^11-10 |
| 1670. | Ar-4 | XYZ-o | R^11-11 |
| 1671. | Ar-4 | XYZ-o | R^11-12 |
| 1672. | Ar-4 | XYZ-o | R^11-13 |
| 1673. | Ar-4 | XYZ-o | R^11-14 |
| 1674. | Ar-4 | XYZ-o | R^11-15 |
| 1675. | Ar-4 | XYZ-o | R^11-16 |
| 1676. | Ar-4 | XYZ-o | R^11-17 |
| 1677. | Ar-4 | XYZ-o | R^11-18 |
| 1678. | Ar-4 | XYZ-o | R^11-19 |
| 1679. | Ar-4 | XYZ-o | R^11-20 |
| 1680. | Ar-4 | XYZ-o | R^11-21 |
| 1681. | Ar-4 | XYZ-p | R^11-1 |
| 1682. | Ar-4 | XYZ-p | R^11-2 |
| 1683. | Ar-4 | XYZ-p | R^11-3 |
| 1684. | Ar-4 | XYZ-p | R^11-4 |
| 1685. | Ar-4 | XYZ-p | R^11-5 |
| 1686. | Ar-4 | XYZ-p | R^11-6 |
| 1687. | Ar-4 | XYZ-p | R^11-7 |
| 1688. | Ar-4 | XYZ-p | R^11-8 |
| 1689. | Ar-4 | XYZ-p | R^11-9 |
| 1690. | Ar-4 | XYZ-p | R^11-10 |
| 1691. | Ar-4 | XYZ-p | R^11-11 |
| 1692. | Ar-4 | XYZ-p | R^11-12 |
| 1693. | Ar-4 | XYZ-p | R^11-13 |
| 1694. | Ar-4 | XYZ-p | R^11-14 |
| 1695. | Ar-4 | XYZ-p | R^11-15 |
| 1696. | Ar-4 | XYZ-p | R^11-16 |
| 1697. | Ar-4 | XYZ-p | R^11-17 |
| 1698. | Ar-4 | XYZ-p | R^11-18 |
| 1699. | Ar-4 | XYZ-p | R^11-19 |
| 1700. | Ar-4 | XYZ-p | R^11-20 |
| 1701. | Ar-4 | XYZ-p | R^11-21 |
| 1702. | Ar-4 | XYZ-q | R^11-1 |
| 1703. | Ar-4 | XYZ-q | R^11-2 |
| 1704. | Ar-4 | XYZ-q | R^11-3 |
| 1705. | Ar-4 | XYZ-q | R^11-4 |
| 1706. | Ar-4 | XYZ-q | R^11-5 |
| 1707. | Ar-4 | XYZ-q | R^11-6 |
| 1708. | Ar-4 | XYZ-q | R^11-7 |
| 1709. | Ar-4 | XYZ-q | R^11-8 |
| 1710. | Ar-4 | XYZ-q | R^11-9 |
| 1711. | Ar-4 | XYZ-q | R^11-10 |
| 1712. | Ar-4 | XYZ-q | R^11-11 |
| 1713. | Ar-4 | XYZ-q | R^11-12 |
| 1714. | Ar-4 | XYZ-q | R^11-13 |
| 1715. | Ar-4 | XYZ-q | R^11-14 |
| 1716. | Ar-4 | XYZ-q | R^11-15 |
| 1717. | Ar-4 | XYZ-q | R^11-16 |
| 1718. | Ar-4 | XYZ-q | R^11-17 |
| 1719. | Ar-4 | XYZ-q | R^11-18 |
| 1720. | Ar-4 | XYZ-q | R^11-19 |
| 1721. | Ar-4 | XYZ-q | R^11-20 |
| 1722. | Ar-4 | XYZ-q | R^11-21 |
| 1723. | Ar-4 | XYZ-r | R^11-1 |
| 1724. | Ar-4 | XYZ-r | R^11-2 |
| 1725. | Ar-4 | XYZ-r | R^11-3 |
| 1726. | Ar-4 | XYZ-r | R^11-4 |
| 1727. | Ar-4 | XYZ-r | R^11-5 |
| 1728. | Ar-4 | XYZ-r | R^11-6 |
| 1729. | Ar-4 | XYZ-r | R^11-7 |
| 1730. | Ar-4 | XYZ-r | R^11-8 |
| 1731. | Ar-4 | XYZ-r | R^11-9 |
| 1732. | Ar-4 | XYZ-r | R^11-10 |
| 1733. | Ar-4 | XYZ-r | R^11-11 |
| 1734. | Ar-4 | XYZ-r | R^11-12 |
| 1735. | Ar-4 | XYZ-r | R^11-13 |
| 1736. | Ar-4 | XYZ-r | R^11-14 |
| 1737. | Ar-4 | XYZ-r | R^11-15 |
| 1738. | Ar-4 | XYZ-r | R^11-16 |
| 1739. | Ar-4 | XYZ-r | R^11-17 |
| 1740. | Ar-4 | XYZ-r | R^11-18 |
| 1741. | Ar-4 | XYZ-r | R^11-19 |
| 1742. | Ar-4 | XYZ-r | R^11-20 |
| 1743. | Ar-4 | XYZ-r | R^11-21 |
| 1744. | Ar-4 | XYZ-s | R^11-1 |
| 1745. | Ar-4 | XYZ-s | R^11-2 |
| 1746. | Ar-4 | XYZ-s | R^11-3 |
| 1747. | Ar-4 | XYZ-s | R^11-4 |
| 1748. | Ar-4 | XYZ-s | R^11-5 |
| 1749. | Ar-4 | XYZ-s | R^11-6 |
| 1750. | Ar-4 | XYZ-s | R^11-7 |
| 1751. | Ar-4 | XYZ-s | R^11-8 |
| 1752. | Ar-4 | XYZ-s | R^11-9 |
| 1753. | Ar-4 | XYZ-s | R^11-10 |
| 1754. | Ar-4 | XYZ-s | R^11-11 |
| 1755. | Ar-4 | XYZ-s | R^11-12 |
| 1756. | Ar-4 | XYZ-s | R^11-13 |
| 1757. | Ar-4 | XYZ-s | R^11-14 |
| 1758. | Ar-4 | XYZ-s | R^11-15 |
| 1759. | Ar-4 | XYZ-s | R^11-16 |
| 1760. | Ar-4 | XYZ-s | R^11-17 |
| 1761. | Ar-4 | XYZ-s | R^11-18 |
| 1762. | Ar-4 | XYZ-s | R^11-19 |
| 1763. | Ar-4 | XYZ-s | R^11-20 |
| 1764. | Ar-4 | XYZ-s | R^11-21 |
| 1765. | Ar-4 | XYZ-t | R^11-1 |
| 1766. | Ar-4 | XYZ-t | R^11-2 |
| 1767. | Ar-4 | XYZ-t | R^11-3 |
| 1768. | Ar-4 | XYZ-t | R^11-4 |
| 1769. | Ar-4 | XYZ-t | R^11-5 |
| 1770. | Ar-4 | XYZ-t | R^11-6 |
| 1771. | Ar-4 | XYZ-t | R^11-7 |
| 1772. | Ar-4 | XYZ-t | R^11-8 |
| 1773. | Ar-4 | XYZ-t | R^11-9 |
| 1774. | Ar-4 | XYZ-t | R^11-10 |
| 1775. | Ar-4 | XYZ-t | R^11-11 |
| 1776. | Ar-4 | XYZ-t | R^11-12 |
| 1777. | Ar-4 | XYZ-t | R^11-13 |
| 1778. | Ar-4 | XYZ-t | R^11-14 |
| 1779. | Ar-4 | XYZ-t | R^11-15 |
| 1780. | Ar-4 | XYZ-t | R^11-16 |
| 1781. | Ar-4 | XYZ-t | R^11-17 |
| 1782. | Ar-4 | XYZ-t | R^11-18 |
| 1783. | Ar-4 | XYZ-t | R^11-19 |
| 1784. | Ar-4 | XYZ-t | R^11-20 |
| 1785. | Ar-4 | XYZ-t | R^11-21 |
| 1786. | Ar-4 | XYZ-u | R^11-1 |
| 1787. | Ar-4 | XYZ-u | R^11-2 |
| 1788. | Ar-4 | XYZ-u | R^11-3 |
| 1789. | Ar-4 | XYZ-u | R^11-4 |
| 1790. | Ar-4 | XYZ-u | R^11-5 |
| 1791. | Ar-4 | XYZ-u | R^11-6 |
| 1792. | Ar-4 | XYZ-u | R^11-7 |
| 1793. | Ar-4 | XYZ-u | R^11-8 |
| 1794. | Ar-4 | XYZ-u | R^11-9 |
| 1795. | Ar-4 | XYZ-u | R^11-10 |
| 1796. | Ar-4 | XYZ-u | R^11-11 |
| 1797. | Ar-4 | XYZ-u | R^11-12 |
| 1798. | Ar-4 | XYZ-u | R^11-13 |
| 1799. | Ar-4 | XYZ-u | R^11-14 |
| 1800. | Ar-4 | XYZ-u | R^11-15 |
| 1801. | Ar-4 | XYZ-u | R^11-16 |
| 1802. | Ar-4 | XYZ-u | R^11-17 |
| 1803. | Ar-4 | XYZ-u | R^11-18 |
| 1804. | Ar-4 | XYZ-u | R^11-19 |
| 1805. | Ar-4 | XYZ-u | R^11-20 |
| 1806. | Ar-4 | XYZ-u | R^11-21 |
| 1807. | Ar-4 | XYZ-v | R^11-1 |
| 1808. | Ar-4 | XYZ-v | R^11-2 |
| 1809. | Ar-4 | XYZ-v | R^11-3 |
| 1810. | Ar-4 | XYZ-v | R^11-4 |
| 1811. | Ar-4 | XYZ-v | R^11-5 |
| 1812. | Ar-4 | XYZ-v | R^11-6 |
| 1813. | Ar-4 | XYZ-v | R^11-7 |
| 1814. | Ar-4 | XYZ-v | R^11-8 |
| 1815. | Ar-4 | XYZ-v | R^11-9 |
| 1816. | Ar-4 | XYZ-v | R^11-10 |
| 1817. | Ar-4 | XYZ-v | R^11-11 |
| 1818. | Ar-4 | XYZ-v | R^11-12 |
| 1819. | Ar-4 | XYZ-v | R^11-13 |
| 1820. | Ar-4 | XYZ-v | R^11-14 |
| 1821. | Ar-4 | XYZ-v | R^11-15 |
| 1822. | Ar-4 | XYZ-v | R^11-16 |
| 1823. | Ar-4 | XYZ-v | R^11-17 |
| 1824. | Ar-4 | XYZ-v | R^11-18 |

TABLE C-continued

|  | Ar | -X-Y-Z- | $R^{11}$ |
|---|---|---|---|
| 1825. | Ar-4 | XYZ-v | $R^{11}$-19 |
| 1826. | Ar-4 | XYZ-v | $R^{11}$-20 |
| 1827. | Ar-4 | XYZ-v | $R^{11}$-21 |
| 1828. | Ar-4 | XYZ-w | $R^{11}$-1 |
| 1829. | Ar-4 | XYZ-w | $R^{11}$-2 |
| 1830. | Ar-4 | XYZ-w | $R^{11}$-3 |
| 1831. | Ar-4 | XYZ-w | $R^{11}$-4 |
| 1832. | Ar-4 | XYZ-w | $R^{11}$-5 |
| 1833. | Ar-4 | XYZ-w | $R^{11}$-6 |
| 1834. | Ar-4 | XYZ-w | $R^{11}$-7 |
| 1835. | Ar-4 | XYZ-w | $R^{11}$-8 |
| 1836. | Ar-4 | XYZ-w | $R^{11}$-9 |
| 1837. | Ar-4 | XYZ-w | $R^{11}$-10 |
| 1838. | Ar-4 | XYZ-w | $R^{11}$-11 |
| 1839. | Ar-4 | XYZ-w | $R^{11}$-12 |
| 1840. | Ar-4 | XYZ-w | $R^{11}$-13 |
| 1841. | Ar-4 | XYZ-w | $R^{11}$-14 |
| 1842. | Ar-4 | XYZ-w | $R^{11}$-15 |
| 1843. | Ar-4 | XYZ-w | $R^{11}$-16 |
| 1844. | Ar-4 | XYZ-w | $R^{11}$-17 |
| 1845. | Ar-4 | XYZ-w | $R^{11}$-18 |
| 1846. | Ar-4 | XYZ-w | $R^{11}$-19 |
| 1847. | Ar-4 | XYZ-w | $R^{11}$-20 |
| 1848. | Ar-4 | XYZ-w | $R^{11}$-21 |
| 1849. | Ar-5 | XYZ-a | $R^{11}$-1 |
| 1850. | Ar-5 | XYZ-a | $R^{11}$-2 |
| 1851. | Ar-5 | XYZ-a | $R^{11}$-3 |
| 1852. | Ar-5 | XYZ-a | $R^{11}$-4 |
| 1853. | Ar-5 | XYZ-a | $R^{11}$-5 |
| 1854. | Ar-5 | XYZ-a | $R^{11}$-6 |
| 1855. | Ar-5 | XYZ-a | $R^{11}$-7 |
| 1856. | Ar-5 | XYZ-a | $R^{11}$-8 |
| 1857. | Ar-5 | XYZ-a | $R^{11}$-9 |
| 1858. | Ar-5 | XYZ-a | $R^{11}$-10 |
| 1859. | Ar-5 | XYZ-a | $R^{11}$-11 |
| 1860. | Ar-5 | XYZ-a | $R^{11}$-12 |
| 1861. | Ar-5 | XYZ-a | $R^{11}$-13 |
| 1862. | Ar-5 | XYZ-a | $R^{11}$-14 |
| 1863. | Ar-5 | XYZ-a | $R^{11}$-15 |
| 1864. | Ar-5 | XYZ-a | $R^{11}$-16 |
| 1865. | Ar-5 | XYZ-a | $R^{11}$-17 |
| 1866. | Ar-5 | XYZ-a | $R^{11}$-18 |
| 1867. | Ar-5 | XYZ-a | $R^{11}$-19 |
| 1868. | Ar-5 | XYZ-a | $R^{11}$-20 |
| 1869. | Ar-5 | XYZ-a | $R^{11}$-21 |
| 1870. | Ar-5 | XYZ-b | $R^{11}$-1 |
| 1871. | Ar-5 | XYZ-b | $R^{11}$-2 |
| 1872. | Ar-5 | XYZ-b | $R^{11}$-3 |
| 1873. | Ar-5 | XYZ-b | $R^{11}$-4 |
| 1874. | Ar-5 | XYZ-b | $R^{11}$-5 |
| 1875. | Ar-5 | XYZ-b | $R^{11}$-6 |
| 1876. | Ar-5 | XYZ-b | $R^{11}$-7 |
| 1877. | Ar-5 | XYZ-b | $R^{11}$-8 |
| 1878. | Ar-5 | XYZ-b | $R^{11}$-9 |
| 1879. | Ar-5 | XYZ-b | $R^{11}$-10 |
| 1880. | Ar-5 | XYZ-b | $R^{11}$-11 |
| 1881. | Ar-5 | XYZ-b | $R^{11}$-12 |
| 1882. | Ar-5 | XYZ-b | $R^{11}$-13 |
| 1883. | Ar-5 | XYZ-b | $R^{11}$-14 |
| 1884. | Ar-5 | XYZ-b | $R^{11}$-15 |
| 1885. | Ar-5 | XYZ-b | $R^{11}$-16 |
| 1886. | Ar-5 | XYZ-b | $R^{11}$-17 |
| 1887. | Ar-5 | XYZ-b | $R^{11}$-18 |
| 1888. | Ar-5 | XYZ-b | $R^{11}$-19 |
| 1889. | Ar-5 | XYZ-b | $R^{11}$-20 |
| 1890. | Ar-5 | XYZ-b | $R^{11}$-21 |
| 1891. | Ar-5 | XYZ-c | $R^{11}$-1 |
| 1892. | Ar-5 | XYZ-c | $R^{11}$-2 |
| 1893. | Ar-5 | XYZ-c | $R^{11}$-3 |
| 1894. | Ar-5 | XYZ-c | $R^{11}$-4 |
| 1895. | Ar-5 | XYZ-c | $R^{11}$-5 |
| 1896. | Ar-5 | XYZ-c | $R^{11}$-6 |
| 1897. | Ar-5 | XYZ-c | $R^{11}$-7 |
| 1898. | Ar-5 | XYZ-c | $R^{11}$-8 |
| 1899. | Ar-5 | XYZ-c | $R^{11}$-9 |
| 1900. | Ar-5 | XYZ-c | $R^{11}$-10 |
| 1901. | Ar-5 | XYZ-c | $R^{11}$-11 |
| 1902. | Ar-5 | XYZ-c | $R^{11}$-12 |
| 1903. | Ar-5 | XYZ-c | $R^{11}$-13 |
| 1904. | Ar-5 | XYZ-c | $R^{11}$-14 |
| 1905. | Ar-5 | XYZ-c | $R^{11}$-15 |
| 1906. | Ar-5 | XYZ-c | $R^{11}$-16 |
| 1907. | Ar-5 | XYZ-c | $R^{11}$-17 |
| 1908. | Ar-5 | XYZ-c | $R^{11}$-18 |
| 1909. | Ar-5 | XYZ-c | $R^{11}$-19 |
| 1910. | Ar-5 | XYZ-c | $R^{11}$-20 |
| 1911. | Ar-5 | XYZ-c | $R^{11}$-21 |
| 1912. | Ar-5 | XYZ-d | $R^{11}$-1 |
| 1913. | Ar-5 | XYZ-d | $R^{11}$-2 |
| 1914. | Ar-5 | XYZ-d | $R^{11}$-3 |
| 1915. | Ar-5 | XYZ-d | $R^{11}$-4 |
| 1916. | Ar-5 | XYZ-d | $R^{11}$-5 |
| 1917. | Ar-5 | XYZ-d | $R^{11}$-6 |
| 1918. | Ar-5 | XYZ-d | $R^{11}$-7 |
| 1919. | Ar-5 | XYZ-d | $R^{11}$-8 |
| 1920. | Ar-5 | XYZ-d | $R^{11}$-9 |
| 1921. | Ar-5 | XYZ-d | $R^{11}$-10 |
| 1922. | Ar-5 | XYZ-d | $R^{11}$-11 |
| 1923. | Ar-5 | XYZ-d | $R^{11}$-12 |
| 1924. | Ar-5 | XYZ-d | $R^{11}$-13 |
| 1925. | Ar-5 | XYZ-d | $R^{11}$-14 |
| 1926. | Ar-5 | XYZ-d | $R^{11}$-15 |
| 1927. | Ar-5 | XYZ-d | $R^{11}$-16 |
| 1928. | Ar-5 | XYZ-d | $R^{11}$-17 |
| 1929. | Ar-5 | XYZ-d | $R^{11}$-18 |
| 1930. | Ar-5 | XYZ-d | $R^{11}$-19 |
| 1931. | Ar-5 | XYZ-d | $R^{11}$-20 |
| 1932. | Ar-5 | XYZ-d | $R^{11}$-21 |
| 1933. | Ar-5 | XYZ-e | $R^{11}$-1 |
| 1934. | Ar-5 | XYZ-e | $R^{11}$-2 |
| 1935. | Ar-5 | XYZ-e | $R^{11}$-3 |
| 1936. | Ar-5 | XYZ-e | $R^{11}$-4 |
| 1937. | Ar-5 | XYZ-e | $R^{11}$-5 |
| 1938. | Ar-5 | XYZ-e | $R^{11}$-6 |
| 1939. | Ar-5 | XYZ-e | $R^{11}$-7 |
| 1940. | Ar-5 | XYZ-e | $R^{11}$-8 |
| 1941. | Ar-5 | XYZ-e | $R^{11}$-9 |
| 1942. | Ar-5 | XYZ-e | $R^{11}$-10 |
| 1943. | Ar-5 | XYZ-e | $R^{11}$-11 |
| 1944. | Ar-5 | XYZ-e | $R^{11}$-12 |
| 1945. | Ar-5 | XYZ-e | $R^{11}$-13 |
| 1946. | Ar-5 | XYZ-e | $R^{11}$-14 |
| 1947. | Ar-5 | XYZ-e | $R^{11}$-15 |
| 1948. | Ar-5 | XYZ-e | $R^{11}$-16 |
| 1949. | Ar-5 | XYZ-e | $R^{11}$-17 |
| 1950. | Ar-5 | XYZ-e | $R^{11}$-18 |
| 1951. | Ar-5 | XYZ-e | $R^{11}$-19 |
| 1952. | Ar-5 | XYZ-e | $R^{11}$-20 |
| 1953. | Ar-5 | XYZ-e | $R^{11}$-21 |
| 1954. | Ar-5 | XYZ-f | $R^{11}$-1 |
| 1955. | Ar-5 | XYZ-f | $R^{11}$-2 |
| 1956. | Ar-5 | XYZ-f | $R^{11}$-3 |
| 1957. | Ar-5 | XYZ-f | $R^{11}$-4 |
| 1958. | Ar-5 | XYZ-f | $R^{11}$-5 |
| 1959. | Ar-5 | XYZ-f | $R^{11}$-6 |
| 1960. | Ar-5 | XYZ-f | $R^{11}$-7 |
| 1961. | Ar-5 | XYZ-f | $R^{11}$-8 |
| 1962. | Ar-5 | XYZ-f | $R^{11}$-9 |
| 1963. | Ar-5 | XYZ-f | $R^{11}$-10 |
| 1964. | Ar-5 | XYZ-f | $R^{11}$-11 |
| 1965. | Ar-5 | XYZ-f | $R^{11}$-12 |
| 1966. | Ar-5 | XYZ-f | $R^{11}$-13 |
| 1967. | Ar-5 | XYZ-f | $R^{11}$-14 |
| 1968. | Ar-5 | XYZ-f | $R^{11}$-15 |
| 1969. | Ar-5 | XYZ-f | $R^{11}$-16 |
| 1970. | Ar-5 | XYZ-f | $R^{11}$-17 |
| 1971. | Ar-5 | XYZ-f | $R^{11}$-18 |
| 1972. | Ar-5 | XYZ-f | $R^{11}$-19 |
| 1973. | Ar-5 | XYZ-f | $R^{11}$-20 |
| 1974. | Ar-5 | XYZ-f | $R^{11}$-21 |
| 1975. | Ar-5 | XYZ-g | $R^{11}$-1 |
| 1976. | Ar-5 | XYZ-g | $R^{11}$-2 |
| 1977. | Ar-5 | XYZ-g | $R^{11}$-3 |
| 1978. | Ar-5 | XYZ-g | $R^{11}$-4 |
| 1979. | Ar-5 | XYZ-g | $R^{11}$-5 |
| 1980. | Ar-5 | XYZ-g | $R^{11}$-6 |

TABLE C-continued

| | Ar | -X-Y-Z- | $R^{11}$ |
|---|---|---|---|
| 1981. | Ar-5 | XYZ-g | $R^{11}$-7 |
| 1982. | Ar-5 | XYZ-g | $R^{11}$-8 |
| 1983. | Ar-5 | XYZ-g | $R^{11}$-9 |
| 1984. | Ar-5 | XYZ-g | $R^{11}$-10 |
| 1985. | Ar-5 | XYZ-g | $R^{11}$-11 |
| 1986. | Ar-5 | XYZ-g | $R^{11}$-12 |
| 1987. | Ar-5 | XYZ-g | $R^{11}$-13 |
| 1988. | Ar-5 | XYZ-g | $R^{11}$-14 |
| 1989. | Ar-5 | XYZ-g | $R^{11}$-15 |
| 1990. | Ar-5 | XYZ-g | $R^{11}$-16 |
| 1991. | Ar-5 | XYZ-g | $R^{11}$-17 |
| 1992. | Ar-5 | XYZ-g | $R^{11}$-18 |
| 1993. | Ar-5 | XYZ-g | $R^{11}$-19 |
| 1994. | Ar-5 | XYZ-g | $R^{11}$-20 |
| 1995. | Ar-5 | XYZ-g | $R^{11}$-21 |
| 1996. | Ar-5 | XYZ-h | $R^{11}$-1 |
| 1997. | Ar-5 | XYZ-h | $R^{11}$-2 |
| 1998. | Ar-5 | XYZ-h | $R^{11}$-3 |
| 1999. | Ar-5 | XYZ-h | $R^{11}$-4 |
| 2000. | Ar-5 | XYZ-h | $R^{11}$-5 |
| 2001. | Ar-5 | XYZ-h | $R^{11}$-6 |
| 2002. | Ar-5 | XYZ-h | $R^{11}$-7 |
| 2003. | Ar-5 | XYZ-h | $R^{11}$-8 |
| 2004. | Ar-5 | XYZ-h | $R^{11}$-9 |
| 2005. | Ar-5 | XYZ-h | $R^{11}$-10 |
| 2006. | Ar-5 | XYZ-h | $R^{11}$-11 |
| 2007. | Ar-5 | XYZ-h | $R^{11}$-12 |
| 2008. | Ar-5 | XYZ-h | $R^{11}$-13 |
| 2009. | Ar-5 | XYZ-h | $R^{11}$-14 |
| 2010. | Ar-5 | XYZ-h | $R^{11}$-15 |
| 2011. | Ar-5 | XYZ-h | $R^{11}$-16 |
| 2012. | Ar-5 | XYZ-h | $R^{11}$-17 |
| 2013. | Ar-5 | XYZ-h | $R^{11}$-18 |
| 2014. | Ar-5 | XYZ-h | $R^{11}$-19 |
| 2015. | Ar-5 | XYZ-h | $R^{11}$-20 |
| 2016. | Ar-5 | XYZ-h | $R^{11}$-21 |
| 2017. | Ar-5 | XYZ-i | $R^{11}$-1 |
| 2018. | Ar-5 | XYZ-i | $R^{11}$-2 |
| 2019. | Ar-5 | XYZ-i | $R^{11}$-3 |
| 2020. | Ar-5 | XYZ-i | $R^{11}$-4 |
| 2021. | Ar-5 | XYZ-i | $R^{11}$-5 |
| 2022. | Ar-5 | XYZ-i | $R^{11}$-6 |
| 2023. | Ar-5 | XYZ-i | $R^{11}$-7 |
| 2024. | Ar-5 | XYZ-i | $R^{11}$-8 |
| 2025. | Ar-5 | XYZ-i | $R^{11}$-9 |
| 2026. | Ar-5 | XYZ-i | $R^{11}$-10 |
| 2027. | Ar-5 | XYZ-i | $R^{11}$-11 |
| 2028. | Ar-5 | XYZ-i | $R^{11}$-12 |
| 2029. | Ar-5 | XYZ-i | $R^{11}$-13 |
| 2030. | Ar-5 | XYZ-i | $R^{11}$-14 |
| 2031. | Ar-5 | XYZ-i | $R^{11}$-15 |
| 2032. | Ar-5 | XYZ-i | $R^{11}$-16 |
| 2033. | Ar-5 | XYZ-i | $R^{11}$-17 |
| 2034. | Ar-5 | XYZ-i | $R^{11}$-18 |
| 2035. | Ar-5 | XYZ-i | $R^{11}$-19 |
| 2036. | Ar-5 | XYZ-i | $R^{11}$-20 |
| 2037. | Ar-5 | XYZ-i | $R^{11}$-21 |
| 2038. | Ar-5 | XYZ-k | $R^{11}$-1 |
| 2039. | Ar-5 | XYZ-k | $R^{11}$-2 |
| 2040. | Ar-5 | XYZ-k | $R^{11}$-3 |
| 2041. | Ar-5 | XYZ-k | $R^{11}$-4 |
| 2042. | Ar-5 | XYZ-k | $R^{11}$-5 |
| 2043. | Ar-5 | XYZ-k | $R^{11}$-6 |
| 2044. | Ar-5 | XYZ-k | $R^{11}$-7 |
| 2045. | Ar-5 | XYZ-k | $R^{11}$-8 |
| 2046. | Ar-5 | XYZ-k | $R^{11}$-9 |
| 2047. | Ar-5 | XYZ-k | $R^{11}$-10 |
| 2048. | Ar-5 | XYZ-k | $R^{11}$-11 |
| 2049. | Ar-5 | XYZ-k | $R^{11}$-12 |
| 2050. | Ar-5 | XYZ-k | $R^{11}$-13 |
| 2051. | Ar-5 | XYZ-k | $R^{11}$-14 |
| 2052. | Ar-5 | XYZ-k | $R^{11}$-15 |
| 2053. | Ar-5 | XYZ-k | $R^{11}$-16 |
| 2054. | Ar-5 | XYZ-k | $R^{11}$-17 |
| 2055. | Ar-5 | XYZ-k | $R^{11}$-18 |
| 2056. | Ar-5 | XYZ-k | $R^{11}$-19 |
| 2057. | Ar-5 | XYZ-k | $R^{11}$-20 |
| 2058. | Ar-5 | XYZ-k | $R^{11}$-21 |
| 2059. | Ar-5 | XYZ-l | $R^{11}$-1 |
| 2060. | Ar-5 | XYZ-l | $R^{11}$-2 |
| 2061. | Ar-5 | XYZ-l | $R^{11}$-3 |
| 2062. | Ar-5 | XYZ-l | $R^{11}$-4 |
| 2063. | Ar-5 | XYZ-l | $R^{11}$-5 |
| 2064. | Ar-5 | XYZ-l | $R^{11}$-6 |
| 2065. | Ar-5 | XYZ-l | $R^{11}$-7 |
| 2066. | Ar-5 | XYZ-l | $R^{11}$-8 |
| 2067. | Ar-5 | XYZ-l | $R^{11}$-9 |
| 2068. | Ar-5 | XYZ-l | $R^{11}$-10 |
| 2069. | Ar-5 | XYZ-l | $R^{11}$-11 |
| 2070. | Ar-5 | XYZ-l | $R^{11}$-12 |
| 2071. | Ar-5 | XYZ-l | $R^{11}$-13 |
| 2072. | Ar-5 | XYZ-l | $R^{11}$-14 |
| 2073. | Ar-5 | XYZ-l | $R^{11}$-15 |
| 2074. | Ar-5 | XYZ-l | $R^{11}$-16 |
| 2075. | Ar-5 | XYZ-l | $R^{11}$-17 |
| 2076. | Ar-5 | XYZ-l | $R^{11}$-18 |
| 2077. | Ar-5 | XYZ-l | $R^{11}$-19 |
| 2078. | Ar-5 | XYZ-l | $R^{11}$-20 |
| 2079. | Ar-5 | XYZ-l | $R^{11}$-21 |
| 2080. | Ar-5 | XYZ-m | $R^{11}$-1 |
| 2081. | Ar-5 | XYZ-m | $R^{11}$-2 |
| 2082. | Ar-5 | XYZ-m | $R^{11}$-3 |
| 2083. | Ar-5 | XYZ-m | $R^{11}$-4 |
| 2084. | Ar-5 | XYZ-m | $R^{11}$-5 |
| 2085. | Ar-5 | XYZ-m | $R^{11}$-6 |
| 2086. | Ar-5 | XYZ-m | $R^{11}$-7 |
| 2087. | Ar-5 | XYZ-m | $R^{11}$-8 |
| 2088. | Ar-5 | XYZ-m | $R^{11}$-9 |
| 2089. | Ar-5 | XYZ-m | $R^{11}$-10 |
| 2090. | Ar-5 | XYZ-m | $R^{11}$-11 |
| 2091. | Ar-5 | XYZ-m | $R^{11}$-12 |
| 2092. | Ar-5 | XYZ-m | $R^{11}$-13 |
| 2093. | Ar-5 | XYZ-m | $R^{11}$-14 |
| 2094. | Ar-5 | XYZ-m | $R^{11}$-15 |
| 2095. | Ar-5 | XYZ-m | $R^{11}$-16 |
| 2096. | Ar-5 | XYZ-m | $R^{11}$-17 |
| 2097. | Ar-5 | XYZ-m | $R^{11}$-18 |
| 2098. | Ar-5 | XYZ-m | $R^{11}$-19 |
| 2099. | Ar-5 | XYZ-m | $R^{11}$-20 |
| 2100. | Ar-5 | XYZ-m | $R^{11}$-21 |
| 2101. | Ar-5 | XYZ-n | $R^{11}$-1 |
| 2102. | Ar-5 | XYZ-n | $R^{11}$-2 |
| 2103. | Ar-5 | XYZ-n | $R^{11}$-3 |
| 2104. | Ar-5 | XYZ-n | $R^{11}$-4 |
| 2105. | Ar-5 | XYZ-n | $R^{11}$-5 |
| 2106. | Ar-5 | XYZ-n | $R^{11}$-6 |
| 2107. | Ar-5 | XYZ-n | $R^{11}$-7 |
| 2108. | Ar-5 | XYZ-n | $R^{11}$-8 |
| 2109. | Ar-5 | XYZ-n | $R^{11}$-9 |
| 2110. | Ar-5 | XYZ-n | $R^{11}$-10 |
| 2111. | Ar-5 | XYZ-n | $R^{11}$-11 |
| 2112. | Ar-5 | XYZ-n | $R^{11}$-12 |
| 2113. | Ar-5 | XYZ-n | $R^{11}$-13 |
| 2114. | Ar-5 | XYZ-n | $R^{11}$-14 |
| 2115. | Ar-5 | XYZ-n | $R^{11}$-15 |
| 2116. | Ar-5 | XYZ-n | $R^{11}$-16 |
| 2117. | Ar-5 | XYZ-n | $R^{11}$-17 |
| 2118. | Ar-5 | XYZ-n | $R^{11}$-18 |
| 2119. | Ar-5 | XYZ-n | $R^{11}$-19 |
| 2120. | Ar-5 | XYZ-n | $R^{11}$-20 |
| 2121. | Ar-5 | XYZ-n | $R^{11}$-21 |
| 2122. | Ar-5 | XYZ-o | $R^{11}$-1 |
| 2123. | Ar-5 | XYZ-o | $R^{11}$-2 |
| 2124. | Ar-5 | XYZ-o | $R^{11}$-3 |
| 2125. | Ar-5 | XYZ-o | $R^{11}$-4 |
| 2126. | Ar-5 | XYZ-o | $R^{11}$-5 |
| 2127. | Ar-5 | XYZ-o | $R^{11}$-6 |
| 2128. | Ar-5 | XYZ-o | $R^{11}$-7 |
| 2129. | Ar-5 | XYZ-o | $R^{11}$-8 |
| 2130. | Ar-5 | XYZ-o | $R^{11}$-9 |
| 2131. | Ar-5 | XYZ-o | $R^{11}$-10 |
| 2132. | Ar-5 | XYZ-o | $R^{11}$-11 |
| 2133. | Ar-5 | XYZ-o | $R^{11}$-12 |
| 2134. | Ar-5 | XYZ-o | $R^{11}$-13 |
| 2135. | Ar-5 | XYZ-o | $R^{11}$-14 |
| 2136. | Ar-5 | XYZ-o | $R^{11}$-15 |

TABLE C-continued

|  | Ar | -X-Y-Z- | R$^{11}$ |
|---|---|---|---|
| 2137. | Ar-5 | XYZ-o | R$^{11}$-16 |
| 2138. | Ar-5 | XYZ-o | R$^{11}$-17 |
| 2139. | Ar-5 | XYZ-o | R$^{11}$-18 |
| 2140. | Ar-5 | XYZ-o | R$^{11}$-19 |
| 2141. | Ar-5 | XYZ-o | R$^{11}$-20 |
| 2142. | Ar-5 | XYZ-o | R$^{11}$-21 |
| 2143. | Ar-5 | XYZ-p | R$^{11}$-1 |
| 2144. | Ar-5 | XYZ-p | R$^{11}$-2 |
| 2145. | Ar-5 | XYZ-p | R$^{11}$-3 |
| 2146. | Ar-5 | XYZ-p | R$^{11}$-4 |
| 2147. | Ar-5 | XYZ-p | R$^{11}$-5 |
| 2148. | Ar-5 | XYZ-p | R$^{11}$-6 |
| 2149. | Ar-5 | XYZ-p | R$^{11}$-7 |
| 2150. | Ar-5 | XYZ-p | R$^{11}$-8 |
| 2151. | Ar-5 | XYZ-p | R$^{11}$-9 |
| 2152. | Ar-5 | XYZ-p | R$^{11}$-10 |
| 2153. | Ar-5 | XYZ-p | R$^{11}$-11 |
| 2154. | Ar-5 | XYZ-p | R$^{11}$-12 |
| 2155. | Ar-5 | XYZ-p | R$^{11}$-13 |
| 2156. | Ar-5 | XYZ-p | R$^{11}$-14 |
| 2157. | Ar-5 | XYZ-p | R$^{11}$-15 |
| 2158. | Ar-5 | XYZ-p | R$^{11}$-16 |
| 2159. | Ar-5 | XYZ-p | R$^{11}$-17 |
| 2160. | Ar-5 | XYZ-p | R$^{11}$-18 |
| 2161. | Ar-5 | XYZ-p | R$^{11}$-19 |
| 2162. | Ar-5 | XYZ-p | R$^{11}$-20 |
| 2163. | Ar-5 | XYZ-p | R$^{11}$-21 |
| 2164. | Ar-5 | XYZ-q | R$^{11}$-1 |
| 2165. | Ar-5 | XYZ-q | R$^{11}$-2 |
| 2166. | Ar-5 | XYZ-q | R$^{11}$-3 |
| 2167. | Ar-5 | XYZ-q | R$^{11}$-4 |
| 2168. | Ar-5 | XYZ-q | R$^{11}$-5 |
| 2169. | Ar-5 | XYZ-q | R$^{11}$-6 |
| 2170. | Ar-5 | XYZ-q | R$^{11}$-7 |
| 2171. | Ar-5 | XYZ-q | R$^{11}$-8 |
| 2172. | Ar-5 | XYZ-q | R$^{11}$-9 |
| 2173. | Ar-5 | XYZ-q | R$^{11}$-10 |
| 2174. | Ar-5 | XYZ-q | R$^{11}$-11 |
| 2175. | Ar-5 | XYZ-q | R$^{11}$-12 |
| 2176. | Ar-5 | XYZ-q | R$^{11}$-13 |
| 2177. | Ar-5 | XYZ-q | R$^{11}$-14 |
| 2178. | Ar-5 | XYZ-q | R$^{11}$-15 |
| 2179. | Ar-5 | XYZ-q | R$^{11}$-16 |
| 2180. | Ar-5 | XYZ-q | R$^{11}$-17 |
| 2181. | Ar-5 | XYZ-q | R$^{11}$-18 |
| 2182. | Ar-5 | XYZ-q | R$^{11}$-19 |
| 2183. | Ar-5 | XYZ-q | R$^{11}$-20 |
| 2184. | Ar-5 | XYZ-q | R$^{11}$-21 |
| 2185. | Ar-5 | XYZ-r | R$^{11}$-1 |
| 2186. | Ar-5 | XYZ-r | R$^{11}$-2 |
| 2187. | Ar-5 | XYZ-r | R$^{11}$-3 |
| 2188. | Ar-5 | XYZ-r | R$^{11}$-4 |
| 2189. | Ar-5 | XYZ-r | R$^{11}$-5 |
| 2190. | Ar-5 | XYZ-r | R$^{11}$-6 |
| 2191. | Ar-5 | XYZ-r | R$^{11}$-7 |
| 2192. | Ar-5 | XYZ-r | R$^{11}$-8 |
| 2193. | Ar-5 | XYZ-r | R$^{11}$-9 |
| 2194. | Ar-5 | XYZ-r | R$^{11}$-10 |
| 2195. | Ar-5 | XYZ-r | R$^{11}$-11 |
| 2196. | Ar-5 | XYZ-r | R$^{11}$-12 |
| 2197. | Ar-5 | XYZ-r | R$^{11}$-13 |
| 2198. | Ar-5 | XYZ-r | R$^{11}$-14 |
| 2199. | Ar-5 | XYZ-r | R$^{11}$-15 |
| 2200. | Ar-5 | XYZ-r | R$^{11}$-16 |
| 2201. | Ar-5 | XYZ-r | R$^{11}$-17 |
| 2202. | Ar-5 | XYZ-r | R$^{11}$-18 |
| 2203. | Ar-5 | XYZ-r | R$^{11}$-19 |
| 2204. | Ar-5 | XYZ-r | R$^{11}$-20 |
| 2205. | Ar-5 | XYZ-r | R$^{11}$-21 |
| 2206. | Ar-5 | XYZ-s | R$^{11}$-1 |
| 2207. | Ar-5 | XYZ-s | R$^{11}$-2 |
| 2208. | Ar-5 | XYZ-s | R$^{11}$-3 |
| 2209. | Ar-5 | XYZ-s | R$^{11}$-4 |
| 2210. | Ar-5 | XYZ-s | R$^{11}$-5 |
| 2211. | Ar-5 | XYZ-s | R$^{11}$-6 |
| 2212. | Ar-5 | XYZ-s | R$^{11}$-7 |
| 2213. | Ar-5 | XYZ-s | R$^{11}$-8 |
| 2214. | Ar-5 | XYZ-s | R$^{11}$-9 |
| 2215. | Ar-5 | XYZ-s | R$^{11}$-10 |
| 2216. | Ar-5 | XYZ-s | R$^{11}$-11 |
| 2217. | Ar-5 | XYZ-s | R$^{11}$-12 |
| 2218. | Ar-5 | XYZ-s | R$^{11}$-13 |
| 2219. | Ar-5 | XYZ-s | R$^{11}$-14 |
| 2220. | Ar-5 | XYZ-s | R$^{11}$-15 |
| 2221. | Ar-5 | XYZ-s | R$^{11}$-16 |
| 2222. | Ar-5 | XYZ-s | R$^{11}$-17 |
| 2223. | Ar-5 | XYZ-s | R$^{11}$-18 |
| 2224. | Ar-5 | XYZ-s | R$^{11}$-19 |
| 2225. | Ar-5 | XYZ-s | R$^{11}$-20 |
| 2226. | Ar-5 | XYZ-s | R$^{11}$-21 |
| 2227. | Ar-5 | XYZ-t | R$^{11}$-1 |
| 2228. | Ar-5 | XYZ-t | R$^{11}$-2 |
| 2229. | Ar-5 | XYZ-t | R$^{11}$-3 |
| 2230. | Ar-5 | XYZ-t | R$^{11}$-4 |
| 2231. | Ar-5 | XYZ-t | R$^{11}$-5 |
| 2232. | Ar-5 | XYZ-t | R$^{11}$-6 |
| 2233. | Ar-5 | XYZ-t | R$^{11}$-7 |
| 2234. | Ar-5 | XYZ-t | R$^{11}$-8 |
| 2235. | Ar-5 | XYZ-t | R$^{11}$-9 |
| 2236. | Ar-5 | XYZ-t | R$^{11}$-10 |
| 2237. | Ar-5 | XYZ-t | R$^{11}$-11 |
| 2238. | Ar-5 | XYZ-t | R$^{11}$-12 |
| 2239. | Ar-5 | XYZ-t | R$^{11}$-13 |
| 2240. | Ar-5 | XYZ-t | R$^{11}$-14 |
| 2241. | Ar-5 | XYZ-t | R$^{11}$-15 |
| 2242. | Ar-5 | XYZ-t | R$^{11}$-16 |
| 2243. | Ar-5 | XYZ-t | R$^{11}$-17 |
| 2244. | Ar-5 | XYZ-t | R$^{11}$-18 |
| 2245. | Ar-5 | XYZ-t | R$^{11}$-19 |
| 2246. | Ar-5 | XYZ-t | R$^{11}$-20 |
| 2247. | Ar-5 | XYZ-t | R$^{11}$-21 |
| 2248. | Ar-5 | XYZ-u | R$^{11}$-1 |
| 2249. | Ar-5 | XYZ-u | R$^{11}$-2 |
| 2250. | Ar-5 | XYZ-u | R$^{11}$-3 |
| 2251. | Ar-5 | XYZ-u | R$^{11}$-4 |
| 2252. | Ar-5 | XYZ-u | R$^{11}$-5 |
| 2253. | Ar-5 | XYZ-u | R$^{11}$-6 |
| 2254. | Ar-5 | XYZ-u | R$^{11}$-7 |
| 2255. | Ar-5 | XYZ-u | R$^{11}$-8 |
| 2256. | Ar-5 | XYZ-u | R$^{11}$-9 |
| 2257. | Ar-5 | XYZ-u | R$^{11}$-10 |
| 2258. | Ar-5 | XYZ-u | R$^{11}$-11 |
| 2259. | Ar-5 | XYZ-u | R$^{11}$-12 |
| 2260. | Ar-5 | XYZ-u | R$^{11}$-13 |
| 2261. | Ar-5 | XYZ-u | R$^{11}$-14 |
| 2262. | Ar-5 | XYZ-u | R$^{11}$-15 |
| 2263. | Ar-5 | XYZ-u | R$^{11}$-16 |
| 2264. | Ar-5 | XYZ-u | R$^{11}$-17 |
| 2265. | Ar-5 | XYZ-u | R$^{11}$-18 |
| 2266. | Ar-5 | XYZ-u | R$^{11}$-19 |
| 2267. | Ar-5 | XYZ-u | R$^{11}$-20 |
| 2268. | Ar-5 | XYZ-u | R$^{11}$-21 |
| 2269. | Ar-5 | XYZ-v | R$^{11}$-1 |
| 2270. | Ar-5 | XYZ-v | R$^{11}$-2 |
| 2271. | Ar-5 | XYZ-v | R$^{11}$-3 |
| 2272. | Ar-5 | XYZ-v | R$^{11}$-4 |
| 2273. | Ar-5 | XYZ-v | R$^{11}$-5 |
| 2274. | Ar-5 | XYZ-v | R$^{11}$-6 |
| 2275. | Ar-5 | XYZ-v | R$^{11}$-7 |
| 2276. | Ar-5 | XYZ-v | R$^{11}$-8 |
| 2277. | Ar-5 | XYZ-v | R$^{11}$-9 |
| 2278. | Ar-5 | XYZ-v | R$^{11}$-10 |
| 2279. | Ar-5 | XYZ-v | R$^{11}$-11 |
| 2280. | Ar-5 | XYZ-v | R$^{11}$-12 |
| 2281. | Ar-5 | XYZ-v | R$^{11}$-13 |
| 2282. | Ar-5 | XYZ-v | R$^{11}$-14 |
| 2283. | Ar-5 | XYZ-v | R$^{11}$-15 |
| 2284. | Ar-5 | XYZ-v | R$^{11}$-16 |
| 2285. | Ar-5 | XYZ-v | R$^{11}$-17 |
| 2286. | Ar-5 | XYZ-v | R$^{11}$-18 |
| 2287. | Ar-5 | XYZ-v | R$^{11}$-19 |
| 2288. | Ar-5 | XYZ-v | R$^{11}$-20 |
| 2289. | Ar-5 | XYZ-v | R$^{11}$-21 |
| 2290. | Ar-5 | XYZ-w | R$^{11}$-1 |
| 2291. | Ar-5 | XYZ-w | R$^{11}$-2 |
| 2292. | Ar-5 | XYZ-w | R$^{11}$-3 |

TABLE C-continued

| | Ar | -X-Y-Z- | R$^{11}$ |
|---|---|---|---|
| 2293. | Ar-5 | XYZ-w | R$^{11}$-4 |
| 2294. | Ar-5 | XYZ-w | R$^{11}$-5 |
| 2295. | Ar-5 | XYZ-w | R$^{11}$-6 |
| 2296. | Ar-5 | XYZ-w | R$^{11}$-7 |
| 2297. | Ar-5 | XYZ-w | R$^{11}$-8 |
| 2298. | Ar-5 | XYZ-w | R$^{11}$-9 |
| 2299. | Ar-5 | XYZ-w | R$^{11}$-10 |
| 2300. | Ar-5 | XYZ-w | R$^{11}$-11 |
| 2301. | Ar-5 | XYZ-w | R$^{11}$-12 |
| 2302. | Ar-5 | XYZ-w | R$^{11}$-13 |
| 2303. | Ar-5 | XYZ-w | R$^{11}$-14 |
| 2304. | Ar-5 | XYZ-w | R$^{11}$-15 |
| 2305. | Ar-5 | XYZ-w | R$^{11}$-16 |
| 2306. | Ar-5 | XYZ-w | R$^{11}$-17 |
| 2307. | Ar-5 | XYZ-w | R$^{11}$-18 |
| 2308. | Ar-5 | XYZ-w | R$^{11}$-19 |
| 2309. | Ar-5 | XYZ-w | R$^{11}$-20 |
| 2310. | Ar-5 | XYZ-w | R$^{11}$-21 |
| 2311. | Ar-6 | XYZ-a | R$^{11}$-1 |
| 2312. | Ar-6 | XYZ-a | R$^{11}$-2 |
| 2313. | Ar-6 | XYZ-a | R$^{11}$-3 |
| 2314. | Ar-6 | XYZ-a | R$^{11}$-4 |
| 2315. | Ar-6 | XYZ-a | R$^{11}$-5 |
| 2316. | Ar-6 | XYZ-a | R$^{11}$-6 |
| 2317. | Ar-6 | XYZ-a | R$^{11}$-7 |
| 2318. | Ar-6 | XYZ-a | R$^{11}$-8 |
| 2319. | Ar-6 | XYZ-a | R$^{11}$-9 |
| 2320. | Ar-6 | XYZ-a | R$^{11}$-10 |
| 2321. | Ar-6 | XYZ-a | R$^{11}$-11 |
| 2322. | Ar-6 | XYZ-a | R$^{11}$-12 |
| 2323. | Ar-6 | XYZ-a | R$^{11}$-13 |
| 2324. | Ar-6 | XYZ-a | R$^{11}$-14 |
| 2325. | Ar-6 | XYZ-a | R$^{11}$-15 |
| 2326. | Ar-6 | XYZ-a | R$^{11}$-16 |
| 2327. | Ar-6 | XYZ-a | R$^{11}$-17 |
| 2328. | Ar-6 | XYZ-a | R$^{11}$-18 |
| 2329. | Ar-6 | XYZ-a | R$^{11}$-19 |
| 2330. | Ar-6 | XYZ-a | R$^{11}$-20 |
| 2331. | Ar-6 | XYZ-a | R$^{11}$-21 |
| 2332. | Ar-6 | XYZ-b | R$^{11}$-1 |
| 2333. | Ar-6 | XYZ-b | R$^{11}$-2 |
| 2334. | Ar-6 | XYZ-b | R$^{11}$-3 |
| 2335. | Ar-6 | XYZ-b | R$^{11}$-4 |
| 2336. | Ar-6 | XYZ-b | R$^{11}$-5 |
| 2337. | Ar-6 | XYZ-b | R$^{11}$-6 |
| 2338. | Ar-6 | XYZ-b | R$^{11}$-7 |
| 2339. | Ar-6 | XYZ-b | R$^{11}$-8 |
| 2340. | Ar-6 | XYZ-b | R$^{11}$-9 |
| 2341. | Ar-6 | XYZ-b | R$^{11}$-10 |
| 2342. | Ar-6 | XYZ-b | R$^{11}$-11 |
| 2343. | Ar-6 | XYZ-b | R$^{11}$-12 |
| 2344. | Ar-6 | XYZ-b | R$^{11}$-13 |
| 2345. | Ar-6 | XYZ-b | R$^{11}$-14 |
| 2346. | Ar-6 | XYZ-b | R$^{11}$-15 |
| 2347. | Ar-6 | XYZ-b | R$^{11}$-16 |
| 2348. | Ar-6 | XYZ-b | R$^{11}$-17 |
| 2349. | Ar-6 | XYZ-b | R$^{11}$-18 |
| 2350. | Ar-6 | XYZ-b | R$^{11}$-19 |
| 2351. | Ar-6 | XYZ-b | R$^{11}$-20 |
| 2352. | Ar-6 | XYZ-b | R$^{11}$-21 |
| 2353. | Ar-6 | XYZ-c | R$^{11}$-1 |
| 2354. | Ar-6 | XYZ-c | R$^{11}$-2 |
| 2355. | Ar-6 | XYZ-c | R$^{11}$-3 |
| 2356. | Ar-6 | XYZ-c | R$^{11}$-4 |
| 2357. | Ar-6 | XYZ-c | R$^{11}$-5 |
| 2358. | Ar-6 | XYZ-c | R$^{11}$-6 |
| 2359. | Ar-6 | XYZ-c | R$^{11}$-7 |
| 2360. | Ar-6 | XYZ-c | R$^{11}$-8 |
| 2361. | Ar-6 | XYZ-c | R$^{11}$-9 |
| 2362. | Ar-6 | XYZ-c | R$^{11}$-10 |
| 2363. | Ar-6 | XYZ-c | R$^{11}$-11 |
| 2364. | Ar-6 | XYZ-c | R$^{11}$-12 |
| 2365. | Ar-6 | XYZ-c | R$^{11}$-13 |
| 2366. | Ar-6 | XYZ-c | R$^{11}$-14 |
| 2367. | Ar-6 | XYZ-c | R$^{11}$-15 |
| 2368. | Ar-6 | XYZ-c | R$^{11}$-16 |
| 2369. | Ar-6 | XYZ-c | R$^{11}$-17 |
| 2370. | Ar-6 | XYZ-c | R$^{11}$-18 |
| 2371. | Ar-6 | XYZ-c | R$^{11}$-19 |
| 2372. | Ar-6 | XYZ-c | R$^{11}$-20 |
| 2373. | Ar-6 | XYZ-c | R$^{11}$-21 |
| 2374. | Ar-6 | XYZ-d | R$^{11}$-1 |
| 2375. | Ar-6 | XYZ-d | R$^{11}$-2 |
| 2376. | Ar-6 | XYZ-d | R$^{11}$-3 |
| 2377. | Ar-6 | XYZ-d | R$^{11}$-4 |
| 2378. | Ar-6 | XYZ-d | R$^{11}$-5 |
| 2379. | Ar-6 | XYZ-d | R$^{11}$-6 |
| 2380. | Ar-6 | XYZ-d | R$^{11}$-7 |
| 2381. | Ar-6 | XYZ-d | R$^{11}$-8 |
| 2382. | Ar-6 | XYZ-d | R$^{11}$-9 |
| 2383. | Ar-6 | XYZ-d | R$^{11}$-10 |
| 2384. | Ar-6 | XYZ-d | R$^{11}$-11 |
| 2385. | Ar-6 | XYZ-d | R$^{11}$-12 |
| 2386. | Ar-6 | XYZ-d | R$^{11}$-13 |
| 2387. | Ar-6 | XYZ-d | R$^{11}$-14 |
| 2388. | Ar-6 | XYZ-d | R$^{11}$-15 |
| 2389. | Ar-6 | XYZ-d | R$^{11}$-16 |
| 2390. | Ar-6 | XYZ-d | R$^{11}$-17 |
| 2391. | Ar-6 | XYZ-d | R$^{11}$-18 |
| 2392. | Ar-6 | XYZ-d | R$^{11}$-19 |
| 2393. | Ar-6 | XYZ-d | R$^{11}$-20 |
| 2394. | Ar-6 | XYZ-d | R$^{11}$-21 |
| 2395. | Ar-6 | XYZ-e | R$^{11}$-1 |
| 2396. | Ar-6 | XYZ-e | R$^{11}$-2 |
| 2397. | Ar-6 | XYZ-e | R$^{11}$-3 |
| 2398. | Ar-6 | XYZ-e | R$^{11}$-4 |
| 2399. | Ar-6 | XYZ-e | R$^{11}$-5 |
| 2400. | Ar-6 | XYZ-e | R$^{11}$-6 |
| 2401. | Ar-6 | XYZ-e | R$^{11}$-7 |
| 2402. | Ar-6 | XYZ-e | R$^{11}$-8 |
| 2403. | Ar-6 | XYZ-e | R$^{11}$-9 |
| 2404. | Ar-6 | XYZ-e | R$^{11}$-10 |
| 2405. | Ar-6 | XYZ-e | R$^{11}$-11 |
| 2406. | Ar-6 | XYZ-e | R$^{11}$-12 |
| 2407. | Ar-6 | XYZ-e | R$^{11}$-13 |
| 2408. | Ar-6 | XYZ-e | R$^{11}$-14 |
| 2409. | Ar-6 | XYZ-e | R$^{11}$-15 |
| 2410. | Ar-6 | XYZ-e | R$^{11}$-16 |
| 2411. | Ar-6 | XYZ-e | R$^{11}$-17 |
| 2412. | Ar-6 | XYZ-e | R$^{11}$-18 |
| 2413. | Ar-6 | XYZ-e | R$^{11}$-19 |
| 2414. | Ar-6 | XYZ-e | R$^{11}$-20 |
| 2415. | Ar-6 | XYZ-e | R$^{11}$-21 |
| 2416. | Ar-6 | XYZ-f | R$^{11}$-1 |
| 2417. | Ar-6 | XYZ-f | R$^{11}$-2 |
| 2418. | Ar-6 | XYZ-f | R$^{11}$-3 |
| 2419. | Ar-6 | XYZ-f | R$^{11}$-4 |
| 2420. | Ar-6 | XYZ-f | R$^{11}$-5 |
| 2421. | Ar-6 | XYZ-f | R$^{11}$-6 |
| 2422. | Ar-6 | XYZ-f | R$^{11}$-7 |
| 2423. | Ar-6 | XYZ-f | R$^{11}$-8 |
| 2424. | Ar-6 | XYZ-f | R$^{11}$-9 |
| 2425. | Ar-6 | XYZ-f | R$^{11}$-10 |
| 2426. | Ar-6 | XYZ-f | R$^{11}$-11 |
| 2427. | Ar-6 | XYZ-f | R$^{11}$-12 |
| 2428. | Ar-6 | XYZ-f | R$^{11}$-13 |
| 2429. | Ar-6 | XYZ-f | R$^{11}$-14 |
| 2430. | Ar-6 | XYZ-f | R$^{11}$-15 |
| 2431. | Ar-6 | XYZ-f | R$^{11}$-16 |
| 2432. | Ar-6 | XYZ-f | R$^{11}$-17 |
| 2433. | Ar-6 | XYZ-f | R$^{11}$-18 |
| 2434. | Ar-6 | XYZ-f | R$^{11}$-19 |
| 2435. | Ar-6 | XYZ-f | R$^{11}$-20 |
| 2436. | Ar-6 | XYZ-f | R$^{11}$-21 |
| 2437. | Ar-6 | XYZ-g | R$^{11}$-1 |
| 2438. | Ar-6 | XYZ-g | R$^{11}$-2 |
| 2439. | Ar-6 | XYZ-g | R$^{11}$-3 |
| 2440. | Ar-6 | XYZ-g | R$^{11}$-4 |
| 2441. | Ar-6 | XYZ-g | R$^{11}$-5 |
| 2442. | Ar-6 | XYZ-g | R$^{11}$-6 |
| 2443. | Ar-6 | XYZ-g | R$^{11}$-7 |
| 2444. | Ar-6 | XYZ-g | R$^{11}$-8 |
| 2445. | Ar-6 | XYZ-g | R$^{11}$-9 |
| 2446. | Ar-6 | XYZ-g | R$^{11}$-10 |
| 2447. | Ar-6 | XYZ-g | R$^{11}$-11 |
| 2448. | Ar-6 | XYZ-g | R$^{11}$-12 |

TABLE C-continued

| | Ar | -X-Y-Z- | $R^{11}$ |
|---|---|---|---|
| 2449. | Ar-6 | XYZ-g | $R^{11}$-13 |
| 2450. | Ar-6 | XYZ-g | $R^{11}$-14 |
| 2451. | Ar-6 | XYZ-g | $R^{11}$-15 |
| 2452. | Ar-6 | XYZ-g | $R^{11}$-16 |
| 2453. | Ar-6 | XYZ-g | $R^{11}$-17 |
| 2454. | Ar-6 | XYZ-g | $R^{11}$-18 |
| 2455. | Ar-6 | XYZ-g | $R^{11}$-19 |
| 2456. | Ar-6 | XYZ-g | $R^{11}$-20 |
| 2457. | Ar-6 | XYZ-g | $R^{11}$-21 |
| 2458. | Ar-6 | XYZ-h | $R^{11}$-1 |
| 2459. | Ar-6 | XYZ-h | $R^{11}$-2 |
| 2460. | Ar-6 | XYZ-h | $R^{11}$-3 |
| 2461. | Ar-6 | XYZ-h | $R^{11}$-4 |
| 2462. | Ar-6 | XYZ-h | $R^{11}$-5 |
| 2463. | Ar-6 | XYZ-h | $R^{11}$-6 |
| 2464. | Ar-6 | XYZ-h | $R^{11}$-7 |
| 2465. | Ar-6 | XYZ-h | $R^{11}$-8 |
| 2466. | Ar-6 | XYZ-h | $R^{11}$-9 |
| 2467. | Ar-6 | XYZ-h | $R^{11}$-10 |
| 2468. | Ar-6 | XYZ-h | $R^{11}$-11 |
| 2469. | Ar-6 | XYZ-h | $R^{11}$-12 |
| 2470. | Ar-6 | XYZ-h | $R^{11}$-13 |
| 2471. | Ar-6 | XYZ-h | $R^{11}$-14 |
| 2472. | Ar-6 | XYZ-h | $R^{11}$-15 |
| 2473. | Ar-6 | XYZ-h | $R^{11}$-16 |
| 2474. | Ar-6 | XYZ-h | $R^{11}$-17 |
| 2475. | Ar-6 | XYZ-h | $R^{11}$-18 |
| 2476. | Ar-6 | XYZ-h | $R^{11}$-19 |
| 2477. | Ar-6 | XYZ-h | $R^{11}$-20 |
| 2478. | Ar-6 | XYZ-h | $R^{11}$-21 |
| 2479. | Ar-6 | XYZ-i | $R^{11}$-1 |
| 2480. | Ar-6 | XYZ-i | $R^{11}$-2 |
| 2481. | Ar-6 | XYZ-i | $R^{11}$-3 |
| 2482. | Ar-6 | XYZ-i | $R^{11}$-4 |
| 2483. | Ar-6 | XYZ-i | $R^{11}$-5 |
| 2484. | Ar-6 | XYZ-i | $R^{11}$-6 |
| 2485. | Ar-6 | XYZ-i | $R^{11}$-7 |
| 2486. | Ar-6 | XYZ-i | $R^{11}$-8 |
| 2487. | Ar-6 | XYZ-i | $R^{11}$-9 |
| 2488. | Ar-6 | XYZ-i | $R^{11}$-10 |
| 2489. | Ar-6 | XYZ-i | $R^{11}$-11 |
| 2490. | Ar-6 | XYZ-i | $R^{11}$-12 |
| 2491. | Ar-6 | XYZ-i | $R^{11}$-13 |
| 2492. | Ar-6 | XYZ-i | $R^{11}$-14 |
| 2493. | Ar-6 | XYZ-i | $R^{11}$-15 |
| 2494. | Ar-6 | XYZ-i | $R^{11}$-16 |
| 2495. | Ar-6 | XYZ-i | $R^{11}$-17 |
| 2496. | Ar-6 | XYZ-i | $R^{11}$-18 |
| 2497. | Ar-6 | XYZ-i | $R^{11}$-19 |
| 2498. | Ar-6 | XYZ-i | $R^{11}$-20 |
| 2499. | Ar-6 | XYZ-i | $R^{11}$-21 |
| 2500. | Ar-6 | XYZ-k | $R^{11}$-1 |
| 2501. | Ar-6 | XYZ-k | $R^{11}$-2 |
| 2502. | Ar-6 | XYZ-k | $R^{11}$-3 |
| 2503. | Ar-6 | XYZ-k | $R^{11}$-4 |
| 2504. | Ar-6 | XYZ-k | $R^{11}$-5 |
| 2505. | Ar-6 | XYZ-k | $R^{11}$-6 |
| 2506. | Ar-6 | XYZ-k | $R^{11}$-7 |
| 2507. | Ar-6 | XYZ-k | $R^{11}$-8 |
| 2508. | Ar-6 | XYZ-k | $R^{11}$-9 |
| 2509. | Ar-6 | XYZ-k | $R^{11}$-10 |
| 2510. | Ar-6 | XYZ-k | $R^{11}$-11 |
| 2511. | Ar-6 | XYZ-k | $R^{11}$-12 |
| 2512. | Ar-6 | XYZ-k | $R^{11}$-13 |
| 2513. | Ar-6 | XYZ-k | $R^{11}$-14 |
| 2514. | Ar-6 | XYZ-k | $R^{11}$-15 |
| 2515. | Ar-6 | XYZ-k | $R^{11}$-16 |
| 2516. | Ar-6 | XYZ-k | $R^{11}$-17 |
| 2517. | Ar-6 | XYZ-k | $R^{11}$-18 |
| 2518. | Ar-6 | XYZ-k | $R^{11}$-19 |
| 2519. | Ar-6 | XYZ-k | $R^{11}$-20 |
| 2520. | Ar-6 | XYZ-k | $R^{11}$-21 |
| 2521. | Ar-6 | XYZ-l | $R^{11}$-1 |
| 2522. | Ar-6 | XYZ-l | $R^{11}$-2 |
| 2523. | Ar-6 | XYZ-l | $R^{11}$-3 |
| 2524. | Ar-6 | XYZ-l | $R^{11}$-4 |
| 2525. | Ar-6 | XYZ-l | $R^{11}$-5 |
| 2526. | Ar-6 | XYZ-l | $R^{11}$-6 |
| 2527. | Ar-6 | XYZ-l | $R^{11}$-7 |
| 2528. | Ar-6 | XYZ-l | $R^{11}$-8 |
| 2529. | Ar-6 | XYZ-l | $R^{11}$-9 |
| 2530. | Ar-6 | XYZ-l | $R^{11}$-10 |
| 2531. | Ar-6 | XYZ-l | $R^{11}$-11 |
| 2532. | Ar-6 | XYZ-l | $R^{11}$-12 |
| 2533. | Ar-6 | XYZ-l | $R^{11}$-13 |
| 2534. | Ar-6 | XYZ-l | $R^{11}$-14 |
| 2535. | Ar-6 | XYZ-l | $R^{11}$-15 |
| 2536. | Ar-6 | XYZ-l | $R^{11}$-16 |
| 2537. | Ar-6 | XYZ-l | $R^{11}$-17 |
| 2538. | Ar-6 | XYZ-l | $R^{11}$-18 |
| 2539. | Ar-6 | XYZ-l | $R^{11}$-19 |
| 2540. | Ar-6 | XYZ-l | $R^{11}$-20 |
| 2541. | Ar-6 | XYZ-l | $R^{11}$-21 |
| 2542. | Ar-6 | XYZ-m | $R^{11}$-1 |
| 2543. | Ar-6 | XYZ-m | $R^{11}$-2 |
| 2544. | Ar-6 | XYZ-m | $R^{11}$-3 |
| 2545. | Ar-6 | XYZ-m | $R^{11}$-4 |
| 2546. | Ar-6 | XYZ-m | $R^{11}$-5 |
| 2547. | Ar-6 | XYZ-m | $R^{11}$-6 |
| 2548. | Ar-6 | XYZ-m | $R^{11}$-7 |
| 2549. | Ar-6 | XYZ-m | $R^{11}$-8 |
| 2550. | Ar-6 | XYZ-m | $R^{11}$-9 |
| 2551. | Ar-6 | XYZ-m | $R^{11}$-10 |
| 2552. | Ar-6 | XYZ-m | $R^{11}$-11 |
| 2553. | Ar-6 | XYZ-m | $R^{11}$-12 |
| 2554. | Ar-6 | XYZ-m | $R^{11}$-13 |
| 2555. | Ar-6 | XYZ-m | $R^{11}$-14 |
| 2556. | Ar-6 | XYZ-m | $R^{11}$-15 |
| 2557. | Ar-6 | XYZ-m | $R^{11}$-16 |
| 2558. | Ar-6 | XYZ-m | $R^{11}$-17 |
| 2559. | Ar-6 | XYZ-m | $R^{11}$-18 |
| 2560. | Ar-6 | XYZ-m | $R^{11}$-19 |
| 2561. | Ar-6 | XYZ-m | $R^{11}$-20 |
| 2562. | Ar-6 | XYZ-m | $R^{11}$-21 |
| 2563. | Ar-6 | XYZ-n | $R^{11}$-1 |
| 2564. | Ar-6 | XYZ-n | $R^{11}$-2 |
| 2565. | Ar-6 | XYZ-n | $R^{11}$-3 |
| 2566. | Ar-6 | XYZ-n | $R^{11}$-4 |
| 2567. | Ar-6 | XYZ-n | $R^{11}$-5 |
| 2568. | Ar-6 | XYZ-n | $R^{11}$-6 |
| 2569. | Ar-6 | XYZ-n | $R^{11}$-7 |
| 2570. | Ar-6 | XYZ-n | $R^{11}$-8 |
| 2571. | Ar-6 | XYZ-n | $R^{11}$-9 |
| 2572. | Ar-6 | XYZ-n | $R^{11}$-10 |
| 2573. | Ar-6 | XYZ-n | $R^{11}$-11 |
| 2574. | Ar-6 | XYZ-n | $R^{11}$-12 |
| 2575. | Ar-6 | XYZ-n | $R^{11}$-13 |
| 2576. | Ar-6 | XYZ-n | $R^{11}$-14 |
| 2577. | Ar-6 | XYZ-n | $R^{11}$-15 |
| 2578. | Ar-6 | XYZ-n | $R^{11}$-16 |
| 2579. | Ar-6 | XYZ-n | $R^{11}$-17 |
| 2580. | Ar-6 | XYZ-n | $R^{11}$-18 |
| 2581. | Ar-6 | XYZ-n | $R^{11}$-19 |
| 2582. | Ar-6 | XYZ-n | $R^{11}$-20 |
| 2583. | Ar-6 | XYZ-n | $R^{11}$-21 |
| 2584. | Ar-6 | XYZ-o | $R^{11}$-1 |
| 2585. | Ar-6 | XYZ-o | $R^{11}$-2 |
| 2586. | Ar-6 | XYZ-o | $R^{11}$-3 |
| 2587. | Ar-6 | XYZ-o | $R^{11}$-4 |
| 2588. | Ar-6 | XYZ-o | $R^{11}$-5 |
| 2589. | Ar-6 | XYZ-o | $R^{11}$-6 |
| 2590. | Ar-6 | XYZ-o | $R^{11}$-7 |
| 2591. | Ar-6 | XYZ-o | $R^{11}$-8 |
| 2592. | Ar-6 | XYZ-o | $R^{11}$-9 |
| 2593. | Ar-6 | XYZ-o | $R^{11}$-10 |
| 2594. | Ar-6 | XYZ-o | $R^{11}$-11 |
| 2595. | Ar-6 | XYZ-o | $R^{11}$-12 |
| 2596. | Ar-6 | XYZ-o | $R^{11}$-13 |
| 2597. | Ar-6 | XYZ-o | $R^{11}$-14 |
| 2598. | Ar-6 | XYZ-o | $R^{11}$-15 |
| 2599. | Ar-6 | XYZ-o | $R^{11}$-16 |
| 2600. | Ar-6 | XYZ-o | $R^{11}$-17 |
| 2601. | Ar-6 | XYZ-o | $R^{11}$-18 |
| 2602. | Ar-6 | XYZ-o | $R^{11}$-19 |
| 2603. | Ar-6 | XYZ-o | $R^{11}$-20 |
| 2604. | Ar-6 | XYZ-o | $R^{11}$-21 |

TABLE C-continued

| | Ar | -X-Y-Z- | $R^{11}$ |
|---|---|---|---|
| 2605. | Ar-6 | XYZ-p | $R^{11}$-1 |
| 2606. | Ar-6 | XYZ-p | $R^{11}$-2 |
| 2607. | Ar-6 | XYZ-p | $R^{11}$-3 |
| 2608. | Ar-6 | XYZ-p | $R^{11}$-4 |
| 2609. | Ar-6 | XYZ-p | $R^{11}$-5 |
| 2610. | Ar-6 | XYZ-p | $R^{11}$-6 |
| 2611. | Ar-6 | XYZ-p | $R^{11}$-7 |
| 2612. | Ar-6 | XYZ-p | $R^{11}$-8 |
| 2613. | Ar-6 | XYZ-p | $R^{11}$-9 |
| 2614. | Ar-6 | XYZ-p | $R^{11}$-10 |
| 2615. | Ar-6 | XYZ-p | $R^{11}$-11 |
| 2616. | Ar-6 | XYZ-p | $R^{11}$-12 |
| 2617. | Ar-6 | XYZ-p | $R^{11}$-13 |
| 2618. | Ar-6 | XYZ-p | $R^{11}$-14 |
| 2619. | Ar-6 | XYZ-p | $R^{11}$-15 |
| 2620. | Ar-6 | XYZ-p | $R^{11}$-16 |
| 2621. | Ar-6 | XYZ-p | $R^{11}$-17 |
| 2622. | Ar-6 | XYZ-p | $R^{11}$-18 |
| 2623. | Ar-6 | XYZ-p | $R^{11}$-19 |
| 2624. | Ar-6 | XYZ-p | $R^{11}$-20 |
| 2625. | Ar-6 | XYZ-p | $R^{11}$-21 |
| 2626. | Ar-6 | XYZ-q | $R^{11}$-1 |
| 2627. | Ar-6 | XYZ-q | $R^{11}$-2 |
| 2628. | Ar-6 | XYZ-q | $R^{11}$-3 |
| 2629. | Ar-6 | XYZ-q | $R^{11}$-4 |
| 2630. | Ar-6 | XYZ-q | $R^{11}$-5 |
| 2631. | Ar-6 | XYZ-q | $R^{11}$-6 |
| 2632. | Ar-6 | XYZ-q | $R^{11}$-7 |
| 2633. | Ar-6 | XYZ-q | $R^{11}$-8 |
| 2634. | Ar-6 | XYZ-q | $R^{11}$-9 |
| 2635. | Ar-6 | XYZ-q | $R^{11}$-10 |
| 2636. | Ar-6 | XYZ-q | $R^{11}$-11 |
| 2637. | Ar-6 | XYZ-q | $R^{11}$-12 |
| 2638. | Ar-6 | XYZ-q | $R^{11}$-13 |
| 2639. | Ar-6 | XYZ-q | $R^{11}$-14 |
| 2640. | Ar-6 | XYZ-q | $R^{11}$-15 |
| 2641. | Ar-6 | XYZ-q | $R^{11}$-16 |
| 2642. | Ar-6 | XYZ-q | $R^{11}$-17 |
| 2643. | Ar-6 | XYZ-q | $R^{11}$-18 |
| 2644. | Ar-6 | XYZ-q | $R^{11}$-19 |
| 2645. | Ar-6 | XYZ-q | $R^{11}$-20 |
| 2646. | Ar-6 | XYZ-q | $R^{11}$-21 |
| 2647. | Ar-6 | XYZ-r | $R^{11}$-1 |
| 2648. | Ar-6 | XYZ-r | $R^{11}$-2 |
| 2649. | Ar-6 | XYZ-r | $R^{11}$-3 |
| 2650. | Ar-6 | XYZ-r | $R^{11}$-4 |
| 2651. | Ar-6 | XYZ-r | $R^{11}$-5 |
| 2652. | Ar-6 | XYZ-r | $R^{11}$-6 |
| 2653. | Ar-6 | XYZ-r | $R^{11}$-7 |
| 2654. | Ar-6 | XYZ-r | $R^{11}$-8 |
| 2655. | Ar-6 | XYZ-r | $R^{11}$-9 |
| 2656. | Ar-6 | XYZ-r | $R^{11}$-10 |
| 2657. | Ar-6 | XYZ-r | $R^{11}$-11 |
| 2658. | Ar-6 | XYZ-r | $R^{11}$-12 |
| 2659. | Ar-6 | XYZ-r | $R^{11}$-13 |
| 2660. | Ar-6 | XYZ-r | $R^{11}$-14 |
| 2661. | Ar-6 | XYZ-r | $R^{11}$-15 |
| 2662. | Ar-6 | XYZ-r | $R^{11}$-16 |
| 2663. | Ar-6 | XYZ-r | $R^{11}$-17 |
| 2664. | Ar-6 | XYZ-r | $R^{11}$-18 |
| 2665. | Ar-6 | XYZ-r | $R^{11}$-19 |
| 2666. | Ar-6 | XYZ-r | $R^{11}$-20 |
| 2667. | Ar-6 | XYZ-r | $R^{11}$-21 |
| 2668. | Ar-6 | XYZ-s | $R^{11}$-1 |
| 2669. | Ar-6 | XYZ-s | $R^{11}$-2 |
| 2670. | Ar-6 | XYZ-s | $R^{11}$-3 |
| 2671. | Ar-6 | XYZ-s | $R^{11}$-4 |
| 2672. | Ar-6 | XYZ-s | $R^{11}$-5 |
| 2673. | Ar-6 | XYZ-s | $R^{11}$-6 |
| 2674. | Ar-6 | XYZ-s | $R^{11}$-7 |
| 2675. | Ar-6 | XYZ-s | $R^{11}$-8 |
| 2676. | Ar-6 | XYZ-s | $R^{11}$-9 |
| 2677. | Ar-6 | XYZ-s | $R^{11}$-10 |
| 2678. | Ar-6 | XYZ-s | $R^{11}$-11 |
| 2679. | Ar-6 | XYZ-s | $R^{11}$-12 |
| 2680. | Ar-6 | XYZ-s | $R^{11}$-13 |
| 2681. | Ar-6 | XYZ-s | $R^{11}$-14 |
| 2682. | Ar-6 | XYZ-s | $R^{11}$-15 |
| 2683. | Ar-6 | XYZ-s | $R^{11}$-16 |
| 2684. | Ar-6 | XYZ-s | $R^{11}$-17 |
| 2685. | Ar-6 | XYZ-s | $R^{11}$-18 |
| 2686. | Ar-6 | XYZ-s | $R^{11}$-19 |
| 2687. | Ar-6 | XYZ-s | $R^{11}$-20 |
| 2688. | Ar-6 | XYZ-s | $R^{11}$-21 |
| 2689. | Ar-6 | XYZ-t | $R^{11}$-1 |
| 2690. | Ar-6 | XYZ-t | $R^{11}$-2 |
| 2691. | Ar-6 | XYZ-t | $R^{11}$-3 |
| 2692. | Ar-6 | XYZ-t | $R^{11}$-4 |
| 2693. | Ar-6 | XYZ-t | $R^{11}$-5 |
| 2694. | Ar-6 | XYZ-t | $R^{11}$-6 |
| 2695. | Ar-6 | XYZ-t | $R^{11}$-7 |
| 2696. | Ar-6 | XYZ-t | $R^{11}$-8 |
| 2697. | Ar-6 | XYZ-t | $R^{11}$-9 |
| 2698. | Ar-6 | XYZ-t | $R^{11}$-10 |
| 2699. | Ar-6 | XYZ-t | $R^{11}$-11 |
| 2700. | Ar-6 | XYZ-t | $R^{11}$-12 |
| 2701. | Ar-6 | XYZ-t | $R^{11}$-13 |
| 2702. | Ar-6 | XYZ-t | $R^{11}$-14 |
| 2703. | Ar-6 | XYZ-t | $R^{11}$-15 |
| 2704. | Ar-6 | XYZ-t | $R^{11}$-16 |
| 2705. | Ar-6 | XYZ-t | $R^{11}$-17 |
| 2706. | Ar-6 | XYZ-t | $R^{11}$-18 |
| 2707. | Ar-6 | XYZ-t | $R^{11}$-19 |
| 2708. | Ar-6 | XYZ-t | $R^{11}$-20 |
| 2709. | Ar-6 | XYZ-t | $R^{11}$-21 |
| 2710. | Ar-6 | XYZ-u | $R^{11}$-1 |
| 2711. | Ar-6 | XYZ-u | $R^{11}$-2 |
| 2712. | Ar-6 | XYZ-u | $R^{11}$-3 |
| 2713. | Ar-6 | XYZ-u | $R^{11}$-4 |
| 2714. | Ar-6 | XYZ-u | $R^{11}$-5 |
| 2715. | Ar-6 | XYZ-u | $R^{11}$-6 |
| 2716. | Ar-6 | XYZ-u | $R^{11}$-7 |
| 2717. | Ar-6 | XYZ-u | $R^{11}$-8 |
| 2718. | Ar-6 | XYZ-u | $R^{11}$-9 |
| 2719. | Ar-6 | XYZ-u | $R^{11}$-10 |
| 2720. | Ar-6 | XYZ-u | $R^{11}$-11 |
| 2721. | Ar-6 | XYZ-u | $R^{11}$-12 |
| 2722. | Ar-6 | XYZ-u | $R^{11}$-13 |
| 2723. | Ar-6 | XYZ-u | $R^{11}$-14 |
| 2724. | Ar-6 | XYZ-u | $R^{11}$-15 |
| 2725. | Ar-6 | XYZ-u | $R^{11}$-16 |
| 2726. | Ar-6 | XYZ-u | $R^{11}$-17 |
| 2727. | Ar-6 | XYZ-u | $R^{11}$-18 |
| 2728. | Ar-6 | XYZ-u | $R^{11}$-19 |
| 2729. | Ar-6 | XYZ-u | $R^{11}$-20 |
| 2730. | Ar-6 | XYZ-u | $R^{11}$-21 |
| 2731. | Ar-6 | XYZ-v | $R^{11}$-1 |
| 2732. | Ar-6 | XYZ-v | $R^{11}$-2 |
| 2733. | Ar-6 | XYZ-v | $R^{11}$-3 |
| 2734. | Ar-6 | XYZ-v | $R^{11}$-4 |
| 2735. | Ar-6 | XYZ-v | $R^{11}$-5 |
| 2736. | Ar-6 | XYZ-v | $R^{11}$-6 |
| 2737. | Ar-6 | XYZ-v | $R^{11}$-7 |
| 2738. | Ar-6 | XYZ-v | $R^{11}$-8 |
| 2739. | Ar-6 | XYZ-v | $R^{11}$-9 |
| 2740. | Ar-6 | XYZ-v | $R^{11}$-10 |
| 2741. | Ar-6 | XYZ-v | $R^{11}$-11 |
| 2742. | Ar-6 | XYZ-v | $R^{11}$-12 |
| 2743. | Ar-6 | XYZ-v | $R^{11}$-13 |
| 2744. | Ar-6 | XYZ-v | $R^{11}$-14 |
| 2745. | Ar-6 | XYZ-v | $R^{11}$-15 |
| 2746. | Ar-6 | XYZ-v | $R^{11}$-16 |
| 2747. | Ar-6 | XYZ-v | $R^{11}$-17 |
| 2748. | Ar-6 | XYZ-v | $R^{11}$-18 |
| 2749. | Ar-6 | XYZ-v | $R^{11}$-19 |
| 2750. | Ar-6 | XYZ-v | $R^{11}$-20 |
| 2751. | Ar-6 | XYZ-v | $R^{11}$-21 |
| 2752. | Ar-6 | XYZ-w | $R^{11}$-1 |
| 2753. | Ar-6 | XYZ-w | $R^{11}$-2 |
| 2754. | Ar-6 | XYZ-w | $R^{11}$-3 |
| 2755. | Ar-6 | XYZ-w | $R^{11}$-4 |
| 2756. | Ar-6 | XYZ-w | $R^{11}$-5 |
| 2757. | Ar-6 | XYZ-w | $R^{11}$-6 |
| 2758. | Ar-6 | XYZ-w | $R^{11}$-7 |
| 2759. | Ar-6 | XYZ-w | $R^{11}$-8 |
| 2760. | Ar-6 | XYZ-w | $R^{11}$-9 |

TABLE C-continued

| | Ar | -X-Y-Z- | $R^{11}$ |
|---|---|---|---|
| 2761. | Ar-6 | XYZ-w | $R^{11}$-10 |
| 2762. | Ar-6 | XYZ-w | $R^{11}$-11 |
| 2763. | Ar-6 | XYZ-w | $R^{11}$-12 |
| 2764. | Ar-6 | XYZ-w | $R^{11}$-13 |
| 2765. | Ar-6 | XYZ-w | $R^{11}$-14 |
| 2766. | Ar-6 | XYZ-w | $R^{11}$-15 |
| 2767. | Ar-6 | XYZ-w | $R^{11}$-16 |
| 2768. | Ar-6 | XYZ-w | $R^{11}$-17 |
| 2769. | Ar-6 | XYZ-w | $R^{11}$-18 |
| 2770. | Ar-6 | XYZ-w | $R^{11}$-19 |
| 2771. | Ar-6 | XYZ-w | $R^{11}$-20 |
| 2772. | Ar-6 | XYZ-w | $R^{11}$-21 |
| 2773. | Ar-7 | XYZ-a | $R^{11}$-1 |
| 2774. | Ar-7 | XYZ-a | $R^{11}$-2 |
| 2775. | Ar-7 | XYZ-a | $R^{11}$-3 |
| 2776. | Ar-7 | XYZ-a | $R^{11}$-4 |
| 2777. | Ar-7 | XYZ-a | $R^{11}$-5 |
| 2778. | Ar-7 | XYZ-a | $R^{11}$-6 |
| 2779. | Ar-7 | XYZ-a | $R^{11}$-7 |
| 2780. | Ar-7 | XYZ-a | $R^{11}$-8 |
| 2781. | Ar-7 | XYZ-a | $R^{11}$-9 |
| 2782. | Ar-7 | XYZ-a | $R^{11}$-10 |
| 2783. | Ar-7 | XYZ-a | $R^{11}$-11 |
| 2784. | Ar-7 | XYZ-a | $R^{11}$-12 |
| 2785. | Ar-7 | XYZ-a | $R^{11}$-13 |
| 2786. | Ar-7 | XYZ-a | $R^{11}$-14 |
| 2787. | Ar-7 | XYZ-a | $R^{11}$-15 |
| 2788. | Ar-7 | XYZ-a | $R^{11}$-16 |
| 2789. | Ar-7 | XYZ-a | $R^{11}$-17 |
| 2790. | Ar-7 | XYZ-a | $R^{11}$-18 |
| 2791. | Ar-7 | XYZ-a | $R^{11}$-19 |
| 2792. | Ar-7 | XYZ-a | $R^{11}$-20 |
| 2793. | Ar-7 | XYZ-a | $R^{11}$-21 |
| 2794. | Ar-7 | XYZ-b | $R^{11}$-1 |
| 2795. | Ar-7 | XYZ-b | $R^{11}$-2 |
| 2796. | Ar-7 | XYZ-b | $R^{11}$-3 |
| 2797. | Ar-7 | XYZ-b | $R^{11}$-4 |
| 2798. | Ar-7 | XYZ-b | $R^{11}$-5 |
| 2799. | Ar-7 | XYZ-b | $R^{11}$-6 |
| 2800. | Ar-7 | XYZ-b | $R^{11}$-7 |
| 2801. | Ar-7 | XYZ-b | $R^{11}$-8 |
| 2802. | Ar-7 | XYZ-b | $R^{11}$-9 |
| 2803. | Ar-7 | XYZ-b | $R^{11}$-10 |
| 2804. | Ar-7 | XYZ-b | $R^{11}$-11 |
| 2805. | Ar-7 | XYZ-b | $R^{11}$-12 |
| 2806. | Ar-7 | XYZ-b | $R^{11}$-13 |
| 2807. | Ar-7 | XYZ-b | $R^{11}$-14 |
| 2808. | Ar-7 | XYZ-b | $R^{11}$-15 |
| 2809. | Ar-7 | XYZ-b | $R^{11}$-16 |
| 2810. | Ar-7 | XYZ-b | $R^{11}$-17 |
| 2811. | Ar-7 | XYZ-b | $R^{11}$-18 |
| 2812. | Ar-7 | XYZ-b | $R^{11}$-19 |
| 2813. | Ar-7 | XYZ-b | $R^{11}$-20 |
| 2814. | Ar-7 | XYZ-b | $R^{11}$-21 |
| 2815. | Ar-7 | XYZ-c | $R^{11}$-1 |
| 2816. | Ar-7 | XYZ-c | $R^{11}$-2 |
| 2817. | Ar-7 | XYZ-c | $R^{11}$-3 |
| 2818. | Ar-7 | XYZ-c | $R^{11}$-4 |
| 2819. | Ar-7 | XYZ-c | $R^{11}$-5 |
| 2820. | Ar-7 | XYZ-c | $R^{11}$-6 |
| 2821. | Ar-7 | XYZ-c | $R^{11}$-7 |
| 2822. | Ar-7 | XYZ-c | $R^{11}$-8 |
| 2823. | Ar-7 | XYZ-c | $R^{11}$-9 |
| 2824. | Ar-7 | XYZ-c | $R^{11}$-10 |
| 2825. | Ar-7 | XYZ-c | $R^{11}$-11 |
| 2826. | Ar-7 | XYZ-c | $R^{11}$-12 |
| 2827. | Ar-7 | XYZ-c | $R^{11}$-13 |
| 2828. | Ar-7 | XYZ-c | $R^{11}$-14 |
| 2829. | Ar-7 | XYZ-c | $R^{11}$-15 |
| 2830. | Ar-7 | XYZ-c | $R^{11}$-16 |
| 2831. | Ar-7 | XYZ-c | $R^{11}$-17 |
| 2832. | Ar-7 | XYZ-c | $R^{11}$-18 |
| 2833. | Ar-7 | XYZ-c | $R^{11}$-19 |
| 2834. | Ar-7 | XYZ-c | $R^{11}$-20 |
| 2835. | Ar-7 | XYZ-c | $R^{11}$-21 |
| 2836. | Ar-7 | XYZ-d | $R^{11}$-1 |
| 2837. | Ar-7 | XYZ-d | $R^{11}$-2 |
| 2838. | Ar-7 | XYZ-d | $R^{11}$-3 |
| 2839. | Ar-7 | XYZ-d | $R^{11}$-4 |
| 2840. | Ar-7 | XYZ-d | $R^{11}$-5 |
| 2841. | Ar-7 | XYZ-d | $R^{11}$-6 |
| 2842. | Ar-7 | XYZ-d | $R^{11}$-7 |
| 2843. | Ar-7 | XYZ-d | $R^{11}$-8 |
| 2844. | Ar-7 | XYZ-d | $R^{11}$-9 |
| 2845. | Ar-7 | XYZ-d | $R^{11}$-10 |
| 2846. | Ar-7 | XYZ-d | $R^{11}$-11 |
| 2847. | Ar-7 | XYZ-d | $R^{11}$-12 |
| 2848. | Ar-7 | XYZ-d | $R^{11}$-13 |
| 2849. | Ar-7 | XYZ-d | $R^{11}$-14 |
| 2850. | Ar-7 | XYZ-d | $R^{11}$-15 |
| 2851. | Ar-7 | XYZ-d | $R^{11}$-16 |
| 2852. | Ar-7 | XYZ-d | $R^{11}$-17 |
| 2853. | Ar-7 | XYZ-d | $R^{11}$-18 |
| 2854. | Ar-7 | XYZ-d | $R^{11}$-19 |
| 2855. | Ar-7 | XYZ-d | $R^{11}$-20 |
| 2856. | Ar-7 | XYZ-d | $R^{11}$-21 |
| 2857. | Ar-7 | XYZ-e | $R^{11}$-1 |
| 2858. | Ar-7 | XYZ-e | $R^{11}$-2 |
| 2859. | Ar-7 | XYZ-e | $R^{11}$-3 |
| 2860. | Ar-7 | XYZ-e | $R^{11}$-4 |
| 2861. | Ar-7 | XYZ-e | $R^{11}$-5 |
| 2862. | Ar-7 | XYZ-e | $R^{11}$-6 |
| 2863. | Ar-7 | XYZ-e | $R^{11}$-7 |
| 2864. | Ar-7 | XYZ-e | $R^{11}$-8 |
| 2865. | Ar-7 | XYZ-e | $R^{11}$-9 |
| 2866. | Ar-7 | XYZ-e | $R^{11}$-10 |
| 2867. | Ar-7 | XYZ-e | $R^{11}$-11 |
| 2868. | Ar-7 | XYZ-e | $R^{11}$-12 |
| 2869. | Ar-7 | XYZ-e | $R^{11}$-13 |
| 2870. | Ar-7 | XYZ-e | $R^{11}$-14 |
| 2871. | Ar-7 | XYZ-e | $R^{11}$-15 |
| 2872. | Ar-7 | XYZ-e | $R^{11}$-16 |
| 2873. | Ar-7 | XYZ-e | $R^{11}$-17 |
| 2874. | Ar-7 | XYZ-e | $R^{11}$-18 |
| 2875. | Ar-7 | XYZ-e | $R^{11}$-19 |
| 2876. | Ar-7 | XYZ-e | $R^{11}$-20 |
| 2877. | Ar-7 | XYZ-e | $R^{11}$-21 |
| 2878. | Ar-7 | XYZ-f | $R^{11}$-1 |
| 2879. | Ar-7 | XYZ-f | $R^{11}$-2 |
| 2880. | Ar-7 | XYZ-f | $R^{11}$-3 |
| 2881. | Ar-7 | XYZ-f | $R^{11}$-4 |
| 2882. | Ar-7 | XYZ-f | $R^{11}$-5 |
| 2883. | Ar-7 | XYZ-f | $R^{11}$-6 |
| 2884. | Ar-7 | XYZ-f | $R^{11}$-7 |
| 2885. | Ar-7 | XYZ-f | $R^{11}$-8 |
| 2886. | Ar-7 | XYZ-f | $R^{11}$-9 |
| 2887. | Ar-7 | XYZ-f | $R^{11}$-10 |
| 2888. | Ar-7 | XYZ-f | $R^{11}$-11 |
| 2889. | Ar-7 | XYZ-f | $R^{11}$-12 |
| 2890. | Ar-7 | XYZ-f | $R^{11}$-13 |
| 2891. | Ar-7 | XYZ-f | $R^{11}$-14 |
| 2892. | Ar-7 | XYZ-f | $R^{11}$-15 |
| 2893. | Ar-7 | XYZ-f | $R^{11}$-16 |
| 2894. | Ar-7 | XYZ-f | $R^{11}$-17 |
| 2895. | Ar-7 | XYZ-f | $R^{11}$-18 |
| 2896. | Ar-7 | XYZ-f | $R^{11}$-19 |
| 2897. | Ar-7 | XYZ-f | $R^{11}$-20 |
| 2898. | Ar-7 | XYZ-f | $R^{11}$-21 |
| 2899. | Ar-7 | XYZ-g | $R^{11}$-1 |
| 2900. | Ar-7 | XYZ-g | $R^{11}$-2 |
| 2901. | Ar-7 | XYZ-g | $R^{11}$-3 |
| 2902. | Ar-7 | XYZ-g | $R^{11}$-4 |
| 2903. | Ar-7 | XYZ-g | $R^{11}$-5 |
| 2904. | Ar-7 | XYZ-g | $R^{11}$-6 |
| 2905. | Ar-7 | XYZ-g | $R^{11}$-7 |
| 2906. | Ar-7 | XYZ-g | $R^{11}$-8 |
| 2907. | Ar-7 | XYZ-g | $R^{11}$-9 |
| 2908. | Ar-7 | XYZ-g | $R^{11}$-10 |
| 2909. | Ar-7 | XYZ-g | $R^{11}$-11 |
| 2910. | Ar-7 | XYZ-g | $R^{11}$-12 |
| 2911. | Ar-7 | XYZ-g | $R^{11}$-13 |
| 2912. | Ar-7 | XYZ-g | $R^{11}$-14 |
| 2913. | Ar-7 | XYZ-g | $R^{11}$-15 |
| 2914. | Ar-7 | XYZ-g | $R^{11}$-16 |
| 2915. | Ar-7 | XYZ-g | $R^{11}$-17 |
| 2916. | Ar-7 | XYZ-g | $R^{11}$-18 |

TABLE C-continued

|  | Ar | -X-Y-Z- | $R^{11}$ |
|---|---|---|---|
| 2917. | Ar-7 | XYZ-g | $R^{11}$-19 |
| 2918. | Ar-7 | XYZ-g | $R^{11}$-20 |
| 2919. | Ar-7 | XYZ-g | $R^{11}$-21 |
| 2920. | Ar-7 | XYZ-h | $R^{11}$-1 |
| 2921. | Ar-7 | XYZ-h | $R^{11}$-2 |
| 2922. | Ar-7 | XYZ-h | $R^{11}$-3 |
| 2923. | Ar-7 | XYZ-h | $R^{11}$-4 |
| 2924. | Ar-7 | XYZ-h | $R^{11}$-5 |
| 2925. | Ar-7 | XYZ-h | $R^{11}$-6 |
| 2926. | Ar-7 | XYZ-h | $R^{11}$-7 |
| 2927. | Ar-7 | XYZ-h | $R^{11}$-8 |
| 2928. | Ar-7 | XYZ-h | $R^{11}$-9 |
| 2929. | Ar-7 | XYZ-h | $R^{11}$-10 |
| 2930. | Ar-7 | XYZ-h | $R^{11}$-11 |
| 2931. | Ar-7 | XYZ-h | $R^{11}$-12 |
| 2932. | Ar-7 | XYZ-h | $R^{11}$-13 |
| 2933. | Ar-7 | XYZ-h | $R^{11}$-14 |
| 2934. | Ar-7 | XYZ-h | $R^{11}$-15 |
| 2935. | Ar-7 | XYZ-h | $R^{11}$-16 |
| 2936. | Ar-7 | XYZ-h | $R^{11}$-17 |
| 2937. | Ar-7 | XYZ-h | $R^{11}$-18 |
| 2938. | Ar-7 | XYZ-h | $R^{11}$-19 |
| 2939. | Ar-7 | XYZ-h | $R^{11}$-20 |
| 2940. | Ar-7 | XYZ-h | $R^{11}$-21 |
| 2941. | Ar-7 | XYZ-i | $R^{11}$-1 |
| 2942. | Ar-7 | XYZ-i | $R^{11}$-2 |
| 2943. | Ar-7 | XYZ-i | $R^{11}$-3 |
| 2944. | Ar-7 | XYZ-i | $R^{11}$-4 |
| 2945. | Ar-7 | XYZ-i | $R^{11}$-5 |
| 2946. | Ar-7 | XYZ-i | $R^{11}$-6 |
| 2947. | Ar-7 | XYZ-i | $R^{11}$-7 |
| 2948. | Ar-7 | XYZ-i | $R^{11}$-8 |
| 2949. | Ar-7 | XYZ-i | $R^{11}$-9 |
| 2950. | Ar-7 | XYZ-i | $R^{11}$-10 |
| 2951. | Ar-7 | XYZ-i | $R^{11}$-11 |
| 2952. | Ar-7 | XYZ-i | $R^{11}$-12 |
| 2953. | Ar-7 | XYZ-i | $R^{11}$-13 |
| 2954. | Ar-7 | XYZ-i | $R^{11}$-14 |
| 2955. | Ar-7 | XYZ-i | $R^{11}$-15 |
| 2956. | Ar-7 | XYZ-i | $R^{11}$-16 |
| 2957. | Ar-7 | XYZ-i | $R^{11}$-17 |
| 2958. | Ar-7 | XYZ-i | $R^{11}$-18 |
| 2959. | Ar-7 | XYZ-i | $R^{11}$-19 |
| 2960. | Ar-7 | XYZ-i | $R^{11}$-20 |
| 2961. | Ar-7 | XYZ-i | $R^{11}$-21 |
| 2962. | Ar-7 | XYZ-k | $R^{11}$-1 |
| 2963. | Ar-7 | XYZ-k | $R^{11}$-2 |
| 2964. | Ar-7 | XYZ-k | $R^{11}$-3 |
| 2965. | Ar-7 | XYZ-k | $R^{11}$-4 |
| 2966. | Ar-7 | XYZ-k | $R^{11}$-5 |
| 2967. | Ar-7 | XYZ-k | $R^{11}$-6 |
| 2968. | Ar-7 | XYZ-k | $R^{11}$-7 |
| 2969. | Ar-7 | XYZ-k | $R^{11}$-8 |
| 2970. | Ar-7 | XYZ-k | $R^{11}$-9 |
| 2971. | Ar-7 | XYZ-k | $R^{11}$-10 |
| 2972. | Ar-7 | XYZ-k | $R^{11}$-11 |
| 2973. | Ar-7 | XYZ-k | $R^{11}$-12 |
| 2974. | Ar-7 | XYZ-k | $R^{11}$-13 |
| 2975. | Ar-7 | XYZ-k | $R^{11}$-14 |
| 2976. | Ar-7 | XYZ-k | $R^{11}$-15 |
| 2977. | Ar-7 | XYZ-k | $R^{11}$-16 |
| 2978. | Ar-7 | XYZ-k | $R^{11}$-17 |
| 2979. | Ar-7 | XYZ-k | $R^{11}$-18 |
| 2980. | Ar-7 | XYZ-k | $R^{11}$-19 |
| 2981. | Ar-7 | XYZ-k | $R^{11}$-20 |
| 2982. | Ar-7 | XYZ-k | $R^{11}$-21 |
| 2983. | Ar-7 | XYZ-l | $R^{11}$-1 |
| 2984. | Ar-7 | XYZ-l | $R^{11}$-2 |
| 2985. | Ar-7 | XYZ-l | $R^{11}$-3 |
| 2986. | Ar-7 | XYZ-l | $R^{11}$-4 |
| 2987. | Ar-7 | XYZ-l | $R^{11}$-5 |
| 2988. | Ar-7 | XYZ-l | $R^{11}$-6 |
| 2989. | Ar-7 | XYZ-l | $R^{11}$-7 |
| 2990. | Ar-7 | XYZ-l | $R^{11}$-8 |
| 2991. | Ar-7 | XYZ-l | $R^{11}$-9 |
| 2992. | Ar-7 | XYZ-l | $R^{11}$-10 |
| 2993. | Ar-7 | XYZ-l | $R^{11}$-11 |
| 2994. | Ar-7 | XYZ-l | $R^{11}$-12 |
| 2995. | Ar-7 | XYZ-l | $R^{11}$-13 |
| 2996. | Ar-7 | XYZ-l | $R^{11}$-14 |
| 2997. | Ar-7 | XYZ-l | $R^{11}$-15 |
| 2998. | Ar-7 | XYZ-l | $R^{11}$-16 |
| 2999. | Ar-7 | XYZ-l | $R^{11}$-17 |
| 3000. | Ar-7 | XYZ-l | $R^{11}$-18 |
| 3001. | Ar-7 | XYZ-l | $R^{11}$-19 |
| 3002. | Ar-7 | XYZ-l | $R^{11}$-20 |
| 3003. | Ar-7 | XYZ-l | $R^{11}$-21 |
| 3004. | Ar-7 | XYZ-m | $R^{11}$-1 |
| 3005. | Ar-7 | XYZ-m | $R^{11}$-2 |
| 3006. | Ar-7 | XYZ-m | $R^{11}$-3 |
| 3007. | Ar-7 | XYZ-m | $R^{11}$-4 |
| 3008. | Ar-7 | XYZ-m | $R^{11}$-5 |
| 3009. | Ar-7 | XYZ-m | $R^{11}$-6 |
| 3010. | Ar-7 | XYZ-m | $R^{11}$-7 |
| 3011. | Ar-7 | XYZ-m | $R^{11}$-8 |
| 3012. | Ar-7 | XYZ-m | $R^{11}$-9 |
| 3013. | Ar-7 | XYZ-m | $R^{11}$-10 |
| 3014. | Ar-7 | XYZ-m | $R^{11}$-11 |
| 3015. | Ar-7 | XYZ-m | $R^{11}$-12 |
| 3016. | Ar-7 | XYZ-m | $R^{11}$-13 |
| 3017. | Ar-7 | XYZ-m | $R^{11}$-14 |
| 3018. | Ar-7 | XYZ-m | $R^{11}$-15 |
| 3019. | Ar-7 | XYZ-m | $R^{11}$-16 |
| 3020. | Ar-7 | XYZ-m | $R^{11}$-17 |
| 3021. | Ar-7 | XYZ-m | $R^{11}$-18 |
| 3022. | Ar-7 | XYZ-m | $R^{11}$-19 |
| 3023. | Ar-7 | XYZ-m | $R^{11}$-20 |
| 3024. | Ar-7 | XYZ-m | $R^{11}$-21 |
| 3025. | Ar-7 | XYZ-n | $R^{11}$-1 |
| 3026. | Ar-7 | XYZ-n | $R^{11}$-2 |
| 3027. | Ar-7 | XYZ-n | $R^{11}$-3 |
| 3028. | Ar-7 | XYZ-n | $R^{11}$-4 |
| 3029. | Ar-7 | XYZ-n | $R^{11}$-5 |
| 3030. | Ar-7 | XYZ-n | $R^{11}$-6 |
| 3031. | Ar-7 | XYZ-n | $R^{11}$-7 |
| 3032. | Ar-7 | XYZ-n | $R^{11}$-8 |
| 3033. | Ar-7 | XYZ-n | $R^{11}$-9 |
| 3034. | Ar-7 | XYZ-n | $R^{11}$-10 |
| 3035. | Ar-7 | XYZ-n | $R^{11}$-11 |
| 3036. | Ar-7 | XYZ-n | $R^{11}$-12 |
| 3037. | Ar-7 | XYZ-n | $R^{11}$-13 |
| 3038. | Ar-7 | XYZ-n | $R^{11}$-14 |
| 3039. | Ar-7 | XYZ-n | $R^{11}$-15 |
| 3040. | Ar-7 | XYZ-n | $R^{11}$-16 |
| 3041. | Ar-7 | XYZ-n | $R^{11}$-17 |
| 3042. | Ar-7 | XYZ-n | $R^{11}$-18 |
| 3043. | Ar-7 | XYZ-n | $R^{11}$-19 |
| 3044. | Ar-7 | XYZ-n | $R^{11}$-20 |
| 3045. | Ar-7 | XYZ-n | $R^{11}$-21 |
| 3046. | Ar-7 | XYZ-o | $R^{11}$-1 |
| 3047. | Ar-7 | XYZ-o | $R^{11}$-2 |
| 3048. | Ar-7 | XYZ-o | $R^{11}$-3 |
| 3049. | Ar-7 | XYZ-o | $R^{11}$-4 |
| 3050. | Ar-7 | XYZ-o | $R^{11}$-5 |
| 3051. | Ar-7 | XYZ-o | $R^{11}$-6 |
| 3052. | Ar-7 | XYZ-o | $R^{11}$-7 |
| 3053. | Ar-7 | XYZ-o | $R^{11}$-8 |
| 3054. | Ar-7 | XYZ-o | $R^{11}$-9 |
| 3055. | Ar-7 | XYZ-o | $R^{11}$-10 |
| 3056. | Ar-7 | XYZ-o | $R^{11}$-11 |
| 3057. | Ar-7 | XYZ-o | $R^{11}$-12 |
| 3058. | Ar-7 | XYZ-o | $R^{11}$-13 |
| 3059. | Ar-7 | XYZ-o | $R^{11}$-14 |
| 3060. | Ar-7 | XYZ-o | $R^{11}$-15 |
| 3061. | Ar-7 | XYZ-o | $R^{11}$-16 |
| 3062. | Ar-7 | XYZ-o | $R^{11}$-17 |
| 3063. | Ar-7 | XYZ-o | $R^{11}$-18 |
| 3064. | Ar-7 | XYZ-o | $R^{11}$-19 |
| 3065. | Ar-7 | XYZ-o | $R^{11}$-20 |
| 3066. | Ar-7 | XYZ-o | $R^{11}$-21 |
| 3067. | Ar-7 | XYZ-p | $R^{11}$-1 |
| 3068. | Ar-7 | XYZ-p | $R^{11}$-2 |
| 3069. | Ar-7 | XYZ-p | $R^{11}$-3 |
| 3070. | Ar-7 | XYZ-p | $R^{11}$-4 |
| 3071. | Ar-7 | XYZ-p | $R^{11}$-5 |
| 3072. | Ar-7 | XYZ-p | $R^{11}$-6 |

TABLE C-continued

|  | Ar | -X-Y-Z- | R[11] |
|---|---|---|---|
| 3073. | Ar-7 | XYZ-p | R[11]-7 |
| 3074. | Ar-7 | XYZ-p | R[11]-8 |
| 3075. | Ar-7 | XYZ-p | R[11]-9 |
| 3076. | Ar-7 | XYZ-p | R[11]-10 |
| 3077. | Ar-7 | XYZ-p | R[11]-11 |
| 3078. | Ar-7 | XYZ-p | R[11]-12 |
| 3079. | Ar-7 | XYZ-p | R[11]-13 |
| 3080. | Ar-7 | XYZ-p | R[11]-14 |
| 3081. | Ar-7 | XYZ-p | R[11]-15 |
| 3082. | Ar-7 | XYZ-p | R[11]-16 |
| 3083. | Ar-7 | XYZ-p | R[11]-17 |
| 3084. | Ar-7 | XYZ-p | R[11]-18 |
| 3085. | Ar-7 | XYZ-p | R[11]-19 |
| 3086. | Ar-7 | XYZ-p | R[11]-20 |
| 3087. | Ar-7 | XYZ-p | R[11]-21 |
| 3088. | Ar-7 | XYZ-q | R[11]-1 |
| 3089. | Ar-7 | XYZ-q | R[11]-2 |
| 3090. | Ar-7 | XYZ-q | R[11]-3 |
| 3091. | Ar-7 | XYZ-q | R[11]-4 |
| 3092. | Ar-7 | XYZ-q | R[11]-5 |
| 3093. | Ar-7 | XYZ-q | R[11]-6 |
| 3094. | Ar-7 | XYZ-q | R[11]-7 |
| 3095. | Ar-7 | XYZ-q | R[11]-8 |
| 3096. | Ar-7 | XYZ-q | R[11]-9 |
| 3097. | Ar-7 | XYZ-q | R[11]-10 |
| 3098. | Ar-7 | XYZ-q | R[11]-11 |
| 3099. | Ar-7 | XYZ-q | R[11]-12 |
| 3100. | Ar-7 | XYZ-q | R[11]-13 |
| 3101. | Ar-7 | XYZ-q | R[11]-14 |
| 3102. | Ar-7 | XYZ-q | R[11]-15 |
| 3103. | Ar-7 | XYZ-q | R[11]-16 |
| 3104. | Ar-7 | XYZ-q | R[11]-17 |
| 3105. | Ar-7 | XYZ-q | R[11]-18 |
| 3106. | Ar-7 | XYZ-q | R[11]-19 |
| 3107. | Ar-7 | XYZ-q | R[11]-20 |
| 3108. | Ar-7 | XYZ-q | R[11]-21 |
| 3109. | Ar-7 | XYZ-r | R[11]-1 |
| 3110. | Ar-7 | XYZ-r | R[11]-2 |
| 3111. | Ar-7 | XYZ-r | R[11]-3 |
| 3112. | Ar-7 | XYZ-r | R[11]-4 |
| 3113. | Ar-7 | XYZ-r | R[11]-5 |
| 3114. | Ar-7 | XYZ-r | R[11]-6 |
| 3115. | Ar-7 | XYZ-r | R[11]-7 |
| 3116. | Ar-7 | XYZ-r | R[11]-8 |
| 3117. | Ar-7 | XYZ-r | R[11]-9 |
| 3118. | Ar-7 | XYZ-r | R[11]-10 |
| 3119. | Ar-7 | XYZ-r | R[11]-11 |
| 3120. | Ar-7 | XYZ-r | R[11]-12 |
| 3121. | Ar-7 | XYZ-r | R[11]-13 |
| 3122. | Ar-7 | XYZ-r | R[11]-14 |
| 3123. | Ar-7 | XYZ-r | R[11]-15 |
| 3124. | Ar-7 | XYZ-r | R[11]-16 |
| 3125. | Ar-7 | XYZ-r | R[11]-17 |
| 3126. | Ar-7 | XYZ-r | R[11]-18 |
| 3127. | Ar-7 | XYZ-r | R[11]-19 |
| 3128. | Ar-7 | XYZ-r | R[11]-20 |
| 3129. | Ar-7 | XYZ-r | R[11]-21 |
| 3130. | Ar-7 | XYZ-s | R[11]-1 |
| 3131. | Ar-7 | XYZ-s | R[11]-2 |
| 3132. | Ar-7 | XYZ-s | R[11]-3 |
| 3133. | Ar-7 | XYZ-s | R[11]-4 |
| 3134. | Ar-7 | XYZ-s | R[11]-5 |
| 3135. | Ar-7 | XYZ-s | R[11]-6 |
| 3136. | Ar-7 | XYZ-s | R[11]-7 |
| 3137. | Ar-7 | XYZ-s | R[11]-8 |
| 3138. | Ar-7 | XYZ-s | R[11]-9 |
| 3139. | Ar-7 | XYZ-s | R[11]-10 |
| 3140. | Ar-7 | XYZ-s | R[11]-11 |
| 3141. | Ar-7 | XYZ-s | R[11]-12 |
| 3142. | Ar-7 | XYZ-s | R[11]-13 |
| 3143. | Ar-7 | XYZ-s | R[11]-14 |
| 3144. | Ar-7 | XYZ-s | R[11]-15 |
| 3145. | Ar-7 | XYZ-s | R[11]-16 |
| 3146. | Ar-7 | XYZ-s | R[11]-17 |
| 3147. | Ar-7 | XYZ-s | R[11]-18 |
| 3148. | Ar-7 | XYZ-s | R[11]-19 |
| 3149. | Ar-7 | XYZ-s | R[11]-20 |
| 3150. | Ar-7 | XYZ-s | R[11]-21 |
| 3151. | Ar-7 | XYZ-t | R[11]-1 |
| 3152. | Ar-7 | XYZ-t | R[11]-2 |
| 3153. | Ar-7 | XYZ-t | R[11]-3 |
| 3154. | Ar-7 | XYZ-t | R[11]-4 |
| 3155. | Ar-7 | XYZ-t | R[11]-5 |
| 3156. | Ar-7 | XYZ-t | R[11]-6 |
| 3157. | Ar-7 | XYZ-t | R[11]-7 |
| 3158. | Ar-7 | XYZ-t | R[11]-8 |
| 3159. | Ar-7 | XYZ-t | R[11]-9 |
| 3160. | Ar-7 | XYZ-t | R[11]-10 |
| 3161. | Ar-7 | XYZ-t | R[11]-11 |
| 3162. | Ar-7 | XYZ-t | R[11]-12 |
| 3163. | Ar-7 | XYZ-t | R[11]-13 |
| 3164. | Ar-7 | XYZ-t | R[11]-14 |
| 3165. | Ar-7 | XYZ-t | R[11]-15 |
| 3166. | Ar-7 | XYZ-t | R[11]-16 |
| 3167. | Ar-7 | XYZ-t | R[11]-17 |
| 3168. | Ar-7 | XYZ-t | R[11]-18 |
| 3169. | Ar-7 | XYZ-t | R[11]-19 |
| 3170. | Ar-7 | XYZ-t | R[11]-20 |
| 3171. | Ar-7 | XYZ-t | R[11]-21 |
| 3172. | Ar-7 | XYZ-u | R[11]-1 |
| 3173. | Ar-7 | XYZ-u | R[11]-2 |
| 3174. | Ar-7 | XYZ-u | R[11]-3 |
| 3175. | Ar-7 | XYZ-u | R[11]-4 |
| 3176. | Ar-7 | XYZ-u | R[11]-5 |
| 3177. | Ar-7 | XYZ-u | R[11]-6 |
| 3178. | Ar-7 | XYZ-u | R[11]-7 |
| 3179. | Ar-7 | XYZ-u | R[11]-8 |
| 3180. | Ar-7 | XYZ-u | R[11]-9 |
| 3181. | Ar-7 | XYZ-u | R[11]-10 |
| 3182. | Ar-7 | XYZ-u | R[11]-11 |
| 3183. | Ar-7 | XYZ-u | R[11]-12 |
| 3184. | Ar-7 | XYZ-u | R[11]-13 |
| 3185. | Ar-7 | XYZ-u | R[11]-14 |
| 3186. | Ar-7 | XYZ-u | R[11]-15 |
| 3187. | Ar-7 | XYZ-u | R[11]-16 |
| 3188. | Ar-7 | XYZ-u | R[11]-17 |
| 3189. | Ar-7 | XYZ-u | R[11]-18 |
| 3190. | Ar-7 | XYZ-u | R[11]-19 |
| 3191. | Ar-7 | XYZ-u | R[11]-20 |
| 3192. | Ar-7 | XYZ-u | R[11]-21 |
| 3193. | Ar-7 | XYZ-v | R[11]-1 |
| 3194. | Ar-7 | XYZ-v | R[11]-2 |
| 3195. | Ar-7 | XYZ-v | R[11]-3 |
| 3196. | Ar-7 | XYZ-v | R[11]-4 |
| 3197. | Ar-7 | XYZ-v | R[11]-5 |
| 3198. | Ar-7 | XYZ-v | R[11]-6 |
| 3199. | Ar-7 | XYZ-v | R[11]-7 |
| 3200. | Ar-7 | XYZ-v | R[11]-8 |
| 3201. | Ar-7 | XYZ-v | R[11]-9 |
| 3202. | Ar-7 | XYZ-v | R[11]-10 |
| 3203. | Ar-7 | XYZ-v | R[11]-11 |
| 3204. | Ar-7 | XYZ-v | R[11]-12 |
| 3205. | Ar-7 | XYZ-v | R[11]-13 |
| 3206. | Ar-7 | XYZ-v | R[11]-14 |
| 3207. | Ar-7 | XYZ-v | R[11]-15 |
| 3208. | Ar-7 | XYZ-v | R[11]-16 |
| 3209. | Ar-7 | XYZ-v | R[11]-17 |
| 3210. | Ar-7 | XYZ-v | R[11]-18 |
| 3211. | Ar-7 | XYZ-v | R[11]-19 |
| 3212. | Ar-7 | XYZ-v | R[11]-20 |
| 3213. | Ar-7 | XYZ-v | R[11]-21 |
| 3214. | Ar-7 | XYZ-w | R[11]-1 |
| 3215. | Ar-7 | XYZ-w | R[11]-2 |
| 3216. | Ar-7 | XYZ-w | R[11]-3 |
| 3217. | Ar-7 | XYZ-w | R[11]-4 |
| 3218. | Ar-7 | XYZ-w | R[11]-5 |
| 3219. | Ar-7 | XYZ-w | R[11]-6 |
| 3220. | Ar-7 | XYZ-w | R[11]-7 |
| 3221. | Ar-7 | XYZ-w | R[11]-8 |
| 3222. | Ar-7 | XYZ-w | R[11]-9 |
| 3223. | Ar-7 | XYZ-w | R[11]-10 |
| 3224. | Ar-7 | XYZ-w | R[11]-11 |
| 3225. | Ar-7 | XYZ-w | R[11]-12 |
| 3226. | Ar-7 | XYZ-w | R[11]-13 |
| 3227. | Ar-7 | XYZ-w | R[11]-14 |
| 3228. | Ar-7 | XYZ-w | R[11]-15 |

TABLE C-continued

| | Ar | -X-Y-Z- | R¹¹ |
|---|---|---|---|
| 3229. | Ar-7 | XYZ-w | R¹¹-16 |
| 3230. | Ar-7 | XYZ-w | R¹¹-17 |
| 3231. | Ar-7 | XYZ-w | R¹¹-18 |
| 3232. | Ar-7 | XYZ-w | R¹¹-19 |
| 3233. | Ar-7 | XYZ-w | R¹¹-20 |
| 3234. | Ar-7 | XYZ-w | R¹¹-21 |
| 3235. | Ar-8 | XYZ-a | R¹¹-1 |
| 3236. | Ar-8 | XYZ-a | R¹¹-2 |
| 3237. | Ar-8 | XYZ-a | R¹¹-3 |
| 3238. | Ar-8 | XYZ-a | R¹¹-4 |
| 3239. | Ar-8 | XYZ-a | R¹¹-5 |
| 3240. | Ar-8 | XYZ-a | R¹¹-6 |
| 3241. | Ar-8 | XYZ-a | R¹¹-7 |
| 3242. | Ar-8 | XYZ-a | R¹¹-8 |
| 3243. | Ar-8 | XYZ-a | R¹¹-9 |
| 3244. | Ar-8 | XYZ-a | R¹¹-10 |
| 3245. | Ar-8 | XYZ-a | R¹¹-11 |
| 3246. | Ar-8 | XYZ-a | R¹¹-12 |
| 3247. | Ar-8 | XYZ-a | R¹¹-13 |
| 3248. | Ar-8 | XYZ-a | R¹¹-14 |
| 3249. | Ar-8 | XYZ-a | R¹¹-15 |
| 3250. | Ar-8 | XYZ-a | R¹¹-16 |
| 3251. | Ar-8 | XYZ-a | R¹¹-17 |
| 3252. | Ar-8 | XYZ-a | R¹¹-18 |
| 3253. | Ar-8 | XYZ-a | R¹¹-19 |
| 3254. | Ar-8 | XYZ-a | R¹¹-20 |
| 3255. | Ar-8 | XYZ-a | R¹¹-21 |
| 3256. | Ar-8 | XYZ-b | R¹¹-1 |
| 3257. | Ar-8 | XYZ-b | R¹¹-2 |
| 3258. | Ar-8 | XYZ-b | R¹¹-3 |
| 3259. | Ar-8 | XYZ-b | R¹¹-4 |
| 3260. | Ar-8 | XYZ-b | R¹¹-5 |
| 3261. | Ar-8 | XYZ-b | R¹¹-6 |
| 3262. | Ar-8 | XYZ-b | R¹¹-7 |
| 3263. | Ar-8 | XYZ-b | R¹¹-8 |
| 3264. | Ar-8 | XYZ-b | R¹¹-9 |
| 3265. | Ar-8 | XYZ-b | R¹¹-10 |
| 3266. | Ar-8 | XYZ-b | R¹¹-11 |
| 3267. | Ar-8 | XYZ-b | R¹¹-12 |
| 3268. | Ar-8 | XYZ-b | R¹¹-13 |
| 3269. | Ar-8 | XYZ-b | R¹¹-14 |
| 3270. | Ar-8 | XYZ-b | R¹¹-15 |
| 3271. | Ar-8 | XYZ-b | R¹¹-16 |
| 3272. | Ar-8 | XYZ-b | R¹¹-17 |
| 3273. | Ar-8 | XYZ-b | R¹¹-18 |
| 3274. | Ar-8 | XYZ-b | R¹¹-19 |
| 3275. | Ar-8 | XYZ-b | R¹¹-20 |
| 3276. | Ar-8 | XYZ-b | R¹¹-21 |
| 3277. | Ar-8 | XYZ-c | R¹¹-1 |
| 3278. | Ar-8 | XYZ-c | R¹¹-2 |
| 3279. | Ar-8 | XYZ-c | R¹¹-3 |
| 3280. | Ar-8 | XYZ-c | R¹¹-4 |
| 3281. | Ar-8 | XYZ-c | R¹¹-5 |
| 3282. | Ar-8 | XYZ-c | R¹¹-6 |
| 3283. | Ar-8 | XYZ-c | R¹¹-7 |
| 3284. | Ar-8 | XYZ-c | R¹¹-8 |
| 3285. | Ar-8 | XYZ-c | R¹¹-9 |
| 3286. | Ar-8 | XYZ-c | R¹¹-10 |
| 3287. | Ar-8 | XYZ-c | R¹¹-11 |
| 3288. | Ar-8 | XYZ-c | R¹¹-12 |
| 3289. | Ar-8 | XYZ-c | R¹¹-13 |
| 3290. | Ar-8 | XYZ-c | R¹¹-14 |
| 3291. | Ar-8 | XYZ-c | R¹¹-15 |
| 3292. | Ar-8 | XYZ-c | R¹¹-16 |
| 3293. | Ar-8 | XYZ-c | R¹¹-17 |
| 3294. | Ar-8 | XYZ-c | R¹¹-18 |
| 3295. | Ar-8 | XYZ-c | R¹¹-19 |
| 3296. | Ar-8 | XYZ-c | R¹¹-20 |
| 3297. | Ar-8 | XYZ-c | R¹¹-21 |
| 3298. | Ar-8 | XYZ-d | R¹¹-1 |
| 3299. | Ar-8 | XYZ-d | R¹¹-2 |
| 3300. | Ar-8 | XYZ-d | R¹¹-3 |
| 3301. | Ar-8 | XYZ-d | R¹¹-4 |
| 3302. | Ar-8 | XYZ-d | R¹¹-5 |
| 3303. | Ar-8 | XYZ-d | R¹¹-6 |
| 3304. | Ar-8 | XYZ-d | R¹¹-7 |
| 3305. | Ar-8 | XYZ-d | R¹¹-8 |
| 3306. | Ar-8 | XYZ-d | R¹¹-9 |
| 3307. | Ar-8 | XYZ-d | R¹¹-10 |
| 3308. | Ar-8 | XYZ-d | R¹¹-11 |
| 3309. | Ar-8 | XYZ-d | R¹¹-12 |
| 3310. | Ar-8 | XYZ-d | R¹¹-13 |
| 3311. | Ar-8 | XYZ-d | R¹¹-14 |
| 3312. | Ar-8 | XYZ-d | R¹¹-15 |
| 3313. | Ar-8 | XYZ-d | R¹¹-16 |
| 3314. | Ar-8 | XYZ-d | R¹¹-17 |
| 3315. | Ar-8 | XYZ-d | R¹¹-18 |
| 3316. | Ar-8 | XYZ-d | R¹¹-19 |
| 3317. | Ar-8 | XYZ-d | R¹¹-20 |
| 3318. | Ar-8 | XYZ-d | R¹¹-21 |
| 3319. | Ar-8 | XYZ-e | R¹¹-1 |
| 3320. | Ar-8 | XYZ-e | R¹¹-2 |
| 3321. | Ar-8 | XYZ-e | R¹¹-3 |
| 3322. | Ar-8 | XYZ-e | R¹¹-4 |
| 3323. | Ar-8 | XYZ-e | R¹¹-5 |
| 3324. | Ar-8 | XYZ-e | R¹¹-6 |
| 3325. | Ar-8 | XYZ-e | R¹¹-7 |
| 3326. | Ar-8 | XYZ-e | R¹¹-8 |
| 3327. | Ar-8 | XYZ-e | R¹¹-9 |
| 3328. | Ar-8 | XYZ-e | R¹¹-10 |
| 3329. | Ar-8 | XYZ-e | R¹¹-11 |
| 3330. | Ar-8 | XYZ-e | R¹¹-12 |
| 3331. | Ar-8 | XYZ-e | R¹¹-13 |
| 3332. | Ar-8 | XYZ-e | R¹¹-14 |
| 3333. | Ar-8 | XYZ-e | R¹¹-15 |
| 3334. | Ar-8 | XYZ-e | R¹¹-16 |
| 3335. | Ar-8 | XYZ-e | R¹¹-17 |
| 3336. | Ar-8 | XYZ-e | R¹¹-18 |
| 3337. | Ar-8 | XYZ-e | R¹¹-19 |
| 3338. | Ar-8 | XYZ-e | R¹¹-20 |
| 3339. | Ar-8 | XYZ-e | R¹¹-21 |
| 3340. | Ar-8 | XYZ-f | R¹¹-1 |
| 3341. | Ar-8 | XYZ-f | R¹¹-2 |
| 3342. | Ar-8 | XYZ-f | R¹¹-3 |
| 3343. | Ar-8 | XYZ-f | R¹¹-4 |
| 3344. | Ar-8 | XYZ-f | R¹¹-5 |
| 3345. | Ar-8 | XYZ-f | R¹¹-6 |
| 3346. | Ar-8 | XYZ-f | R¹¹-7 |
| 3347. | Ar-8 | XYZ-f | R¹¹-8 |
| 3348. | Ar-8 | XYZ-f | R¹¹-9 |
| 3349. | Ar-8 | XYZ-f | R¹¹-10 |
| 3350. | Ar-8 | XYZ-f | R¹¹-11 |
| 3351. | Ar-8 | XYZ-f | R¹¹-12 |
| 3352. | Ar-8 | XYZ-f | R¹¹-13 |
| 3353. | Ar-8 | XYZ-f | R¹¹-14 |
| 3354. | Ar-8 | XYZ-f | R¹¹-15 |
| 3355. | Ar-8 | XYZ-f | R¹¹-16 |
| 3356. | Ar-8 | XYZ-f | R¹¹-17 |
| 3357. | Ar-8 | XYZ-f | R¹¹-18 |
| 3358. | Ar-8 | XYZ-f | R¹¹-19 |
| 3359. | Ar-8 | XYZ-f | R¹¹-20 |
| 3360. | Ar-8 | XYZ-f | R¹¹-21 |
| 3361. | Ar-8 | XYZ-g | R¹¹-1 |
| 3362. | Ar-8 | XYZ-g | R¹¹-2 |
| 3363. | Ar-8 | XYZ-g | R¹¹-3 |
| 3364. | Ar-8 | XYZ-g | R¹¹-4 |
| 3365. | Ar-8 | XYZ-g | R¹¹-5 |
| 3366. | Ar-8 | XYZ-g | R¹¹-6 |
| 3367. | Ar-8 | XYZ-g | R¹¹-7 |
| 3368. | Ar-8 | XYZ-g | R¹¹-8 |
| 3369. | Ar-8 | XYZ-g | R¹¹-9 |
| 3370. | Ar-8 | XYZ-g | R¹¹-10 |
| 3371. | Ar-8 | XYZ-g | R¹¹-11 |
| 3372. | Ar-8 | XYZ-g | R¹¹-12 |
| 3373. | Ar-8 | XYZ-g | R¹¹-13 |
| 3374. | Ar-8 | XYZ-g | R¹¹-14 |
| 3375. | Ar-8 | XYZ-g | R¹¹-15 |
| 3376. | Ar-8 | XYZ-g | R¹¹-16 |
| 3377. | Ar-8 | XYZ-g | R¹¹-17 |
| 3378. | Ar-8 | XYZ-g | R¹¹-18 |
| 3379. | Ar-8 | XYZ-g | R¹¹-19 |
| 3380. | Ar-8 | XYZ-g | R¹¹-20 |
| 3381. | Ar-8 | XYZ-g | R¹¹-21 |
| 3382. | Ar-8 | XYZ-h | R¹¹-1 |
| 3383. | Ar-8 | XYZ-h | R¹¹-2 |
| 3384. | Ar-8 | XYZ-h | R¹¹-3 |

TABLE C-continued

|  | Ar | -X-Y-Z- | R^11 |
|---|---|---|---|
| 3385. | Ar-8 | XYZ-h | R^11-4 |
| 3386. | Ar-8 | XYZ-h | R^11-5 |
| 3387. | Ar-8 | XYZ-h | R^11-6 |
| 3388. | Ar-8 | XYZ-h | R^11-7 |
| 3389. | Ar-8 | XYZ-h | R^11-8 |
| 3390. | Ar-8 | XYZ-h | R^11-9 |
| 3391. | Ar-8 | XYZ-h | R^11-10 |
| 3392. | Ar-8 | XYZ-h | R^11-11 |
| 3393. | Ar-8 | XYZ-h | R^11-12 |
| 3394. | Ar-8 | XYZ-h | R^11-13 |
| 3395. | Ar-8 | XYZ-h | R^11-14 |
| 3396. | Ar-8 | XYZ-h | R^11-15 |
| 3397. | Ar-8 | XYZ-h | R^11-16 |
| 3398. | Ar-8 | XYZ-h | R^11-17 |
| 3399. | Ar-8 | XYZ-h | R^11-18 |
| 3400. | Ar-8 | XYZ-h | R^11-19 |
| 3401. | Ar-8 | XYZ-h | R^11-20 |
| 3402. | Ar-8 | XYZ-h | R^11-21 |
| 3403. | Ar-8 | XYZ-i | R^11-1 |
| 3404. | Ar-8 | XYZ-i | R^11-2 |
| 3405. | Ar-8 | XYZ-i | R^11-3 |
| 3406. | Ar-8 | XYZ-i | R^11-4 |
| 3407. | Ar-8 | XYZ-i | R^11-5 |
| 3408. | Ar-8 | XYZ-i | R^11-6 |
| 3409. | Ar-8 | XYZ-i | R^11-7 |
| 3410. | Ar-8 | XYZ-i | R^11-8 |
| 3411. | Ar-8 | XYZ-i | R^11-9 |
| 3412. | Ar-8 | XYZ-i | R^11-10 |
| 3413. | Ar-8 | XYZ-i | R^11-11 |
| 3414. | Ar-8 | XYZ-i | R^11-12 |
| 3415. | Ar-8 | XYZ-i | R^11-13 |
| 3416. | Ar-8 | XYZ-i | R^11-14 |
| 3417. | Ar-8 | XYZ-i | R^11-15 |
| 3418. | Ar-8 | XYZ-i | R^11-16 |
| 3419. | Ar-8 | XYZ-i | R^11-17 |
| 3420. | Ar-8 | XYZ-i | R^11-18 |
| 3421. | Ar-8 | XYZ-i | R^11-19 |
| 3422. | Ar-8 | XYZ-i | R^11-20 |
| 3423. | Ar-8 | XYZ-i | R^11-21 |
| 3424. | Ar-8 | XYZ-k | R^11-1 |
| 3425. | Ar-8 | XYZ-k | R^11-2 |
| 3426. | Ar-8 | XYZ-k | R^11-3 |
| 3427. | Ar-8 | XYZ-k | R^11-4 |
| 3428. | Ar-8 | XYZ-k | R^11-5 |
| 3429. | Ar-8 | XYZ-k | R^11-6 |
| 3430. | Ar-8 | XYZ-k | R^11-7 |
| 3431. | Ar-8 | XYZ-k | R^11-8 |
| 3432. | Ar-8 | XYZ-k | R^11-9 |
| 3433. | Ar-8 | XYZ-k | R^11-10 |
| 3434. | Ar-8 | XYZ-k | R^11-11 |
| 3435. | Ar-8 | XYZ-k | R^11-12 |
| 3436. | Ar-8 | XYZ-k | R^11-13 |
| 3437. | Ar-8 | XYZ-k | R^11-14 |
| 3438. | Ar-8 | XYZ-k | R^11-15 |
| 3439. | Ar-8 | XYZ-k | R^11-16 |
| 3440. | Ar-8 | XYZ-k | R^11-17 |
| 3441. | Ar-8 | XYZ-k | R^11-18 |
| 3442. | Ar-8 | XYZ-k | R^11-19 |
| 3443. | Ar-8 | XYZ-k | R^11-20 |
| 3444. | Ar-8 | XYZ-k | R^11-21 |
| 3445. | Ar-8 | XYZ-l | R^11-1 |
| 3446. | Ar-8 | XYZ-l | R^11-2 |
| 3447. | Ar-8 | XYZ-l | R^11-3 |
| 3448. | Ar-8 | XYZ-l | R^11-4 |
| 3449. | Ar-8 | XYZ-l | R^11-5 |
| 3450. | Ar-8 | XYZ-l | R^11-6 |
| 3451. | Ar-8 | XYZ-l | R^11-7 |
| 3452. | Ar-8 | XYZ-l | R^11-8 |
| 3453. | Ar-8 | XYZ-l | R^11-9 |
| 3454. | Ar-8 | XYZ-l | R^11-10 |
| 3455. | Ar-8 | XYZ-l | R^11-11 |
| 3456. | Ar-8 | XYZ-l | R^11-12 |
| 3457. | Ar-8 | XYZ-l | R^11-13 |
| 3458. | Ar-8 | XYZ-l | R^11-14 |
| 3459. | Ar-8 | XYZ-l | R^11-15 |
| 3460. | Ar-8 | XYZ-l | R^11-16 |
| 3461. | Ar-8 | XYZ-l | R^11-17 |
| 3462. | Ar-8 | XYZ-l | R^11-18 |
| 3463. | Ar-8 | XYZ-l | R^11-19 |
| 3464. | Ar-8 | XYZ-l | R^11-20 |
| 3465. | Ar-8 | XYZ-l | R^11-21 |
| 3466. | Ar-8 | XYZ-m | R^11-1 |
| 3467. | Ar-8 | XYZ-m | R^11-2 |
| 3468. | Ar-8 | XYZ-m | R^11-3 |
| 3469. | Ar-8 | XYZ-m | R^11-4 |
| 3470. | Ar-8 | XYZ-m | R^11-5 |
| 3471. | Ar-8 | XYZ-m | R^11-6 |
| 3472. | Ar-8 | XYZ-m | R^11-7 |
| 3473. | Ar-8 | XYZ-m | R^11-8 |
| 3474. | Ar-8 | XYZ-m | R^11-9 |
| 3475. | Ar-8 | XYZ-m | R^11-10 |
| 3476. | Ar-8 | XYZ-m | R^11-11 |
| 3477. | Ar-8 | XYZ-m | R^11-12 |
| 3478. | Ar-8 | XYZ-m | R^11-13 |
| 3479. | Ar-8 | XYZ-m | R^11-14 |
| 3480. | Ar-8 | XYZ-m | R^11-15 |
| 3481. | Ar-8 | XYZ-m | R^11-16 |
| 3482. | Ar-8 | XYZ-m | R^11-17 |
| 3483. | Ar-8 | XYZ-m | R^11-18 |
| 3484. | Ar-8 | XYZ-m | R^11-19 |
| 3485. | Ar-8 | XYZ-m | R^11-20 |
| 3486. | Ar-8 | XYZ-m | R^11-21 |
| 3487. | Ar-8 | XYZ-n | R^11-1 |
| 3488. | Ar-8 | XYZ-n | R^11-2 |
| 3489. | Ar-8 | XYZ-n | R^11-3 |
| 3490. | Ar-8 | XYZ-n | R^11-4 |
| 3491. | Ar-8 | XYZ-n | R^11-5 |
| 3492. | Ar-8 | XYZ-n | R^11-6 |
| 3493. | Ar-8 | XYZ-n | R^11-7 |
| 3494. | Ar-8 | XYZ-n | R^11-8 |
| 3495. | Ar-8 | XYZ-n | R^11-9 |
| 3496. | Ar-8 | XYZ-n | R^11-10 |
| 3497. | Ar-8 | XYZ-n | R^11-11 |
| 3498. | Ar-8 | XYZ-n | R^11-12 |
| 3499. | Ar-8 | XYZ-n | R^11-13 |
| 3500. | Ar-8 | XYZ-n | R^11-14 |
| 3501. | Ar-8 | XYZ-n | R^11-15 |
| 3502. | Ar-8 | XYZ-n | R^11-16 |
| 3503. | Ar-8 | XYZ-n | R^11-17 |
| 3504. | Ar-8 | XYZ-n | R^11-18 |
| 3505. | Ar-8 | XYZ-n | R^11-19 |
| 3506. | Ar-8 | XYZ-n | R^11-20 |
| 3507. | Ar-8 | XYZ-n | R^11-21 |
| 3508. | Ar-8 | XYZ-o | R^11-1 |
| 3509. | Ar-8 | XYZ-o | R^11-2 |
| 3510. | Ar-8 | XYZ-o | R^11-3 |
| 3511. | Ar-8 | XYZ-o | R^11-4 |
| 3512. | Ar-8 | XYZ-o | R^11-5 |
| 3513. | Ar-8 | XYZ-o | R^11-6 |
| 3514. | Ar-8 | XYZ-o | R^11-7 |
| 3515. | Ar-8 | XYZ-o | R^11-8 |
| 3516. | Ar-8 | XYZ-o | R^11-9 |
| 3517. | Ar-8 | XYZ-o | R^11-10 |
| 3518. | Ar-8 | XYZ-o | R^11-11 |
| 3519. | Ar-8 | XYZ-o | R^11-12 |
| 3520. | Ar-8 | XYZ-o | R^11-13 |
| 3521. | Ar-8 | XYZ-o | R^11-14 |
| 3522. | Ar-8 | XYZ-o | R^11-15 |
| 3523. | Ar-8 | XYZ-o | R^11-16 |
| 3524. | Ar-8 | XYZ-o | R^11-17 |
| 3525. | Ar-8 | XYZ-o | R^11-18 |
| 3526. | Ar-8 | XYZ-o | R^11-19 |
| 3527. | Ar-8 | XYZ-o | R^11-20 |
| 3528. | Ar-8 | XYZ-o | R^11-21 |
| 3529. | Ar-8 | XYZ-p | R^11-1 |
| 3530. | Ar-8 | XYZ-p | R^11-2 |
| 3531. | Ar-8 | XYZ-p | R^11-3 |
| 3532. | Ar-8 | XYZ-p | R^11-4 |
| 3533. | Ar-8 | XYZ-p | R^11-5 |
| 3534. | Ar-8 | XYZ-p | R^11-6 |
| 3535. | Ar-8 | XYZ-p | R^11-7 |
| 3536. | Ar-8 | XYZ-p | R^11-8 |
| 3537. | Ar-8 | XYZ-p | R^11-9 |
| 3538. | Ar-8 | XYZ-p | R^11-10 |
| 3539. | Ar-8 | XYZ-p | R^11-11 |
| 3540. | Ar-8 | XYZ-p | R^11-12 |

TABLE C-continued

|  | Ar | -X-Y-Z- | $R^{11}$ |
|---|---|---|---|
| 3541. | Ar-8 | XYZ-p | $R^{11}$-13 |
| 3542. | Ar-8 | XYZ-p | $R^{11}$-14 |
| 3543. | Ar-8 | XYZ-p | $R^{11}$-15 |
| 3544. | Ar-8 | XYZ-p | $R^{11}$-16 |
| 3545. | Ar-8 | XYZ-p | $R^{11}$-17 |
| 3546. | Ar-8 | XYZ-p | $R^{11}$-18 |
| 3547. | Ar-8 | XYZ-p | $R^{11}$-19 |
| 3548. | Ar-8 | XYZ-p | $R^{11}$-20 |
| 3549. | Ar-8 | XYZ-p | $R^{11}$-21 |
| 3550. | Ar-8 | XYZ-q | $R^{11}$-1 |
| 3551. | Ar-8 | XYZ-q | $R^{11}$-2 |
| 3552. | Ar-8 | XYZ-q | $R^{11}$-3 |
| 3553. | Ar-8 | XYZ-q | $R^{11}$-4 |
| 3554. | Ar-8 | XYZ-q | $R^{11}$-5 |
| 3555. | Ar-8 | XYZ-q | $R^{11}$-6 |
| 3556. | Ar-8 | XYZ-q | $R^{11}$-7 |
| 3557. | Ar-8 | XYZ-q | $R^{11}$-8 |
| 3558. | Ar-8 | XYZ-q | $R^{11}$-9 |
| 3559. | Ar-8 | XYZ-q | $R^{11}$-10 |
| 3560. | Ar-8 | XYZ-q | $R^{11}$-11 |
| 3561. | Ar-8 | XYZ-q | $R^{11}$-12 |
| 3562. | Ar-8 | XYZ-q | $R^{11}$-13 |
| 3563. | Ar-8 | XYZ-q | $R^{11}$-14 |
| 3564. | Ar-8 | XYZ-q | $R^{11}$-15 |
| 3565. | Ar-8 | XYZ-q | $R^{11}$-16 |
| 3566. | Ar-8 | XYZ-q | $R^{11}$-17 |
| 3567. | Ar-8 | XYZ-q | $R^{11}$-18 |
| 3568. | Ar-8 | XYZ-q | $R^{11}$-19 |
| 3569. | Ar-8 | XYZ-q | $R^{11}$-20 |
| 3570. | Ar-8 | XYZ-q | $R^{11}$-21 |
| 3571. | Ar-8 | XYZ-r | $R^{11}$-1 |
| 3572. | Ar-8 | XYZ-r | $R^{11}$-2 |
| 3573. | Ar-8 | XYZ-r | $R^{11}$-3 |
| 3574. | Ar-8 | XYZ-r | $R^{11}$-4 |
| 3575. | Ar-8 | XYZ-r | $R^{11}$-5 |
| 3576. | Ar-8 | XYZ-r | $R^{11}$-6 |
| 3577. | Ar-8 | XYZ-r | $R^{11}$-7 |
| 3578. | Ar-8 | XYZ-r | $R^{11}$-8 |
| 3579. | Ar-8 | XYZ-r | $R^{11}$-9 |
| 3580. | Ar-8 | XYZ-r | $R^{11}$-10 |
| 3581. | Ar-8 | XYZ-r | $R^{11}$-11 |
| 3582. | Ar-8 | XYZ-r | $R^{11}$-12 |
| 3583. | Ar-8 | XYZ-r | $R^{11}$-13 |
| 3584. | Ar-8 | XYZ-r | $R^{11}$-14 |
| 3585. | Ar-8 | XYZ-r | $R^{11}$-15 |
| 3586. | Ar-8 | XYZ-r | $R^{11}$-16 |
| 3587. | Ar-8 | XYZ-r | $R^{11}$-17 |
| 3588. | Ar-8 | XYZ-r | $R^{11}$-18 |
| 3589. | Ar-8 | XYZ-r | $R^{11}$-19 |
| 3590. | Ar-8 | XYZ-r | $R^{11}$-20 |
| 3591. | Ar-8 | XYZ-r | $R^{11}$-21 |
| 3592. | Ar-8 | XYZ-s | $R^{11}$-1 |
| 3593. | Ar-8 | XYZ-s | $R^{11}$-2 |
| 3594. | Ar-8 | XYZ-s | $R^{11}$-3 |
| 3595. | Ar-8 | XYZ-s | $R^{11}$-4 |
| 3596. | Ar-8 | XYZ-s | $R^{11}$-5 |
| 3597. | Ar-8 | XYZ-s | $R^{11}$-6 |
| 3598. | Ar-8 | XYZ-s | $R^{11}$-7 |
| 3599. | Ar-8 | XYZ-s | $R^{11}$-8 |
| 3600. | Ar-8 | XYZ-s | $R^{11}$-9 |
| 3601. | Ar-8 | XYZ-s | $R^{11}$-10 |
| 3602. | Ar-8 | XYZ-s | $R^{11}$-11 |
| 3603. | Ar-8 | XYZ-s | $R^{11}$-12 |
| 3604. | Ar-8 | XYZ-s | $R^{11}$-13 |
| 3605. | Ar-8 | XYZ-s | $R^{11}$-14 |
| 3606. | Ar-8 | XYZ-s | $R^{11}$-15 |
| 3607. | Ar-8 | XYZ-s | $R^{11}$-16 |
| 3608. | Ar-8 | XYZ-s | $R^{11}$-17 |
| 3609. | Ar-8 | XYZ-s | $R^{11}$-18 |
| 3610. | Ar-8 | XYZ-s | $R^{11}$-19 |
| 3611. | Ar-8 | XYZ-s | $R^{11}$-20 |
| 3612. | Ar-8 | XYZ-s | $R^{11}$-21 |
| 3613. | Ar-8 | XYZ-t | $R^{11}$-1 |
| 3614. | Ar-8 | XYZ-t | $R^{11}$-2 |
| 3615. | Ar-8 | XYZ-t | $R^{11}$-3 |
| 3616. | Ar-8 | XYZ-t | $R^{11}$-4 |
| 3617. | Ar-8 | XYZ-t | $R^{11}$-5 |
| 3618. | Ar-8 | XYZ-t | $R^{11}$-6 |
| 3619. | Ar-8 | XYZ-t | $R^{11}$-7 |
| 3620. | Ar-8 | XYZ-t | $R^{11}$-8 |
| 3621. | Ar-8 | XYZ-t | $R^{11}$-9 |
| 3622. | Ar-8 | XYZ-t | $R^{11}$-10 |
| 3623. | Ar-8 | XYZ-t | $R^{11}$-11 |
| 3624. | Ar-8 | XYZ-t | $R^{11}$-12 |
| 3625. | Ar-8 | XYZ-t | $R^{11}$-13 |
| 3626. | Ar-8 | XYZ-t | $R^{11}$-14 |
| 3627. | Ar-8 | XYZ-t | $R^{11}$-15 |
| 3628. | Ar-8 | XYZ-t | $R^{11}$-16 |
| 3629. | Ar-8 | XYZ-t | $R^{11}$-17 |
| 3630. | Ar-8 | XYZ-t | $R^{11}$-18 |
| 3631. | Ar-8 | XYZ-t | $R^{11}$-19 |
| 3632. | Ar-8 | XYZ-t | $R^{11}$-20 |
| 3633. | Ar-8 | XYZ-t | $R^{11}$-21 |
| 3634. | Ar-8 | XYZ-u | $R^{11}$-1 |
| 3635. | Ar-8 | XYZ-u | $R^{11}$-2 |
| 3636. | Ar-8 | XYZ-u | $R^{11}$-3 |
| 3637. | Ar-8 | XYZ-u | $R^{11}$-4 |
| 3638. | Ar-8 | XYZ-u | $R^{11}$-5 |
| 3639. | Ar-8 | XYZ-u | $R^{11}$-6 |
| 3640. | Ar-8 | XYZ-u | $R^{11}$-7 |
| 3641. | Ar-8 | XYZ-u | $R^{11}$-8 |
| 3642. | Ar-8 | XYZ-u | $R^{11}$-9 |
| 3643. | Ar-8 | XYZ-u | $R^{11}$-10 |
| 3644. | Ar-8 | XYZ-u | $R^{11}$-11 |
| 3645. | Ar-8 | XYZ-u | $R^{11}$-12 |
| 3646. | Ar-8 | XYZ-u | $R^{11}$-13 |
| 3647. | Ar-8 | XYZ-u | $R^{11}$-14 |
| 3648. | Ar-8 | XYZ-u | $R^{11}$-15 |
| 3649. | Ar-8 | XYZ-u | $R^{11}$-16 |
| 3650. | Ar-8 | XYZ-u | $R^{11}$-17 |
| 3651. | Ar-8 | XYZ-u | $R^{11}$-18 |
| 3652. | Ar-8 | XYZ-u | $R^{11}$-19 |
| 3653. | Ar-8 | XYZ-u | $R^{11}$-20 |
| 3654. | Ar-8 | XYZ-u | $R^{11}$-21 |
| 3655. | Ar-8 | XYZ-v | $R^{11}$-1 |
| 3656. | Ar-8 | XYZ-v | $R^{11}$-2 |
| 3657. | Ar-8 | XYZ-v | $R^{11}$-3 |
| 3658. | Ar-8 | XYZ-v | $R^{11}$-4 |
| 3659. | Ar-8 | XYZ-v | $R^{11}$-5 |
| 3660. | Ar-8 | XYZ-v | $R^{11}$-6 |
| 3661. | Ar-8 | XYZ-v | $R^{11}$-7 |
| 3662. | Ar-8 | XYZ-v | $R^{11}$-8 |
| 3663. | Ar-8 | XYZ-v | $R^{11}$-9 |
| 3664. | Ar-8 | XYZ-v | $R^{11}$-10 |
| 3665. | Ar-8 | XYZ-v | $R^{11}$-11 |
| 3666. | Ar-8 | XYZ-v | $R^{11}$-12 |
| 3667. | Ar-8 | XYZ-v | $R^{11}$-13 |
| 3668. | Ar-8 | XYZ-v | $R^{11}$-14 |
| 3669. | Ar-8 | XYZ-v | $R^{11}$-15 |
| 3670. | Ar-8 | XYZ-v | $R^{11}$-16 |
| 3671. | Ar-8 | XYZ-v | $R^{11}$-17 |
| 3672. | Ar-8 | XYZ-v | $R^{11}$-18 |
| 3673. | Ar-8 | XYZ-v | $R^{11}$-19 |
| 3674. | Ar-8 | XYZ-v | $R^{11}$-20 |
| 3675. | Ar-8 | XYZ-v | $R^{11}$-21 |
| 3676. | Ar-8 | XYZ-w | $R^{11}$-1 |
| 3677. | Ar-8 | XYZ-w | $R^{11}$-2 |
| 3678. | Ar-8 | XYZ-w | $R^{11}$-3 |
| 3679. | Ar-8 | XYZ-w | $R^{11}$-4 |
| 3680. | Ar-8 | XYZ-w | $R^{11}$-5 |
| 3681. | Ar-8 | XYZ-w | $R^{11}$-6 |
| 3682. | Ar-8 | XYZ-w | $R^{11}$-7 |
| 3683. | Ar-8 | XYZ-w | $R^{11}$-8 |
| 3684. | Ar-8 | XYZ-w | $R^{11}$-9 |
| 3685. | Ar-8 | XYZ-w | $R^{11}$-10 |
| 3686. | Ar-8 | XYZ-w | $R^{11}$-11 |
| 3687. | Ar-8 | XYZ-w | $R^{11}$-12 |
| 3688. | Ar-8 | XYZ-w | $R^{11}$-13 |
| 3689. | Ar-8 | XYZ-w | $R^{11}$-14 |
| 3690. | Ar-8 | XYZ-w | $R^{11}$-15 |
| 3691. | Ar-8 | XYZ-w | $R^{11}$-16 |
| 3692. | Ar-8 | XYZ-w | $R^{11}$-17 |
| 3693. | Ar-8 | XYZ-w | $R^{11}$-18 |
| 3694. | Ar-8 | XYZ-w | $R^{11}$-19 |
| 3695. | Ar-8 | XYZ-w | $R^{11}$-20 |
| 3696. | Ar-8 | XYZ-w | $R^{11}$-21 |

TABLE C-continued

|  | Ar | -X-Y-Z- | R[11] |
|---|---|---|---|
| 3697. | Ar-1 | XYZ-a | R[11]-22 |
| 3698. | Ar-1 | XYZ-b | R[11]-22 |
| 3699. | Ar-1 | XYZ-c | R[11]-22 |
| 3700. | Ar-1 | XYZ-d | R[11]-22 |
| 3701. | Ar-1 | XYZ-e | R[11]-22 |
| 3702. | Ar-1 | XYZ-f | R[11]-22 |
| 3703. | Ar-1 | XYZ-g | R[11]-22 |
| 3704. | Ar-1 | XYZ-h | R[11]-22 |
| 3705. | Ar-1 | XYZ-i | R[11]-22 |
| 3706. | Ar-1 | XYZ-k | R[11]-22 |
| 3707. | Ar-1 | XYZ-l | R[11]-22 |
| 3708. | Ar-1 | XYZ-m | R[11]-22 |
| 3709. | Ar-1 | XYZ-n | R[11]-22 |
| 3710. | Ar-1 | XYZ-o | R[11]-22 |
| 3711. | Ar-1 | XYZ-p | R[11]-22 |
| 3712. | Ar-1 | XYZ-q | R[11]-22 |
| 3713. | Ar-1 | XYZ-r | R[11]-22 |
| 3714. | Ar-1 | XYZ-s | R[11]-22 |
| 3715. | Ar-1 | XYZ-t | R[11]-22 |
| 3716. | Ar-1 | XYZ-u | R[11]-22 |
| 3717. | Ar-1 | XYZ-v | R[11]-22 |
| 3718. | Ar-1 | XYZ-w | R[11]-22 |
| 3719. | Ar-2 | XYZ-a | R[11]-22 |
| 3720. | Ar-2 | XYZ-b | R[11]-22 |
| 3721. | Ar-2 | XYZ-c | R[11]-22 |
| 3722. | Ar-2 | XYZ-d | R[11]-22 |
| 3723. | Ar-2 | XYZ-e | R[11]-22 |
| 3724. | Ar-2 | XYZ-f | R[11]-22 |
| 3725. | Ar-2 | XYZ-g | R[11]-22 |
| 3726. | Ar-2 | XYZ-h | R[11]-22 |
| 3727. | Ar-2 | XYZ-i | R[11]-22 |
| 3728. | Ar-2 | XYZ-k | R[11]-22 |
| 3729. | Ar-2 | XYZ-l | R[11]-22 |
| 3730. | Ar-2 | XYZ-m | R[11]-22 |
| 3731. | Ar-2 | XYZ-n | R[11]-22 |
| 3732. | Ar-2 | XYZ-o | R[11]-22 |
| 3733. | Ar-2 | XYZ-p | R[11]-22 |
| 3734. | Ar-2 | XYZ-q | R[11]-22 |
| 3735. | Ar-2 | XYZ-r | R[11]-22 |
| 3736. | Ar-2 | XYZ-s | R[11]-22 |
| 3737. | Ar-2 | XYZ-t | R[11]-22 |
| 3738. | Ar-2 | XYZ-u | R[11]-22 |
| 3739. | Ar-2 | XYZ-v | R[11]-22 |
| 3740. | Ar-2 | XYZ-w | R[11]-22 |
| 3741. | Ar-3 | XYZ-a | R[11]-22 |
| 3742. | Ar-3 | XYZ-b | R[11]-22 |
| 3743. | Ar-3 | XYZ-c | R[11]-22 |
| 3744. | Ar-3 | XYZ-d | R[11]-22 |
| 3745. | Ar-3 | XYZ-e | R[11]-22 |
| 3746. | Ar-3 | XYZ-f | R[11]-22 |
| 3747. | Ar-3 | XYZ-g | R[11]-22 |
| 3748. | Ar-3 | XYZ-h | R[11]-22 |
| 3749. | Ar-3 | XYZ-i | R[11]-22 |
| 3750. | Ar-3 | XYZ-k | R[11]-22 |
| 3751. | Ar-3 | XYZ-l | R[11]-22 |
| 3752. | Ar-3 | XYZ-m | R[11]-22 |
| 3753. | Ar-3 | XYZ-n | R[11]-22 |
| 3754. | Ar-3 | XYZ-o | R[11]-22 |
| 3755. | Ar-3 | XYZ-p | R[11]-22 |
| 3756. | Ar-3 | XYZ-q | R[11]-22 |
| 3757. | Ar-3 | XYZ-r | R[11]-22 |
| 3758. | Ar-3 | XYZ-s | R[11]-22 |
| 3759. | Ar-3 | XYZ-t | R[11]-22 |
| 3760. | Ar-3 | XYZ-u | R[11]-22 |
| 3761. | Ar-3 | XYZ-v | R[11]-22 |
| 3762. | Ar-3 | XYZ-w | R[11]-22 |
| 3763. | Ar-4 | XYZ-a | R[11]-22 |
| 3764. | Ar-4 | XYZ-b | R[11]-22 |
| 3765. | Ar-4 | XYZ-c | R[11]-22 |
| 3766. | Ar-4 | XYZ-d | R[11]-22 |
| 3767. | Ar-4 | XYZ-e | R[11]-22 |
| 3768. | Ar-4 | XYZ-f | R[11]-22 |
| 3769. | Ar-4 | XYZ-g | R[11]-22 |
| 3770. | Ar-4 | XYZ-h | R[11]-22 |
| 3771. | Ar-4 | XYZ-i | R[11]-22 |
| 3772. | Ar-4 | XYZ-k | R[11]-22 |
| 3773. | Ar-4 | XYZ-l | R[11]-22 |
| 3774. | Ar-4 | XYZ-m | R[11]-22 |
| 3775. | Ar-4 | XYZ-n | R[11]-22 |
| 3776. | Ar-4 | XYZ-o | R[11]-22 |
| 3777. | Ar-4 | XYZ-p | R[11]-22 |
| 3778. | Ar-4 | XYZ-q | R[11]-22 |
| 3779. | Ar-4 | XYZ-r | R[11]-22 |
| 3780. | Ar-4 | XYZ-s | R[11]-22 |
| 3781. | Ar-4 | XYZ-t | R[11]-22 |
| 3782. | Ar-4 | XYZ-u | R[11]-22 |
| 3783. | Ar-4 | XYZ-v | R[11]-22 |
| 3784. | Ar-4 | XYZ-w | R[11]-22 |
| 3785. | Ar-5 | XYZ-a | R[11]-22 |
| 3786. | Ar-5 | XYZ-b | R[11]-22 |
| 3787. | Ar-5 | XYZ-c | R[11]-22 |
| 3788. | Ar-5 | XYZ-d | R[11]-22 |
| 3789. | Ar-5 | XYZ-e | R[11]-22 |
| 3790. | Ar-5 | XYZ-f | R[11]-22 |
| 3791. | Ar-5 | XYZ-g | R[11]-22 |
| 3792. | Ar-5 | XYZ-h | R[11]-22 |
| 3793. | Ar-5 | XYZ-i | R[11]-22 |
| 3794. | Ar-5 | XYZ-k | R[11]-22 |
| 3795. | Ar-5 | XYZ-l | R[11]-22 |
| 3796. | Ar-5 | XYZ-m | R[11]-22 |
| 3797. | Ar-5 | XYZ-n | R[11]-22 |
| 3798. | Ar-5 | XYZ-o | R[11]-22 |
| 3799. | Ar-5 | XYZ-p | R[11]-22 |
| 3800. | Ar-5 | XYZ-q | R[11]-22 |
| 3801. | Ar-5 | XYZ-r | R[11]-22 |
| 3802. | Ar-5 | XYZ-s | R[11]-22 |
| 3803. | Ar-5 | XYZ-t | R[11]-22 |
| 3804. | Ar-5 | XYZ-u | R[11]-22 |
| 3805. | Ar-5 | XYZ-v | R[11]-22 |
| 3806. | Ar-5 | XYZ-w | R[11]-22 |
| 3807. | Ar-6 | XYZ-a | R[11]-22 |
| 3808. | Ar-6 | XYZ-b | R[11]-22 |
| 3809. | Ar-6 | XYZ-c | R[11]-22 |
| 3810. | Ar-6 | XYZ-d | R[11]-22 |
| 3811. | Ar-6 | XYZ-e | R[11]-22 |
| 3812. | Ar-6 | XYZ-f | R[11]-22 |
| 3813. | Ar-6 | XYZ-g | R[11]-22 |
| 3814. | Ar-6 | XYZ-h | R[11]-22 |
| 3815. | Ar-6 | XYZ-i | R[11]-22 |
| 3816. | Ar-6 | XYZ-k | R[11]-22 |
| 3817. | Ar-6 | XYZ-l | R[11]-22 |
| 3818. | Ar-6 | XYZ-m | R[11]-22 |
| 3819. | Ar-6 | XYZ-n | R[11]-22 |
| 3820. | Ar-6 | XYZ-o | R[11]-22 |
| 3821. | Ar-6 | XYZ-p | R[11]-22 |
| 3822. | Ar-6 | XYZ-q | R[11]-22 |
| 3823. | Ar-6 | XYZ-r | R[11]-22 |
| 3824. | Ar-6 | XYZ-s | R[11]-22 |
| 3825. | Ar-6 | XYZ-t | R[11]-22 |
| 3826. | Ar-6 | XYZ-u | R[11]-22 |
| 3827. | Ar-6 | XYZ-v | R[11]-22 |
| 3828. | Ar-6 | XYZ-w | R[11]-22 |
| 3829. | Ar-7 | XYZ-a | R[11]-22 |
| 3830. | Ar-7 | XYZ-b | R[11]-22 |
| 3831. | Ar-7 | XYZ-c | R[11]-22 |
| 3832. | Ar-7 | XYZ-d | R[11]-22 |
| 3833. | Ar-7 | XYZ-e | R[11]-22 |
| 3834. | Ar-7 | XYZ-f | R[11]-22 |
| 3835. | Ar-7 | XYZ-g | R[11]-22 |
| 3836. | Ar-7 | XYZ-h | R[11]-22 |
| 3837. | Ar-7 | XYZ-i | R[11]-22 |
| 3838. | Ar-7 | XYZ-k | R[11]-22 |
| 3839. | Ar-7 | XYZ-l | R[11]-22 |
| 3840. | Ar-7 | XYZ-m | R[11]-22 |
| 3841. | Ar-7 | XYZ-n | R[11]-22 |
| 3842. | Ar-7 | XYZ-o | R[11]-22 |
| 3843. | Ar-7 | XYZ-p | R[11]-22 |
| 3844. | Ar-7 | XYZ-q | R[11]-22 |
| 3845. | Ar-7 | XYZ-r | R[11]-22 |
| 3846. | Ar-7 | XYZ-s | R[11]-22 |
| 3847. | Ar-7 | XYZ-t | R[11]-22 |
| 3848. | Ar-7 | XYZ-u | R[11]-22 |
| 3849. | Ar-7 | XYZ-v | R[11]-22 |
| 3850. | Ar-7 | XYZ-w | R[11]-22 |
| 3851. | Ar-8 | XYZ-a | R[11]-22 |
| 3852. | Ar-8 | XYZ-b | R[11]-22 |

TABLE C-continued

|  | Ar | -X-Y-Z- | R[11] |
|---|---|---|---|
| 3853. | Ar-8 | XYZ-c | R[11]-22 |
| 3854. | Ar-8 | XYZ-d | R[11]-22 |
| 3855. | Ar-8 | XYZ-e | R[11]-22 |
| 3856. | Ar-8 | XYZ-f | R[11]-22 |
| 3857. | Ar-8 | XYZ-g | R[11]-22 |
| 3858. | Ar-8 | XYZ-h | R[11]-22 |
| 3859. | Ar-8 | XYZ-i | R[11]-22 |
| 3860. | Ar-8 | XYZ-k | R[11]-22 |
| 3861. | Ar-8 | XYZ-l | R[11]-22 |
| 3862. | Ar-8 | XYZ-m | R[11]-22 |
| 3863. | Ar-8 | XYZ-n | R[11]-22 |
| 3864. | Ar-8 | XYZ-o | R[11]-22 |
| 3865. | Ar-8 | XYZ-p | R[11]-22 |
| 3866. | Ar-8 | XYZ-q | R[11]-22 |
| 3867. | Ar-8 | XYZ-r | R[11]-22 |
| 3868. | Ar-8 | XYZ-s | R[11]-22 |
| 3869. | Ar-8 | XYZ-t | R[11]-22 |
| 3870. | Ar-8 | XYZ-u | R[11]-22 |
| 3871. | Ar-8 | XYZ-v | R[11]-22 |
| 3872. | Ar-8 | XYZ-w | R[11]-22 |
| 3873. | Ar-1 | XYZ-a | R[11]-23 |
| 3874. | Ar-1 | XYZ-b | R[11]-23 |
| 3875. | Ar-1 | XYZ-c | R[11]-23 |
| 3876. | Ar-1 | XYZ-d | R[11]-23 |
| 3877. | Ar-1 | XYZ-e | R[11]-23 |
| 3878. | Ar-1 | XYZ-f | R[11]-23 |
| 3879. | Ar-1 | XYZ-g | R[11]-23 |
| 3880. | Ar-1 | XYZ-h | R[11]-23 |
| 3881. | Ar-1 | XYZ-i | R[11]-23 |
| 3882. | Ar-1 | XYZ-k | R[11]-23 |
| 3883. | Ar-1 | XYZ-l | R[11]-23 |
| 3884. | Ar-1 | XYZ-m | R[11]-23 |
| 3885. | Ar-1 | XYZ-n | R[11]-23 |
| 3886. | Ar-1 | XYZ-o | R[11]-23 |
| 3887. | Ar-1 | XYZ-p | R[11]-23 |
| 3888. | Ar-1 | XYZ-q | R[11]-23 |
| 3889. | Ar-1 | XYZ-r | R[11]-23 |
| 3890. | Ar-1 | XYZ-s | R[11]-23 |
| 3891. | Ar-1 | XYZ-t | R[11]-23 |
| 3892. | Ar-1 | XYZ-u | R[11]-23 |
| 3893. | Ar-1 | XYZ-v | R[11]-23 |
| 3894. | Ar-1 | XYZ-w | R[11]-23 |
| 3895. | Ar-2 | XYZ-a | R[11]-23 |
| 3896. | Ar-2 | XYZ-b | R[11]-23 |
| 3897. | Ar-2 | XYZ-c | R[11]-23 |
| 3898. | Ar-2 | XYZ-d | R[11]-23 |
| 3899. | Ar-2 | XYZ-e | R[11]-23 |
| 3900. | Ar-2 | XYZ-f | R[11]-23 |
| 3901. | Ar-2 | XYZ-g | R[11]-23 |
| 3902. | Ar-2 | XYZ-h | R[11]-23 |
| 3903. | Ar-2 | XYZ-i | R[11]-23 |
| 3904. | Ar-2 | XYZ-k | R[11]-23 |
| 3905. | Ar-2 | XYZ-l | R[11]-23 |
| 3906. | Ar-2 | XYZ-m | R[11]-23 |
| 3907. | Ar-2 | XYZ-n | R[11]-23 |
| 3908. | Ar-2 | XYZ-o | R[11]-23 |
| 3909. | Ar-2 | XYZ-p | R[11]-23 |
| 3910. | Ar-2 | XYZ-q | R[11]-23 |
| 3911. | Ar-2 | XYZ-r | R[11]-23 |
| 3912. | Ar-2 | XYZ-s | R[11]-23 |
| 3913. | Ar-2 | XYZ-t | R[11]-23 |
| 3914. | Ar-2 | XYZ-u | R[11]-23 |
| 3915. | Ar-2 | XYZ-v | R[11]-23 |
| 3916. | Ar-2 | XYZ-w | R[11]-23 |
| 3917. | Ar-3 | XYZ-a | R[11]-23 |
| 3918. | Ar-3 | XYZ-b | R[11]-23 |
| 3919. | Ar-3 | XYZ-c | R[11]-23 |
| 3920. | Ar-3 | XYZ-d | R[11]-23 |
| 3921. | Ar-3 | XYZ-e | R[11]-23 |
| 3922. | Ar-3 | XYZ-f | R[11]-23 |
| 3923. | Ar-3 | XYZ-g | R[11]-23 |
| 3924. | Ar-3 | XYZ-h | R[11]-23 |
| 3925. | Ar-3 | XYZ-i | R[11]-23 |
| 3926. | Ar-3 | XYZ-k | R[11]-23 |
| 3927. | Ar-3 | XYZ-l | R[11]-23 |
| 3928. | Ar-3 | XYZ-m | R[11]-23 |
| 3929. | Ar-3 | XYZ-n | R[11]-23 |
| 3930. | Ar-3 | XYZ-o | R[11]-23 |
| 3931. | Ar-3 | XYZ-p | R[11]-23 |
| 3932. | Ar-3 | XYZ-q | R[11]-23 |
| 3933. | Ar-3 | XYZ-r | R[11]-23 |
| 3934. | Ar-3 | XYZ-s | R[11]-23 |
| 3935. | Ar-3 | XYZ-t | R[11]-23 |
| 3936. | Ar-3 | XYZ-u | R[11]-23 |
| 3937. | Ar-3 | XYZ-v | R[11]-23 |
| 3938. | Ar-3 | XYZ-w | R[11]-23 |
| 3939. | Ar-4 | XYZ-a | R[11]-23 |
| 3940. | Ar-4 | XYZ-b | R[11]-23 |
| 3941. | Ar-4 | XYZ-c | R[11]-23 |
| 3942. | Ar-4 | XYZ-d | R[11]-23 |
| 3943. | Ar-4 | XYZ-e | R[11]-23 |
| 3944. | Ar-4 | XYZ-f | R[11]-23 |
| 3945. | Ar-4 | XYZ-g | R[11]-23 |
| 3946. | Ar-4 | XYZ-h | R[11]-23 |
| 3947. | Ar-4 | XYZ-i | R[11]-23 |
| 3948. | Ar-4 | XYZ-k | R[11]-23 |
| 3949. | Ar-4 | XYZ-l | R[11]-23 |
| 3950. | Ar-4 | XYZ-m | R[11]-23 |
| 3951. | Ar-4 | XYZ-n | R[11]-23 |
| 3952. | Ar-4 | XYZ-o | R[11]-23 |
| 3953. | Ar-4 | XYZ-p | R[11]-23 |
| 3954. | Ar-4 | XYZ-q | R[11]-23 |
| 3955. | Ar-4 | XYZ-r | R[11]-23 |
| 3956. | Ar-4 | XYZ-s | R[11]-23 |
| 3957. | Ar-4 | XYZ-t | R[11]-23 |
| 3958. | Ar-4 | XYZ-u | R[11]-23 |
| 3959. | Ar-4 | XYZ-v | R[11]-23 |
| 3960. | Ar-4 | XYZ-w | R[11]-23 |
| 3961. | Ar-5 | XYZ-a | R[11]-23 |
| 3962. | Ar-5 | XYZ-b | R[11]-23 |
| 3963. | Ar-5 | XYZ-c | R[11]-23 |
| 3964. | Ar-5 | XYZ-d | R[11]-23 |
| 3965. | Ar-5 | XYZ-e | R[11]-23 |
| 3966. | Ar-5 | XYZ-f | R[11]-23 |
| 3967. | Ar-5 | XYZ-g | R[11]-23 |
| 3968. | Ar-5 | XYZ-h | R[11]-23 |
| 3969. | Ar-5 | XYZ-i | R[11]-23 |
| 3970. | Ar-5 | XYZ-k | R[11]-23 |
| 3971. | Ar-5 | XYZ-l | R[11]-23 |
| 3972. | Ar-5 | XYZ-m | R[11]-23 |
| 3973. | Ar-5 | XYZ-n | R[11]-23 |
| 3974. | Ar-5 | XYZ-o | R[11]-23 |
| 3975. | Ar-5 | XYZ-p | R[11]-23 |
| 3976. | Ar-5 | XYZ-q | R[11]-23 |
| 3977. | Ar-5 | XYZ-r | R[11]-23 |
| 3978. | Ar-5 | XYZ-s | R[11]-23 |
| 3979. | Ar-5 | XYZ-t | R[11]-23 |
| 3980. | Ar-5 | XYZ-u | R[11]-23 |
| 3981. | Ar-5 | XYZ-v | R[11]-23 |
| 3982. | Ar-5 | XYZ-w | R[11]-23 |
| 3983. | Ar-6 | XYZ-a | R[11]-23 |
| 3984. | Ar-6 | XYZ-b | R[11]-23 |
| 3985. | Ar-6 | XYZ-c | R[11]-23 |
| 3986. | Ar-6 | XYZ-d | R[11]-23 |
| 3987. | Ar-6 | XYZ-e | R[11]-23 |
| 3988. | Ar-6 | XYZ-f | R[11]-23 |
| 3989. | Ar-6 | XYZ-g | R[11]-23 |
| 3990. | Ar-6 | XYZ-h | R[11]-23 |
| 3991. | Ar-6 | XYZ-i | R[11]-23 |
| 3992. | Ar-6 | XYZ-k | R[11]-23 |
| 3993. | Ar-6 | XYZ-l | R[11]-23 |
| 3994. | Ar-6 | XYZ-m | R[11]-23 |
| 3995. | Ar-6 | XYZ-n | R[11]-23 |
| 3996. | Ar-6 | XYZ-o | R[11]-23 |
| 3997. | Ar-6 | XYZ-p | R[11]-23 |
| 3998. | Ar-6 | XYZ-q | R[11]-23 |
| 3999. | Ar-6 | XYZ-r | R[11]-23 |
| 4000. | Ar-6 | XYZ-s | R[11]-23 |
| 4001. | Ar-6 | XYZ-t | R[11]-23 |
| 4002. | Ar-6 | XYZ-u | R[11]-23 |
| 4003. | Ar-6 | XYZ-v | R[11]-23 |
| 4004. | Ar-6 | XYZ-w | R[11]-23 |
| 4005. | Ar-7 | XYZ-a | R[11]-23 |
| 4006. | Ar-7 | XYZ-b | R[11]-23 |
| 4007. | Ar-7 | XYZ-c | R[11]-23 |
| 4008. | Ar-7 | XYZ-d | R[11]-23 |

TABLE C-continued

| | Ar | -X-Y-Z- | $R^{11}$ |
|---|---|---|---|
| 4009. | Ar-7 | XYZ-e | $R^{11}$-23 |
| 4010. | Ar-7 | XYZ-f | $R^{11}$-23 |
| 4011. | Ar-7 | XYZ-g | $R^{11}$-23 |
| 4012. | Ar-7 | XYZ-h | $R^{11}$-23 |
| 4013. | Ar-7 | XYZ-i | $R^{11}$-23 |
| 4014. | Ar-7 | XYZ-k | $R^{11}$-23 |
| 4015. | Ar-7 | XYZ-l | $R^{11}$-23 |
| 4016. | Ar-7 | XYZ-m | $R^{11}$-23 |
| 4017. | Ar-7 | XYZ-n | $R^{11}$-23 |
| 4018. | Ar-7 | XYZ-o | $R^{11}$-23 |
| 4019. | Ar-7 | XYZ-p | $R^{11}$-23 |
| 4020. | Ar-7 | XYZ-q | $R^{11}$-23 |
| 4021. | Ar-7 | XYZ-r | $R^{11}$-23 |
| 4022. | Ar-7 | XYZ-s | $R^{11}$-23 |
| 4023. | Ar-7 | XYZ-t | $R^{11}$-23 |
| 4024. | Ar-7 | XYZ-u | $R^{11}$-23 |
| 4025. | Ar-7 | XYZ-v | $R^{11}$-23 |
| 4026. | Ar-7 | XYZ-w | $R^{11}$-23 |
| 4027. | Ar-8 | XYZ-a | $R^{11}$-23 |
| 4028. | Ar-8 | XYZ-b | $R^{11}$-23 |
| 4029. | Ar-8 | XYZ-c | $R^{11}$-23 |
| 4030. | Ar-8 | XYZ-d | $R^{11}$-23 |
| 4031. | Ar-8 | XYZ-e | $R^{11}$-23 |
| 4032. | Ar-8 | XYZ-f | $R^{11}$-23 |
| 4033. | Ar-8 | XYZ-g | $R^{11}$-23 |
| 4034. | Ar-8 | XYZ-h | $R^{11}$-23 |
| 4035. | Ar-8 | XYZ-i | $R^{11}$-23 |
| 4036. | Ar-8 | XYZ-k | $R^{11}$-23 |
| 4037. | Ar-8 | XYZ-l | $R^{11}$-23 |
| 4038. | Ar-8 | XYZ-m | $R^{11}$-23 |
| 4039. | Ar-8 | XYZ-n | $R^{11}$-23 |
| 4040. | Ar-8 | XYZ-o | $R^{11}$-23 |
| 4041. | Ar-8 | XYZ-p | $R^{11}$-23 |
| 4042. | Ar-8 | XYZ-q | $R^{11}$-23 |
| 4043. | Ar-8 | XYZ-r | $R^{11}$-23 |
| 4044. | Ar-8 | XYZ-s | $R^{11}$-23 |
| 4045. | Ar-8 | XYZ-t | $R^{11}$-23 |
| 4046. | Ar-8 | XYZ-u | $R^{11}$-23 |
| 4047. | Ar-8 | XYZ-v | $R^{11}$-23 |
| 4048. | Ar-8 | XYZ-w | $R^{11}$-23 |
| 4049. | Ar-1 | XYZ-a | $R^{11}$-24 |
| 4050. | Ar-1 | XYZ-b | $R^{11}$-24 |
| 4051. | Ar-1 | XYZ-c | $R^{11}$-24 |
| 4052. | Ar-1 | XYZ-d | $R^{11}$-24 |
| 4053. | Ar-1 | XYZ-e | $R^{11}$-24 |
| 4054. | Ar-1 | XYZ-f | $R^{11}$-24 |
| 4055. | Ar-1 | XYZ-g | $R^{11}$-24 |
| 4056. | Ar-1 | XYZ-h | $R^{11}$-24 |
| 4057. | Ar-1 | XYZ-i | $R^{11}$-24 |
| 4058. | Ar-1 | XYZ-k | $R^{11}$-24 |
| 4059. | Ar-1 | XYZ-l | $R^{11}$-24 |
| 4060. | Ar-1 | XYZ-m | $R^{11}$-24 |
| 4061. | Ar-1 | XYZ-n | $R^{11}$-24 |
| 4062. | Ar-1 | XYZ-o | $R^{11}$-24 |
| 4063. | Ar-1 | XYZ-p | $R^{11}$-24 |
| 4064. | Ar-1 | XYZ-q | $R^{11}$-24 |
| 4065. | Ar-1 | XYZ-r | $R^{11}$-24 |
| 4066. | Ar-1 | XYZ-s | $R^{11}$-24 |
| 4067. | Ar-1 | XYZ-t | $R^{11}$-24 |
| 4068. | Ar-1 | XYZ-u | $R^{11}$-24 |
| 4069. | Ar-1 | XYZ-v | $R^{11}$-24 |
| 4070. | Ar-1 | XYZ-w | $R^{11}$-24 |
| 4071. | Ar-2 | XYZ-a | $R^{11}$-24 |
| 4072. | Ar-2 | XYZ-b | $R^{11}$-24 |
| 4073. | Ar-2 | XYZ-c | $R^{11}$-24 |
| 4074. | Ar-2 | XYZ-d | $R^{11}$-24 |
| 4075. | Ar-2 | XYZ-e | $R^{11}$-24 |
| 4076. | Ar-2 | XYZ-f | $R^{11}$-24 |
| 4077. | Ar-2 | XYZ-g | $R^{11}$-24 |
| 4078. | Ar-2 | XYZ-h | $R^{11}$-24 |
| 4079. | Ar-2 | XYZ-i | $R^{11}$-24 |
| 4080. | Ar-2 | XYZ-k | $R^{11}$-24 |
| 4081. | Ar-2 | XYZ-l | $R^{11}$-24 |
| 4082. | Ar-2 | XYZ-m | $R^{11}$-24 |
| 4083. | Ar-2 | XYZ-n | $R^{11}$-24 |
| 4084. | Ar-2 | XYZ-o | $R^{11}$-24 |
| 4085. | Ar-2 | XYZ-p | $R^{11}$-24 |
| 4086. | Ar-2 | XYZ-q | $R^{11}$-24 |
| 4087. | Ar-2 | XYZ-r | $R^{11}$-24 |
| 4088. | Ar-2 | XYZ-s | $R^{11}$-24 |
| 4089. | Ar-2 | XYZ-t | $R^{11}$-24 |
| 4090. | Ar-2 | XYZ-u | $R^{11}$-24 |
| 4091. | Ar-2 | XYZ-v | $R^{11}$-24 |
| 4092. | Ar-2 | XYZ-w | $R^{11}$-24 |
| 4093. | Ar-3 | XYZ-a | $R^{11}$-24 |
| 4094. | Ar-3 | XYZ-b | $R^{11}$-24 |
| 4095. | Ar-3 | XYZ-c | $R^{11}$-24 |
| 4096. | Ar-3 | XYZ-d | $R^{11}$-24 |
| 4097. | Ar-3 | XYZ-e | $R^{11}$-24 |
| 4098. | Ar-3 | XYZ-f | $R^{11}$-24 |
| 4099. | Ar-3 | XYZ-g | $R^{11}$-24 |
| 4100. | Ar-3 | XYZ-h | $R^{11}$-24 |
| 4101. | Ar-3 | XYZ-i | $R^{11}$-24 |
| 4102. | Ar-3 | XYZ-k | $R^{11}$-24 |
| 4103. | Ar-3 | XYZ-l | $R^{11}$-24 |
| 4104. | Ar-3 | XYZ-m | $R^{11}$-24 |
| 4105. | Ar-3 | XYZ-n | $R^{11}$-24 |
| 4106. | Ar-3 | XYZ-o | $R^{11}$-24 |
| 4107. | Ar-3 | XYZ-p | $R^{11}$-24 |
| 4108. | Ar-3 | XYZ-q | $R^{11}$-24 |
| 4109. | Ar-3 | XYZ-r | $R^{11}$-24 |
| 4110. | Ar-3 | XYZ-s | $R^{11}$-24 |
| 4111. | Ar-3 | XYZ-t | $R^{11}$-24 |
| 4112. | Ar-3 | XYZ-u | $R^{11}$-24 |
| 4113. | Ar-3 | XYZ-v | $R^{11}$-24 |
| 4114. | Ar-3 | XYZ-w | $R^{11}$-24 |
| 4115. | Ar-4 | XYZ-a | $R^{11}$-24 |
| 4116. | Ar-4 | XYZ-b | $R^{11}$-24 |
| 4117. | Ar-4 | XYZ-c | $R^{11}$-24 |
| 4118. | Ar-4 | XYZ-d | $R^{11}$-24 |
| 4119. | Ar-4 | XYZ-e | $R^{11}$-24 |
| 4120. | Ar-4 | XYZ-f | $R^{11}$-24 |
| 4121. | Ar-4 | XYZ-g | $R^{11}$-24 |
| 4122. | Ar-4 | XYZ-h | $R^{11}$-24 |
| 4123. | Ar-4 | XYZ-i | $R^{11}$-24 |
| 4124. | Ar-4 | XYZ-k | $R^{11}$-24 |
| 4125. | Ar-4 | XYZ-l | $R^{11}$-24 |
| 4126. | Ar-4 | XYZ-m | $R^{11}$-24 |
| 4127. | Ar-4 | XYZ-n | $R^{11}$-24 |
| 4128. | Ar-4 | XYZ-o | $R^{11}$-24 |
| 4129. | Ar-4 | XYZ-p | $R^{11}$-24 |
| 4130. | Ar-4 | XYZ-q | $R^{11}$-24 |
| 4131. | Ar-4 | XYZ-r | $R^{11}$-24 |
| 4132. | Ar-4 | XYZ-s | $R^{11}$-24 |
| 4133. | Ar-4 | XYZ-t | $R^{11}$-24 |
| 4134. | Ar-4 | XYZ-u | $R^{11}$-24 |
| 4135. | Ar-4 | XYZ-v | $R^{11}$-24 |
| 4136. | Ar-4 | XYZ-w | $R^{11}$-24 |
| 4137. | Ar-5 | XYZ-a | $R^{11}$-24 |
| 4138. | Ar-5 | XYZ-b | $R^{11}$-24 |
| 4139. | Ar-5 | XYZ-c | $R^{11}$-24 |
| 4140. | Ar-5 | XYZ-d | $R^{11}$-24 |
| 4141. | Ar-5 | XYZ-e | $R^{11}$-24 |
| 4142. | Ar-5 | XYZ-f | $R^{11}$-24 |
| 4143. | Ar-5 | XYZ-g | $R^{11}$-24 |
| 4144. | Ar-5 | XYZ-h | $R^{11}$-24 |
| 4145. | Ar-5 | XYZ-i | $R^{11}$-24 |
| 4146. | Ar-5 | XYZ-k | $R^{11}$-24 |
| 4147. | Ar-5 | XYZ-l | $R^{11}$-24 |
| 4148. | Ar-5 | XYZ-m | $R^{11}$-24 |
| 4149. | Ar-5 | XYZ-n | $R^{11}$-24 |
| 4150. | Ar-5 | XYZ-o | $R^{11}$-24 |
| 4151. | Ar-5 | XYZ-p | $R^{11}$-24 |
| 4152. | Ar-5 | XYZ-q | $R^{11}$-24 |
| 4153. | Ar-5 | XYZ-r | $R^{11}$-24 |
| 4154. | Ar-5 | XYZ-s | $R^{11}$-24 |
| 4155. | Ar-5 | XYZ-t | $R^{11}$-24 |
| 4156. | Ar-5 | XYZ-u | $R^{11}$-24 |
| 4157. | Ar-5 | XYZ-v | $R^{11}$-24 |
| 4158. | Ar-5 | XYZ-w | $R^{11}$-24 |
| 4159. | Ar-6 | XYZ-a | $R^{11}$-24 |
| 4160. | Ar-6 | XYZ-b | $R^{11}$-24 |
| 4161. | Ar-6 | XYZ-c | $R^{11}$-24 |
| 4162. | Ar-6 | XYZ-d | $R^{11}$-24 |
| 4163. | Ar-6 | XYZ-e | $R^{11}$-24 |
| 4164. | Ar-6 | XYZ-f | $R^{11}$-24 |

TABLE C-continued

|  | Ar | -X-Y-Z- | $R^{11}$ |
|---|---|---|---|
| 4165. | Ar-6 | XYZ-g | $R^{11}$-24 |
| 4166. | Ar-6 | XYZ-h | $R^{11}$-24 |
| 4167. | Ar-6 | XYZ-i | $R^{11}$-24 |
| 4168. | Ar-6 | XYZ-k | $R^{11}$-24 |
| 4169. | Ar-6 | XYZ-l | $R^{11}$-24 |
| 4170. | Ar-6 | XYZ-m | $R^{11}$-24 |
| 4171. | Ar-6 | XYZ-n | $R^{11}$-24 |
| 4172. | Ar-6 | XYZ-o | $R^{11}$-24 |
| 4173. | Ar-6 | XYZ-p | $R^{11}$-24 |
| 4174. | Ar-6 | XYZ-q | $R^{11}$-24 |
| 4175. | Ar-6 | XYZ-r | $R^{11}$-24 |
| 4176. | Ar-6 | XYZ-s | $R^{11}$-24 |
| 4177. | Ar-6 | XYZ-t | $R^{11}$-24 |
| 4178. | Ar-6 | XYZ-u | $R^{11}$-24 |
| 4179. | Ar-6 | XYZ-v | $R^{11}$-24 |
| 4180. | Ar-6 | XYZ-w | $R^{11}$-24 |
| 4181. | Ar-7 | XYZ-a | $R^{11}$-24 |
| 4182. | Ar-7 | XYZ-b | $R^{11}$-24 |
| 4183. | Ar-7 | XYZ-c | $R^{11}$-24 |
| 4184. | Ar-7 | XYZ-d | $R^{11}$-24 |
| 4185. | Ar-7 | XYZ-e | $R^{11}$-24 |
| 4186. | Ar-7 | XYZ-f | $R^{11}$-24 |
| 4187. | Ar-7 | XYZ-g | $R^{11}$-24 |
| 4188. | Ar-7 | XYZ-h | $R^{11}$-24 |
| 4189. | Ar-7 | XYZ-i | $R^{11}$-24 |
| 4190. | Ar-7 | XYZ-k | $R^{11}$-24 |
| 4191. | Ar-7 | XYZ-l | $R^{11}$-24 |
| 4192. | Ar-7 | XYZ-m | $R^{11}$-24 |
| 4193. | Ar-7 | XYZ-n | $R^{11}$-24 |
| 4194. | Ar-7 | XYZ-o | $R^{11}$-24 |
| 4195. | Ar-7 | XYZ-p | $R^{11}$-24 |
| 4196. | Ar-7 | XYZ-q | $R^{11}$-24 |
| 4197. | Ar-7 | XYZ-r | $R^{11}$-24 |
| 4198. | Ar-7 | XYZ-s | $R^{11}$-24 |
| 4199. | Ar-7 | XYZ-t | $R^{11}$-24 |
| 4200. | Ar-7 | XYZ-u | $R^{11}$-24 |
| 4201. | Ar-7 | XYZ-v | $R^{11}$-24 |
| 4202. | Ar-7 | XYZ-w | $R^{11}$-24 |
| 4203. | Ar-8 | XYZ-a | $R^{11}$-24 |
| 4204. | Ar-8 | XYZ-b | $R^{11}$-24 |
| 4205. | Ar-8 | XYZ-c | $R^{11}$-24 |
| 4206. | Ar-8 | XYZ-d | $R^{11}$-24 |
| 4207. | Ar-8 | XYZ-e | $R^{11}$-24 |
| 4208. | Ar-8 | XYZ-f | $R^{11}$-24 |
| 4209. | Ar-8 | XYZ-g | $R^{11}$-24 |
| 4210. | Ar-8 | XYZ-h | $R^{11}$-24 |
| 4211. | Ar-8 | XYZ-i | $R^{11}$-24 |
| 4212. | Ar-8 | XYZ-k | $R^{11}$-24 |
| 4213. | Ar-8 | XYZ-l | $R^{11}$-24 |
| 4214. | Ar-8 | XYZ-m | $R^{11}$-24 |
| 4215. | Ar-8 | XYZ-n | $R^{11}$-24 |
| 4216. | Ar-8 | XYZ-o | $R^{11}$-24 |
| 4217. | Ar-8 | XYZ-p | $R^{11}$-24 |
| 4218. | Ar-8 | XYZ-q | $R^{11}$-24 |
| 4219. | Ar-8 | XYZ-r | $R^{11}$-24 |
| 4220. | Ar-8 | XYZ-s | $R^{11}$-24 |
| 4221. | Ar-8 | XYZ-t | $R^{11}$-24 |
| 4222. | Ar-8 | XYZ-u | $R^{11}$-24 |
| 4223. | Ar-8 | XYZ-v | $R^{11}$-24 |
| 4224. | Ar-8 | XYZ-w | $R^{11}$-24 |
| 4225. | Ar-1 | XYZ-a | $R^{11}$-25 |
| 4226. | Ar-1 | XYZ-b | $R^{11}$-25 |
| 4227. | Ar-1 | XYZ-c | $R^{11}$-25 |
| 4228. | Ar-1 | XYZ-d | $R^{11}$-25 |
| 4229. | Ar-1 | XYZ-e | $R^{11}$-25 |
| 4230. | Ar-1 | XYZ-f | $R^{11}$-25 |
| 4231. | Ar-1 | XYZ-g | $R^{11}$-25 |
| 4232. | Ar-1 | XYZ-h | $R^{11}$-25 |
| 4233. | Ar-1 | XYZ-i | $R^{11}$-25 |
| 4234. | Ar-1 | XYZ-k | $R^{11}$-25 |
| 4235. | Ar-1 | XYZ-l | $R^{11}$-25 |
| 4236. | Ar-1 | XYZ-m | $R^{11}$-25 |
| 4237. | Ar-1 | XYZ-n | $R^{11}$-25 |
| 4238. | Ar-1 | XYZ-o | $R^{11}$-25 |
| 4239. | Ar-1 | XYZ-p | $R^{11}$-25 |
| 4240. | Ar-1 | XYZ-q | $R^{11}$-25 |
| 4241. | Ar-1 | XYZ-r | $R^{11}$-25 |
| 4242. | Ar-1 | XYZ-s | $R^{11}$-25 |
| 4243. | Ar-1 | XYZ-t | $R^{11}$-25 |
| 4244. | Ar-1 | XYZ-u | $R^{11}$-25 |
| 4245. | Ar-1 | XYZ-v | $R^{11}$-25 |
| 4246. | Ar-1 | XYZ-w | $R^{11}$-25 |
| 4247. | Ar-2 | XYZ-a | $R^{11}$-25 |
| 4248. | Ar-2 | XYZ-b | $R^{11}$-25 |
| 4249. | Ar-2 | XYZ-c | $R^{11}$-25 |
| 4250. | Ar-2 | XYZ-d | $R^{11}$-25 |
| 4251. | Ar-2 | XYZ-e | $R^{11}$-25 |
| 4252. | Ar-2 | XYZ-f | $R^{11}$-25 |
| 4253. | Ar-2 | XYZ-g | $R^{11}$-25 |
| 4254. | Ar-2 | XYZ-h | $R^{11}$-25 |
| 4255. | Ar-2 | XYZ-i | $R^{11}$-25 |
| 4256. | Ar-2 | XYZ-k | $R^{11}$-25 |
| 4257. | Ar-2 | XYZ-l | $R^{11}$-25 |
| 4258. | Ar-2 | XYZ-m | $R^{11}$-25 |
| 4259. | Ar-2 | XYZ-n | $R^{11}$-25 |
| 4260. | Ar-2 | XYZ-o | $R^{11}$-25 |
| 4261. | Ar-2 | XYZ-p | $R^{11}$-25 |
| 4262. | Ar-2 | XYZ-q | $R^{11}$-25 |
| 4263. | Ar-2 | XYZ-r | $R^{11}$-25 |
| 4264. | Ar-2 | XYZ-s | $R^{11}$-25 |
| 4265. | Ar-2 | XYZ-t | $R^{11}$-25 |
| 4266. | Ar-2 | XYZ-u | $R^{11}$-25 |
| 4267. | Ar-2 | XYZ-v | $R^{11}$-25 |
| 4268. | Ar-2 | XYZ-w | $R^{11}$-25 |
| 4269. | Ar-3 | XYZ-a | $R^{11}$-25 |
| 4270. | Ar-3 | XYZ-b | $R^{11}$-25 |
| 4271. | Ar-3 | XYZ-c | $R^{11}$-25 |
| 4272. | Ar-3 | XYZ-d | $R^{11}$-25 |
| 4273. | Ar-3 | XYZ-e | $R^{11}$-25 |
| 4274. | Ar-3 | XYZ-f | $R^{11}$-25 |
| 4275. | Ar-3 | XYZ-g | $R^{11}$-25 |
| 4276. | Ar-3 | XYZ-h | $R^{11}$-25 |
| 4277. | Ar-3 | XYZ-i | $R^{11}$-25 |
| 4278. | Ar-3 | XYZ-k | $R^{11}$-25 |
| 4279. | Ar-3 | XYZ-l | $R^{11}$-25 |
| 4280. | Ar-3 | XYZ-m | $R^{11}$-25 |
| 4281. | Ar-3 | XYZ-n | $R^{11}$-25 |
| 4282. | Ar-3 | XYZ-o | $R^{11}$-25 |
| 4283. | Ar-3 | XYZ-p | $R^{11}$-25 |
| 4284. | Ar-3 | XYZ-q | $R^{11}$-25 |
| 4285. | Ar-3 | XYZ-r | $R^{11}$-25 |
| 4286. | Ar-3 | XYZ-s | $R^{11}$-25 |
| 4287. | Ar-3 | XYZ-t | $R^{11}$-25 |
| 4288. | Ar-3 | XYZ-u | $R^{11}$-25 |
| 4289. | Ar-3 | XYZ-v | $R^{11}$-25 |
| 4290. | Ar-3 | XYZ-w | $R^{11}$-25 |
| 4291. | Ar-4 | XYZ-a | $R^{11}$-25 |
| 4292. | Ar-4 | XYZ-b | $R^{11}$-25 |
| 4293. | Ar-4 | XYZ-c | $R^{11}$-25 |
| 4294. | Ar-4 | XYZ-d | $R^{11}$-25 |
| 4295. | Ar-4 | XYZ-e | $R^{11}$-25 |
| 4296. | Ar-4 | XYZ-f | $R^{11}$-25 |
| 4297. | Ar-4 | XYZ-g | $R^{11}$-25 |
| 4298. | Ar-4 | XYZ-h | $R^{11}$-25 |
| 4299. | Ar-4 | XYZ-i | $R^{11}$-25 |
| 4300. | Ar-4 | XYZ-k | $R^{11}$-25 |
| 4301. | Ar-4 | XYZ-l | $R^{11}$-25 |
| 4302. | Ar-4 | XYZ-m | $R^{11}$-25 |
| 4303. | Ar-4 | XYZ-n | $R^{11}$-25 |
| 4304. | Ar-4 | XYZ-o | $R^{11}$-25 |
| 4305. | Ar-4 | XYZ-p | $R^{11}$-25 |
| 4306. | Ar-4 | XYZ-q | $R^{11}$-25 |
| 4307. | Ar-4 | XYZ-r | $R^{11}$-25 |
| 4308. | Ar-4 | XYZ-s | $R^{11}$-25 |
| 4309. | Ar-4 | XYZ-t | $R^{11}$-25 |
| 4310. | Ar-4 | XYZ-u | $R^{11}$-25 |
| 4311. | Ar-4 | XYZ-v | $R^{11}$-25 |
| 4312. | Ar-4 | XYZ-w | $R^{11}$-25 |
| 4313. | Ar-5 | XYZ-a | $R^{11}$-25 |
| 4314. | Ar-5 | XYZ-b | $R^{11}$-25 |
| 4315. | Ar-5 | XYZ-c | $R^{11}$-25 |
| 4316. | Ar-5 | XYZ-d | $R^{11}$-25 |
| 4317. | Ar-5 | XYZ-e | $R^{11}$-25 |
| 4318. | Ar-5 | XYZ-f | $R^{11}$-25 |
| 4319. | Ar-5 | XYZ-g | $R^{11}$-25 |
| 4320. | Ar-5 | XYZ-h | $R^{11}$-25 |

TABLE C-continued

| | Ar | -X-Y-Z- | R[11] |
|---|---|---|---|
| 4321. | Ar-5 | XYZ-i | R[11]-25 |
| 4322. | Ar-5 | XYZ-k | R[11]-25 |
| 4323. | Ar-5 | XYZ-l | R[11]-25 |
| 4324. | Ar-5 | XYZ-m | R[11]-25 |
| 4325. | Ar-5 | XYZ-n | R[11]-25 |
| 4326. | Ar-5 | XYZ-o | R[11]-25 |
| 4327. | Ar-5 | XYZ-p | R[11]-25 |
| 4328. | Ar-5 | XYZ-q | R[11]-25 |
| 4329. | Ar-5 | XYZ-r | R[11]-25 |
| 4330. | Ar-5 | XYZ-s | R[11]-25 |
| 4331. | Ar-5 | XYZ-t | R[11]-25 |
| 4332. | Ar-5 | XYZ-u | R[11]-25 |
| 4333. | Ar-5 | XYZ-v | R[11]-25 |
| 4334. | Ar-5 | XYZ-w | R[11]-25 |
| 4335. | Ar-6 | XYZ-a | R[11]-25 |
| 4336. | Ar-6 | XYZ-b | R[11]-25 |
| 4337. | Ar-6 | XYZ-c | R[11]-25 |
| 4338. | Ar-6 | XYZ-d | R[11]-25 |
| 4339. | Ar-6 | XYZ-e | R[11]-25 |
| 4340. | Ar-6 | XYZ-f | R[11]-25 |
| 4341. | Ar-6 | XYZ-g | R[11]-25 |
| 4342. | Ar-6 | XYZ-h | R[11]-25 |
| 4343. | Ar-6 | XYZ-i | R[11]-25 |
| 4344. | Ar-6 | XYZ-k | R[11]-25 |
| 4345. | Ar-6 | XYZ-l | R[11]-25 |
| 4346. | Ar-6 | XYZ-m | R[11]-25 |
| 4347. | Ar-6 | XYZ-n | R[11]-25 |
| 4348. | Ar-6 | XYZ-o | R[11]-25 |
| 4349. | Ar-6 | XYZ-p | R[11]-25 |
| 4350. | Ar-6 | XYZ-q | R[11]-25 |
| 4351. | Ar-6 | XYZ-r | R[11]-25 |
| 4352. | Ar-6 | XYZ-s | R[11]-25 |
| 4353. | Ar-6 | XYZ-t | R[11]-25 |
| 4354. | Ar-6 | XYZ-u | R[11]-25 |
| 4355. | Ar-6 | XYZ-v | R[11]-25 |
| 4356. | Ar-6 | XYZ-w | R[11]-25 |
| 4357. | Ar-7 | XYZ-a | R[11]-25 |
| 4358. | Ar-7 | XYZ-b | R[11]-25 |
| 4359. | Ar-7 | XYZ-c | R[11]-25 |
| 4360. | Ar-7 | XYZ-d | R[11]-25 |
| 4361. | Ar-7 | XYZ-e | R[11]-25 |
| 4362. | Ar-7 | XYZ-f | R[11]-25 |
| 4363. | Ar-7 | XYZ-g | R[11]-25 |
| 4364. | Ar-7 | XYZ-h | R[11]-25 |
| 4365. | Ar-7 | XYZ-i | R[11]-25 |
| 4366. | Ar-7 | XYZ-k | R[11]-25 |
| 4367. | Ar-7 | XYZ-l | R[11]-25 |
| 4368. | Ar-7 | XYZ-m | R[11]-25 |
| 4369. | Ar-7 | XYZ-n | R[11]-25 |
| 4370. | Ar-7 | XYZ-o | R[11]-25 |
| 4371. | Ar-7 | XYZ-p | R[11]-25 |
| 4372. | Ar-7 | XYZ-q | R[11]-25 |
| 4373. | Ar-7 | XYZ-r | R[11]-25 |
| 4374. | Ar-7 | XYZ-s | R[11]-25 |
| 4375. | Ar-7 | XYZ-t | R[11]-25 |
| 4376. | Ar-7 | XYZ-u | R[11]-25 |
| 4377. | Ar-7 | XYZ-v | R[11]-25 |
| 4378. | Ar-7 | XYZ-w | R[11]-25 |
| 4379. | Ar-8 | XYZ-a | R[11]-25 |
| 4380. | Ar-8 | XYZ-b | R[11]-25 |
| 4381. | Ar-8 | XYZ-c | R[11]-25 |
| 4382. | Ar-8 | XYZ-d | R[11]-25 |
| 4383. | Ar-8 | XYZ-e | R[11]-25 |
| 4384. | Ar-8 | XYZ-f | R[11]-25 |
| 4385. | Ar-8 | XYZ-g | R[11]-25 |
| 4386. | Ar-8 | XYZ-h | R[11]-25 |
| 4387. | Ar-8 | XYZ-i | R[11]-25 |
| 4388. | Ar-8 | XYZ-k | R[11]-25 |
| 4389. | Ar-8 | XYZ-l | R[11]-25 |
| 4390. | Ar-8 | XYZ-m | R[11]-25 |
| 4391. | Ar-8 | XYZ-n | R[11]-25 |
| 4392. | Ar-8 | XYZ-o | R[11]-25 |
| 4393. | Ar-8 | XYZ-p | R[11]-25 |
| 4394. | Ar-8 | XYZ-q | R[11]-25 |
| 4395. | Ar-8 | XYZ-r | R[11]-25 |
| 4396. | Ar-8 | XYZ-s | R[11]-25 |
| 4397. | Ar-8 | XYZ-t | R[11]-25 |
| 4398. | Ar-8 | XYZ-u | R[11]-25 |
| 4399. | Ar-8 | XYZ-v | R[11]-25 |
| 4400. | Ar-8 | XYZ-w | R[11]-25 |
| 4401. | Ar-1 | XYZ-a | R[11]-26 |
| 4402. | Ar-1 | XYZ-b | R[11]-26 |
| 4403. | Ar-1 | XYZ-c | R[11]-26 |
| 4404. | Ar-1 | XYZ-d | R[11]-26 |
| 4405. | Ar-1 | XYZ-e | R[11]-26 |
| 4406. | Ar-1 | XYZ-f | R[11]-26 |
| 4407. | Ar-1 | XYZ-g | R[11]-26 |
| 4408. | Ar-1 | XYZ-h | R[11]-26 |
| 4409. | Ar-1 | XYZ-i | R[11]-26 |
| 4410. | Ar-1 | XYZ-k | R[11]-26 |
| 4411. | Ar-1 | XYZ-l | R[11]-26 |
| 4412. | Ar-1 | XYZ-m | R[11]-26 |
| 4413. | Ar-1 | XYZ-n | R[11]-26 |
| 4414. | Ar-1 | XYZ-o | R[11]-26 |
| 4415. | Ar-1 | XYZ-p | R[11]-26 |
| 4416. | Ar-1 | XYZ-q | R[11]-26 |
| 4417. | Ar-1 | XYZ-r | R[11]-26 |
| 4418. | Ar-1 | XYZ-s | R[11]-26 |
| 4419. | Ar-1 | XYZ-t | R[11]-26 |
| 4420. | Ar-1 | XYZ-u | R[11]-26 |
| 4421. | Ar-1 | XYZ-v | R[11]-26 |
| 4422. | Ar-1 | XYZ-w | R[11]-26 |
| 4423. | Ar-2 | XYZ-a | R[11]-26 |
| 4424. | Ar-2 | XYZ-b | R[11]-26 |
| 4425. | Ar-2 | XYZ-c | R[11]-26 |
| 4426. | Ar-2 | XYZ-d | R[11]-26 |
| 4427. | Ar-2 | XYZ-e | R[11]-26 |
| 4428. | Ar-2 | XYZ-f | R[11]-26 |
| 4429. | Ar-2 | XYZ-g | R[11]-26 |
| 4430. | Ar-2 | XYZ-h | R[11]-26 |
| 4431. | Ar-2 | XYZ-i | R[11]-26 |
| 4432. | Ar-2 | XYZ-k | R[11]-26 |
| 4433. | Ar-2 | XYZ-l | R[11]-26 |
| 4434. | Ar-2 | XYZ-m | R[11]-26 |
| 4435. | Ar-2 | XYZ-n | R[11]-26 |
| 4436. | Ar-2 | XYZ-o | R[11]-26 |
| 4437. | Ar-2 | XYZ-p | R[11]-26 |
| 4438. | Ar-2 | XYZ-q | R[11]-26 |
| 4439. | Ar-2 | XYZ-r | R[11]-26 |
| 4440. | Ar-2 | XYZ-s | R[11]-26 |
| 4441. | Ar-2 | XYZ-t | R[11]-26 |
| 4442. | Ar-2 | XYZ-u | R[11]-26 |
| 4443. | Ar-2 | XYZ-v | R[11]-26 |
| 4444. | Ar-2 | XYZ-w | R[11]-26 |
| 4445. | Ar-3 | XYZ-a | R[11]-26 |
| 4446. | Ar-3 | XYZ-b | R[11]-26 |
| 4447. | Ar-3 | XYZ-c | R[11]-26 |
| 4448. | Ar-3 | XYZ-d | R[11]-26 |
| 4449. | Ar-3 | XYZ-e | R[11]-26 |
| 4450. | Ar-3 | XYZ-f | R[11]-26 |
| 4451. | Ar-3 | XYZ-g | R[11]-26 |
| 4452. | Ar-3 | XYZ-h | R[11]-26 |
| 4453. | Ar-3 | XYZ-i | R[11]-26 |
| 4454. | Ar-3 | XYZ-k | R[11]-26 |
| 4455. | Ar-3 | XYZ-l | R[11]-26 |
| 4456. | Ar-3 | XYZ-m | R[11]-26 |
| 4457. | Ar-3 | XYZ-n | R[11]-26 |
| 4458. | Ar-3 | XYZ-o | R[11]-26 |
| 4459. | Ar-3 | XYZ-p | R[11]-26 |
| 4460. | Ar-3 | XYZ-q | R[11]-26 |
| 4461. | Ar-3 | XYZ-r | R[11]-26 |
| 4462. | Ar-3 | XYZ-s | R[11]-26 |
| 4463. | Ar-3 | XYZ-t | R[11]-26 |
| 4464. | Ar-3 | XYZ-u | R[11]-26 |
| 4465. | Ar-3 | XYZ-v | R[11]-26 |
| 4466. | Ar-3 | XYZ-w | R[11]-26 |
| 4467. | Ar-4 | XYZ-a | R[11]-26 |
| 4468. | Ar-4 | XYZ-b | R[11]-26 |
| 4469. | Ar-4 | XYZ-c | R[11]-26 |
| 4470. | Ar-4 | XYZ-d | R[11]-26 |
| 4471. | Ar-4 | XYZ-e | R[11]-26 |
| 4472. | Ar-4 | XYZ-f | R[11]-26 |
| 4473. | Ar-4 | XYZ-g | R[11]-26 |
| 4474. | Ar-4 | XYZ-h | R[11]-26 |
| 4475. | Ar-4 | XYZ-i | R[11]-26 |
| 4476. | Ar-4 | XYZ-k | R[11]-26 |

TABLE C-continued

|  | Ar | -X-Y-Z- | $R^{11}$ |
|---|---|---|---|
| 4477. | Ar-4 | XYZ-l | $R^{11}$-26 |
| 4478. | Ar-4 | XYZ-m | $R^{11}$-26 |
| 4479. | Ar-4 | XYZ-n | $R^{11}$-26 |
| 4480. | Ar-4 | XYZ-o | $R^{11}$-26 |
| 4481. | Ar-4 | XYZ-p | $R^{11}$-26 |
| 4482. | Ar-4 | XYZ-q | $R^{11}$-26 |
| 4483. | Ar-4 | XYZ-r | $R^{11}$-26 |
| 4484. | Ar-4 | XYZ-s | $R^{11}$-26 |
| 4485. | Ar-4 | XYZ-t | $R^{11}$-26 |
| 4486. | Ar-4 | XYZ-u | $R^{11}$-26 |
| 4487. | Ar-4 | XYZ-v | $R^{11}$-26 |
| 4488. | Ar-4 | XYZ-w | $R^{11}$-26 |
| 4489. | Ar-5 | XYZ-a | $R^{11}$-26 |
| 4490. | Ar-5 | XYZ-b | $R^{11}$-26 |
| 4491. | Ar-5 | XYZ-c | $R^{11}$-26 |
| 4492. | Ar-5 | XYZ-d | $R^{11}$-26 |
| 4493. | Ar-5 | XYZ-e | $R^{11}$-26 |
| 4494. | Ar-5 | XYZ-f | $R^{11}$-26 |
| 4495. | Ar-5 | XYZ-g | $R^{11}$-26 |
| 4496. | Ar-5 | XYZ-h | $R^{11}$-26 |
| 4497. | Ar-5 | XYZ-i | $R^{11}$-26 |
| 4498. | Ar-5 | XYZ-k | $R^{11}$-26 |
| 4499. | Ar-5 | XYZ-l | $R^{11}$-26 |
| 4500. | Ar-5 | XYZ-m | $R^{11}$-26 |
| 4501. | Ar-5 | XYZ-n | $R^{11}$-26 |
| 4502. | Ar-5 | XYZ-o | $R^{11}$-26 |
| 4503. | Ar-5 | XYZ-p | $R^{11}$-26 |
| 4504. | Ar-5 | XYZ-q | $R^{11}$-26 |
| 4505. | Ar-5 | XYZ-r | $R^{11}$-26 |
| 4506. | Ar-5 | XYZ-s | $R^{11}$-26 |
| 4507. | Ar-5 | XYZ-t | $R^{11}$-26 |
| 4508. | Ar-5 | XYZ-u | $R^{11}$-26 |
| 4509. | Ar-5 | XYZ-v | $R^{11}$-26 |
| 4510. | Ar-5 | XYZ-w | $R^{11}$-26 |
| 4511. | Ar-6 | XYZ-a | $R^{11}$-26 |
| 4512. | Ar-6 | XYZ-b | $R^{11}$-26 |
| 4513. | Ar-6 | XYZ-c | $R^{11}$-26 |
| 4514. | Ar-6 | XYZ-d | $R^{11}$-26 |
| 4515. | Ar-6 | XYZ-e | $R^{11}$-26 |
| 4516. | Ar-6 | XYZ-f | $R^{11}$-26 |
| 4517. | Ar-6 | XYZ-g | $R^{11}$-26 |
| 4518. | Ar-6 | XYZ-h | $R^{11}$-26 |
| 4519. | Ar-6 | XYZ-i | $R^{11}$-26 |
| 4520. | Ar-6 | XYZ-k | $R^{11}$-26 |
| 4521. | Ar-6 | XYZ-l | $R^{11}$-26 |
| 4522. | Ar-6 | XYZ-m | $R^{11}$-26 |
| 4523. | Ar-6 | XYZ-n | $R^{11}$-26 |
| 4524. | Ar-6 | XYZ-o | $R^{11}$-26 |
| 4525. | Ar-6 | XYZ-p | $R^{11}$-26 |
| 4526. | Ar-6 | XYZ-q | $R^{11}$-26 |
| 4527. | Ar-6 | XYZ-r | $R^{11}$-26 |
| 4528. | Ar-6 | XYZ-s | $R^{11}$-26 |
| 4529. | Ar-6 | XYZ-t | $R^{11}$-26 |
| 4530. | Ar-6 | XYZ-u | $R^{11}$-26 |
| 4531. | Ar-6 | XYZ-v | $R^{11}$-26 |
| 4532. | Ar-6 | XYZ-w | $R^{11}$-26 |
| 4533. | Ar-7 | XYZ-a | $R^{11}$-26 |
| 4534. | Ar-7 | XYZ-b | $R^{11}$-26 |
| 4535. | Ar-7 | XYZ-c | $R^{11}$-26 |
| 4536. | Ar-7 | XYZ-d | $R^{11}$-26 |
| 4537. | Ar-7 | XYZ-e | $R^{11}$-26 |
| 4538. | Ar-7 | XYZ-f | $R^{11}$-26 |
| 4539. | Ar-7 | XYZ-g | $R^{11}$-26 |
| 4540. | Ar-7 | XYZ-h | $R^{11}$-26 |
| 4541. | Ar-7 | XYZ-i | $R^{11}$-26 |
| 4542. | Ar-7 | XYZ-k | $R^{11}$-26 |
| 4543. | Ar-7 | XYZ-l | $R^{11}$-26 |
| 4544. | Ar-7 | XYZ-m | $R^{11}$-26 |
| 4545. | Ar-7 | XYZ-n | $R^{11}$-26 |
| 4546. | Ar-7 | XYZ-o | $R^{11}$-26 |
| 4547. | Ar-7 | XYZ-p | $R^{11}$-26 |
| 4548. | Ar-7 | XYZ-q | $R^{11}$-26 |
| 4549. | Ar-7 | XYZ-r | $R^{11}$-26 |
| 4550. | Ar-7 | XYZ-s | $R^{11}$-26 |
| 4551. | Ar-7 | XYZ-t | $R^{11}$-26 |
| 4552. | Ar-7 | XYZ-u | $R^{11}$-26 |
| 4553. | Ar-7 | XYZ-v | $R^{11}$-26 |
| 4554. | Ar-7 | XYZ-w | $R^{11}$-26 |
| 4555. | Ar-8 | XYZ-a | $R^{11}$-26 |
| 4556. | Ar-8 | XYZ-b | $R^{11}$-26 |
| 4557. | Ar-8 | XYZ-c | $R^{11}$-26 |
| 4558. | Ar-8 | XYZ-d | $R^{11}$-26 |
| 4559. | Ar-8 | XYZ-e | $R^{11}$-26 |
| 4560. | Ar-8 | XYZ-f | $R^{11}$-26 |
| 4561. | Ar-8 | XYZ-g | $R^{11}$-26 |
| 4562. | Ar-8 | XYZ-h | $R^{11}$-26 |
| 4563. | Ar-8 | XYZ-i | $R^{11}$-26 |
| 4564. | Ar-8 | XYZ-k | $R^{11}$-26 |
| 4565. | Ar-8 | XYZ-l | $R^{11}$-26 |
| 4566. | Ar-8 | XYZ-m | $R^{11}$-26 |
| 4567. | Ar-8 | XYZ-n | $R^{11}$-26 |
| 4568. | Ar-8 | XYZ-o | $R^{11}$-26 |
| 4569. | Ar-8 | XYZ-p | $R^{11}$-26 |
| 4570. | Ar-8 | XYZ-q | $R^{11}$-26 |
| 4571. | Ar-8 | XYZ-r | $R^{11}$-26 |
| 4572. | Ar-8 | XYZ-s | $R^{11}$-26 |
| 4573. | Ar-8 | XYZ-t | $R^{11}$-26 |
| 4574. | Ar-8 | XYZ-u | $R^{11}$-26 |
| 4575. | Ar-8 | XYZ-v | $R^{11}$-26 |
| 4576. | Ar-8 | XYZ-w | $R^{11}$-26 |
| 4577. | Ar-1 | XYZ-a | $R^{11}$-27 |
| 4578. | Ar-1 | XYZ-b | $R^{11}$-27 |
| 4579. | Ar-1 | XYZ-c | $R^{11}$-27 |
| 4580. | Ar-1 | XYZ-d | $R^{11}$-27 |
| 4581. | Ar-1 | XYZ-e | $R^{11}$-27 |
| 4582. | Ar-1 | XYZ-f | $R^{11}$-27 |
| 4583. | Ar-1 | XYZ-g | $R^{11}$-27 |
| 4584. | Ar-1 | XYZ-h | $R^{11}$-27 |
| 4585. | Ar-1 | XYZ-i | $R^{11}$-27 |
| 4586. | Ar-1 | XYZ-k | $R^{11}$-27 |
| 4587. | Ar-1 | XYZ-l | $R^{11}$-27 |
| 4588. | Ar-1 | XYZ-m | $R^{11}$-27 |
| 4589. | Ar-1 | XYZ-n | $R^{11}$-27 |
| 4590. | Ar-1 | XYZ-o | $R^{11}$-27 |
| 4591. | Ar-1 | XYZ-p | $R^{11}$-27 |
| 4592. | Ar-1 | XYZ-q | $R^{11}$-27 |
| 4593. | Ar-1 | XYZ-r | $R^{11}$-27 |
| 4594. | Ar-1 | XYZ-s | $R^{11}$-27 |
| 4595. | Ar-1 | XYZ-t | $R^{11}$-27 |
| 4596. | Ar-1 | XYZ-u | $R^{11}$-27 |
| 4597. | Ar-1 | XYZ-v | $R^{11}$-27 |
| 4598. | Ar-1 | XYZ-w | $R^{11}$-27 |
| 4599. | Ar-2 | XYZ-a | $R^{11}$-27 |
| 4600. | Ar-2 | XYZ-b | $R^{11}$-27 |
| 4601. | Ar-2 | XYZ-c | $R^{11}$-27 |
| 4602. | Ar-2 | XYZ-d | $R^{11}$-27 |
| 4603. | Ar-2 | XYZ-e | $R^{11}$-27 |
| 4604. | Ar-2 | XYZ-f | $R^{11}$-27 |
| 4605. | Ar-2 | XYZ-g | $R^{11}$-27 |
| 4606. | Ar-2 | XYZ-h | $R^{11}$-27 |
| 4607. | Ar-2 | XYZ-i | $R^{11}$-27 |
| 4608. | Ar-2 | XYZ-k | $R^{11}$-27 |
| 4609. | Ar-2 | XYZ-l | $R^{11}$-27 |
| 4610. | Ar-2 | XYZ-m | $R^{11}$-27 |
| 4611. | Ar-2 | XYZ-n | $R^{11}$-27 |
| 4612. | Ar-2 | XYZ-o | $R^{11}$-27 |
| 4613. | Ar-2 | XYZ-p | $R^{11}$-27 |
| 4614. | Ar-2 | XYZ-q | $R^{11}$-27 |
| 4615. | Ar-2 | XYZ-r | $R^{11}$-27 |
| 4616. | Ar-2 | XYZ-s | $R^{11}$-27 |
| 4617. | Ar-2 | XYZ-t | $R^{11}$-27 |
| 4618. | Ar-2 | XYZ-u | $R^{11}$-27 |
| 4619. | Ar-2 | XYZ-v | $R^{11}$-27 |
| 4620. | Ar-2 | XYZ-w | $R^{11}$-27 |
| 4621. | Ar-3 | XYZ-a | $R^{11}$-27 |
| 4622. | Ar-3 | XYZ-b | $R^{11}$-27 |
| 4623. | Ar-3 | XYZ-c | $R^{11}$-27 |
| 4624. | Ar-3 | XYZ-d | $R^{11}$-27 |
| 4625. | Ar-3 | XYZ-e | $R^{11}$-27 |
| 4626. | Ar-3 | XYZ-f | $R^{11}$-27 |
| 4627. | Ar-3 | XYZ-g | $R^{11}$-27 |
| 4628. | Ar-3 | XYZ-h | $R^{11}$-27 |
| 4629. | Ar-3 | XYZ-i | $R^{11}$-27 |
| 4630. | Ar-3 | XYZ-k | $R^{11}$-27 |
| 4631. | Ar-3 | XYZ-l | $R^{11}$-27 |
| 4632. | Ar-3 | XYZ-m | $R^{11}$-27 |

TABLE C-continued

|  | Ar | -X-Y-Z- | R$^{11}$ |
|---|---|---|---|
| 4633. | Ar-3 | XYZ-n | R$^{11}$-27 |
| 4634. | Ar-3 | XYZ-o | R$^{11}$-27 |
| 4635. | Ar-3 | XYZ-p | R$^{11}$-27 |
| 4636. | Ar-3 | XYZ-q | R$^{11}$-27 |
| 4637. | Ar-3 | XYZ-r | R$^{11}$-27 |
| 4638. | Ar-3 | XYZ-s | R$^{11}$-27 |
| 4639. | Ar-3 | XYZ-t | R$^{11}$-27 |
| 4640. | Ar-3 | XYZ-u | R$^{11}$-27 |
| 4641. | Ar-3 | XYZ-v | R$^{11}$-27 |
| 4642. | Ar-3 | XYZ-w | R$^{11}$-27 |
| 4643. | Ar-4 | XYZ-a | R$^{11}$-27 |
| 4644. | Ar-4 | XYZ-b | R$^{11}$-27 |
| 4645. | Ar-4 | XYZ-c | R$^{11}$-27 |
| 4646. | Ar-4 | XYZ-d | R$^{11}$-27 |
| 4647. | Ar-4 | XYZ-e | R$^{11}$-27 |
| 4648. | Ar-4 | XYZ-f | R$^{11}$-27 |
| 4649. | Ar-4 | XYZ-g | R$^{11}$-27 |
| 4650. | Ar-4 | XYZ-h | R$^{11}$-27 |
| 4651. | Ar-4 | XYZ-i | R$^{11}$-27 |
| 4652. | Ar-4 | XYZ-k | R$^{11}$-27 |
| 4653. | Ar-4 | XYZ-l | R$^{11}$-27 |
| 4654. | Ar-4 | XYZ-m | R$^{11}$-27 |
| 4655. | Ar-4 | XYZ-n | R$^{11}$-27 |
| 4656. | Ar-4 | XYZ-o | R$^{11}$-27 |
| 4657. | Ar-4 | XYZ-p | R$^{11}$-27 |
| 4658. | Ar-4 | XYZ-q | R$^{11}$-27 |
| 4659. | Ar-4 | XYZ-r | R$^{11}$-27 |
| 4660. | Ar-4 | XYZ-s | R$^{11}$-27 |
| 4661. | Ar-4 | XYZ-t | R$^{11}$-27 |
| 4662. | Ar-4 | XYZ-u | R$^{11}$-27 |
| 4663. | Ar-4 | XYZ-v | R$^{11}$-27 |
| 4664. | Ar-4 | XYZ-w | R$^{11}$-27 |
| 4665. | Ar-5 | XYZ-a | R$^{11}$-27 |
| 4666. | Ar-5 | XYZ-b | R$^{11}$-27 |
| 4667. | Ar-5 | XYZ-c | R$^{11}$-27 |
| 4668. | Ar-5 | XYZ-d | R$^{11}$-27 |
| 4669. | Ar-5 | XYZ-e | R$^{11}$-27 |
| 4670. | Ar-5 | XYZ-f | R$^{11}$-27 |
| 4671. | Ar-5 | XYZ-g | R$^{11}$-27 |
| 4672. | Ar-5 | XYZ-h | R$^{11}$-27 |
| 4673. | Ar-5 | XYZ-i | R$^{11}$-27 |
| 4674. | Ar-5 | XYZ-k | R$^{11}$-27 |
| 4675. | Ar-5 | XYZ-l | R$^{11}$-27 |
| 4676. | Ar-5 | XYZ-m | R$^{11}$-27 |
| 4677. | Ar-5 | XYZ-n | R$^{11}$-27 |
| 4678. | Ar-5 | XYZ-o | R$^{11}$-27 |
| 4679. | Ar-5 | XYZ-p | R$^{11}$-27 |
| 4680. | Ar-5 | XYZ-q | R$^{11}$-27 |
| 4681. | Ar-5 | XYZ-r | R$^{11}$-27 |
| 4682. | Ar-5 | XYZ-s | R$^{11}$-27 |
| 4683. | Ar-5 | XYZ-t | R$^{11}$-27 |
| 4684. | Ar-5 | XYZ-u | R$^{11}$-27 |
| 4685. | Ar-5 | XYZ-v | R$^{11}$-27 |
| 4686. | Ar-5 | XYZ-w | R$^{11}$-27 |
| 4687. | Ar-6 | XYZ-a | R$^{11}$-27 |
| 4688. | Ar-6 | XYZ-b | R$^{11}$-27 |
| 4689. | Ar-6 | XYZ-c | R$^{11}$-27 |
| 4690. | Ar-6 | XYZ-d | R$^{11}$-27 |
| 4691. | Ar-6 | XYZ-e | R$^{11}$-27 |
| 4692. | Ar-6 | XYZ-f | R$^{11}$-27 |
| 4693. | Ar-6 | XYZ-g | R$^{11}$-27 |
| 4694. | Ar-6 | XYZ-h | R$^{11}$-27 |
| 4695. | Ar-6 | XYZ-i | R$^{11}$-27 |
| 4696. | Ar-6 | XYZ-k | R$^{11}$-27 |
| 4697. | Ar-6 | XYZ-l | R$^{11}$-27 |
| 4698. | Ar-6 | XYZ-m | R$^{11}$-27 |
| 4699. | Ar-6 | XYZ-n | R$^{11}$-27 |
| 4700. | Ar-6 | XYZ-o | R$^{11}$-27 |
| 4701. | Ar-6 | XYZ-p | R$^{11}$-27 |
| 4702. | Ar-6 | XYZ-q | R$^{11}$-27 |
| 4703. | Ar-6 | XYZ-r | R$^{11}$-27 |
| 4704. | Ar-6 | XYZ-s | R$^{11}$-27 |
| 4705. | Ar-6 | XYZ-t | R$^{11}$-27 |
| 4706. | Ar-6 | XYZ-u | R$^{11}$-27 |
| 4707. | Ar-6 | XYZ-v | R$^{11}$-27 |
| 4708. | Ar-6 | XYZ-w | R$^{11}$-27 |
| 4709. | Ar-7 | XYZ-a | R$^{11}$-27 |
| 4710. | Ar-7 | XYZ-b | R$^{11}$-27 |
| 4711. | Ar-7 | XYZ-c | R$^{11}$-27 |
| 4712. | Ar-7 | XYZ-d | R$^{11}$-27 |
| 4713. | Ar-7 | XYZ-e | R$^{11}$-27 |
| 4714. | Ar-7 | XYZ-f | R$^{11}$-27 |
| 4715. | Ar-7 | XYZ-g | R$^{11}$-27 |
| 4716. | Ar-7 | XYZ-h | R$^{11}$-27 |
| 4717. | Ar-7 | XYZ-i | R$^{11}$-27 |
| 4718. | Ar-7 | XYZ-k | R$^{11}$-27 |
| 4719. | Ar-7 | XYZ-l | R$^{11}$-27 |
| 4720. | Ar-7 | XYZ-m | R$^{11}$-27 |
| 4721. | Ar-7 | XYZ-n | R$^{11}$-27 |
| 4722. | Ar-7 | XYZ-o | R$^{11}$-27 |
| 4723. | Ar-7 | XYZ-p | R$^{11}$-27 |
| 4724. | Ar-7 | XYZ-q | R$^{11}$-27 |
| 4725. | Ar-7 | XYZ-r | R$^{11}$-27 |
| 4726. | Ar-7 | XYZ-s | R$^{11}$-27 |
| 4727. | Ar-7 | XYZ-t | R$^{11}$-27 |
| 4728. | Ar-7 | XYZ-u | R$^{11}$-27 |
| 4729. | Ar-7 | XYZ-v | R$^{11}$-27 |
| 4730. | Ar-7 | XYZ-w | R$^{11}$-27 |
| 4731. | Ar-8 | XYZ-a | R$^{11}$-27 |
| 4732. | Ar-8 | XYZ-b | R$^{11}$-27 |
| 4733. | Ar-8 | XYZ-c | R$^{11}$-27 |
| 4734. | Ar-8 | XYZ-d | R$^{11}$-27 |
| 4735. | Ar-8 | XYZ-e | R$^{11}$-27 |
| 4736. | Ar-8 | XYZ-f | R$^{11}$-27 |
| 4737. | Ar-8 | XYZ-g | R$^{11}$-27 |
| 4738. | Ar-8 | XYZ-h | R$^{11}$-27 |
| 4739. | Ar-8 | XYZ-i | R$^{11}$-27 |
| 4740. | Ar-8 | XYZ-k | R$^{11}$-27 |
| 4741. | Ar-8 | XYZ-l | R$^{11}$-27 |
| 4742. | Ar-8 | XYZ-m | R$^{11}$-27 |
| 4743. | Ar-8 | XYZ-n | R$^{11}$-27 |
| 4744. | Ar-8 | XYZ-o | R$^{11}$-27 |
| 4745. | Ar-8 | XYZ-p | R$^{11}$-27 |
| 4746. | Ar-8 | XYZ-q | R$^{11}$-27 |
| 4747. | Ar-8 | XYZ-r | R$^{11}$-27 |
| 4748. | Ar-8 | XYZ-s | R$^{11}$-27 |
| 4749. | Ar-8 | XYZ-t | R$^{11}$-27 |
| 4750. | Ar-8 | XYZ-u | R$^{11}$-27 |
| 4751. | Ar-8 | XYZ-v | R$^{11}$-27 |
| 4752. | Ar-8 | XYZ-w | R$^{11}$-27 |
| 4753. | Ar-1 | XYZ-a | R$^{11}$-28 |
| 4754. | Ar-1 | XYZ-b | R$^{11}$-28 |
| 4755. | Ar-1 | XYZ-c | R$^{11}$-28 |
| 4756. | Ar-1 | XYZ-d | R$^{11}$-28 |
| 4757. | Ar-1 | XYZ-e | R$^{11}$-28 |
| 4758. | Ar-1 | XYZ-f | R$^{11}$-28 |
| 4759. | Ar-1 | XYZ-g | R$^{11}$-28 |
| 4760. | Ar-1 | XYZ-h | R$^{11}$-28 |
| 4761. | Ar-1 | XYZ-i | R$^{11}$-28 |
| 4762. | Ar-1 | XYZ-k | R$^{11}$-28 |
| 4763. | Ar-1 | XYZ-l | R$^{11}$-28 |
| 4764. | Ar-1 | XYZ-m | R$^{11}$-28 |
| 4765. | Ar-1 | XYZ-n | R$^{11}$-28 |
| 4766. | Ar-1 | XYZ-o | R$^{11}$-28 |
| 4767. | Ar-1 | XYZ-p | R$^{11}$-28 |
| 4768. | Ar-1 | XYZ-q | R$^{11}$-28 |
| 4769. | Ar-1 | XYZ-r | R$^{11}$-28 |
| 4770. | Ar-1 | XYZ-s | R$^{11}$-28 |
| 4771. | Ar-1 | XYZ-t | R$^{11}$-28 |
| 4772. | Ar-1 | XYZ-u | R$^{11}$-28 |
| 4773. | Ar-1 | XYZ-v | R$^{11}$-28 |
| 4774. | Ar-1 | XYZ-w | R$^{11}$-28 |
| 4775. | Ar-2 | XYZ-a | R$^{11}$-28 |
| 4776. | Ar-2 | XYZ-b | R$^{11}$-28 |
| 4777. | Ar-2 | XYZ-c | R$^{11}$-28 |
| 4778. | Ar-2 | XYZ-d | R$^{11}$-28 |
| 4779. | Ar-2 | XYZ-e | R$^{11}$-28 |
| 4780. | Ar-2 | XYZ-f | R$^{11}$-28 |
| 4781. | Ar-2 | XYZ-g | R$^{11}$-28 |
| 4782. | Ar-2 | XYZ-h | R$^{11}$-28 |
| 4783. | Ar-2 | XYZ-i | R$^{11}$-28 |
| 4784. | Ar-2 | XYZ-k | R$^{11}$-28 |
| 4785. | Ar-2 | XYZ-l | R$^{11}$-28 |
| 4786. | Ar-2 | XYZ-m | R$^{11}$-28 |
| 4787. | Ar-2 | XYZ-n | R$^{11}$-28 |
| 4788. | Ar-2 | XYZ-o | R$^{11}$-28 |

TABLE C-continued

|  | Ar | -X-Y-Z- | $R^{11}$ |
|---|---|---|---|
| 4789. | Ar-2 | XYZ-p | $R^{11}$-28 |
| 4790. | Ar-2 | XYZ-q | $R^{11}$-28 |
| 4791. | Ar-2 | XYZ-r | $R^{11}$-28 |
| 4792. | Ar-2 | XYZ-s | $R^{11}$-28 |
| 4793. | Ar-2 | XYZ-t | $R^{11}$-28 |
| 4794. | Ar-2 | XYZ-u | $R^{11}$-28 |
| 4795. | Ar-2 | XYZ-v | $R^{11}$-28 |
| 4796. | Ar-2 | XYZ-w | $R^{11}$-28 |
| 4797. | Ar-3 | XYZ-a | $R^{11}$-28 |
| 4798. | Ar-3 | XYZ-b | $R^{11}$-28 |
| 4799. | Ar-3 | XYZ-c | $R^{11}$-28 |
| 4800. | Ar-3 | XYZ-d | $R^{11}$-28 |
| 4801. | Ar-3 | XYZ-e | $R^{11}$-28 |
| 4802. | Ar-3 | XYZ-f | $R^{11}$-28 |
| 4803. | Ar-3 | XYZ-g | $R^{11}$-28 |
| 4804. | Ar-3 | XYZ-h | $R^{11}$-28 |
| 4805. | Ar-3 | XYZ-i | $R^{11}$-28 |
| 4806. | Ar-3 | XYZ-k | $R^{11}$-28 |
| 4807. | Ar-3 | XYZ-l | $R^{11}$-28 |
| 4808. | Ar-3 | XYZ-m | $R^{11}$-28 |
| 4809. | Ar-3 | XYZ-n | $R^{11}$-28 |
| 4810. | Ar-3 | XYZ-o | $R^{11}$-28 |
| 4811. | Ar-3 | XYZ-p | $R^{11}$-28 |
| 4812. | Ar-3 | XYZ-q | $R^{11}$-28 |
| 4813. | Ar-3 | XYZ-r | $R^{11}$-28 |
| 4814. | Ar-3 | XYZ-s | $R^{11}$-28 |
| 4815. | Ar-3 | XYZ-t | $R^{11}$-28 |
| 4816. | Ar-3 | XYZ-u | $R^{11}$-28 |
| 4817. | Ar-3 | XYZ-v | $R^{11}$-28 |
| 4818. | Ar-3 | XYZ-w | $R^{11}$-28 |
| 4819. | Ar-4 | XYZ-a | $R^{11}$-28 |
| 4820. | Ar-4 | XYZ-b | $R^{11}$-28 |
| 4821. | Ar-4 | XYZ-c | $R^{11}$-28 |
| 4822. | Ar-4 | XYZ-d | $R^{11}$-28 |
| 4823. | Ar-4 | XYZ-e | $R^{11}$-28 |
| 4824. | Ar-4 | XYZ-f | $R^{11}$-28 |
| 4825. | Ar-4 | XYZ-g | $R^{11}$-28 |
| 4826. | Ar-4 | XYZ-h | $R^{11}$-28 |
| 4827. | Ar-4 | XYZ-i | $R^{11}$-28 |
| 4828. | Ar-4 | XYZ-k | $R^{11}$-28 |
| 4829. | Ar-4 | XYZ-l | $R^{11}$-28 |
| 4830. | Ar-4 | XYZ-m | $R^{11}$-28 |
| 4831. | Ar-4 | XYZ-n | $R^{11}$-28 |
| 4832. | Ar-4 | XYZ-o | $R^{11}$-28 |
| 4833. | Ar-4 | XYZ-p | $R^{11}$-28 |
| 4834. | Ar-4 | XYZ-q | $R^{11}$-28 |
| 4835. | Ar-4 | XYZ-r | $R^{11}$-28 |
| 4836. | Ar-4 | XYZ-s | $R^{11}$-28 |
| 4837. | Ar-4 | XYZ-t | $R^{11}$-28 |
| 4838. | Ar-4 | XYZ-u | $R^{11}$-28 |
| 4839. | Ar-4 | XYZ-v | $R^{11}$-28 |
| 4840. | Ar-4 | XYZ-w | $R^{11}$-28 |
| 4841. | Ar-5 | XYZ-a | $R^{11}$-28 |
| 4842. | Ar-5 | XYZ-b | $R^{11}$-28 |
| 4843. | Ar-5 | XYZ-c | $R^{11}$-28 |
| 4844. | Ar-5 | XYZ-d | $R^{11}$-28 |
| 4845. | Ar-5 | XYZ-e | $R^{11}$-28 |
| 4846. | Ar-5 | XYZ-f | $R^{11}$-28 |
| 4847. | Ar-5 | XYZ-g | $R^{11}$-28 |
| 4848. | Ar-5 | XYZ-h | $R^{11}$-28 |
| 4849. | Ar-5 | XYZ-i | $R^{11}$-28 |
| 4850. | Ar-5 | XYZ-k | $R^{11}$-28 |
| 4851. | Ar-5 | XYZ-l | $R^{11}$-28 |
| 4852. | Ar-5 | XYZ-m | $R^{11}$-28 |
| 4853. | Ar-5 | XYZ-n | $R^{11}$-28 |
| 4854. | Ar-5 | XYZ-o | $R^{11}$-28 |
| 4855. | Ar-5 | XYZ-p | $R^{11}$-28 |
| 4856. | Ar-5 | XYZ-q | $R^{11}$-28 |
| 4857. | Ar-5 | XYZ-r | $R^{11}$-28 |
| 4858. | Ar-5 | XYZ-s | $R^{11}$-28 |
| 4859. | Ar-5 | XYZ-t | $R^{11}$-28 |
| 4860. | Ar-5 | XYZ-u | $R^{11}$-28 |
| 4861. | Ar-5 | XYZ-v | $R^{11}$-28 |
| 4862. | Ar-5 | XYZ-w | $R^{11}$-28 |
| 4863. | Ar-6 | XYZ-a | $R^{11}$-28 |
| 4864. | Ar-6 | XYZ-b | $R^{11}$-28 |
| 4865. | Ar-6 | XYZ-c | $R^{11}$-28 |
| 4866. | Ar-6 | XYZ-d | $R^{11}$-28 |
| 4867. | Ar-6 | XYZ-e | $R^{11}$-28 |
| 4868. | Ar-6 | XYZ-f | $R^{11}$-28 |
| 4869. | Ar-6 | XYZ-g | $R^{11}$-28 |
| 4870. | Ar-6 | XYZ-h | $R^{11}$-28 |
| 4871. | Ar-6 | XYZ-i | $R^{11}$-28 |
| 4872. | Ar-6 | XYZ-k | $R^{11}$-28 |
| 4873. | Ar-6 | XYZ-l | $R^{11}$-28 |
| 4874. | Ar-6 | XYZ-m | $R^{11}$-28 |
| 4875. | Ar-6 | XYZ-n | $R^{11}$-28 |
| 4876. | Ar-6 | XYZ-o | $R^{11}$-28 |
| 4877. | Ar-6 | XYZ-p | $R^{11}$-28 |
| 4878. | Ar-6 | XYZ-q | $R^{11}$-28 |
| 4879. | Ar-6 | XYZ-r | $R^{11}$-28 |
| 4880. | Ar-6 | XYZ-s | $R^{11}$-28 |
| 4881. | Ar-6 | XYZ-t | $R^{11}$-28 |
| 4882. | Ar-6 | XYZ-u | $R^{11}$-28 |
| 4883. | Ar-6 | XYZ-v | $R^{11}$-28 |
| 4884. | Ar-6 | XYZ-w | $R^{11}$-28 |
| 4885. | Ar-7 | XYZ-a | $R^{11}$-28 |
| 4886. | Ar-7 | XYZ-b | $R^{11}$-28 |
| 4887. | Ar-7 | XYZ-c | $R^{11}$-28 |
| 4888. | Ar-7 | XYZ-d | $R^{11}$-28 |
| 4889. | Ar-7 | XYZ-e | $R^{11}$-28 |
| 4890. | Ar-7 | XYZ-f | $R^{11}$-28 |
| 4891. | Ar-7 | XYZ-g | $R^{11}$-28 |
| 4892. | Ar-7 | XYZ-h | $R^{11}$-28 |
| 4893. | Ar-7 | XYZ-i | $R^{11}$-28 |
| 4894. | Ar-7 | XYZ-k | $R^{11}$-28 |
| 4895. | Ar-7 | XYZ-l | $R^{11}$-28 |
| 4896. | Ar-7 | XYZ-m | $R^{11}$-28 |
| 4897. | Ar-7 | XYZ-n | $R^{11}$-28 |
| 4898. | Ar-7 | XYZ-o | $R^{11}$-28 |
| 4899. | Ar-7 | XYZ-p | $R^{11}$-28 |
| 4900. | Ar-7 | XYZ-q | $R^{11}$-28 |
| 4901. | Ar-7 | XYZ-r | $R^{11}$-28 |
| 4902. | Ar-7 | XYZ-s | $R^{11}$-28 |
| 4903. | Ar-7 | XYZ-t | $R^{11}$-28 |
| 4904. | Ar-7 | XYZ-u | $R^{11}$-28 |
| 4905. | Ar-7 | XYZ-v | $R^{11}$-28 |
| 4906. | Ar-7 | XYZ-w | $R^{11}$-28 |
| 4907. | Ar-8 | XYZ-a | $R^{11}$-28 |
| 4908. | Ar-8 | XYZ-b | $R^{11}$-28 |
| 4909. | Ar-8 | XYZ-c | $R^{11}$-28 |
| 4910. | Ar-8 | XYZ-d | $R^{11}$-28 |
| 4911. | Ar-8 | XYZ-e | $R^{11}$-28 |
| 4912. | Ar-8 | XYZ-f | $R^{11}$-28 |
| 4913. | Ar-8 | XYZ-g | $R^{11}$-28 |
| 4914. | Ar-8 | XYZ-h | $R^{11}$-28 |
| 4915. | Ar-8 | XYZ-i | $R^{11}$-28 |
| 4916. | Ar-8 | XYZ-k | $R^{11}$-28 |
| 4917. | Ar-8 | XYZ-l | $R^{11}$-28 |
| 4918. | Ar-8 | XYZ-m | $R^{11}$-28 |
| 4919. | Ar-8 | XYZ-n | $R^{11}$-28 |
| 4920. | Ar-8 | XYZ-o | $R^{11}$-28 |
| 4921. | Ar-8 | XYZ-p | $R^{11}$-28 |
| 4922. | Ar-8 | XYZ-q | $R^{11}$-28 |
| 4923. | Ar-8 | XYZ-r | $R^{11}$-28 |
| 4924. | Ar-8 | XYZ-s | $R^{11}$-28 |
| 4925. | Ar-8 | XYZ-t | $R^{11}$-28 |
| 4926. | Ar-8 | XYZ-u | $R^{11}$-28 |
| 4927. | Ar-8 | XYZ-v | $R^{11}$-28 |
| 4928. | Ar-8 | XYZ-w | $R^{11}$-28 |

Compounds I are in particular a compound of the formula Ia.2, wherein $R^1$ is a radical —XYZ—$R^{11}$, where Ar, —XYZ— and $R^{11}$ are as defined in the rows 464, 480, 481, 482, 483, 568, 589, 591, 592, 593, 594, 595, 596, 598, 599, 600, 602, 603, 604, 605, 631, 640, 673, 682, 715, 724, 736, 745, 757, 845, 904, 913, 3725, 3901, 4077, 4253, 4429, 4605 and 4781 of table C.

Compound I is in particular a compound of the formula Ia.3, wherein $R^1$ is a radical —XYZ—$R^{11}$, where Ar, —XYZ— and $R^{11}$ are as defined in row 598 of table C.

Compound I is in particular a compound of the formula Ia.4, wherein $R^1$ is a radical —XYZ—$R^{11}$, where Ar, —XYZ— and $R^{11}$ are as defined in row 598 of table C.

Compound I is in particular a compound of the formula Ia.5, wherein $R^1$ is a radical —XYZ—$R^{11}$, where Ar, —XYZ— and $R^{11}$ are as defined in row 598 of table C.

Compound I is in particular a compound of the formula Ia.6, wherein $R^1$ is a radical —XYZ—$R^{11}$, where Ar, —XYZ— and $R^{11}$ are as defined in row 598 of table C.

Compound I is in particular a compound of the formula Ia.15, wherein $R^1$ is a radical —XYZ—$R^{11}$, where Ar, —XYZ— and $R^{11}$ are as defined in row 598 of table C.

Compound I is in particular a compound of the formula Ia.16, wherein $R^1$ is a radical —XYZ—$R^{11}$, where Ar, —XYZ— and $R^{11}$ are as defined in rows 589 or 598 of table C.

Compound I is in particular a compound of the formula Ia.17, wherein $R^1$ is a radical —XYZ—$R^{11}$, where Ar, —XYZ— and $R^{11}$ are as defined in rows 598 of table C.

Compound I is in particular a compound of the formula Ia.25, wherein $R^1$ is a radical —XYZ—$R^{11}$, where Ar, —XYZ— and $R^{11}$ are as defined in row 598 of table C.

Compound I is in particular a compound of the formula Ia.37, wherein $R^1$ is a radical —XYZ—$R^{11}$, where Ar, —XYZ— and $R^{11}$ are as defined in row 598 of table C.

Compound I is in particular a compound of the formula Ia.49, wherein $R^1$ is a radical —XYZ—$R^{11}$, where Ar, —XYZ— and $R^{11}$ are as defined in row 598 of table C.

Compound I is in particular a compound of the formula Ia.50, wherein $R^1$ is a radical —XYZ—$R^{11}$, where Ar, —XYZ— and $R^{11}$ are as defined in row 598 of table C.

Compound I is in particular a compound of the formula Ib.1, wherein $R^1$ is a radical —XYZ—$R^{11}$, where $R^3$ is methyl and Ar, —XYZ— and $R^{11}$ are as defined in row 598 of table C.

Compounds I are in particular a compound of the formula Ib.3 wherein $R^1$ is a radical —XYZ—$R^{11}$, where Ar, —XYZ— and $R^{11}$ are as defined in rows 598, 600, 605 and 4605 of table C.

Compound I is in particular a compound of the formula Ib.11, wherein $R^1$ is a radical —XYZ—$R^{11}$, where $R^3$ is methyl and Ar, —XYZ— and $R^{11}$ are as defined in row 598 of table C.

Compound I is in particular a compound of the formula Ib.14, wherein $R^1$ is a radical —XYZ—$R^{11}$, where Ar, —XYZ— and $R^{11}$ are as defined in row 598 of table C.

Compound I is in particular a compound of the formula Ib.16, wherein $R^1$ is a radical —XYZ—$R^{11}$, where Ar, —XYZ— and $R^{11}$ are as defined in row 598 of table C.

Compound I is in particular a compound of the formula Ib.17, wherein $R^1$ is a radical —XYZ—$R^{11}$, where Ar, —XYZ— and $R^{11}$ are as defined in row 598 of table C.

Compound I is in particular a compound of the formula Ic.37, wherein $R^1$ is a radical —XYZ—$R^{11}$, where Ar, —XYZ— and $R^{11}$ are as defined in row 598 of table C.

Compound I is in particular a compound of the formula Ic.45, wherein $R^1$ is a radical —XYZ—$R^{11}$, where $R^6$ is methyl and Ar, —XYZ— and $R^{11}$ are as defined in row 598 of table C.

Compound I is in particular a compound of the formula Ic.61, wherein $R^1$ is a radical —XYZ—$R^{11}$, where Ar, —XYZ— and $R^{11}$ are as defined in row 598 of table C.

The present invention relates in particular to the compounds of examples 1, 2, 3, 4, 5, 6, 7, 8, 9 and 10 to their tautomers, their stereoisomers, their N-oxide and to the agriculturally or veterinarily salts thereof.

Examples of the compounds of the present invention are also the following compound 1 to 63:

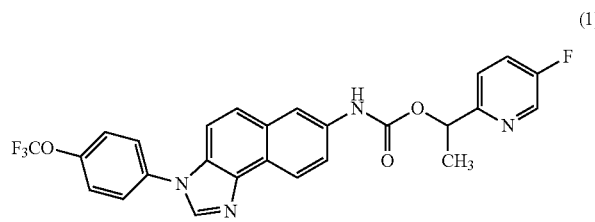

(1)

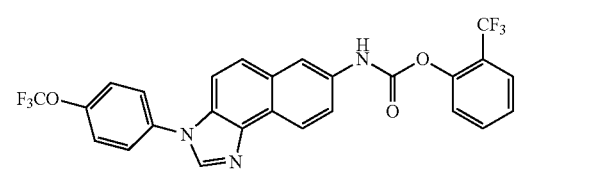

(2)

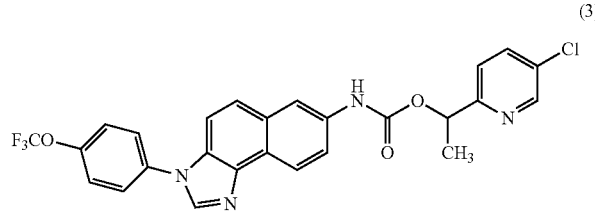

(3)

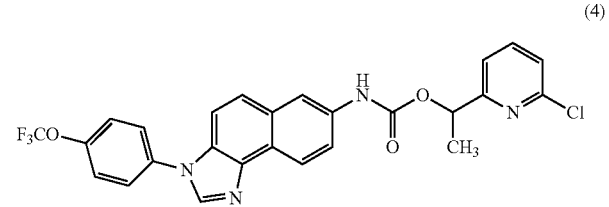

(4)

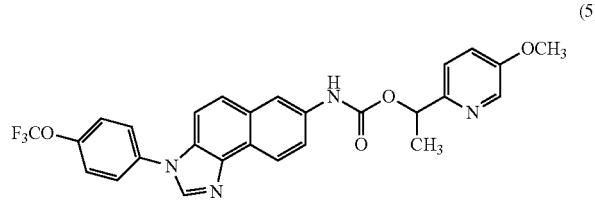

(5)

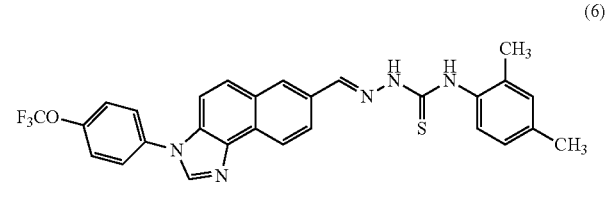

(6)

-continued

-continued
(23)
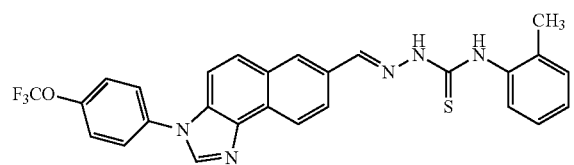
(24)
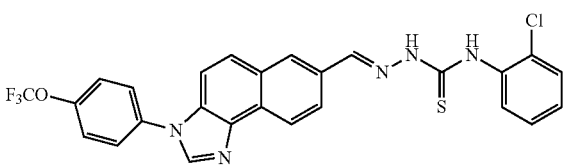
(25)
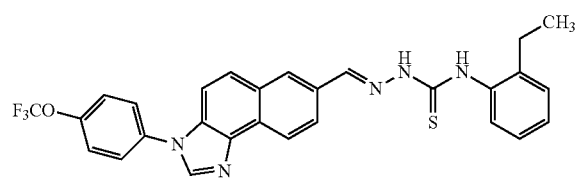
(26)
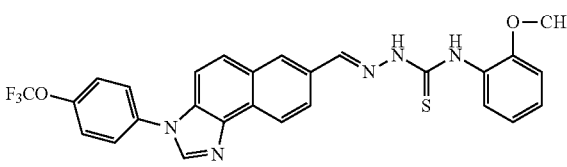
(27)
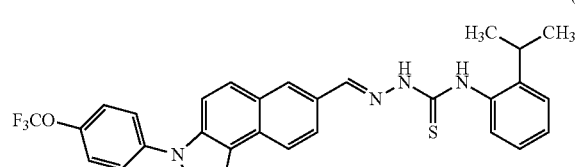
(28)
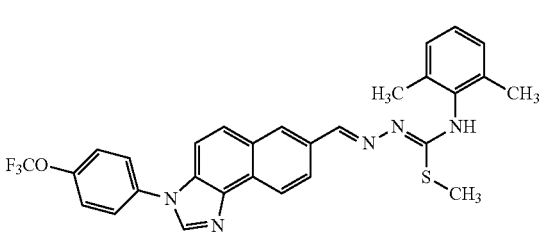
(29)
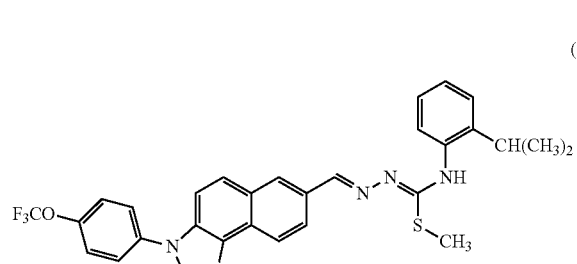
(30)
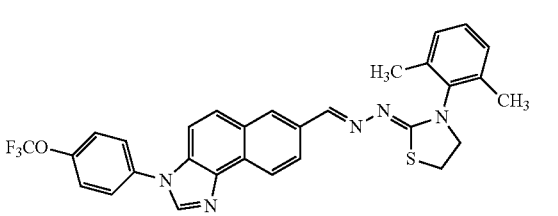
(31)
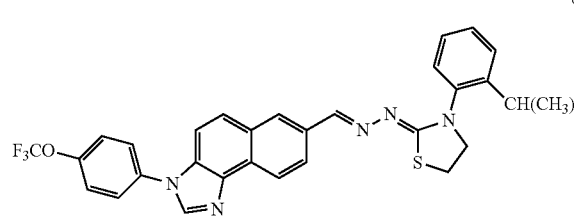
(32)
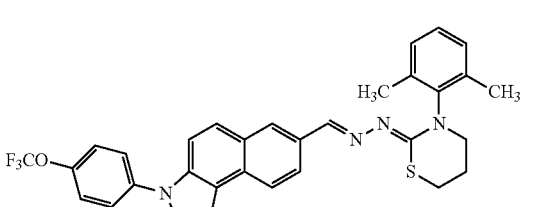
(33)
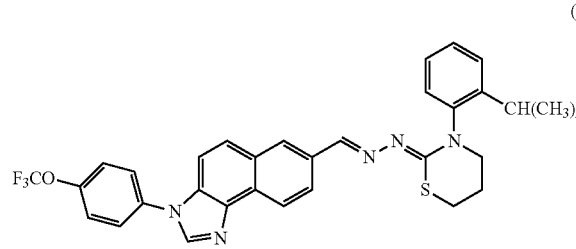
(34)
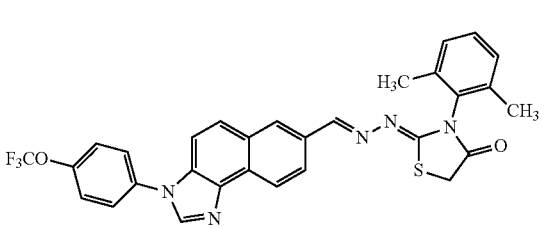
(35)
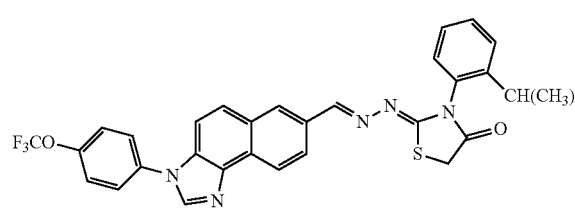
(36)
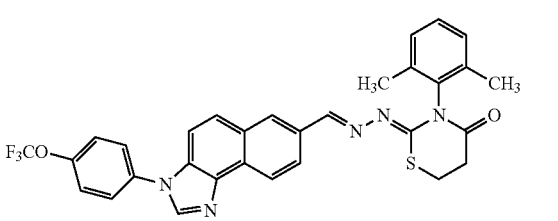

-continued
(37)
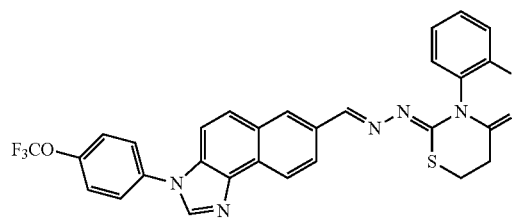
(38)
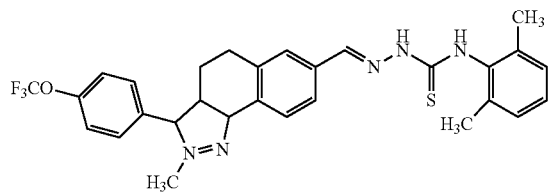
(39)
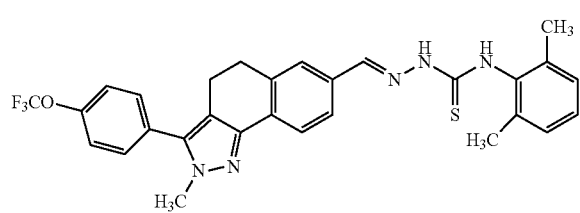
(40)
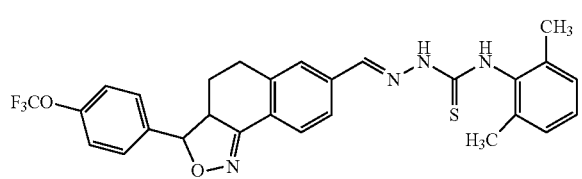
(41)
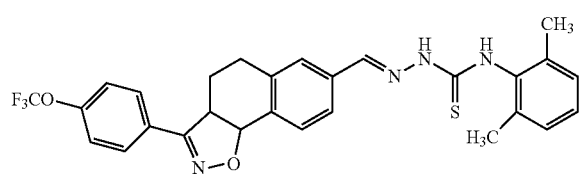
(42)
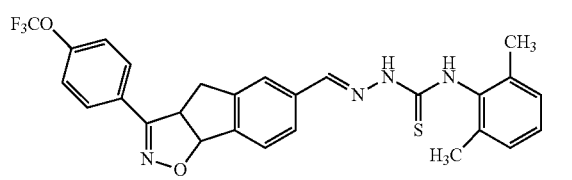
(43)
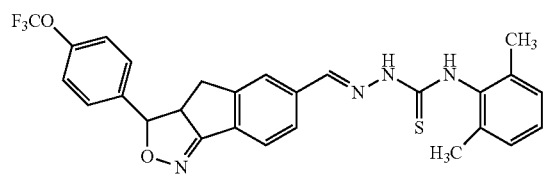
(44)
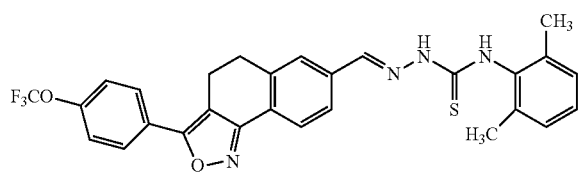
(45)
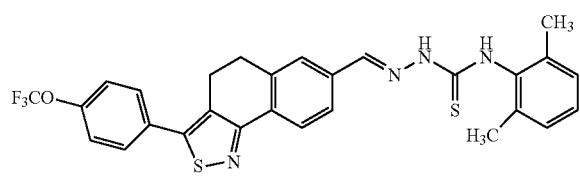
(46)
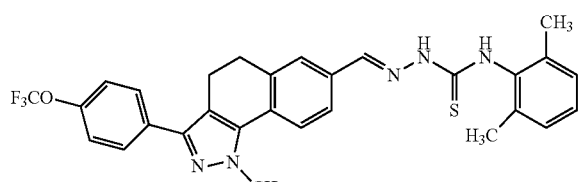
(47)
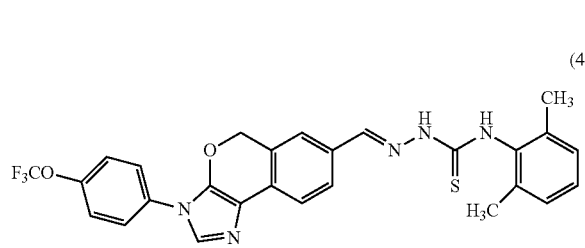
(48)
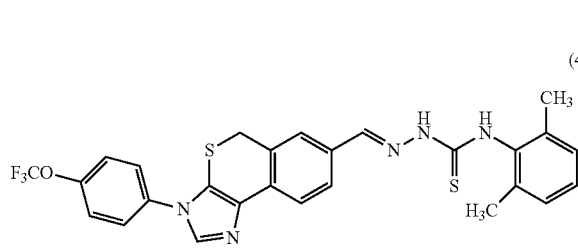
(49)
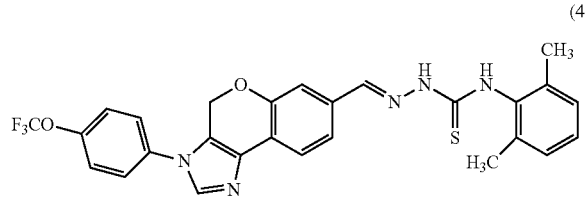
(50)
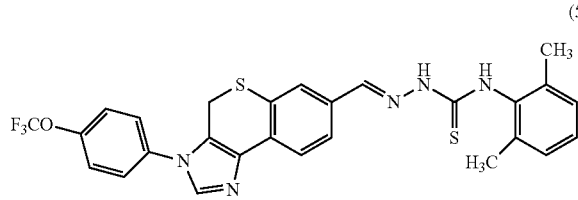

-continued
(51)
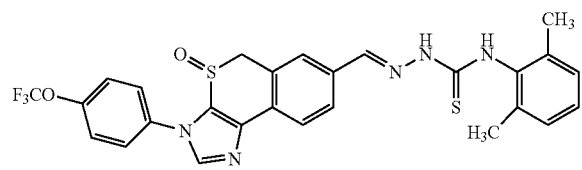
(52)
(53)
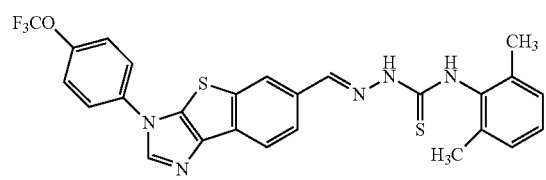
(54)
(55)
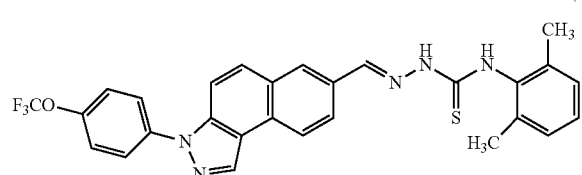
(56)
(57)
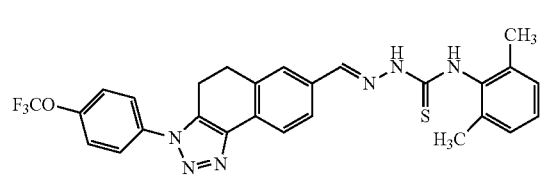
(58)
(59)
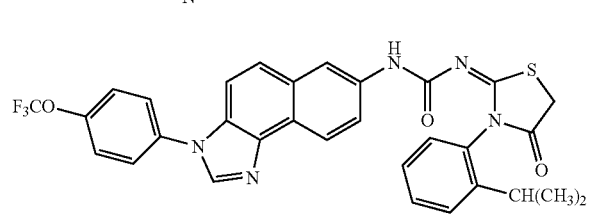
(60)
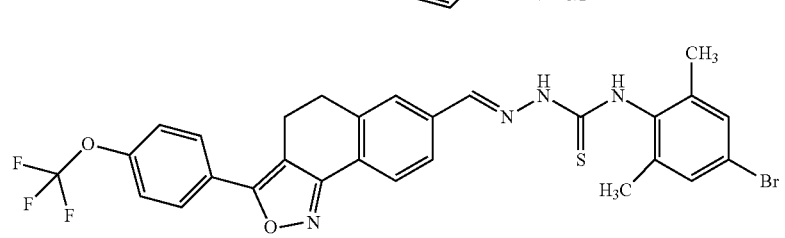
(61)
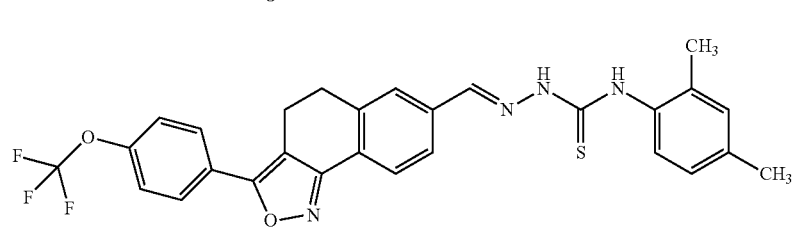
(62)
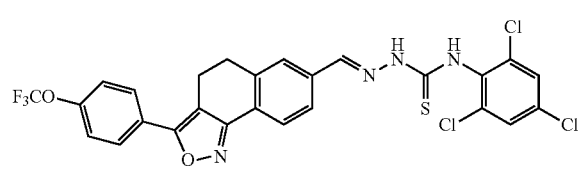
(63)
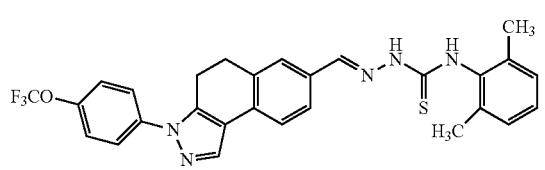

Also preferred compounds of the invention are compounds C-1 to C-132.

The compounds of the formula (I) can be prepared by the standard methods of organic chemistry, e.g. by the methods described hereinafter in schemes 1 to 25 and in the synthesis descriptions of the working examples. In schemes 1 to 25, the radicals Ar, $A^1$, $A^2$, $A^3$, $C^1$, $C^2$, Q, X, Y, Z, R, $R^1$, $R^{11}$, $R^{Q3}$, $R^{Q3a}$, $R^{Q3b}$, $R^{Q4}$, $R^{Q4a}$, $R^{Q4b}$, $R^{x3}$, $R^{x3a}$, $R^{x1a}$, $R^{y1}$, $R^{y2}$, $R^z$ and the index k are as defined above for formula (I), if not otherwise specified.

Methyleneamino-thiourea compounds of formula (I), i.e. compounds of formula (I) in which X is a —C($R^{x3}$)=N—, Y is —N($R^{y2}$)—C(=S)—, and Z is N—$R^z$ can be performed in accordance with the methods described in the examples and by analogy to the methods described in WO 2011/017504. These compounds can be prepared according to routes (A), (B) or (C) shown in Scheme 1.

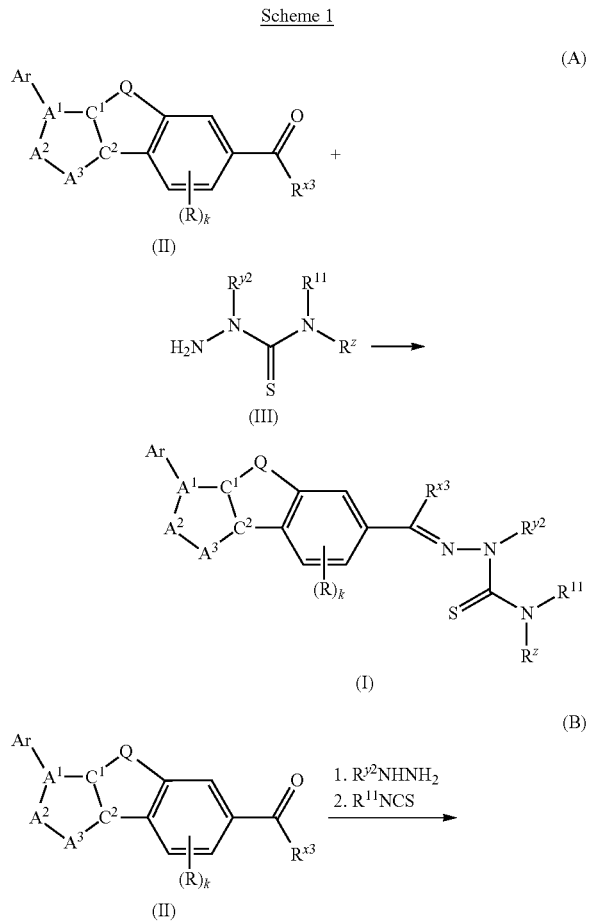

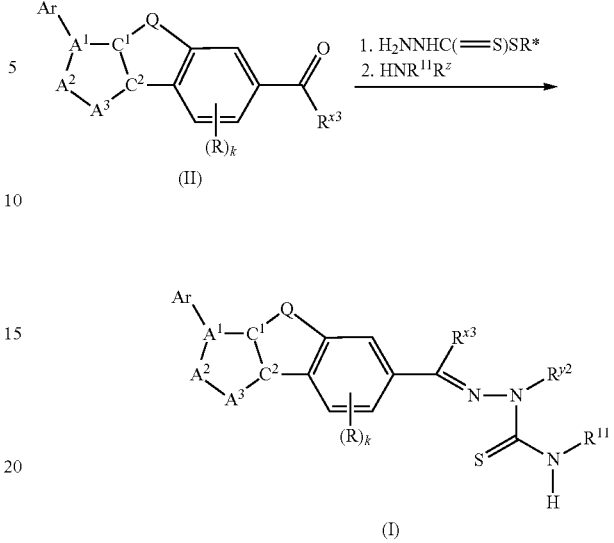

In Scheme 1, R* is $C_1$-$C_6$-alkyl, preferably methyl or ethyl.

According to route (A) of Scheme 1, an aldehyde or ketone compound of the formula (II) is reacted with a thiosemicarbazide of the formula (III) in the presence or in the absence of a solvent. Suitable solvents are polar protic solvents. If the reaction is performed in the absence of a solvent, the thiosemicarbazide compound of the formula (III) usually also act as solvent. Compounds of the formula (III) are commercially available or can be prepared according to standard procedures of the organic chemistry.

According to route (B) of Scheme 1, an aldehyde or ketone compound of the formula (II) is first reacted with a hydrazine of the formula $R^{y2}$NHNH$_2$ followed by the reaction with an isocyanate of the formula $R^{11}$—NCS. Usually, the reaction is carried out in a polar aprotic solvent such as tetrahydrofuran.

According to route (C) of Scheme 1, an aldehyde or ketone compound of the formula (II) is first reacted a hydrazinecarbodithioate of the formula H$_2$NNHC(=S)SR*, where R* is $C_1$-$C_6$-alkyl followed by the reaction with an amine of the formula HNR$^{11}$R$^z$ in a polar aprotic solvent such as dimethylformamide.

For converting compounds of formula (I) in which $R^z$ is H into compounds (I) in which $R^z$ is not H, compounds of formula (I) in which $R^z$ is H can be reacted with compounds of formula $R^z$-Lg, wherein $R^z$ is not H and Lg is a leaving group, such as a bromine, chlorine or iodine atom or a tosylate, mesylate or triflate, to yield compounds of formula (I), wherein $R^z$ is different from H. The reaction is suitably carried out in the presence of a base such as sodium hydride or potassium hydride, suitably in a polar aprotic solvent such as N,N-dimethylformamide, tetrahydrofuran, dioxane, acetonitrile, dimethylsulfoxide or pyridine, or mixtures of these solvents, in a temperature range of from 0° C. and 100 C.

Methyleneamino-urea compounds of formula (I), i.e. compounds of formula (I) in which X is a —C($R^{x3}$)=N—, Y is —N($R^{y1}$)—C(=O)—, and Z is N—$R^z$ can be prepared as shown in the Scheme 2 below.

Scheme 2

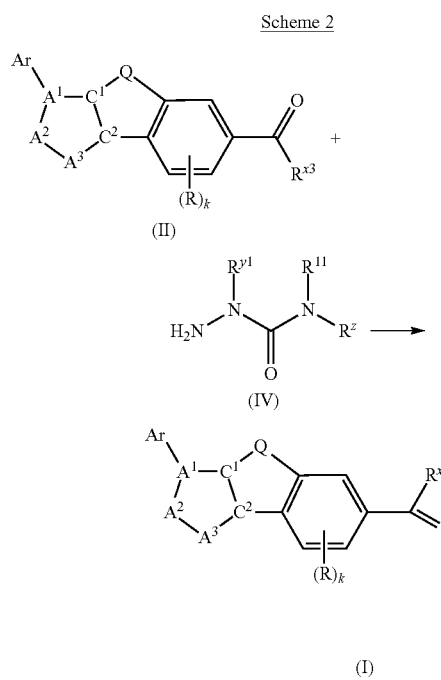

The reaction shown in Scheme 2 can be performed by analogy to the method (A) described in Scheme 1. Compounds of the formula (IV) are known or can be prepared according to standard procedures.

Urea compounds of the formula (I) and carbamate compounds of formula (I), i.e. compounds of formula (I) in which X is a single bond, Y is —N($R^{y1}$)—C(=O)—, and Z is O or N—$R^z$ can be prepared as shown in the Scheme 3 below by analogy to the method described in Synthesis, 2010, 2990-2966.

Scheme 3

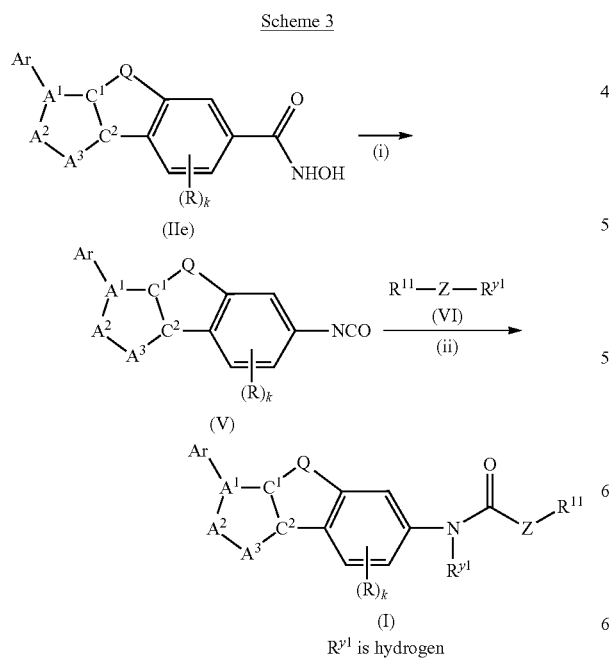

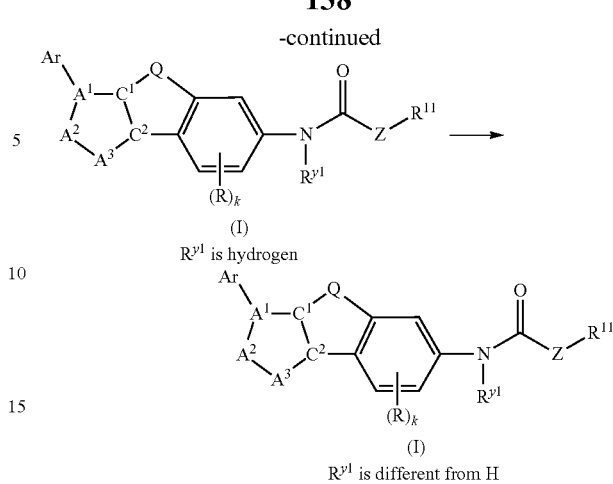

In step (i) of Scheme 3, the isocyanate of the formula (V) is obtained via Lossen rearrangement of the hydroxamic acid of the formula (IIe). To this end, the hydroxamic acid of the formula (IIe) is reacted with 1-propanephosphonic acid cyclic anhydride (T3P) in the presence of a base. The base is preferably N-methylmorpholine. In step (ii) of Scheme 3, the isocyanate (V) is trapped with an alcohol or amine of the formula (VI) to give the corresponding carbamate or urea compound of the formula (I).

For converting compounds of formula (I) in which $R^{y1}$ is H into compounds (I) in which $R^{y1}$ is not H, compounds of formula (I) in which $R^{y1}$ is H can be reacted with compounds of formula $R^{y1}$-Lg, wherein $R^{y1}$ is not H and Lg is a leaving group, such as a bromine, chlorine or iodine atom or a tosylate, mesylate or triflate, to yield compounds of formula (I), wherein $R^{y1}$ is different from H. The reaction is suitably carried out in the presence of a base such as sodium hydride or potassium hydride, suitably in a polar aprotic solvent such as N,N-dimethylformamide, tetrahydrofuran, dioxane, acetonitrile, dimethylsulfoxide or pyridine, or mixtures of these solvents, in a temperature range of from 0° C. and 100 C.

Carbamate compounds of the formula (I), in which X is a single bond, Y is —N($R^{y1}$)—C(=O)—, and Z is O can also be prepared as shown in the Scheme 4 below and in analogy to the methods described in WO 2011/017513.

Scheme 4

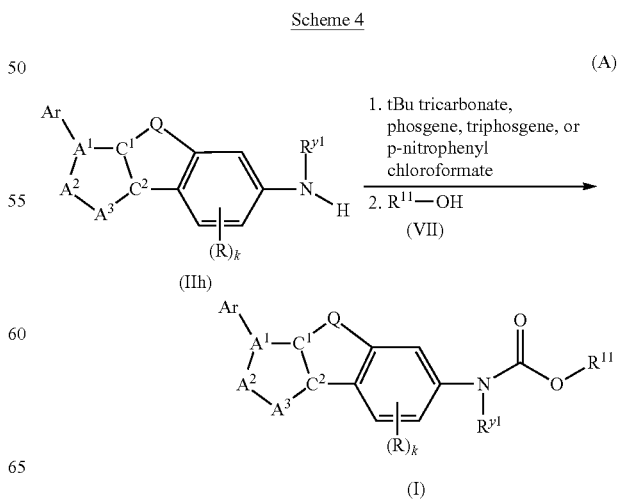

-continued

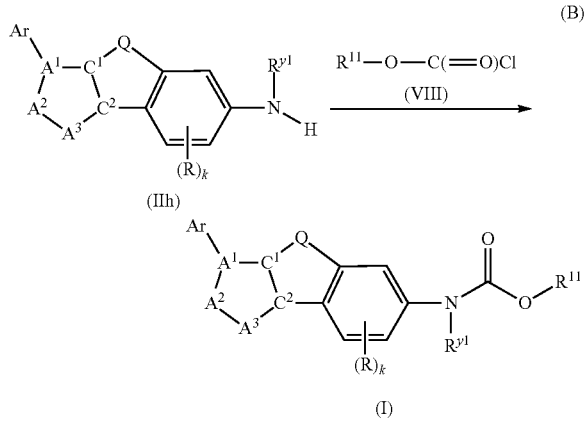

The reaction shown in route (A) of Scheme 4 can be performed by analogy to Ia (IIh) into either an isocyanate or p-nitrophenyl carbamate followed by treatment with an alcohol of the formula (VII) and an organic or inorganic base. According to route (B) of Scheme 4, the compound of the formula (IIh) is reacted with a chloroformate of the formula (VIII). The chloroformate of the formula (VIII) is generated from the alcohol of the formula (VII) by treatment with phosgene or triphosgene in the presence of a base, e.g. pyridine.

Compounds of formula (I), in which X is —N($R^{x2}$)—C(=O)—, Y is —N=C((S)—$R^{y3}$, and Z is N—$R^z$ can be prepared by analogy to the methods described in WO 2013/009791, especially in schemes 1 to 11.

Compounds of formula (I), in which X is —N($R^{x2}$)—C(=O)—, Y is —N=C((O)—$R^{y3}$, and Z is N—$R^z$ can be prepared by analogy to the methods described in WO 2013/009791, especially in schemes 1, 2 and 3.

Compounds of formula (I), in which X is —N($R^{x2}$)—C(=O)—, Y is —N=C((O)—$R^{y3}$, and Z is N—$R^z$ and $R^{y3}$ together with $R^z$ form an $C_2$-$C_6$-alkylene group, wherein a $CH_2$ moiety may be replaced by a carbonyl group and/or wherein 1 or 2 $CH_2$ moieties may be replaced by O or S and/or wherein the alkylene group may be substituted 1, 2, 3, 4, 5 or 6 radicals $R^{hh}$ can be prepared by analogy to the methods described in US 2012/0202687.

Compounds of the formula (II) can be prepared by analogy to the methods described in in literature and in accordance with the methods described in the examples. Usually compounds of the formula (II) are prepared by the reactions shown in the following Scheme 5. Compounds of the formula (II) correspond to the compound of the formula (INT), wherein $R^{1a}$ is (C=O)$R^{x3a}$. Compounds of the formula (IIb) correspond to the compound of the formula (INT), wherein $R^{1a}$ is CN. Compounds of the formula (IIh) correspond to the compound of the formula (INT), wherein $R^{1a}$ is (N($R^{x1a}$)H.

Scheme 5

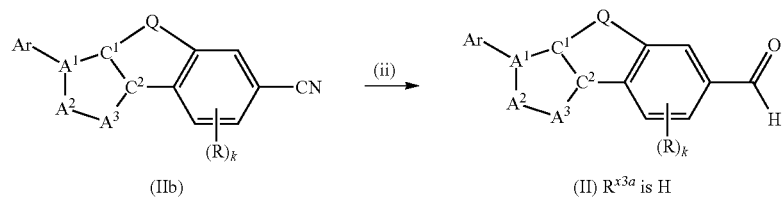

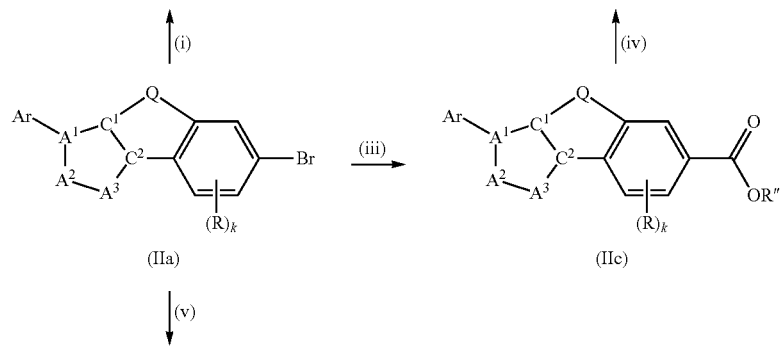

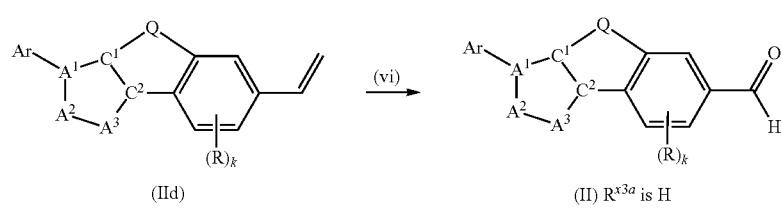

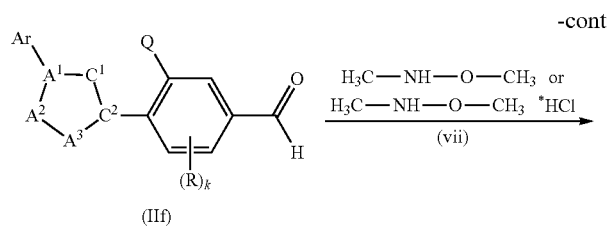
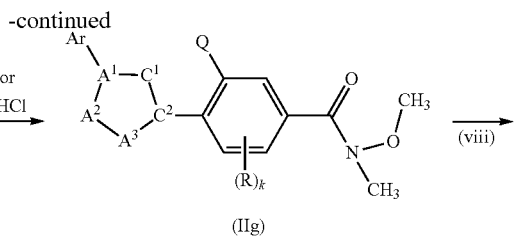

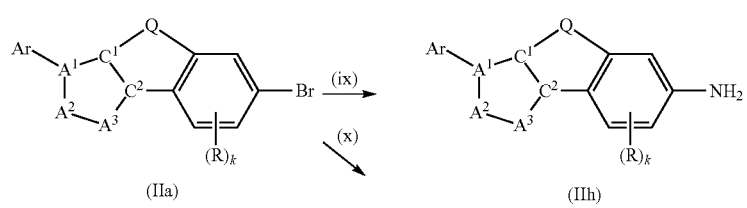

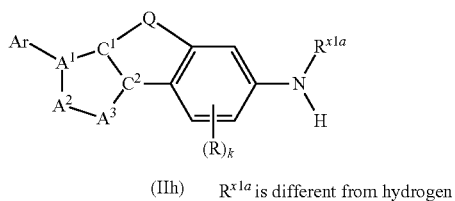

(IIh)  $R^{x1a}$ is different from hydrogen

In Scheme 5, R" is $C_1$-$C_6$-alkyl and Hal is halogen, preferably chlorine or bromine, in particular bromine.

Suitable reaction conditions for performing the preparation of the cyanide compound of the formula (IIb) (reaction step (i) of Scheme 5) by a Pd-catalyzed aromatic cyanation reaction of an aryl bromide of the formula (IIa) with an alkalimetal cyanide, preferably NaCN, can be taken from Journal of the American Chemical Society, 133 (28), 10999-11005; 2011. The reduction of a cyanide compound (IIb) to an aldehyde compound (II) shown in step (ii) of Scheme 5 can be performed with a metal alkoxyaluminum hydride. Suitable alkoxyaluminum hydrides are lithium alkoxyaluminum hydrides and sodium alkoxyaluminum hydrides, e.g. Na[Al(OC$_2$H$_5$)$_3$H]. Suitable reaction conditions for step (ii) of Scheme 5 can be taken from Organic Reactions (Hooboken, N.J., United States), pp 36, 1988. The conversion of the aryl bromide (IIa) into the ester compound (IIc) is shown in reaction step (iii) of Scheme 5. Suitable reaction conditions for the palladium-catalysed reaction can be taken from Journal of Medicinal Chemistry, 52 (22), 7258-7272; 2009. Suitable reaction conditions for performing the palladium catalyzed reaction step (iv) of Scheme 5 can be taken from Synlett, (6), 869-872; 2006. Suitable reaction conditions for performing the reaction step (v) of Scheme 5 can be taken from Journal of the American Chemical Society, 124(22), 6343-6348, 2002. Suitable reaction conditions for performing the reaction step (vi) of Scheme 5 can be taken from European Journal of Medicinal Chemistry, 49, 310-323; 2012.

Compounds of the formula (IIe) can be prepared by reacting methyl or ethyl carboxylic esters of the formula (IIc) with hydroxylamine. The reaction can be performed in analogy to the method described in J. Org. Chem., 2009, 74, 3540-3543.

Compounds of the formula (II) can also be prepared by reacting an acid halide of the formula (IIf) with N,O-dimethylhydroxyamide or N,O-dimethylhydroxyamide hydrochloride to give the corresponding Weinreb-amide of the formula (IIg) as shown in reaction step (vii) of Scheme 5, followed by treating the Weinreb-amide (IIg) with an organometallic reagent, e.g. a Grignard reagent of the formula $R^{x3a}$MgBr or an organolithium reagent of the formula $R^{x3a}$Li as shown in step (viii) of Scheme 5. Reduction of the Weinreb amide (IIg) with lithium aluminum hydride affords compounds of the formula (II), wherein $R^{x3}$ is hydrogen. The acid halide of the formula (IIf) can be prepared from the ester compound of the formula (IIc) according to standard methods.

Compounds of the formula (IIh), wherein $R^{x1a}$ is hydrogen, can be prepared by reacting a compound of the formula (IIa) with an alkali metal azide, preferably sodium azide in the presence of copper(I) as shown in reaction step (ix) of Scheme 5. Compounds of the formula (IIh), wherein $R^{x1a}$ is different from hydrogen can be prepared by reacting a compound of the formula (IIa) with a primary amine of the formula $R^{x1a}$NH$_2$ in the sense of a Buchwald-Hartwig amination as shown in reaction step (x) of Scheme 5.

Compounds of the formula IIa, wherein $A^1$ is N can be prepared by analogy to the methods described in literature and in accordance with the methods described in the examples. Usually compounds of the formula (IIa), where $A^1$ is N, are prepared as shown in the following Scheme 6.

Scheme 6

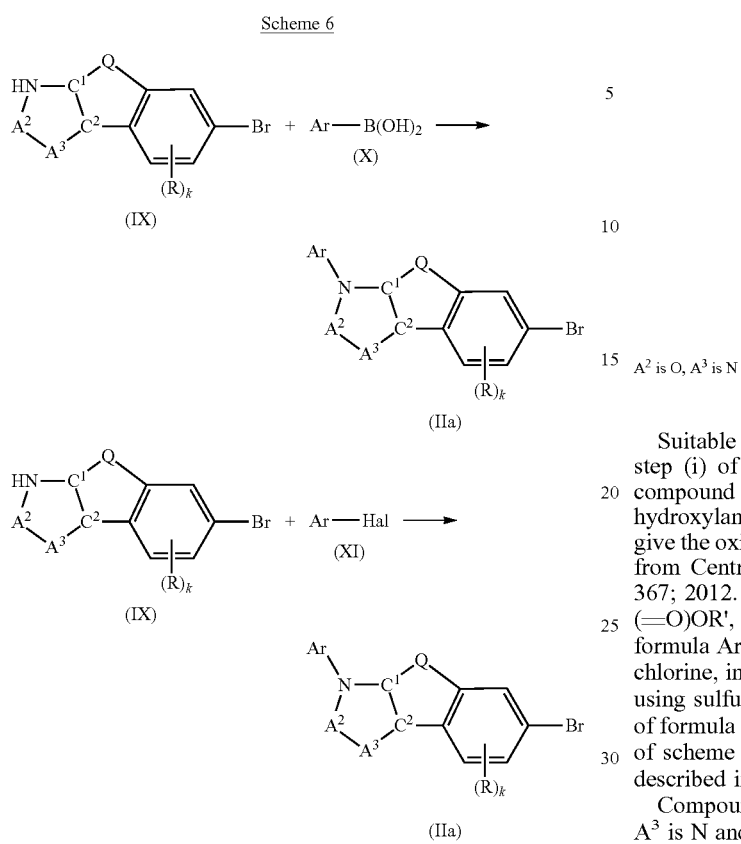

$A^1 = N$

In Scheme 6, Hal is bromine or iodine, preferably bromine. Compounds of the formula (IIa), where $A^1$ is N can be prepared via copper-catalyzed coupling of an arylbromide compound of the formula (IX) with a boronic acid of the formula (X) in the presence of a base in analogy to the method shown in ACS Medicinal Chemistry Letters, 4(2), 293-296; 2013. Alternatively, the compound of formula (IIa), where $A^1$ is N, can be prepared by reacting a compound of formula (IX) with an aryl halide of the formula (XI) in analogy to the method shown in Journal of Medicinal Chemistry, 56(5), 1865-1877, 2013. Compounds of the formula (X) and (XI) are known.

Compounds of the formula IIa, wherein $A^1$ is C, $A^2$ is O, $A^3$ is N and Q is —C($R^{Q3a}R^{Q3b}$)—C($R^{Q4a}R^{Q4b}$)—, can be prepared by analogy to the methods described in literature and as shown in the following Scheme 7.

Scheme 7

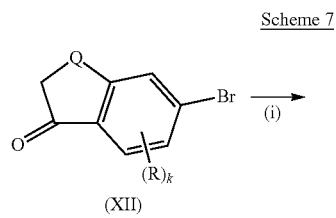

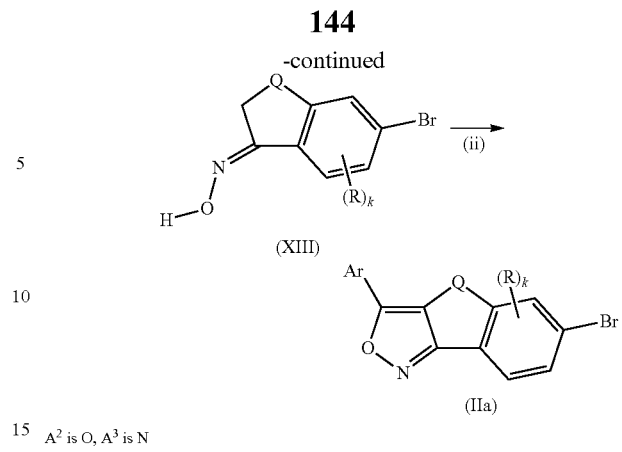

$A^2$ is O, $A^3$ is N

Suitable reaction conditions for performing the reaction step (i) of scheme 7, namely the reaction of the ketone compound of the formula (XII) with hydroxylamine or hydroxylamine hydrochloride in the presence of a base to give the oxime compound of the formula (XIII) can be taken from Central European Journal of Chemistry 10(2), 360-367; 2012. Cyclisation with an ester of the formula Ar—C(=O)OR', where R' is $C_1$-$C_6$-alkyl, or an acid halide of the formula Ar—C(=O)Hal, where Hal is halogen, preferably chlorine, in the presence of a base followed by dehydration using sulfuric acid or Burgees reagent yield the compound of formula (IIa) as outlined in step (ii) of scheme 7. Step (ii) of scheme 7 can be performed in analogy to the methods described in WO 2011/059784.

Compounds of the formula IIa, wherein $A^1$ is C, $A^2$ is NH, $A^3$ is N and Q is —C($R^{Q3a}R^{Q3b}$)—C($R^{Q4a}R^{Q4b}$)—, can be prepared by analogy to the methods described in literature and as shown in the following Scheme 8.

Scheme 8

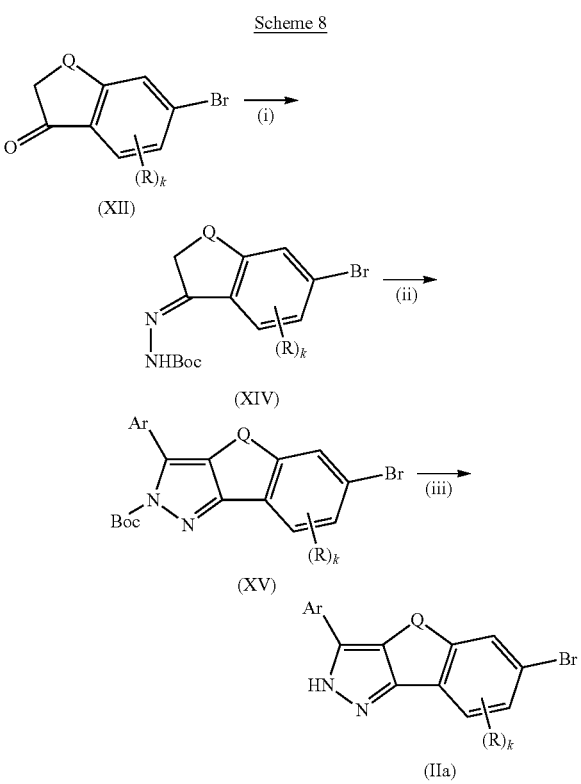

145

-continued

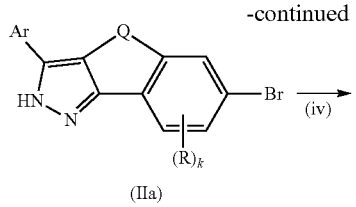

(IIa)

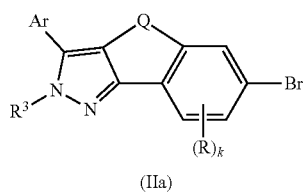

(IIa)

In Scheme 8, Boc means tert-butyloxycarbonyl. Step (i) of Scheme 8 can be performed by analogy to a conventional derivatization of ketones into their hydrazones by reacting a ketone compound (XII) with hydrazinecarboxylic acid 1,1-dimethylester to give a corresponding hydrazone compound (XIII). A suitable method has been described in Synthetic Communications, 26(19), 3659-3669 (1996). In step (ii) of Scheme 8, the hyrazone compound (XIII) is metalated with a strong base, e.g. a lithium amide base such as lithium diisopropylamide, and then reacted with the aromatic ester of the formula Ar—C(=O)OR, where R is $C_1$-$C_6$-alkyl followed by acid cyclization to give the Boc-protected pyrazole of the formula (XIV) in analogy to the method described in Synthetic Communications, 26(19), 3659-3669 (1996). Removal of the tert-butyloxycarbonyl group from the compound (XIV) to give the compound of formula (IIa) is shown in step (iii) of Scheme 8. The removal can be performed by analogy to conventional methods. For converting compounds of formula (IIa) in which $R^3$ is H into compounds (IIa) in which $R^3$ is not H, compounds of formula (IIa) in which $R^3$ is H can be reacted with compounds of formula $R^3$-Lg, wherein $R^3$ is not H and Lg is a leaving group, such as a bromine, chlorine or iodine atom or a tosylate, mesylate or triflate, to yield compounds of formula (I), wherein $R^{y1}$ is different from H.

Compounds of the formula IIa, wherein $A^1$ is N, $A^2$ is N, $A^3$ is C($R^7$) with $R^7$ is hydrogen and Q is —C($R^{Q3a}R^{Q3b}$)—C($R^{Q4a}R^{Q4b}$)—, can be prepared by analogy to the methods described in literature and as shown in the following Scheme 9.

Scheme 9

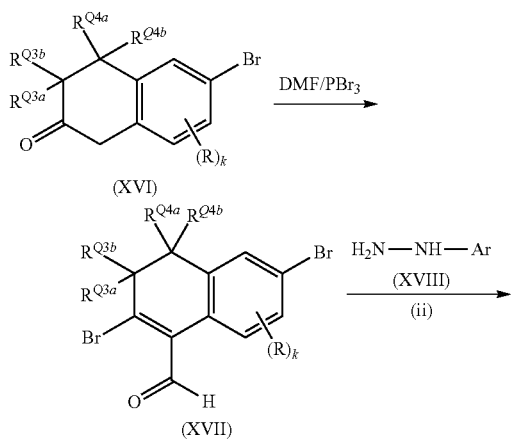

146

-continued

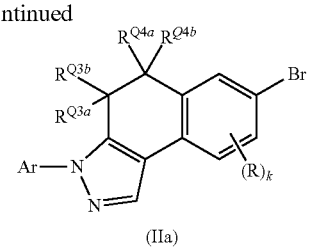

(IIa)

In Scheme 9, DMF means N,N-dimethylformamide. In step (i) of Scheme 9, the cyclohexanone compound of the formula (XVI) is treated with dimethylformamide and phosphorus tribromide or phosphorus oxybromide in the sense of a Vilsmeier-Haack reaction to give the aldehyde compound (XVII). The reaction is usually carried out in a chlorinated hydrocarbon such as dichloromethane or trichloroethylene. The reaction can be performed in analogy to the method described in Chemical Communications, 48(89), 10975-10977; 2012. In step (ii) of Scheme 9, the aldehyde compound (XVII) is cyclized with an arylhydrazine of the formula (XVIII) in the presence of a palladium catalyst and a phosphorus chelating ligand together with a base such as NaO-tert-butyl to give 1-aryl-1H-pyrazole compounds (IIa). The reaction can be performed in analogy to the method described in Tetrahedron, 62 (26), p. 6133-6442 (2006).

Compounds of the formula IIa, wherein $A^1$ is N, $A^2$ is N, $A^3$ is C($R^7$) and $R^7$ is hydrogen and Q is —C($R^{Q3a}$)=C($R^{Q4a}$)—, can be prepared by analogy to the methods described in literature and as shown in the following Scheme 10.

Scheme 10

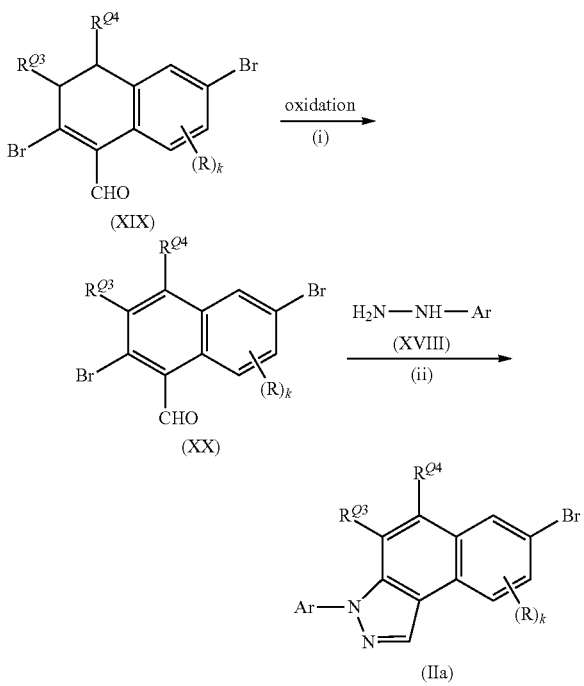

In step (i) of Scheme 10, the 1,2-dihydronaphthalene compound (XIX) is converted to the naphthalene compound (XX) by oxidation with an oxidation agent. A suitable oxidation agent is 2,3-dichloro-5,6-dicyanobenzoquinone.

Suitable reaction conditions for performing step (i) of scheme 10 can be taken from Bioorganic & Medicinal Chemistry 11(4), 521-528, 2003. Step (ii) of Scheme 10 can be performed in analogy to step (ii) of Scheme 9. The 1,2-dihydronaphthalene compound (XIX) can be obtained in analogy to the method described for the preparation of compounds of formula (XVI), where $R^{Q3a}$ and $R^{Q4a}$ are each hydrogen.

Compounds of the formula IIa, wherein $A^1$ is N, $A^2$ is $CR^2$, $A^3$ is $CR^7$ and Q is —C($R^{Q3a}R^{Q3b}$)—C($R^{Q4a}R^{Q4b}$)—, can be prepared by analogy to the methods described in literature and as shown in the following Scheme 11.

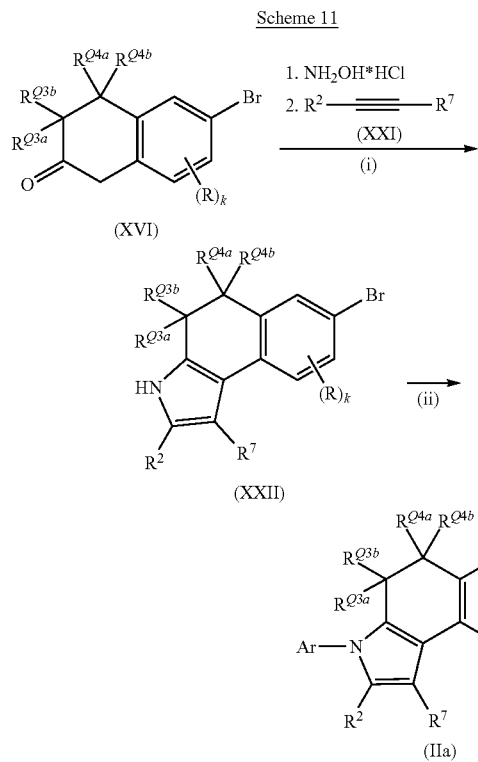

Scheme 11

(XVI)

(XXII)

(IIa)

In step (i) of Scheme 11, the ketone compound (XVI), hydroxylamine hydrochloride and an acetylene compound (XXI) react in a one pot reaction to give 4,5-dihydrobenz[e]indole of the formula (XXII). The reaction in step (i) of Scheme 11 can be performed in analogy to the method described in Tetrahedron 51(13), 1690-1692, 2010. Step (ii) of Scheme 11 can be performed in analogy to the method described in Scheme 6.

Compounds of the formula IIa, wherein $A^1$ is N, $A^2$ is N, $A^3$ is N and Q is —C($R^{Q3a}R^{Q3b}$)—C($R^{Q4a}R^{Q4b}$)—, can be prepared by analogy to the methods described in literature and as shown in the following Scheme 12.

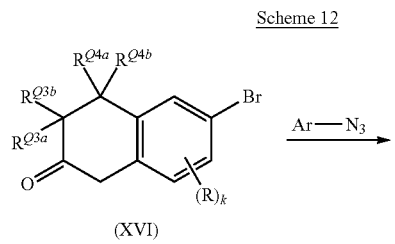

Scheme 12

(XVI)

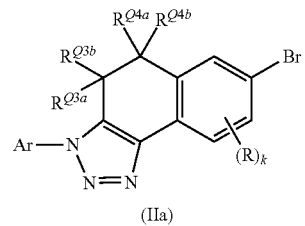

(IIa)

According to scheme 12, compounds of the formula (IIa) can be prepared by reacting a ketone compound of the formula (XV) with an arylazide in a sense of a Huisgen [3+2] cycloaddition. This reaction can be performed by analogy to the method described in Chemistry—A European Journal, 18(19), 6088-6093, S6088/1-6088/47; 2012.

Compounds of the formula IIa, wherein $A^1$ is N, $A^2$ is N, $A^3$ is N and Q is —C($R^{Q3}$)=C($R^{Q4}$)—, can be prepared by analogy to the methods described in literature and as shown in the following Scheme 13.

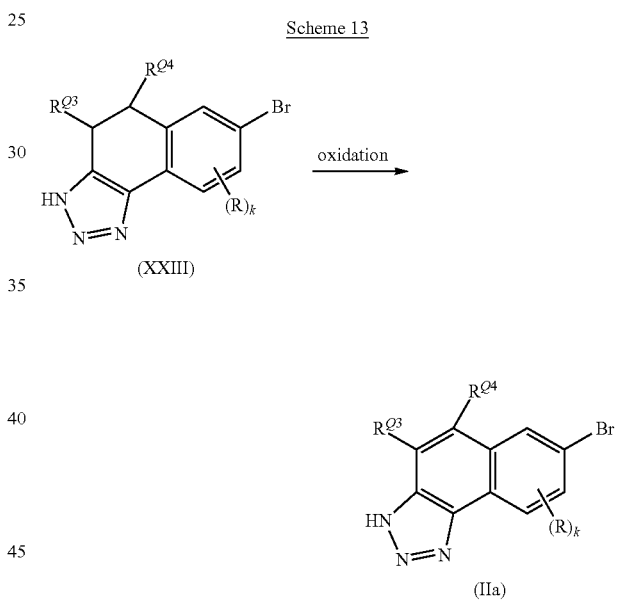

Scheme 13

(XXIII)

(IIa)

The oxidation in Scheme 13 can be performed in analogy to step (i) of Scheme 10. The compounds of the formula (XXIII) can be prepared in analogy to the reaction shown in Scheme 12.

As a rule, compounds of the formula (IIa), where Q is —C($R^{Q3a}R^{Q3b}$)—C($R^{Q4a}R^{Q4b}$)— can be converted into compounds of the formula (IIa), where Q is Q is —C($R^{Q3}$)=C($R^{Q4}$)— according to the method described in step (i) of Scheme 10. (korrekt?)

Some of the reactions shown in the Schemes below may be performed in analogy to the reactions shown in the Schemes above.

Compounds of the formula IIa, wherein $A^1$ is C, $A^2$ is N($R^3$), $A^3$ is N, $C^1$ is CH and Q is —C($R^{Q3a}R^{Q3b}$)—C($R^{Q4a}R^{Q4b}$)—, can be prepared by analogy to the methods described in literature and as shown in the following Scheme 14.

Scheme 14

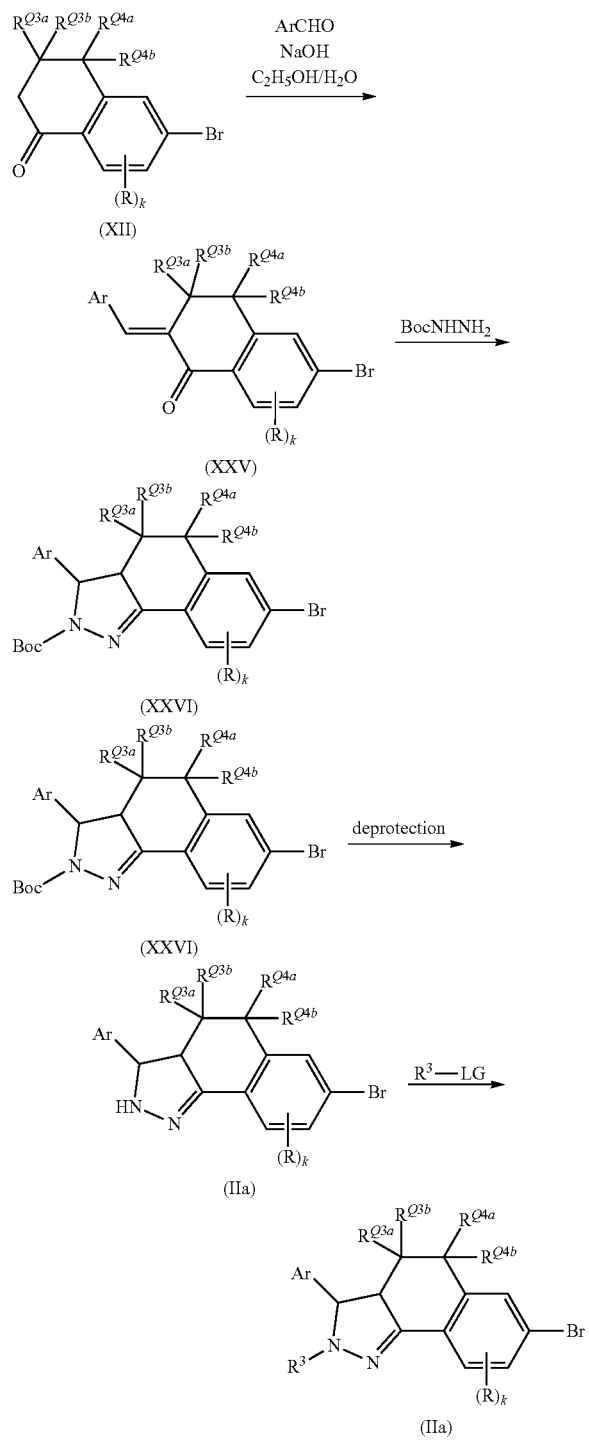

Scheme 15

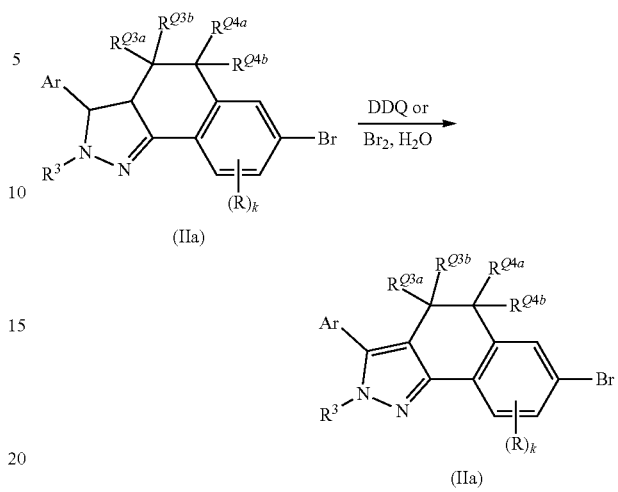

In Scheme 15, DDQ is 2,3-dichloro-5,6-dicyano-1,4-benzoquinone.

Compounds of the formula IIa, wherein $A^1$ is C, $A^2$ is O, $A^3$ is N, $C^1$ is C and Q is —C($R^{Q3a}R^{Q3b}$)—C($R^{Q4a}R^{Q4b}$)—, can be prepared by analogy to the methods described in literature and as shown in the following Scheme 16.

Scheme 16

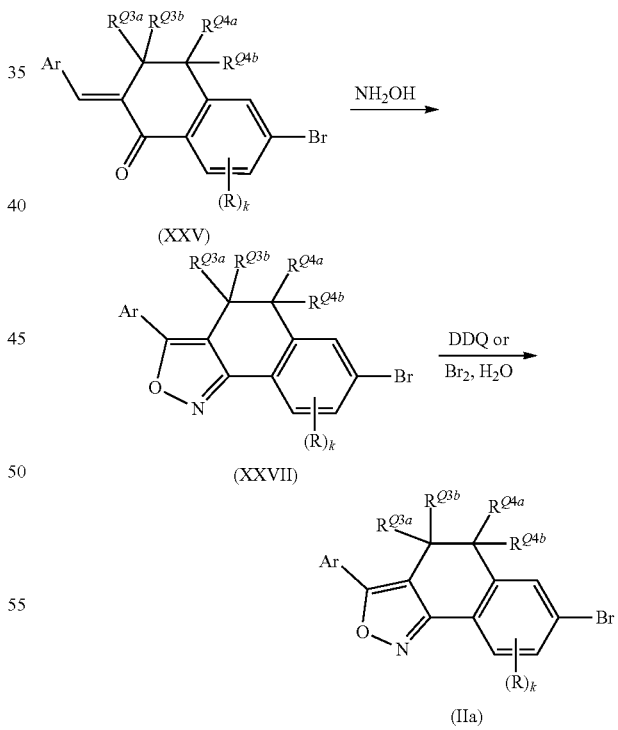

In Scheme 14, Boc means tert-butyloxycarbonyl and LG is a leaving group, such as a bromine, chlorine or iodine atom or a tosylate, mesylate or triflate.

Compounds of the formula IIa, wherein $A^1$ is C, $A^2$ is N($R^3$), $A^3$ is N, $C^1$ is C and Q is —C($R^{Q3a}R^{Q3b}$)—C($R^{Q4a}R^{Q4b}$)—, can be prepared by analogy to the methods described in literature and as shown in the following Scheme 15.

In Scheme 16, DDQ is 2,3-dichloro-5,6-dicyano-1,4-benzoquinone.

Compounds of the formula IIa, wherein $A^1$ is N, $A^2$ is CH, $A^3$ is N, $C^1$ is C and Q is —OC($R^{Q4a}R^{Q4b}$)—, can be prepared by analogy to the methods described in literature and as shown in the following Scheme 17.

Scheme 17

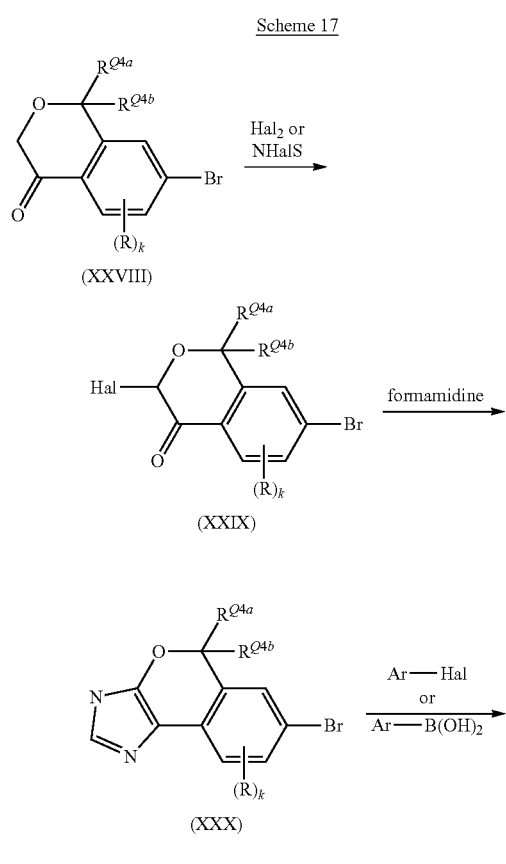

In Scheme 17, Hal is halogen, preferably bromine, chlorine or iodine and NHalS is N-halogenosuccinimide, preferably N-bromosuccinimide.

Compounds of the formula IIa, wherein $A^1$ is N, $A^2$ is CH, $A^3$ is N, $C^1$ is C and Q is —SC($R^{Q4a}R^{Q4b}$)—, can be prepared by analogy to the methods described in literature and as shown in the following Scheme 18.

Scheme 18

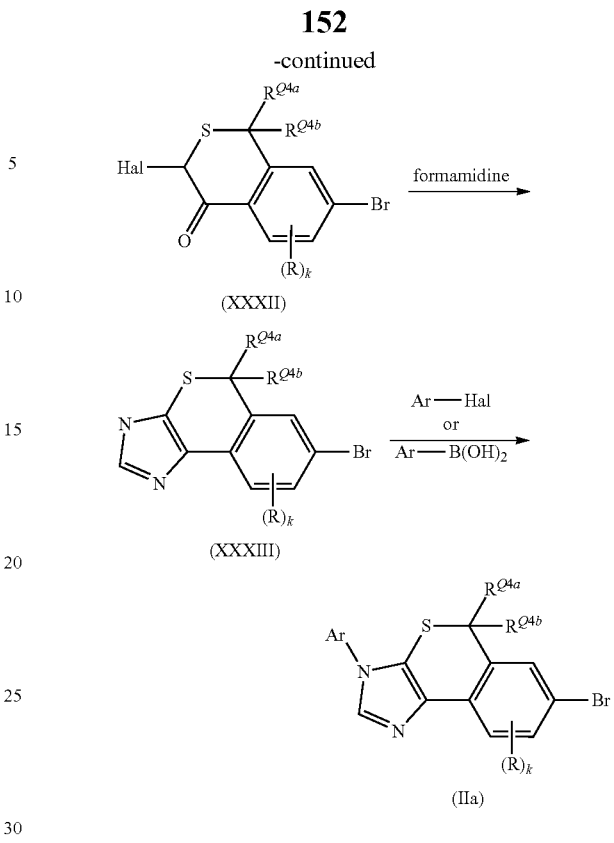

In Scheme 18, Hal is halogen, preferably bromine, chlorine or iodine and NHalS is N-halogenosuccinimide, preferably N-bromosuccinimide.

Compounds of the formula IIa, wherein $A^1$ is N, $A^2$ is CH, $A^3$ is N, $C^1$ is C and Q is —S(=O)C($R^{Q4a}R^{Q4b}$)— or —S(=O)$_2$C($R^{Q4a}R^{Q4b}$)—, can be prepared by treating a compound of the formula (IIa), where $A^1$ is N, $A^2$ is CH, $A^3$ is N, $C^1$ is C and Q is —SC($R^{Q4a}R^{Q4b}$)—, with an oxidazing agent such as 3-chloroperoxybenzoic acid or RuCl$_3$/NaIO$_4$.

Compounds of the formula IIa, wherein $A^1$ is N, $A^2$ is CH, $A^3$ is N, $C^1$ is CH and Q is —C($R^{Q4a}R^{Q4b}$)—O—, where $R^{Q4a}$ and $R^{Q4b}$ are both hydrogen, can be prepared by analogy to the methods described in literature and as shown in the following Scheme 19.

Scheme 19

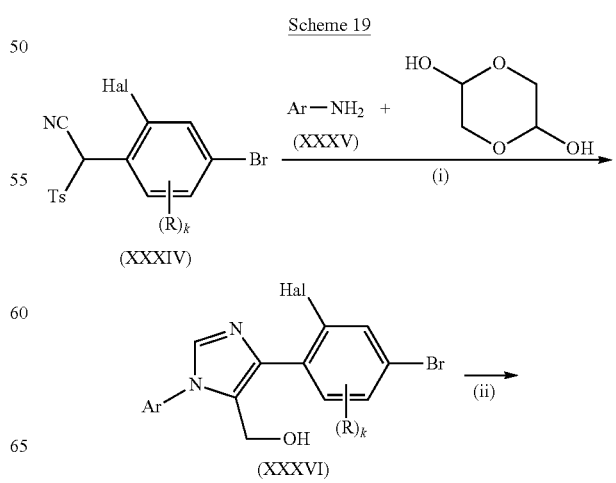

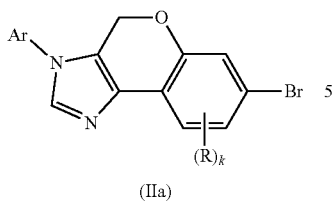

(IIa)

In Scheme 19, Ts is tosyl and Hal is halogen. In step (i) of Scheme 19, the cyano compound (XXXIV) is treated with an amine (XXXV) and glyoaldehyde, dimer to form the imidazolyl compound (XXXVI). The reaction can be performed in analogy to the method described in WO 2004/013141. Step (ii) of Scheme 19 is performed under copper or palladium catalysis.

Compounds of the formula IIa, wherein $A^1$ is N, $A^2$ is CH, $A^3$ is N, $C^1$ is CH and Q is —C($R^{Q4a}R^{Q4b}$)—S—, where $R^{Q4a}$ and $R^{Q4b}$ are both hydrogen, can be prepared by analogy to the methods described in literature and as shown in the following Scheme 20.

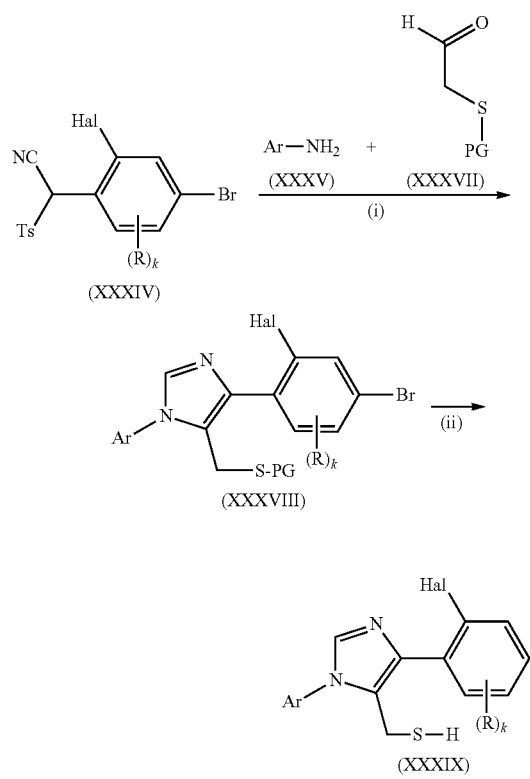

In Scheme 20, Ts is tosyl, Hal is halogen and PG is a sulfur protection group such as PMB (p-methoxybenzyl).

In step (i) of Scheme 19, the cyano compound (XXXIV) is treated with an amine (XXXV) and a protected sulfanylacetaldehyde (XXXVII) to form the imidazolyl compound (XXXVIII). In step (ii) of Scheme 20, the sulfur is deprotected according to standard methods in the organic chemistry. Step (iii) of Scheme 20 is performed under copper or palladium catalysis to give the compound (IIa).

Compounds of the formula IIa, wherein $A^1$ is N, $A^2$ is CH, $A^3$ is N, $C^1$ is CH and Q is —C($R^{Q4a}R^{Q4b}$)—S(O)— or C($R^{Q4a}R^{Q4b}$)—S(O)$_2$—, where $R^{Q4a}$ and $R^{Q4b}$ are both hydrogen can be prepared by treating a compound of the formula (IIa), where $A^1$ is N, $A^2$ is CH, $A^3$ is N, $C^1$ is C and Q is —SC($R^{Q4a}R^{Q4b}$)—, with an oxidazing agent such as 3-chloroperoxybenzoic acid or RuCl$_3$/NaIO$_4$.

Compounds of the formula (IIa), wherein $A^1$ is N, $A^2$ is CH, $A^3$ is N, $C^1$ is C and Q is —N($R^{Q2}$)—C(=O)—, can be prepared by analogy to the methods described in literature and as shown in the following Scheme 21.

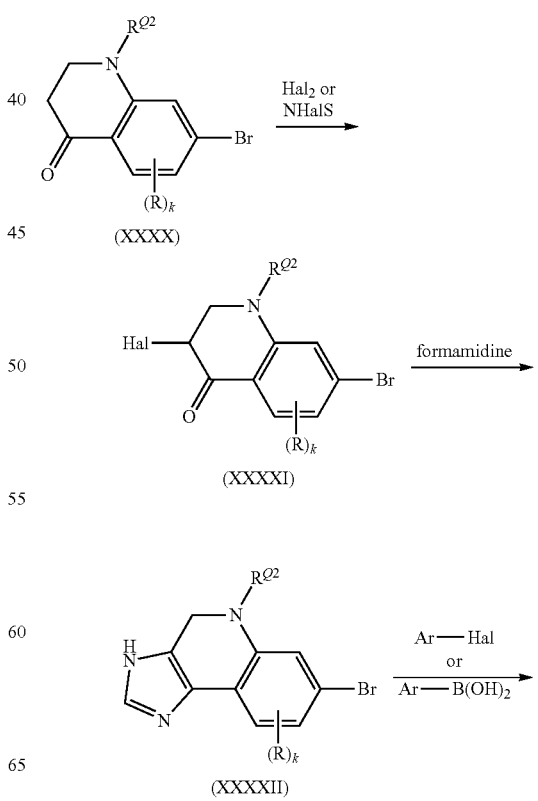

-continued

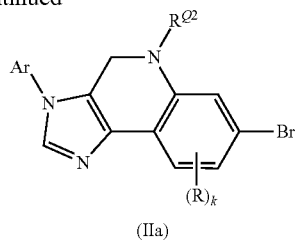

(IIa)

In Scheme 21, Hal is halogen, preferably bromine, chlorine or iodine and NHalS is N-halogenosuccinimide, preferably N-bromosuccinimide.

Compounds of the formula (IIa), wherein $A^1$ is N, $A^2$ is CH, $A^3$ is N, $C^1$ is C and Q is —C($R^{Q4a}R^{Q4b}$)—N($R^{Q2}$)—, can be prepared by analogy to the methods described in literature and as shown in the following Scheme 22.

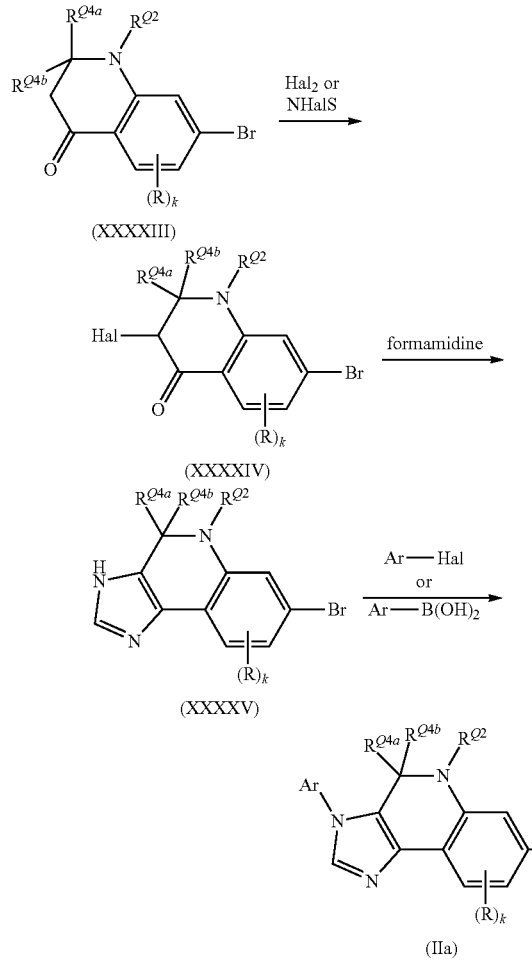

In Scheme 22, Hal is halogen, preferably bromine, chlorine or iodine and NHalS is N-halogenosuccinimide, preferably N-bromosuccinimide.

Compounds of the formula (IIa), wherein $A^1$ is N, $A^2$ is CH, $A^3$ is N, $C^1$ is C and Q is —N($R^{Q2}$)—C($R^{Q4a}R^{Q4b}$)—, can be prepared by analogy to the methods described in literature and as shown in the following Scheme 23.

Scheme 23

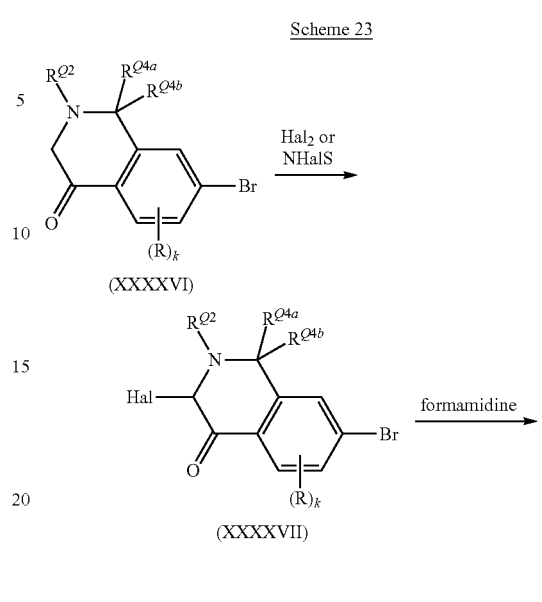

In Scheme 23, Hal is halogen, preferably bromine, chlorine or iodine and NHalS is N-halogenosuccinimide, preferably N-bromosuccinimide.

Compounds of the formula (IIa), wherein $A^1$ is N, $A^2$ is CH, $A^3$ is N, $C^1$ is C and Q is —N($R^{Q2}$)—C(O)—, can be prepared by analogy to the methods described in literature and as shown in the following Scheme 24.

Scheme 24

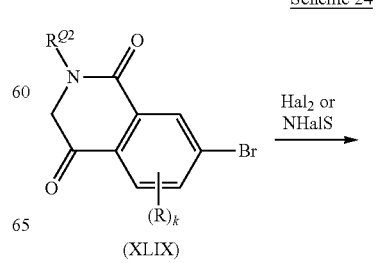

(XLIX)

-continued

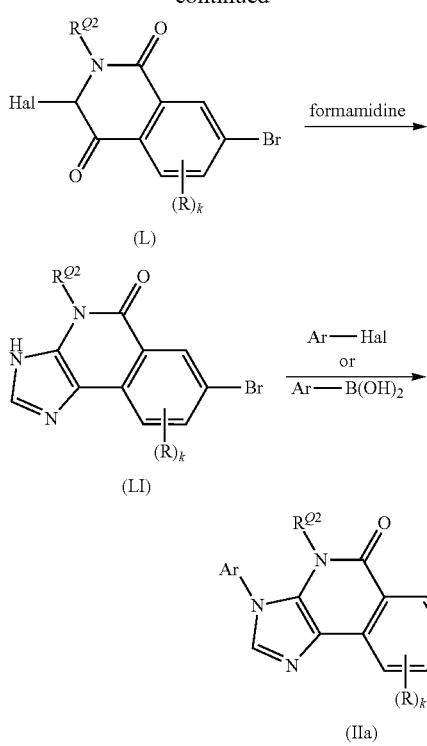

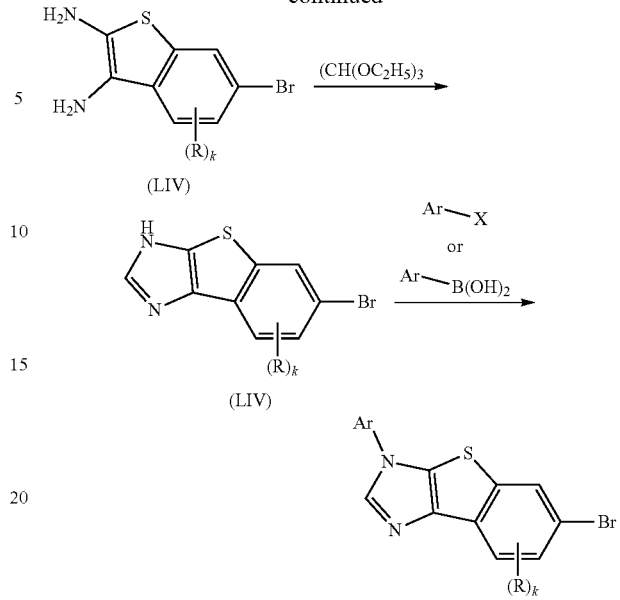

In Scheme 24, Hal is halogen, preferably bromine, chlorine or iodine and NHalS is N-halogenosuccinimide, preferably N-bromosuccinimide.

Compounds of the formula (IIa), wherein $A^1$ is N, $A^2$ is CH, $A^3$ is N, $C^1$ is C and Q is S can be prepared by analogy to the methods described in literature and as shown in the following Scheme 25.

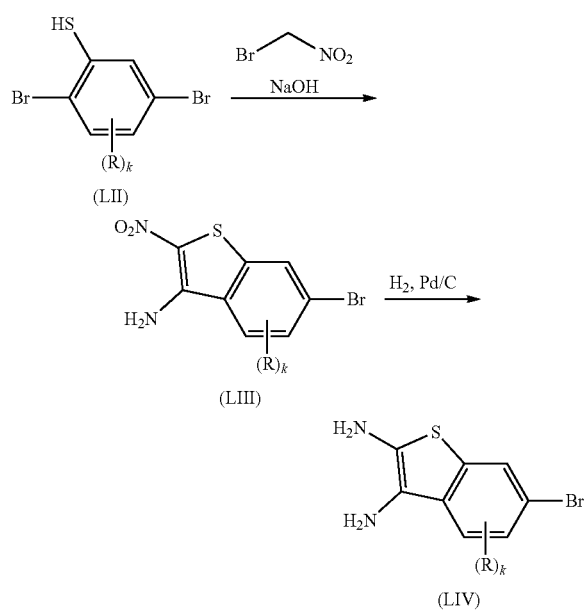

As a rule, the compounds of formula (I), especially (Ia), (Ib), (Ic) and (Id), including their stereoisomers, N-oxides and salts, as well as their precursors in the synthesis process, can be prepared by the methods described above or by customary modifications of the synthesis routes described. If individual compounds can not be prepared via the above-described routes, they can be prepared by derivatization of other compounds (I) or the respective precursor. For example, in individual cases, certain compounds of formula (I) can advantageously be prepared from other compounds of formula (I) by derivatization, e.g. by ester hydrolysis, amidation, esterification, ether cleavage, olefination, reduction, oxidation and the like, or by customary modifications of the synthesis routes described.

The reaction mixtures are worked up in the customary manner, for example by mixing with water, separating the phases, and, if appropriate, purifying the crude products by chromatography, for example on alumina or on silica gel. Some of the intermediates and end products may be obtained in the form of colorless or pale brown viscous oils which are freed or purified from volatile components under reduced pressure and at moderately elevated temperature. If the intermediates and end products are obtained as solids, they may be purified by recrystallization or trituration with an appropriate solvent.

Due to their excellent activity, the compounds of the present invention may be used for controlling invertebrate pests.

Accordingly, the present invention also provides a method for controlling invertebrate pests which method comprises treating the pests, their food supply, their habitat or their breeding ground or a cultivated plant, plant propagation materials (such as seed), soil, area, material or environment in which the pests are growing or may grow, or the materials, cultivated plants, plant propagation materials (such as seed), soils, surfaces or spaces to be protected from pest attack or infestation with a pesticidally effective amount of a compound of the present invention or a composition as defined above. The invention also relates to the use of a compound of the invention, of a stereoisomer and/or of an agriculturally or veterinarily acceptable salt thereof for combating invertebrate pests.

Preferably, the method of the invention serves for protecting plant propagation material (such as seed) and the plant which grows therefrom from invertebrate pest attack or infestation and comprises treating the plant propagation material (such as seed) with a pesticidally effective amount of a compound of the present invention as defined above or with a pesticidally effective amount of an agricultural composition as defined above and below. The method of the invention is not limited to the protection of the "substrate" (plant, plant propagation materials, soil material etc.) which has been treated according to the invention, but also has a preventive effect, thus, for example, according protection to a plant which grows from a treated plant propagation materials (such as seed), the plant itself not having been treated.

Alternatively preferably, the method of the invention serves for protecting plants from attack or infestation by invertebrate pests, which method comprises treating the plants with a pesticidally effective amount of at least one compound of the invention, a stereoisomer thereof and/or at least one agriculturally acceptable salt thereof.

In the sense of the present invention, "invertebrate pests" are preferably selected from arthropods and nematodes, more preferably from harmful insects, arachnids and nematodes, and even more preferably from insects, acarids and nematodes. In the sense of the present invention, "invertebrate pests" are most preferably insects.

The invention further provides an agricultural composition for combating invertebrate pests, which comprises such an amount of at least one compound according to the invention and at least one inert liquid and/or solid agronomically acceptable carrier that has a pesticidal action and, if desired, at least one surfactant.

Such a composition may comprise a single active compound of the present invention or a mixture of several active compounds of the present invention. The composition according to the present invention may comprise an individual isomer or mixtures of isomers or a salt as well as individual tautomers or mixtures of tautomers.

The compounds of the present invention, including their salts, stereoisomers and tautomers, are in particular suitable for efficiently controlling arthropodal pests such as arachnids, myriapedes and insects as well as nematodes. They are especially suitable for efficiently combating or controlling the following pests:

insects from the order of the lepidopterans (Lepidoptera), for example *Acronicta major, Adoxophyes orana, Aedia leucomelas, Agrotis* spp. such as *Agrotis fucosa, Agrotis segetum, Agrotis ypsilon; Alabama argillacea, Anticarsia gemmatalis, Anticarsia* spp., *Argyresthia conjugella, Autographa gamma, Barathra brassicae, Bucculatrix thurberiella, Bupalus piniarius, Cacoecia murinana, Cacoecia podana, Capua reticulana, Carpocapsa pomonella, Cheimatobia brumata, Chilo* spp. such as *Chilo suppressalis; Choristoneura fumiferana, Choristoneura occidentalis, Cirphis unipuncta, Clysia ambiguella, Cnaphalocerus* spp., *Cydia pomonella, Dendrolimus pini, Diaphania nitidalis, Diatraea grandiosella, Earias insulana, Elasmopalpus lignosellus, Ephestia cautella, Ephestia kuehniella, Eupoecilia ambiguella, Euproctis chrysorrhoea, Euxoa* spp., *Evetria bouliana, Feltia* spp. such as *Feltia subterranean; Galleria mellonella, Grapholitha funebrana, Grapholitha molesta, Helicoverpa* spp. such as *Helicoverpa armigera, Helicoverpa zea; Heliothis* spp. such as *Heliothis armigera, Heliothis virescens, Heliothis zea; Hellula undalis, Hibernia defoliaria, Hofmannophila pseudospretella, Homona magnanima, Hyphantria cunea, Hyponomeuta padella, Hyponomeuta malinellus, Keiferia lycopersicella, Lambdina fiscellaria, Laphygma* spp. such as *Laphygma exigua; Leucoptera coffeella, Leucoptera scitella, Lithocolletis blancardella, Lithophane antennata, Lobesia botrana, Loxagrotis albicosta, Loxostege sticticalis, Lymantria* spp. such as *Lymantria dispar, Lymantria monacha; Lyonetia clerkella, Malacosoma neustria, Mamestra* spp. such as *Mamestra brassicae; Mocis repanda, Mythimna separata, Orgyia pseudotsugata, Oria* spp., *Ostrinia* spp. such as *Ostrinia nubilalis; Oulema oryzae, Panolis flammea, Pectinophora* spp. such as *Pectinophora gossypiella; Peridroma saucia, Phalera bucephala, Phthorimaea* spp. such as *Phthorimaea operculella; Phyllocnistis citrella, Pieris* spp. such as *Pieris brassicae, Pieris rapae; Plathypena scabra, Plutella maculipennis, Plutella xylostella, Prodenia* spp., *Pseudaletia* spp., *Pseudoplusia includens, Pyrausta nubilalis, Rhyacionia frustrana, Scrobipalpula absoluta, Sitotroga cerealella, Sparganothis pilleriana, Spodoptera* spp. such as *Spodoptera frugiperda, Spodoptera littoralis, Spodoptera litura; Thaumatopoea pityocampa, Thermesia gemmatalis, Tinea pellionella, Tineola bisselliella, Tortrix viridana, Trichoplusia* spp. such as *Trichoplusia ni; Tuta absoluta*, and *Zeiraphera canadensis,* beetles (Coleoptera), for example *Acanthoscehdes obtectus, Adoretus* spp., *Agelastica alni, Agrilus sinuatus, Agriotes* spp. such as *Agriotes fuscicollis, Agriotes lineatus, Agriotes obscurus; Amphimallus solstitialis, Anisandrus dispar, Anobium punctatum, Anomala rufocuprea, Anoplophora* spp. such as *Anoplophora glabripennis; Anthonomus* spp. such as *Anthonomus grandis, Anthonomus pomorum; Anthrenus* spp., *Aphthona euphoridae, Apogonia* spp., *Athous haemorrhoidalis, Atomaria* spp. such as *Atomaria linearis; Attagenus* spp., *Aulacophora femoralis, Blastophagus piniperda, Blitophaga undata, Bruchidius obtectus, Bruchus* spp. such as *Bruchus lentis, Bruchus pisorum, Bruchus rufimanus; Byctiscus betulae, Callosobruchus chinensis, Cassida nebulosa, Cerotoma trifurcata, Cetonia aurata, Ceuthorrhynchus* spp. such as *Ceuthorrhynchus assimilis, Ceuthorrhynchus napi; Chaetocnema tibialis, Cleonus mendicus, Conoderus* spp. such as *Conoderus vespertinus; Cosmopolites* spp., *Costelytra zealandica, Crioceris asparagi, Cryptorhynchus lapathi, Ctenicera* ssp. such as *Ctenicera destructor; Curculio* spp., *Dectes texanus, Dermestes* spp., *Diabrotica* spp. such as *Diabrotica 12-punctata Diabrotica speciosa, Diabrotica longicornis, Diabrotica semipunctata, Diabrotica virgifera; Epilachna* spp. such as *Epilachna varivestis, Epilachna vigintioctomaculata; Epitrix* spp. such as *Epitrix hirtipennis; Eutinobothrus brasiliensis, Faustinus cubae, Gibbium psylloides, Heteronychus arator, Hylamorpha elegans, Hylobius abietis, Hylotrupes bajulus, Hypera brunneipennis, Hypera postica, Hypothenemus* spp., *Ips typographus, Lachnosterna consanguinea, Lema bilineata, Lema melanopus, Leptinotarsa* spp. such as *Leptinotarsa decemlineata; Limonius californicus, Lissorhoptrus oryzophilus, Lissorhoptrus oryzophilus, Lixus* spp., *Lyctus* spp. such as *Lyctus bruneus; Melanotus communis, Meligethes* spp. such as *Meligethes aeneus; Melolontha hippocastani, Melolontha melolontha, Migdolus* spp., *Monochamus* spp. such as *Monochamus alternatus; Naupactus xanthographus, Niptus hololeucus, Oryctes rhinoceros, Oryzaephilus surinamensis, Otiorrhynchus sulcatus, Otiorrhynchus ovatus, Otiorrhynchus sulcatus, Oulema oryzae, Oxycetonia jucunda, Phaedon cochleariae, Phyllobius pyri, Phyllopertha horticola, Phyllophaga* spp., *Phyllotreta* spp. such as

*Phyllotreta chrysocephala, Phyllotreta nemorum, Phyllotreta striolata; Phyllophaga* spp., *Phyllopertha horticola, Popillia japonica, Premnotrypes* spp., *Psylliodes chrysocephala, Ptinus* spp., *Rhizobius ventralis, Rhizopertha dominica, Sitona lineatus, Sitophilus* spp. such as *Sitophilus granaria, Sitophilus zeamais; Sphenophorus* spp. such as *Sphenophorus levis; Sternechus* spp. such as *Sternechus subsignatus; Symphyletes* spp., *Tenebrio molitor, Tribolium* spp. such as *Tribolium castaneum; Trogoderma* spp., *Tychius* spp., *Xylotrechus* spp., and *Zabrus* spp. such as *Zabrus tenebrioides*, flies, mosquitoes (Diptera), e.g. *Aedes* spp. such as *Aedes aegypti, Aedes albopictus, Aedes vexans; Anastrepha ludens, Anopheles* spp. such as *Anopheles albimanus, Anopheles crucians, Anopheles freeborni, Anopheles gambiae, Anopheles leucosphyrus, Anopheles maculipennis, Anopheles minimus, Anopheles quadrimaculatus, Anopheles sinensis; Bibio hortulanus, Calliphora erythrocephala, Calliphora vicina, Cerafitis capitata, Ceratitis capitata, Chrysomyia* spp. such as *Chrysomya bezziana, Chrysomya hominivorax, Chrysomya macellaria; Chrysops atlanticus, Chrysops discalis, Chrysops silacea, Cochliomyia* spp. such as *Cochliomyia hominivorax; Contarinia* spp. such as *Contarinia sorghicola; Cordylobia anthropophaga, Culex* spp. such as *Culex nigripalpus, Culex pipiens, Culex quinquefasciatus, Culex tarsalis, Culex tritaeniorhynchus; Culicoides furens, Culiseta inornata, Culiseta melanura, Cuterebra* spp., *Dacus cucurbitae, Dacus oleae, Dasineura brassicae, Delia* spp. such as *Delia antique, Delia coarctata, Delia platura, Delia radicum; Dermatobia hominis, Drosophila* spp., *Fannia* spp. such as *Fannia canicularis; Gastraphilus* spp. such as *Gasterophilus intestinalis; Geomyza Tripunctata, Glossina fuscipes, Glossina morsitans, Glossina palpalis, Glossina tachinoides, Haematobia irritans, Haplodiplosis equestris, Hippelates* spp., *Hylemyia* spp. such as *Hylemyia platura; Hypoderma* spp. such as *Hypoderma lineata; Hyppobosca* spp., *Leptoconops torrens, Liriomyza* spp. such as *Liriomyza sativae, Liriomyza trifolii; Lucilia* spp. such as *Lucilia caprina, Lucilia cuprina, Lucilia sericata; Lycoria pectoralis, Mansonia titillanus, Mayetiola* spp. such as *Mayetiola destructor; Musca* spp. such as *Musca autumnalis, Musca domestica; Muscina stabulans, Oestrus* spp. such as *Oestrus ovis; Opomyza florum, Oscinella* spp. such as *Oscinella frit; Pegomya hysocyami, Phlebotomus argentipes, Phorbia* spp. such as *Phorbia antiqua, Phorbia brassicae, Phorbia coarctata; Prosimulium mixtum, Psila rosae, Psorophora columbiae, Psorophora discolor, Rhagoletis cerasi, Rhagoletis pomonella, Sarcophaga* spp. such as *Sarcophaga haemorrhoidalis; Simulium vittatum, Stomoxys* spp. such as *Stomoxys calcitrans; Tabanus* spp. such as *Tabanus atratus, Tabanus bovinus, Tabanus lineola, Tabanus similis; Tannia* spp., *Tipula oleracea, Tipula paludosa,* and *Wohlfahrtia* spp., thrips (Thysanoptera), e.g. *Baliothrips biformis, Dichromothrips corbetti, Dichromothrips* ssp., *Enneothrips flavens, Frankliniella* spp. such as *Frankliniella fusca, Frankliniella occidentalis, Frankliniella tritici; Heliothrips* spp., *Hercinothrips femoralis, Kakothrips* spp., *Rhipiphorothrips cruentatus, Scirtothrips* spp. such as *Scirtothrips citri; Taeniothrips cardamoni, Thrips* spp. such as *Thrips oryzae, Thrips palmi, Thrips tabaci;* termites (Isoptera), e.g. *Calotermes flavicollis, Coptotermes formosanus, Heterotermes aureus, Heterotermes longiceps, Heterotermes tenuis, Leucotermes flavipes, Odontotermes* spp., *Reticulitermes* spp. such as *Reticulitermes speratus, Reticulitermes flavipes, Reticulitermes grassei, Reticulitermes lucifugus, Reticulitermes santonensis, Reticulitermes virginicus; Termes natalensis,* cockroaches (Blattaria-Blattodea), e.g. *Acheta domesticus, Blatta orientalis, Blattella asahinae, Blattella germanica, Gryllotalpa* spp., *Leucophaea maderae, Locusta* spp., *Melanoplus* spp., *Periplaneta americana, Periplaneta australasiae, Periplaneta brunnea, Periplaneta fuligginosa, Periplaneta japonica,* bugs, aphids, leafhoppers, whiteflies, scale insects, cicadas (Hemiptera), e.g. *Acrosternum* spp. such as *Acrosternum hilare; Acyrthosipon* spp. such as *Acyrthosiphon onobrychis, Acyrthosiphon pisum; Adelges laricis, Aeneolamia* spp., *Agonoscena* spp., *Aleurodes* spp., *Aleurolobus barodensis, Aleurothrixus* spp., *Amrasca* spp., *Anasa tristis, Antestiopsis* spp., *Anuraphis cardui, Aonidiella* spp., *Aphanostigma piri, Aphidula nasturtii, Aphis* spp. such as *Aphis fabae, Aphis forbesi, Aphis gossypii, Aphis grossulariae, Aphis pomi, Aphis sambuci, Aphis schneideri, Aphis spiraecola; Arboridia apicalis, Arilus critatus, Aspidiella* spp., *Aspidiotus* spp., *Atanus* spp., *Aulacorthum solani, Bemisia* spp. such as *Bemisia argentifolii, Bemisia tabaci; Blissus* spp. such as *Blissus leucopterus; Brachycaudus cardui, Brachycaudus helichrysi, Brachycaudus persicae, Brachycaudus prunicola, Brachycolus* spp., *Brevicoryne brassicae, Calligypona marginata, Calocoris* spp., *Campylomma livida, Capitophorus horni, Carneocephala fulgida, Cavelerius* spp., *Ceraplastes* spp., *Ceratovacuna lanigera, Cercopidae, Cerosipha gossypii, Chaetosiphon fragaefolii, Chionaspis tegalensis, Chlorita onukii, Chromaphis juglandicola, Chrysomphalus ficus, Cicadulina mbila, Cimex* spp. such as *Cimex hemipterus, Cimex lectularius; Coccomytilus halli, Coccus* spp., *Creontiades dilutus, Cryptomyzus ribis, Cryptomyzus ribis, Cyrtopeltis notatus, Dalbulus* spp., *Dasynus piperis, Dialeurades* spp., *Diaphorina* spp., *Diaspis* spp., *Dichelops furcatus, Diconocoris hewetti, Doralis* spp., *Dreyfusia nordmannianae, Dreyfusia piceae, Drosicha* spp., *Dysaphis* spp. such as *Dysaphis plantaginea, Dysaphis pyri, Dysaphis radicola; Dysaulacorthum pseudosolani, Dysdercus* spp. such as *Dysdercus cingulatus, Dysdercus intermedius; Dysmicoccus* spp., *Empoasca* spp. such as *Empoasca fabae, Empoasca solana; Eriosoma* spp., *Erythroneura* spp., *Eurygaster* spp. such as *Eurygaster integriceps; Euscelis bilobatus, Euschistus* spp. such as *Euschistuos heros, Euschistus impictiventris, Euschistus servus; Geococcus coffeae, Halyomorpha* spp. such as *Halyomorpha halys; Heliopeltis* spp., *Homalodisca coagulata, Horcias nobilellus, Hyalopterus pruni, Hyperomyzus lactucae, Icerya* spp., *Idiocerus* spp., *Idioscopus* spp., *Laodelphax striatellus, Lecanium* spp., *Lepidosaphes* spp., *Leptocorisa* spp., *Leptoglossus phyllopus, Lipaphis erysimi, Lygus* spp. such as *Lygus hesperus, Lygus lineolaris, Lygus pratensis; Macropes excavatus, Macrosiphum* spp. such as *Macrosiphum rosae, Macrosiphum avenae, Macrosiphum euphorbiae; Mahanarva fimbriolata, Megacopta cribraria, Megoura viciae, Melanaphis pyrarius, Melanaphis sacchari, Metcafiella* spp., *Metopolophium dirhodum, Miridae* spp., *Monellia costalis, Monelliopsis pecanis, Myzus* spp. such as *Myzus ascalonicus, Myzus cerasi, Myzus persicae, Myzus varians; Nasonovia ribis-nigri, Nephotettix* spp. such as *Nephotettix malayanus, Nephotettix nigropictus, Nephotettix parvus, Nephotettix virescens; Nezara* spp. such as *Nezara viridula; Nilaparvata lugens, Oebalus* spp., *Oncometopia* spp., *Orthezia praelonga, Parabemisia myricae, Paratrioza* spp., *Parlatoria* spp., *Pemphigus* spp. such as *Pemphigus bursarius; Pentomidae, Peregrinus maidis, Perkinsiella saccharicida, Phenacoccus* spp., *Phloeomyzus passerinii, Phorodon humuli, Phylloxera* spp., *Piesma* quadrata, Piezodorus spp. such as Piezodorus guildinii, Pinnaspis aspidistrae, Planococcus spp., Protopulvinaria pyriformis, Psallus seriatus, Pseudacysta persea, Pseudaulacaspis pentagona, Pseudococcus spp. such as Pseudococcus comstocki; Psylla spp. such as Psylla mali, Psylla piri; Pteromalus spp., Pyrilla spp., Quadraspidiotus spp., Quesada gigas, Rastrococcus spp., Reduvius senilis, Rhodnius spp., Rhopalomyzus ascalonicus, Rhopalosiphum spp. such as Rhopalosiphum pseudobrassicas, Rhopalosiphum insertum, Rhopalosiphum maidis, Rhopalosiphum padi; Sagatodes spp., Sahlbergella singularis, Saissetia spp., Sappaphis mala, Sappaphis mali, Scaphoides titanus, Schizaphis graminum, Schizoneura lanuginosa, Scotinophora spp., Selenaspidus articulatus, Sitobion avenae, Sogata spp., Sogatella furcifera, Solubea insularis, Stephanitis nashi, Stictocephala festina, Tenalaphara malayensis, Thyanta spp. such as Thyanta perditor; Tibraca spp., Tinocallis caryaefoliae, Tomaspis spp., Toxoptera spp. such as Toxoptera aurantii; Trialeurodes spp. such as Trialeurodes vaporariorum; Triatoma spp., Trioza spp., Typhlocyba spp., Unaspis spp. such as Unaspis yanonensis; and Viteus vitifolii, ants, bees, wasps, sawflies (Hymenoptera), e.g. Athalia rosae, Atta capiguara, Atta cephalotes, Atta cephalotes, Atta laevigata, Atta robusta, Atta sexdens, Atta texana, Bombus spp., Camponotus floridanus, Crematogaster spp., Dasymutilla occidentalis, Diprion spp., Dolichovespula maculata, Hoplocampa spp. such as Hoplocampa minuta, Hoplocampa testudinea; Lasius spp. such as Lasius niger, Linepithema humile, Monomorium pharaonis, Paravespula germanica, Paravespula pennsylvanica, Paravespula vulgaris, Pheidole megacephala, Pogonomyrmex barbatus, Pogonomyrmex californicus, Polistes rubiginosa, Solenopsis geminata, Solenopsis invicta, Solenopsis richteri, Solenopsis xyloni, Vespa spp. such as Vespa crabro, and Vespula squamosa, crickets, grasshoppers, locusts (Orthoptera), e.g. Acheta domestica, Calliptamus italicus, Chortoicetes terminifera, Dociostaurus maroccanus, Gryllotalpa africana, Gryllotalpa gryllotalpa, Hieroglyphus daganensis, Kraussaria angulifera, Locusta migratoria, Locustana pardalina, Melanoplus bivittatus, Melanoplus femurrubrum, Melanoplus mexicanus, Melanoplus sanguinipes, Melanoplus spretus, Nomadacris septemfasciata, Oedaleus senegalensis, Schistocerca americana, Schistocerca gregaria, Tachycines asynamorus, and Zonozerus variegatus, arachnids (Arachnida), such as acari, e.g. of the families Argasidae, Ixodidae and Sarcoptidae, such as Amblyomma spp. (e.g. Amblyomma americanum, Amblyomma variegatum, Amblyomma maculatum), Argas spp. (e.g. Argas persicus), Boophilus spp. (e.g. Boophilus annulatus, Boophilus decoloratus, Boophilus microplus), Dermacentor silvarum, Dermacentor andersoni, Dermacentor variabilis, Hyalomma spp. (e.g. Hyalomma truncatum), Ixodes spp. (e.g. Ixodes ricinus, Ixodes rubicundus, Ixodes scapularis, Ixodes holocyclus, Ixodes pacificus), Ornithodorus spp. (e.g. Ornithodorus moubata, Ornithodorus hermsi, Ornithodorus turicata), Ornithonyssus bacoti, Otobius megnini, Dermanyssus gallinae, Psoroptes spp. (e.g. Psoroptes ovis), Rhipicephalus spp. (e.g. Rhipicephalus sanguineus, Rhipicephalus appendiculatus, Rhipicephalus evertsi), Rhizoglyphus spp., Sarcoptes spp. (e.g. Sarcoptes scabiei), and Eriophyidae spp. such as Acaria sheldoni, Aculops spp. (e.g. Aculops pelekassi) Aculus spp. (e.g. Aculus schlechtendali), Epitrimerus pyri, Phyllocoptruta oleivora and Eriophyes spp. (e.g. Eriophyes sheldoni); Tarsonemidae spp. such as Hemitarsonemus spp., Phytonemus pallidus and Polyphagotarsonemus latus, Stenotarsonemus spp.; Tenuipalpidae spp. such as Brevipalpus spp. (e.g. Brevipalpus phoenicis); Tetranychidae spp. such as Eotetranychus spp., Eutetranychus spp., Oligonychus spp., Tetranychus cinnabarinus, Tetranychus kanzawai, Tetranychus pacificus, Tetranychus telarius and Tetranychus urticae; Bryobia praetiosa, Panonychus spp. (e.g. Panonychus ulmi, Panonychus citri), Metatetranychus spp. and Oligonychus spp. (e.g. Oligonychus pratensis), Vasates lycopersici; Araneida, e.g. Latrodectus mactans, and Loxosceles reclusa. And Acarus siro, Chorioptes spp., Scorpio maurus, fleas (Siphonaptera), e.g. Ceratophyllus spp., Ctenocephalides felis, Ctenocephalides canis, Xenopsylla cheopis, Pulex irritans, Tunga penetrans, and Nosopsyllus fasciatus, silverfish, firebrat (Thysanura), e.g. Lepisma saccharina and Thermobia domestica, centipedes (Chilopoda), e.g. Geophilus spp., Scutigera spp. such as Scutigera coleoptrata;

millipedes (Diplopoda), e.g. Blaniulus guttulatus, Narceus spp.,

Earwigs (Dermaptera), e.g. forficula auricularia, lice (Phthiraptera), e.g. Damalinia spp., Pediculus spp. such as Pediculus humanus capitis, Pediculus humanus corporis; Pthirus pubis, Haematopinus spp. such as Haematopinus eurysternus, Haematopinus suis; Linognathus spp. such as Linognathus vituli; Bovicola bovis, Menopon gallinae, Menacanthus stramineus and Solenopotes capillatus, Trichodectes spp., springtails (Collembola), e.g. Onychiurus ssp. such as Onychiurus armatus, They are also suitable for controlling nematodes: plant parasitic nematodes such as root knot nematodes, Meloidogyne hapla, Meloidogyne incognita, Meloidogyne javanica, and other Meloidogyne species; cyst-forming nematodes, Globodera rostochiensis and other Globodera species; Heterodera avenae, Heterodera glycines, Heterodera schachtii, Heterodera trifolii, and other Heterodera species; Seed gall nematodes, Anguina species; Stem and foliar nematodes, Aphelenchoides species such as Aphelenchoides besseyi; Sting nematodes, Belonolaimus longicaudatus and other Belonolaimus species; Pine nematodes, Bursaphelenchus lignicolus Mamiya et Kiyohara, Bursaphelenchus xylophilus and other Bursaphelenchus species; Ring nematodes, Criconema species, Criconemella species, Criconemoides species, Mesocriconema species; Stem and bulb nematodes, Ditylenchus destructor, Ditylenchus dipsaci and other Ditylenchus species; Awl nematodes, Dolichodorus species; Spiral nematodes, Helicotylenchus multicinctus and other Helicotylenchus species; Sheath and sheathoid nematodes, Hemicycliophora species and Hemicriconemoides species; Hirshmanniella species; Lance nematodes, Hoploaimus species; false rootknot nematodes, Nacobbus species; Needle nematodes, Longidorus elongatus and other Longidorus species; Lesion nematodes, Pratylenchus brachyurus, Pratylenchus neglectus, Pratylenchus penetrans, Pratylenchus curvitatus, Pratylenchus goodeyi and other Pratylenchus species; Burrowing nematodes, Radopholus similis and other Radopholus species; Reniform nematodes, Rotylenchus robustus, Rotylenchus reniformis and other Rotylenchus species; Scutellonema species; Stubby root nematodes, Trichodorus primitivus and other Trichodorus species, Paratrichodorus species; Stunt nematodes, Tylenchorhynchus claytoni, Tylenchorhynchus dubius and other Tylenchorhynchus species; Citrus nematodes, Tylenchulus species such as Tylenchulus semipenetrans; Dagger nematodes, Xiphinema species; and other plant parasitic nematode species.

Examples of further pest species which may be controlled by compounds of formula (I) include: from the class of the Bivalva, for example, *Dreissena* spp.; from the class of the Gastropoda, for example, *Arion* spp., *Biomphalaria* spp., *Bulinus* spp., *Deroceras* spp., *Galba* spp., *Lymnaea* spp., *Oncomelania* spp., *Succinea* spp.; from the class of the helminths, for example, *Ancylostoma duodenale, Ancylostoma ceylanicum, Acylostoma braziliensis, Ancylostoma* spp., *Ascaris lumbricoides, Ascaris* spp., *Brugia malayi, Brugia timori, Bunostomum* spp., *Chabertia* spp., *Clonorchis* spp., *Cooperia* spp., *Dicrocoelium* spp., *Dictyocaulus filaria, Diphyllobothrium latum, Dracunculus medinensis, Echinococcus granulosus, Echinococcus multilocularis, Enterobius vermicularis, Faciola* spp., *Haemonchus* spp. such as *Haemonchus contortus; Heterakis* spp., *Hymenolepis nana, Hyostrongulus* spp., *Loa Loa, Nematodirus* spp., *Oesophagostomum* spp., *Opisthorchis* spp., *Onchocerca volvulus, Ostertagia* spp., *Paragonimus* spp., *Schistosomen* spp., *Strongyloides fuelleborni, Strongyloides stercora lis, Stronyloides* spp., *Taenia saginata, Taenia solium, Trichinella spiralis, Trichinella nativa, Trichinella britovi, Trichinella nelsoni, Trichinella pseudopsiralis, Trichostrongulus* spp., *Trichuris trichiura, Wuchereria bancrofti*; from the order of the Isopoda, for example, *Armadillidium vulgare, Oniscus asellus, Porcellio scaber*; from the order of the Symphyla, for example, *Scutigerella immaculata;*

Further examples of pest species which may be controlled by compounds of formula (I) include: *Anisoplia austriaca, Apamea* spp., *Austroasca viridigrisea, Baliothrips biformis, Caenorhabditis elegans, Cephus* spp., *Ceutorhynchus napi, Chaetocnema aridula, Chilo auricilius, Chilo indicus, Chilo polychrysus, Chortiocetes terminifera, Cnaphalocroci medinalis, Cnaphalocrosis* spp., *Colias eurytheme, Collops* spp., *Cornitermes cumulans, Creontiades* spp., *Cyclocephala* spp., *Dalbulus maidis, Deraceras reticulatum, Diatrea saccharalis, Dichelops furcatus, Dicladispa armigera, Diloboderus* spp. such as *Diloboderus abderus; Edessa* spp., *Epinotia* spp., *Formicidae, Geocoris* spp., *Globitermes sulfureus, Gryllotalpidae, Halotydeus destructor, Hipnodes bicolor, Hydrellia philippina, Julus* spp., *Laodelphax* spp., *Leptocorsia acuta, Leptocorsia oratorius, Liogenys fuscus, Lucillia* spp., *Lyogenys fuscus, Mahanarva* spp., *Maladera matrida, Marasmia* spp., *Mastotermes* spp., *Mealybugs, Megascelis* ssp, *Metamasius hemipterus, Microtheca* spp., *Mocis latipes, Murgantia* spp., *Mythemina separata, Neocapritermes opacus, Neocapritermes parvus, Neomegalotomus* spp., *Neotermes* spp., *Nymphula depunctalis, Oebalus pugnax, Orseolia* spp. such as *Orseolia oryzae; Oxycaraenus hyalinipennis, Plusia* spp., *Pomacea canaliculata, Procornitermes* ssp, *Procornitermes triacifer, Psylloides* spp., *Rachiplusia* spp., *Rhodopholus* spp., *Scaptocoris castanea, Scaptocoris* spp., *Scirpophaga* spp. such as *Scirpophaga incertulas, Scirpophaga innotata; Scotinophara* spp. such as *Scotinophara coarctata; Sesamia* spp. such as *Sesamia inferens, Sogaella frucifera, Solenapsis geminata, Spississtilus* spp., Stalk borer, *Stenchaetothrips biformis, Steneotarsonemus spinki, Sylepta derogata, Telehin licus, Trichostrongylus* spp.

The compounds of the present invention, including their salts, stereoisomers and tautomers, are particularly useful for controlling insects, preferably sucking or piercing and chewing and biting insects such as insects from the genera Lepidoptera, Coleoptera and Hemiptera, in particular Lepidoptera, Coleoptera and true bugs.

The compounds of the present invention, including their salts, stereoisomers and tautomers, are moreover useful for controlling insects of the orders Thysanoptera, Diptera (especially flies, mosquitos), Hymenoptera (especially ants) and Isoptera (especially termites.

The compounds of the present invention, including their salts, stereoisomers and tautomers, are particularly useful for controlling insects of the orders Lepidoptera and Coleoptera.

The invention also relates to agrochemical compositions comprising an auxiliary and at least one compound I according to the invention.

An agrochemical composition comprises a pesticidally effective amount of a compound I. The term "effective amount" denotes an amount of the composition or of the compounds I, which is sufficient for controlling harmful fungi on cultivated plants or in the protection of materials and which does not result in a substantial damage to the treated plants. Such an amount can vary in a broad range and is dependent on various factors, such as the species to be controlled, the treated cultivated plant or material, the climatic conditions and the specific compound I used.

The compounds I, their N-oxides and salts can be converted into customary types of agrochemical compositions, e.g. solutions, emulsions, suspensions, dusts, powders, pastes, granules, pressings, capsules, and mixtures thereof. Examples for composition types are suspensions (e.g. SC, OD, FS), emulsifiable concentrates (e.g. EC), emulsions (e.g. EW, EO, ES, ME), capsules (e.g. CS, ZC), pastes, pastilles, wettable powders or dusts (e.g. WP, SP, WS, DP, DS), pressings (e.g. BR, TB, DT), granules (e.g. WG, SG, GR, FG, GG, MG), insecticidal articles (e.g. LN), as well as gel formulations for the treatment of plant propagation materials such as seeds (e.g. GF).

These and further compositions types are defined in the "Catalogue of pesticide formulation types and international coding system", Technical Monograph No. 2, $6^{th}$ Ed. May 2008, CropLife International.

The compositions are prepared in a known manner, such as described by Mollet and Grubemann, Formulation technology, Wiley VCH, Weinheim, 2001; or Knowles, New developments in crop protection product formulation, Agrow Reports DS243, T&F Informa, London, 2005.

Suitable auxiliaries are solvents, liquid carriers, solid carriers or fillers, surfactants, dispersants, emulsifiers, wetters, adjuvants, solubilizers, penetration enhancers, protective colloids, adhesion agents, thickeners, humectants, repellents, attractants, feeding stimulants, compatibilizers, bactericides, anti-freezing agents, anti-foaming agents, colorants, tackifiers and binders.

Suitable solvents and liquid carriers are water and organic solvents, such as mineral oil fractions of medium to high boiling point, e.g. kerosene, diesel oil; oils of vegetable or animal origin; aliphatic, cyclic and aromatic hydrocarbons, e.g. toluene, paraffin, tetrahydronaphthalene, alkylated naphthalenes; alcohols, e.g. ethanol, propanol, butanol, benzylalcohol, cyclohexanol; glycols; DMSO; ketones, e.g. cyclohexanone; esters, e.g. lactates, carbonates, fatty acid esters, gamma-butyrolactone; fatty acids; phosphonates; amines; amides, e.g. N-methylpyrrolidone, fatty acid dimethylamides; and mixtures thereof.

Suitable solid carriers or fillers are mineral earths, e.g. silicates, silica gels, talc, kaolins, limestone, lime, chalk, clays, dolomite, diatomaceous earth, bentonite, calcium sulfate, magnesium sulfate, magnesium oxide; polysaccharides, e.g. cellulose, starch; fertilizers, e.g. ammonium sulfate, ammonium phosphate, ammonium nitrate, ureas; products of vegetable origin, e.g. cereal meal, tree bark meal, wood meal, nutshell meal, and mixtures thereof.

Suitable surfactants are surface-active compounds, such as anionic, cationic, nonionic and amphoteric surfactants, block polymers, polyelectrolytes, and mixtures thereof. Such surfactants can be used as emusifier, dispersant, solubilizer, wetter, penetration enhancer, protective colloid, or adjuvant. Examples of surfactants are listed in McCutcheon's, Vol. 1: Emulsifiers & Detergents, McCutcheon's Directories, Glen Rock, USA, 2008 (International Ed. or North American Ed.).

Suitable anionic surfactants are alkali, alkaline earth or ammonium salts of sulfonates, sulfates, phosphates, carboxylates, and mixtures thereof. Examples of sulfonates are alkylarylsulfonates, diphenylsulfonates, alpha-olefin sulfonates, lignine sulfonates, sulfonates of fatty acids and oils, sulfonates of ethoxylated alkylphenols, sulfonates of alkoxylated arylphenols, sulfonates of condensed naphthalenes, sulfonates of dodecyl- and tridecylbenzenes, sulfonates of naphthalenes and alkylnaphthalenes, sulfosuccinates or sulfosuccinamates. Examples of sulfates are sulfates of fatty acids and oils, of ethoxylated alkylphenols, of alcohols, of ethoxylated alcohols, or of fatty acid esters. Examples of phosphates are phosphate esters. Examples of carboxylates are alkyl carboxylates, and carboxylated alcohol or alkylphenol ethoxylates.

Suitable nonionic surfactants are alkoxylates, N-substituted fatty acid amides, amine oxides, esters, sugar-based surfactants, polymeric surfactants, and mixtures thereof. Examples of alkoxylates are compounds such as alcohols, alkylphenols, amines, amides, arylphenols, fatty acids or fatty acid esters which have been alkoxylated with 1 to 50 equivalents. Ethylene oxide and/or propylene oxide may be employed for the alkoxylation, preferably ethylene oxide. Examples of N-substituted fatty acid amides are fatty acid glucamides or fatty acid alkanolamides. Examples of esters are fatty acid esters, glycerol esters or monoglycerides. Examples of sugar-based surfactants are sorbitans, ethoxylated sorbitans, sucrose and glucose esters or alkylpolyglucosides. Examples of polymeric surfactants are home- or copolymers of vinylpyrrolidone, vinylalcohols, or vinylacetate.

Suitable cationic surfactants are quaternary surfactants, for example quaternary ammonium compounds with one or two hydrophobic groups, or salts of long-chain primary amines. Suitable amphoteric surfactants are alkylbetains and imidazolines. Suitable block polymers are block polymers of the A-B or A-B-A type comprising blocks of polyethylene oxide and polypropylene oxide, or of the A-B-C type comprising alkanol, polyethylene oxide and polypropylene oxide. Suitable polyelectrolytes are polyacids or polybases. Examples of polyacids are alkali salts of polyacrylic acid or polyacid comb polymers. Examples of polybases are polyvinylamines or polyethyleneamines.

Suitable adjuvants are compounds, which have a neglectable or even no pesticidal activity themselves, and which improve the biological performance of the compound I on the target. Examples are surfactants, mineral or vegetable oils, and other auxilaries. Further examples are listed by Knowles, Adjuvants and additives, Agrow Reports DS256, T&F Informa UK, 2006, chapter 5.

Suitable thickeners are polysaccharides (e.g. xanthan gum, carboxymethylcellulose), anorganic clays (organically modified or unmodified), polycarboxylates, and silicates.

Suitable bactericides are bronopol and isothiazolinone derivatives such as alkylisothiazolinones and benzisothiazolinones.

Suitable anti-freezing agents are ethylene glycol, propylene glycol, urea and glycerin.

Suitable anti-foaming agents are silicones, long chain alcohols, and salts of fatty acids.

Suitable colorants (e.g. in red, blue, or green) are pigments of low water solubility and water-soluble dyes. Examples are inorganic colorants (e.g. iron oxide, titan oxide, iron hexacyanoferrate) and organic colorants (e.g. alizarin-, azo- and phthalocyanine colorants).

Suitable tackifiers or binders are polyvinylpyrrolidons, polyvinylacetates, polyvinyl alcohols, polyacrylates, biological or synthetic waxes, and cellulose ethers.

Examples for composition types and their preparation are:

i) Water-Soluble Concentrates (SL, LS)

10-60 wt % of a compound I according to the invention and 5-15 wt % wetting agent (e.g. alcohol alkoxylates) are dissolved in water and/or in a water-soluble solvent (e.g. alcohols) ad 100 wt %. The active substance dissolves upon dilution with water.

ii) Dispersible Concentrates (DC)

5-25 wt % of a compound I according to the invention and 1-10 wt % dispersant (e.g. polyvinylpyrrolidone) are dissolved in organic solvent (e.g. cyclohexanone) ad 100 wt %. Dilution with water gives a dispersion.

iii) Emulsifiable Concentrates (EC)

15-70 wt % of a compound I according to the invention and 5-10 wt % emulsifiers (e.g. calcium dodecylbenzenesulfonate and castor oil ethoxylate) are dissolved in water-insoluble organic solvent (e.g. aromatic hydrocarbon) ad 100 wt %. Dilution with water gives an emulsion.

iv) Emulsions (EW, EO, ES)

5-40 wt % of a compound I according to the invention and 1-10 wt % emulsifiers (e.g. calcium dodecylbenzenesulfonate and castor oil ethoxylate) are dissolved in 20-40 wt % water-insoluble organic solvent (e.g. aromatic hydrocarbon). This mixture is introduced into water ad 100 wt % by means of an emulsifying machine and made into a homogeneous emulsion. Dilution with water gives an emulsion.

v) Suspensions (SC, OD, FS)

In an agitated ball mill, 20-60 wt % of a compound I according to the invention are comminuted with addition of 2-10 wt % dispersants and wetting agents (e.g. sodium lignosulfonate and alcohol ethoxylate), 0.1-2 wt % thickener (e.g. xanthan gum) and water ad 100 wt % to give a fine active substance suspension. Dilution with water gives a stable suspension of the active substance. For FS type composition up to 40 wt % binder (e.g. polyvinylalcohol) is added.

vi) Water-Dispersible Granules and Water-Soluble Granules (WG, SG)

50-80 wt % of a compound I according to the invention are ground finely with addition of dispersants and wetting agents (e.g. sodium lignosulfonate and alcohol ethoxylate) ad 100 wt % and prepared as water-dispersible or water-soluble granules by means of technical appliances (e.g. extrusion, spray tower, fluidized bed). Dilution with water gives a stable dispersion or solution of the active substance.

vii) Water-Dispersible Powders and Water-Soluble Powders (WP, SP, WS)

50-80 wt % of a compound I according to the invention are ground in a rotor-stator mill with addition of 1-5 wt % dispersants (e.g. sodium lignosulfonate), 1-3 wt % wetting agents (e.g. alcohol ethoxylate) and solid carrier (e.g. silica gel) ad 100 wt %. Dilution with water gives a stable dispersion or solution of the active substance.

viii) Gel (GW, GF)

In an agitated ball mill, 5-25 wt % of a compound I according to the invention are comminuted with addition of 3-10 wt % dispersants (e.g. sodium lignosulfonate), 1-5 wt % thickener (e.g. carboxymethylcellulose) and water ad 100 wt % to give a fine suspension of the active substance. Dilution with water gives a stable suspension of the active substance.

iv) Microemulsion (ME)

5-20 wt % of a compound I according to the invention are added to 5-30 wt % organic solvent blend (e.g. fatty acid dimethylamide and cyclohexanone), 10-25 wt % surfactant blend (e.g. alkohol ethoxylate and arylphenol ethoxylate), and water ad 100%. This mixture is stirred for 1 h to produce spontaneously a thermodynamically stable microemulsion.

iv) Microcapsules (CS)

An oil phase comprising 5-50 wt % of a compound I according to the invention, 0-40 wt % water insoluble organic solvent (e.g. aromatic hydrocarbon), 2-15 wt % acrylic monomers (e.g. methylmethacrylate, methacrylic acid and a di- or triacrylate) are dispersed into an aqueous solution of a protective colloid (e.g. polyvinyl alcohol). Radical polymerization initiated by a radical initiator results in the formation of poly(meth)acrylate microcapsules. Alternatively, an oil phase comprising 5-50 wt % of a compound I according to the invention, 0-40 wt % water insoluble organic solvent (e.g. aromatic hydrocarbon), and an isocyanate monomer (e.g. diphenylmethene-4,4'-diisocyanatae) are dispersed into an aqueous solution of a protective colloid (e.g. polyvinyl alcohol). The addition of a polyamine (e.g. hexamethylenediamine) results in the formation of a polyurea microcapsules. The monomers amount to 1-10 wt %. The wt % relate to the total CS composition.

ix) Dustable Powders (DP, DS)

1-10 wt % of a compound I according to the invention are ground finely and mixed intimately with solid carrier (e.g. finely divided kaolin) ad 100 wt %.

x) Granules (GR, FG)

0.5-30 wt % of a compound I according to the invention is ground finely and associated with solid carrier (e.g. silicate) ad 100 wt %. Granulation is achieved by extrusion, spray-drying or the fluidized bed.

xi) Ultra-Low Volume Liquids (UL)

1-50 wt % of a compound I according to the invention are dissolved in organic solvent (e.g. aromatic hydrocarbon) ad 100 wt %.

The compositions types i) to xi) may optionally comprise further auxiliaries, such as 0.1-1 wt % bactericides, 5-15 wt % anti-freezing agents, 0.1-1 wt % anti-foaming agents, and 0.1-1 wt % colorants.

The agrochemical compositions generally comprise between 0.01 and 95%, preferably between 0.1 and 90%, and in particular between 0.5 and 75%, by weight of active substance. The active substances are employed in a purity of from 90% to 100%, preferably from 95% to 100% (according to NMR spectrum).

Solutions for seed treatment (LS), Suspoemulsions (SE), flowable concentrates (FS), powders for dry treatment (DS), water-dispersible powders for slurry treatment (WS), water-soluble powders (SS), emulsions (ES), emulsifiable concentrates (EC) and gels (GF) are usually employed for the purposes of treatment of plant propagation materials, particularly seeds. The compositions in question give, after two-to-tenfold dilution, active substance concentrations of from 0.01 to 60% by weight, preferably from 0.1 to 40% by weight, in the ready-to-use preparations. Application can be carried out before or during sowing. Methods for applying compound I and compositions thereof, respectively, on to plant propagation material, especially seeds include dressing, coating, pelleting, dusting, soaking and in-furrow application methods of the propagation material. Preferably, compound I or the compositions thereof, respectively, are applied on to the plant propagation material by a method such that germination is not induced, e.g. by seed dressing, pelleting, coating and dusting.

When employed in plant protection, the amounts of active substances applied are, depending on the kind of effect desired, from 0.001 to 2 kg per ha, preferably from 0.005 to 2 kg per ha, more preferably from 0.05 to 0.9 kg per ha, and in particular from 0.1 to 0.75 kg per ha.

In treatment of plant propagation materials such as seeds, e.g. by dusting, coating or drenching seed, amounts of active substance of from 0.1 to 1000 g, preferably from 1 to 1000 g, more preferably from 1 to 100 g and most preferably from 5 to 100 g, per 100 kilogram of plant propagation material (preferably seeds) are generally required.

When used in the protection of materials or stored products, the amount of active substance applied depends on the kind of application area and on the desired effect. Amounts customarily applied in the protection of materials are 0.001 g to 2 kg, preferably 0.005 g to 1 kg, of active substance per cubic meter of treated material.

Various types of oils, wetters, adjuvants, fertilizer, or micronutrients, and further pesticides (e.g. herbicides, insecticides, fungicides, growth regulators, safeners) may be added to the active substances or the compositions comprising them as premix or, if appropriate not until immediately prior to use (tank mix). These agents can be admixed with the compositions according to the invention in a weight ratio of 1:100 to 100:1, preferably 1:10 to 10:1.

The user applies the composition according to the invention usually from a predosage device, a knapsack sprayer, a spray tank, a spray plane, or an irrigation system. Usually, the agrochemical composition is made up with water, buffer, and/or further auxiliaries to the desired application concentration and the ready-to-use spray liquor or the agrochemical composition according to the invention is thus obtained. Usually, 20 to 2000 liters, preferably 50 to 400 liters, of the ready-to-use spray liquor are applied per hectare of agricultural useful area.

According to one embodiment, individual components of the composition according to the invention such as parts of a kit or parts of a binary or ternary mixture may be mixed by the user himself in a spray tank and further auxiliaries may be added, if appropriate.

In a further embodiment, either individual components of the composition according to the invention or partially premixed components, e.g. components comprising compounds I and/or active substances from the groups M) or F) (see below), may be mixed by the user in a spray tank and further auxiliaries and additives may be added, if appropriate.

In a further embodiment, either individual components of the composition according to the invention or partially premixed components, e. g. components comprising compounds I and/or active substances from the groups M.1 to M.UN.X or F.I to F.XII, can be applied jointly (e.g. after tank mix) or consecutively.

The following list M of pesticides, grouped according the Mode of Action Classification of the Insecticide Resistance Action Committee (IRAC), together with which the compounds according to the invention can be used and with which potential synergistic effects might be produced, is intended to illustrate the possible combinations, but not to impose any limitation:

M.1 Acetylcholine esterase (AChE) inhibitors from the class of

M.1A carbamates, for example aldicarb, alanycarb, bendiocarb, benfuracarb, butocarboxim, butoxycarboxim, carbaryl, carbofuran, carbosulfan, ethiofencarb, fenobucarb, formetanate, furathiocarb, isoprocarb, methiocarb, methomyl, metolcarb, oxamyl, pirimicarb, propoxur, thiodicarb, thiofanox, trimethacarb, XMC, xylylcarb and triazamate; or from the class of M.1B organophosphates, for example acephate, azamethiphos, azinphos-ethyl, azinphosmethyl, cadusafos, chlorethoxyfos, chlorfenvinphos, chlormephos, chlorpyrifos, chlorpyrifos-methyl, coumaphos, cyanophos, demeton-S-methyl, diazinon, dichlorvos/DDVP, dicrotophos, dimethoate, dimethylvinphos, disulfoton, EPN, ethion, ethoprophos, famphur, fenamiphos, fenitrothion, fenthion, fosthiazate, heptenophos, imicyafos, isofenphos, isopropyl O-(methoxyaminothio-phosphoryl) salicylate, isoxathion, malathion, mecarbam, methamidophos, methidathion, mevinphos, monocrotophos, naled, omethoate, oxydemeton-methyl, parathion, parathion-methyl, phenthoate, phorate, phosalone, phosmet, phosphamidon, phoxim, pirimiphos-methyl, profenofos, propetamphos, prothiofos, pyraclofos, pyridaphenthion, quinalphos, sulfotep, tebupirimfos, temephos, terbufos, tetrachlorvinphos, thiometon, triazophos, trichlorfon and vamidothion;

M.2. GABA-gated chloride channel antagonists such as:

M.2A cyclodiene organochlorine compounds, as for example endosulfan or chlordane; or M.2B fiproles (phenylpyrazoles), as for example ethiprole, fipronil, flufiprole, pyrafluprole and pyriprole;

M.3 Sodium channel modulators from the class of

M.3A pyrethroids, for example acrinathrin, allethrin, d-cis-trans allethrin, d-trans allethrin, bifenthrin, bioallethrin, bioallethrin S-cylclopentenyl, bioresmethrin, cycloprothrin, cyfluthrin, beta-cyfluthrin, cyhalothrin, lambda-cyhalothrin, gammacyhalothrin, cypermethrin, alpha-cypermethrin, beta-cypermethrin, theta-cypermethrin, zeta-cypermethrin, cyphenothrin, deltamethrin, empenthrin, esfenvalerate, etofenprox, fenpropathrin, fenvalerate, flucythrinate, flumethrin, tau-fluvalinate, halfenprox, imiprothrin, meperfluthrin, metofluthrin, momfluorothrin, permethrin, phenothrin, prallethrin, profluthrin, pyrethrin (pyrethrum), resmethrin, silafluofen, tefluthrin, tetramethylfluthrin, tetramethrin, tralomethrin and transfluthrin; or M.3B sodium channel modulators such as DDT or methoxychlor;

M.4 Nicotinic acetylcholine receptor agonists (nAChR) from the class of

M.4A neonicotinoids, for example acteamiprid, chlothianidin, dinotefuran, imidacloprid, nitenpyram, thiacloprid and thiamethoxam; or the compounds M.4A.1: 1-[(6-chloro-3-pyridinyl)methyl]-2,3,5,6,7,8-hexahydro-9-nitro-(5S,8R)-5,8-Epoxy-1H-imidazo[1,2-a]azepine; or M.4A.2: 1-[(6-chloro-3-pyridyl)methyl]-2-nitro-1-[(E)-pentylideneamino]guanidine; or M4.A.3: 1-[(6-chloro-3-pyridyl)methyl]-7-methyl-8-nitro-5-propoxy-3,5,6,7-tetrahydro-2H-imidazo[1,2-a]pyridine;

or M.4B nicotine.

M.5 Nicotinic acetylcholine receptor allosteric activators from the class of spinosyns, for example spinosad or spinetoram;

M.6 Chloride channel activators from the class of avermectins and milbemycins, for example abamectin, emamectin benzoate, ivermectin, lepimectin or milbemectin;

M.7 Juvenile hormone mimics, such as

M.7A juvenile hormone analogues as hydroprene, kinoprene and methoprene; or others as M.7B fenoxycarb or M.7C pyriproxyfen;

M.8 miscellaneous non-specific (multi-site) inhibitors, for example

M.8A alkyl halides as methyl bromide and other alkyl halides, or

M.8B chloropicrin, or M.8C sulfuryl fluoride, or M.8D borax, or M.8E tartar emetic;

M.9 Selective homopteran feeding blockers, for example

M.9B pymetrozine, or M.9C flonicamid;

M.10 Mite growth inhibitors, for example

M.10A clofentezine, hexythiazox and diflovidazin, or M.10B etoxazole;

M.11 Microbial disruptors of insect midgut membranes, for example *bacillus thuringiensis* or *bacillus sphaericus* and the insecticdal proteins they produce such as *bacillus thuringiensis* subsp. *israelensis, bacillus sphaericus, bacillus thuringiensis* subsp. *aizawai, bacillus thuringiensis* subsp. *kurstaki* and *bacillus thuringiensis* subsp. *tenebrionis*, or the Bt crop proteins: Cry1Ab, Cry1Ac, Cry1Fa, Cry2Ab, mCry3A, Cry3Ab, Cry3Bb and Cry34/35Ab1;

M.12 Inhibitors of mitochondrial ATP synthase, for example M.12A diafenthiuron, or M.12B organotin miticides such as azocyclotin, cyhexatin or fenbutatin oxide, or M.12C propargite, or M.12D tetradifon;

M.13 Uncouplers of oxidative phosphorylation via disruption of the proton gradient, for example chlorfenapyr, DNOC or sulfluramid;

M.14 Nicotinic acetylcholine receptor (nAChR) channel blockers, for example nereistoxin analogues as bensultap, cartap hydrochloride, thiocyclam or thiosultap sodium;

M.15 Inhibitors of the chitin biosynthesis type 0, such as benzoylureas as for example bistrifluron, chlorfluazuron, diflubenzuron, flucycloxuron, flufenoxuron, hexaflumuron, lufenuron, novaluron, noviflumuron, teflubenzuron or triflumuron;

M.16 Inhibitors of the chitin biosynthesis type 1, as for example buprofezin;

M.17 Moulting disruptors, Dipteran, as for example cyromazine;

M.18 Ecdyson receptor agonists such as diacylhydrazines, for example methoxyfenozide, tebufenozide, halofenozide, fufenozide or chromafenozide;

M.19 Octopamin receptor agonists, as for example amitraz;

M.20 Mitochondrial complex III electron transport inhibitors, for example

M.20A hydramethylnon, or M.20B acequinocyl, or M.20C fluacrypyrim;

M.21 Mitochondrial complex I electron transport inhibitors, for example

M.21A METI acaricides and insecticides such as fenazaquin, fenpyroximate, pyrimidifen, pyridaben, tebufenpyrad or tolfenpyrad, or M.21B rotenone;

M.22 Voltage-dependent sodium channel blockers, for example

M.22A indoxacarb, or M.22B metaflumizone, or M.22C 1-[(E)-[2-(4-cyanophenyl)-1-[3-(trifluoromethyl)phenyl]ethylidene]amino]-3-[4-(difluoromethoxy)phenyl]urea;

M.23 Inhibitors of the of acetyl CoA carboxylase, such as Tetronic and Tetramic acid derivatives, for example spirodiclofen, spiromesifen or spirotetramat;

M.24 Mitochondrial complex IV electron transport inhibitors, for example

M.24A phosphine such as aluminium phosphide, calcium phosphide, phosphine or zinc phosphide, or M.24B cyanide.

M.25 Mitochondrial complex II electron transport inhibitors, such as beta-ketonitrile derivatives, for example cyenopyrafen or cyflumetofen;

M.28 Ryanodine receptor-modulators from the class of diamides, as for example flubendiamide, chlorantraniliprole (Rynaxypyr®), cyantraniliprole (Cyazypyr®), or the phthalamide compounds M.28.1: (R)-3-Chlor-N1-{2-methyl-4-[1,2,2,2-tetrafluor-1-(trifluormethyl)ethyl]phenyl}-N2-(1-methyl-2-methylsulfonylethyl)phthalamid and M.28.2: (S)-3-Chlor-N1-{2-methyl-4-[1,2,2,2-tetrafluor-1-(trifluormethyl)ethyl]phenyl}-N2-(1-methyl-2-methylsulfonylethyl)phthalamid, or the compound M.28.3: 3-bromo-N-{2-bromo-4-chloro-6-[(1-cyclopropylethyl)carbamoyl]phenyl}-1-(3-chlorpyridin-2-yl)-1H-pyrazole-5-carboxamide (proposed ISO name: cyclaniliprole), or the compound M.28.4: methyl-2-[3,5-dibromo-2-({[3-bromo-1-(3-chlorpyridin-2-yl)-1H-pyrazol-5-yl]carbonyl}amino)benzoyl]-1,2-dimethylhydrazinecarboxylate; or a compound selected from M.28.5a) to M.28.5l):

M.28.5a) N-[4,6-dichloro-2-[(diethyl-lambda-4-sulfanylidene)carbamoyl]-phenyl]-2-(3-chloro-2-pyridyl)-5-(trifluoromethyl)pyrazole-3-carboxamide;

M.28.5b) N-[4-chloro-2-[(diethyl-lambda-4-sulfanylidene)carbamoyl]-6-methyl-phenyl]-2-(3-chloro-2-pyridyl)-5-(trifluoromethyl)pyrazole-3-carboxamide;

M.28.5c) N-[4-chloro-2-[(di-2-propyl-lambda-4-sulfanylidene)carbamoyl]-6-methyl-phenyl]-2-(3-chloro-2-pyridyl)-5-(trifluoromethyl)pyrazole-3-carboxamide;

M.28.5d) N-[4,6-dichloro-2-[(di-2-propyl-lambda-4-sulfanylidene)carbamoyl]-phenyl]-2-(3-chloro-2-pyridyl)-5-(trifluoromethyl)pyrazole-3-carboxamide;

M.28.5e) N-[4,6-dichloro-2-[(diethyl-lambda-4-sulfanylidene)carbamoyl]-phenyl]-2-(3-chloro-2-pyridyl)-5-(difluoromethyl)pyrazole-3-carboxamide;

M.28.5f) N-[4,6-dibromo-2-[(di-2-propyl-lambda-4-sulfanylidene)carbamoyl]-phenyl]-2-(3-chloro-2-pyridyl)-5-(trifluoromethyl)pyrazole-3-carboxamide;

M.28.5g) N-[4-chloro-2-[(di-2-propyl-lambda-4-sulfanylidene)carbamoyl]-6-cyano-phenyl]-2-(3-chloro-2-pyridyl)-5-(trifluoromethyl)pyrazole-3-carboxamide;

M.28.5h) N-[4,6-dibromo-2-[(diethyl-lambda-4-sulfanylidene)carbamoyl]-phenyl]-2-(3-chloro-2-pyridyl)-5-(trifluoromethyl)pyrazole-3-carboxamide;

M.28.5i) N-[2-(5-amino-1,3,4-thiadiazol-2-yl)-4-chloro-6-methyl-phenyl]-5-bromo-2-(3-chloro-2-pyridyl)pyrazole-3-carboxamide;

M.28.5j) 5-chloro-2-(3-chloro-2-pyridyl)-N-[2,4-dichloro-6-[(1-cyano-1-methyl-ethyl)carbamoyl]phenyl]pyrazole-3-carboxamide;

M.28.5k) 5-bromo-N-[2,4-dichloro-6-(methylcarbamoyl)phenyl]-2-(3,5-dichloro-2-pyridyl)pyrazole-3-carboxamide;

M.28.5l) N-[2-(tert-butylcarbamoyl)-4-chloro-6-methyl-phenyl]-2-(3-chloro-2-pyridyl)-5-(fluoromethoxy)pyrazole-3-carboxamide; or a compound selected from M.28.6 N2-(1-cyano-1-methyl-ethyl)-N1-(2,4-dimethylphenyl)-3-iodo-phthalamide; or M.28.7 3-chloro-N2-(1-cyano-1-methyl-ethyl)-N1-(2,4-dimethylphenyl)phthalamide;

M.UN.X insecticidal active compounds of unknown or uncertain mode of action, as for example afidopyropen, azadirachtin, amidoflumet, benzoximate, bifenazate, bromopropylate, chinomethionat, cryolite, dicofol, flufenerim, flometoquin, fluensulfone, flupyradifurone, piperonyl butoxide, pyridalyl, pyrifluquinazon, sulfoxaflor, pyflubumide or the compounds M.UN.X.1: 4-[5-(3,5-Dichloro-phenyl)-5-trifluoromethyl-4,5-dihydro-isoxazol-3-yl]-2-methyl-N-[(2,2,2-trifluoroethylcarbamoyl)-methyl]-benzamide, or the compound M.UN.X.2: 4-[5-[3-chloro-5-(trifluoromethyl)phenyl]-5-(trifluoromethyl)-4H-isoxazol-3-yl]-N-[2-oxo-2-(2,2,2-trifluoroethylamino)ethyl]naphthalene-1-carboxamide, or the compound M.UN.X.3: 11-(4-chloro-2,6-dimethylphenyl)-12-hydroxy-1,4-dioxa-9-azadispiro[4.2.4.2]-tetradec-11-en-10-one, or the compound M.UN.X.4: 3-(4'-fluoro-2,4-dimethylbiphenyl-3-yl)-4-hydroxy-8-oxa-1-azaspiro[4.5]dec-3-en-2-one, or the compound M.UN.X.5: 1-[2-fluoro-4-methyl-5-[(2,2,2-trifluoroethyl)sulfinyl]phenyl]-3-(trifluoromethyl)-1H-1,2,4-triazole-5-amine, or actives on basis of *bacillus firmus* (Votivo, 1-1582); or M.UN.X.6; a compound selected from the group of M.UN.X.6a) (E/Z)—N-[1-[(6-chloro-3-pyridyl)methyl]-2-pyridylidene]-2,2,2-trifluoro-acetamide;

M.UN.X.6b) (E/Z)—N-[1-[(6-chloro-5-fluoro-3-pyridyl)methyl]-2-pyridylidene]-2,2,2-trifluoro-acetamide;

M.UN.X.6c) (E/Z)-2,2,2-trifluoro-N-[1-[(6-fluoro-3-pyridyl)methyl]-2-pyridylidene]acetamide;

M.UN.X.6d) (E/Z)—N-[1-[(6-bromo-3-pyridyl)methyl]-2-pyridylidene]-2,2,2-trifluoro-acetamide;

M.UN.X.6e) (E/Z)—N-[1-[1-(6-chloro-3-pyridyl)ethyl]-2-pyridylidene]-2,2,2-trifluoro-acetamide;

M.UN.X.6f) (E/Z)—N-[1-[(6-chloro-3-pyridyl)methyl]-2-pyridylidene]-2,2-difluoroacetamide;

M.UN.X.6g) (E/Z)-2-chloro-N-[1-[(6-chloro-3-pyridyl)methyl]-2-pyridylidene]-2,2-difluoroacetamide;

M.UN.X.6h) (E/Z)—N-[1-[(2-chloropyrimidin-5-yl)methyl]-2-pyridylidene]-2,2,2-trifluoroacetamide and M.UN.X.6i) (E/Z)—N-[1-[(6-chloro-3-pyridyl)methyl]-2-pyridylidene]-2,2,3,3,3-pentafluoropropanamide.); or of the compounds M.UN.X.7: 3-[3-chloro-5-(trifluoromethyl)phenyl]-4-oxo-1-(pyrimidin-5-ylmethyl)pyrido[1,2-a]pyrimidin-1-ium-2-olate; or M.UN.X.8: 8-chloro-N-[2-chloro-5-methoxyphenyl)sulfonyl]-6-trifluoromethyl)imidazo[1,2-a]pyridine-2-carboxamide; or M.UN.X.9: 4-[5-(3,5-dichlorophenyl)-5-(trifluoromethyl)-4H-isoxazol-3-yl]-2-methyl-N-(1-oxothietan-3-yl)benzamide; or M.UN.X.10: 5-[3-[2,6-dichloro-4-(3,3-dichloroallyloxy)phenoxy]propoxy]-1H-pyrazole.

The commercially available compounds of the group M listed above may be found in The Pesticide Manual, 15th Edition, C. D. S. Tomlin, British Crop Protection Council (2011) among other publications.

The quinoline derivative flometoquin is shown in WO2006/013896. The aminofuranone compounds flupyradifurone is known from WO 2007/115644. The sulfoximine compound sulfoxaflor is known from WO2007/149134. The pyrethroid momfluorothrin is known from U.S. Pat. No. 6,908,945. The pyrazole acaricide pyflubumide is known from WO2007/020986. The isoxazoline compounds have been described likewise M.UN.X.1 in WO2005/085216, M.UN.X.2 in WO2009/002809 and in WO2011/149749 and the isoxazoline M.UN.X.9 in WO2013/050317. The pyripyropene derivative afidopyropen has been described in WO 2006/129714. The spiroketal-substituted cyclic ketoenol derivative M.UN.X.3 is known from WO2006/089633 and the biphenyl-substituted spirocyclic ketoenol derivative M.UN.X.4 from WO2008/067911. Finally triazoylphenylsulfide like M.UN.X.5 have been described in WO2006/043635 and biological control agents on basis of *bacillus firmus* in WO2009/124707. The neonicotionids 4A.1 is known from WO20120/069266 and WO2011/06946, the M.4.A.2 from WO2013/003977, the M4.A.3. from WO2010/069266.

The Metaflumizone analogue M.22C is described in CN 10171577. The phthalamides M.28.1 and M.28.2 are both known from WO 2007/101540. The anthranilamide M.28.3 has been described in WO2005/077934. The hydrazide compound M.28.4 has been described in WO 2007/043677. The anthranilamides M.28.5a) to M.28.5h) can be prepared as described in WO 2007/006670, WO2013/024009 and WO2013/024010, the anthranilamide M.28.5i is described in WO2011/085575, the M.28.5j) in WO2008/134969, the M.28.5k) in US2011/046186 and the M.28.51) in WO2012/034403. The diamide compounds M.28.6 and M.28.7 can be found in CN102613183.

The compounds M.UN.X.6a) to M.UN.X.6i) listed in M.UN.X.6 have been described in WO2012/029672. The mesoionic antagonist compound M.UN.X.7 was described in WO2012/092115, the nematicide M.UN.X.8 in WO2013/055584 and the Pyridalyl-type analogue M.UN.X.10 in WO2010/060379.

The following list F of active substances, in conjunction with which the compounds according to the invention can be used, is intended to illustrate the possible combinations but does not limit them:

F.I) Respiration Inhibitors

F.I-1) Inhibitors of complex III at Qo site:

strobilurins: azoxystrobin, coumethoxystrobin, coumoxystrobin, dimoxystrobin, enestroburin, fluoxastrobin, kresoxim-methyl, metominostrobin, orysastrobin, picoxystrobin, pyraclostrobin, pyrametostrobin, pyraoxystrobin, pyribencarb, triclopyricarb/chlorodincarb, trifloxystrobin, 2-[2-(2,5-dimethyl-phenoxymethyl)-phenyl]-3-methoxyacrylic acid methyl ester and 2 (2-(3-(2,6-dichlorophenyl)-1-methyl-allylideneaminooxymethyl)-phenyl)-2-methoxyimino-N methyl-acetamide;

oxazolidinediones and imidazolinones: famoxadone, fenamidone;

F.I-2) Inhibitors of complex II (e.g. carboxamides):

carboxanilides: benodanil, benzovindiflupyr, bixafen, boscalid, carboxin, fenfuram, fenhexamid, fluopyram, flutolanil, furametpyr, isopyrazam, isotianil, mepronil, oxycarboxin, penflufen, penthiopyrad, sedaxane, tecloftalam, thifluzamide, tiadinil, 2-amino-4 methyl-thiazole-5-carboxanilide, N-(3',4',5' trifluorobiphenyl-2 yl)-3-difluoromethyl-1-methyl-1H-pyrazole-4 carboxamide (fluxapyroxad), N-(4'-trifluoromethylthiobiphenyl-2-yl)-3 difluoromethyl-1-methyl-1H pyrazole-4-carboxamide, N-(2-(1,3,3-trimethyl-butyl)-phenyl)-1,3-dimethyl-5 fluoro-1H-pyrazole-4 carboxamide, 3-(difluoromethyl)-1-methyl-N-(1,1,3-trimethylindan-4-yl)pyrazole-4-carboxamide, 3-(trifluoromethyl)-1-methyl-N-(1,1,3-trimethylindan-4-yl)pyrazole-4-carboxamide, 1,3-dimethyl-N-(1,1,3-trimethylindan-4-yl)pyrazole-4-carboxamide, 3-(trifluoromethyl)-1,5-dimethyl-N-(1,1,3-trimethylindan-4-yl)pyrazole-4-carboxamide, 3-(difluoromethyl)-1,5-dimethyl-N-(1,1,3-trimethylindan-4-yl)pyrazole-4-carboxamide, 1,3,5-trimethyl-N-(1,1,3-trimethylindan-4-yl)pyrazole-4-carboxamide, 3-(difluoromethyl)-1-methyl-N-(1,1,3-trimethylindan-4-yl)pyrazole-4-carboxamide, 3-(trifluoromethyl)-1-methyl-N-(1,1,3-trimethylindan-4-yl)pyrazole-4-carboxamide, 1,3-dimethyl-N-(1,1,3-trimethylindan-4-yl)pyrazole-4-carboxamide, 3-(trifluoromethyl)-1,5-dimethyl-N-(1,1,3-trimethylindan-4-yl)pyrazole-4-carboxamide, 3-(difluoromethyl)-1,5-dimethyl-N-(1,1,3-trimethylindan-4-yl)pyrazole-4-carboxamide, 1,3,5-trimethyl-N-(1,1,3-trimethylindan-4-yl)pyrazole-4-carboxamide;

F.I-3) Inhibitors of complex III at Qi site: cyazofamid, amisulbrom, [(3S,6S,7R,8R)-8-benzyl-3-[(3-acetoxy-4-methoxy-pyridine-2-carbonyl)amino]-6-methyl-4,9-dioxo-1,5-dioxonan-7-yl]2-methylpropanoate, [(3S,6S,7R,8R)-8-benzyl-3-[[3-(acetoxymethoxy)-4-methoxy-pyridine-2-carbonyl]amino]-6-methyl-4,9-dioxo-1,5-dioxonan-7-yl]2-methylpropanoate, [(3S,6S,7R,8R)-8-benzyl-3-[(3-isobutoxycarbonyloxy-4-methoxy-pyridine-2-carbonyl) amino]-6-methyl-4,9-dioxo-1,5-dioxonan-7-yl]2-methylpropanoate, [(3S,6S,7R,8R)-8-benzyl-3-[[3-(1,3-benzodioxol-5-ylmethoxy)-4-methoxy-pyridine-2-carbonyl]amino]-6-methyl-4,9-dioxo-1,5-dioxonan-7-yl]2-methylpropanoate, 3S,6S,7R,8R)-3-[[(3-hydroxy-4-methoxy-2-pyridinyl)carbonyl]amino]-6-methyl-4,9-dioxo-8-(phenylmethyl)-1,5-dioxonan-7-yl 2-methylpropanoate;

F.I-4) Other respiration inhibitors (complex I, uncouplers) diflumetorim; (5,8-difluoroquinazolin-4-yl)-{2-[2-fluoro-4-(4-trifluoromethylpyridin-2-yloxy)-phenyl]-ethyl}-amine; tecnazen; ametoctradin; silthiofam; nitrophenyl derivates: binapacryl, dinobuton, dinocap, fluazinam, ferimzone, nitrthal-isopropyl, and including organometal compounds: fentin salts, such as fentin-acetate, fentin chloride or fentin hydroxide;

F.II) Sterol biosynthesis inhibitors (SBI fungicides)

F.II-1) C14 demethylase inhibitors (DMI fungicides, e.g. triazoles, imidazoles) triazoles: azaconazole, bitertanol, bromuconazole, cyproconazole, difenoconazole, diniconazole, diniconazole-M, epoxiconazole, fenbuconazole, fluquinconazole, flusilazole, flutriafol, hexaconazole, imibenconazole, ipconazole, metconazole, myclobutanil, paclobutrazole, penconazole, propiconazole, prothioconazole, simeconazole, tebuconazole, tetraconazole, triadimefon, triadimenol, triticonazole, uniconazole, 1-[rel-(2S;3R)-3-(2-chlorophenyl)-2-(2,4-difluorophenyl)-oxiranylmethyl]-5-thiocyanato-1H-[1,2,4]triazole, 2-[rel-(2S;3R)-3-(2-chlorophenyl)-2-(2,4-difluorophenyl)-oxiranylmethyl]-2H-[1,2,4]triazole-3-thiol;

imidazoles: imazalil, pefurazoate, oxpoconazole, prochloraz, triflumizole;

pyrimidines, pyridines and piperazines: fenarimol, nuarimol, pyrifenox, triforine, 1-[rel-(2S;3R)-3-(2-chlorophenyl)-2-(2,4-difluorophenyl)-oxiranylmethyl]-5-thiocyanato-1H-[1,2,4]triazole, 2-[rel-(2S;3R)-3-(2-chlorophenyl)-2-(2,4-difluorophenyl)oxiranylmethyl]-2H-[1,2,4]triazole-3-thiol;

F.II-2) Delta14-reductase inhitors (Amines, e.g. morpholines, piperidines)

morpholines: aldimorph, dodemorph, dodemorph-acetate, fenpropimorph, tridemorph;

piperidines: fenpropidin, piperalin; spiroketalamines: spiroxamine;

F.II-3) Inhibitors of 3-keto reductase: hydroxyanilides: fenhexamid;

F.III) Nucleic acid synthesis inhibitors

F.III-1) RNA, DNA synthesis phenylamides or acyl amino acid fungicides: benalaxyl, benalaxyl-M, kiralaxyl, metalaxyl, metalaxyl-M (mefenoxam), ofurace, oxadixyl;

isoxazoles and iosothiazolones: hymexazole, octhilinone;

F.III-2) DNA topisomerase inhibitors: oxolinic acid;

F.III-3) Nucleotide metabolism (e.g. adenosin-deaminase), hydroxy(2-amino)pyrimidines: bupirimate;

F.IV) Inhibitors of cell division and or cytoskeleton

F.IV-1) Tubulin inhibitors: benzimidazoles and thiophanates: benomyl, carbendazim, fuberidazole, thiabendazole, thiophanate-methyl;

triazolopyrimidines: 5-chloro-7 (4-methylpiperidin-1-yl)-6-(2,4,6-trifluorophenyl)[1,2,4]triazolo[1,5a]pyrimidine;

F.IV-2) Other cell division inhibitors benzamides and phenyl acetamides: diethofencarb, ethaboxam, pencycuron, fluopicolide, zoxamide;

F.IV-3) Actin inhibitors: benzophenones: metrafenone, pyriofenone;

F.V) Inhibitors of amino acid and protein synthesis

F.V-1) Methionine synthesis inhibitors (anilino-pyrimidines)

anilino-pyrimidines: cyprodinil, mepanipyrim, nitrapyrin, pyrimethanil;

F.V-2) Protein synthesis inhibitors (anilino-pyrimidines)

antibiotics: blasticidin-S, kasugamycin, kasugamycin hydrochloride-hydrate, mildiomycin, streptomycin, oxytetracyclin, polyoxine, validamycin A;

F.VI) Signal transduction inhibitors

F.VI-1) MAP/Histidine kinase inhibitors (e.g. anilino-pyrimidines)

dicarboximides: fluoroimid, iprodione, procymidone, vinclozolin;

phenylpyrroles: fenpiclonil, fludioxonil;

F.VI-2) G protein inhibitors: quinolines: quinoxyfen;

F.VII) Lipid and membrane synthesis inhibitors

F.VII-1) Phospholipid biosynthesis inhibitors organophosphorus compounds: edifenphos, iprobenfos, pyrazophos;

dithiolanes: isoprothiolane;

F.VII-2) Lipid peroxidation: aromatic hydrocarbons: dicloran, quintozene, tecnazene, tolclofos-methyl, biphenyl, chloroneb, etridiazole;

F.VII-3) Carboxyl acid amides (CAA fungicides)

cinnamic or mandelic acid amides: dimethomorph, flumorph, mandiproamid, pyrimorph;

valinamide carbamates: benthiavalicarb, iprovalicarb, pyribencarb, valifenalate and N-(1-(1-(4-cyano-phenyl)ethanesulfonyl)-but-2-yl) carbamic acid-(4-fluorophenyl) ester;

F.VII-4) Compounds affecting cell membrane permeability and fatty acids:

1-[4-[4-[5-(2,6-difluorophenyl)-4,5-dihydro-3-isoxazolyl]-2-thiazolyl]-1-piperidinyl]-2-[5-methyl-3-(trifluoromethyl)-1H-pyrazol-1-yl]ethanone, carbamates: propamocarb, propamocarb-hydrochlorid, F.VII-5) fatty acid amide hydrolase inhibitors: 1-[4-[4-[5-(2,6-difluorophenyl)-4,5-dihydro-3-isoxazolyl]-2-thiazolyl]-1-piperidinyl]-2-[5-methyl-3-(trifluoromethyl)-1H-pyrazol-1-yl]ethanone;

F.VIII) Inhibitors with Multi Site Action

F.VIII-1) Inorganic active substances: Bordeaux mixture, copper acetate, copper hydroxide, copper oxychloride, basic copper sulfate, sulfur;

F.VIII-2) Thio- and dithiocarbamates: ferbam, mancozeb, maneb, metam, methasulphocarb, metiram, propineb, thiram, zineb, ziram;

F.VIII-3) Organochlorine compounds (e.g. phthalimides, sulfamides, chloronitriles):

anilazine, chlorothalonil, captafol, captan, folpet, dichlofluanid, dichlorophen, flusulfamide, hexachlorobenzene, pentachlorphenole and its salts, phthalide, tolylfluanid, N-(4-chloro-2-nitro-phenyl)-N-ethyl-4-methyl-benzenesulfonamide;

F.VIII-4) Guanidines and other: guanidine, dodine, dodine free base, guazatine, guazatine-acetate, iminoctadine, iminoctadine-triacetate, iminoctadine-tris(albesilate), 2,6-dimethyl-1H,5H-[1,4]dithiino[2,3-c:5,6-c']dipyrrole-1,3,5,7(2H,6H)-tetraone;

F.VIII-5) Ahtraquinones: dithianon;

F.IX) Cell wall synthesis inhibitors

F.IX-1) Inhibitors of glucan synthesis: validamycin, polyoxin B;

F.IX-2) Melanin synthesis inhibitors: pyroquilon, tricyclazole, carpropamide, dicyclomet, fenoxanil;

F.X) Plant defense inducers

F.X-1) Salicylic acid pathway: acibenzolar-S-methyl;

F.X-2) Others: probenazole, isotianil, tiadinil, prohexadione-calcium;

phosphonates: fosetyl, fosetyl-aluminum, phosphorous acid and its salts;

F.XI) Unknown mode of action:bronopol, chinomethionat, cyflufenamid, cymoxanil, dazomet, debacarb, diclomezine, difenzoquat, difenzoquat-methylsulfate, diphenylamin, fenpyrazamine, flumetover, flusulfamide, flutianil, methasulfocarb, nitrapyrin, nitrothal-isopropyl, oxathiapiprolin, oxin-copper, proquinazid, tebufloquin, tecloftalam, triazoxide, 2-butoxy-6-iodo-3-propylchromen-4-one, N-(cyclopropylmethoxyimino-(6-difluoro-methoxy-2,3-difluoro-phenyl)-methyl)-2-phenyl acetamide, N'-(4-(4-chloro-3-trifluoromethyl-phenoxy)-2,5-dimethyl-phenyl)-N-ethyl-N methyl formamidine, N'(4-(4-fluoro-3-trifluoromethyl-phenoxy)-2,5-dimethyl-phenyl)-N-ethyl-N-methyl formamidine, N'-(2-methyl-5-trifluoromethyl-4-(3-trimethylsilanyl-propoxy)-phenyl)-N-ethyl-N-methyl formamidine, N'-(5-difluoromethyl-2 methyl-4-(3-trimethylsilanyl-propoxy)-phenyl)-N-ethyl-N-methyl formamidine, 2-{1-[2-(5-methyl-3-trifluoromethyl-pyrazole-1-yl)-acetyl]-piperidin-4-yl}-thiazole-4-carboxylic acid methyl(1,2,3,4-tetrahydro-naphthalen-1-yl)-amide, 2-{1-[2-(5-methyl-3-trifluoromethyl-pyrazole-1-yl)-acetyl]-piperidin-4-yl}-thiazole-4-carboxylic acid methyl-(R)-1,2,3,4-tetrahydro-naphthalen-1-yl-amide, methoxy-acetic acid 6-tert-butyl-8-fluoro-2,3-dimethyl-quinolin-4-yl ester and N-Methyl-2-{1-[(5-methyl-3-trifluoromethyl-1H-pyrazol-1-yl)-acetyl]-piperidin-4-yl}-N-[(1R)-1,2,3,4-tetrahydronaphthalen-1-yl]-4-thiazolecarboxamide, 3-[5-(4-chloro-phenyl)-2,3-dimethyl-isoxazolidin-3 yl]-pyridine, pyrisoxazole, 5-amino-2-isopropyl-3-oxo-4-ortho-tolyl-2,3-dihydro-pyrazole-1 carbothioic acid S-allyl ester, N-(6-methoxy-pyridin-3-yl)cyclopropanecarboxylic acid amide, 5-chloro-1 (4,6-dimethoxy-pyrimidin-2-yl)-2-methyl-1H-benzoimidazole, 2-(4-chloro-phenyl)-N-[4-(3,4-dimethoxy-phenyl)-isoxazol-5-yl]-2-prop-2-ynyloxy-acetamide.

F.XII) Growth regulators: abscisic acid, amidochlor, ancymidol, 6-benzylaminopurine, brassinolide, butralin, chlormequat (chlormequat chloride), choline chloride, cyclanilide, daminozide, dikegulac, dimethipin, 2,6-dimethylpuridine, ethephon, flumetralin, flurprimidol, fluthiacet, forchlorfenuron, gibberellic acid, inabenfide, indole-3-acetic acid, maleic hydrazide, mefluidide, mepiquat (mepiquat chloride), naphthaleneacetic acid, N 6-benzyladenine, paclobutrazol, prohexadione (prohexadione-calcium), prohydrojasmon, thidiazuron, triapenthenol, tributyl phosphorotrithioate, 2,3,5 tri iodobenzoic acid, trinexapac-ethyl and uniconazole;

F.XIII) Biological control agents

*Ampelomyces quisqualis* (e.g. AQ 10® from Intrachem Bio GmbH & Co. KG, Germany), *Aspergillus flavus* (e.g. AFLAGUARD® from Syngenta, CH), *Aureobasidium pullulans* (e.g. BOTECTOR® from bio-ferm GmbH, Germany), *Bacillus pumilus* (e.g. NRRL Accession No. B-30087 in SONATA® and BALLAD® Plus from Agra-Quest Inc., USA), *Bacillus subtilis* (e.g. isolate NRRL-Nr. B-21661 in RHAPSODY®, SERENADE® MAX and SERENADE® ASO from AgraQuest Inc., USA), *Bacillus subtilis* var. *amyloliquefaciens* FZB24 (e.g. TAEGRO® from Novozyme Biologicals, Inc., USA), *Candida oleophila* 1-82 (e.g. ASPIRE® from Ecogen Inc., USA), *Candida saitoana* (e.g. BIOCURE® (in mixture with lysozyme) and BIOCOAT® from Micro Flo Company, USA (BASF SE) and Arysta), Chitosan (e.g. ARMOUR-ZEN from BotriZen Ltd., NZ), *Clonostachys rosea* f. *catenulata*, also named *Gliocladium catenulatum* (e.g. isolate J1446: PRESTOP® from Verdera, Finland), *Coniothyrium minitans* (e.g. CONTANS® from Prophyta, Germany), *Cryphonectria parasitica* (e.g. *Endothia parasitica* from CNICM, France), *Cryptococcus albidus* (e.g. YIELD PLUS® from Anchor BioTechnologies, South Africa), *Fusarium oxysporum* (e.g. BIOFOX® from S.I.A.P.A., Italy, FUSACLEAN® from Natural Plant Protection, France), *Metschnikowia fructicola* (e.g. SHEMER® from Agrogreen, Israel), *Microdochium dimerum* (e.g. ANTIBOT® from Agrauxine, France), *Phlebiopsis gigantea* (e.g. ROTSOP® from Verdera, Finland), *Pseudozyma flocculosa* (e.g. SPORODEX® from Plant Products Co. Ltd., Canada), *Pythium oligandrum* DV74 (e.g. POLYVERSUM® from Remeslo SSRO, Biopreparaty, Czech Rep.), *Reynoutria sachlinensis* (e.g. REGALIA® from Marrone BioInnovations, USA), *Talaromyces flavus* V117b (e.g. PROTUS® from Prophyta, Germany), *Trichoderma asperellum* SKT-1 (e.g. ECO-HOPE® from Kumiai Chemical Industry Co., Ltd., Japan), *T. atroviride* LC52 (e.g. SENTINEL® from Agrimm Technologies Ltd, NZ), *T. harzianum* T-22 (e.g. PLANTSHIELD® der Firma BioWorks Inc., USA), *T. harzianum* TH 35 (e.g. ROOT PRO® from Mycontrol Ltd., Israel), *T. harzianum* T-39 (e.g. TRICHODEX® and *TRICHODERMA* 2000® from Mycontrol Ltd., Israel and Makhteshim Ltd., Israel), *T. harzianum* and *T. viride* (e.g. TRICHOPEL from Agrimm Technologies Ltd, NZ), *T. harzianum* ICC012 and *T. viride* ICC080 (e.g. REMEDIER® WP from Isagro Ricerca, Italy), *T. polysporum* and *T. harzianum* (e.g. BINAB® from BINAB BioInnovation AB, Sweden), *T. stromaticum* (e.g. TRICOVAB® from C.E.P.L.A.C., Brazil), *T. virens* GL-21 (e.g. SOILGARD® from Certis LLC, USA), *T. viride* (e.g. TRIECO® from Ecosense Labs. (India) Pvt. Ltd., Indien, BIO-CURE® F from T. Stanes & Co. Ltd., Indien), *T. viride* TV1 (e.g. *T. viride* TV1 from Agribiotec srl, Italy), *Ulocladium oudemansii* HRU3 (e.g. BOTRY-ZEN® from Botry-Zen Ltd, NZ).

The commercially available compounds II of the group F listed above may be found in The Pesticide Manual, 15th Edition, C. D. S. Tomlin, British Crop Protection Council (2011) among other publications. Their preparation and their activity against harmful fungi is known (cf.: http://www.alanwood.net/pesticides/); these substances are commercially available. The compounds described by IUPAC nomenclature, their preparation and their fungicidal activity are also known (cf. Can. J. Plant Sci. 48(6), 587-94, 1968; EP A 141 317; EP-A 152 031; EP-A 226 917; EP A 243 970; EP A 256 503; EP-A 428 941; EP-A 532 022; EP-A 1 028 125; EP-A 1 035 122; EP A 1 201 648; EP A 1122 244, JP 2002316902; DE 19650197; DE 10021412; DE 102005009458; U.S. Pat. Nos. 3,296,272; 3,325,503; WO 98/46608; WO 99/14187; WO 99/24413; WO 99/27783; WO 00/29404; WO 00/46148; WO 00/65913; WO 01/54501; WO 01/56358; WO 02/22583; WO 02/40431; WO 03/10149; WO 03/11853; WO 03/14103; WO 03/16286; WO 03/53145; WO 03/61388; WO 03/66609; WO 03/74491; WO 04/49804; WO 04/83193; WO 05/120234; WO 05/123689; WO 05/123690; WO 05/63721; WO 05/87772; WO 05/87773; WO 06/15866; WO 06/87325; WO 06/87343; WO 07/82098; WO 07/90624, WO 11/028657).

The compounds of the invention may be mixed with soil, peat or other rooting media for the protection of plants against seed-borne, soil-borne or foliar fungal diseases.

Examples of suitable synergists for use in the compositions include piperonyl butoxide, sesamex, safroxan and dodecyl imidazole.

Suitable herbicides and plant-growth regulators for inclusion in the compositions will depend upon the intended target and the effect required.

An example of a rice selective herbicide which may be included is propanil. An example of a plant growth regulator for use in cotton is PIX™.

Some mixtures may comprise active ingredients which have significantly different physical, chemical or biological properties such that they do not easily lend themselves to the same.

The invertebrate pest (also referred to as "animal pest"), i.e. the insects, arachnids and nematodes, the plant, soil or water in which the plant is growing or may grow can be contacted with the compounds of the present invention or composition(s) comprising them by any application method known in the art. As such, "contacting" includes both direct contact (applying the compounds/compositions directly on the invertebrate pest or plant—typically to the foliage, stem or roots of the plant) and indirect contact (applying the compounds/compositions to the locus of the invertebrate pest or plant).

The compounds of the present invention or the pesticidal compositions comprising them may be used to protect growing plants and crops from attack or infestation by animal pests, especially insects, acaridae or arachnids by contacting the plant/crop with a pesticidally effective amount of compounds of the present invention. The term "crop" refers both to growing and harvested crops.

The compounds of the present invention and the compositions comprising them are particularly important in the control of a multitude of insects on various cultivated plants, such as cereal, root crops, oil crops, vegetables, spices, ornamentals, for example seed of durum and other wheat, barley, oats, rye, maize (fodder maize and sugar maize/sweet and field corn), soybeans, oil crops, crucifers, cotton, sunflowers, bananas, rice, oilseed rape, turnip rape, sugarbeet, fodder beet, eggplants, potatoes, grass, lawn, turf, fodder grass, tomatoes, leeks, pumpkin/squash, cabbage, iceberg lettuce, pepper, cucumbers, melons, *Brassica* species, melons, beans, peas, garlic, onions, carrots, tuberous plants such as potatoes, sugar cane, tobacco, grapes, petunias, geranium/pelargoniums, pansies and impatiens.

The compounds of the present invention are employed as such or in form of compositions by treating the insects or the plants, plant propagation materials, such as seeds, soil, surfaces, materials or rooms to be protected from insecticidal attack with an insecticidally effective amount of the active compounds. The application can be carried out both before and after the infection of the plants, plant propagation materials, such as seeds, soil, surfaces, materials or rooms by the insects.

Moreover, invertebrate pests may be controlled by contacting the target pest, its food supply, habitat, breeding ground or its locus with a pesticidally effective amount of compounds of the present invention. As such, the application may be carried out before or after the infection of the locus, growing crops, or harvested crops by the pest.

The compounds of the present invention can also be applied preventively to places at which occurrence of the pests is expected.

The compounds of the present invention may be also used to protect growing plants from attack or infestation by pests by contacting the plant with a pesticidally effective amount of compounds of the present invention. As such, "contacting" includes both direct contact (applying the compounds/compositions directly on the pest and/or plant—typically to the foliage, stem or roots of the plant) and indirect contact (applying the compounds/compositions to the locus of the pest and/or plant).

"Locus" means a habitat, breeding ground, plant, seed, soil, area, material or environment in which a pest or parasite is growing or may grow.

In general, "pesticidally effective amount" means the amount of active ingredient needed to achieve an observable effect on growth, including the effects of necrosis, death, retardation, prevention, and removal, destruction, or otherwise diminishing the occurrence and activity of the target organism. The pesticidally effective amount can vary for the various compounds/compositions used in the invention. A pesticidally effective amount of the compositions will also vary according to the prevailing conditions such as desired pesticidal effect and duration, weather, target species, locus, mode of application, and the like.

In the case of soil treatment or of application to the pests dwelling place or nest, the quantity of active ingredient ranges from 0.0001 to 500 g per 100 m$^2$, preferably from 0.001 to 20 g per 100 m$^2$.

Customary application rates in the protection of materials are, for example, from 0.01 g to 1000 g of active compound per m$^2$ treated material, desirably from 0.1 g to 50 g per m$^2$.

Insecticidal compositions for use in the impregnation of materials typically contain from 0.001 to 95 weight %, preferably from 0.1 to 45 weight %, and more preferably from 1 to 25 weight % of at least one repellent and/or insecticide.

For use in treating crop plants, the rate of application of the active ingredients of this invention may be in the range of 0.1 g to 4000 g per hectare, desirably from 5 g to 500 g per hectare, more desirably from 5 g to 200 g per hectare.

The compounds of the present invention are effective through both contact (via soil, glass, wall, bed net, carpet, plant parts or animal parts), and ingestion (bait, or plant part).

The compounds of the present invention may also be applied against non-crop insect pests, such as ants, termites, wasps, flies, mosquitos, crickets, or cockroaches. For use against said non-crop pests, compounds of the present invention are preferably used in a bait composition.

The bait can be a liquid, a solid or a semisolid preparation (e.g. a gel). Solid baits can be formed into various shapes and forms suitable to the respective application e.g. granules, blocks, sticks, disks. Liquid baits can be filled into various devices to ensure proper application, e.g. open containers, spray devices, droplet sources, or evaporation sources. Gels can be based on aqueous or oily matrices and can be formulated to particular necessities in terms of stickyness, moisture retention or aging characteristics.

The bait employed in the composition is a product, which is sufficiently attractive to incite insects such as ants, termites, wasps, flies, mosquitos, crickets etc. or cockroaches to eat it. The attractiveness can be manipulated by using feeding stimulants or sex pheromones. Food stimulants are chosen, for example, but not exclusively, from animal and/or plant proteins (meat-, fish- or blood meal, insect parts, egg yolk), from fats and oils of animal and/or plant origin, or mono-, oligo- or polyorganosaccharides, especially from sucrose, lactose, fructose, dextrose, glucose, starch, pectin or even molasses or honey. Fresh or decaying parts of fruits, crops, plants, animals, insects or specific parts thereof can also serve as a feeding stimulant. Sex pheromones are known to be more insect specific. Specific pheromones are described in the literature and are known to those skilled in the art.

For use in bait compositions, the typical content of active ingredient is from 0.001 weight % to 15 weight %, desirably from 0.001 weight % to 5% weight % of active ingredient.

Formulations of compounds of the present invention as aerosols (e.g in spray cans), oil sprays or pump sprays are highly suitable for the non-professional user for controlling pests such as flies, fleas, ticks, mosquitos or cockroaches. Aerosol recipes are preferably composed of the active compound, solvents such as lower alcohols (e.g. methanol, ethanol, propanol, butanol), ketones (e.g. acetone, methyl ethyl ketone), paraffin hydrocarbons (e.g. kerosenes) having boiling ranges of approximately 50 to 250° C., dimethylformamide, N-methylpyrrolidone, dimethyl sulfoxide, aromatic hydrocarbons such as toluene, xylene, water, furthermore auxiliaries such as emulsifiers such as sorbitol monooleate, oleyl ethoxylate having 3-7 mol of ethylene oxide, fatty alcohol ethoxylate, perfume oils such as ethereal oils, esters of medium fatty acids with lower alcohols, aromatic carbonyl compounds, if appropriate stabilizers such as sodium benzoate, amphoteric surfactants, lower epoxides, triethyl orthoformate and, if required, propellants such as propane, butane, nitrogen, compressed air, dimethyl ether, carbon dioxide, nitrous oxide, or mixtures of these gases.

The oil spray formulations differ from the aerosol recipes in that no propellants are used.

For use in spray compositions, the content of active ingredient is from 0.001 to 80 weights %, preferably from 0.01 to 50 weight % and most preferably from 0.01 to 15 weight %.

The compounds of the present invention and its respective compositions can also be used in mosquito and fumigating coils, smoke cartridges, vaporizer plates or long-term vaporizers and also in moth papers, moth pads or other heat-independent vaporizer systems.

Methods to control infectious diseases transmitted by insects (e.g. malaria, dengue and yellow fever, lymphatic filariasis, and leishmaniasis) with compounds of the present invention and its respective compositions also comprise treating surfaces of huts and houses, air spraying and impregnation of curtains, tents, clothing items, bed nets, tsetse-fly trap or the like. Insecticidal compositions for application to fibers, fabric, knitgoods, nonwovens, netting material or foils and tarpaulins preferably comprise a mixture including the insecticide, optionally a repellent and at least one binder. Suitable repellents for example are N,N-Diethyl-meta-toluamide (DEET), N,N-diethylphenylacetamide (DEPA), 1-(3-cyclohexan-1-yl-carbonyl)-2-methylpiperine, (2-hydroxymethylcyclohexyl) acetic acid lactone, 2-ethyl-1,3-hexandiol, indalone, Methylneodecanamide (MNDA), a pyrethroid not used for insect control such as {(+/−)-3-allyl-2-methyl-4-oxocyclopent-2-(+)-enyl-(+)-trans-chrysantemate (Esbiothrin), a repellent derived from or identical with plant extracts like limonene, eugenol, (+)-Eucamalol (1), (−)-1-epi-eucamalol or crude plant extracts from plants like *Eucalyptus maculata, Vitex rotun-*

*difolia, Cymbopogan martinii, Cymbopogan citratus* (lemon grass), *Cymopogan nartdus* (citronella). Suitable binders are selected for example from polymers and copolymers of vinyl esters of aliphatic acids (such as such as vinyl acetate and vinyl versatate), acrylic and methacrylic esters of alcohols, such as butyl acrylate, 2-ethylhexylacrylate, and methyl acrylate, mono- and di-ethylenically unsaturated hydrocarbons, such as styrene, and aliphatic diens, such as butadiene.

The impregnation of curtains and bednets is done in general by dipping the textile material into emulsions or dispersions of the insecticide or spraying them onto the nets.

The compounds of the present invention and their compositions can be used for protecting wooden materials such as trees, board fences, sleepers, etc. and buildings such as houses, outhouses, factories, but also construction materials, furniture, leathers, fibers, vinyl articles, electric wires and cables etc. from ants and/or termites, and for controlling ants and termites from doing harm to crops or human being (e.g. when the pests invade into houses and public facilities). The compounds of the present invention are applied not only to the surrounding soil surface or into the under-floor soil in order to protect wooden materials but it can also be applied to lumbered articles such as surfaces of the under-floor concrete, alcove posts, beams, plywoods, furniture, etc., wooden articles such as particle boards, half boards, etc. and vinyl articles such as coated electric wires, vinyl sheets, heat insulating material such as styrene foams, etc. In case of application against ants doing harm to crops or human beings, the ant controller of the present invention is applied to the crops or the surrounding soil, or is directly applied to the nest of ants or the like.

The compounds of the present invention are also suitable for the treatment of plant propagation material, especially seeds, in order to protect them from insect pest, in particular from soil-living insect pests and the resulting plant's roots and shoots against soil pests and foliar insects.

The compounds of the present invention are particularly useful for the protection of the seed from soil pests and the resulting plant's roots and shoots against soil pests and foliar insects. The protection of the resulting plant's roots and shoots is preferred. More preferred is the protection of resulting plant's shoots from piercing and sucking insects, wherein the protection from aphids is most preferred.

The present invention therefore comprises a method for the protection of seeds from insects, in particular from soil insects and of the seedlings' roots and shoots from insects, in particular from soil and foliar insects, said method comprising contacting the seeds before sowing and/or after pregermination with a compound of the present invention, including a salt thereof. Particularly preferred is a method, wherein the plant's roots and shoots are protected, more preferably a method, wherein the plants shoots are protected form piercing and sucking insects, most preferably a method, wherein the plants shoots are protected from aphids.

The term seed embraces seeds and plant propagules of all kinds including but not limited to true seeds, seed pieces, suckers, corms, bulbs, fruit, tubers, grains, cuttings, cut shoots and the like and means in a preferred embodiment true seeds.

The term seed treatment comprises all suitable seed treatment techniques known in the art, such as seed dressing, seed coating, seed dusting, seed soaking and seed pelleting.

The present invention also comprises seeds coated with or containing the active compound.

The term "coated with and/or containing" generally signifies that the active ingredient is for the most part on the surface of the propagation product at the time of application, although a greater or lesser part of the ingredient may penetrate into the propagation product, depending on the method of application. When the said propagation product is (re)planted, it may absorb the active ingredient.

Suitable seed is seed of cereals, root crops, oil crops, vegetables, spices, ornamentals, for example seed of durum and other wheat, barley, oats, rye, maize (fodder maize and sugar maize/sweet and field corn), soybeans, oil crops, crucifers, cotton, sunflowers, bananas, rice, oilseed rape, turnip rape, sugarbeet, fodder beet, eggplants, potatoes, grass, lawn, turf, fodder grass, tomatoes, leeks, pumpkin/ squash, cabbage, iceberg lettuce, pepper, cucumbers, melons, *Brassica* species, melons, beans, peas, garlic, onions, carrots, tuberous plants such as potatoes, sugar cane, tobacco, grapes, petunias, geranium/pelargoniums, pansies and impatiens.

In addition, the active compound may also be used for the treatment seeds from plants, which tolerate the action of herbicides or fungicides or insecticides owing to breeding, including genetic engineering methods.

For example, the active compound can be employed in treatment of seeds from plants, which are resistant to herbicides from the group consisting of the sulfonylureas, imidazolinones, glufosinate-ammonium or glyphosate-isopropylammonium and analogous active substances (see for example, EP-A 242 236, EP-A 242 246) (WO 92/00377) (EP-A 257 993, U.S. Pat. No. 5,013,659) or in transgenic crop plants, for example cotton, with the capability of producing *Bacillus thuringiensis* toxins (Bt toxins) which make the plants resistant to certain pests (EP-A 142 924, EP-A 193 259), Furthermore, the active compound can be used also for the treatment of seeds from plants, which have modified characteristics in comparison with existing plants consist, which can be generated for example by traditional breeding methods and/or the generation of mutants, or by recombinant procedures). For example, a number of cases have been described of recombinant modifications of crop plants for the purpose of modifying the starch synthesized in the plants (e.g. WO 92/11376, WO 92/14827, WO 91/19806) or of transgenic crop plants having a modified fatty acid composition (WO 91/13972).

The seed treatment application of the active compound is carried out by spraying or by dusting the seeds before sowing of the plants and before emergence of the plants.

Compositions which are especially useful for seed treatment are e.g.:

A Soluble concentrates (SL, LS)
D Emulsions (EW, EO, ES)
E Suspensions (SC, OD, FS)
F Water-dispersible granules and water-soluble granules (WG, SG)
G Water-dispersible powders and water-soluble powders (WP, SP, WS)
H Gel-Formulations (GF)
I Dustable powders (DP, DS)

Conventional seed treatment formulations include for example flowable concentrates FS, solutions LS, powders for dry treatment DS, water dispersible powders for slurry treatment WS, water-soluble powders SS and emulsion ES and EC and gel formulation GF. These formulations can be applied to the seed diluted or undiluted. Application to the seeds is carried out before sowing, either directly on the seeds or after having pregerminated the latter.

In a preferred embodiment a FS formulation is used for seed treatment. Typcially, a FS formulation may comprise 1-800 g/l of active ingredient, 1-200 g/l Surfactant, 0 to 200 g/l antifreezing agent, 0 to 400 g/l of binder, 0 to 200 g/l of a pigment and up to 1 liter of a solvent, preferably water.

Especially preferred FS formulations of compounds of the present invention for seed treatment usually comprise from 0.1 to 80% by weight (1 to 800 g/l) of the active ingredient, from 0.1 to 20% by weight (1 to 200 g/l) of at least one surfactant, e.g. 0.05 to 5% by weight of a wetter and from 0.5 to 15% by weight of a dispersing agent, up to 20% by weight, e.g. from 5 to 20% of an anti-freeze agent, from 0 to 15% by weight, e.g. 1 to 15% by weight of a pigment and/or a dye, from 0 to 40% by weight, e.g. 1 to 40% by weight of a binder (sticker/adhesion agent), optionally up to 5% by weight, e.g. from 0.1 to 5% by weight of a thickener, optionally from 0.1 to 2% of an anti-foam agent, and optionally a preservative such as a biocide, antioxidant or the like, e.g. in an amount from 0.01 to 1% by weight and a filler/vehicle up to 100% by weight.

Seed Treatment formulations may additionally also comprise binders and optionally colorants.

Binders can be added to improve the adhesion of the active materials on the seeds after treatment. Suitable binders are homo- and copolymers from alkylene oxides like ethylene oxide or propylene oxide, polyvinylacetate, polyvinylalcohols, polyvinylpyrrolidones, and copolymers thereof, ethylene-vinyl acetate copolymers, acrylic homo- and copolymers, polyethyleneamines, polyethyleneamides and polyethyleneimines, polysaccharides like celluloses, tylose and starch, polyolefin homo- and copolymers like olefin/maleic anhydride copolymers, polyurethanes, polyesters, polystyrene homo and copolymers.

Optionally, also colorants can be included in the formulation. Suitable colorants or dyes for seed treatment formulations are Rhodamin B, C.I. Pigment Red 112, C.I. Solvent Red 1, pigment blue 15:4, pigment blue 15:3, pigment blue 15:2, pigment blue 15:1, pigment blue 80, pigment yellow 1, pigment yellow 13, pigment red 112, pigment red 48:2, pigment red 48:1, pigment red 57:1, pigment red 53:1, pigment orange 43, pigment orange 34, pigment orange 5, pigment green 36, pigment green 7, pigment white 6, pigment brown 25, basic violet 10, basic violet 49, acid red 51, acid red 52, acid red 14, acid blue 9, acid yellow 23, basic red 10, basic red 108.

Examples of a gelling agent is carrageen (Satiagel®)

In the treatment of seed, the application rates of the compounds of the present invention are generally from 0.01 g to 10 kg per 100 kg of seed, preferably from 0.05 g to 5 kg per 100 kg of seed, more preferably from 0.1 g to 1000 g per 100 kg of seed and in particular from 0.1 g to 200 g per 100 kg of seed.

The invention therefore also relates to seed comprising a compound of the present invention, including an agriculturally useful salt of it, as defined herein. The amount of the compound of the present invention, including an agriculturally useful salt thereof will in general vary from 0.01 g to 10 kg per 100 kg of seed, preferably from 0.05 g to 5 kg per 100 kg of seed, in particular from 0.1 g to 1000 g per 100 kg of seed. For specific crops such as lettuce the rate can be higher.

Methods which can be employed for treating the seed are, in principle, all suitable seed treatment and especially seed dressing techniques known in the art, such as seed coating (e.g. seed pelleting), seed dusting and seed imbibition (e.g. seed soaking). Here, "seed treatment" refers to all methods that bring seeds and the compounds of the present invention into contact with each other, and "seed dressing" to methods of seed treatment which provide the seeds with an amount of the compounds of the present invention, i.e. which generate a seed comprising a compound of the present invention. In principle, the treatment can be applied to the seed at any time from the harvest of the seed to the sowing of the seed. The seed can be treated immediately before, or during, the planting of the seed, for example using the "planter's box" method. However, the treatment may also be carried out several weeks or months, for example up to 12 months, before planting the seed, for example in the form of a seed dressing treatment, without a substantially reduced efficacy being observed.

Expediently, the treatment is applied to unsown seed. As used herein, the term "unsown seed" is meant to include seed at any period from the harvest of the seed to the sowing of the seed in the ground for the purpose of germination and growth of the plant.

Specifically, a procedure is followed in the treatment in which the seed is mixed, in a suitable device, for example a mixing device for solid or solid/liquid mixing partners, with the desired amount of seed treatment formulations, either as such or after previous dilution with water, until the composition is distributed uniformly on the seed. If appropriate, this is followed by a drying step.

The compounds of the present invention, including their stereoisomers, veterinarily acceptable salts or N-oxides, are in particular also suitable for being used for combating parasites in and on animals.

An object of the present invention is therefore also to provide new methods to control parasites in and on animals. Another object of the invention is to provide safer pesticides for animals. Another object of the invention is further to provide pesticides for animals that may be used in lower doses than existing pesticides. And another object of the invention is to provide pesticides for animals, which provide a long residual control of the parasites.

The invention also relates to compositions comprising a parasiticidally effective amount of compounds of the present invention, including their stereoisomers, veterinarily acceptable salts or N-oxides, and an acceptable carrier, for combating parasites in and on animals.

The present invention also provides a method for treating, controlling, preventing and protecting animals against infestation and infection by parasites, which comprises orally, topically or parenterally administering or applying to the animals a parasiticidally effective amount of a compound of the present invention, including its stereoisomers, veterinarily acceptable salts or N-oxides, or a composition comprising it.

The invention also provides the use of a compound of the present invention, including its stereoisomers, veterinarily acceptable salts or N-oxides, for treating or protecting an animal from infestation or infection by invertebrate pests.

The invention also provides a process for the preparation of a composition for treating, controlling, preventing or protecting animals against infestation or infection by parasites which comprises a parasiticidally effective amount of a compound of the present invention, including its stereoisomers, veterinarily acceptable salts or N-oxides, or a composition comprising it.

Activity of compounds against agricultural pests does not suggest their suitability for control of endo- and ectoparasites in and on animals which requires, for example, low, non-emetic dosages in the case of oral application, metabolic compatibility with the animal, low toxicity, and a safe handling.

Surprisingly it has now been found that compounds of formula (I) and their stereoisomers, veterinarily acceptable salts, tautomers and N-oxides, are suitable for combating endo- and ectoparasites in and on animals.

The compounds of the present invention, especially compounds of formula (I) and their stereoisomers, veterinarily acceptable salts, tautomers and N-oxides, and compositions comprising them are preferably used for controlling and preventing infestations of and infections in animals including warm-blooded animals (including humans) and fish. They are for example suitable for controlling and preventing infestations and infections in mammals such as cattle, sheep, swine, camels, deer, horses, pigs, poultry, rabbits, goats, dogs and cats, water buffalo, donkeys, fallow deer and reindeer, and also in fur-bearing animals such as mink, chinchilla and raccoon, birds such as hens, geese, turkeys and ducks and fish such as fresh- and salt-water fish such as trout, carp and eels.

Compounds of the present invention, including their stereoisomers, veterinarily acceptable salts or N-oxides, and compositions comprising them are preferably used for controlling and preventing infestations and infections in domestic animals, such as dogs or cats.

Infestations in warm-blooded animals and fish include, but are not limited to, lice, biting lice, ticks, nasal bots, keds, biting flies, muscoid flies, flies, myiasitic fly larvae, chiggers, gnats, mosquitoes and fleas.

The compounds of the present invention, including their stereoisomers, veterinarily acceptable salts or N-oxides, and compositions comprising them are suitable for systemic and/or non-systemic control of ecto- and/or endoparasites. They are active against all or some stages of development.

The compounds of the present invention are especially useful for combating parasites of the following orders and species, respectively:

fleas (Siphonaptera), e.g. *Ctenocephalides felis, Ctenocephalides canis, Xenopsylla cheopis, Pulex irritans, Tunga penetrans*, and *Nosopsyllus fasciatus*, cockroaches (Blattaria-Blattodea), e.g. *Blattella germanica, Blattella asahinae, Periplaneta americana, Periplaneta japonica, Periplaneta brunnea, Periplaneta fuligginosa, Periplaneta australasiae*, and *Blatta orientalis*, flies, mosquitoes (Diptera), e.g. *Aedes aegypti, Aedes albopictus, Aedes vexans, Anastrepha ludens, Anopheles maculipennis, Anopheles crucians, Anopheles albimanus, Anopheles gambiae, Anopheles freeborni, Anopheles leucosphyrus, Anopheles minimus, Anopheles quadrimaculatus, Calliphora vicina, Chrysomya bezziana, Chrysomya hominivorax, Chrysomya macellaria, Chrysops discalis, Chrysops silacea, Chrysops atlanticus, Cochliomyia hominivorax, Cordylobia anthropophaga, Culicoides furens, Culex pipiens, Culex nigripalpus, Culex quinquefasciatus, Culex tarsalis, Culiseta inornata, Culiseta melanura, Dermatobia hominis, Fannia canicularis, Gasterophilus intestinalis, Glossina morsitans, Glossina palpalis, Glossina fuscipes, Glossina tachinoides, Haematobia irritans, Haplodiplosis equestris, Hippelates* spp., *Hypoderma lineata, Leptoconops torrens, Lucilia caprina, Lucilia cuprina, Lucilia sericata, Lycoria pectoralis, Mansonia* spp., *Musca domestica, Muscina stabulans, Oestrus ovis, Phlebotomus argentipes, Psorophora columbiae, Psorophora discolor, Prosimulium mixtum, Sarcophaga haemorrhoidalis, Sarcophaga* sp., *Simulium vittatum, Stomoxys calcitrans, Tabanus bovinus, Tabanus atratus, Tabanus lineola*, and *Tabanus similis*, lice (Phthiraptera), e.g. *Pediculus humanus capitis, Pediculus humanus corporis, Pthirus pubis, Haematopinus eurysternus, Haematopinus suis, Linognathus vituli, Bovicola bovis, Menopon gallinae, Menacanthus stramineus* and *Solenopotes capillatus*.

ticks and parasitic mites (Parasitiformes): ticks (Ixodida), e.g. *Ixodes scapularis, Ixodes holocyclus, Ixodes pacificus, Rhiphicephalus sanguineus, Dermacentor andersoni, Dermacentor variabilis, Amblyomma americanum, Ambryomma maculatum, Ornithodorus hermsi, Ornithodorus turicata* and parasitic mites (Mesostigmata), e.g. *Ornithonyssus bacoti* and *Dermanyssus gallinae*, Actinedida (Prostigmata) und Acaridida (Astigmata) e.g. *Acarapis* spp., *Cheyletiella* spp., *Ornithocheyletia* spp., *Myobia* spp., *Psorergates* spp., *Demodex* spp., *Trombicula* spp., *Listrophorus* spp., *Acarus* spp., *Tyrophagus* spp., *Caloglyphus* spp., *Hypodectes* spp., *Pterolichus* spp., *Psoroptes* spp., *Chorioptes* spp., *Otodectes* spp., *Sarcoptes* spp., *Notoedres* spp., *Knemidocoptes* spp., *Cytodites* spp., and *Laminosioptes* spp., Bugs (Heteropterida): *Cimex lectularius, Cimex hemipterus, Reduvius senilis, Triatoma* spp., *Rhodnius* ssp., *Panstrongylus* ssp. and *Arilus critatus*, Anoplurida, e.g. *Haematopinus* spp., *Linognathus* spp., *Pediculus* spp., *Phtirus* spp., and *Solenopotes* spp, Mallophagida (suborders Arnblycerina and Ischnocerina), e.g. *Trimenopon* spp., *Menopon* spp., *Trinoton* spp., *Bovicola* spp., *Werneckiella* spp., *Lepikentron* spp., *Trichodectes* spp., and *Felicola* spp, Roundworms Nematoda:

Wipeworms and Trichinosis (Trichosyringida), e.g. Trichinellidae (*Trichinella* spp.), (Trichuridae) *Trichuris* spp., *Capillaria* spp, Rhabditida, e.g. *Rhabditis* spp, *Strongyloides* spp., *Helicephalobus* spp, Strongylida, e.g. *Strongylus* spp., *Ancylostoma* spp., *Necator americanus, Bunostomum* spp. (Hookworm), *Trichostrongylus* spp., *Haemonchus contortus., Ostertagia* spp., *Cooperia* spp., *Nematodirus* spp., *Dictyocaulus* spp., *Cyathostoma* spp., *Oesophagostomum* spp., *Stephanurus dentatus, Ollulanus* spp., *Chabertia* spp., *Stephanurus dentatus, Syngamus trachea, Ancylostoma* spp., *Uncinaria* spp., *Globocephalus* spp., *Necator* spp., *Metastrongylus* spp., *Muellerius capillaris, Protostrongylus* spp., *Angiostrongylus* spp., *Parelaphostrongylus* spp. *Aleurostrongylus abstrusus*, and *Dioctophyma renale*, Intestinal roundworms (Ascaridida), e.g. *Ascaris lumbricoides, Ascaris suum, Ascaridia galli, Parascaris equorum, Enterobius vermicularis* (Threadworm), *Toxocara canis, Toxascaris leonine, Skrjabinema* spp., and *Oxyuris equi*, Camallanida, e.g. *Dracunculus medinensis* (guinea worm)

Spirurida, e.g. *Thelazia* spp. *Wuchereria* spp., *Brugia* spp., *Onchocerca* spp., *Dirofilari* spp. a, *Dipetalonema* spp., *Setaria* spp., *Elaeophora* spp., *Spirocerca lupi*, and *Habronema* spp., Thorny headed worms (Acanthocephala), e.g. *Acanthocephalus* spp., *Macracanthorhynchus hirudinaceus* and *Oncicola* spp., Planarians (Plathelminthes):

Flukes (Trematoda), e.g. *Faciola* spp., *Fascioloides magna, Paragonimus* spp., *Dicrocoelium* spp., *Fasciolopsis buski, Clonorchis sinensis, Schistosoma* spp., *Trichobilharzia* spp., *Alaria alata, Paragonimus* spp., and *Nanocyetes* spp., Cercomeromorpha, in particular Cestoda (Tapeworms), e.g. *Diphyllobothrium* spp., *Tenia* spp., *Echinococcus* spp., *Dipylidium caninum, Multiceps* spp., *Hymenolepis* spp.,

*Mesocestoides* spp., *Vampirolepis* spp., *Moniezia* spp., *Anoplocephala* spp., *Sirometra* spp., *Anoplocephala* spp., and *Hymenolepis* spp.

The present invention relates to the therapeutic and the non-therapeutic use of compounds of the present invention and compositions comprising them for controlling and/or combating parasites in and/or on animals. The compounds of the present invention and compositions comprising them may be used to protect the animals from attack or infestation by parasites by contacting them with a parasiticidally effective amount of compounds of the present invention and compositions containing them.

The compounds of the present invention and compositions comprising them can be effective through both contact (via soil, glass, wall, bed net, carpet, blankets or animal parts) and ingestion (e.g. baits). As such, "contacting" includes both direct contact (applying the pesticidal mixtures/compositions containing the compounds of the present invention directly on the parasite, which may include an indirect contact at its locus-P, and optionally also administrating the pesticidal mixtures/composition directly on the animal to be protected) and indirect contact (applying the compounds/compositions to the locus of the parasite). The contact of the parasite through application to its locus is an example of a non-therapeutic use of compounds of the present invention. "Locus-P" as used above means the habitat, food supply, breeding ground, area, material or environment in which a parasite is growing or may grow outside of the animal.

In general, "parasiticidally effective amount" means the amount of active ingredient needed to achieve an observable effect on growth, including the effects of necrosis, death, retardation, prevention, and removal, destruction, or otherwise diminishing the occurrence and activity of the target organism. The parasiticidally effective amount can vary for the various compounds/compositions of the present invention. A parasiticidally effective amount of the compositions will also vary according to the prevailing conditions such as desired parasiticidal effect and duration, target species, mode of application, and the like.

The compounds of the present invention can also be applied preventively to places at which occurrence of the pests or parasites are expected.

Administration can be carried out both prophylactically and therapeutically.

Administration of the active compounds is carried out directly or in the form of suitable preparations, orally, topically/dermally or parenterally.

EXAMPLES

The present invention is now illustrated in further details by the following examples, without imposing any limitation thereto.

Compounds can be characterized e.g. by coupled High Performance Liquid Chromatography/mass spectrometry (HPLC/MS), by $^1$H-NMR and/or by their melting points. Analytical HPLC—Method 1: Phenomenex Kinetex 1.7 µm XB-C18 100 A; 50×2.1 mm. Elution: acetonitrile+0.1% trifluoroacetic acid (TFA)/water+0.1% trifluoroacetic acid (TFA) in a ratio of from 5:95 to 95:5 in 1.5 minutes at 50° C. Method 2: BEH C18 1.7 µm; 50×2.1 mm. Elution: acetonitrile+0.1% formic acid (FA)/water+0.1% 0.1% formic acid (FA) in a ratio of from 5:95 to 95:5 in 5 minutes at 40° C. Method 3: Agilent Eclipse Plus C18, 50×4.6 mm, ID 5 µm; Elution: A=10 mM Amm. Formate (0.1% Formic Acid), B=Acetonitrile (0.1% Formic Acid), Flow=1.2 ml/min. at 30° C.; Gradient:=10% B to 100% B-3 min, hold for 1 min, 1 min-10% B. Run Time=5.01 min.

$^e$H-NMR: The signals are characterized by chemical shift (ppm, δ [delta]) vs. tetramethylsilane, respectively CDCl$_3$ for $^{13}$C-NMR, by their multiplicity and by their integral (relative number of hydrogen atoms given). The following abbreviations are used to characterize the multiplicity of the signals: m=multiplett, q=quartett, t=triplett, d=doublet and s=singulett.

Abbreviations used are: d for day(s), h for hour(s), min for minute(s), r.t./room temperature for 20-25° C., Rt for retension time; DMSO for dimethyl sulfoxide, OAc for acetate, EtOAc for ethyl acetate, THF for tetrahydrofuran, and t-BuOH for tert-butanol.

Synthesis Examples

| | Structure | IUPAC |
|---|---|---|
| C-1 | 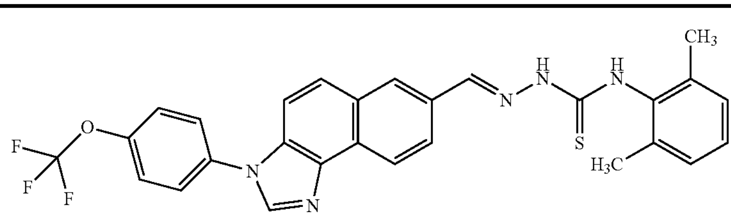 | 1-(2,6-dimethylphenyl)-3-[(E)-[3-[4-(trifluoromethoxy)phenyl]benzo[e]benzimidazol-7-yl]methyleneamino]thiourea |
| C-2 | 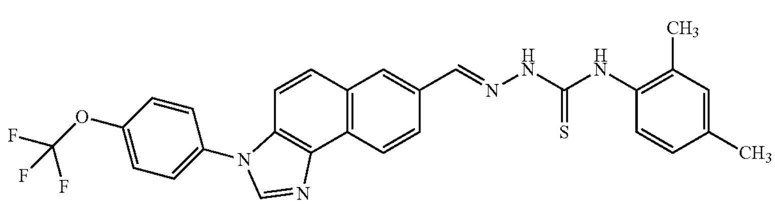 [SMILES: Cc1ccc(NC(=S)N/N=C/c2ccc3c(ccc4c3ncn4-c3ccc(OC(F)(F)F)cc3)c2)c(C)c1] | 1-(2,4-dimethylphenyl)-3-[(E)-[3-[4-(trifluoromethoxy)phenyl]benzo[e]benzimidazol-7-yl]methyleneamino]thiourea |

-continued

| Structure | IUPAC |
|---|---|
| C-3 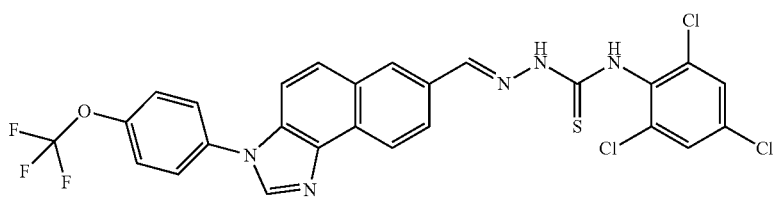 [SMILES: FC(F)(F)Oc1ccc(-n2cnc3c4ccc(/C=N/NC(=S)Nc5c(Cl)cc(Cl)cc5Cl)cc4ccc32)cc1] | 1-(2,4,6-trichlorophenyl)-3-[(E)-[3-[4-(trifluoromethoxy)phenyl]benzo[e]benzimidazol-7-yl]methyleneamino]thiourea |
| C-4 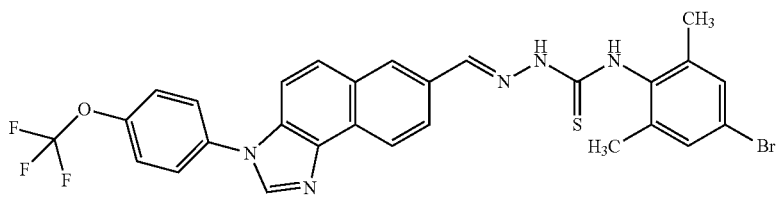 [SMILES: Cc1cc(Br)cc(C)c1NC(=S)N/N=C/c1ccc2c(ccc3c2ncn3-c2ccc(OC(F)(F)F)cc2)c1] | 1-(4-bromo-2,6-dimethyl-phenyl)-3-[(E)-[3-[4-(trifluoromethoxy)phenyl]benzo[e]benzimidazol-7-yl]methyleneamino]thiourea |
| C-5 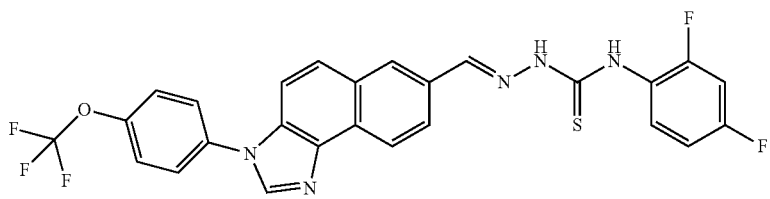 [SMILES: Fc1ccc(NC(=S)N/N=C/c2ccc3c(ccc4c3ncn4-c3ccc(OC(F)(F)F)cc3)c2)c(F)c1] | 1-(2,4-difluorophenyl)-3-[(E)-[3-[4-(trifluoromethoxy)phenyl]benzo[e]benzimidazol-7-yl]methyleneamino]thiourea |
| C-6 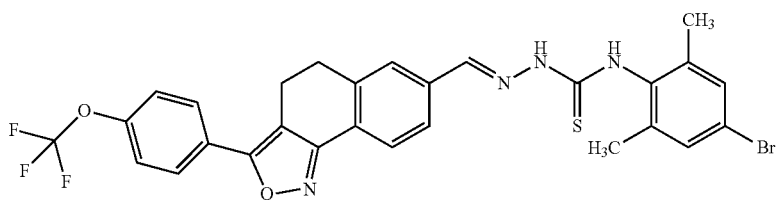 [SMILES: Cc1cc(Br)cc(C)c1NC(=S)N/N=C/c1ccc2c(c1)CCc1c-2noc1-c1ccc(OC(F)(F)F)cc1] | 1-(4-bromo-2,6-dimethyl-phenyl)-3-[(E)-[3-[4-(trifluoromethoxy)phenyl]-4,5-dihydrobenzo[g][2,1]benzoxazol-7-yl]methyleneamino]thiourea |
| C-7 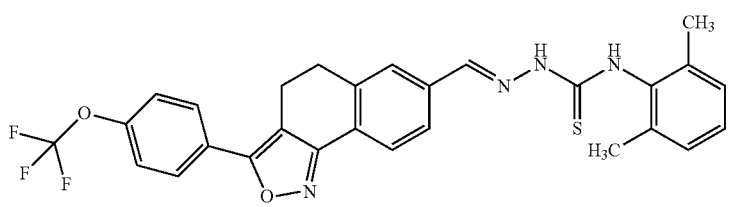 [SMILES: Cc1cccc(C)c1NC(=S)N/N=C/c1ccc2c(c1)CCc1c-2noc1-c1ccc(OC(F)(F)F)cc1] | 1-(2,6-dimethylphenyl)-3-[(E)-[3-[4-(trifluoromethoxy)phenyl]-4,5-dihydrobenzo[g][2,1]benzoxazol-7-yl]methyleneamino]thiourea |
| C-8 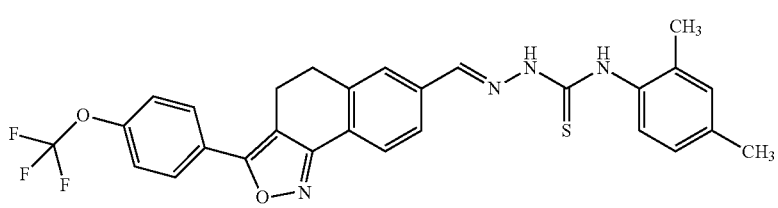 [SMILES: Cc1ccc(NC(=S)N/N=C/c2ccc3c(c2)CCc2c-3noc2-c2ccc(OC(F)(F)F)cc2)c(C)c1] | 1-(2,4-dimethylphenyl)-3-[(E)-[3-[4-(trifluoromethoxy)phenyl]-4,5-dihydrobenzo[g][2,1]benzoxazol-7-yl]methyleneamino]thiourea |
| C-9 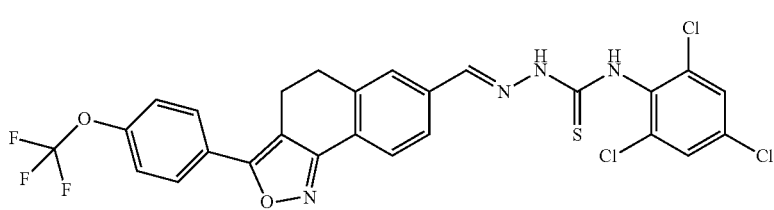 [SMILES: FC(F)(F)Oc1ccc(-c2onc3c2CCc2cc(/C=N/NC(=S)Nc4c(Cl)cc(Cl)cc4Cl)ccc2-3)cc1] | 1-(2,4,6-trichlorophenyl)-3-[(E)-[3-[4-(trifluoromethoxy)phenyl]-4,5-dihydrobenzo[g][2,1]benzoxazol-7-yl]methyleneamino]thiourea |

| Structure | IUPAC |
|---|---|
| C-10 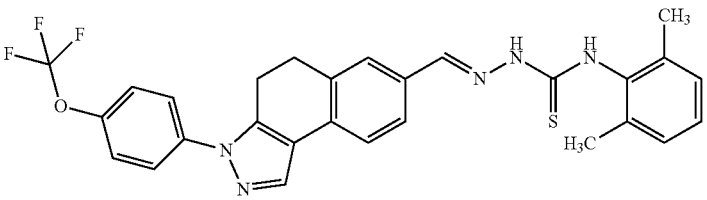 | 1-(2,6-dimethylphenyl)-3-[(E)-[3-[4-(trifluoromethoxy)phenyl]-4,5-dihydrobenzo[e]indazol-7-yl]methyleneamino]thiourea |
| C-11 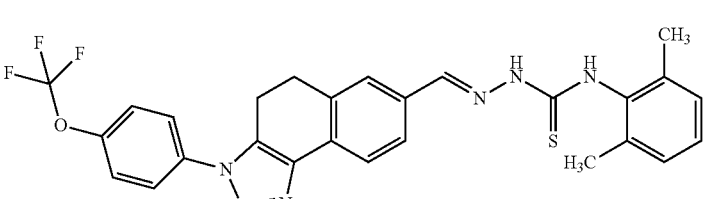 | 1-(2,6-dimethylphenyl)-3-[(E)-[3-[4-(trifluoromethoxy)phenyl]-4,5-dihydrobenzo[e]benzotriazol-7-yl]methyleneamino]thiourea |
| C-12 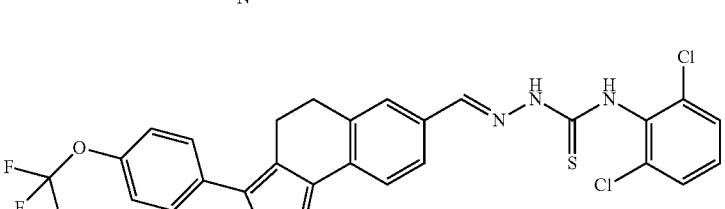 | 1-(2,6-dichlorophenyl)-3-[(E)-[3-[4-(trifluoromethoxy)phenyl]-4,5-dihydrobenzo[g][2,1]benzoxazol-7-yl]methyleneamino]thiourea |
| C-13 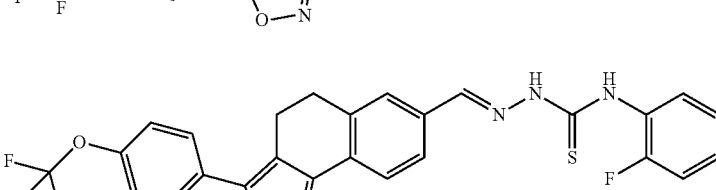 | 1-(2,4-difluorophenyl)-3-[(E)-[3-[4-(trifluoromethoxy)phenyl]-4,5-dihydrobenzo[g][2,1]benzoxazol-7-yl]methyleneamino]thiourea |
| C-14 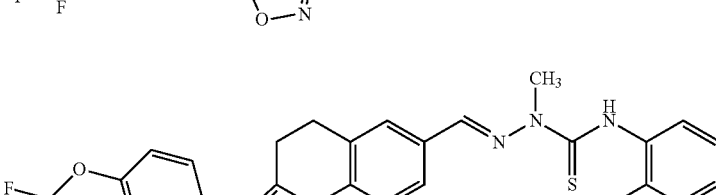 | 3-(2,4-dichlorophenyl)-1-methyl-1-[(E)-[3-[4-(trifluoromethoxy)phenyl]-4,5-dihydrobenzo[g][2,1]benzoxazol-7-yl]methyleneamino]thiourea |
| C-15 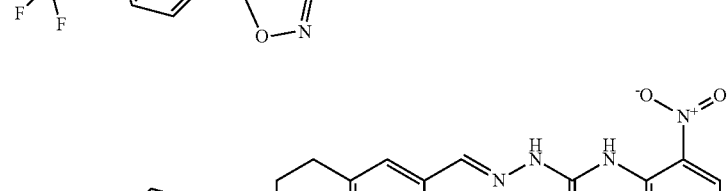 | 1-(2-nitrophenyl)-3-[[3-[4-(trifluoromethoxy)phenyl]-5,6-dihydro-4H-benzo[g][2,1]benzoxazol-7-ylidene]methylimino]thiourea |
| C-16 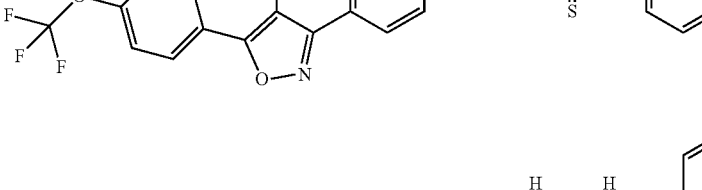 | 1-(1-naphthyl)-3-[(E)-[3-[4-(trifluoromethoxy)phenyl]-4,5-dihydrobenzo[g][2,1]benzoxazol-7-yl]methyleneamino]thiourea |

| Structure | IUPAC |
|---|---|
| C-17 | 1-(2-ethylphenyl)-3-[[3-[4-(trifluoromethoxy)phenyl]-5,6-dihydro-4H-benzo[g][2,1]benzoxazol-7-ylidene]methylimino]thiourea |
| C-18 | 1-[2-chloro-5-(trifluoromethyl)phenyl]-3-[(E)-[3-[4-(trifluoromethoxy)phenyl]-4,5-dihydrobenzo[g][2,1]benzoxazol-7-yl]methyleneamino]thiourea |
| C-19 | 1-(2-ethylphenyl)-3-[[3-[4-(trifluoromethoxy)phenyl]-5,8-dihydro-4H-benzo[e]indazol-7-ylidene]methylimino]thiourea |
| C-20 | 1-(2,4,6-trichlorophenyl)-3-[(E)-[3-[4-(trifluoromethoxy)phenyl]-4,5-dihydrobenzo[e]indazol-7-yl]methyleneamino]thiourea |
| C-21 | 1-(5-chloro-2-methyl-phenyl)-3-[(E)-[3-[4-(trifluoromethoxy)phenyl]benzo[e]benzimidazol-7-yl]methyleneamino]thiourea |
| C-22 | 3-(2-ethylphenyl)-1-[[3-[4-(trifluoromethoxy)phenyl]-9aH-benzo[e]benzimidazol-7-ylidene]methylimino]isothiourea |
| C-23 | 3-(o-tolyl)-1-[[3-[4-(trifluoromethoxy)phenyl]-9aH-benzo[e]benzimidazol-7-ylidene]methylimino]isothiourea |

-continued

| | Structure | IUPAC |
|---|---|---|
| C-24 | 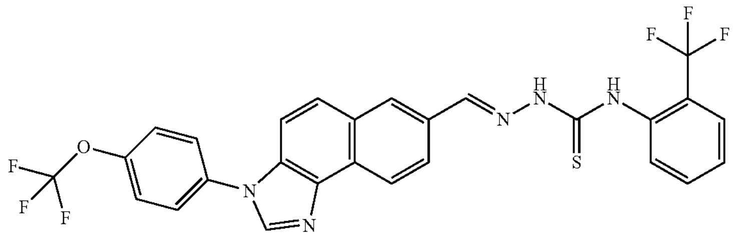 [SMILES: FC(F)(F)Oc1ccc(-n2cnc3c4ccc(/C=N/NC(=S)Nc5ccccc5C(F)(F)F)cc4ccc32)cc1] | 1-[[3-[4-(trifluoromethoxy)phenyl]-9aH-benzo[e]benzimidazol-7-ylidene]methylimino]-3-[2-(trifluoromethyl)phenyl]isothiourea |
| C-25 | 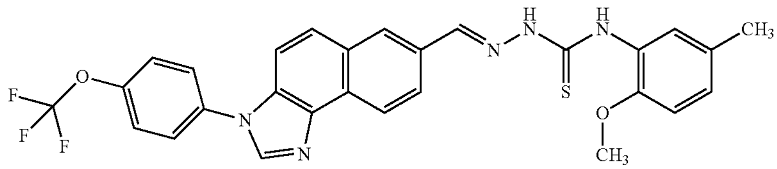 [SMILES: COc1ccc(C)cc1NC(=S)N/N=C/c1ccc2c(ccc3c2ncn3-c2ccc(OC(F)(F)F)cc2)c1] | 1-(2-methoxy-5-methyl-phenyl)-3-[(E)-[3-[4-(trifluoromethoxy)phenyl]benzo[e]benzimidazol-7-yl]methyleneamino]thiourea |
| C-26 | 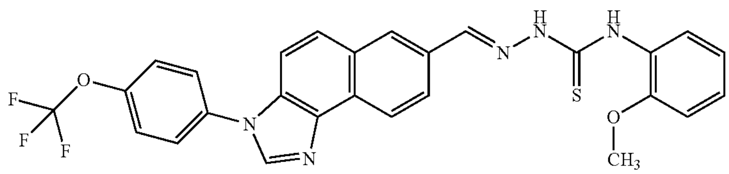 [SMILES: COc1ccccc1NC(=S)N/N=C/c1ccc2c(ccc3c2ncn3-c2ccc(OC(F)(F)F)cc2)c1] | 3-(2-methoxyphenyl)-1-[[3-[4-(trifluoromethoxy)phenyl]-9aH-benzo[e]benzimidazol-7-ylidene]methylimino]isothiourea |
| C-27 | 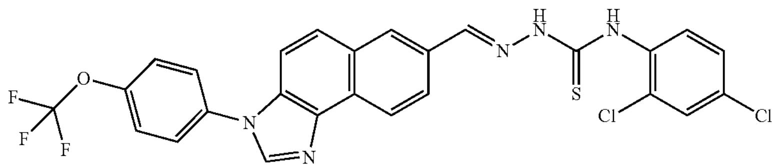 [SMILES: FC(F)(F)Oc1ccc(-n2cnc3c4ccc(/C=N/NC(=S)Nc5ccc(Cl)cc5Cl)cc4ccc32)cc1] | 1-(2,4-dichlorophenyl)-3-[(E)-[3-[4-(trifluoromethoxy)phenyl]benzo[e]benzimidazol-7-yl]methyleneamino]thiourea |
| C-28 | 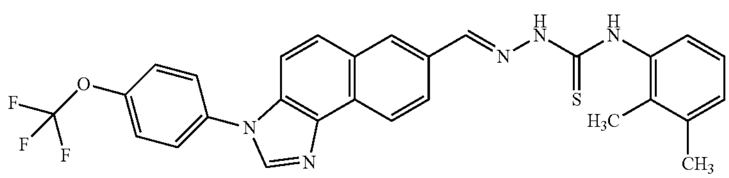 [SMILES: Cc1cccc(NC(=S)N/N=C/c2ccc3c(ccc4c3ncn4-c3ccc(OC(F)(F)F)cc3)c2)c1C] | 1-(2,3-dimethylphenyl)-3-[(E)-[3-[4-(trifluoromethoxy)phenyl]benzo[e]benzimidazol-7-yl]methyleneamino]thiourea |
| C-29 | 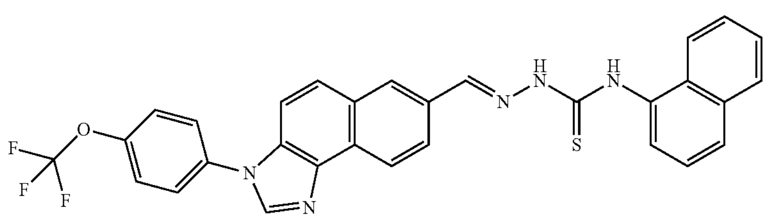 [SMILES: FC(F)(F)Oc1ccc(-n2cnc3c4ccc(/C=N/NC(=S)Nc5cccc6ccccc56)cc4ccc32)cc1] | 1-(2H-naphthalen-1-ylidene)-3-[[3-[4-(trifluoromethoxy)phenyl]-9aH-benzo[e]benzimidazol-7-ylidene]methylimino]thiourea |
| C-30 | 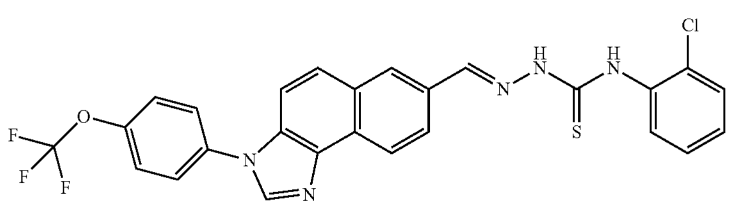 | 3-(2-chlorophenyl)-1-[[3-[4-(trifluoromethoxy)phenyl]-8H-benzo[e]benzimidazol-7-ylidene]methylimino]isothiourea |
| C-31 | 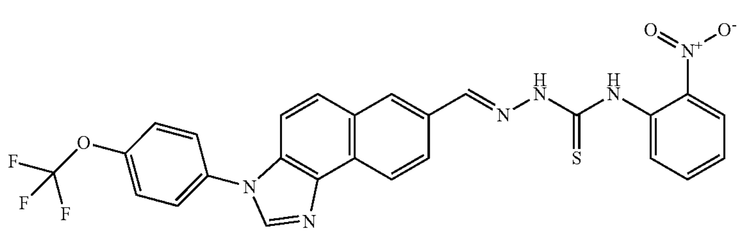 [SMILES: O=[N+]([O-])c1ccccc1NC(=S)N/N=C/c1ccc2c(ccc3c2ncn3-c2ccc(OC(F)(F)F)cc2)c1] | 3-(2-nitrophenyl)-1-[[3-[4-(trifluoromethoxy)phenyl]-9aH-benzo[e]benzimidazol-7-ylidene]methylimino]isothiourea |

-continued

| Structure | IUPAC |
|---|---|
| C-32 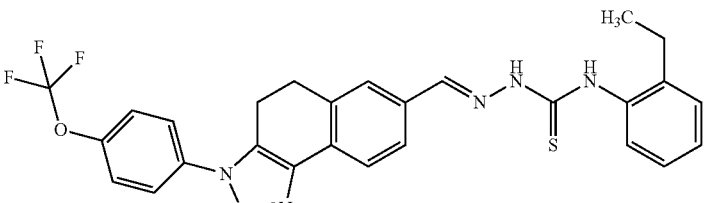 | 1-(2-ethylphenyl)-3-[[3-[4-(trifluoromethoxy)phenyl]-5,6-dihydro-4H-benzo[e]benzotriazol-7-ylidene]methylimino]thiourea |
| C-33 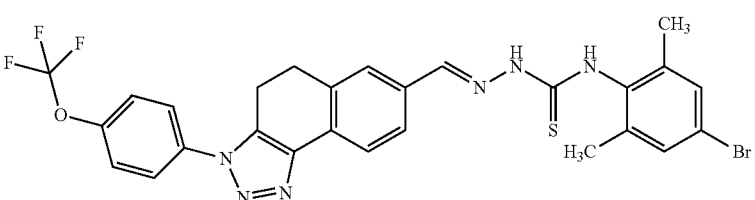 | 1-(4-bromo-2,6-dimethyl-phenyl)-3-[(E)-[3-[4-(trifluoromethoxy)phenyl]-4,5-dihydrobenzo[e]benzotriazol-7-yl]methyleneamino]thiourea |
| C-34 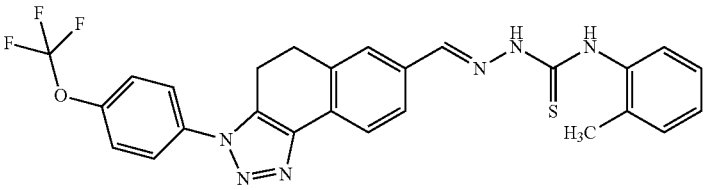 [SMILES: Cc1ccccc1NC(=S)N/N=C/c1ccc2c(c1)CCc1c-2nnn1-c1ccc(OC(F)(F)F)cc1] | 1-(o-tolyl)-3-[[3-[4-(trifluoromethoxy)phenyl]-5,8-dihydro-4H-benzo[e]benzotriazol-7-ylidene]methylimino]thiourea |
| C-35 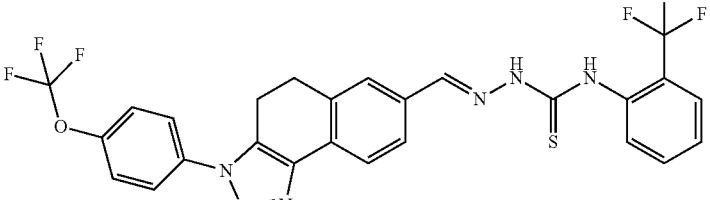 | 1-[[3-[4-(trifluoromethoxy)phenyl]-5,8-dihydro-4H-benzo[e]benzotriazol-7-ylidene]methylimino]-3-[2-(trifluoromethyl)phenyl]thiourea |
| C-36 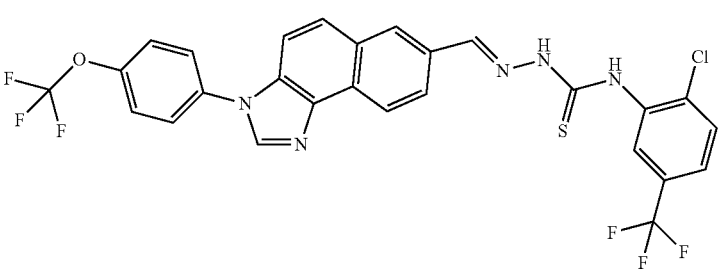 [SMILES: FC(F)(F)Oc1ccc(-n2cnc3c4ccc(/C=N/NC(=S)Nc5cc(C(F)(F)F)ccc5Cl)cc4ccc32)cc1] | 1-[2-chloro-5-(trifluoromethyl)phenyl]-3-[(E)-[3-[4-(trifluoromethoxy)phenyl]benzo[e]benzimidazol-7-yl]methyleneamino]thiourea |
| C-37 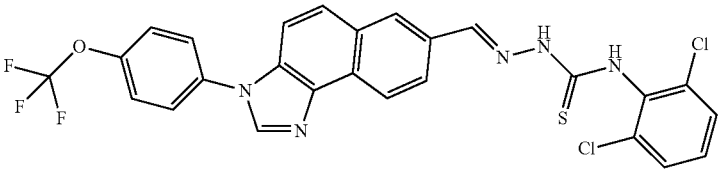 | 1-(2,6-dichlorophenyl)-3-[(E)-[3-[4-(trifluoromethoxy)phenyl]benzo[e]benzimidazol-7-yl]methyleneamino]thiourea |
| C-38 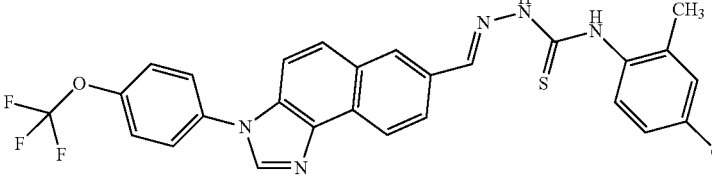 | 1-(4-chloro-2-methyl-phenyl)-3-[(E)-[3-[4-(trifluoromethoxy)phenyl]benzo[e]benzimidazol-7-yl]methyleneamino]thiourea |

-continued

| | Structure | IUPAC |
|---|---|---|
| C-39 | 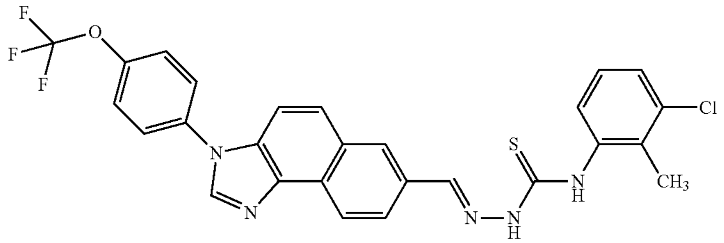 [SMILES: Cc1c(Cl)cccc1NC(=S)N/N=C/c1ccc2c(ccc3c2ncn3-c2ccc(OC(F)(F)F)cc2)c1] | 1-(3-chloro-2-methyl-phenyl)-3-[(E)-[3-[4-(trifluoromethoxy)phenyl]benzo[e]benzimidazol-7-yl]methyleneamino]thiourea |
| C-40 | 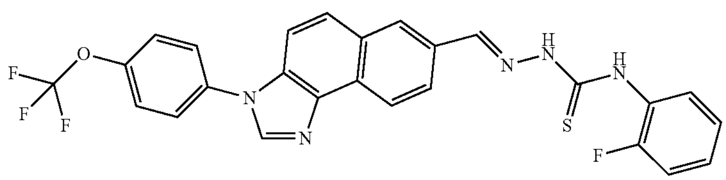 [SMILES: Fc1ccccc1NC(=S)N/N=C/c1ccc2c(ccc3c2ncn3-c2ccc(OC(F)(F)F)cc2)c1] | 3-(2-fluorophenyl)-1-[[3-[4-(trifluoromethoxy)phenyl]-5H-benzo[e]benzimidazol-7-ylidene]methylimino]isothiourea |
| C-41 | 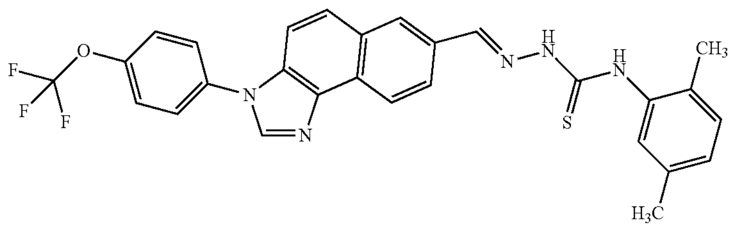 [SMILES: Cc1ccc(C)c(NC(=S)N/N=C/c2ccc3c(ccc4c3ncn4-c3ccc(OC(F)(F)F)cc3)c2)c1] | 1-(2,5-dimethylphenyl)-3-[(E)-[3-[4-(trifluoromethoxy)phenyl]benzo[e]benzimidazol-7-yl]methyleneamino]thiourea |
| C-42 | 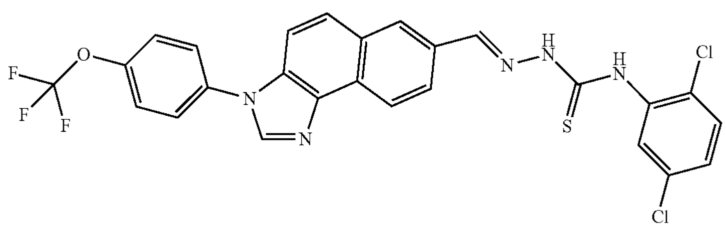 [SMILES: FC(F)(F)Oc1ccc(-n2cnc3c4ccc(/C=N/NC(=S)Nc5cc(Cl)ccc5Cl)cc4ccc32)cc1] | 1-(2,5-dichlorophenyl)-3-[(E)-[3-[4-(trifluoromethoxy)phenyl]benzo[e]benzimidazol-7-yl]methyleneamino]thiourea |
| C-43 | 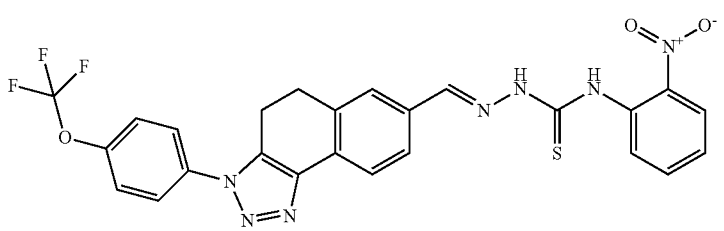 [SMILES: O=[N+]([O-])c1ccccc1NC(=S)N/N=C/c1ccc2c(c1)CCc1c-2nnn1-c1ccc(OC(F)(F)F)cc1] | 1-(2-nitrophenyl)-3-[[3-[4-(trifluoromethoxy)phenyl]-5,6-dihydro-4H-benzo[e]benzotriazol-7-ylidene]methylimino]thiourea |
| C-44 | 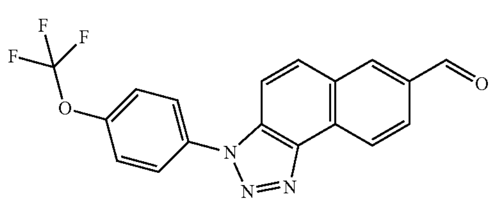 [SMILES: O=Cc1ccc2c(ccc3c2nnn3-c2ccc(OC(F)(F)F)cc2)c1] | 3-[4-(trifluoromethoxy)phenyl]benzo[e]indazole-7-carbaldehyde |
| C-45 | 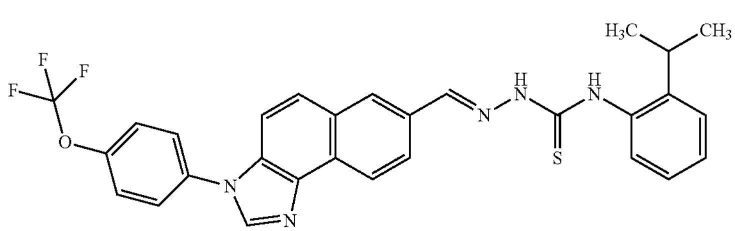 [SMILES: CC(C)c1ccccc1NC(=S)N/N=C/c1ccc2c(ccc3c2ncn3-c2ccc(OC(F)(F)F)cc2)c1] | 1-(2-isopropylphenyl)-3-[[3-[4-(trifluoromethoxy)phenyl]-3aH-benzo[e]benzimidazol-7-ylidene]methylimino]thiourea |

-continued

| Structure | IUPAC |
|---|---|
| C-46 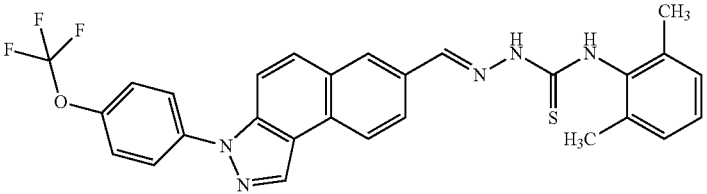 [SMILES: Cc1cccc(C)c1NC(=S)N/N=C/c1ccc2c(ccc3c2cnn3-c2ccc(OC(F)(F)F)cc2)c1] | 1-(2,6-dimethylphenyl)-3-[(E)-[3-[4-(trifluoromethoxy)phenyl]benzo[e]indazol-7-yl]methyleneamino]thiourea |
| C-47 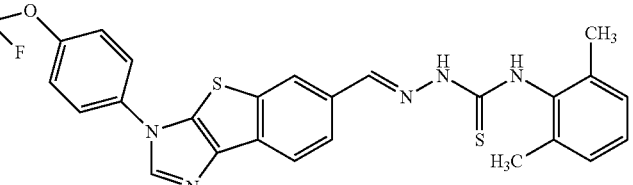 | 1-(2,6-dimethylphenyl)-3-[(E)-[3-[4-(trifluoromethoxy)phenyl]benzothiopheno[2,3-d]imidazol-6-yl]methyleneamino]thiourea |
| C-48 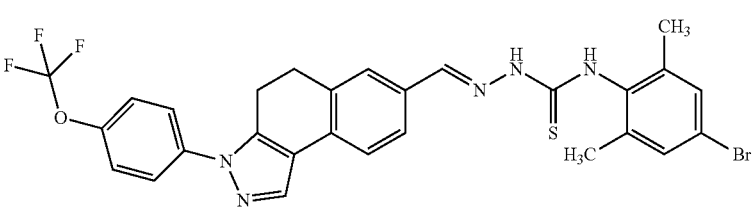 [SMILES: Cc1cc(Br)cc(C)c1NC(=S)N/N=C/c1ccc2c(c1)CCc1c-2cnn1-c1ccc(OC(F)(F)F)cc1] | 1-(4-bromo-2,6-dimethyl-phenyl)-3-[(E)-[3-[4-(trifluoromethoxy)phenyl]-4,5-dihydrobenzo[e]indazol-7-yl]methyleneamino]thiourea |
| C-49 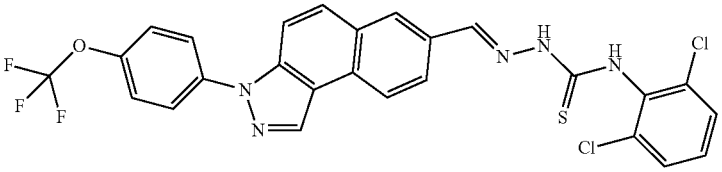 | 1-(2,6-dichlorophenyl)-3-[(E)-[3-[4-(trifluoromethoxy)phenyl]benzo[e]indazol-7-yl]methyleneamino]thiourea |
| C-50 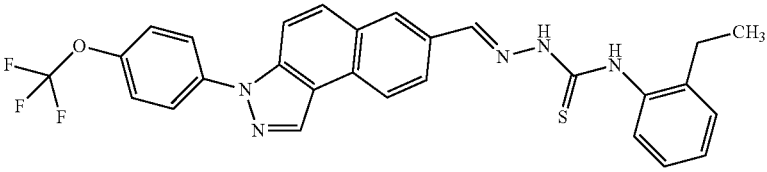 [SMILES: CCc1ccccc1NC(=S)N/N=C/c1ccc2c(ccc3c2cnn3-c2ccc(OC(F)(F)F)cc2)c1] | 1-(2-ethylphenyl)-3-[[3-[4-(trifluoromethoxy)phenyl]-5H-benzo[e]indazol-7-ylidene]methylimino]thiourea |
| C-51 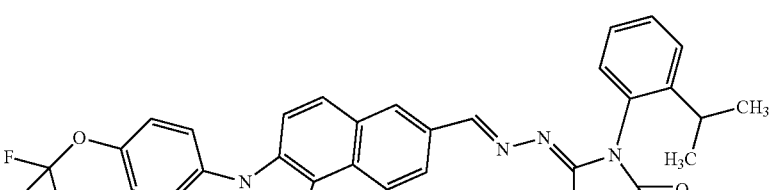 | (2Z)-3-(2-isopropylphenyl)-2-[(E)-[3-[4-(trifluoromethoxy)phenyl]benzo[e]benzimidazol-7-yl]methylenehydrazono]thiazolidin-4-one |
| C-52 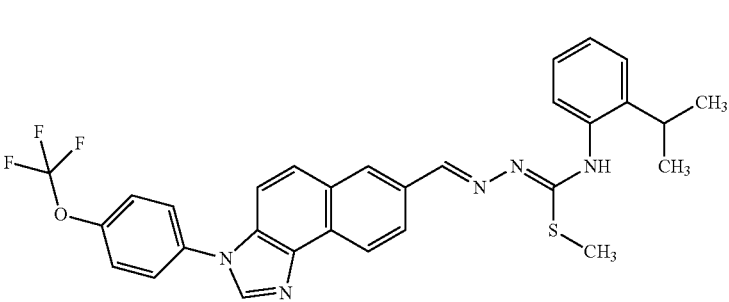 [SMILES: CS/C(=N\N=C\c1ccc2c(ccc3c2ncn3-c2ccc(OC(F)(F)F)cc2)c1)Nc1ccccc1C(C)C] | 3-(2-isopropylphenyl)-2-methyl-1-[[3-[4-(trifluoromethoxy)phenyl]-3aH-benzo[e]benzimidazol-7-ylidene]methylimino]isothiourea |

-continued

| Structure | IUPAC |
|---|---|
| C-53 | (E)-3-(2-isopropylphenyl)-N-[(E)-[3-[4-(trifluoromethoxy)phenyl]benzo[e]benzimidazol-7-yl]methyleneamino]thiazolidin-2-imine |
| C-54 | 1-(2,6-dimethylphenyl)-3-[(E)-[3-[4-(trifluoromethoxy)phenyl]benzo[e]benzotriazol-7-yl]methyleneamino]thiourea |
| C-54 | (E)-3-(2-isopropylphenyl)-N-[(E)-[3-[4-(trifluoromethoxy)phenyl]benzo[e]benzimidazol-7-yl]methyleneamino]-1,3-thiazinan-2-imine |
| C-55 | 1-(5-chloro-2-pyridyl)ethyl N-[3-[4-(trifluoromethoxy)phenyl]benzo[e]benzimidazol-7-yl]carbamate |
| C-56 | 1-(2,6-dichlorophenyl)-3-[(E)-[3-[4-(trifluoromethoxy)phenyl]benzo[e]benzotriazol-7-yl]methyleneamino]thiourea |
| C-57 | 1-(2,6-dimethylphenyl)-3-[1-[3-[4-(trifluoromethoxy)phenyl]-4,5-dihydrobenzo[e]benzimidazol-7-yl]vinylimino]thiourea |
| C-58 | 1-(2,6-dichlorophenyl)-3-[1-[3-[4-(trifluoromethoxy)phenyl]-4,5-dihydrobenzo[e]benzimidazol-7-yl]vinylimino]thiourea |

| | Structure | IUPAC |
|---|---|---|
| C-59 | 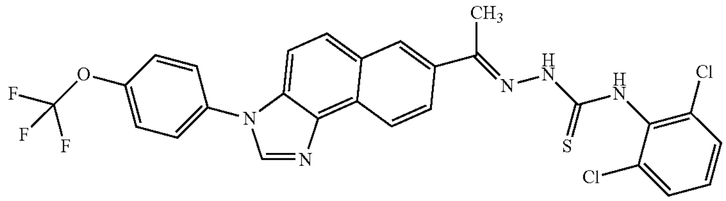 [SMILES: C/C(=N\NC(=S)Nc1c(Cl)cccc1Cl)c1ccc2c(ccc3c2ncn3-c2ccc(OC(F)(F)F)cc2)c1] | 1-(2-chloro-6-methyl-phenyl)-3-[(E)-[3-[4-(trifluoromethoxy)phenyl]benzo[e]benzotriazol-7-yl]methyleneamino]thiourea |
| C-60 | 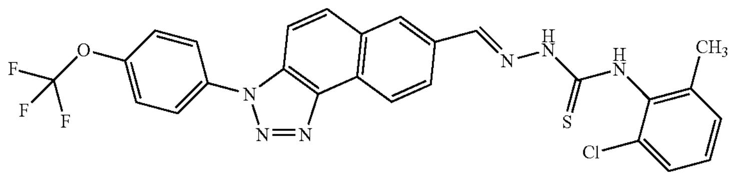 [SMILES: Cc1cccc(Cl)c1NC(=S)N/N=C/c1ccc2c(ccc3c2nnn3-c2ccc(OC(F)(F)F)cc2)c1] | 1-(2,6-diethylphenyl)-3-[(E)-[3-[4-(trifluoromethoxy)phenyl]benzo[e]benzotriazol-7-yl]methyleneamino]thiourea |
| C-61 | 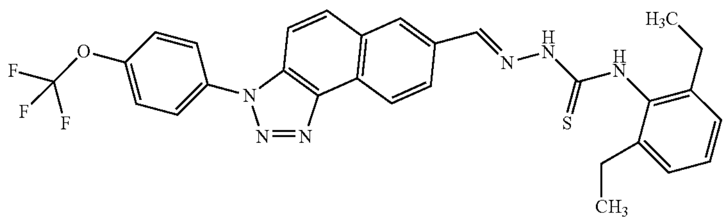 [SMILES: CCc1cccc(CC)c1NC(=S)N/N=C/c1ccc2c(ccc3c2nnn3-c2ccc(OC(F)(F)F)cc2)c1] | 1-(2-ethyl-6-methyl-phenyl)-3-[(E)-[3-[4-(trifluoromethoxy)phenyl]benzo[e]benzotriazol-7-yl]methyleneamino]thiourea |
| C-62 | 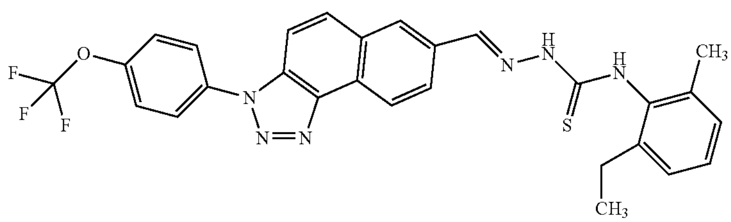 [SMILES: CCc1cccc(C)c1NC(=S)N/N=C/c1ccc2c(ccc3c2nnn3-c2ccc(OC(F)(F)F)cc2)c1] | 1-(3-methyl-2-pyridyl)-3-[(E)-[3-[4-(trifluoromethoxy)phenyl]benzo[e]benzimidazol-7-yl]methyleneamino]thiourea |
| C-63 | 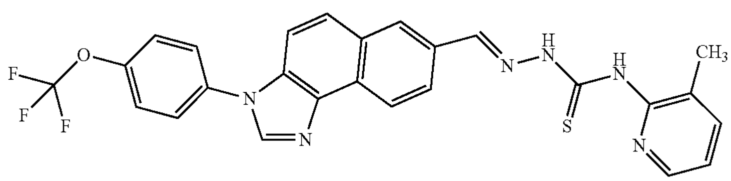 [SMILES: Cc1cccnc1NC(=S)N/N=C/c1ccc2c(ccc3c2ncn3-c2ccc(OC(F)(F)F)cc2)c1] | 1-(2-iodophenyl)-3-[[3-[4-(trifluoromethoxy)phenyl]-5H-benzo[e]benzimidazol-7-ylidene]methylimino]thiourea |
| C-64 | 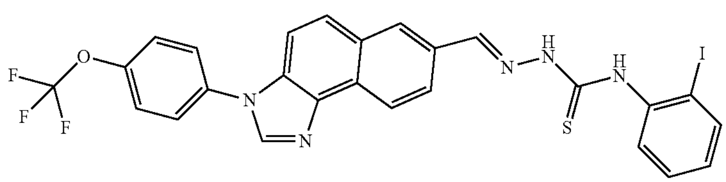 [SMILES: FC(F)(F)Oc1ccc(-n2cnc3c4ccc(/C=N/NC(=S)Nc5ccccc5I)cc4ccc32)cc1] | 1-(2-methoxy-6-methyl-phenyl)-3-[(E)-[3-[4-(trifluoromethoxy)phenyl]benzo[e]benzimidazol-7-yl]methyleneamino]thiourea |
| C-65 | 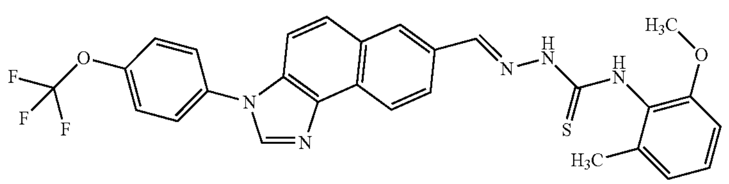 [SMILES: COc1cccc(C)c1NC(=S)N/N=C/c1ccc2c(ccc3c2ncn3-c2ccc(OC(F)(F)F)cc2)c1] | 1-(2,6-dibromophenyl)-3-[(E)-[3-[4-(trifluoromethoxy)phenyl]benzo[e]benzimidazol-7-yl]methyleneamino]thiourea |
| C-66 | 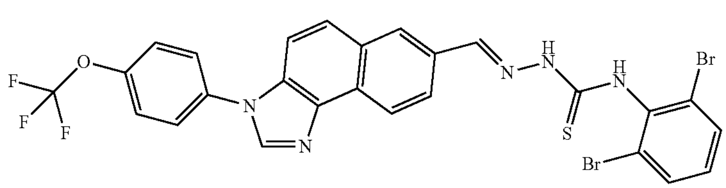 [SMILES: FC(F)(F)Oc1ccc(-n2cnc3c4ccc(/C=N/NC(=S)Nc5c(Br)cccc5Br)cc4ccc32)cc1] | 1-(2-bromophenyl)-3-[[3-[4-(trifluoromethoxy)phenyl]-5H-benzo[e]benzimidazol-7-ylidene]methylimino]thiourea |

-continued

| | Structure | IUPAC |
|---|---|---|
| C-67 | 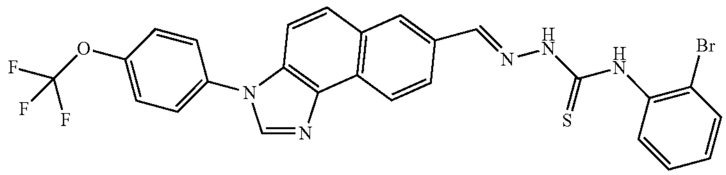 [SMILES: FC(F)(F)Oc1ccc(-n2cnc3c4ccc(/C=N/NC(=S)Nc5ccccc5Br)cc4ccc32)cc1] | 1-(3-ethyl-2-pyridyl)-3-[(E)-[3-[4-(trifluoromethoxy)phenyl]benzo[e]benzimidazol-7-yl]methyleneamino]thiourea |
| C-68 | 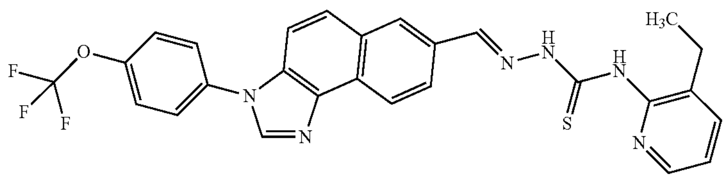 [SMILES: CCc1cccnc1NC(=S)N/N=C/c1ccc2c(ccc3c2ncn3-c2ccc(OC(F)(F)F)cc2)c1] | 1-(3,5-dimethylisoxazol-4-yl)-3-[(E)-[3-[4-(trifluoromethoxy)phenyl]benzo[e]benzimidazol-7-yl]methyleneamino]thiourea |
| C-69 | 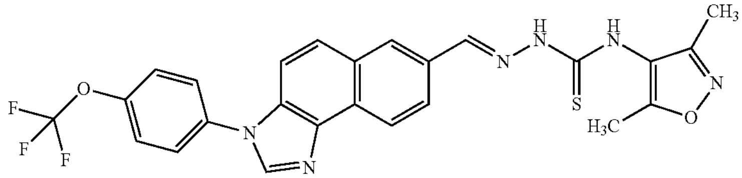 [SMILES: Cc1noc(C)c1NC(=S)N/N=C/c1ccc2c(ccc3c2ncn3-c2ccc(OC(F)(F)F)cc2)c1] | 1-(2,6-diethylphenyl)-3-[(E)-[3-[4-(trifluoromethoxy)phenyl]benzo[e]benzimidazol-7-yl]methyleneamino]thiourea |
| C-70 | 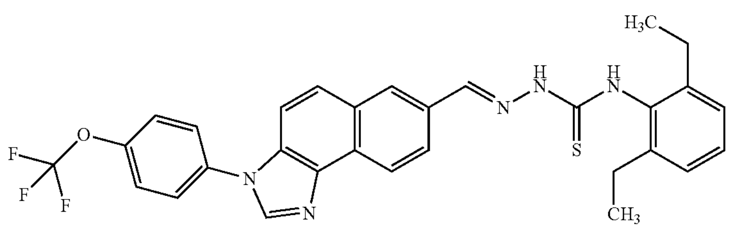 [SMILES: CCc1cccc(CC)c1NC(=S)N/N=C/c1ccc2c(ccc3c2ncn3-c2ccc(OC(F)(F)F)cc2)c1] | 1-(2,6-difluorophenyl)-3-[(E)-[3-[4-(trifluoromethoxy)phenyl]benzo[e]benzimidazol-7-yl]methyleneamino]thiourea |
| C-71 | 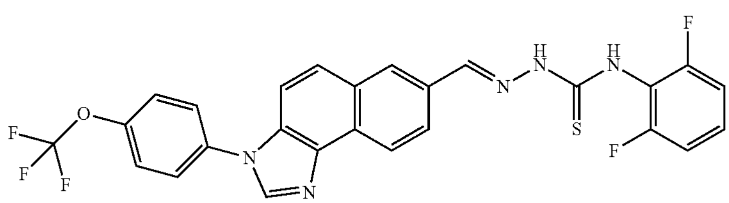 [SMILES: Fc1cccc(F)c1NC(=S)N/N=C/c1ccc2c(ccc3c2ncn3-c2ccc(OC(F)(F)F)cc2)c1] | 1-(2,6-dimethylphenyl)-3-[(E)-[3-[4-(trifluoromethoxy)phenyl]benzo[g][1,2]benzoxazol-7-yl]methyleneamino]thiourea |
| C-72 | 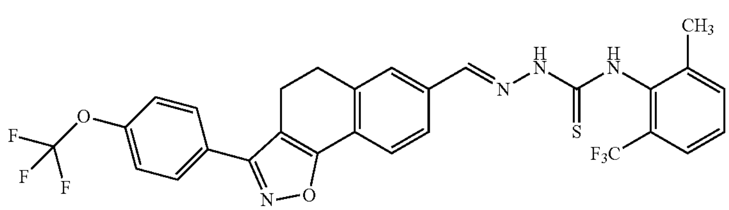 [SMILES: Cc1cccc(C(F)(F)F)c1NC(=S)N/N=C/c1ccc2c(c1)CCc1c(-c3ccc(OC(F)(F)F)cc3)noc1-2] | 1-(3-pyridyl)-3-[(E)-[3-[4-(trifluoromethoxy)phenyl]benzo[e]benzimidazol-7-yl]methyleneamino]thiourea |
| C-73 | 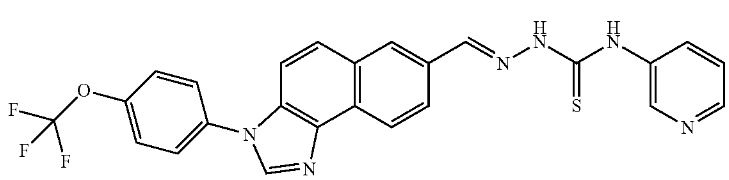 [SMILES: FC(F)(F)Oc1ccc(-n2cnc3c4ccc(/C=N/NC(=S)Nc5cccnc5)cc4ccc32)cc1] | 1-(2-chloro-6-methyl-phenyl)-3-[(E)-[3-[4-(trifluoromethylsulfanyl)phenyl]benzo[e]benzimidazol-7-yl]methyleneamino]thiourea |
| C-74 | 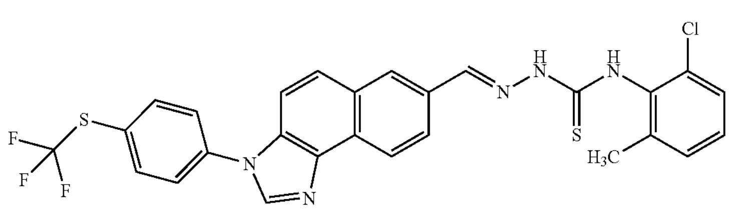 [SMILES: Cc1cccc(Cl)c1NC(=S)N/N=C/c1ccc2c(ccc3c2ncn3-c2ccc(SC(F)(F)F)cc2)c1] | 1-(2,6-dimethylphenyl)-3-[(E)-[3-[4-(trifluoromethylsulfanyl)phenyl]benzo[e]benzimidazol-7-yl]methyleneamino]thiourea |

-continued

| | Structure | IUPAC |
|---|---|---|
| C-75 | 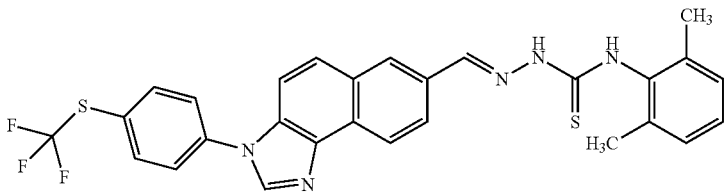 [SMILES: Cc1cccc(C)c1NC(=S)N/N=C/c1ccc2c(ccc3c2ncn3-c2ccc(SC(F)(F)F)cc2)c1] | 1-(2-ethyl-6-methyl-phenyl)-3-[(E)-[3-[4-(trifluoromethylsulfanyl)phenyl]benzo[e]benzimidazol-7-yl]methyleneamino]thiourea |
| C-76 | 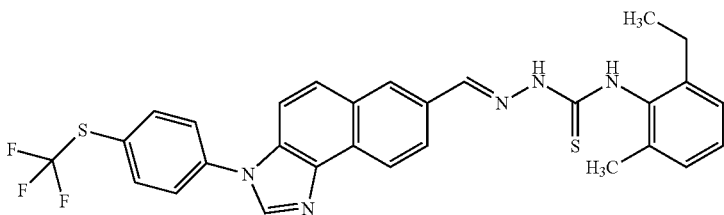 [SMILES: CCc1cccc(C)c1NC(=S)N/N=C/c1ccc2c(ccc3c2ncn3-c2ccc(SC(F)(F)F)cc2)c1] | 1-(2-chloro-6-methyl-phenyl)-3-[(E)-[3-[4-(trifluoromethyl)phenyl]benzo[e]benzimidazol-7-yl]methyleneamino]thiourea |
| C-77 | 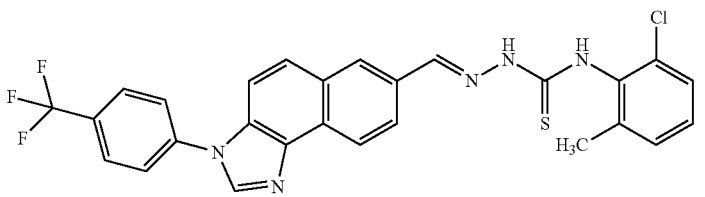 | 1-(2-ethyl-6-methyl-phenyl)-3-[(E)-[3-[4-(trifluoromethyl)phenyl]benzo[e]benzimidazol-7-yl]methyleneamino]thiourea |
| C-78 | 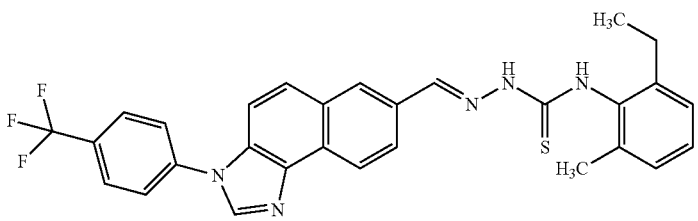 [SMILES: CCc1cccc(C)c1NC(=S)N/N=C/c1ccc2c(ccc3c2ncn3-c2ccc(C(F)(F)F)cc2)c1] | 1-(2-chloro-6-methyl-phenyl)-3-[(E)-[3-[4-(trifluoromethoxy)phenyl]benzo[e]benzimidazol-7-yl]methyleneamino]thiourea |
| C-79 | 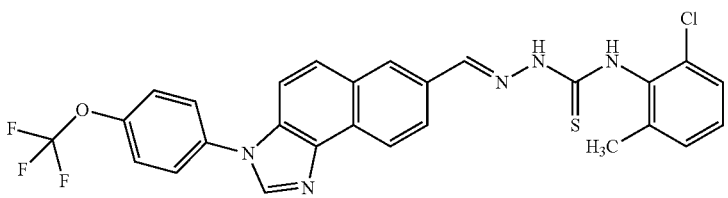 [SMILES: Cc1cccc(Cl)c1NC(=S)N/N=C/c1ccc2c(ccc3c2ncn3-c2ccc(OC(F)(F)F)cc2)c1] | 1-(3,5-dimethylisoxazol-4-yl)-3-[(E)-[3-[4-(trifluoromethoxy)phenyl]benzo[e]benzotriazol-7-yl]methyleneamino]thiourea |
| C-80 | 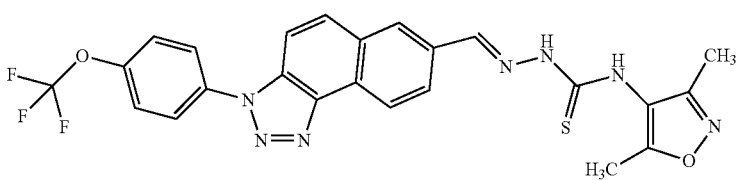 [SMILES: Cc1noc(C)c1NC(=S)N/N=C/c1ccc2c(ccc3c2nnn3-c2ccc(OC(F)(F)F)cc2)c1] | 1-(3-ethyl-2-pyridyl)-3-[(E)-[3-[4-(trifluoromethoxy)phenyl]benzo[e]benzotriazol-7-yl]methyleneamino]thiourea |
| C-81 | 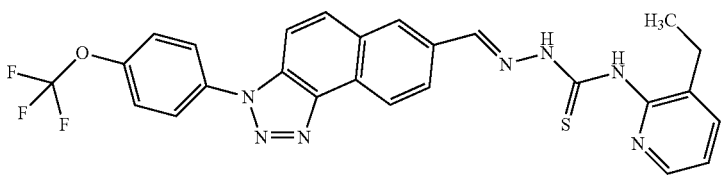 [SMILES: CCc1cccnc1NC(=S)N/N=C/c1ccc2c(ccc3c2nnn3-c2ccc(OC(F)(F)F)cc2)c1] | 1-(2-ethyl-6-methyl-phenyl)-3-[1-[3-[4-(trifluoromethoxy)phenyl]-4,5-dihydrobenzo[e]benzimidazol-7-yl]vinylimino]thiourea |

-continued

| | Structure | IUPAC |
|---|---|---|
| C-82 | 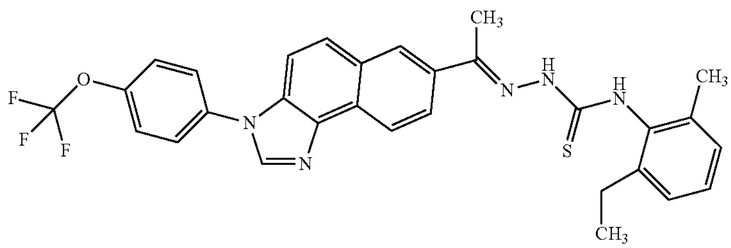 [SMILES: CCc1cccc(C)c1NC(=S)N/N=C(\C)c1ccc2c(ccc3c2ncn3-c2ccc(OC(F)(F)F)cc2)c1] | 1-(2,6-dimethylphenyl)-3-[(E)-[3-[4-(trifluoromethoxy)phenyl]-4,5-dihydrobenzo[g][2,1]benzothiazol-7-yl]methyleneamino]thiourea |
| C-83 | 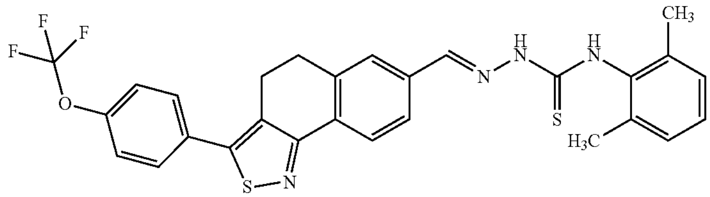 [SMILES: Cc1cccc(C)c1NC(=S)N/N=C/c1ccc2c(c1)CCc1c-2nsc1-c1ccc(OC(F)(F)F)cc1] | 1-(2,6-dimethylphenyl)-3-[(E)-[3-[4-(trifluoromethoxy)phenyl]benzo[g][2,1]benzoxazol-7-yl]methyleneamino]thiourea |
| C-84 | 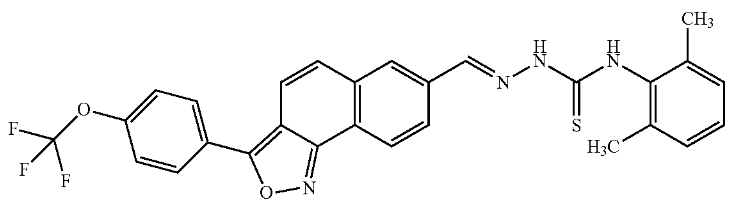 [SMILES: Cc1cccc(C)c1NC(=S)N/N=C/c1ccc2c(ccc3c(-c4ccc(OC(F)(F)F)cc4)onc32)c1] | 3-(2,6-dimethylphenyl)-1-methyl-1-[(E)-[3-[4-(trifluoromethoxy)phenyl]benzo[e]benzimidazol-7-yl]methyleneamino]thiourea |
| C-85 | 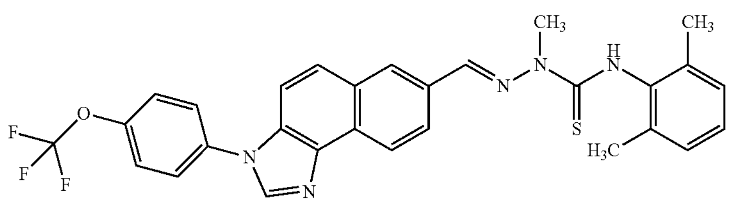 [SMILES: Cc1cccc(C)c1NC(=S)N(C)/N=C/c1ccc2c(ccc3c2ncn3-c2ccc(OC(F)(F)F)cc2)c1] | 1-(2,6-dimethylphenyl)-3-[(E)-[3-[4-(trifluoromethyl)phenyl]benzo[e]benzimidazol-7-yl]methyleneamino]thiourea |
| C-86 | 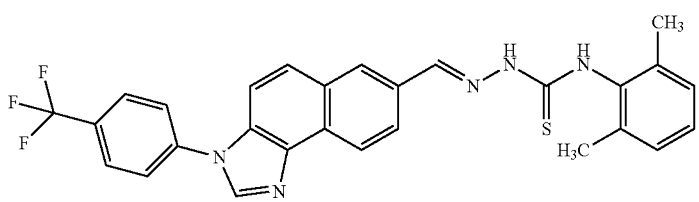 [SMILES: Cc1cccc(C)c1NC(=S)N/N=C/c1ccc2c(ccc3c2ncn3-c2ccc(C(F)(F)F)cc2)c1] | 1-methyl-3-(o-tolyl)-1-[(E)-[3-[4-(trifluoromethoxy)phenyl]benzo[e]benzimidazol-7-yl]methyleneamino]thiourea |
| C-87 | 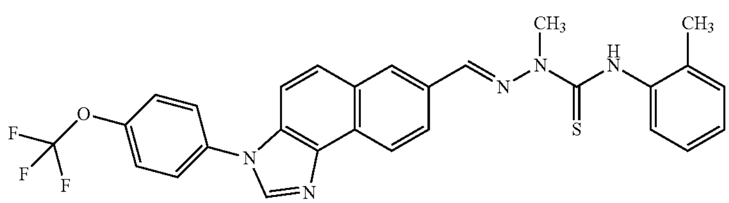 [SMILES: Cc1ccccc1NC(=S)N(C)/N=C/c1ccc2c(ccc3c2ncn3-c2ccc(OC(F)(F)F)cc2)c1] | 1-(2,6-dimethylphenyl)-3-[(E)-[3-[4-(trifluoromethoxy)phenyl]benzo[g][2,1]benzothiazol-7-yl]methyleneamino]thiourea |
| C-88 | 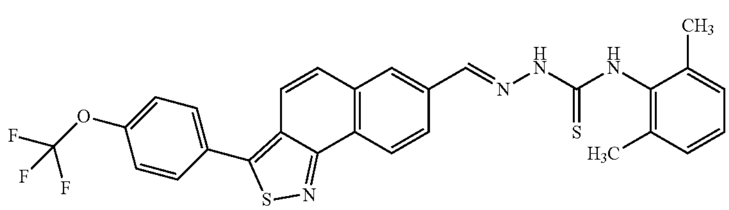 [SMILES: Cc1cccc(C)c1NC(=S)N/N=C/c1ccc2c(ccc3c(-c4ccc(OC(F)(F)F)cc4)snc32)c1] | 1-phenyl-3-[(E)-[3-[4-(trifluoromethoxy)phenyl]benzo[e]benzimidazol-7-yl]methyleneamino]urea |

-continued

| | Structure | IUPAC |
|---|---|---|
| C-89 | 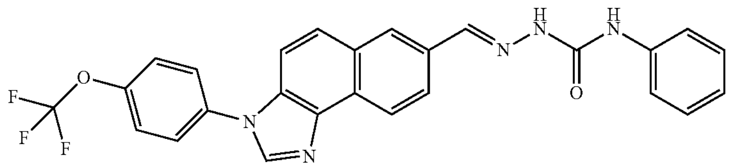 [SMILES: O=C(N/N=C/c1ccc2c(ccc3c2ncn3-c2ccc(OC(F)(F)F)cc2)c1)Nc1ccccc1] | 3-(o-tolyl)-1-[[3-[4-(trifluoromethoxy)phenyl]-8H-benzo[e]benzimidazol-7-ylidene]methylimino]isourea |
| C-90 | 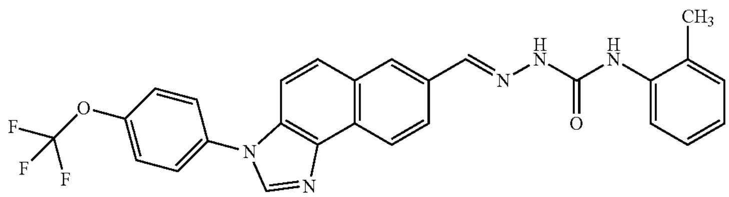 [SMILES: Cc1ccccc1NC(=O)N/N=C/c1ccc2c(ccc3c2ncn3-c2ccc(OC(F)(F)F)cc2)c1] | 1-(2-chloro-6-methyl-phenyl)-3-[(E)-[2-methyl-3-[4-(trifluoromethoxy)phenyl]benzo[g]indazol-7-yl]methyleneamino]thiourea |
| C-91 | 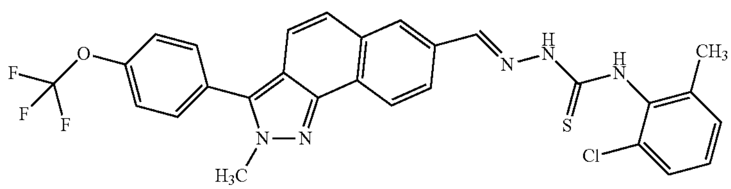 | 1-(2-ethyl-6-methyl-phenyl)-3-[(E)-[2-methyl-3-[4-(trifluoromethoxy)phenyl]benzo[g]indazol-7-yl]methyleneamino]thiourea |
| C-92 | 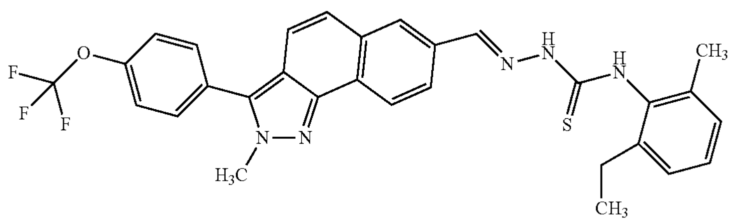 [SMILES: CCc1cccc(C)c1NC(=S)N/N=C/c1ccc2c(ccc3c(-c4ccc(OC(F)(F)F)cc4)n(C)nc32)c1] | 1-(2,6-diethylphenyl)-3-[(E)-[2-methyl-3-[4-(trifluoromethoxy)phenyl]benzo[g]indazol-7-yl]methyleneamino]thiourea |
| C-93 | 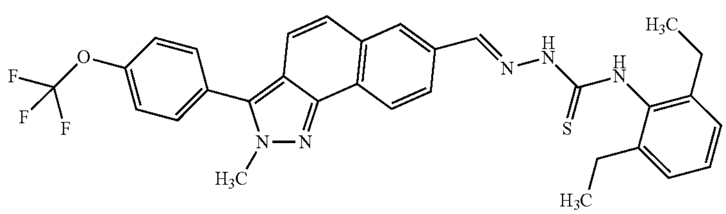 [SMILES: CCc1cccc(CC)c1NC(=S)N/N=C/c1ccc2c(ccc3c(-c4ccc(OC(F)(F)F)cc4)n(C)nc32)c1] | 1-(2,6-dimethylphenyl)-3-[(E)-[2-methyl-3-[4-(trifluoromethoxy)phenyl]-3,3a,4,5-tetrahydrobenzo[g]indazol-7-yl]methyleneamino]thiourea |
| C-94 | 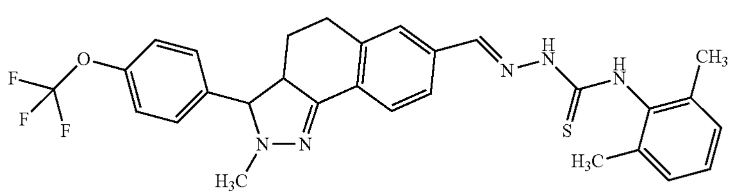 [SMILES: Cc1cccc(C)c1NC(=S)N/N=C/c1ccc2c(c1)CCC1C2=NN(C)C1c1ccc(OC(F)(F)F)cc1] | 1-(2,6-dichlorophenyl)-3-[(E)-[2-methyl-3-[4-(trifluoromethoxy)phenyl]-3,3a,4,5-tetrahydrobenzo[g]indazol-7-yl]methyleneamino]thiourea |
| C-95 | 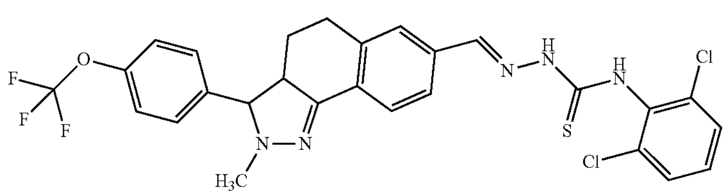 [SMILES: CN1N=C2c3ccc(/C=N/NC(=S)Nc4c(Cl)cccc4Cl)cc3CCC2C1c1ccc(OC(F)(F)F)cc1] | 1-(2,6-dimethylphenyl)-3-[(E)-[2-methyl-3-[4-(trifluoromethoxy)phenyl]benzo[g]indazol-7-yl]methyleneamino]thiourea |
| C-96 | 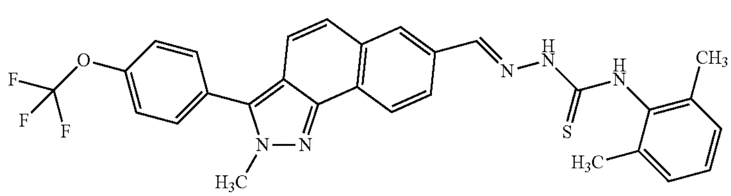 [SMILES: Cc1cccc(C)c1NC(=S)N/N=C/c1ccc2c(ccc3c(-c4ccc(OC(F)(F)F)cc4)n(C)nc32)c1] | 1-(2-methoxy-6-methyl-phenyl)-3-[(E)-[2-methyl-3-[4-(trifluoromethoxy)phenyl]benzo[g]indazol-7-yl]methyleneamino]thiourea |

| Structure | IUPAC |
|---|---|
| C-97 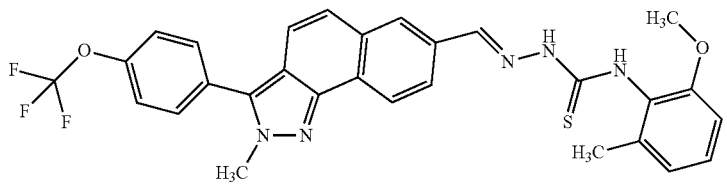 [SMILES: COc1cccc(C)c1NC(=S)N/N=C/c1ccc2c(ccc3c(-c4ccc(OC(F)(F)F)cc4)n(C)nc32)c1] | 1-(2,6-dibromophenyl)-3-[(E)-[2-methyl-3-[4-(trifluoromethoxy)phenyl]benzo[g]indazol-7-yl]methyleneamino]thiourea |
| C-98 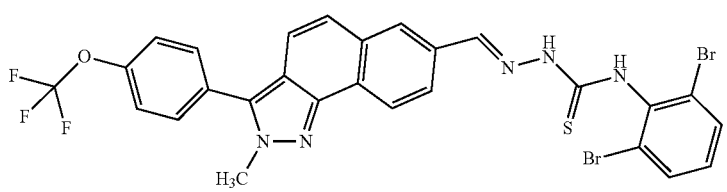 | 1-(2,6-dichlorophenyl)-3-[(E)-[2-methyl-3-[4-(trifluoromethoxy)phenyl]benzo[g]indazol-7-yl]methyleneamino]thiourea |
| C-99 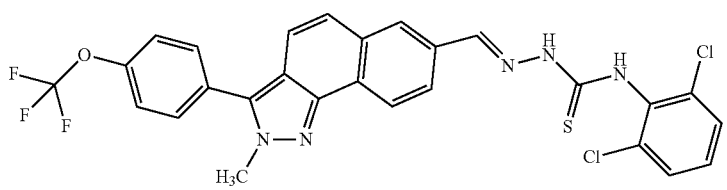 [SMILES: Cn1nc2c(ccc3cc(/C=N/NC(=S)Nc4c(Br)cccc4Br)ccc32)c1-c1ccc(OC(F)(F)F)cc1] | 3-(2-chlorophenyl)-1-[[3-[4-(trifluoromethoxy)phenyl]-8H-benzo[e]benzimidazol-7-ylidene]methylimino]isourea |
| C-100 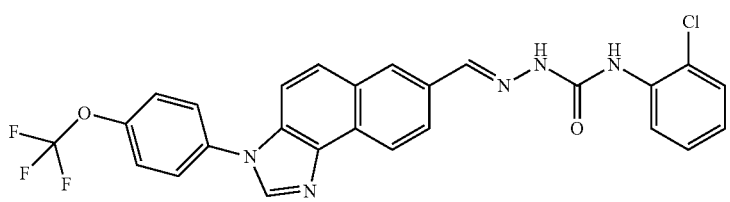 [SMILES: O=C(N/N=C/c1ccc2c(ccc3c2ncn3-c2ccc(OC(F)(F)F)cc2)c1)Nc1ccccc1Cl] | 1-(3-methyl-2-pyridyl)-3-[(E)-[2-methyl-3-[4-(trifluoromethoxy)phenyl]benzo[g]indazol-7-yl]methyleneamino]thiourea |
| C-101 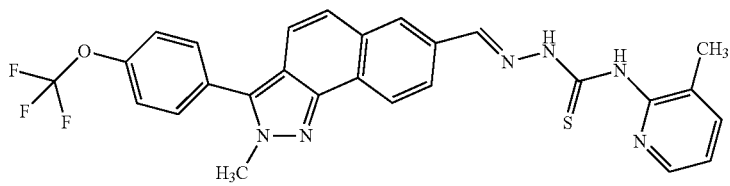 [SMILES: Cc1cccnc1NC(=S)N/N=C/c1ccc2c(ccc3c(-c4ccc(OC(F)(F)F)cc4)n(C)nc32)c1] | 1-(3-iodo-2-pyridyl)-3-[(E)-[2-methyl-3-[4-(trifluoromethoxy)phenyl]benzo[g]indazol-7-yl]methyleneamino]thiourea |
| C-102 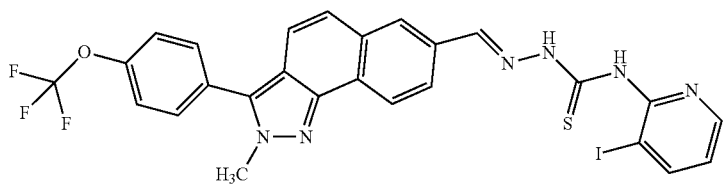 [SMILES: Cn1nc2c(ccc3cc(/C=N/NC(=S)Nc4ncccc4I)ccc32)c1-c1ccc(OC(F)(F)F)cc1] | 1-(2-methyl-6-methylsulfanyl-phenyl)-3-[(E)-[3-[4-(trifluoromethoxy)phenyl]benzo[e]benzimidazol-7-yl]methyleneamino]thiourea |
| C-103 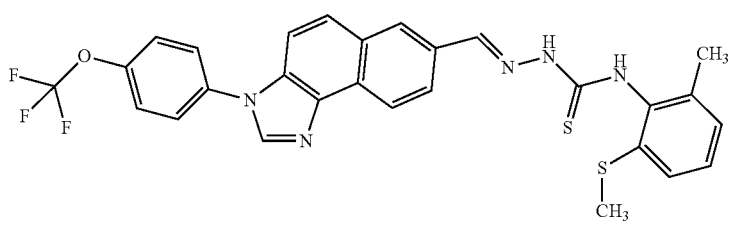 [SMILES: CSc1cccc(C)c1NC(=S)N/N=C/c1ccc2c(ccc3c2ncn3-c2ccc(OC(F)(F)F)cc2)c1] | 1-(2-methyl-6-methylsulfinyl-phenyl)-3-[(E)-[3-[4-(trifluoromethoxy)phenyl]benzo[e]benzimidazol-7-yl]methyleneamino]thiourea |

-continued

| | Structure | IUPAC |
|---|---|---|
| C-104 | 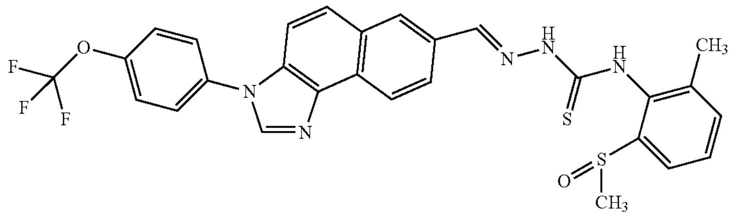 [SMILES: Cc1cccc(S(C)=O)c1NC(=S)N/N=C/c1ccc2c(ccc3c2ncn3-c2ccc(OC(F)(F)F)cc2)c1] | 1-(2,6-dimethylphenyl)-3-[(E)-[3-(p-tolyl)benzo[e]benzimidazol-7-yl]methyleneamino]thiourea |
| C-105 | 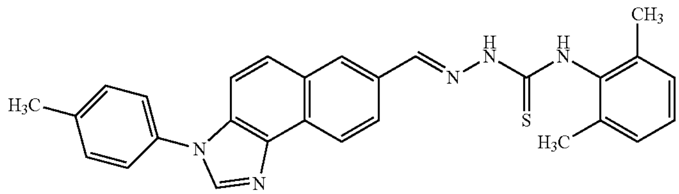 [SMILES: Cc1ccc(-n2cnc3c4ccc(/C=N/NC(=S)Nc5c(C)cccc5C)cc4ccc32)cc1] | 1-[(E)-[3-(4-chlorophenyl)benzo[e]benzimidazol-7-yl]methyleneamino]-3-(2,6-dimethylphenyl)thiourea |
| C-106 | 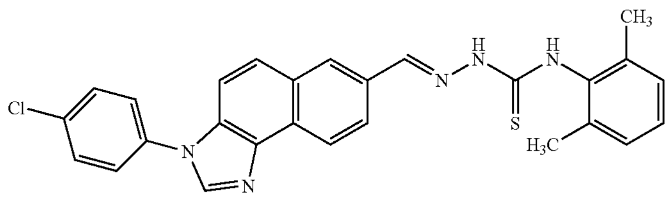 [SMILES: Cc1cccc(C)c1NC(=S)N/N=C/c1ccc2c(ccc3c2ncn3-c2ccc(Cl)cc2)c1] | 1-(2,6-dimethylphenyl)-3-[(E)-[2-methyl-3-[4-(trifluoromethoxy)phenyl]-4,5-dihydrobenzo[g]indazol-7-yl]methyleneamino]thiourea |
| C-107 | 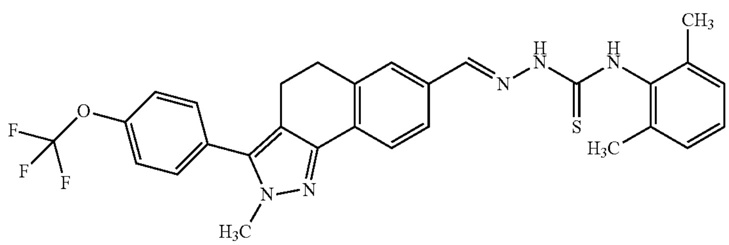 [SMILES: Cc1cccc(C)c1NC(=S)N/N=C/c1ccc2c(c1)CCc1c-2nn(C)c1-c1ccc(OC(F)(F)F)cc1] | 1-(2,6-dimethylphenyl)-3-[(E)-[3-[6-(trifluoromethyl)-3-pyridyl]benzo[e]benzimidazol-7-yl]methyleneamino]thiourea |
| C-108 | 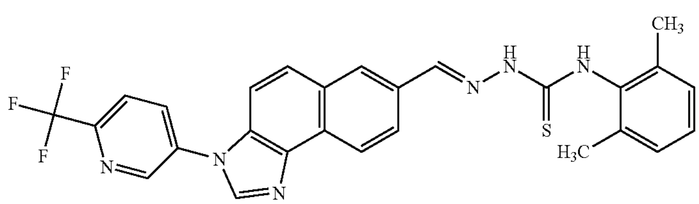 [SMILES: Cc1cccc(C)c1NC(=S)N/N=C/c1ccc2c(ccc3c2ncn3-c2ccc(C(F)(F)F)nc2)c1] | 1-(2,6-dimethylphenyl)-3-[(E)-[3-[5-(trifluoromethyl)-2-pyridyl]benzo[e]benzimidazol-7-yl]methyleneamino]thiourea |
| C-109 | 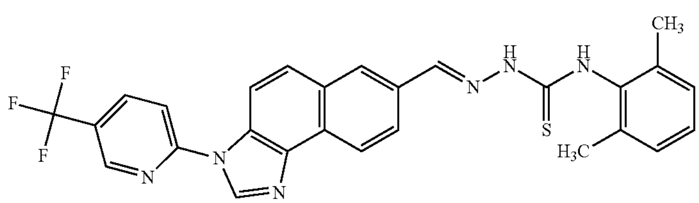 [SMILES: Cc1cccc(C)c1NC(=S)N/N=C/c1ccc2c(ccc3c2ncn3-c2ccc(C(F)(F)F)cn2)c1] | 1-(2,6-dimethylphenyl)-3-[(E)-[3-[4-(1,1,2,2,2-pentafluoroethyl)phenyl]benzo[e]benzimidazol-7-yl]methyleneamino]thiourea |
| C-110 | 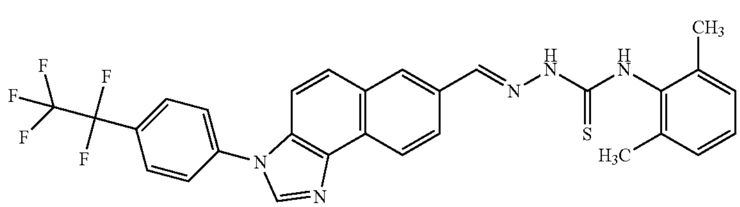 [SMILES: Cc1cccc(C)c1NC(=S)N/N=C/c1ccc2c(ccc3c2ncn3-c2ccc(C(F)(F)C(F)(F)F)cc2)c1] | 1-[[3-(3,5-dichlorophenyl)-9aH-benzo[e]benzimidazol-7-ylidene]methylimino]-3-(2,6-dimethylphenyl)isothiourea |

-continued

| Structure | IUPAC |
|---|---|
| C-111 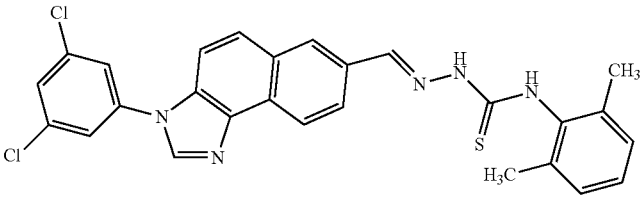 [SMILES: Cc1cccc(C)c1NC(=S)N/N=C/c1ccc2c(ccc3c2ncn3-c2cc(Cl)cc(Cl)c2)c1] | 1-[[3-[3-chloro-5-(trifluoromethyl)-2-pyridyl]-3aH-benzo[e]benzimidazol-7-ylidene]methylimino]-3-(2,6-dimethylphenyl)thiourea |
| C-112 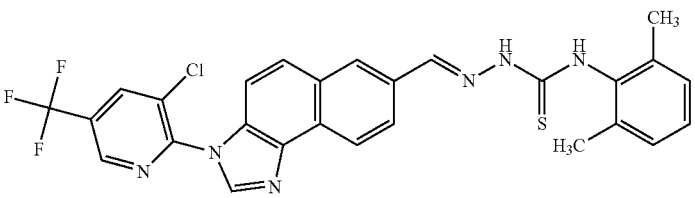 [SMILES: Cc1cccc(C)c1NC(=S)N/N=C/c1ccc2c(ccc3c2ncn3-c2ncc(C(F)(F)F)cc2Cl)c1] | 1-(2,6-dimethylphenyl)-3-[[3-[2-fluoro-4-(trifluoromethyl)phenyl]-3aH-benzo[e]benzimidazol-7-ylidene]methylimino]thiourea |
| C-113 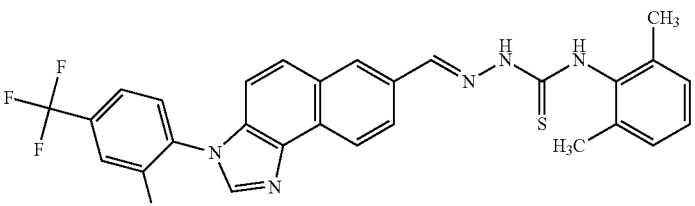 | 1-[[3-[2-chloro-4-(trifluoromethyl)phenyl]-3aH-benzo[e]benzimidazol-7-ylidene]methylimino]-3-(2,6-dimethylphenyl)thiourea |
| C-114 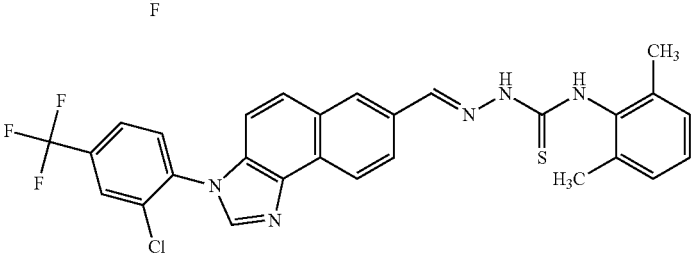 | (1Z)-1-[4-hydroxy-3-(2-isopropylphenyl)thiazol-2-ylidene]-3-[3-[4-(trifluoromethoxy)phenyl]-9aH-benzo[e]benzimidazol-7-ylidene]urea |
| C-115 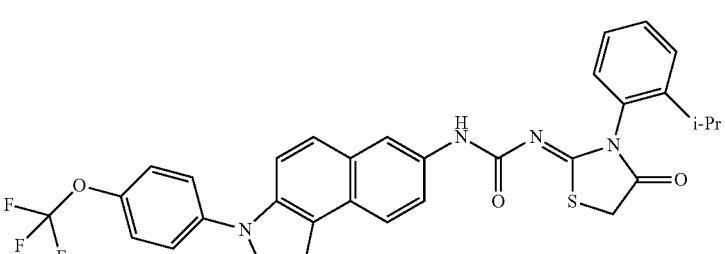 | (1Z)-1-[4-oxo-3-[2-(trifluoromethyl)phenyl]thiazolidin-2-ylidene]-3-[3-[4-(trifluoromethoxy)phenyl]-8H-benzo[e]benzimidazol-7-ylidene]urea |
| C-116 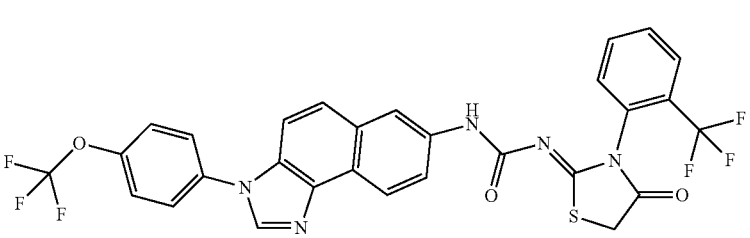 [SMILES: O=C(/N=C1\SCC(=O)N1c1ccccc1C(F)(F)F)Nc1ccc2c(ccc3c2ncn3-c2ccc(OC(F)(F)F)cc2)c1] | 3-[N-(2-isopropylphenyl)-C-sulfanyl-carbonimidoyl]-1-[3-[4-(trifluoromethoxy)phenyl]-9aH-benzo[e]benzimidazol-7-ylidene]isourea |
| C-117 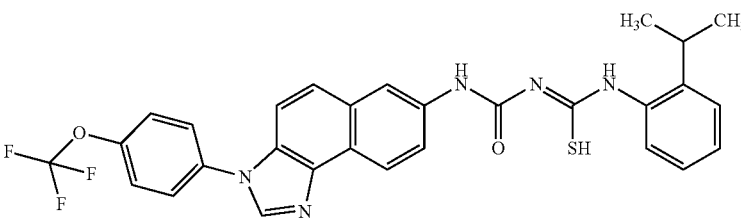 [SMILES: CC(C)c1ccccc1N/C(S)=N/C(=O)Nc1ccc2c(ccc3c2ncn3-c2ccc(OC(F)(F)F)cc2)c1] | (2Z)-3-(2,6-dimethylphenyl)-5,5-dimethyl-2-[(E)-[3-[4-(trifluoromethoxy)phenyl]benzo[e]benzimidazol-7-yl]methylenehydrazono]thiazolidin-4-one |

-continued

| Structure | IUPAC |
|---|---|
| C-118 | (2Z)-3-(2,6-dimethylphenyl)-2-[(E)-[3-[4-(trifluoromethoxy)phenyl]benzo[e]benzimidazol-7-yl]methylenehydrazono]thiazolidin-4-one |
| C-119 | (E)-3-(2,6-dimethylphenyl)-N-[(E)-[3-[4-(trifluoromethoxy)phenyl]benzo[e]benzimidazol-7-yl]methyleneamino]-1,3-thiazinan-2-imine |
| C-120 | (2Z)-3-(2,6-dimethylphenyl)-5-methyl-2-[(E)-[3-[4-(trifluoromethoxy)phenyl]benzo[e]benzimidazol-7-yl]methylenehydrazono]thiazolidin-4-one |
| C-121 | (E)-3-(2,6-dimethylphenyl)-N-[(E)-[3-[4-(trifluoromethoxy)phenyl]benzo[e]benzimidazol-7-yl]methyleneamino]thiazolidin-2-imine |
| C-122 | 1-(2-pyridyl)ethyl N-[3-[4-(trifluoromethoxy)phenyl]benzo[e]benzimidazol-7-yl]carbamate |
| C-123 | 1-(2-methoxyphenyl)ethyl N-[3-[4-(trifluoromethoxy)phenyl]-9aH-benzo[e]benzimidazol-7-ylidene]carbamate |

-continued

| Structure | IUPAC |
|---|---|
| C-124 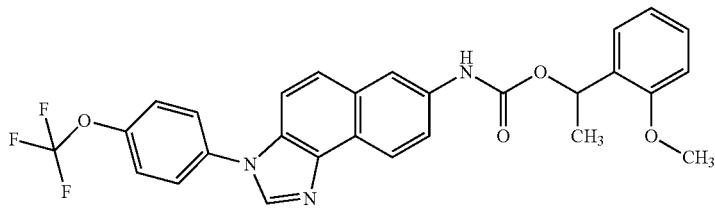 [SMILES: COc1ccccc1C(C)OC(=O)Nc1ccc2c(ccc3c2ncn3-c2ccc(OC(F)(F)F)cc2)c1] | 1-(2,4-difluorophenyl)ethyl N-[3-[4-(trifluoromethoxy)phenyl]benzo[e]benzimidazol-7-yl]carbamate |
| C-125 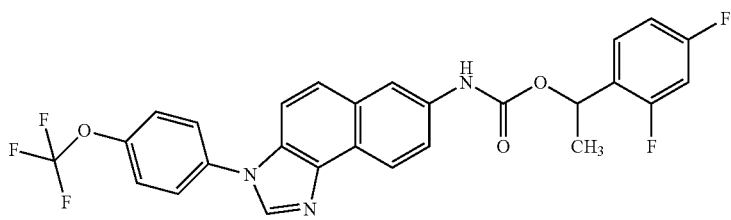 [SMILES: CC(OC(=O)Nc1ccc2c(ccc3c2ncn3-c2ccc(OC(F)(F)F)cc2)c1)c1ccc(F)cc1F] | o-tolyl N-[3-[4-(trifluoromethoxy)phenyl]-9aH-benzo[e]benzimidazol-7-ylidene]carbamate |
| C-126 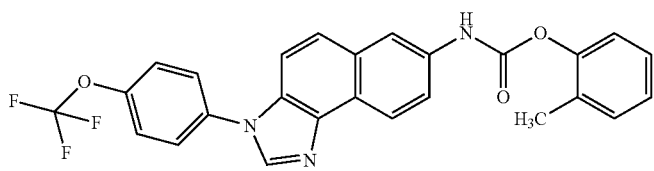 [SMILES: Cc1ccccc1OC(=O)Nc1ccc2c(ccc3c2ncn3-c2ccc(OC(F)(F)F)cc2)c1] | 1-(2-isopropylphenyl)-3-[[2-methyl-3-[4-(trifluoromethoxy)phenyl]-4,9a-dihydrochromeno[4,3-c]pyrazol-7-ylidene]methylimino]thiourea |
| C-127 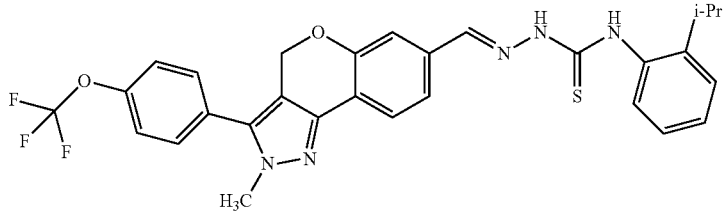 [SMILES: CC(C)c1ccccc1NC(=S)N/N=C/c1ccc2c(c1)OCc1c-2nn(C)c1-c1ccc(OC(F)(F)F)cc1] | (2Z)-3-(2,6-dimethylphenyl)-2-[(E)-[2-methyl-3-[4-(trifluoromethoxy)phenyl]-4H-chromeno[4,3-c]pyrazol-7-yl]methylenehydrazono]thiazolidin-4-one |
| C-128 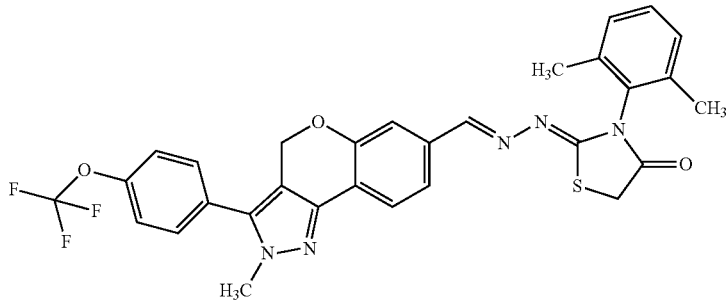 [SMILES: Cc1cccc(C)c1N1C(=O)CS/C1=N\N=C\c1ccc2c(c1)OCc1c-2nn(C)c1-c1ccc(OC(F)(F)F)cc1] | 1-(2,6-dimethylphenyl)-3-[(E)-[2-methyl-3-[4-(trifluoroethoxy)phenyl]benzo[e]benzimidazol-7-yl]methyleneamino]thiourea |
| C-129 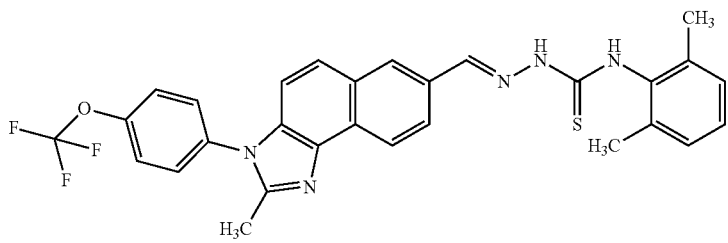 [SMILES: Cc1cccc(C)c1NC(=S)N/N=C/c1ccc2c(ccc3c2nc(C)n3-c2ccc(OC(F)(F)F)cc2)c1] | 3-(2-isopropylphenyl)-1-[[2-methyl-3-[4-(trifluoromethoxy)phenyl]-5H-benzo[e]benzimidazol-7-ylidene]methylimino]isothiourea |

| Structure | IUPAC |
|---|---|
| C-130 | (2Z)-3-(2,6-dimethylphenyl)-2-[(E)-[2-methyl-3-[4-(trifluoromethoxy)phenyl]benzo[e]benzimidazol-7-yl]methylenehydrazono]thiazolidin-4-one |
| C-131 | 1-(2,6-dimethylphenyl)-3-[(E)-[2-methyl-3-[4-(trifluoromethoxy)phenyl]-4H-chromeno[4,3-c]pyrazol-7-yl]methyleneamino]thiourea |
| C-132 | 1-(2,6-dimethylphenyl)-3-[(E)-[3-[4-(trifluoromethoxy)phenyl]benzo[e]benzimidazol-7-yl]methyleneamino]thiourea |

Example 1

1-(2,6-dimethylphenyl)-3-[(E)-[3-[4-(trifluoromethoxy)phenyl]benzo[e]benzimidazol-7-yl]methyleneamino]thiourea (compound C-1)

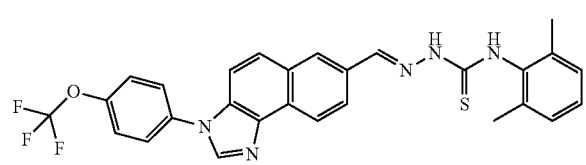 [SMILES: Cc1cccc(C)c1NC(=S)N/N=C/c1ccc2c(ccc3c2ncn3-c2ccc(OC(F)(F)F)cc2)c1]

Step 1: 7-bromo-3H-benzo[e]benzimidazole

A stirred solution of 6-bromonaphthalene-1,2-diamine (prepared as described in WO 2011/087740; 0.6 g, 2.5 mmol) in formic acid (5 mL) was heated at 80° C. for 16 h. The reaction mixture was then concentrated to dryness. The concentrate was triturated with 1:1 $CH_2Cl_2$/EtOAc and the resultant brown precipitate was isolated by filtration to give 200 mg (32% yield) of the title compound. The title compound was used without further purification in the next step. LC/MS (method 1): $R_t$: 0.76 min; MS: m/z=247 (M)$^+$; $^1$H NMR (DMSO-$d_6$): 9.4 (s, 1 H), 8.57 (d, 1H), 8.45 (s, 1 H), 7.87-8.03 (m, 3 H)

Step 2: 7-bromo-3-[4-(trifluoromethoxy)phenyl]benzo[e]benzimidazole

A solution of the product of step 1 (0.5 g, 2.0 mmol), [4-(trifluoromethoxy)phenyl]-boronic acid (0.62 g, 3.0 mmol), copper (II) acetate (0.37 g, 2.0 mmol) and triethylamine (0.5 g, 5.0 mmol) in 1:1 pyridine/THF (10 mL) was stirred at room temperature for 16 h and then at 55° C. for additional 24 h. The reaction mixture was then concentrated to dryness, diluted with $CH_2Cl_2$ and washed with an aqueous solution of citric acid (10%) and a saturated aqueous solution of copper sulfate. The organic layer was dried ($MgSO_4$), concentrated and purified by column chromatography eluting with a gradient of cyclohexane/EtOAc to afford 7-bromo-3-[4-(trifluoromethoxy)phenyl]-benzo[e]benzimidazole (120 mg, 15% yield). LC/MS (method 1): $R_t$=1.29 min; MS: m/z=407 (M$^+$).

Step 3: 3-[4-(trifluoromethoxy)phenyl]-7-vinyl-benzo[e]benzimidazole

A stirred solution of the product of step 2 (150 mg, 0.37 mmol), tributyl(vinyl)tin (0.18 g, 0.55 mmol) and (1,1'-bis(diphenylphosphino)ferrocene)palladium(II) dichloride (53 mg, 0.07 mmol) in toluene (10 mL) was heated 100° C. for 16 h. The reaction mixture was then diluted with toluene and washed with a saturated aqueous solution of potassium fluoride. The organic layer was dried ($MgSO_4$), concentrated and purified by column chromatography eluting with a gradient of cyclohexane/EtOAc to afford 3-[4-(trifluoromethoxy)phenyl]-7-vinyl-benzo[e]benzimidazole (100 mg, 77% yield). LC/MS (method 1): Rt=1.19 min; MS: m/z=355 (M+1).

Step 4: 3-[4-(trifluoromethoxy)phenyl]benzo[e]benzimidazole-7-carbaldehyde

A solution of the product of step 4 (100 mg, 0.28 mmol), osmium tetroxide (0.05 mL, 2.5% in t-BuOH), sodium periodate (0.18 g, 0.85 mmol) in 1:1 THF/water (2 mL) was stirred at room temperature for 16 h. The reaction mixture was concentrated, diluted with EtOAc and then water was added. The organic phase was dried (MgSO$_4$), concentrated and purified by column chromatography eluting with a gradient of cyclohexane/EtOAc to afford 3-[4-(trifluoromethoxy)phenyl]benzo[e]benzimidazole-7-carbaldehyde (50 mg, 50% yield). LC/MS (method 1): Rt=1.12 min; MS: m/z=357 (M+1).

Step 5: 1-(2,6-dimethylphenyl)-3-[(E)-[3-[4-(trifluoromethoxy)phenyl]benzo[e]benzimidazol-7-yl]methyleneamino]thiourea A stirred solution of the product of step 4 (50 mg, 0.14 mmol) and 1-amino-3-(2,6-dimethylphenyl)thiourea (82 mg, 0.42 mmol) was heated at 70° C. for 16 h. The reaction mixture was then concentrated and purified by column chromatography eluting with a gradient of dichloromethane/methanol to afford 1-(2,6-dimethylphenyl)-3-[(E)-[3-[4-(trifluoromethoxy)phenyl]benzo[e]benzimidazol-7-yl]methyleneamino]thiourea (40 mg, 48% yield). LC/MS (method 1): Rt=1.24 min; MS: m/z=534 (M+1).

Example 2

1-(4-bromo-2,6-dimethyl-phenyl)-3-[(E)-[3-[4-(trifluoromethoxy)phenyl]-4,5-dihydrobenzo[g][2,1]benzoxazol-7-yl]methyleneamino]thiourea (compound C-6)

filtered and concentrated under reduced pressure to afford a brown oil (4.6 g) which was used without further purification. A portion (3.6 g) of resultant brown oil was dissolved in toluene (50 mL), TsOH (100 mg) was added and the stirred mixture was heated at 50° C. for 5 h. The reaction mixture was then concentrated and purified by flash chromatography eluting with a gradient of cyclohexane/EtOAc to afford 7-bromo-3-[4-(trifluoromethoxy)phenyl]-4,5-dihydrobenzo[g][2,1]benzoxazole (3.4 g 98% yield) as a white solid.

Step 2: 3-[4-(trifluoromethoxy)phenyl]-7-vinyl-4,5-dihydrobenzo[g][2,1]benzoxazole A stirred solution of the product of step 1 (3.4 g, 8.3 mmol), tributyl(vinyl)tin (3.94 g, 12.3 mmol) and (1,1'-bis(diphenylphosphino)ferrocene)palladium(II) dichloride (1.12 g, 1.66 mmol) in toluene (100 mL) was heated 100° C. for 16 h. The reaction mixture was then diluted with toluene and washed with a saturated aqueous solution of potassium fluoride. The organic layer was dried (MgSO$_4$), concentrated and purified by column chromatography eluting with a gradient of cyclohexane/EtOAc to afford (3-[4-(trifluoromethoxy)phenyl]-7-vinyl-4,5-dihydrobenzo[g][2,1]benzoxazole, 3.0 g 99% yield). LC/MS (method 1): Rt=1.50 min; MS: m/z=358 (M+).

Step 3: 3-[4-(trifluoromethoxy)phenyl]-4,5-dihydrobenzo[g][2,1]benzoxazole-7-carbaldehyde A solution of the product of step 2 (3.0 g), osmium tetroxide (1 mL, 2.5% in t-BuOH), sodium periodate (4.31 g, 3 mmol) in 1:1 THF/water (20 mL) was stirred at room temperature for 16 h. The reaction mixture was concentrated, diluted with EtOAc and then water was added. The organic phase was dried (MgSO$_4$), concentrated and purified by column chromatography eluting with a gradient of cyclohexane/EtOAc to afford 3-[4-(trifluoromethoxy)phenyl]-4,5-dihydrobenzo[g][2,1]benzoxazole-7-carbaldehyde (1.7 g 70% yield). LC/MS (method 1): R$_t$=1.21 min; MS: m/z=360 (M+1).

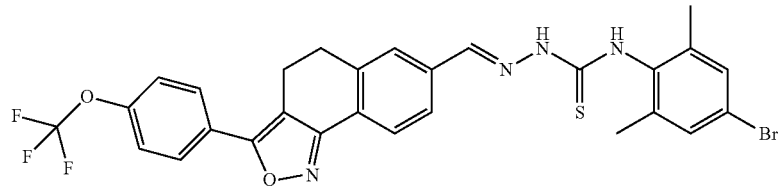 [SMILES: Cc1cc(Br)cc(C)c1NC(=S)N/N=C/c1ccc2c(c1)CCc1c-2noc1-c1ccc(OC(F)(F)F)cc1]

Step 1: 7-bromo-3-[4-(trifluoromethoxy)phenyl]-4,5-dihydrobenzo[g][2,1]benzoxazole To a stirred solution of diisopropylamine (2.6 g, 26 mmol) in THF (25 mL) at −78° C. was added n-BuLi (1.6 M in hexanes, 16 mL, 26 mmol) dropwise over 5 min. After 30 min, the reaction was allowed to warm to 0° C. then a solution of 6-bromotetralin-1-one oxime (2.5 g, 10.4 mmol) in THF (10 mL) was added dropwise. After 15 min, a solution of methyl 4-(trifluoromethoxy)benzoate (2.75 g, 12.5 mmol) in THF (10 mL) was then added and the reaction was stirred at 0° C. for 30 min. The reaction was then quenched with an aqueous solution of NH$_4$Cl and extracted with EtOAc. The organic layer was dried over MgSO4, Step 4: 1-(4-bromo-2,6-dimethyl-phenyl)-3-[(E)-[3-[4-(trifluoromethoxy)phenyl]-4,5-dihydrobenzo[g][2,1]benzoxazol-7-yl]methyleneamino]thiourea A stirred solution of the product of step 3 (100 mg, 0.28 mmol) and 1-amino-3-(4-bromo-2,6-dimethylphenyl)thiourea (91 mg, 0.33 mmol) was heated at 70° C. for 2 h. The reaction was then allowed to cool to room temperature and 1-(4-bromo-2,6-dimethyl-phenyl)-3-[(E)-[3-[4-(trifluoromethoxy)phenyl]-4,5-dihydrobenzo[g][2,1]benzoxazol-7-yl]methyleneamino]thiourea isolated as a precipitate by vacuum filtration (70 mg, 41% yield). LC/MS (method 1): Rt=1.52 min; MS: m/z=616 (M+1). $^1$H NMR (400 MHz, CDCl$_3$) δ 9.53 (s, 1H), 8.55 (s, 1H), 8.06 (d, J=8.1 Hz, 1H), 7.90-7.79 (m, 4H), 7.72-7.62 (m, 2H), 7.44-7.29 (m, 5H), 3.08 (s, 4H), 2.31 (s, 6H).

Example 3

1-(2,6-dimethylphenyl)-3-[(E)-[3-[4-(trifluoromethyl)phenyl]benzo[e]benzimidazol-7-yl]methyleneamino]thiourea (compound C-86)

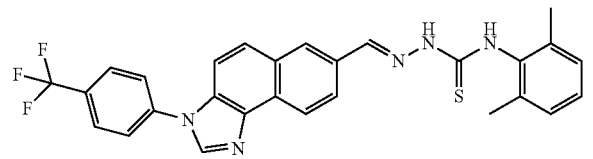 [SMILES: Cc1cccc(C)c1NC(=S)N/N=C/c1ccc2c(ccc3c2ncn3-c2ccc(C(F)(F)F)cc2)c1]

A stirred solution of 3-[4-(trifluoromethyl)phenyl]benzo[e]benzimidazole-7-carbaldehyde (100 mg, 0.28 mmol) and 1-amino-3-(4-bromo-2,6-dimethylphenyl)thiourea (60 mg, 0.31 mmol) was heated at 70° C. in ethanol (3 mL) for 2 h. The reaction was then allowed to cool to room temperature, the precipitate was isolated by filtration purified by column reverse-phase chromatography eluting with a gradient of acetonitrile/water to afford 1-(2,6-dimethylphenyl)-3-[(E)-[3-[4-(trifluoromethyl)phenyl]benzo[e]benzimidazol-7-yl]methyleneamino]thiourea (36 mg, 24% yield). LC/MS (method 1): Rt=1.29 min; MS: m/z=518 (M+). $^1$H NMR (400 MHz, THF-ds) δ 10.90 (s, 1H), 9.37 (s, 1H), 8.64 (d, J=8.6 Hz, 1H), 8.21 (d, J=8.7 Hz, 2H), 8.02-7.91 (m, 4H), 7.81 (d, J=2.2 Hz, 2H), 7.05 (s, 2H), 2.04 (s, 6H).

Example 4

1-(2,6-dimethylphenyl)-3-[(E)-[3-[4-(trifluoromethoxy)phenyl]benzo[g][1,2]benzoxazol-7-yl]methyleneamino]thiourea (compound C-72)

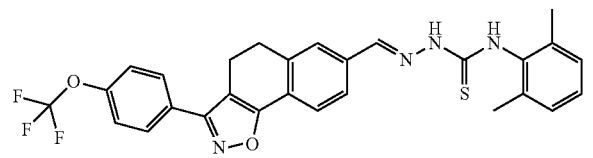 [SMILES: Cc1cccc(C)c1NC(=S)N/N=C/c1ccc2c(c1)CCc1c(-c3ccc(OC(F)(F)F)cc3)noc1-2]

Step 1: 6-bromotetralin-1-ol

A solution of 6-bromoteralone (5 g, 22.2 mmol) and sodium borohydride (1 g, 0.03 mol) in ethanol (100 ml) were stirred at room temperature overnight. The reaction was diluted with EtOAc and water was added. The organic phase was dried (MgSO$_4$), and concentrated to give 6-bromotetralin-1-ol (4.1 g, 81% yield) which was used without further purification.

Step 2: 7-bromo-1,2-dihydronaphthalene

A stirred solution of the product of step 1 (4.1 g, 18.1 mmol) and a catalytic amount of p-toluenesulfonic acid in benzene (150 mL) were stirred at reflux for 20 min. The reaction was washed with aqueous NaHCO$_3$ and extracted with EtOAc, dried and concentrated to give 7-bromo-1,2-dihydronaphthalene (3.6 g, 95% yield) which was used without further purification.

Step 3: 7-bromo-3-[4-(trifluoromethoxy)phenyl]-3a,4,5,9b-tetrahydrobenzo[g][1,2]benzoxazole To a stirred solution of the product of step 2 (3.6 g, 0.02 mol) and (1Z)—N-hydroxy-4-(trifluoromethoxy)benzimidoyl chloride (6.5 g 0.03 mol) in CH$_2$Cl$_2$ at 0° C. was added triethylamine (6 mL, 0.04 mol). The reaction was allowed to warm to room temperature and stirred overnight. The reaction was then purified by column chromatography eluting with a gradient of cyclohexane/EtOAc to afford 7-bromo-3-[4-(trifluoromethoxy)phenyl]-3a,4,5,9b-tetrahydrobenzo[g][1,2]benzoxazole (1.7 g, 24% yield). LC/MS (method 1): R$_t$=1.429 min; MS: m/z=412.5 (M+).

Step 4: 7-bromo-3-[4-(trifluoromethoxy)phenyl]-4,5-dihydrobenzo[g][1,2]benzoxazole A stirred solution of the product of step 3 (1.65 g, 4 mmol) and DDQ (1.8 g, 8 mmol) in toluene (50 mL) were heated at 100° C. for 16 h. The reaction was then allowed to cool to room temperature and purified by column chromatography eluting with a gradient of cyclohexane/EtOAc to afford 7-bromo-3-[4-(trifluoromethoxy)phenyl]-4,5-dihydrobenzo[g][1,2]benzoxazole (700 mg, 43% yield).

Step 5: 3-[4-(trifluoromethoxy)phenyl]-7-vinyl-4,5-dihydrobenzo[g][1,2]benzoxazole A stirred solution of the product of step 4 (700 mg, 1.7 mmol), tributyl(vinyl)tin (815 mg, 2.57 mmol) and (1,1'-bis(diphenylphosphino)ferrocene)palladium(II) dichloride (232 mg, 0.34 mmol) in toluene (20 mL) was heated at 100° C. for 16 h. The reaction mixture was then diluted with toluene and washed with a saturated aqueous solution of potassium fluoride. The organic layer was dried (MgSO$_4$), concentrated and purified by column chromatography eluting with a gradient of cyclohexane/EtOAc to afford 3-[4-(trifluoromethoxy)phenyl]-7-vinyl-4,5-dihydrobenzo[g][1,2]benzoxazole (350 mg, 57% yield).

Step 6: 3-[4-(trifluoromethoxy)phenyl]-4,5-dihydrobenzo[g][1,2]benzoxazole-7-carbaldehyde A solution of the product of step 5 (350 mg, 0.79 mmol), osmium tetroxide (2.5% in t-BuOH, 400 mg, 0.04 mmol), sodium periodate (0.51 mg, 2.31 mmol) in THF/water (1:1, 20 mL) was stirred at room temperature for 16 h. The reaction mixture was concentrated, diluted with EtOAc and then water was added. The organic phase was dried (MgSO$_4$), concentrated and purified by column chromatography eluting with a gradient of cyclohexane/EtOAc to afford 3-[4-(trifluoromethoxy)phenyl]-4,5-dihydrobenzo[g][1,2]benzoxazole-7-carbaldehyde (200 mg, 71% yield). LC/MS (method 1): R$_t$=1.388 min; MS: m/z=357.8.

Step 7: 1-(2,6-dimethylphenyl)-3-[(E)-[3-[4-(trifluoromethoxy)phenyl]-4,5-dihydrobenzo[g][1,2]benzoxazol-7-yl]methyleneamino]thiourea A stirred solution of the product of step 6 (200 mg, 0.56 mmol) and 1-amino-3-(2,6-dimethylphenyl)thiourea (131 mg, 0.67 mmol) was heated at 70° C. for 2 h. The reaction was then allowed to cool to room temperature, the precipitate was isolated by filtration purified by column reverse-phase chromatography eluting with a gradient of acetonitrile/water to afford 1-(2,6-dimethylphenyl)-3-[(E)-[3-[4-(trifluoromethoxy)phenyl]benzo[g][1,2]benzoxazol-7-yl]methyleneamino]thiourea (110 mg, 37% yield). LC/MS (method 1): Rt=1.504 min; MS: m/z=535 (M+). 1H NMR (500 MHz, CDCl$_3$) δ 10.03 (s, 1H), 8.67 (s, 1H), 7.93 (s, 1H), 7.88-7.75 (m, 4H), 7.67-7.60 (m, 2H), 7.35 (d, J=8.2 Hz, 3H), 7.28-7.19 (m, 1H), 7.17 (d, J=7.6 Hz, 2H), 3.15 (t, J=7.8 Hz, 2H), 3.01 (t, J=7.8 Hz, 2H), 2.35 (s, 6H).

Example 5

1-methyl-3-(o-tolyl)-1-[(E)-[3-[4-(trifluoromethoxy)phenyl]benzo[e]benzimidazol-7-yl]methyleneamino]thiourea (compound C-87)

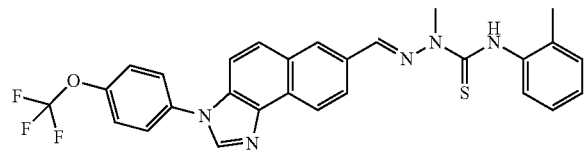 [SMILES: Cc1ccccc1NC(=S)N(C)/N=C/c1ccc2c(ccc3c2ncn3-c2ccc(OC(F)(F)F)cc2)c1]

A stirred solution of the product of 3-[4-(trifluoromethoxy)phenyl]benzo[e]benzimidazole-7-carbaldehyde (100 mg, 0.28 mmol) and 1-amino-1-methyl-3-(o-tolyl)thiourea (66 mg, 0.34 mmol) was heated at 70° C. in ethanol (3 mL) for 2 h. The reaction mixture was allowed to cool to room temperature, concentrated and purified by column chromatography eluting with a gradient of dichloromethane/methanol to afford 1-methyl-3-(o-tolyl)-1-[(E)-[3-[4-(trifluoromethoxy)phenyl]benzo[e]benzimidazol-7-yl]methyleneamino]thiourea (111 mg, 67% yield). LC/MS (method 1): Rt=1.345 min; MS: m/z=533.9 (M+1).

Example 6

1-(2,6-dimethylphenyl)-3-[(E)-[2-methyl-3-[4-(trifluoromethoxy)phenyl]-4,5-dihydrobenzo[g]indazol-7-yl]methyleneamino]thiourea (compound C-107)

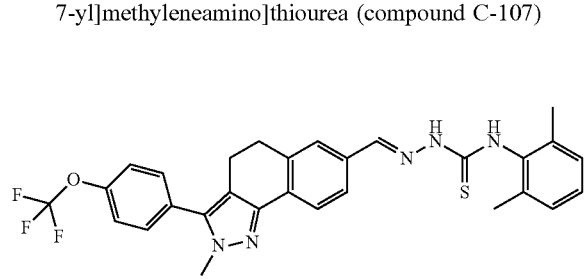

A stirred solution of 2-methyl-3-[4-(trifluoromethoxy)phenyl]-4,5-dihydrobenzo[g]indazole-7-carbaldehyde and 1-amino-3-(2,6-dimethylphenyl)thiourea ethanol was heated at 70° C. in ethanol (3 mL) for 2 h. The reaction was then allowed to cool to room temperature. The precipitate was isolated by vacuum filtration to give 1-(2,6-dimethylphenyl)-3-[(E)-[2-methyl-3-[4-(trifluoromethoxy)phenyl]-4,5-dihydrobenzo[g]indazol-7-yl]methyleneamino]thiourea (55 mg, 57% yield). LC/MS (method 1): Rt=1.467 min; MS: m/z=549.6 (M+). 1H NMR (400 MHz, CDCl$_3$) δ 9.28 (s, 1H), 8.67 (s, 1H), 7.93 (d, J=7.9 Hz, 1H), 7.59 (d, J=11.7 Hz, 2H), 7.46-7.32 (m, 4H), 7.25-7.12 (m, 3H), 3.91 (s, 3H), 2.99 (t, J=7.3 Hz, 2H), 2.74 (t, J=7.3 Hz, 2H), 2.34 (s, 6H).

Example 7

1-(2,6-dimethylphenyl)-3-[(E)-1-[3-[4-(trifluoromethoxy)phenyl]benzo[e]benzimidazol-7-yl]ethylideneamino]thiourea (compound C-58)

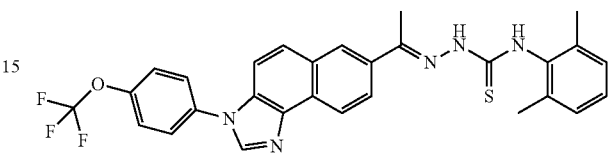

A stirred solution of 1-[3-[4-(trifluoromethoxy)phenyl]benzo[e]benzimidazol-7-yl]ethanone (100 mg, 0.27 mmol) and 1-amino-3-(2,6-dimethylphenyl)thiourea (63 mg, 0.32 mmol) in ethanol was heated at 60° C. in ethanol (3 mL) for 16 h. The reaction mixture was allowed to cool to room temperature and the precipitate that had formed was filtered and purified by column chromatography eluting with a gradient of cyclohexane/EtOAc to afford 1-(2,6-dimethylphenyl)-3-[(E)-1-[3-[4-(trifluoromethoxy)phenyl]benzo[e]benzimidazol-7-yl]ethylideneamino]thiourea (58 mg, 39% yield). LC/MS (method 1): Rt=1.3 min; MS: m/z=548.9 (M+1). $^1$H NMR (400 MHz, DMSO-d$_6$) δ 10.57 (s, 1H), 9.91 (s, 1H), 8.69-8.58 (m, 3H), 8.46 (d, J=9.1 Hz, 1H), 7.93 (dd, J=9.0, 7.4 Hz, 3H), 7.80 (d, J=8.9 Hz, 1H), 7.69 (d, J=8.4 Hz, 2H), 7.20-7.09 (m, 1H), 7.14 (s, 2H), 7.05 (d, J=7.8 Hz, OH), 2.53 (s, 3H), 2.23 (s, 6H).

Example 8

1-(2-ethyl-6-methyl-phenyl)-3-[(E)-1-[3-[4-(trifluoromethoxy)phenyl]benzo[e]benzimidazol-7-yl]ethylideneamino]thiourea (compound C-82)

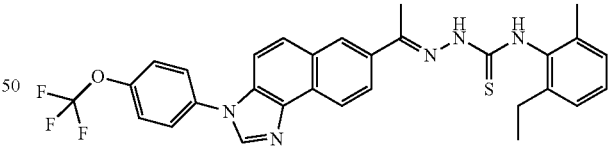

A stirred solution of 1-[3-[4-(trifluoromethoxy)phenyl]benzo[e]benzimidazol-7-yl]ethanone (100 mg, 0.27 mmol) and 1-amino-3-(2-ethyl-6-methyl-phenyl)thiourea (68 mg, 0.32 mmol) in propanol (3 mL) with a catalytic amount of acetic acid was heated at 90° C. for 16 h. The reaction mixture was allowed to cool to room temperature and the precipitate that had formed was filtered and purified by column chromatography eluting with a gradient of dichloromethane/methanol to afford 1-(2-ethyl-6-methyl-phenyl)-3-[(E)-1-[3-[4-(trifluoromethoxy)phenyl]benzo[e]benzimidazol-7-yl]ethylideneamino]thiourea (22 mg, 15% yield). LC/MS (method 1): R$_t$=1.342 min;

MS: m/z=562.9 (M+1).

Example XX 2-methyl-3-[4-(trifluoromethoxy)phenyl]-4,5-dihydrobenzo[g]indazole-7-carbaldehyde; 2-methyl-3-[4-(trifluoromethoxy)phenyl]benzo[g]indazole-7-carbaldehyde

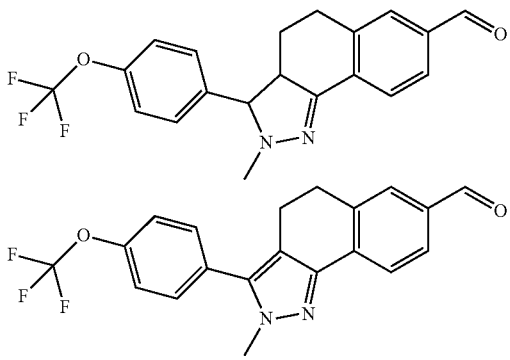

Step 1: (2E)-6-bromo-2-[[4-(trifluoromethoxy)phenyl]methylene]tetralin-1-one To a mixture of 6-bromotetralin-1-one (4.0 g, 17.77 mmol) and NaOH (177.7 mg, 4.44 mmol) in EtOH (30 mL) was added 4-(trifluoromethoxy)benzaldehyde (3.4 g, 17.77 mmol) dropwise at room temperature. The reaction mixture was stirred at room temperature overnight. The resulting precipitate was collected by filtration. The crude product was washed with EtOH to give (2E)-6-bromo-2-[[4-(trifluoromethoxy)phenyl]methylene]tetralin-1-one (5 g, yield: 70.8%). $^1$H NMR (400 MHz, CDCl$_3$): 8.01~7.99 (m, 2H), 7.84~7.45 (m, 4H), 7.29~7.27 (m, 2H), 3.12~3.09 (m, 2H), 2.96~2.93 (m, 2H)

Step 2: 7-bromo-2-methyl-3-[4-(trifluoromethoxy)phenyl]-3,3a,4,5-tetrahydrobenzo[g]indazole To a solution of the product of step 1 (4.0 g, 10.0 mmol) in EtOH (100 mL) was added MeNHNH$_2$ (40% in water, 11.6 g, 100 mmol) dropwise at room temperature. The reaction mixture was heated to reflux and stirred at that temperature for 5 h. The reaction mixture was concentrated and the residue was purified by flash chromatography to give 7-bromo-2-methyl-3-[4-(trifluoromethoxy)phenyl]-3,3a,4,5-tetrahydrobenzo[g]indazole (4 g, yield: 93.4%). $^1$H NMR (400 MHz, CDCl$_3$): 7.82~7.80 (m, 2H), 7.52~7.33 (m, 4H), 7.26~7.24 (m, 3H), 3.73~3.70 (d, 1H, J=13.2), 3.15~3.09 (m, 1H), 2.88~2.86 (m, 2H), 2.82 (s, 3H), 2.15~2.13 (m, 1H), 1.88~1.78 (m, 1H).

Step 3: 2-methyl-3-[4-(trifluoromethoxy)phenyl]-7-vinyl-3,3a,4,5-tetrahydrobenzo[g]indazole To a mixture of the product of step 2 (600 mg, 1.41 mmol) and tributyl(vinyl)stannane (671 mg, 2.12 mmol) in dry toluene (10 mL) was added Pd(PPh$_3$)$_4$ (162 mg, 0.14 mmol) at room temperature under N$_2$ atmosphere. The reaction mixture was heated to 100° C. and stirred at that temperature for 6 h, then cooled to room temperature and partitioned between water and EtOAc. The combined organic layers were washed with water and brine, dried over Na$_2$SO$_4$, then concentrated. The residue was filtered through silica gel (EtOAc) to give 2-methyl-3-[4-(trifluoromethoxy)phenyl]-7-vinyl-3,3a,4,5-tetrahydrobenzo[g]indazole (450 mg) which was used without further purification. $^1$H NMR (400 MHz, CDCl$_3$): 7.92-7.90 (m, 1H), 7.53-7.51 (m, 2H), 7.32-7.19 (m, 4H), 6.72-6.65 (m, 1H), 5.80-5.76 (d, J=17.2, 1H), 5.29-5.26 (d, J=10.8, 1H), 3.72-3.68 (d, J=14, 1H), 3.15-3.10 (m, 1H), 2.91-2.88 (m, 2H), 2.82 (s, 3H), 2.17-2.13 (m, 1H), 1.87-1.82 (m, 1H).

Step 4: 2-methyl-3-[4-(trifluoromethoxy)phenyl]-4,5-dihydrobenzo[g]indazole-7-carbaldehyde To a solution of the product of step 3 (380 mg, 1.0 mmol) in H2O (20 mL) and dioxane (40 mL) was added OsO$_4$ (26 mg, 0.1 mmol) at room temperature. After 5 min at room temperature, NaIO$_4$ (1.1 g, 5.11 mmol) was added portionwise. The reaction mixture was stirred at room temperature for 4 h. The reaction mixture was quenched with sat. Na$_2$S$_2$O$_3$ solution and then extracted with EtOAc. The combined organic layers were washed with water and brine, dried over Na$_2$SO$_4$, then concentrated. The residue was purified by flash chromatography to give 2-methyl-3-[4-(trifluoromethoxy)phenyl]-4,5-dihydrobenzo[g]indazole-7-carbaldehyde as light yellow solid (270 mg). $^1$H NMR (400 MHz, CDCl$_3$): 9.89 (s, 1H), 8.00 (d, 1H), 7.64 (d, 1H), 7.60 (s, 1H), 7.43 (d, 2H), 7.20 (d, 2H), 3.74 (d, J=13.6, 1H), 3.11~3.07 (m, 1H), 2.91~2.85 (m, 2H), 2.78 (s, 3H), 1.83~1.77 (m, 1H). Continued elution then afforded 2-methyl-3-[4-(trifluoromethoxy)phenyl]benzo[g]indazole-7-carbaldehyde as reddish solid (66 mg). $^1$H NMR (400 MHz, CDCl$_3$): 9.99 (s, 1H), 8.04~8.02 (m, 1H), 7.82~7.78 (m, 2H), 7.44~7.42 (m, 2H), 7.38~7.36 (m, 2H), 3.93 (s, 3H), 3.05~3.02 (t, J=7.4, 2H), 2.78~2.74 (t, J=7.4, 2H).

Example 9

1-(2,6-dimethylphenyl)-3-[(E)-[2-methyl-3-[4-(trifluoromethoxy)phenyl]-3,3a,4,5-tetrahydrobenzo[g]indazol-7-yl]methyleneamino]thiourea (compound C-94)

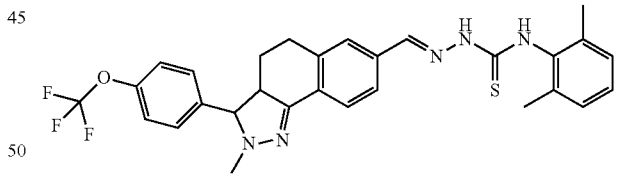

A stirred solution of 2-methyl-3-[4-(trifluoromethoxy)phenyl]-3,3a,4,5-tetrahydrobenzo[g]indazole-7-carbaldehyde (100 mg, 0.27 mmol) and 1-amino-3-(2,6-dimethylphenyl)thiourea (62 mg, 0.32 mmol) in ethanol (3 mL) was heated at 60° C. for 16 h. The reaction mixture was allowed to cool to room temperature and the precipitate that had formed was filtered and purified by column chromatography eluting with a gradient of cyclohexane/EtOAc to afford 1-(2,6-dimethylphenyl)-3-[(E)-[2-methyl-3-[4-(trifluoromethoxy)phenyl]-3,3a,4,5-tetrahydrobenzo[g]indazol-7-yl]methyleneamino]thiourea (32 mg, 22% yield). LC/MS (method 1): Rt=1,524 min;

MS: m/z=552 (M+1). 1H NMR (500 MHz, CDCl$_3$) δ 10.62 (s, 1H), 8.67 (s, 1H), 7.95 (d, J=8.4 Hz, 2H), 7.52 (dd, J=17.2, 8.8 Hz, 3H), 7.42 (s, 1H), 7.32-7.09 (m, 6H), 3.75

(d, J=13.8 Hz, 1H), 3.12 (td, J=13.2, 4.9 Hz, 1H), 2.96-2.86 (m, 2H), 2.83 (s, 3H), 2.33 (s, 6H), 2.16 (dt, J=13.1, 3.9 Hz, 1H), 2.04 (s, 1H).

Example 10

2-methyl-3-[4-(trifluoromethoxy)phenyl]benzo[g]indazole-7-carbaldehyde

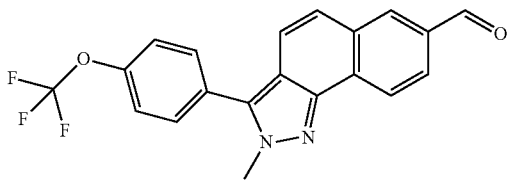 [SMILES: Cn1nc2c(ccc3cc(C=O)ccc32)c1-c1ccc(OC(F)(F)F)cc1]

Step 1: 7-bromo-2-methyl-3-[4-(trifluoromethoxy)phenyl]benzo[g]indazole

To a solution of 7-bromo-2-methyl-3-[4-(trifluoromethoxy)phenyl]-3,3a,4,5-tetrahydrobenzo[g]indazole (4.3 g, 10.1 mmol) in 1,4-dioxane (150 mL) was added DDQ (11.5 g, 50.6 mmol) portionwise at room temperature. The reaction mixture was heated to reflux and stirred at that temperature overnight under $N_2$ atmosphere. The reaction mixture was cooled to room temperature, and then filtered. The filtrate was concentrated and the residue diluted with EtOAc, washed with water and brine, dried over Na2SO4, then concentrated. The residue was purified by flash chromatography to give 7-bromo-2-methyl-3-[4-(trifluoromethoxy)phenyl]benzo[g]indazole (3.6 g, yield: 90.8%). $^1$H NMR (400 MHz, CDCl3): 8.49~8.47 (m, 1H), 7.98~7.71 (m, 2H), 7.69~7.44 (m, 5H), 7.32~7.29 (m, 1H), 4.21 (s, 3H).

Step 2: methyl 2-methyl-3-[4-(trifluoromethoxy)phenyl]benzo[g]indazole-7-carboxylate To a mixture of the product of step 1 (2 g, 4.75 mmol), Et$_3$N (1 g, 9.5 mmol), DPPP (600 mg, 1.42 mmol) and Pd(OAc)$_2$ (250 mg, 0.95 mmol) in MeOH (20 mL) and DMF (20 mL) was stirred at 100° C. under CO atmosphere (3 MPa) for 24 h. The reaction mixture cooled to room temperature, and concentrated. The residue diluted with EtOAc, washed with water and brine, dried over Na$_2$SO$_4$, then concentrated. The residue was purified by column chromatography to give methyl 2-methyl-3-[4-(trifluoromethoxy)phenyl]benzo[g]indazole-7-carboxylate (1.6 g, yield: 84.2%). $^1$H NMR (400 MHz, CDCl$_3$): 8.67~8.57 (m, 2H), 8.25~8.23 (m, 1H), 7.62~7.60 (m, 2H), 7.48~7.44 (m, 4H), 4.24 (s, 3H), 4.00 (s, 3H).

Step 3: [2-methyl-3-[4-(trifluoromethoxy)phenyl]benzo[g]indazol-7-yl]methanol

To a solution of the product of step 2 (1.6 g, 4.0 mmol) in dry PhMe (20 mL) was added DIBAL-H (1.0 M in PhMe, 16 mL, 16 mmol) drop-wise at −20° C. under N2 atmosphere. The resulting mixture warmed to 0° C. and stirred for 3 hr. The mixture was quenched with the solution of NH4Cl slowly and filtered. The filtrate diluted with EtOAc, washed with water and brine, dried over Na2SO4, then concentrated to dryness to give [2-methyl-3-[4-(trifluoromethoxy)phenyl] benzo[g]indazol-7-yl]methanol (1.2 g, yield: 80.6%) which was directly without purification. $^1$H NMR (400 MHz, CDCl$_3$): 8.61~8.59 (m, 2H), 7.82~7.60 (m, 4H), 7.45~7.40 (m, 4H), 4.90 (s, 2H), 4.21 (s, 3H).

Step 4: 2-methyl-3-[4-(trifluoromethoxy)phenyl] benzo[g]indazole-7-carbaldehyde

To a solution of the product of step 3 (1.2 g, 3.22 mmol) in CHCl$_3$ (20 mL) was added MnO$_2$ (2.3 g, 25.8 mmol) portionwise at room temperature. The resulting mixture heated to 60° C. and stirred for 3 h. The mixture was cooled to RT and filtered. The filtrate was concentrated and the residue was purified by column chromatography to give compound 2-methyl-3-[4-(trifluoromethoxy)phenyl]benzo[g]indazole-7-carbaldehyde (930 mg, yield: 78%). 1H NMR (400 MHz, CDCl3): 10.19 (s, 1H), 8.75-8.73 (m, 2H), 8.35 (s, 1H), 8.12-8.10 (m, 1H), 7.63-7.61 (m, 2H), 7.52-7.45 (m, 4H), 4.25 (s, 3H).

Example 11

(1Z)-1-[(2-isopropylanilino)-sulfanyl-methylene]-3-[3-[4-(trifluoromethoxy)phenyl]benzo[e]benzimidazol-7-yl]urea (compound C-117)

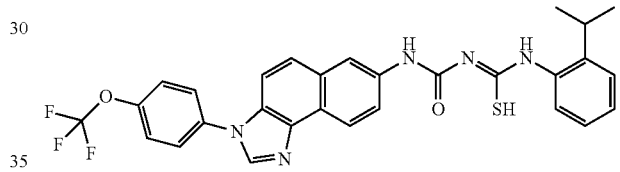

Step 1: tert-butyl-N-(6-bromo-2-naphthyl)carbamate

To a cooled solution of 6-bromonaphthalene-2-carboxylic acid (50 g, 0.2 mol) in t-butanol (350 mL) triethylamine (30 g, 0.3 mol) was added slowly. Diphenylphosphoryl azide (60 g, 0.22 mol) was then added and the reaction mixture was stirred at 80° C. for 16 h. The mixture was allowed to cool to room temperature, then poured into saturated NaHCO$_3$ solution. The precipitate that had formed was filtered to give tert-butyl-N-(6-bromo-2-naphthyl)carbamate (65 g) which was used without further purification.

Step 2: tert-butyl N-(6-bromo-1-nitro-2-naphthyl)carbamate

To a cooled solution of the product of step 1 (65 g, 0.2 mol) in acetic acid (500 mL), fuming nitric acid (40 mL) was added slowly. The reaction mixture immediately turned to a dark red and a red precipitate formed within a few minutes. The mixture was then poured onto ice water. The precipitate was filtered and washed with water and oven-dried to give tert-butyl N-(6-bromo-1-nitro-2-naphthyl)carbamate (102 g) which was used without further purification.

Step 3: 6-bromonaphthalene-1,2-diamine

To a cooled solution of of the product of step 2 (75 g, 0.2 mol) in methanol (400 mL), SnCl$_2$.2H$_2$O (212 g, 0.61 mol) was added. The reaction mixture was stirred at reflux for 16 h. The reaction mixture was then concentrated to dryness, diluted with water and adjusted to an alkaline pH with aqueous NaHCO₃ than NaOH solutions and extracted with EtOAc. The organic layer was dried (MgSO₄) and concentrated to give 6-bromonaphthalene-1,2-diamine (35 g) which was used without further purification in the next step.

Step 4: 7-bromo-3H-benzo[e]benzimidazole

The product of step 3 (35 g, 0.15 mol) in formic acid (350 mL) was heated to 80° C. for 3 h. The reaction mixture was then concentrated to dryness, diluted with water and the yellow precipitate was filtered and washed with water and oven-dried. The filtrate was purified by column chromatography eluting with a gradient of cyclohexane/EtOAc to afford 7-bromo-3H-benzo[e]benzimidazole (30 g, 82% combined yield). LC/MS (method 1): R$_f$=0.873 min; MS: m/z=247 (M+).

Step 5: 7-bromo-3-[4-(trifluoromethoxy)phenyl]benzo[e]benzimidazole

A stirred solution of the product of step 4 (15 g, 0.06 mol) and 1-fluoro-4-(trifluoromethoxy)benzene (21 g, 0.12 mol) and Cs₂CO₃ (50 g, 0.15 mol) in DMF (250 mL) was heated to 160° C. for 16 h. The reaction mixture was diluted with water and extracted with EtOAc. The organic layer was dried (MgSO₄) and concentrated to give 7-bromo-3-[4-(trifluoromethoxy)phenyl]benzo[e]benzimidazole 16 g (65% yield) which was used without further purification. LC/MS (method 1): R$_f$=1.304 min; MS: m/z=406.7 (M+).

Step 6: methyl 3-[4-(trifluoromethoxy)phenyl]benzo[e]benzimidazole-7-carboxylate To a stirred suspension of the product of step 5 (7.5 g, 18.2 mmol), [1,1'-bis(diphenylphosphino)ferrocene]dichloropalladium(II) (2.3 g, 2.7 mmol) and Na₂CO₃ (3 g, 28 mmol) in methanol (70 mL), carbon monoxide was pressed onto the flask by use of a 2 L gas burette and heated to 60° C. for 16 h. The reaction mixture was then concentrated to dryness and diluted with EtOAc and filtrated to remove the catalyst. The filtrate was washed with an aqueous HCl solution (5%). The organic layer was dried (MgSO₄) and concentrated to give methyl 3-[4-(trifluoromethoxy)phenyl]benzo[e]benzimidazole-7-carboxylate (7 g) which was used without further purification.

Step 7: 3-[4-(trifluoromethoxy)phenyl]benzo[e]benzimidazole-7-carboxylic acid

A solution of the product of step 6 (7 g, 0.02 mol) and LiOH H₂O (1.3 g, 0.05 mol) in THF/water (3:1, 20 mL) was stirred at room temperature overnight. The reaction mixture was then concentrated to dryness and purified by column chromatography eluting with a gradient of acetonitrile/water to give 3-[4-(trifluoromethoxy)phenyl]benzo[e]benzimidazole-7-carboxylic acid (2.3 g, 34% yield).

Step 8: 3-[4-(trifluoromethoxy)phenyl]benzo[e]benzimidazole-7-carbonyl azide

To solution of the product of step 7 (1.3 g, 3.5 mmol) in isopropanol (20 mL), diphenylphosphoryl azide (1.92 g, 7 mmol) and triethylamine (706 mg, 7 mmol) were added and the mixture was stirred at room temperature overnight. The reaction mixture was then concentrated to dryness, diluted with EtOAc and washed with an aqueous NaHCO₃ solution. The organic layer was dried (MgSO₄) and purified by column chromatography eluting with a gradient of cyclohexane/EtOAc to give 3-[4-(trifluoromethoxy)phenyl]benzo[e]benzimidazole-7-carbonyl azide (1.1 g, 80% yield).

Step 9: (1Z)-1-[(2-isopropylanilino)-sulfanyl-methylene]-3-[3-[4-(trifluoromethoxy)phenyl]benzo[e]benzimidazol-7-yl]urea A solution of the product of step 8 (1.1 g, 2.8 mmol) in toluene (20 mL) was heated to 100° C. The reaction was then allowed to cool to roo temperature and (2-isopropylphenyl)thiourea (646 mg, 3.32 mmol) and cesium carbonate (2.26 g, 7 mmol) were added and the reaction was stirred overnight. The reaction mixture was diluted with EtOAc and washed with an aqueous NaHCO₃ solution. The organic layer was dried (MgSO₄) and purified by column chromatography eluting with a gradient of cyclohexane/EtOAc to give (1Z)-1-[(2-isopropylanilino)-sulfanyl-methylene]-3-[3-[4-(trifluoromethoxy)phenyl]benzo[e]benzimidazol-7-yl]urea (204 mg, 13% yield). LC/MS (method 1): R$_f$=1.304 min; MS: m/s: 564 (M+). ¹H NMR (400 MHz, DMSO-d₆) δ 11.76 (s, 1H), 10.28 (s, 1H), 9.56 (s, 1H), 8.65 (s, 1H), 8.53 (d, J=8.8 Hz, 1H), 8.21 (d, J=2.1 Hz, 1H), 7.95-7.86 (m, 2H), 7.85-7.73 (m, 2H), 7.69 (ddd, J=8.7, 4.0, 1.6 Hz, 3H), 7.41 (ddd, J=12.8, 7.8, 1.5 Hz, 2H), 7.28 (dtd, J=25.8, 7.4, 1.6 Hz, 2H), 3.09 (p, J=6.9 Hz, 1H), 1.21 (d, J=6.9 Hz, 7H).

Example 12

(1Z)-1-[3-(2-isopropylphenyl)-4-oxo-thiazolidin-2-ylidene]-3-[3-[4(trifluoromethoxy)phenyl]benzo[e]benzimidazol-7-yl]urea (compound C-115)

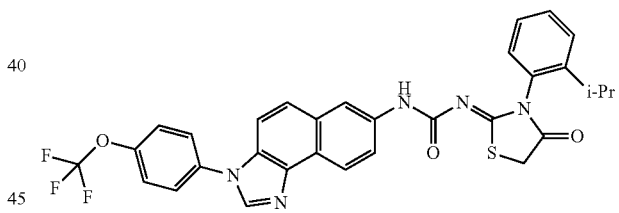

Step 1: (1Z)-1-[3-(2-isopropylphenyl)-4-oxo-thiazolidin-2-ylidene]-3-[3-[4-(trifluoromethoxy)phenyl]benzo[e]benzimidazol-7-yl]urea A solution of compound C—XX (115 mg, 0.2 mmol), sodium acetate (66 mg, 0.8 mmol) and methyl 2-bromoacetate (62 mg, 0.4 mmol) in ethanol (3 mL) was heated to 60° C. overnight. The reaction was allowed to cool to room temperature and purified by column chromatography eluting with a gradient of cyclohexane/EtOAc to give (1Z)-1-[3-(2-isopropylphenyl)-4-oxo-thiazolidin-2-ylidene]-3-[3-[4-(trifluoromethoxy)phenyl]benzo[e]benzimidazol-7-yl]urea (77 mg, 56% yield). LC/MS (method 1): Rt=1.203 min; MS: m/z 603.9 (M+). ¹H NMR (400 MHz, CDCl₃) δ 8.53 (d, J=8.8 Hz, 1H), 8.38 (d, J=2.1 Hz, 1H), 8.07 (s, 1H), 7.74-7.64 (m, 2H), 7.61-7.50 (m, 3H), 7.51-7.40 (m, 5H), 7.36-7.24 (m, 1H), 7.08 (d, J=7.7 Hz, 1H), 3.96 (d, J=3.6 Hz, 2H), 2.74 (hept, J=6.9 Hz, 1H), 2.03 (d, J=1.2 Hz, 1H), 1.29-1.17 (m, 7H).

Example 13

1-(5-chloro-2-pyridyl)ethyl N-[3-[4-(trifluoromethoxy)phenyl]benzo[e]benzimidazol-7-yl]carbamate (compound C-56)

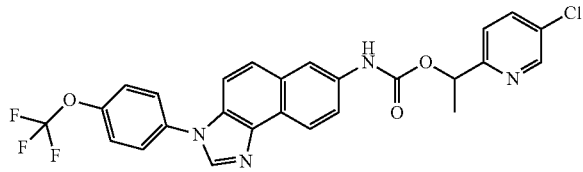 [SMILES: CC(OC(=O)Nc1ccc2c(ccc3c2ncn3-c2ccc(OC(F)(F)F)cc2)c1)c1ccc(Cl)cn1]

Step 1: 1-(5-chloropyridin-2-yl)ethanol

To a stirred solution of 1-(5-chloropyridin-2-yl)ethanone (4.0 g, 26 mmol) in methanol (40 mL) was added NaBH$_4$ (1.98 g, 52 mmol) at 0° C. The reaction mixture was stirred at 0° C. to room temperature for 1 h. Solvent was then removed under and the reaction was basified with an aqueous NaHCO$_3$ solution (50 mL) and extracted with EtOAc. The organic layer was separated, dried over Na$_2$SO$_4$ and concentrated to afford crude compound, which was purified by column chromatography eluting with a gradient of EtOAc/hexane to obtain 1-(5-chloropyridin-2-yl)ethanol (2.0 g, 50% yield). $^1$H NMR (400 MHz, CDCl$_3$) δ 8.50 (d, J=2.3 Hz, 1H), 7.67 (dd, J=8.4, 2.4 Hz, 1H), 7.29-7.24 (m, 1H), 4.89 (dd, J=6.7, 2.9 Hz, 1H), 3.71 (d, J=4.1 Hz, 1H), 1.50 (d, J=6.6 Hz, 3H).

Step 2: 1-(5-chloropyridin-2-yl)ethyl 3-(4-(trifluoromethoxy)phenyl)-3H-naphtho[1,2-d]imidazol-7-ylcarbamate To a stirred solution of 3-(4-(trifluoromethoxy)phenyl)-3H-naphtho[1,2-d]imidazole-7-carboxylic acid (300 mg, 0.81 mmol) in toluene (10 mL) were added diphenylphosphoryl azide (220 mg, 0.81 mmol), triethylamine (122 mg, 1.20 mmol) and 1-(5-chloropyridin-2-yl)ethanol (126 mg, 0.81 mmol). The reaction mixture was heated at 100° C. for 16 h. Toluene was removed under vacuum to afford crude compound, which was purified by column chromatography eluting with a gradient of EtOAc/hexane to obtain 1-(5-chloropyridin-2-yl)ethyl 3-(4-(trifluoromethoxy)phenyl)-3H-naphtho[1,2-d]imidazol-7-ylcarbamate (90 mg, 22% yield). LC/MS (method 1): R$_t$=2.69 min; MS: m/z 527.09 (M+). $^1$H NMR (400 MHz, CDCl$_3$) δ 8.63-8.59 (d, 1H), 8.57 (br, s, 1H), 8.15 (d, J=14.6 Hz, 2H), 7.72-7.64 (m, 2H), 7.64-7.42 (m, 6H), 7.38 (d, J=8.4 Hz, 1H), 5.96 (q, J=6.7 Hz, 1H), 1.68 (d, J=6.7 Hz, 3H).

Example 14

(Z)-3-(2-isopropylphenyl)-2-((E)-((3-(4-(trifluoromethoxy)phenyl)-3H-naphtho[1,2-d]imidazol-7-yl)methylene)hydrazono)thiazolidin-4-one (compound C-51)

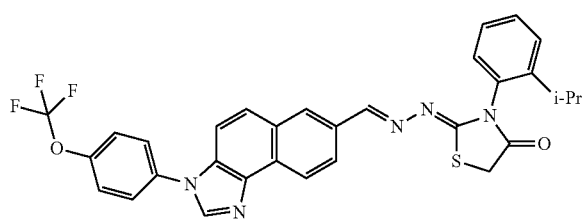 [SMILES: CC(C)c1ccccc1N1C(=O)CS/C1=N\N=C\c1ccc2c(ccc3c2ncn3-c2ccc(OC(F)(F)F)cc2)c1]

To a stirred solution of (E)-N-(2-isopropylphenyl)-2-((3-(4-(trifluoromethoxy)phenyl)-3H-naphtho[1,2-d]imidazol-7-yl)methylene)hydrazinecarbothioamide (120 mg, 0.21 mmol) in ethanol (5 mL) was added methyl bromoacetate (0.04 mL, 0.043 mmol) and the reaction mixture was heated to 80° C. for 3 h. The resultatant precipitate was isolated by filtration and purified by column chromatography eluting with a gradient of EtOAc/hexane to obtain to obtain (Z)-3-(2-isopropylphenyl)-2-((E)-((3-(4-(trifluoromethoxy)phenyl)-3H-naphtho[1,2-d]imidazol-7-yl)methylene)hydrazono)thiazolidin-4-one (84 mg, 66% yield). LC/MS (method 2): R$_t$=3.05 min; MS: m/z=588.09 (M+). $^1$H NMR (400 MHz, DMSO-d$_6$): δ 8.91 (s, 1H), 8.64 (d, J=8.7 Hz, 1H), 8.50 (s, 1H), 8.32 (s, 1H), 8.19-8.11 (d, 1H), 7.97-7.88 (m, 3H), 7.81 (d, J=9.0 Hz, 1H), 7.70 (d, J=8.3 Hz, 2H), 7.56-7.45 (m, 2H), 7.39-7.32 (m, 1H), 7.28 (d, J=7.7 Hz, 1H), 4.33-4.11 (m, 2H), 2.88-2.76 (m, 1H), 1.17 (dd, J=14.4, 6.8 Hz, 6H).

Example 15

(Z)-3-(2-isopropylphenyl)-2-((E)-((3-(4-(trifluoromethoxy)phenyl)-3H-naphtho[1,2-d]imidazol-7-yl)methylene)hydrazono)-1,3-thiazinane (C-55)

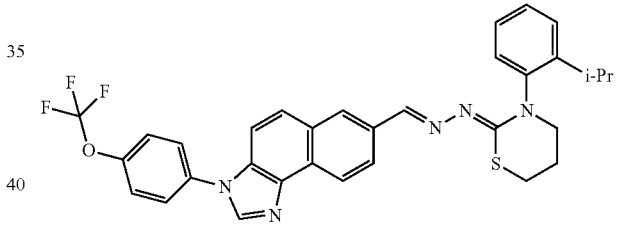

To a stirred solution of (E)-N-(2-isopropylphenyl)-2-((3-(4-(trifluoromethoxy)phenyl)-3H-naphtho[1,2-d]imidazol-7-yl)methylene)hydrazinecarbothioamide (300 mg, 0.55 mmol) in butanone (6 mL) was added K$_2$CO$_3$ (303 mg, 2.2 mmol) and 1-bromo-3-chloropropane (129 mg, 0.83 mmol) and the reaction mixture was heated at reflux for 8 h. The reaction mixture was then diluted with EtOAc (25 mL), filtered and solvent was removed under vacuum. The resultant crude compound was purified by column chromatography eluting with a gradient of EtOAc/hexane to obtain a solid which was further triturated with ether (5 ml) and filtered to afford (Z)-3-(2-isopropylphenyl)-2-((E)-((3-(4-(trifluoromethoxy)phenyl)-3H-naphtho[1,2-d]imidazol-7-yl)methylene)hydrazono)-1,3-thiazinane (107 mg, 33% yield). LC/MS (method 2): R$_t$=2.59 min; MS: m/z=588.11 (M+). $^1$H NMR (400 MHz, DMSO-d$_6$) δ 8.66 (s, 1H), 8.50-8.48 (d, J=8.6 Hz, 1H), 8.14-8.02 (m, 3H), 7.91-7.89 (d, J=8.6 Hz, 2H), 7.77 (q, J=8.9 Hz, 2H), 7.68-7.66 (d, J=8.4 Hz, 2H), 7.41-7.39 (d, J=7.6 Hz, 1H), 7.30 (ddd, J=13.4, 6.1, 2.1 Hz, 1H), 7.25 (dd, J=5.2, 1.9 Hz, 2H), 3.74 (m, 1H), 3.50-3.39 (m, 1H), 3.18-2.97 (m, 3H), 2.36-2.15 (m, 2H), 1.19 (dd, J=12.3, 6.8 Hz, 6H).

Example 16

(1Z,N'E)-methyl N-2-isopropylphenyl-N'-((3-(4-(trifluoromethoxy)phenyl)-3H-naphtho[1,2-d]imidazol-7-yl)methylene)carbamohydrazonothioate (compound C-52)

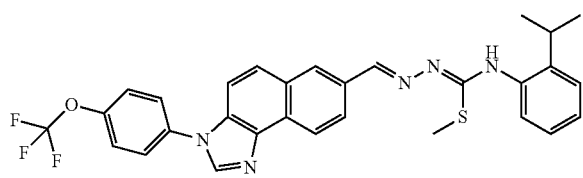 [SMILES: CS/C(=N\N=C\c1ccc2c(ccc3c2ncn3-c2ccc(OC(F)(F)F)cc2)c1)Nc1ccccc1C(C)C]

To a stirred solution of (E)-N-(2-isopropylphenyl)-2-((3-(4-(trifluoromethoxy)phenyl)-3H-naphtho[1,2-d]imidazol-7-yl)methylene)hydrazinecarbothioamide (200 mg, 0.36 mmol) in ethanol (3 mL) was added methyliodide (0.07 mL, 1.09 mmol) and the reaction mixture was heated at 80° C. for 3 h. The resultant solid was removed by filtration and the filtrate was concentrated to afford crude product, which was purified by column chromatography eluting with a gradient of EtOAc/hexane to obtain a solid which was further triturated with ether (5 ml) and filtered to afford (1Z,N'E)-methyl N-2-isopropylphenyl-N'((3-(4-(trifluoromethoxy)phenyl)-3H-naphtho[1,2-d]imidazol-7-yl)methylene)carbamohydrazonothioate (82 mg, 41% yield). LC/MS (method 2): $R_t$=2.92; m/z=562.15 (M+). $^1$H NMR (400 MHz, CDCl$_3$): δ 8.73-8.63 (m, 2H), 8.31 (s, 1H), 8.27-8.21 (d, 1H), 8.18-8.17 (d, J=5.2 Hz, 2H), 7.81-7.79 (d, J=8.4 Hz, 1H), 7.65-7.58 (m, 3H), 7.49-7.46 (d, J=8.4 Hz, 2H), 7.38-7.28 (m, 3H), 7.21 (t, J=7.6 Hz, 1H), 3.33 (p, J=6.9 Hz, 1H), 2.48 (s, 3H), 1.30 (d, J=6.8 Hz, 6H).

Example 17

(E)-N-(2,6-dimethylphenyl)-2-((3-(4-(trifluoromethoxy)phenyl)-4,5-dihydro-3H-benzo[e]indazol-7-yl)methylene)hydrazinecarbothioamide (compound C-10)

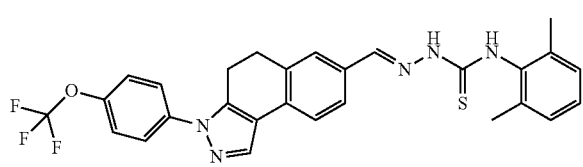 [SMILES: Cc1cccc(C)c1NC(=S)N/N=C/c1ccc2c(c1)CCc1c-2cnn1-c1ccc(OC(F)(F)F)cc1]

Step 1: 2,6-dibromo-3,4-dihydronaphthalene-1-carbaldehyde

To a stirred solution of 6-bromo-3,4-dihydronaphthalen-2(1H)-one (3.0 g, 13.3 mmol) in DMF (15 mL) was added POBr$_3$ (7.65 g, 26.7 mmol) at 0° C. The reaction mixture was then stirred at 0° C. to room temperature for 3 h. The reaction mixture was then quenched with ice water and the resultant precipitate was isolated by filtration and to afford 2,6-dibromo-3,4-dihydronaphthalene-1-carbaldehyde (3.0 g, 71% yield). $^1$H NMR (400 MHz, CDCl$_3$): δ 10.29 (d, J=0.9 Hz, 1H), 7.89 (d, J=8.5 Hz, 1H), 7.41-7.34 (m, 1H), 7.30 (dd, J=2.0, 1.0 Hz, 1H), 3.07-2.97 (m, 2H), 2.87 (t, J=7.7 Hz, 2H).

Step 2: 7-bromo-3-(4-(trifluoromethoxy)phenyl)-4,5-dihydro-3H-benzo[e]indazole To a stirred solution of the product of step 1 (1.5 g, 4.8 mmol) in AcOH (10 mL) was added [4-(trifluoromethoxy)phenyl]hydrazine (1.0 g, 4.8 mmol). The reaction mixture was heated at 100° C. for 1 h then concentrated under reduced pressure to afford crude compound, which purified by column chromatography eluting with a gradient of EtOAc/hexane to obtain 7-bromo-3-(4-(trifluoromethoxy)phenyl)-4,5-dihydro-3H-benzo[e]indazole (400 mg, 21% yield). $^1$H NMR (400 MHz, CDCl$_3$): δ 7.93 (s, 1H), 7.57-7.51 (m, 2H), 7.41-7.30 (m, 5H), 3.01 (s, 4H).

Step 3: 3-(4-(trifluoromethoxy)phenyl)-4,5-dihydro-3H-benzo[e]indazole-7-carbaldehyde To a stirred solution of the product of step 2 (200 mg, 0.49 mmol) in THF (10 mL) at -78° C. was added n-BuLi (0.45 mL, 1.6 M). After 30 min, DMF (72 mg, 0.98 mmol) was added and stirring was continued for another 1 h. The reaction mixture was then quenched with water (10 mL) and extracted with EtOAc. The organic layer was separated, dried over Na$_2$SO$_4$ and concentrated to afford 3-(4-(trifluoromethoxy)phenyl)-4,5-dihydro-3H-benzo[e]indazole-7-carbaldehyde (200 mg), which was used without further purification. LC/MS (method 2): $R_t$=2.38; MS: m/z=359.13 (M+).

Step 4: (E)-N-(2,6-dimethylphenyl)-2-((3-(4-(trifluoromethoxy)phenyl)-4,5-dihydro-3H-benzo[e]indazol-7-yl)methylene)hydrazinecarbothioamide To a stirred solution of the product of step 3 (400 mg, 1.4 mmol) in ethanol (5 mL) was added N-(2,6-dimethylphenyl)hydrazinecarbothioamide (218 mg, 1.1 mmol) and the reaction mixture was heated at reflux for 3 h. The reaction mixture was then concentrated under reduced pressure to afford crude compound, which purified by column chromatography eluting with a gradient of EtOAc/hexane to obtain (E)-N-(2,6-dimethylphenyl)-2-((3-(4-(trifluoromethoxy)phenyl)-4,5-dihydro-3H-benzo[e]indazol-7-yl)methylene)hydrazinecarbothioamide (45 mg, 6% yield). LC/MS (method 2): $R_t$=3.00 min; MS: m/z=536.27 (M+). $^1$H NMR (400 MHz, CDCl$_3$): δ 9.24 (s, 1H), 8.35 (s, 1H), 7.92 (s, 1H), 7.78 (d, J=1.9 Hz, 1H), 7.65 (s, 1H), 7.40 (t, J=7.1 Hz, 2H), 7.27 (d, J=7.1 Hz, 1H), 7.23-7.11 (m, 4H), 7.08 (d, J=7.4 Hz, 2H), 3.03 (t, J=7.8 Hz, 2H), 2.78 (t, J=7.6 Hz, 2H), 2.19 (s, 6H).

Example 18

(E)-N-(2,6-dimethylphenyl)-2-((3-(4-(trifluoromethoxy)phenyl)-3H-benzo[e]indazol-7-yl)methylene)hydrazinecarbothioamide (compound C-46)

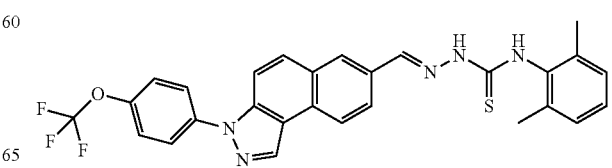

Step 1: 7-bromo-3-(4-(trifluoromethoxy)phenyl)-3H-benzo[e]indazole

To a stirred solution of 7-bromo-3-(4-(trifluoromethoxy)phenyl)-4,5-dihydro-3H-benzo[e]indazole (1.3 g, 3.2 mmol) in toluene (20 mL) was added DDQ (1.4 g, 6.4 mmol) and the reaction mixture was heated at 100° C. for 16 h. The reaction mixture was then filtered through Celite and filtrate was concentrated to afford crude compound, which purified by column chromatography eluting with a gradient of EtOAc/hexane) to obtain 7-bromo-3-(4-(trifluoromethoxy)phenyl)-3H-benzo[e]indazole (850 mg, 65% yield). LC/MS (method 2): $R_t$=4.52; MS: m/z=407.01. $^1$H NMR (400 MHz, CDCl$_3$): δ 8.60 (d, J=0.9 Hz, 1 H), 8.16 (d, J=8.7 Hz, 1H), 8.11 (d, J=2.0 Hz, 1 H), 7.82-7.69 (m, 5 H), 7.43 (d, J=8.4 Hz, 2 H).

Step 2: 3-(4-(trifluoromethoxy)phenyl)-7-vinyl-3H-benzo[e]indazole

To a stirred solution of the product of step 1 (750 mg, 1.85 mmol) in toluene (20 mL) was added tributyl(vinyl)stannane (600 mg, 1.85 mmol) and (1,1'-bis(diphenylphosphino)ferrocene)palladium(II) dichloride (200 mg, 0.184 mmol). The reaction mixture was heated at 100° C. for 16 h then filtered through celite and filtrate concentrated to afford 3-(4-(trifluoromethoxy)phenyl)-7-vinyl-3H-benzo[e]indazole (700 mg) which was used without further purification.

Step 3: 3-(4-(trifluoromethoxy)phenyl)-3H-benzo[e]indazole-7-carbaldehyde

To a stirred solution of the product of step 2 (700 mg, 1.97 mmol) in dioxane:water (5:1, 25 mL) were added NaIO$_4$ (840 mg, 3.93 mmol) and OsO$_4$ (143 mg, 0.560 mmol). The reaction mixture was then stirred at room temperature for 1 h, diluted with EtOAc and washed with water. The organic layer was separated, dried over Na$_2$SO$_4$ and concentrated to afford crude compound, which purified by column chromatography eluting with a gradient of EtOAc/hexane) to obtain 3-(4-(trifluoromethoxy)phenyl)-3H-benzo[e]indazole-7-carbaldehyde (150 mg, 33% yield). $^1$H NMR (400 MHz, CDCl$_3$): δ 10.19 (s, 1 H), 8.69 (d, J=1.0 Hz, 1 H), 8.47 (d, J=1.6 Hz, 1 H), 8.40 (d, J=8.4 Hz, 1 H), 8.17 (dd, J=8.4, 1.6 Hz, 1 H), 7.95 (d, J=9.1 Hz, 1 H), 7.86-7.78 (m, 3 H), 7.45 (d, J=8.4 Hz, 2 H).

Step 4: (E)-N-(2,6-dimethylphenyl)-2-((3-(4-(trifluoromethoxy)phenyl)-3H-benzo[e]indazol-7-yl)methylene)hydrazinecarbothioamide To a stirred solution of the product of step 3 (80 mg, 0.22 mmol) and N-(2,6-dimethylphenyl)hydrazinecarbothioamide (43 mg, 0.22 mmol) in ethanol (5 mL) was added catalytic amount of acetic acid and the reaction mixture was heated at reflux for 2 h. The resultant solid was isolated by filtration and dried to obtain (E)-N-(2,6-dimethylphenyl)-2-((3-(4-(trifluoromethoxy)phenyl)-3H-benzo[e]indazol-7-yl)methylene)hydrazinecarbothioamide (50 mg, 42% yield). LC/MS (method 2): $R_t$=3.10 min; MS: m/z=534.09 (M+). $^1$H NMR (400 MHz, DMSO-d$_6$): δ 11.82 (s, 1 H), 9.94 (s, 1 H), 9.02 (s, 1 H), 8.48-8.44 (m, 2 H), 8.41 (s, 1 H), 8.33 (s, 1 H), 8.02-7.93 (m, 4 H), 7.64 (d, J=8.4 Hz, 2 H), 7.14 (d, J=1.7 Hz, 3 H), 2.23 (s, 6 H).

Example 19

(7-bromo-3-(4-(trifluoromethoxy)phenyl)-3H-naphtho[1,2-d][1,2,3]triazole

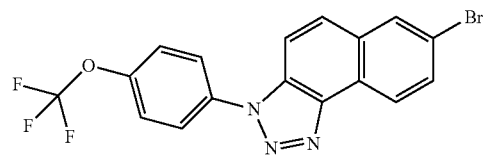 [SMILES: FC(F)(F)Oc1ccc(-n2nnc3c4ccc(Br)cc4ccc32)cc1]

Step 1: 1-azido-4-(trifluoromethoxy)benzene

To a stirred solution of 4-(trifluoromethoxy)aniline (5.0 g, 13.5 mmol) in aqueous HCl (6 M, 75 mL) at 0° C. was added NaNO$_2$ (2.14 g, 31.1 mmol) in H$_2$O. After 15 min NaN$_3$ (2.0 g, 31 mmol) was added and stirring was continued at 0° C. to room temperature for 2 h. The reaction mixture was then diluted with CH$_2$Cl$_2$ and washed with water. The organic layer was separated, dried over Na$_2$SO$_4$ and concentrated to afford 1-azido-4-(trifluoromethoxy)benzene (5.0 g, 86% yield) which was used without further purification.

Step 2: 7-bromo-3-(4-(trifluoromethoxy)phenyl)-4,5-dihydro-3H-naphtho[1,2-d][1,2,3]triazole To a stirred solution of 6-bromo-3,4-dihydronaphthalen-2(1H)-one (5.0 g, 22.32 mmol) in DMSO (50 mL) were added L-proline (500 mg, 4.46 mmol) and the product of step 1 (4.5 g, 22 mmol). The reaction mixture was stirred at room temperature for 16 h (TLC). The reaction mixture was then diluted with EtOAc and washed with water. The organic layer was separated, dried over Na$_2$SO$_4$ and concentrated to afford crude compound, which purified by column chromatography eluting with a gradient of EtOAc/hexane) to obtain 7-bromo-3-(4-(trifluoromethoxy)phenyl)-4,5-dihydro-3H-naphtho[1,2-d][1,2,3]triazole (2.0 g, 22% yield). LC/MS (method 2): Rt=2.44; MS: m/z=410.10. $^1$H NMR (400 MHz, CDCl$_3$): δ 7.88 (d, J=8.1 Hz, 1 H), 7.66-7.60 (m, 2 H), 7.48 (dd, J=8.1, 2.0 Hz, 1 H), 7.45-7.39 (m, 3 H), 3.19-2.99 (m, 4 H).

Step 3: (7-bromo-3-(4-(trifluoromethoxy)phenyl)-3H-naphtho[1,2-d][1,2,3]triazole To a stirred solution of the product of step 2 (1.0 g, 2.4 mmol) in toluene (20 mL) was added DDQ (1.1 g, 4.88 mmol) and the reaction mixture was stirred at 100° C. for 16 h. The reaction mixture was filtered through Celite and the filtrate was concentrated to afford crude compound, which purified by column chromatography eluting with a gradient of EtOAc/hexane) to obtain (7-bromo-3-(4-(trifluoromethoxy)phenyl)-3H-naphtho[1,2-d][1,2,3]triazole (400 mg, 40% yield). LC/MS (method 2): $R_t$=3.07; MS: m/z=407.88 (M+).

Example 20

3-(4-(trifluoromethoxy)phenyl)-4,5-dihydronaphtho[1,2-c]isothiazole-7-carbaldehyde

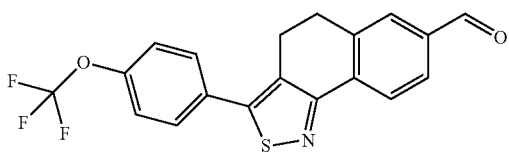 [SMILES: O=Cc1ccc2c(c1)CCc1c-2nsc1-c1ccc(OC(F)(F)F)cc1]

Step 1: 7-bromo-3-(4-(trifluoromethoxy)phenyl)-4,5-dihydronaphtho[1,2-c]isoxazole To a stirred solution of (Z)-6-bromo-3,4-dihydronaphthalen-1(2H)-one oxime (4.5 g, 19 mmol) in THF (40 mL) at 0° C. was added LDA (2 M, 23.5 mL). After 1 h methyl 4-(trifluoromethoxy)benzoate (10.34 g, 47.1 mmol) was added and stirring was continued from 0° C. to room temperature for 2 h. The reaction mixture was quenched with a saturated aqueous solution of NH₄Cl (10 mL), diluted with EtOAc and washed with water. The organic layer was separated, dried over Na₂SO₄ and concentrated. The resultant solid was dissolved in toluene and heated in at reflux for 1 h in a catalytic amount of p-TsOH. The reaction mixture was then diluted with EtOAc and washed with water. The organic layer was separated, dried over Na₂SO₄ and concentrated to afford 7-bromo-3-(4-(trifluoromethoxy)phenyl)-4,5-dihydronaphtho[1,2-c]isoxazole which was used without further purification.

Step 2: 7-bromo-3-(4-(trifluoromethoxy)phenyl)-4,5-dihydronaphtho[1,2-c]isothiazole To the product of step 1 (1.0 g, 2.4 mmol) was added imidazole (415 mg, 6.1 mmol) followed by P₂S₅ (1.35 g, 6.1 mmol) and the reaction mixture was heated at 160° C. for 3 h. Dilution with CH₂Cl₂ (100 mL), filtration and concentration of the filtrate to afford crude compound which purified by column chromatography eluting with a gradient of EtOAc/hexane to obtain 7-bromo-3-(4-(trifluoromethoxy)phenyl)-4,5-dihydronaphtho[1,2-c]isothiazole (500 mg, 50% yield). LC/MS (method 2): $R_t$=3.45; MS: m/z=425.94. $^1$H NMR (400 MHz, CDCl₃): δ 8.00 (d, J=8.2 Hz, 1H), 7.54-7.45 (m, 4H), 7.38-7.31 (m, 2H), 3.04-2.94 (m, 4H).

Step 3: 3-(4-(trifluoromethoxy)phenyl)-4,5-dihydronaphtho[1,2-c]isothiazole-7-carbaldehyde To a stirred solution of the product of step 1 (550 mg, 1.29 mmol) in THF (5.5 mL) at −78° C. was added n-BuLi (0.77 mL, 1.9 mmol). After 45 min DMF (0.15 mL, 1.9 mmol) was added and stirring was continued for 30 min. The reaction mixture was quenched with a saturated solution of NH₄Cl (4 mL), diluted with EtOAc and washed with water. The organic layer was separated, dried over Na₂SO₄ and concentrated to afford crude compound, which purified by column chromatography eluting with a gradient of EtOAc/hexane) to obtain 3-(4-(trifluoromethoxy)phenyl)-4,5-dihydronaphtho[1,2-c]isothiazole-7-carbaldehyde (90 mg, 16% yield). LC/MS (method 2): Rt=4.34; MS: m/z=375.99. $^1$H NMR (400 MHz, CDCl₃): δ 10.44 (s, 1H), 8.16-8.12 (m, 1H), 8.08 (d, J=2.4 Hz, 1H), 7.78 (dd, J=8.6, 2.4 Hz, 1H), 7.50 (dq, J=8.6, 1.7 Hz, 1H), 7.39-7.35 (m, 2H), 7.32-7.28 (m, 1H), 3.03 (qd, J=6.5, 5.8, 3.6 Hz, 4H).

Example 21

7-bromo-3-(4-(trifluoromethoxy)phenyl)naphtho[1,2-c]isoxazole

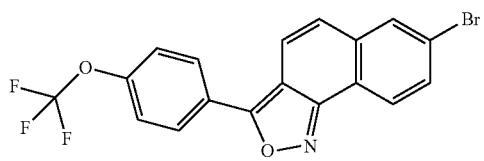 [SMILES: FC(F)(F)Oc1ccc(-c2onc3c2ccc2cc(Br)ccc23)cc1]

Step 1: 7-bromo-3-(4-(trifluoromethoxy)phenyl)naphtho[1,2-c]isoxazole

To a stirred solution of 7-bromo-3-(4-(trifluoromethoxy)phenyl)-4,5-dihydronaphtho[1,2-c]isoxazole (2.0 g, 4.89 mmol) in AcOH (20 mL) was added activated MnO₂ (2.13 g, 24.5 mmol). The reaction mixture was heated in a sealed tube at 160° C. for 48 h then poured into ice water (100 mL), diluted with EtOAc (200 mL) and filtered through Celite. The organic layer was separated, dried over Na₂SO₄ and concentrated to afford crude compound, which was purified by column chromatography eluting with a gradient of EtOAc/hexane to obtain to obtain 7-bromo-3-(4-(trifluoromethoxy)phenyl)naphtho[1,2-c]isoxazole (700 mg, 35% yield). LC/MS (method 2): Rt=4.65; MS: m/z=407.93 (M+). $^1$H NMR (400 MHz, CDCl₃): δ 8.42 (d, J=8.5 Hz, 1H), 8.09-8.01 (m, 2H), 7.92 (d, J=1.9 Hz, 1H), 7.74 (dd, J=8.5, 1.9 Hz, 1H), 7.61 (d, J=9.3 Hz, 1H), 7.46-7.38 (m, 2H), 7.28 (s, 1H).

Example 22

7-bromo-3-(4-(trifluoromethoxy)phenyl)naphtho[1,2-c]isothiazole

To a stirred solution of 7-bromo-3-(4-(trifluoromethoxy)phenyl)-4,5-dihydronaphtho[1,2-c]isothiazole (850 mg, 1.99 mmol) in AcOH (8.5 mL) was added activated MnO₂ (1.73 g, 19.9 mmol). The reaction mixture was heated in a sealed tube at 160° C. for 36 h then poured into ice water (100 mL), diluted with EtOAc (200 mL) and filtered through Celite. The organic layer was separated, dried over Na₂SO₄ and concentrated to afford crude compound, which was purified by column chromatography eluting with a gradient of EtOAc/hexane to obtain to obtain 7-bromo-3-(4-(trifluoromethoxy)phenyl)naphtho[1,2-c]isothiazole (400 mg, 48% yield). LC/MS (method 2): Rt=3.61; MS: m/z=423.76 (M+). $^1$H NMR (400 MHz, CDCl₃): δ 8.70 (d, J=8.6 Hz, 1H), 7.97

(d, J=1.9 Hz, 1H), 7.77 (dd, J=8.7, 1.9 Hz, 1H), 7.74-7.68 (m, 2H), 7.64 (d, J=9.3 Hz, 1H), 7.47-7.40 (m, 3H).

Example 23

(E)-2-((3-(3,5-dichlorophenyl)-3H-naphtho[1,2-d]imidazol-7-yl)methylene)-N-(2,6-dimethylphenyl)hydrazinecarbothioamide (compound C-111)

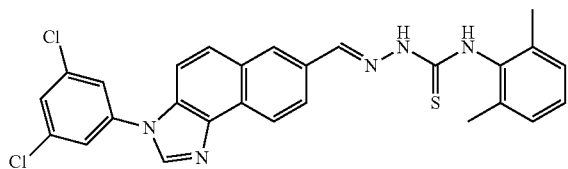 [SMILES: Cc1cccc(C)c1NC(=S)N/N=C/c1ccc2c(ccc3c2ncn3-c2cc(Cl)cc(Cl)c2)c1]

Step 1: 3-(3,5-dichlorophenyl)-3H-naphtho[1,2-d]imidazole-7-carbaldehyde

To a stirred solution of 3H-naphtho[1,2-d]imidazole-7-carbaldehyde (1.2 g, 6.12 mmol) and 3,5-dichlorophenylboronic acid (1.74 g, 9.18 mmol) in $CH_2Cl_2$ (24 mL) were added triethylamine (2.62 mL 18.4 mmol), pyridine (0.8 mL, 9.2 mmol), 4 A° molecular sieves (500 mg) and copper acetate (1.67 g, 9.2 mmol). The reaction mixture was stirred at room temperature for 16 h then filtered over Celite. The reaction mixture was diluted with $CH_2Cl_2$ and washed with aqueous HCl (2 M, 20 mL). The organic layer was then separated, dried over $Na_2SO_4$ and concentrated to afford crude compound, which was purified by column chromatography eluting with a gradient of EtOAc/hexane to obtain to obtain impure 3-(3,5-dichlorophenyl)-3H-naphtho[1,2-d]imidazole-7-carbaldehyde (600 mg, 19% purity by HPLC) and which was used without further purification. LC/MS (method 2): $R_t$=3.30 min; MS: m/z=341 (M+).

Step 2: 3(E)-2-((3-(3,5-dichlorophenyl)-3H-naphtho[1,2-d]imidazol-7-yl)methylene)-N-(2,6-dimethylphenyl)hydrazinecarbothioamide To a stirred solution of 3-(3,5-dichlorophenyl)-3H-naphtho[1,2-d]imidazole-7-carbaldehyde (600 mg) and N-(2,6-dimethylphenyl)hydrazinecarbothioamide (206 mg, 1.06 mmol) in ethanol (10 mL) was added catalytic amount of acetic acid. The reaction mixture was then heated at reflux for 1 h. The resultant solid was isolated by filtration and purified by preparative HPLC to obtain 3(E)-2-((3-(3,5-dichlorophenyl)-3H-naphtho[1,2-d]imidazol-7-yl)methylene)-N-(2,6-dimethylphenyl)hydrazinecarbothioamide (52 mg). $^1$H NMR (400 MHz, DMSO-$d_6$): δ 11.83 (s, 1H), 9.96 (s, 1H), 8.71 (s, 1H), 8.51-8.34 (m, 4H), 7.94-7.83 (m, 5H), 7.12 (s, 3H), 2.23 (s, 6H).

Example 24

3-[4-(trifluoromethylsulfanyl)phenyl]benzo[e]benzimidazole-7-carbaldehyde

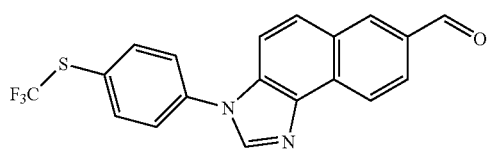 [SMILES: O=Cc1ccc2c(ccc3c2ncn3-c2ccc(SC(F)(F)F)cc2)c1]

Step 1: 2-bromo-6-methoxy-naphthalene

To a mixture of 6-bromonaphthalen-2-ol (50.0 g, 0.23 mol) and $Cs_2CO_3$ (88.1 g, 0.27 mol) in acetone (600 mL) was added MeI (35.2 g, 0.25 mol) dropwise at 0° C. The mixture was allowed to warm to 26° C. and stirred overnight. The reaction was filtered via filter paper. The organic layer was evaporated in vacuum to give 2-bromo-6-methoxynaphthalene (51.8 g, yield: 97%). 1H NMR (400 MHz, $CDCl_3$): 8.01 (s, 1H), 7.88~7.90 (d, J=8 MHz, 1H), 7.66~7.68 (m, 1H), 7.56~7.58 (d, J=8 MHz, 1H), 7.37~7.39 (d, J=8 MHz, 1H), 4.05 (s, 3H).

Step 2: 6-bromo-2-methoxy-1-nitro-naphthalene

A mixture of $HNO_3$ (10 mL) and AcOH (70 mL) was added to a mixture of the product of step 1 (50 g, 0.21 mol) in AcOH (350 mL) dropwise at 25° C. The mixture was heated to 50° C. and stirred for 2.5 h. The reaction was cooled to 25° C. and filtered off with suction and washed with AcOH to give the 6-bromo-2-methoxy-1-nitro-naphthalene (48.3 g, yield: 81.2%). $^1$H NMR (400 MHz, $CDCl_3$): 8.01 (s, 1H), 7.88~7.90 (d, J=8 MHz, 1H), 7.66~7.68 (m, 1H), 7.56~7.58 (d, J=8 MHz, 1H), 7.37~7.39 (d, J=8 MHz, 1H), 4.05 (s, 3H).

Step 3: 2-methoxy-1-nitro-6-vinyl-naphthalene

To a mixture of the product of step 2 (17.2 g, 61.0 mmol), 4,4,5,5-tetramethyl-2-vinyl-1,3,2-dioxaborolane (14.1 g, 91.5 mmol) and KF (7.1 g, 122.0 mmol) in $THF/H_2O$ (V/V=4:1, 350 mL) was added $Pd(PPh_3)Cl_2$ (4.3 g, 6.10 mmol) under $N_2$. The mixture was heated to reflux and stirred overnight. The reaction was cooled and diluted with EtOAc. The organic layer was separated, dried and concentrated to dryness. The residue was purified by silica gel chromatography to give 2-methoxy-1-nitro-6-vinyl-naphthalene (12.4 g, yield: 89%). $^1$H NMR (400 MHz, $CDCl_3$): 7.91~7.94 (d, J=12 MHz, 1H), 7.74~7.76 (m, 2H), 7.63~7.66 (d, J=12 MHz, 1H), 7.31~7.34 (d, J=12 MHz, 1H), 6.81~6.88 (m, 1H), 5.86~5.90 (d, J=16 MHz, 1H), 5.37~5.40 (d, J=12 MHz, 1H), 4.03 (s, 3H).

Step 4: 1-nitro-6-vinyl-naphthalen-2-ol

To a mixture of the product of step 3 (20.8 g, 90.8 mmol) in dry DCM (1.0 L) was added $BBr_3$ (33.8 mL, 363 mmol) between −70 and −65° C. under $N_2$. The mixture was stirred for 0.5 h at −70° C. The reaction was quenched with $H_2O$ at −60° C. The mixture was allowed to warm to 24° C. The organic layer was separated and the water phase was extracted with EtOAc. The combined organic layers were dried and concentrated to dryness. The residue was purified by silica gel chromatography to give the 1-nitro-6-vinyl-naphthalen-2-ol (16.2 g, yield: 83%). $^1$H NMR (400 MHz, DMSO-$d_6$): 11.43 (s, Ar—OH, 1H), 8.00~8.02 (d, J=8 MHz, 1H), 7.96 (s, 1H), 7.83~7.85 (d, J=8 MHz, 1H), 7.54~7.56 (d, J=8 MHz, 1H), 7.32~7.34 (d, J=8 MHz, 1H), 6.84~6.91 (m, 1H), 5.94~5.98 (d, J=16 MHz, 1H), 5.35~5.38 (d, J=12 MHz, 1H).

Step 5: (1-nitro-6-vinyl-2-naphthyl)trifluoromethanesulfonate

To a mixture of the product of step 4 (10.0 g, 46.5 mmol) and $Et_3N$ (5.6 g, 55.8 mmol) in DCM (1.0 L) was added $Tf_2O$ (14.4 g, 51.2 mmol) dropwise at 0° C. under $N_2$. The mixture was stirred for 1.5 h at 0° C. The reaction was quenched with H₂O at 0° C. The organic layer was separated, dried and concentrated to dryness. The residue was purified by silica gel chromatography to give (1-nitro-6-vinyl-2-naphthyl)trifluoromethanesulfonate (13.6 g, yield: 84.0%). ¹H NMR (400 MHz, CDCl₃): 8.06~8.08 (d, J=8 MHz, 1H), 7.87~7.91 (m, 3H), 7.52~7.54 (d, J=8 MHz, 1H), 6.86~6.93 (m, 1H), 5.97~5.01 (d, J=16 MHz, 1H), 5.51~5.54 (d, J=12 MHz, 1H).

Step 6: 1-nitro-N-[4-(trifluoromethylsulfanyl)phenyl]-6-vinyl-naphthalen-2-amine To a mixture of the product of step 5 (8.0 g, 23.0 mmol), 4-(trifluoromethylsulfanyl)aniline (4.4 g, 23.0 mmol), PPh₃ (6.0 g, 23.0 mmol) and K₂CO₃ (6.4 g, 46.0 mmol) in dry toluene (400 mL) was added Pd(PPh₃)₄ (32.0 g, 51.2 mmol) under N₂. The mixture was heated to 110° C. and stirred overnight. The reaction was quenched with H2O and filtered via Celite pad. The organic layer was separated, dried and concentrated to dryness. The residue was purified by silica gel chromatography to give 1-nitro-N-[4-(trifluoromethylsulfanyl)phenyl]-6-vinyl-naphthalen-2-amine (2.0 g, yield: 22%). ¹H NMR (400 MHz, CDCl₃): 9.06 (s, 1H), 8.34~8.36 (d, J=8 MHz, 1H), 7.82~7.84 (d, J=8 MHz, 1H), 7.77~7.79 (d, J=8 MHz, 1H), 7.66~7.69 (m, 3H), 7.48~7.50 (d, J=8 MHz, 1H), 7.29 (s, 1H), 6.81~6.88 (m, 1H), 5.88~5.92 (d, J=16 MHz, 1H), 5.38~5.41 (d, J=12 MHz, 1H).

Step 7: N2-[4-(trifluoromethylsulfanyl)phenyl]-6-vinyl-naphthalene-1,2-diamine

To the product of step 6 (1.6 g, 4.10 mmol), NH₄Cl (2.2 g, 40.1 mmol) and H₂O (10 mL) in EtOH (30 mL) was added Fe (2.3 g, 40.1 mmol) under N₂ at 90° C. The mixture then was stirred and detected by TLC. When the starting material was consumed completely, the reaction mixture was cooled and filtered via Celite pad. The organic layer was concentrated to dryness. The residue was partitioned between EtOAc and H₂O. The organic layer was separated, dried over Na₂SO₄ and concentrated to dryness to give N2-[4-(trifluoromethylsulfanyl)phenyl]-6-vinyl-naphthalene-1,2-diamine (1.2 g) which was used without further purification.

Step 8: 3-[4-(trifluoromethylsulfanyl)phenyl]-7-vinyl-benzo[e]benzimidazole

A mixture of the product of step 7 (3.4 g, 9.44 mmol) in DMF-DMA (60 mL) was heated to 70° C. and stirred for 4 h. The reaction was concentrated to dryness. The residue was purified by silica gel chromatography to give 3-[4-(trifluoromethylsulfanyl)phenyl]-7-vinyl-benzo[e]benzimidazole (2.4 g, 68.6%)¹H NMR (400 MHz, CDCl₃): 8.64~8.66 (d, J=8 MHz, 1H), 8.21 (s, 1H), 7.91~7.93 (m, 3H), 7.85~7.87 (d, J=8 MHz, 1H), 7.76~7.78 (d, J=8 MHz, 1H), 7.64~7.68 (m, 3H), 6.91~6.98 (m, 1H), 5.91~5.95 (d, J=16 MHz, 1H), 5.35~5.38 (d, J=12 MHz, 1H).

Step 9: 3-[4-(trifluoromethylsulfanyl)phenyl]benzo[e]benzimidazole-7-carbaldehyde A mixture of the product of step 8 (0.9 g, 2.43 mmol) in dioxane (100 mL) and H₂O (20 mL) was added OsO₄ (62 mg, 0.24 mmol), then added NaIO₄ (2.6 g, 12.2 mmol) in portionwise at 22° C. and stirred. When the starting material was consumed completely, the reaction was quenched with aq. Na₂S₂O₃, and extracted with EtOAc. The organic layer was dried and concentrated to dryness. The residue was purified by silica gel chromatography to give 3-[4-(trifluoromethylsulfanyl)phenyl]benzo[e]benzimidazole-7-carbaldehyde (502 mg, 55%). ¹H NMR (400 MHz, CDCl₃): 10.22 (s, Ar—CHO, 1H), 8.80~8.82 (d, J=8 MHz, 1H), 8.50 (s, 1H), 8.28 (s, 1H), 7.17~7.20 (dd, J=4 MHz, 8 MHz, 1H), 7.94~7.96 (d, J=8 MHz, 3H), 7.75~7.77 (d, J=8 MHz, 1H), 7.67~7.69 (d, J=8 MHz, 2H).

Example 25

(2Z)-3-(2,6-dimethylphenyl)-2-[(E)-[3-[4-(trifluoromethoxy)phenyl]benzo[e]benzimidazol-7-yl]methylenehydrazono]thiazolidin-4-one (compound C-119)

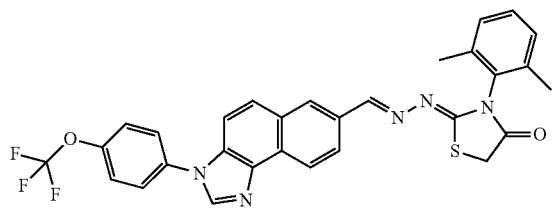

Step 1: 1-(2,6-dimethylphenyl)-3-[(E)-[3-[4-(trifluoromethoxy)phenyl]benzo[e]benzimidazol-7-yl]methyleneamino]thiourea A mixture of 3-[4-(trifluoromethoxy)phenyl]benzo[e]benzimidazole-7-carbaldehyde (1 g, 2.81 mmol) and 1-amino-3-(2,6-dimethylphenyl)thiourea (0.55 g, 2.81 mmol) in ethanol was heated at 80° C. for 12 h. The reaction mixture was allowed to cool to RT and the precipitated solid was collected by filtration. The solid compound was washed with cold ethanol and dried under vacuum to afford 1.3 g of 1-(2,6-dimethylphenyl)-3-[(E)-[3-[4-(trifluoromethoxy)phenyl]benzo[e]benzimidazol-7-yl]methyleneamino]thiourea. LC/MS (Method 3): Rt: 3.15 min; MS: m/z=534.1 (M+1); ¹H NMR (DMSO-d₆): 11.85 (s, 1 H), 9.97 (s, 1H), 8.69 (s, 1H), 8.44-8.52 (m, 2H), 8.38 (d, J=12 Hz, 2H), 7.93-7.89 (m, 3H), 7.82 (d, J=9 Hz, 1H), 7.70 (d, J=8.1 Hz, 2H), 7.15-7.14 (m, 3 H), 2.27 (s, 6H).

Step 2: (2Z)-3-(2,6-dimethylphenyl)-2-[(E)-[3-[4-(trifluoromethoxy)phenyl]benzo[e]benzimidazol-7-yl]methylenehydrazono]thiazolidin-4-one To a solution of (2Z)-3-(2,6-dimethylphenyl)-2-[(E)-[3-[4-(trifluoromethoxy)phenyl]benzo[e]benzimidazol-7-yl]methylenehydrazono]thiazolidin-4-one (0.1 g, 0.19 mmol) and Sodium acetate (0.05 g, 0.56 mmol) in 10 mL of ethanol was added Methyl bromoacetate (0.03 mL, 0.28 mmol) and the resultant mixture stirred between 25-30° C. for 48 h. The reaction mixture was evaporated under vacuum and 20 mL of water was added to the residue and then extracted with EtOAc (2×20 mL). The combined organic layer was dried over anhydrous sodium sulphate and concentrated under vacuum a residue which was recrystallized using a mixture of Dichloromethane:n-pentane (1:5) to afford 0.1 g (93%) of (2Z)-3-(2,6-dimethylphenyl)-2-[(E)-[3-[4-(trifluoromethoxy)phenyl]benzo[e]benzimidazol-7-yl]methylenehydrazono]thiazolidin-4-one. LC/MS (Method 3): R_t: 3.474 min; MS: m/z=574 (M+1). ¹H NMR (DMSO-d₆): 8.71 (s, 1

H), 8.60 (d, J=8.4 Hz, 1H), 8.51 (s, 1H), 8.29 (s, 1H), 7.79-8.15 (m, 4H), 7.70 (d, J=8.4 Hz, 2H), 7.25-7.22 (m, 3H), 4.30 (s, 2H), 2.13 (s, 6H).

Example 26

(2Z)-3-(2,6-dimethylphenyl)-5,5-dimethyl-2-[(E)-[3-[4-(trifluoromethoxy)phenyl]benzo[e]benzimidazol-7-yl]methylenehydrazono]thiazolidin-4-one (compound C-118)

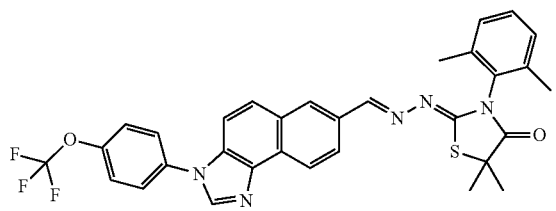 [SMILES: Cc1cccc(C)c1N1C(=O)C(C)(C)S/C1=N\N=C\c1ccc2c(ccc3c2ncn3-c2ccc(OC(F)(F)F)cc2)c1]

To a stirred solution of (2Z)-3-(2,6-dimethylphenyl)-2-[(E)-[3-[4-(trifluoromethoxy)phenyl]benzo[e]benzimidazol-7-yl]methylenehydrazono]thiazolidin-4-one (170 mg, 0.3 mmol) in DMF at 0° C. was added NaH (50 mg, 1.19 mmol). The reaction mixture stirred for 5 min and Methyl iodide (0.06 mL, 0.89 mmol) was added. The reaction mixture was stirred at 30° C. for 2 h. The reaction was quenched with ice cold water (20 mL) and was extracted with EtOAc (2×20 mL). The combined organic layer was washed with brine, dried over Sodium sulphate and evaporate under vacuum to get a crude product which was purified by silica gel column chromatography eluting with a gradient of n-Heptane and chloroform to afford (2Z)-3-(2,6-dimethylphenyl)-5,5-dimethyl-2-[(E)-[3-[4-(trifluoromethoxy)phenyl]benzo[e]benzimidazol-7-yl]methylenehydrazono]thiazolidin-4-one (110 mg, 61%). LC/MS (Method 3): $R_t$=3.76 min; MS: m/z=602 (M+1). $^1$H NMR (DMSO-d$_6$): 8.64 (s, 1 H), 8.52 (d, J=8.4 Hz, 1H), 8.44 (s, 1H), 8.22 (s, 1H), 8.05 (d, J=9 Hz, 1H), 7.77-7.78 (m, 4H), 7.63 (d, J=9 Hz, 2H), 7.16-7.26 (m, 3H), 2.06 (s, 6H), 1.68 (s, 6H).

Example 27

3-(2,6-dimethylphenyl)-5-methyl-2-[(E)-[3-[4-(trifluoromethoxy)phenyl]benzo[e]benzimidazol-7-yl]methylenehydrazono]thiazolidin-4-one (compound C-121)

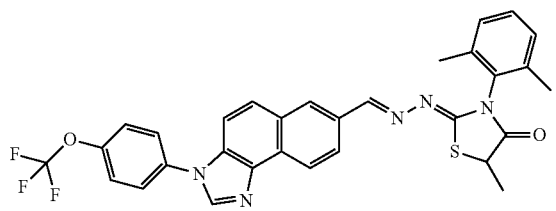 [SMILES: Cc1cccc(C)c1N1C(=O)C(C)S/C1=N\N=C\c1ccc2c(ccc3c2ncn3-c2ccc(OC(F)(F)F)cc2)c1]

To a solution of 1-(2,6-dimethylphenyl)-3-[(E)-[3-[4-(trifluoromethoxy)phenyl]benzo[e]benzimidazol-7-yl]methyleneamino]thiourea (0.15 g, 0.28 mmol) and sodium acetate (0.07 g, 0.84 mmol) in 15 mL of EtOH was added methyl 2-bromopropanoate (0.04 mL, 0.42 mmol) The mixture heated at 60° C. for 24 h. The EtOH was evaporated under vacuum and 20 mL of water was added and the mixture extracted with EtOAc (2×20 mL). The combined organic layer was dried over Na$_2$SO$_4$ and concentrated under vacuum to get a residue which was purified by silica gel column chromatography eluting with a gradient of n-Heptane/chloroform to afford 0.12 g (73%) of 3-(2,6-dimethylphenyl)-5-methyl-2-[(E)-[3-[4-(trifluoromethoxy)phenyl]benzo[e]benzimidazol-7-yl]methylenehydrazono]thiazolidin-4-one. LC/MS (Method 3): $R_t$: 3.638 min; MS: m/z=588 (M+1). $^1$H NMR (DMSO-d$_6$): 8.71 (s, 1 H), 8.59 (d, J=8.4 Hz, 1H), 8.51 (s, 1H), 8.30 (s, 1H), 8.14 (d, J=9 Hz, 1H), 7.90-7.79 (m, 4H), 7.70 (d, J=9 Hz, 2H), 7.31-7.23 (m, 3H), 4.61 (q, J=6 Hz, 1H), 2.14 (s, 3H), 2.11 (s, 3H), 1.69 (d, J=6 Hz, 3H).

Example 28

1-(2,6-dimethylphenyl)-3-[2-methyl-3-[4-(trifluoromethoxy)phenyl]-4H-chromeno[4,3-c]pyrazol-7-yl]methyleneamino]thiourea (compound C-132)

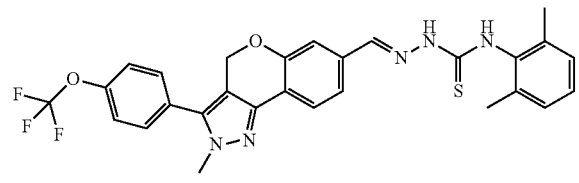 [SMILES: Cc1cccc(C)c1NC(=S)N/N=C/c1ccc2c(c1)OCc1c-2nn(C)c1-c1ccc(OC(F)(F)F)cc1]

Step 1: 7-bromo-3-[[4-(trifluoromethoxy)phenyl]methylene]chroman-4-one

To a stirred solution of 7-bromochromane-4-one (1.8 g, 7.9 mmol) in Acetic acid (10 mL) at 0° C. was added 4-(trifluoromethoxy)benzaldehyde (1.2 mL, 8.5 mmol) and consulfuric acid (5 mL). The mixture was stirred at 30° C. for 3 h and subsequently diluted with water and neutralized with solid NaHCO$_3$. The mixture was extracted with EtOAc (2×20 mL) and the organic layer was dried over Sodium sulfate and evaporated under vacuum to afford 7-bromo-3-[[4-(trifluoromethoxy)phenyl]methylene]chroman-4-one (2.7 g, 85%). $^1$H NMR (CDCl$_3$): 7.78-7.83 (2H, m), 7.13-7.30 (m, 6H), 5.28 (2 H, d, J=1.8 Hz).

Step 2: 7-bromo-2-methyl-3-[4-(trifluoromethoxy)phenyl]-3a,4-dihydro-3H-chromeno[4,3-c]pyrazole To a stirred solution of methyl hydrazine sulphate (1.17 g, 8.0 mmol) in ethanol (25 mL) was added Triethyl amine (1.35 g, 13.0 mmol) and stirred for 5 min. 7-bromo-3-[[4-(trifluoromethoxy)phenyl]methylene]chroman-4-one (2.7 g, 6.7 mmol) was added and the mixture was heated at 80° C. for 1 h. The reaction mixture was poured into ice water. The precipitated solid was filtered and washed with cold methanol to afford 7-bromo-2-methyl-3-[4-(trifluoromethoxy)phenyl]-3a,4-dihydro-3H-chromeno[4,3-c]pyrazole (2.3 g, 79% yield). LC/MS (Method 3): $R_t$: 3.75 min; MS: m/z=427 (M+1), $^1$H NMR (CDCl$_3$): 7.56-7.59 (1H, m), 7.42 (2H, d, J=8.7 Hz), 7.19-7.22 (2H, m), 7.03-7.08 (2H, m).

Step 3: 7-bromo-2-methyl-3-[4-(trifluoromethoxy)phenyl]-4H-chromeno[4,3-c]pyrazole To a stirred solution of 7-bromo-2-methyl-3-[4-(trifluoromethoxy)phenyl]-3a,4-dihydro-3H-chromeno[4,3-c]pyrazole (2.3 g, 5.4 mmol) in Carbontetrachloride (30 mL) was added Sodium bicarbonate (1.36 g, 16.0 mmol) and Bromine (0.3 mL, 5.6 mmol). The mixture was stirred at 0° C. for 3 h. The reaction mixture was diluted with water and extracted with EtOAc. The organic layer was dried over sodium sulphate and concentrated under vacuum to afford 7-bromo-2-methyl-3-[4-(trifluoromethoxy)phenyl]-4H-chromeno[4,3-c]pyrazole (1.45 g, 63%). LC/MS (Method 3): Rt: 3.67 min; MS: m/z=425 (M+1), $^1$H NMR (CDCl$_3$): 7.67 (1H, d, J=8.1 Hz), 7.33 (4H, s), 7.12 (2H, d, J=11.4 Hz), 5.17 (2H, s), 3.89 (3H, s).

Step 4: 2-methyl-3-[4-(trifluoromethoxy)phenyl]-7-vinyl-4H-chromeno[4,3-c]pyrazole A stirred solution of 7-bromo-2-methyl-3-[4-(trifluoromethoxy)phenyl]-4H-chromeno[4,3-c]pyrazole (1.45 g, 3.4 mmol) in Toluene was degassed with nitrogen gas. Tri n-butyl vinyl tin (1 mL, 3.4 mmol) and PdCl$_2$(dppf)$_2$ (0.124 g, 7.6 mmol) were added. The mixture was heated at 100° C. for 2 h. The reaction mixture was diluted with EtOAc and filtered through Celite. The filtrate was washed with water and dried over sodium sulfate and concentrated under vacuum to afford 7-bromo-2-methyl-3-[4-(trifluoromethoxy)phenyl]-4H-chromeno[4,3-c]pyrazole (0.75 g, 62%). LC/MS (Method 3): R$_t$: 3.53 min; MS: m/z=373 (M+1), $^1$H NMR (CDCl$_3$): 7.66 (1H, d, J=7.8 Hz), 7.21 (4H, m), 6.98-7.05 (2H, m), 6.56-6.66 (1H, m), 5.70 (1H, d, J=17.7 Hz), 5.14-5.22 (3H, m), 3.82 (3H, s).

Step 5: 2-methyl-3-[4-(trifluoromethoxy)phenyl]-4H-chromeno[4,3-c]pyrazole-7-carbaldehyde To a stirred solution of 2-methyl-3-[4-(trifluoromethoxy)phenyl]-7-vinyl-4H-chromeno[4,3-c]pyrazole (0.75 g, 2.0 mmol) in dioxane (8 mL) was added osmium tetroxide (0.025 g, 0.1 mmol) in water (8 mL), Sodium periodate (0.86 g, 4.0 mmol). The mixture was stirred at 30° C. for 4 h. The reaction mixture was quenched with Sodium sulfite solution and extracted with EtOAc. The organic layer was dried over Sodium sulfate and concentrated under vacuum to afford 2-methyl-3-[4-(trifluoromethoxy)phenyl]-4H-chromeno[4,3-c]pyrazole-7-carbaldehyde (0.6 g, 80%). LC/MS (Method 3): R$_t$: 3.169 min; MS: m/z=375 (M+1).

Step 6: 1-(2,6-dimethylphenyl)-3-[(E)-[2-methyl-3-[4-(trifluoromethoxy)phenyl]-4H-chromeno[4,3-c]pyrazol-7-yl]methyleneamino]thiourea To a stirred solution of 2-methyl-3-[4-(trifluoromethoxy)phenyl]-4H-chromeno[4,3-c]pyrazole-7-carbaldehyde (0.6 g, 1.6 mmol) in ethanol (15 mL) was added 1-amino-3-(2,6-dimethylphenyl)thiourea (0.312 g, 1.6 mmol). The mixture was heated at 80° C. for 3 h. The reaction mixture was cooled to 0° C. The precipitated solid was filtered and dried to afford 1-(2,6-dimethylphenyl)-3-[(E)-[2-methyl-3-[4-(trifluoromethoxy)phenyl]-4H-chromeno [4,3-c]pyrazol-7-yl]methyleneamino]thiourea (0.63 g, 71%). LC/MS (Method 3): R$_t$: 3.4 min; MS: m/z=551 (M+1), $^1$H NMR (CDCl$_3$): 11.74 (1H, s), 9.94 (1H, s), 8.05 (1H, s), 7.70 (1H, s), 7.63-7.66 (3H, m), 7.53 (2H, d, J=8.4 Hz), 7.4 (1H, d), 7.11 (3H, s), 5.27 (2H, s), 3.87 (3H, s), 2.17 (6H, s).

Example 29

1-(2,6-dimethylphenyl)-3-[2-methyl-3-[4-(trifluoromethoxy)phenyl]benzo[e]benzimidazol-7-yl]methyleneamino]thiourea (compound C-129)

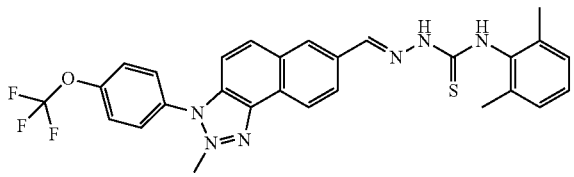

Step 1: 2-methyl-3-[4-(trifluoromethoxy)phenyl]-7-vinyl-benzo[e]benzimidazole

To a solution of 3-[4-(trifluoromethoxy)phenyl]-7-vinyl-benzo[e]benzimidazole (1.5 g, 4.23 mmol) in Tetrahydrofuran (100 mL) at –78° C. was added a solution of 2.0 M butyl lithium (4.23 mL, 8.45 mmol) in hexane and stirred for 1 h. Methyl iodide (1.2 g, 8.45 mmol) was added and stirred for another 1 h. The reaction mixture was allowed to warm up to ~10° C. and sat. ammonium chloride solution was added and the mixture partitioned between water and EtOAc. The organic layer was dried (Sodium sulphate) and evaporated under vacuum and the residue purified by column chromatography (silica gel 230-400; 25% EtOAc in Heptane) to afford 2-methyl-3-[4-(trifluoromethoxy)phenyl]-7-vinyl-benzo[e]benzimidazole (0.61 g, 39%). LC/MS (Method 3): R$_t$: 9.373 min; MS: m/z=368 (M+); $^1$H NMR (CDCl$_3$): 8.41-8.38 (m, 1H), 7.64-7.62 (m, 2H), 7.41 (d, 1H, J=9 Hz), 3.27 (m, 3H), 7.05-7.00 (m, 2H), 6.75-6.65 (m, 1H), 5.69 (dd, 1H, J=0.7 Hz, and 17 Hz), 5.12 (dd, 1H, 0.63 Hz and 11 Hz), 2.42 (s, 3H).

Step 2: (2-methyl-3-[4-(trifluoromethoxy)phenyl] benzo[e]benzimidazole-7-carbaldehyde)

To a stirred solution of 2-methyl-3-[4-(trifluoromethoxy)phenyl]-7-vinyl-benzo[e]benzimidazole (0.61 g, 1.72 mmol) in Dioxane (8 mL) was added Osmium tetroxide (0.02 g, 0.09 mmol) in water (8 mL) and Sodium periodate (0.74 g, 3.44 mmol) at RT. The mixture was stirred for 4 and subsequently sodium sulfite solution was added. The reaction mixture was extracted with EtOAc and the extracts were combined and dried over Sodium sulfate and evaporated under vacuum to afford (2-methyl-3-[4-(trifluoromethoxy) phenyl]benzo[e]benzimidazole-7-carbaldehyde) (0.41 g, 64%). LC/MS (Method 3): R$_t$: 2.95 min; MS: m/z=370 (M+1)$^1$H NMR (CDCl$_3$): 10.17 (s, 1H), 8.73 (d, 1H, J=8.5 Hz), 8.43 (s, 1H), 8.12 (d, 1H, J=8.4 Hz), 7.79 (d, 1H, J=8.7 Hz), 7.49 (s, 4H), 7.34 (d, 1H, J=9 Hz), 2.63 (s, 3H).

Step 3: 1-(2,6-dimethylphenyl)-3-[2-methyl-3-[4-(trifluoromethoxy)phenyl]benzo[e]benzimidazol-7-yl]methyleneamino]thiourea To a solution of (2-methyl-3-[4-(trifluoromethoxy)phenyl]benzo[e]benzimidazole-7-carbaldehyde) (0.3 g, 0.81 mmol) in ethanol (15 mL) was added 1-amino-3-(2,6-dimethylphenyl)thiourea (0.16 g, 0.81 mmol) at room temperature. The reaction mixture heated to 80° C. for 10 h. The reaction mixture was cooled to 5° C. and the solid obtained was filtered, washed with pentane and dried to afford 1-(2,6-dimethylphenyl)-3-[2-methyl-3-[4-(trifluoromethoxy)phenyl]benzo[e]benzimidazol-7-yl]methyleneamino]thiourea (0.44 g, 78%); LC/MS (Method 3): $R_t$: 3.247 min; MS: m/z=548 (M+1); $^1$H NMR (DMSO-$d_6$): 11.83 (s, 1H), 9.97 (s, 1H), 8.84 (s, 2H), 8.32-8.29 (m, 2H), 7.81-7.75 (m, 3H), 7.70-7.67 (m, 2H), 7.37 (d, 1H, J=9 Hz), 7.13 (s, 3H), 2.54 (s, 3H), 2.22 (s, 6H).

Example 30

6-bromo-2-methyl-3-[4-(trifluoromethoxy)phenyl]-4H-indeno[1,2-c]pyrazole and 6-bromo-1-methyl-3-[4-(trifluoromethoxy)phenyl]-2,4-dihydroindeno[1,2-c]pyrazole

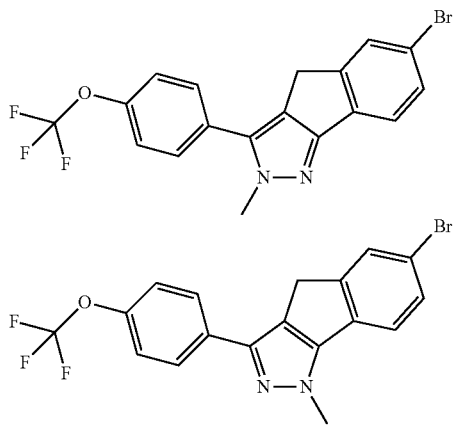

Step 1: (2Z)-5-bromo-2-[methylsulfanyl-[4-(trifluoromethoxy)phenyl]methylene]indan-1-one To a suspension of NaH (60% dispersion in mineral oil, 508 mg, 13 mmol) in DMF (10 mL) a solution of methyl 4-(trifluoromethoxy)methyl 4-(trifluoromethoxy)benzenecarbodithioate (3.5 g, 14 mmol) and 5-bromoindan-1-one (2.4 g, 12 mmol) in DMF (15 mL) was added slowly. The reaction mixture was allowed to warm to room temperature and stirred for 1 h. The mixture was again cooled to 0° C. and iodomethane (2 g, 14 mmol) was added slowly. The reaction mixture was allowed to warm to room temperature overnight, then poured into water, and extracted with EtOAc. The organic layer was dried (MgSO$_4$) and purified by column chromatography eluting with a gradient of cyclohexane/ethyl acetate to give (2Z)-5-bromo-2-[methylsulfanyl-[4-(trifluoromethoxy)phenyl]methylene]indan-1-one (2.8 g, 56% yield). LC/MS (method 1): $R_t$: 1.476 min; MS: m/z=430.3 (M+1)

Step 2: 6-bromo-2-methyl-3-[4-(trifluoromethoxy)phenyl]-4H-indeno[1,2-c]pyrazole and 6-bromo-1-methyl-3-[4-(trifluoromethoxy)phenyl]-2,4-dihydroindeno[1,2-c]pyrazole The product of step 1 (190 mg, 0.44 mmol) and methylhydrazine (0.15 mL, 2.9 mmol) in propanol (5 mL) was stirred at 90° C. overnight. The reaction mixture was then concentrated to dryness, diluted with EtOAc and washed with water. The organic layer was dried (MgSO4) and purified by column chromatography eluting with a gradient of cyclohexane/ethyl acetate to give 6-bromo-2-methyl-3-[4-(trifluoromethoxy)phenyl]-4H-indeno[1,2-c]pyrazole (50 mg, 26% yield). LC/MS (method 1): Rt: 1,434 min; MS: m/z=410.7 (M+1). $^1$H NMR (500 MHz, CDCl$_3$) δ 7.67-7.58 (m, 2H), 7.57-7.46 (m, 3H), 7.37 (ddt, J=7.6, 2.0, 1.0 Hz, 2H), 3.99 (s, 3H), 3.66 (s, 2H). Continued elution afforded 6-bromo-1-methyl-3-[4-(trifluoromethoxy)phenyl]-2,4-dihydroindeno[1,2-c]pyrazole (20 mg, 11% yield). LC/MS (method 1): $R_t$: 1,487 min; MS: m/z=408.8 (M+1). $^1$H NMR (500 MHz, CDCl$_3$) δ 7.89-7.81 (m, 2H), 7.70-7.66 (m, 1H), 7.55-7.44 (m, 1H), 7.42 (d, J=8.1 Hz, 1H), 7.28 (ddt, J=7.7, 2.1, 1.1 Hz, 3H), 4.15 (s, 3H), 3.74 (s, 2H).

Example 31

1-(2,4-dichlorophenyl)-3-[(E)-[3-[4-(trifluoromethoxy)phenyl]benzo[e]benzimidazol-7-yl]methyleneamino]thiourea (C-27)

$^1$H NMR (400 MHz, DMSO-$d_6$) δ 12.08 (s, 1H), 10.04 (s, 1H), 8.70 (s, 1H), 8.54 (dd, J=8.7, 3.0 Hz, 1H), 8.48, 8.34 (m, 3H), 8.05 (d, J=2.5 Hz, 1H), 7.98, 7.86 (m, 3H), 7.82 (d, J=8.9 Hz, 1H), 7.73, 7.66 (m, 2H), 7.53 (td, J=8.9, 6.2 Hz, 1H), 7.43, 7.32 (m, 1H), 7.14 (tdd, J=8.6, 3.0, 1.3 Hz, 1H).

By analogy to the procedure described in example 1 to 30 the compounds C-2 to C-5, C-7 to C9, C-11 to C-45, C-47 to C-50, C-53, C-54, C-57, C-59 to C-81, C-83, C-85, C87 to C-93, C-95 to C-106, C108 to C-110, C-112 to C-114, C-116, C-120, C-122 to C127 and C-130 to C-132 as described in the following table S.1, have been prepared.

TABLE S.1

| Cmp. | M+ | Rt |
|---|---|---|
| C-1 | 534.8 | 1.28 |
| C-2 | 534.2 | 1.28 |
| C-3 | 610.1 | 1.31 |
| C-4 | 612.2 | 1.32 |
| C-5 | 560.7 | 1.24 |
| C-6 | 616.7 | 1.54 |
| C-7 | 537 | 1.48 |
| C-8 | 536.9 | 1.5 |
| C-9 | 612.8 | 1.51 |
| C-10 | 536.3 | 3 |
| C-11 | 539.9 | 2.15* |
| C-12 | 579.4 | 1.46 |
| C-13 | 545 | 1.46 |
| C-14 | 591.8 | 1.67 |
| C-15 | 554.9 | 1.57 |
| C-16 | 559.8 | 1.5 |
| C-17 | 537.8 | 1.51 |
| C-18 | | |
| C-19 | 537.1 | 1.46 |
| C-20 | 612.6 | 1.48 |
| C-21 | 554.7 | 1.36 |
| C-22 | 534.8 | 1.3 |
| C-23 | 520.7 | 1.26 |
| C-24 | 574.8 | 1.3 |
| C-25 | 550.8 | 1.34 |
| C-26 | 536.9 | 1.29 |
| C-27 | | |
| C-28 | 534.9 | 1.29 |
| C-29 | 556.8 | 1.29 |
| C-30 | 540.7 | 1.3 |
| C-31 | 551.7 | 1.3 |
| C-32 | 537.1 | 1.38 |
| C-33 | 617.6 | 1.43 |
| C-34 | 523.8 | 1.34 |
| C-35 | 577.8 | 1.38 |
| C-36 | 608.8 | 1.41 |
| C-37 | 574.7 | 1.25 |
| C-38 | 554.8 | 1.32 |
| C-39 | 554.8 | 1.31 |

TABLE S.1-continued

| Cmp. | M+ | Rt |
|---|---|---|
| C-40 | 524.7 | 1.25 |
| C-41 | 354.8 | 1.3 |
| C-42 | 574.7 | 1.39 |
| C-43 | 554.8 | 1.39 |
| C-44 | 359.2 | 2.81* |
| C-45 | 548.3 | 2.87* |
| C-46 | 534.1 | 3.10* |
| C-47 | 540.1 | 2.86* |
| C-48 | 614.7 | 1.49 |
| C-49 | 574.8 | 1.43 |
| C-50 | 534.8 | 1.48 |
| C-51 | 588 | 1.37 |
| C-52 | 562.2 | 2.92* |
| C-53 | 574 | 3.05* |
| C-54 | 534.9 | 2.96* |
| C-54 | 535.9 | 1.42 |
| C-55 | 588.1 | 2.77* |
| C-56 | 527.1 | 2.69* |
| C-57 | 575.7 | 1.39 |
| C-58 | 548.9 | 1.3 |
| C-59 | 588.8 | 1.28 |
| C-60 | 555.8 | 1.41 |
| C-61 | 563.9 | 1.48 |
| C-62 | 549.8 | 1.46 |
| C-63 | 521.8 | 1.07 |
| C-64 | 632.8 | 1.32 |
| C-65 | 550.9 | 1.24 |
| C-66 | 664.7 | 1.28 |
| C-67 | 584.9 | 1.32 |
| C-68 | 535.8 | 1.11 |
| C-69 | 525 | 1.17 |
| C-70 | 562 | 1.35 |
| C-71 | 542.7 | 1.22 |
| C-72 | 554.9 | 1.52 |
| C-73 | 507.7 | 0.99 |
| C-74 | 570.7 | 1.34 |
| C-75 | 550 | 1.35 |
| C-76 | 564 | 1.38 |
| C-77 | 538 | 1.28 |
| C-78 | 533 | 1.33 |
| C-79 | 553.9 | 1.25 |
| C-80 | 525.9 | 1.28 |
| C-81 | 535.9 | 1.2 |
| C-82 | 562.9 | 1.34 |
| C-83 | 553.1 | 3.25* |
| C-84 | 535.1 | 3.21* |
| C-85 | 548.9 | 1.38 |
| C-86 | 518.8 | 1.29 |
| C-87 | 533.9 | 1.35 |
| C-88 | 550.8 | 4.55* |
| C-89 | 489.9 | 1.16 |
| C-90 | 489.9 | 1.16 |
| C-91 | 567.9 | 1.4 |
| C-92 | 561.9 | 1.44 |
| C-93 | 576 | 1.47 |
| C-94 | 552 | 1.52 |
| C-95 | 591.8 | 1.49 |
| C-96 | 547.9 | 1.41 |
| C-97 | 563.9 | 1.37 |
| C-98 | 677.2 | 1.39 |
| C-99 | 587.8 | 1.38 |
| C-100 | 523.8 | 1.25 |
| C-101 | 535.8 | 1.2 |
| C-102 | 645.8 | 1.46 |
| C-103 | 565.9 | 1.23 |
| C-104 | 581.9 | 1.1 |
| C-105 | 464 | 3.89* |
| C-106 | 484.1 | 2.70* |
| C-107 | 549.6 | 1.47 |
| C-108 | 519.4 | 3.14* |
| C-109 | 519.4 | 3.58* |
| C-110 | 568.4 | 3.48* |
| C-111 | 518.3 | 1.15 |
| C-112 | 553.3 | 3.30* |
| C-113 | 536.4 | 3.26* |
| C-114 | 552.4 | 3.38* |
| C-115 | 603.9 | 1.2 |
| C-116 | 629.9 | 1.19 |
| C-117 | 564 | 1.3 |
| C-118 | 601.6 | 3.77# |
| C-119 | 573 | 3.47# |
| C-120 | 573.5 | 3.58# |
| C-121 | 587.6 | 3.64# |
| C-122 | 559.6 | 3.61# |
| C-123 | 492.4 | 2.88# |
| C-124 | 521.4 | 3.36# |
| C-125 | 521.4 | 3.41# |
| C-126 | 477.4 | 3.26# |
| C-127 | 564 | 3.54# |
| C-128 | 592 | 3.61# |
| C-129 | 548 | 3.24# |
| C-130 | 562 | 3.39# |
| C-131 | 588 | 3.46# |
| C-132 | 552 | 3.4# |

*Analytical HPLC: method 2
Analytical HPLC: method 3
Com. = compound

II. Evaluation of Pesticidal Activity:

The activity of the compounds of formula I of the present invention can be demonstrated and evaluated by the following biological test.

B.1 Diamond Back Moth (*Plutella xylostella*)

The active compound was dissolved at the desired concentration in a mixture of 1:1 (vol:vol) distilled water: aceteone. Surfactant (Kinetic HV) was added at a rate of 0.01% (vol/vol). The test solution was prepared at the day of use.

Leaves of cabbage were dipped in test solution and air-dried. Treated leaves were placed in petri dishes lined with moist filter paper and inoculated with ten $3^{rd}$ instar larvae. Mortality was recorded 72 hours after treatment. Feeding damages were also recorded using a scale of 0-100%.

In this test, the compounds C-1, C-2, C-3, C-4, C-5, C-21, C-22, C-23, C-24, C-26, C27, C-29, C-30, C-37, C-38, C-40, C-41, C-45, C-46, C-47, C-50, C-51, C-52, C-53, C55, C-56, C-58, C-65, C-66, C-67, C-68, C-70, C-74, C-75, C-76, C-77, C-78, C-79, C82, C-85, C-86, C-87, C-89, C-90, C-91, C-92, C-93, C-94, C-95, C-96, C-97, C-98, C99, C-101, C-103, C-104, C-107, C-108, C-109 at 500 ppm, showed a mortality of at least 75% in comparison with untreated controls.

B.2 Orchid *thrips* (*dichromothrips corbetti*)

*Dichromothrips corbetti* adults used for bioassay were obtained from a colony maintained continuously under laboratory conditions. For testing purposes, the test compound is diluted in a 1:1 mixture of acetone:water (vol:vol), plus Kinetic HV at a rate of 0.01% v/v.

*Thrips* potency of each compound was evaluated by using a floral-immersion technique. All petals of individual, intact orchid flowers were dipped into treatment solution and allowed to dry in Petri dishes. Treated petals were placed into individual resealable plastic along with about 20 adult *thrips*. All test arenas were held under continuous light and a temperature of about 28° C. for duration of the assay. After 3 days, the numbers of live *thrips* were counted on each petal. The percent mortality was recorded 72 hours after treatment.

In this test, the compound C-1 at 300 ppm, showed a mortality of at least 75% in comparison with untreated controls.

B.3 Boll Weevil (*Anthonomus grandis*)

For evaluating control of boll weevil (*Anthonomus grandis*) the test unit consisted of 96-well-microtiter plates containing an insect diet and 5-10 *A. grandis* eggs.

The compounds were formulated using a solution containing 75% v/v water and 25% v/v DMSO. Different concentrations of formulated compounds were sprayed onto the insect diet at 5 μl, using a custom built micro atomizer, at two replications.

After application, microtiter plates were incubated at about 25±1° C. and about 75±5% relative humidity for 5 days. Egg and larval mortality was then visually assessed.

In this test, compounds C-1, C-2, C-3, C-4, C-5, C-21, C-22, C-23, C-24, C-25, C-26, C-27, C-28, C-29, C-31, C-32, C-33, C-37, C-38, C-39, C-40, C-41, C-42, C-45, C-46, C-47, C-49, C-50, C-51, C-52, C-53, C-55, C-56, C-58, C-59, C-61, C-63, C-64, C-65, C-66, C-67, C-68, C-70, C-71, C-73, C-74, C-75, C-76, C-77, C-78, C-79, C-85, C-86, C-87, C-89, C-90, C-91, C-92, C-93, C-94, C-95, C-96, C-97, C-98, C-99, C-101, C102, C-103, C-104, C-105, C-106, C-107, C-108, C-109, C-110, C-112, C-113, C-115, C-116, C-117 at 800 ppm showed at least 75% mortality in comparison with untreated controls.

B.4 Cowpea Aphid (*aphis craccivora*)

The active compound is dissolved at the desired concentration in a mixture of 1:1 (vol:vol) distilled water:acetone. Surfactant (Kinetic HV) is added at a rate of 0.01% (vol/vol). The test solution is prepared at the day of use.

Potted cowpea plants were colonized with approximately 50-100 aphids of various stages by manually transferring a leaf tissue cut from infested plant 24 hours before application. Plants were sprayed after the pest population has been recorded. Treated plants are maintained on light carts at about 28° C. Percent mortality was assessed after 72 hours.

In this test, compounds C-34, C-87 at 500 ppm showed at least 75% mortality in comparison with untreated controls.

B.5 Silverleaf Whitefly (*Bemisia argentifoli*)

The active compounds were formulated by a Tecan liquid handler in 100% cyclohexanone as a 10,000 ppm solution supplied in tubes. The 10,000 ppm solution was serially diluted in 100% cyclohexanone to make interim solutions. These served as stock solutions for which final dilutions were made by the Tecan in 50% acetone:50% water (v/v) into 5 or 10 ml glass vials. A nonionic surfactant (Kinetic®) was included in the solution at a volume of 0.01% (v/v). The vials were then inserted into an automated electrostatic sprayer equipped with an atomizing nozzle for application to plants/insects.

Cotton plants at the cotyledon stage (one plant per pot) were sprayed by an automated electrostatic plant sprayer equipped with an atomizing spray nozzle. The plants were dried in the sprayer fume hood and then removed from the sprayer. Each pot was placed into a plastic cup and about 10 to 12 whitefly adults (approximately 3-5 days old) were introduced. The insects were collected using an aspirator and a nontoxic Tygon® tubing connected to a barrier pipette tip. The tip, containing the collected insects, was then gently inserted into the soil containing the treated plant, allowing insects to crawl out of the tip to reach the foliage for feeding. Cups were covered with a reusable screened lid. Test plants were maintained in a growth room at about 25° C. and about 20-40% relative humidity for 3 days, avoiding direct exposure to fluorescent light (24 hour photoperiod) to prevent trapping of heat inside the cup. Mortality was assessed 3 days after treatment, compared to untreated control plants.

In this test, compounds C-19, C-24, C-51, C-52, C-53, C-55, C-70, C-74, C-75, C-76, C-77, C-78, C-100, C-103, C-109 at 300 ppm showed at least 75% mortality in comparison with untreated controls.

B.6 Mediterranean Fruitfly (*Ceratitis capitata*)

For evaluating control of Mediterranean fruitfly (*Ceratitis capitata*) the test unit consisted of microtiter plates containing an insect diet and 50-80 *C. capitata* eggs.

The compounds were formulated using a solution containing 75% v/v water and 25% v/v DMSO. Different concentrations of formulated compounds were sprayed onto the insect diet at 5 μl, using a custom built micro atomizer, at two replications.

After application, microtiter plates were incubated at about 28±1° C. and about 80±5% relative humidity for 5 days. Egg and larval mortality was then visually assessed.

In this test, compounds C-1, C-2, C-3, C-4, C-5, C-9, C-11, C-21, C-22, C-23, C-24, C25, C-26, C-27, C-28, C-29, C-34, C-37, C-38, C-39, C-40, C-41, C-45, C-46, C-47, C50, C-51, C-52, C-53, C-55, C-56, C-58, C-59, C-63, C-64, C-65, C-66, C-67, C-68, C70, C-71, C-74, C-75, C-76, C-77, C-78, C-79, C-84, C-85, C-86, C-87, C-91, C-92, C93, C-96, C-97, C-98, C-99, C-101, C-103, C-104, C-105, C-106, C-107, C-108, C-109, C-110, C-112, C-113, C-115, C-117 at 800 ppm showed at least 75% mortality in comparison with untreated controls.

B.7 Tobacco Budworm (*Heliothis virescens*) I

For evaluating control of tobacco budworm (*Heliothis virescens*) the test unit consisted of 96-well-microtiter plates containing an insect diet and 15-25 *H. virescens* eggs. The compounds were formulated using a solution containing 75% v/v water and 25% v/v DMSO. Different concentrations of formulated compounds were sprayed onto the insect diet at 10 μl, using a custom built micro atomizer, at two replications.

After application, microtiter plates were incubated at about 28±1° C. and about 80±5% relative humidity for 5 days. Egg and larval mortality was then visually assessed.

In this test, compounds C-1, C-2, C-3, C-4, C-5, C-7, C-11, C-21, C-22, C-23, C-26, C28, C-29, C-31, C-33, C-37, C-38, C-39, C-41, C-45, C-46, C-47, C-49, C-50, C-51, C52, C-53, C-54, C-55, C-56, C-58, C-59, C-61, C-62, C-63, C-64, C-65, C-66, C-67, C68, C-70, C-71, C-74, C-75, C-76, C-77, C-78, C-79, C-84, C-85, C-86, C-88, C-89, C90, C-91, C-92, C-93, C-94, C-95, C-96, C-97, C-98, C-99, C-101, C-103, C-104, C105, C-106, C-107, C-108, C-109, C-110, C-112, C-113, C-115, C-116, C-117 at 800 ppm showed at least 75% mortality in comparison with untreated controls.

B.8 Vetch Aphid (*Megoura viciae*)

For evaluating control of vetch aphid (*Megoura viciae*) through contact or systemic means the test unit consisted of 24-well-microtiter plates containing broad bean leaf disks.

The compounds were formulated using a solution containing 75% v/v water and 25% v/v DMSO. Different concentrations of formulated compounds were sprayed onto the leaf disks at 2.5 μl, using a custom built micro atomizer, at two replications.

After application, the leaf disks were air-dried and 5-8 adult aphids placed on the leaf disks inside the microtiter plate wells. The aphids were then allowed to suck on the treated leaf disks and incubated at about 23±1° C. and about 50±5% relative humidity for 5 days. Aphid mortality and fecundity was then visually assessed.

In this test, compounds C-5, C-18, C-43, C-53, C-56, C-86, C-105 at 2500 ppm showed at least 75% mortality in comparison with untreated controls.

B.9 Green Peach Aphid (*Myzus persicae*)

The active compounds were formulated by a Tecan liquid handler in 100% cyclohexa none as a 10,000 ppm solution supplied in tubes. The 10,000 ppm solution was serially diluted in 100% cyclohexanone to make interim solutions. These served as stock solutions for which final dilutions were made by the Tecan in 50% acetone:50% water (v/v) into 5 or 10 ml glass vials. A nonionic surfactant (Kinetic®) was included in the solution at a volume of 0.01% (v/v). The vials were then inserted into an automated electrostatic sprayer equipped with an atomizing nozzle for application to plants/insects.

Bell pepper plants at the first true-leaf stage were infested prior to treatment by placing heavily infested leaves from the main colony on top of the treatment plants. Aphids were allowed to transfer overnight to accomplish an infestation of 30-50 aphids per plant and the host leaves were removed. The infested plants were then sprayed by an automated electrostatic plant sprayer equipped with an atomizing spray nozzle. The plants were dried in the sprayer fume hood, removed, and then maintained in a growth room under fluorescent lighting in a 24-hr photoperiod at about 25° C. and about 20-40% relative humidity. Aphid mortality on the treated plants, relative to mortality on untreated control plants, was determined after 5 days.

In this test, compounds C-1, C-2, C-4, C-7, C-25, C-31, C-43, C-51, C-52, C-57, C-58, C-70, C-75, C-76, C-77, C-79, C-84, C-86, C-92, C-108, C-109, C-110, C-113 at 800 ppm showed at least 75% mortality in comparison with untreated controls.

B.10 Southern Armyworm (*Spodoptera eridania*), 2nd Instar Larvae

The active compounds were formulated by a Tecan liquid handler in 100% cyclohexanone as a 10,000 ppm solution supplied in tubes. The 10,000 ppm solution was serially diluted in 100% cyclohexanone to make interim solutions. These served as stock solutions for which final dilutions were made by the Tecan in 50% acetone:50% water (v/v) into 5 or 10 ml glass vials. A nonionic surfactant (Kinetic®) was included in the solution at a volume of 0.01% (v/v). The vials were then inserted into an automated electrostatic sprayer equipped with an atomizing nozzle for application to plants/insects.

Lima bean plants (variety Sieva) were grown 2 plants to a pot and selected for treatment at the $1^{st}$ true leaf stage. Test solutions were sprayed onto the foliage by an automated electrostatic plant sprayer equipped with an atomizing spray nozzle. The plants were dried in the sprayer fume hood and then removed from the sprayer. Each pot was placed into perforated plastic bags with a zip closure. About 10 to 11 armyworm larvae were placed into the bag and the bags zipped closed. Test plants were maintained in a growth room at about 25° C. and about 20-40% relative humidity for 4 days, avoiding direct exposure to fluorescent light (24 hour photoperiod) to prevent trapping of heat inside the bags. Mortality and reduced feeding were assessed 4 days after treatment, compared to untreated control plants.

In this test, compounds C-1, C-22, C-23, C-25, C-51, C-52, C-53, C-55, C-56, C-58, C66, C-68, C-70, C-71, C-74, C-75, C-76, C-77, C-78, C-79, C-85, C-86, C-103, C-104, C-106, C-107, C-108 at 300 ppm showed at least 75% mortality in comparison with untreated controls.

B.11 Yellow Fever Mosquito (*Aedes aegypti*)

For evaluating control of yellow fever mosquito (*Aedes aegypti*) the test unit consisted of 96-well-microtiter plates containing 200 μl of tap water per well and 5-15 freshly hatched *A. aegypti* larvae.

The active compounds were formulated using a solution containing 75% (v/v) water and 25% (v/v) DMSO. Different concentrations of formulated compounds or mixtures were sprayed onto the insect diet at 2.5 μl, using a custom built micro atomizer, at two replications.

After application, microtiter plates were incubated at 28+1° C., 80+5% RH for 2 days. Larval mortality was then visually assessed. In this test, compounds C-1, C-4, C-22, C37, C-41, C-47, C-51, C-53, C-55, C-56, C-58, C-65, C-70, C-74, C-75, C-76, C-77, C78, C-79, C-85, C-86, C-87, C-88, C-92, C-93, C-94, C-96, C-97, C-103, C-104, C-106, C-107, C-108, C-109, C-110, C-112, C-113, C-115, C-117 at 800 ppm showed at least 75% mortality in comparison with untreated controls.

B.12 Orchid *thrips* (*dichromothrips corbetti*)

*Dichromothrips corbetti* adults used for bioassay were obtained from a colony maintained continuously under laboratory conditions. For testing purposes, the test compound is diluted in a 1:1 mixture of acetone:water (vol:vol), plus Kinetic HV at a rate of 0.01% v/v.

*Thrips* potency of each compound was evaluated by using a floral-immersion technique. All petals of individual, intact orchid flowers were dipped into treatment solution and allowed to dry in Petri dishes. Treated petals were placed into individual resealable plastic along with about 20 adult *thrips*. All test arenas were held under continuous light and a temperature of about 28° C. for duration of the assay. After 3 days, the numbers of live *thrips* were counted on each petal. The percent mortality was recorded 72 hours after treatment.

In this test, compounds C-1, C-4, C-7, C-9, C-21, C-22, C-23, C-24, C-30, C-37, C-38, C-41, C-45, C-51, C-52, C-53, C-55, C-58, C-65, C-66, C-70, C-75, C-76, C-77, C-78, C-79, C-82, C-85, C-86, C-92, C-93, C-94, C-96, C-99, C-101, C-103, C-104, C-107, C-108 at 500 ppm showed at least 75% mortality in comparison with untreated controls.

We claim:
1. A compound of the formula (I)

wherein
$C^1$ is C or CH
$C^2$ is C or CH
$A^1$ is N or C
$A^2$ is N, $C(R^2)$, $N(R^3)$, O, S or $C(R^4,R^5)$; and
$A^3$ is N, O, S, $N(R^6)$, $C(R^7)$ or $C(R^8,R^9)$;
where one or two non-adjacent bonds in the 5-membered ring formed by $C^1$, $C^2$, $A^1$, $A^2$ and $A^3$ are double bonds, while the others are single bonds, provided that the bond between $A^1$ and $A^2$ or the bond between $A^1$ and $C^1$ or the bond between $A^2$ and $A^3$ or the bond between $C^1$ and $C^2$ or the bond between $A^3$ and $C^2$ is a double bond further provided that at least one of $A^1$, $A^2$ and $A^3$ is N, $N(R^3)$ or $N(R^6)$,
and where
$R^2$, $R^7$ independently of each other, are selected from the group consisting of hydrogen, halogen, $N_3$, OH, CN, $NO_2$, —SCN, —$SF_5$, $C_1$-$C_6$-alkyl, $C_1$-$C_6$-haloalkyl, $C_1$-$C_6$-alkoxy, $C_1$-$C_6$-haloalkoxy, $C_2$-$C_6$-alkenyl, tri-$C_1$-$C_6$-alkylsilyl, $C_2$-$C_6$-alkynyl, $C_1$-$C_6$- alkoxy-$C_1$-$C_4$-alkyl, $C_1$-$C_6$-alkoxy-$C_1$-$C_4$-alkoxy, $C_3$-$C_6$-cycloalkyl, $C_3$-$C_6$-cycloalkoxy, $C_3$-$C_6$-cycloalkyl-$C_1$-$C_4$-alkyl, $C_3$-$C_6$-cycloalkoxy-$C_1$-$C_4$-alkyl, where the alkyl, cycloalkyl, cycloalkoxy and alkoxy parts of the last 6 mentioned radicals are unsubstituted or partially or completely halogenated, C(O)—OR$^a$, NR$^b$R$^c$, $C_1$-$C_6$-alkylen-NR$^b$R$^c$, O—$C_1$-$C_6$-alkylen-NR$^b$R$^c$, $C_1$-$C_6$-alkylen-CN, NH—$C_1$-$C_6$-alkylen-NR$^b$R$^c$, C(O)—NR$^b$R$^c$, C(O)—R$^d$, SO$_2$NR$^b$R$^c$ and S(=O)$_m$R$^e$;

R$^3$, R$^6$ independently of each other, are selected from the group consisting of hydrogen, $C_1$-$C_6$-alkyl, $C_1$-$C_6$-haloalkyl, $C_1$-$C_6$-alkoxy, $C_1$-$C_6$-haloalkoxy, $C_2$-$C_6$-alkenyl, $C_2$-$C_6$-alkynyl, $C_1$-$C_6$-alkoxy-$C_1$-$C_4$-alkyl, $C_1$-$C_6$-alkoxy-$C_1$-$C_4$-alkoxy, $C_3$-$C_6$-cycloalkyl, $C_3$-$C_6$-cycloalkoxy, $C_3$-$C_6$-cycloalkyl-$C_1$-$C_4$-alkyl, $C_3$-$C_6$-cycloalkoxy-$C_1$-$C_4$-alkyl, where the alkyl, cycloalkyl, cycloalkoxy and alkoxy parts of the last 6 mentioned radicals are unsubstituted or partially or completely halogenated, C(O)—OR$^a$, NR$^b$R$^c$, $C_1$-$C_6$-alkylen-NR$^b$R$^c$, O—$C_1$-$C_6$-alkylen-NR$^b$R$^c$, $C_1$-$C_6$-alkylen-CN, NH—$C_1$-$C_6$-alkylen-NR$^b$R$^c$, C(O)—NR$^b$R$^c$, C(O)—R$^d$, SO$_2$NR$^b$R$^c$, S(=O)$_m$R$^e$, phenyl and benzyl, where the phenyl ring in the last 2 radicals is unsubstituted or carry 1, 2, 3, 4 or 5 radicals R$^f$;

R$^4$, R$^5$ independently of each other are selected from the group consisting of hydrogen, halogen, CN, $C_1$-$C_4$-alkyl, $C_1$-$C_4$-haloalkyl, $C_1$-$C_4$-alkoxy, $C_1$-$C_4$-haloalkoxy, $C_1$-$C_4$-alkylthio and $C_1$-$C_4$-haloalkylthio or C(R$^4$,R$^5$) may be a carbonyl group or thiocarbonyl group;

R$^8$, R$^9$ independently of each other are selected from the group consisting of hydrogen, halogen, CN, $C_1$-$C_4$-alkyl, $C_1$-$C_4$-haloalkyl, $C_1$-$C_4$-alkoxy, $C_1$-$C_4$-haloalkoxy, $C_1$-$C_4$-alkylthio and $C_1$-$C_4$-haloalkylthio or C(R$^8$,R$^9$) may be a carbonyl group or thiocarbonyl group;

Ar is phenyl or 5- or 6-membered hetaryl, which are unsubstituted or carry 1, 2, 3 or 4 radicals R$^{Ar}$, which are identical or different, where R$^{Ar}$ independently of each other, are selected from the group consisting of halogen, N$_3$, OH, CN, NO$_2$, —SCN, —SF$_5$, $C_1$-$C_6$-alkyl, $C_1$-$C_6$-haloalkyl, $C_1$-$C_6$-alkoxy, $C_1$-$C_6$-haloalkoxy, $C_2$-$C_6$-alkenyl, tri-$C_1$-$C_6$-alkylsilyl, $C_2$-$C_6$-alkynyl, $C_1$-$C_6$-alkoxy-$C_1$-$C_4$-alkyl, $C_1$-$C_6$-alkoxy-$C_1$-$C_4$-alkoxy, $C_3$-$C_6$-cycloalkyl, $C_3$-$C_6$-cycloalkoxy, $C_3$-$C_6$-cycloalkyl-$C_1$-$C_4$-alkyl, $C_3$-$C_6$-cycloalkoxy-$C_1$-$C_4$-alkyl, where the alkyl, cycloalkyl, cycloalkoxy and alkoxy parts of the last 6 mentioned radicals are unsubstituted or partially or completely halogenated, C(O)—OR$^a$, NR$^b$R$^c$, $C_1$-$C_6$-alkylen-NR$^b$R$^c$, O—$C_1$-$C_6$-alkylen-NR$^b$R$^c$, $C_1$-$C_6$-alkylen-CN, NH—$C_1$-$C_6$-alkylen-NR$^b$R$^c$, C(O)—NR$^b$R$^c$, C(O)—R$^d$, SO$_2$NR$^b$R$^c$ and S(=O)$_m$R$^e$, one radical may also be phenyl, phenoxy, phenylcarbonyl, phenylthio or benzyl, where the phenyl ring in the last 5 radicals is unsubstituted or carry 1, 2, 3, 4 or 5 radicals R$^f$;

Q is —O—, —S—, —S(=O)—, —S(=O)$_2$—, —C(R$^{Q2a}$R$^{Q2b}$)—, —N(R$^{Q1}$)—, —N(R$^{Q2}$)—C(=O)—, —O—C(=O)—, —C(R$^{Q3}$)=C(R$^{Q4}$)—, —C(R$^{Q3a}$R$^{Q3b}$)—C(R$^{Q4a}$R$^{Q4b}$)—, —C(R$^{Q3a}$R$^{Q3b}$)—C(=O)—, —O—C(R$^{Q4a}$R$^{Q4b}$)—, —S(=O)$_n$—C(R$^{Q4a}$R$^{Q4b}$)— or —N(R$^{Q2}$)—C(R$^{Q4a}$R$^{Q4b}$)—, where n is 0, 1 or 2;

R$^{Q1}$, R$^{Q2}$ independently of each other are selected from the group consisting of hydrogen, $C_1$-$C_6$-alkyl, $C_1$-$C_6$-haloalkyl, $C_1$-$C_6$-alkoxy, $C_1$-$C_6$-haloalkoxy, $C_2$-$C_6$-alkenyl, $C_2$-$C_6$-alkynyl, $C_1$-$C_6$-alkoxy-$C_1$-$C_4$-alkyl, $C_1$-$C_6$-alkoxy-$C_1$-$C_4$-alkoxy, $C_3$-$C_6$-cycloalkyl, $C_3$-$C_6$-cycloalkoxy, $C_3$-$C_6$-cycloalkyl-$C_1$-$C_4$-alkyl, $C_3$-$C_6$-cycloalkoxy-$C_1$-$C_4$-alkyl, where the alkyl, cycloalkyl, cycloalkoxy and alkoxy parts of the last 6 mentioned radicals are unsubstituted or partially or completely halogenated, C(O)—OR$^a$, NR$^b$R$^c$, $C_1$-$C_6$-alkylen-NR$^b$R$^c$, $C_1$-$C_6$-alkylen-CN, C(O)—NR$^b$R$^c$, C(O)—R$^d$, SO$_2$NR$^b$R$^c$, S(=O)$_m$R$^e$, phenyl and benzyl, where the phenyl ring in the last 2 radicals is unsubstituted or carry 1, 2, 3, 4 or 5 radicals R$^f$;

R$^{Q3}$, R$^{Q4}$ independently of each other, are selected from the group consisting of hydrogen, halogen, OH, CN, $C_1$-$C_4$-alkyl, $C_1$-$C_4$-haloalkyl, $C_1$-$C_4$-alkoxy, $C_1$-$C_4$-haloalkoxy, C(O)—OR$^a$, NR$^b$R$^c$, $C_1$-$C_6$-alkylen-NR$^b$R$^c$, O—$C_1$-$C_6$-alkylen-NR$^b$R$^c$, $C_1$-$C_6$-alkylen-CN, NH—$C_1$-$C_6$-alkylen-NR$^b$R$^c$, C(O)—NR$^b$R$^c$, C(O)—R$^d$, SO$_2$NR$^b$R$^c$ and S(=O)$_m$R$^e$;

R$^{Q2a}$, R$^{Q2b}$ independently of each other, are selected from the group consisting of hydrogen, halogen, CN, $C_1$-$C_4$-alkyl, $C_1$-$C_4$-haloalkyl, $C_1$-$C_4$-alkoxy, $C_1$-$C_4$-haloalkoxy, $C_1$-$C_4$-alkylthio and $C_1$-$C_4$-haloalkylthio or —C(R$^{Q2a}$R$^{Q2b}$)— is C=O or C=S;

R$^{Q3a}$, R$^{Q3b}$ independently of each other, are selected from the group consisting of hydrogen, halogen, CN, $C_1$-$C_4$-alkyl, $C_1$-$C_4$-haloalkyl, $C_1$-$C_4$-alkoxy, $C_1$-$C_4$-haloalkoxy, $C_1$-$C_4$-alkylthio and $C_1$-$C_4$-haloalkylthio;

R$^{Q4a}$, R$^{Q4b}$ independently of each other, are selected from the group consisting of hydrogen, halogen, CN, $C_1$-$C_4$-alkyl, $C_1$-$C_4$-haloalkyl, $C_1$-$C_4$-alkoxy, $C_1$-$C_4$-haloalkoxy, $C_1$-$C_4$-alkylthio and $C_1$-$C_4$-haloalkylthio;

R$^1$ is a moiety of the formula —X—Y—Z—R$^{11}$, where R$^{11}$ is selected from the group consisting of $C_1$-$C_6$-alkyl, $C_1$-$C_6$-haloalkyl, $C_2$-$C_6$-alkenyl, $C_2$-$C_6$-alkynyl, $C_1$-$C_6$-alkoxy-$C_1$-$C_4$-alkyl, $C_3$-$C_6$-cycloalkyl, $C_3$-$C_6$-cycloalkyl-$C_1$-$C_4$-alkyl, $C_3$-$C_6$-cycloalkoxy-$C_1$-$C_4$-alkyl, where the alkyl, cycloalkyl, cycloalkoxy and alkoxy parts of the last four mentioned radicals are unsubstituted or partially or completely halogenated, $C_1$-$C_6$-alkylen-NR$^b$R$^c$, $C_1$-$C_6$-alkylen-CN, C(O)—NR$^b$R$^c$, C(O)—R$^d$, aryl, arylcarbonyl, aryl-$C_1$-$C_4$-alkyl, aryloxy-$C_1$-$C_4$-alkyl, hetaryl, hetarylcarbonyl, hetaryl-$C_1$-$C_4$-alkyl and hetaryloxy-$C_1$-$C_4$-alkyl, where the aryl and hetaryl rings in the last 8 radicals are unsubstituted or carry 1, 2, 3, 4 or 5 radicals R$^g$ and where hetaryl is a 5- or 6-membered monocyclic hetaryl or a 8-, 9- or 10-membered bicyclic hetaryl;

X is a single bond, NR$^{x1}$, or a bivalent group —N(R$^{x2}$)—C(=O)—, where C=(O) is bound to Y, —N(R$^{x2}$)—C(=S)—, where C=(S) is bound to Y, or a bivalent group —C(R$^{x3}$)=N—, where the nitrogen is bound to Y, Y is a bivalent group —N(R$^{y1}$)—C(=O)—, —N(R$^{y2}$)—C(=S)—, —N=C((O)$_p$—R$^{y3}$)— or —N=C((S)$_p$—R$^{y3}$)—, where the nitrogen atom in the four groups is bound to X and where p is 0 or 1, Z is O, S or N—R$^z$, and where R$^{x1}$, R$^{x2}$ independently of each other, are selected from the group consisting of hydrogen, $C_1$-$C_6$-alkyl, $C_1$-$C_6$-haloalkyl, $C_2$-$C_6$-alkenyl, $C_2$-$C_6$-alkynyl, $C_1$-$C_6$-alkoxy-$C_1$-$C_4$-alkyl, $C_3$-$C_6$-cycloalkyl, $C_3$-$C_6$-cycloalkyl-$C_1$-$C_4$-alkyl, $C_3$-$C_6$-cycloalkoxy-$C_1$-$C_4$-alkyl, where the alkyl, cycloalkyl, cycloalkoxy and alkoxy parts of the last four mentioned radicals are unsubstituted or partially or completely halogenated, C(O)—OR$^a$, $C_1$-$C_6$-alkylen-NR$^b$R$^c$, $C_1$-$C_6$-alkylen-CN, C(O)—NR$^b$R$^c$, C(O)—R$^d$, SO$_2$NR$^b$R$^c$, S(=O)$_m$R$^e$, phenyl and benzyl, where the phenyl ring in the last 2 radicals is unsubstituted or carry 1, 2, 3, 4 or 5 radicals R$^f$;

R$^{x3}$ is selected from the group consisting of hydrogen, halogen, CN, $C_1$-$C_6$-alkyl, $C_1$-$C_6$-haloalkyl, $C_1$-$C_6$-alkoxy, $C_1$-$C_6$-haloalkoxy, $C_2$-$C_6$-alkenyl, tri-$C_1$-$C_6$-alkylsilyl, $C_2$-$C_6$-alkynyl, $C_1$-$C_6$-alkoxy-$C_1$-$C_4$-alkyl, $C_1$-$C_6$-alkoxy-$C_1$-$C_4$-alkoxy, $C_3$-$C_6$-cycloalkyl, $C_3$-$C_6$-cycloalkoxy, $C_3$-$C_6$-cycloalkoxy-$C_1$-$C_4$-alkyl, $C_3$-$C_6$-cycloalkyl-$C_1$-$C_4$-alkyl, where the alkyl, cycloalkyl, cycloalkoxy and alkoxy parts of the last 6 mentioned radicals are unsubstituted or partially or completely halogenated, $C_1$-$C_6$-alkylen-NR$^b$R$^c$, O—$C_1$-$C_6$-alkylen-NR$^b$R$^c$, $C_1$-$C_6$-alkylen-CN, NH—$C_1$-$C_6$-alkylen-NR$^b$R$^c$, C(O)—NR$^b$R$^c$, C(O)—R$^d$, phenyl, phenoxy, phenylcarbonyl, phenylthio and benzyl, where the phenyl ring in the last 5 radicals is unsubstituted or carry 1, 2, 3, 4 or 5 radicals R$^f$;

p is 0 or 1;

R$^{y1}$, R$^{y2}$ independently of each other, are selected from the group consisting of hydrogen, $C_1$-$C_6$-alkyl, $C_1$-$C_6$-haloalkyl, $C_2$-$C_6$-alkenyl, $C_2$-$C_6$-alkynyl, $C_1$-$C_6$-alkoxy-$C_1$-$C_4$-alkyl, $C_1$-$C_6$-alkoxy-$C_1$-$C_4$-alkoxy, $C_3$-$C_6$-cycloalkyl, $C_3$-$C_6$-cycloalkyl-$C_1$-$C_4$-alkyl, $C_3$-$C_6$-cycloalkoxy-$C_1$-$C_4$-alkyl, where the alkyl, cycloalkyl, cycloalkoxy and alkoxy parts of the last 4 mentioned radicals are unsubstituted or partially or completely halogenated, C(O)—OR$^a$, $C_1$-$C_6$-alkylen-NR$^b$R$^c$, $C_1$-$C_6$-alkylen-CN, C(O)—NR$^b$R$^c$, C(O)—R$^d$, SO$_2$NR$^b$R$^c$, S(=O)$_m$R$^e$, phenyl and benzyl, where the phenyl ring in the last 2 radicals is unsubstituted or carry 1, 2, 3, 4 or 5 radicals R$^f$;

R$^{y3}$ is selected from the group consisting of hydrogen, $C_1$-$C_6$-alkyl, $C_1$-$C_6$-haloalkyl, $C_1$-$C_6$-alkoxy, $C_1$-$C_6$-haloalkoxy, $C_2$-$C_6$-alkenyl, tri-$C_1$-$C_6$-alkylsilyl, $C_2$-$C_6$-alkynyl, $C_1$-$C_6$-alkoxy-$C_1$-$C_4$-alkyl, $C_3$-$C_6$-cycloalkyl, $C_3$-$C_6$-cycloalkoxy-$C_1$-$C_4$-alkyl, $C_3$-$C_6$-cycloalkyl-$C_1$-$C_4$-alkyl, where the alkyl, cycloalkyl and alkoxy parts of the last four mentioned radicals are unsubstituted or partially or completely halogenated, $C_1$-$C_6$-alkylen-NR$^b$R$^c$, $C_1$-$C_6$-alkylen-CN, C(O)—NR$^b$R$^c$, C(O)—R$^d$, phenyl, phenylcarbonyl and benzyl, where the phenyl ring in the last 3 radicals is unsubstituted or carry 1, 2, 3, 4 or 5 radicals R$^f$;

R$^z$ is selected from the group consisting of hydrogen, $C_1$-$C_6$-alkyl, $C_1$-$C_6$-haloalkyl, $C_2$-$C_6$-alkenyl, $C_2$-$C_6$-alkynyl, $C_1$-$C_6$-alkoxy-$C_1$-$C_4$-alkyl, $C_3$-$C_6$-cycloalkyl, $C_3$-$C_6$-cycloalkyl-$C_1$-$C_4$-alkyl, $C_3$-$C_6$-cycloalkoxy-$C_1$-$C_4$-alkyl, where the alkyl, cycloalkyl, cycloalkoxy and alkoxy parts of the last 4 mentioned radicals are unsubstituted or partially or completely halogenated, C(O)—OR$^a$, $C_1$-$C_6$-alkylen-NR$^b$R$^c$, $C_1$-$C_6$-alkylen-CN, C(O)—NR$^b$R$^c$, C(O)—R$^d$, SO$_2$NR$^b$R$^c$, S(=O)$_m$R$^e$, phenyl and benzyl, where the phenyl ring in the last 2 radicals is unsubstituted or carry 1, 2, 3, 4 or 5 radicals R$^f$, or R$^z$ together with R$^{y3}$, if present, may also form a $C_2$-$C_6$-alkylene group, wherein a CH$_2$ moiety may be replaced by a carbonyl group and/or wherein 1 or 2 CH$_2$ moieties may be replaced by O or S and/or wherein the alkylene group may be substituted 1, 2, 3, 4, 5 or 6 radicals R$^{hh}$;

k is 0, 1, 2 or 3;

R is selected from the group consisting of halogen, N$_3$, OH, CN, NO$_2$, —SCN, —SF$_5$, $C_1$-$C_6$-alkyl, $C_1$-$C_6$-haloalkyl, $C_1$-$C_6$-alkoxy, $C_1$-$C_6$-haloalkoxy, $C_2$-$C_6$-alkenyl, tri-$C_1$-$C_6$-alkylsilyl, $C_2$-$C_6$-alkynyl, $C_1$-$C_6$-alkoxy-$C_1$-$C_4$-alkyl, $C_1$-$C_6$-alkoxy-$C_1$-$C_4$-alkoxy, $C_3$-$C_6$-cycloalkyl, $C_3$-$C_6$-cycloalkoxy, $C_3$-$C_6$-cycloalkyl-$C_1$-$C_4$-alkyl, $C_3$-$C_6$-cycloalkoxyx-$C_1$-$C_4$-alkyl, where the alkyl, cycloalkyl, cycloalkoxy and alkoxy parts of the last 6 mentioned radicals are unsubstituted or partially or completely halogenated, C(O)—OR$^a$, NR$^b$R$^c$, $C_1$-$C_6$-alkylen-NR$^b$R$^c$, O—$C_1$-$C_6$-alkylen-NR$^b$R$^c$, $C_1$-$C_6$-alkylen-CN, NH—$C_1$-$C_6$-alkylen-NR$^b$R$^c$, C(O)—NR$^b$R$^c$, C(O)—R$^d$, SO$_2$NR$^b$R$^c$ and S(=O)$_m$R$^e$, one radical may also be phenyl, phenoxy, phenylcarbonyl, phenylthio or benzyl, where the phenyl ring in the last 5 radicals is unsubstituted or carry 1, 2, 3, 4 or 5 radicals R$^f$;

it being possible for k=2 or 3 that R are identical or different;

and where each m is independently 0, 1 or 2;

each R$^a$ is selected from the group consisting of hydrogen, $C_1$-$C_6$-alkyl, $C_1$-$C_6$-haloalkyl, $C_2$-$C_6$-alkenyl, $C_2$-$C_6$-alkynyl, $C_1$-$C_6$-alkoxy-$C_1$-$C_4$-alkyl, $C_3$-$C_6$-cycloalkyl, $C_3$-$C_6$-cycloalkyl-$C_1$-$C_4$-alkyl, $C_3$-$C_6$-cycloalkoxy-$C_1$-$C_4$-alkyl, where the alkyl, cycloalkyl, cycloalkoxy and alkoxy parts of the last 4 mentioned radicals are unsubstituted or partially or completely halogenated, $C_1$-$C_6$-alkylen-NR$^b$R$^c$, $C_1$-$C_6$-alkylen-CN, phenyl and benzyl, where the phenyl ring in the last 2 radicals is unsubstituted or carry 1, 2, 3, 4 or 5 radicals R$^f$;

each R$^b$ is selected from the group consisting of hydrogen, $C_1$-$C_6$-alkyl, $C_1$-$C_6$-haloalkyl, $C_2$-$C_6$-alkenyl, $C_2$-$C_6$-alkynyl, $C_1$-$C_6$-alkoxy-$C_1$-$C_4$-alkyl, $C_3$-$C_6$-cycloalkyl, $C_3$-$C_6$-cycloalkyl-$C_1$-$C_4$-alkyl, $C_3$-$C_6$-cycloalkoxy-$C_1$-$C_4$-alkyl, where the alkyl, cycloalkyl, cycloalkoxy and alkoxy parts of the last 4 mentioned radicals are unsubstituted or partially or completely halogenated, $C_1$-$C_6$-alkylen-CN, phenyl and benzyl, where the phenyl ring in the last 2 radicals is unsubstituted or carry 1, 2, 3, 4 or 5 radicals R$^f$;

each R$^c$ is selected from the group consisting of hydrogen, $C_1$-$C_6$-alkyl, $C_1$-$C_6$-haloalkyl, $C_2$-$C_6$-alkenyl, $C_2$-$C_6$-alkynyl, $C_1$-$C_6$-alkoxy-$C_1$-$C_4$-alkyl, $C_3$-$C_6$-cycloalkyl, $C_3$-$C_6$-cycloalkyl-$C_1$-$C_4$-alkyl, $C_3$-$C_6$-cycloalkoxy-$C_1$-$C_4$-alkyl, where the alkyl, cycloalkyl, cycloalkoxy and alkoxy parts of the last 4 mentioned radicals are unsubstituted or partially or completely halogenated, $C_1$-$C_6$-alkylen-CN, phenyl and benzyl, where the phenyl ring in the last 2 radicals is unsubstituted or carry 1, 2, 3, 4 or 5 radicals R$^f$;

each moiety NR$^b$R$^c$ may also form an N-bound, saturated 5- to 8-membered heterocycle, which in addition to the nitrogen atom may have 1 or 2 further heteroatoms or heteroatom moieties selected from O, S(=O)$_m$ and N—R', where R' is hydrogen or $C_1$-$C_6$-alkyl and where the N-bound heterocycle is unsubstituted or carries 1, 2, 3, 4, 5 or 6 radicals selected from halogen, $C_1$-$C_4$-alkyl, $C_1$-$C_4$-haloalkyl, $C_1$-$C_4$-alkoxy and $C_1$-$C_4$-haloalkoxy;

each $R^d$ is selected from the group consisting of hydrogen, $C_1$-$C_6$-alkyl, $C_1$-$C_6$-haloalkyl, $C_2$-$C_6$-alkenyl, $C_2$-$C_6$-alkynyl, $C_1$-$C_6$-alkoxy-$C_1$-$C_4$-alkyl, $C_3$-$C_6$-cycloalkyl, $C_3$-$C_6$-cycloalkyl-$C_1$-$C_4$-alkyl, $C_3$-$C_6$-cycloalkoxy-$C_1$-$C_4$-alkyl, where the alkyl, cycloalkyl, cycloalkoxy and alkoxy parts of the last 4 mentioned radicals are unsubstituted or partially or completely halogenated, phenyl and benzyl, where the phenyl ring in the last 2 radicals is unsubstituted or carry 1, 2, 3, 4 or 5 radicals $R^f$;

each $R^e$ is selected from the group consisting of $C_1$-$C_6$-alkyl, $C_1$-$C_6$-haloalkyl, $C_3$-$C_6$-cycloalkyl, $C_3$-$C_6$-cycloalkyl-$C_1$-$C_4$-alkyl, where the alkyl and cycloalkyl parts of the last 2 mentioned radicals are unsubstituted or partially or completely halogenated, phenyl and benzyl, where the phenyl ring in the last 2 radicals is unsubstituted or carry 1, 2, 3, 4 or 5 radicals $R^f$;

each $R^f$ is selected from the group consisting of halogen, $N_3$, OH, CN, $NO_2$, —SCN, —$SF_5$, $C_1$-$C_6$-alkyl, $C_1$-$C_6$-haloalkyl, $C_1$-$C_6$-alkoxy, $C_1$-$C_6$-haloalkoxy, $C_2$-$C_6$-alkenyl, tri-$C_1$-$C_6$-alkylsilyl, $C_2$-$C_6$-alkynyl, $C_1$-$C_6$-alkoxy-$C_1$-$C_4$-alkyl, $C_1$-$C_6$-alkoxy-$C_1$-$C_4$-alkoxy, $C_3$-$C_6$-cycloalkyl, $C_3$-$C_6$-cycloalkoxy, $C_3$-$C_6$-cycloalkyl-$C_1$-$C_4$-alkyl, $C_3$-$C_6$-cycloalkoxyx-$C_1$-$C_4$-alkyl, where the alkyl, cycloalkyl, cycloalkoxy and alkoxy parts of the last 6 mentioned radicals are unsubstituted or partially or completely halogenated, $C(O)$—$OR^a$, $NR^bR^c$, $C_1$-$C_6$-alkylen-$NR^bR^c$, O—$C_1$-$C_6$-alkylen-$NR^bR^c$, $C_1$-$C_6$-alkylen-CN, NH—$C_1$-$C_6$-alkylen-$NR^bR^c$, $C(O)$—$NR^bR^c$, $C(O)$—$R^d$, $SO_2NR^bR^c$ and $S(=O)_mR^e$;

each $R^g$ is selected from the group consisting of halogen, $N_3$, OH, CN, $NO_2$, —SCN, —$SF_5$, $C_1$-$C_6$-alkyl, $C_1$-$C_6$-haloalkyl, $C_1$-$C_6$-alkoxy, $C_1$-$C_6$-haloalkoxy, $C_2$-$C_6$-alkenyl, tri-$C_1$-$C_6$-alkylsilyl, $C_2$-$C_6$-alkynyl, $C_1$-$C_6$-alkoxy-$C_1$-$C_4$-alkyl, $C_1$-$C_6$-alkoxy-$C_1$-$C_4$-alkoxy, $C_3$-$C_6$-cycloalkyl, $C_3$-$C_6$-cycloalkoxy, $C_3$-$C_6$-cycloalkyl-$C_1$-$C_4$-alkyl, $C_3$-$C_6$-cycloalkoxy-$C_1$-$C_4$-alkyl, where the alkyl, cycloalkyl, cycloalkoxy and alkoxy parts of the last 6 mentioned radicals are unsubstituted or partially or completely halogenated, $C(O)$—$OR^a$, $NR^bR^c$, $C_1$-$C_6$-alkylen-$NR^bR^c$, O—$C_1$-$C_6$-alkylen-$NR^bR^c$, $C_1$-$C_6$-alkylen-CN, NH—$C_1$-$C_6$-alkylen-$NR^bR^c$, $C(O)$—$NR^bR^c$, $C(O)$—$R^d$, $SO_2NR^bR^c$ and $S(=O)_mR^e$;

each $R^{hh}$ is selected from halogen, $C_1$-$C_6$-alkyl, $C_3$-$C_6$-cycloalkyl, or CN;

or an N-oxide, stereoisomer, tautomer or agriculturally or veterinarily acceptable salt thereof.

2. The compound of claim 1, which is a compound of the formulae Ia, Ib, Ic, Id or Ie, an N-oxide, stereoisomer, tautomer or agriculturally or veterinarily acceptable salt thereof (Ia)

(Ib)

(Ic)

(Id)

where in formula Ia
$A^{2a}$ is N or $C(R^2)$; and
$A^{3a}$ is N or $C(R^7)$;
where in formula Ib
$C^1$ is CH or C, provided that ---- indicates a single bond, if $C^1$ is CH or a double bond, if $C^1$ is C,
$A^{2b}$ is $N(R^3)$, O or S; and
$A^{3b}$ is N or $C(R^7)$;
provided that one or both of $A^{2b}$ and $A^{3b}$ are $N(R^3)$ or N, respectively;
where in formula Ic
$C^1$ and $C^2$ are both CH or both C provided that ---- indicates a single bond, if $C^1$ and $C^2$ are CH or a double bond, if $C^1$ and $C^2$ are C,
$A^{2c}$ is N or $C(R^2)$; and
$A^{3c}$ is O, S, $N(R^6)$ or $C(R^8,R^9)$;
where in formula Id
$A^{2d}$ is $N(R^3)$, O, S or $C(R^4,R^5)$; and
$A^{3d}$ is O, S, $N(R^6)$ or $C(R^8,R^9)$;
provided that at least one of $A^{2d}$ and $A^{3d}$ is different from O and S and further provided that the bond between $A^{2d}$ and $A^{3d}$ is a single bond.

3. The compound of claim 2, which is a compound of the formula Ia, where either $A^{2a}$ is N and $A^{3a}$ is $C(R^7)$ or $A^{2a}$ is $C(R^2)$ and $A^{3a}$ is N, or an N-oxide, stereoisomer or agriculturally or veterinarily acceptable salt thereof.

4. The compound of claim 1, wherein Q is —O—, —S—, —C($R^{Q2a}R^{Q2b}$)—, —N($R^{Q2}$)—C(=O)—, —C($R^{Q3}$)=C($R^{Q4}$)—, —C($R^{Q3a}R^{Q3b}$)—C($R^{Q4a}R^{Q4b}$)—, —O—C($R^{Q4a}R^{Q4b}$)—, —S(=O)$_n$—C($R^{Q4a}R^{Q4b}$)— or —N($R^{Q2}$)—C($R^{Q4a}R^{Q4b}$)—.

5. The compound of claim 4, where Q is selected from the group consisting of O, S, —$CH_2$—, —CH=CH—, —$CH_2CH_2$—, O—$CH_2$, —S(=O)—$CH_2$—, —N($R^{Q2}$)—C(=O)— and —N($R^{Q2}$)—$CH_2$—.

6. The compound of claim 5, where Q is selected from the group consisting of O, S, —$CH_2$—, —CH=CH—, —$CH_2CH_2$—, O—$CH_2$, —S(=O)—$CH_2$—, —N(R')—C(=O)— and —N(R')—$CH_2$—, wherein R' is hydrogen or methyl.

7. The compound of claim 1, which is a compound of the formula, (Ia.1)

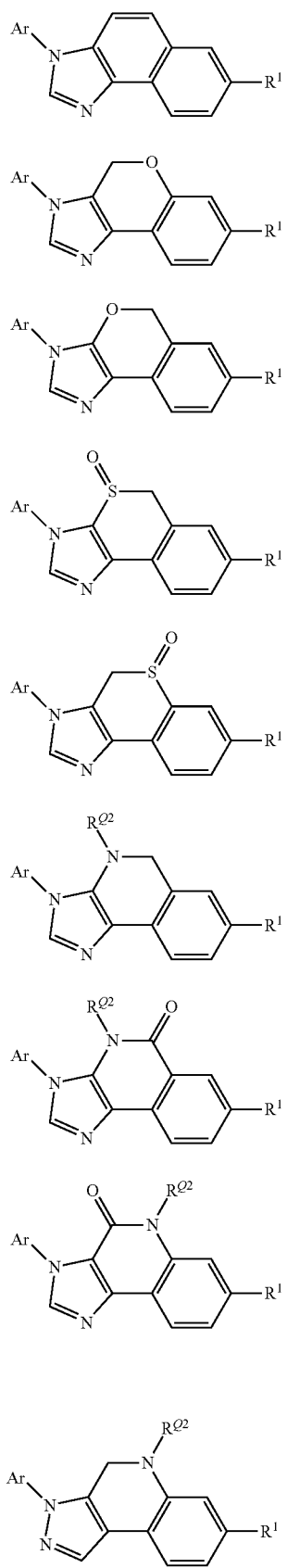
Ia.2
Ia.3
Ia.4
Ia.5
Ia.6
Ia.7
Ia.8
Ia.9
Ia.10
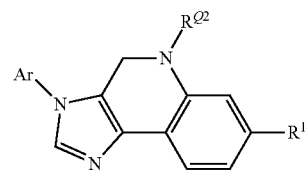 Ia.11
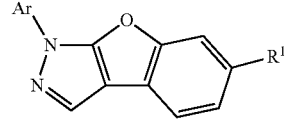 Ia.12
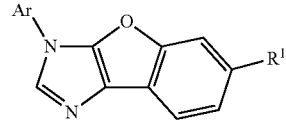 Ia.13
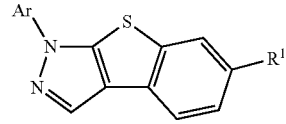 Ia.14
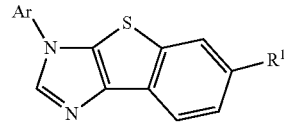 Ia.15
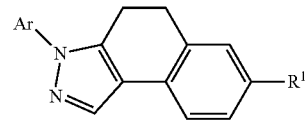 Ia.16
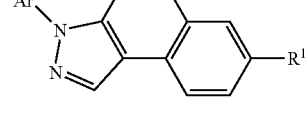 Ia.17
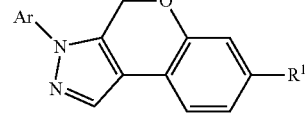 Ia.18
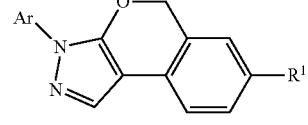 Ia.19
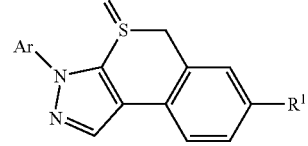 Ia.20
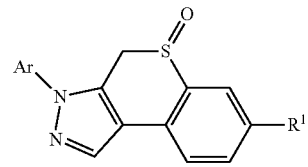 Ia.21

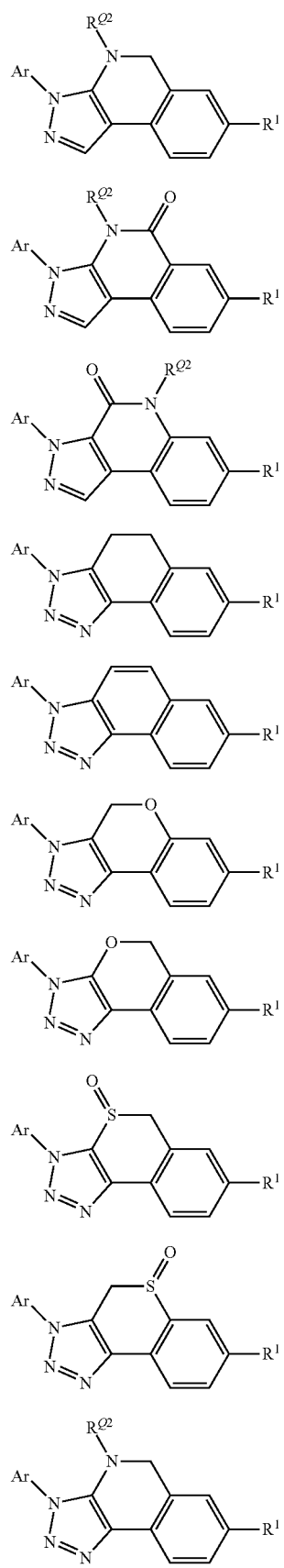
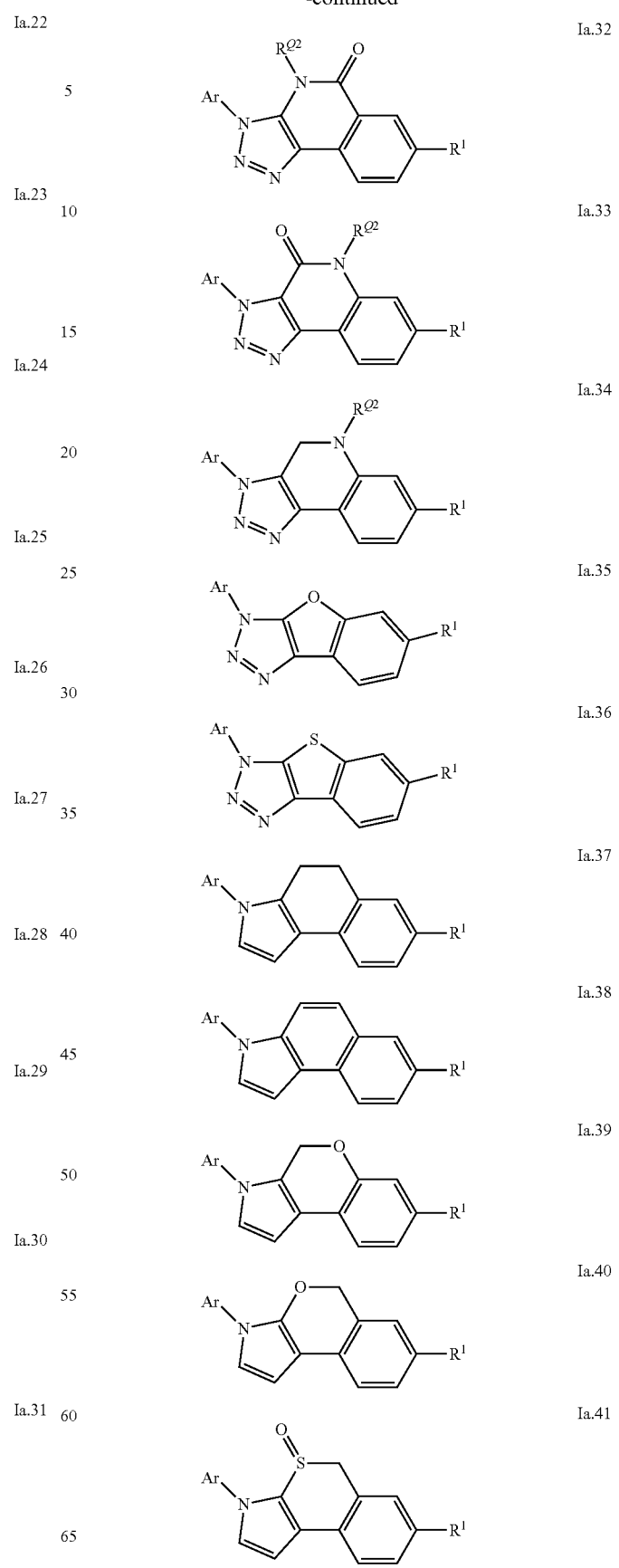

wherein $R^{Q2}$ is in particular hydrogen, $C_1$-$C_4$-alkyl, $C_3$-$C_6$-cycloalkyl, $C_3$-$C_6$-cycloalkymethyl or benzyl; or an N-oxide, stereoisomer, tautomer or agriculturally or veterinarily acceptable salt thereof.

8. The compound of claim 1, which is a compound of the formula

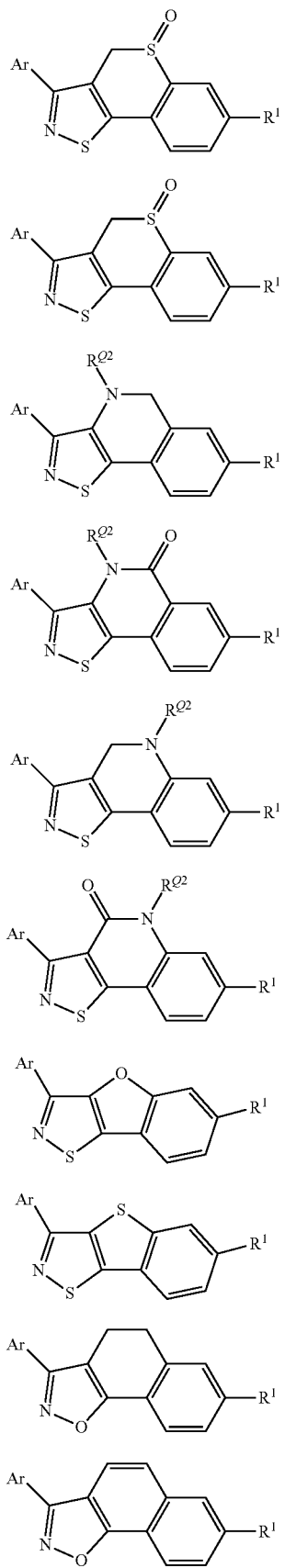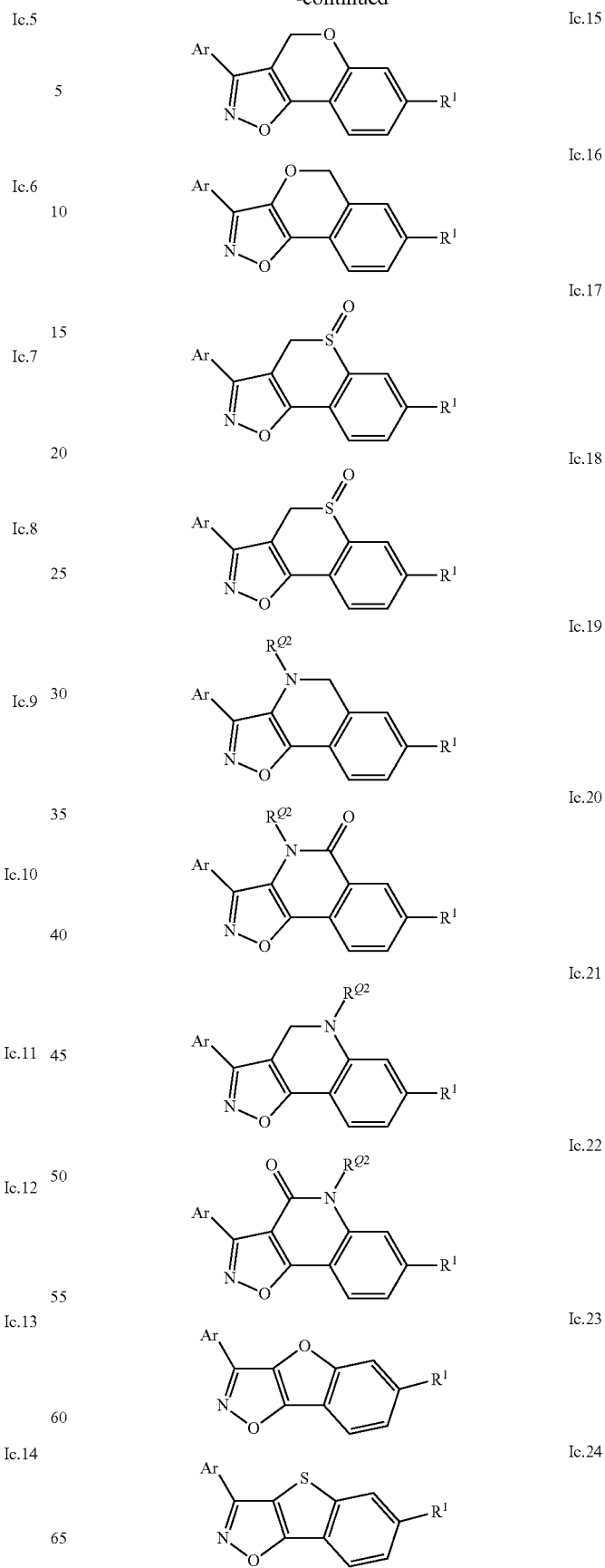

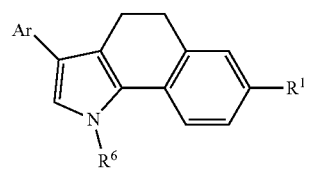 Ic.25
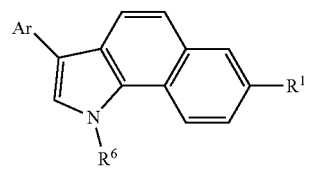 Ic.26
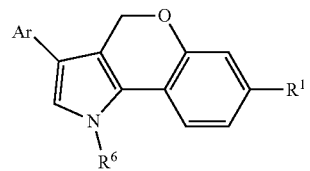 Ic.27
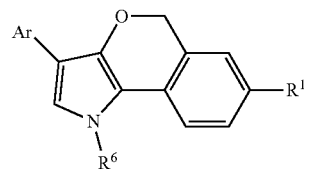 Ic.28
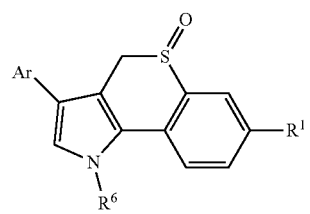 Ic.29
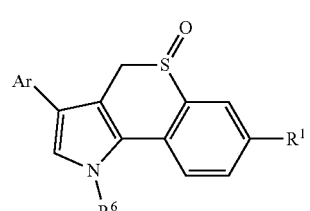 Ic.30
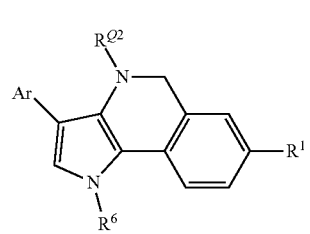 Ic.31
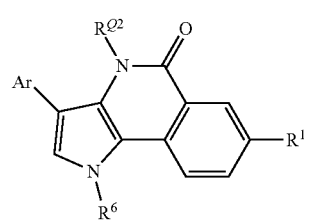 Ic.32
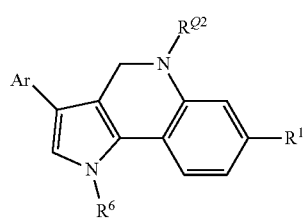 Ic.33
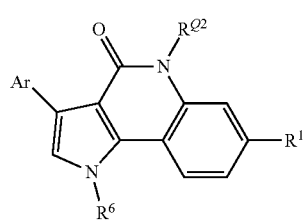 Ic.34
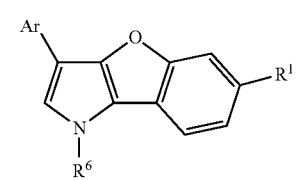 Ic.35
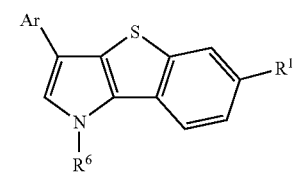 Ic.36
Ic.37
Ic.38
Ic.39
Ic.40
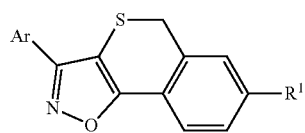 Ic.41

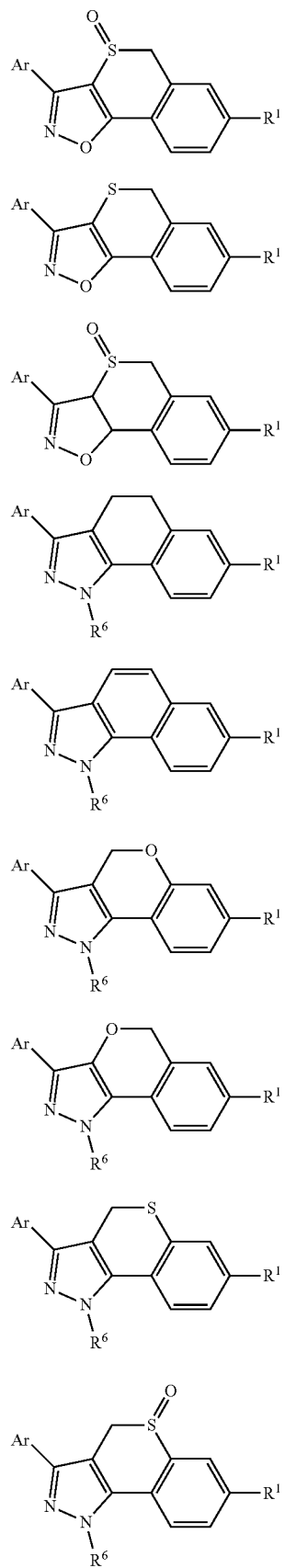
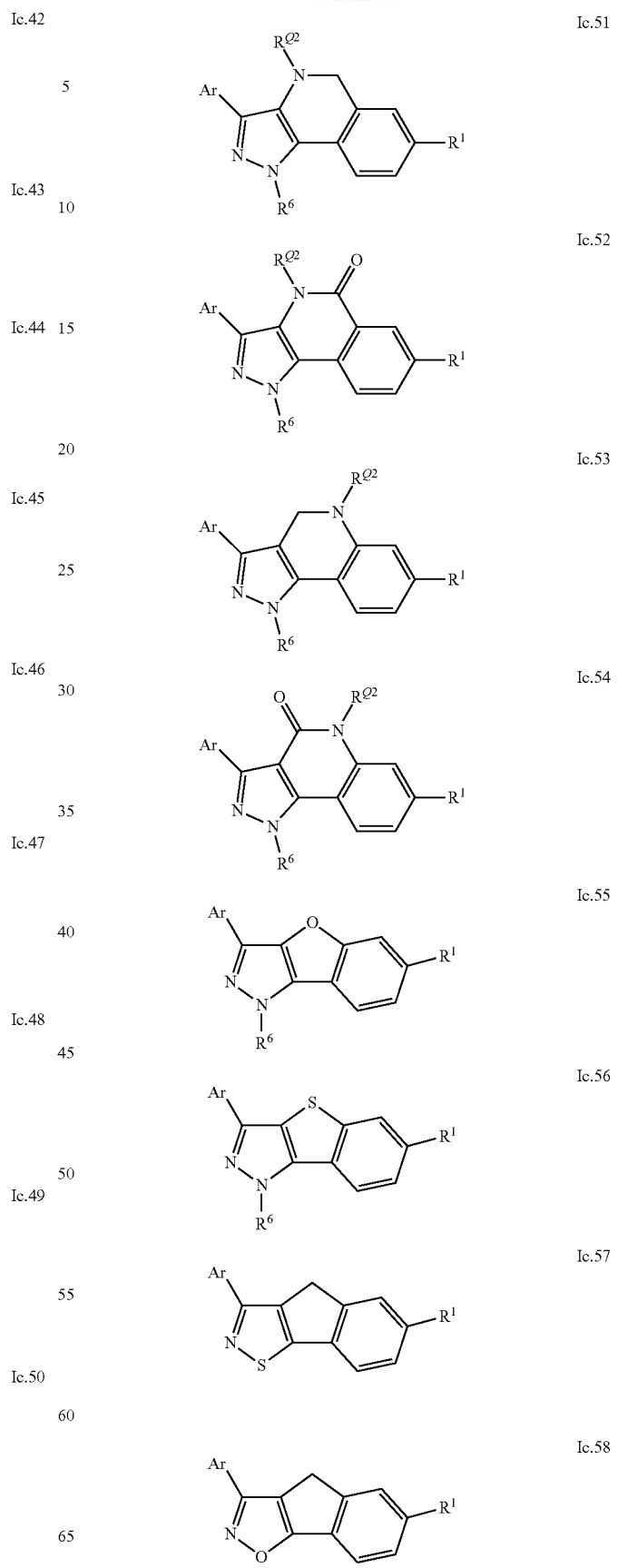

wherein $R^{Q2}$ is in particular hydrogen, $C_1$-$C_4$-alkyl, $C_3$-$C_6$-cycloalkyl, $C_3$-$C_6$-cycloalkymethyl or benzyl; or an N-oxide, stereoisomer, tautomer or agriculturally or veterinarily acceptable salt thereof.

9. The compound of claim 1, which is a compound of the formulae

-continued

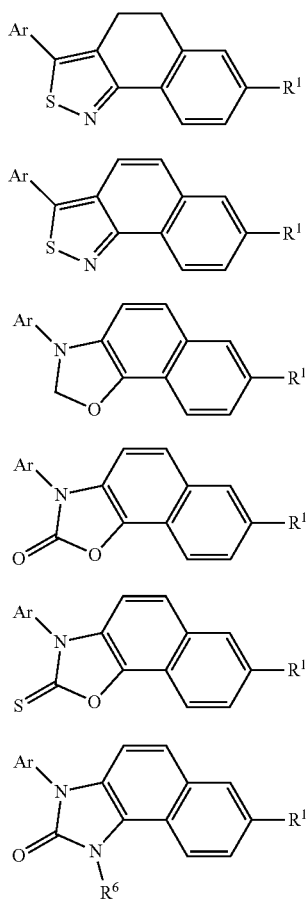

or an N-oxide, stereoisomer, tautomer or agriculturally or veterinarily acceptable salt thereof.

10. The compound of claim 1, where Ar is phenyl or pyridyl, which carries 1, 2 or 3 radicals $R^{Ar}$.

11. The compound of claim 1, where $R^{Ar}$ is selected from the group consisting of halogen, $C_1$-$C_6$-alkyl, $C_1$-$C_6$-haloalkyl, $C_1$-$C_6$-alkoxy, $C_1$-$C_6$-haloalkoxy and S—$R^e$, where $R^e$ is $C_1$-$C_6$-alkyl or $C_1$-$C_6$-haloalkyl.

12. The compound of claim 1, where Ar is phenyl, which carries one radical $R^{Ar}$ in the 4-position, or 3-pyridyl, which carries one radical $R^{Ar}$ in the 6-position and where phenyl and pyridyl may carry 1 or 2 further radicals $R^{Ar}$.

13. The compound of claim 12, where radical $R^{Ar}$ in the 6-position of 3-pyridyl and the radical $R^{Ar}$ in the 4-position of phenyl is selected from the group consisting of $C_1$-$C_4$-haloalkyl, $C_1$-$C_4$-haloalkoxy and S—$R^e$, where $R^e$ is $C_1$-$C_4$-haloalkyl.

14. The compound of claim 13, where Ar is selected from 4-trifluoromethylphenyl, 4-trifluoromethoxyphenyl, 4-(pentafluoroethoxy)phenyl, 4-(trifluoromethylthio)phenyl, 6-trifluoro-3-pyridyl, 6-trifluoromethoxy-3-pyridyl, 6-(pentafluoroethoxy)-3-pyridyl and 6-(trifluoromethylthio)3-pyridyl.

15. The compound of claim 1, where $R^1$ is a radical of one of the following formulae $R^1$-a to $R^1$-v:

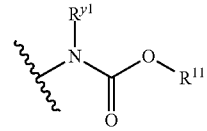

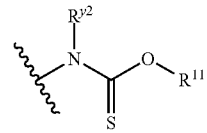

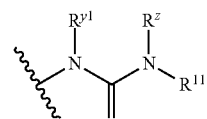

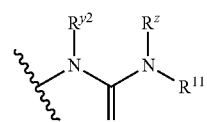

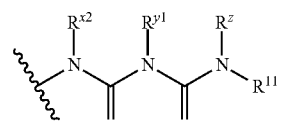

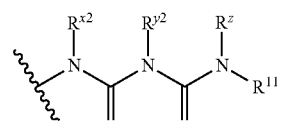

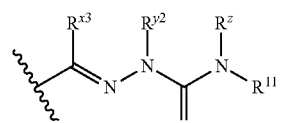

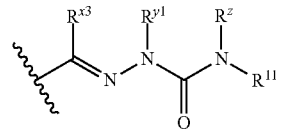

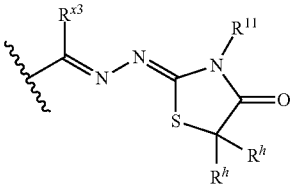

-continued

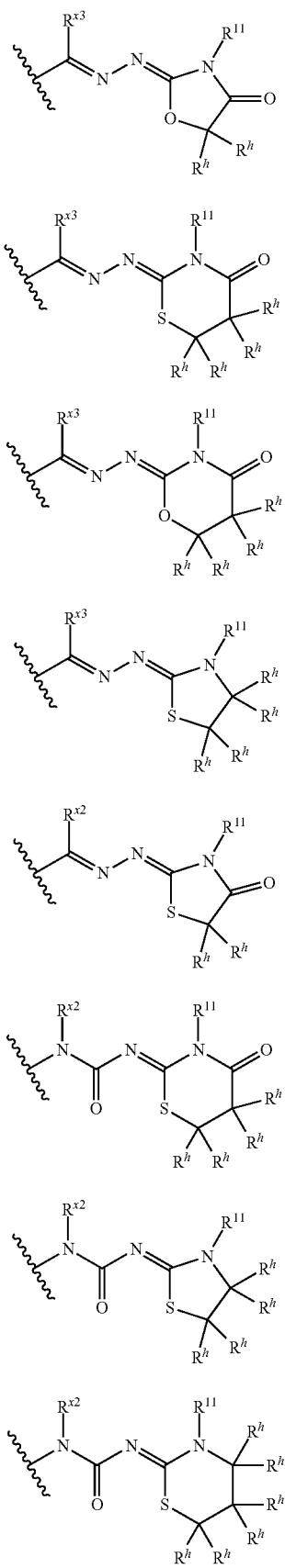

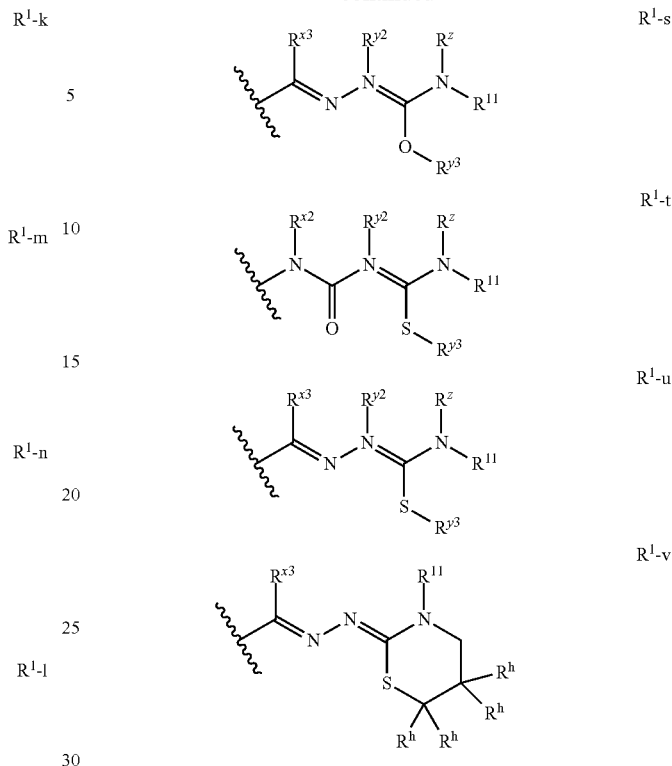

wherein

R$^h$ is hydrogen or has one of the meanings given for R$^{hh}$.

16. The compound of claim 1, where R$^{11}$ is aryl, aryl-C$_1$-C$_4$-alkyl, hetaryl, or hetaryl-C$_1$-C$_4$-alkyl, where the aryl and hetaryl rings in the last 4 radicals are unsubstituted or carry 1, 2, 3, 4 or 5 radicals R$^g$ and where hetaryl is a 5- or 6-membered monocyclic hetaryl.

17. The compound of claim 1, where R$^{11}$ is phenyl, benzyl, 1-phenylethyl, pyridyl, pyridyl-methyl and 1-(pyridyl)ethyl, where phenyl and pyridyl in the last 6 radicals carries 1, 2 or 3 radicals R$^g$.

18. The compound of claim 1, where R$^g$ is selected from the group consisting of halogen, C$_1$-C$_6$-alkyl, C$_1$-C$_6$-haloalkyl, C$_1$-C$_6$-alkoxy, C$_1$-C$_6$-haloalkoxy and S—R$^e$, where R$^e$ is C$_1$-C$_6$-alkyl or C$_1$-C$_6$-haloalkyl.

19. The compound of claim 1, where R$^{11}$ is 2-chlorophenyl, 2-fluorophenyl, 2-methylphenyl, 2-ethylphenyl, 2-isopropylphenyl, 2-trifluoromethyphenyl, 2-methoxyphenyl, 2,4-dichlorophenyl, 2,4-difluorophenyl, 2,4-dimethylphenyl, 2,5-dimethylphenyl, 2,5-dichlorophenyl, 2-methyl-5-methoxyphenyl, 2,6-dichlorophenyl, 2,6-difluorophenyl, 2,6-dimethylphenyl, 2,4,6-trifluorophenyl, 2,4,6-trichlorophenyl, 2,4,6-trimethylphenyl, 2-methyl-4-chlorophenyl, 2-methyl-5-chlorophenyl, 2-chloro-5-trifluoromethylphenyl, 2,6-dimethyl-4-bromophenyl, 1-(5-chloro-2-pyridyl)ethyl, 1-(5-fluoro-2-pyridyl)ethyl, 1-(5-methoxy-2-pyridyl)ethyl or 1-(6-chloro-2-pyridyl)ethyl.

20. The compound of claim 1, which is selected from the group consisting of compounds 1-(2,6-dimethylphenyl)-3-[(E)-[3-[4-(trifluoromethoxy)phenyl]benzo[e]benzimidazol-7-yl]methyleneamino]thiourea; 1-(2,4-dimethylphenyl)-3-[(E)-[3-[4-(trifluoromethoxy)phenyl]benzo[e]benzimidazol-7-yl]methyleneamino]thiourea; 1-(2,4,6-trichlorophenyl)-3-[(E)-[3-[4-(trifluoromethoxy)phenyl]benzo[e]benzimidazol-7-yl]methyleneamino]thiourea; 1-(4- bromo-2,6-dimethyl-phenyl)-3-[(E)-[3-[4-(trifluoromethoxy)phenyl]benzo[e]benzimidazol-7-yl]methyleneamino]thiourea; 1-(2,4-difluorophenyl)-3-[(E)-[3-[4-(trifluoromethoxy)phenyl]benzo[e]benzimidazol-7-yl]methyleneamino]thiourea; 1-(4-bromo-2,6-dimethyl-phenyl)-3-[(E)-[3-[4-(trifluoromethoxy)phenyl]-4,5-dihydrobenzo[g][2,1]benzoxazol-7-yl]methyleneamino]thiourea; 1-(2,6-dimethylphenyl)-3-[(E)-[3-[4-(trifluoromethoxy)phenyl]-4,5-dihydrobenzo[g][2,1]benzoxazol-7-yl]methyleneamino]thiourea; 1-(2,4-dimethylphenyl)-3-[(E)-[3-[4-(trifluoromethoxy)phenyl]-4,5-dihydrobenzo[g][2,1]benzoxazol-7-yl]methyleneamino]thiourea; 1-(2,4,6-trichlorophenyl)-3-[(E)-[3-[4-(trifluoromethoxy)phenyl]-4,5-dihydrobenzo[g][2,1]benzoxazol-7-yl]methyleneamino]thiourea; 1-(2,6-dimethylphenyl)-3-[(E)-[3-[4-(trifluoromethoxy)phenyl]-4,5-dihydrobenzo[e]indazol-7-yl]methyleneamino]thiourea; 1-(2,6-dimethylphenyl)-3-[(E)-[3-[4-(trifluoromethoxy)phenyl]-4,5-dihydrobenzo[e]benzotriazol-7-yl]methyleneamino]thiourea; 1-(2,6-dichlorophenyl)-3-[(E)-[3-[4-(trifluoromethoxy)phenyl]-4,5-dihydrobenzo[g][2,1]benzoxazol-7-yl]methyleneamino]thiourea; 1-(2,4-difluorophenyl)-3-[(E)-[3-[4-(trifluoromethoxy)phenyl]-4,5-dihydrobenzo[g][2,1]benzoxazol-7-yl]methyleneamino]thiourea; 3-(2,4-dichlorophenyl)-1-methyl-1-[(E)-[3-[4-(trifluoromethoxy)phenyl]-4,5-dihydrobenzo[g][2,1]benzoxazol-7-yl]methyleneamino]thiourea; 1-(2-nitrophenyl)-3-[[3-[4-(trifluoromethoxy)phenyl]-5,6-dihydro-4H-benzo[g][2,1]benzoxazol-7-ylidene]methylimino]thiourea; 1-(1-naphthyl)-3-[(E)-[3-[4-(trifluoromethoxy)phenyl]-4,5-dihydrobenzo[g][2,1]benzoxazol-7-yl]methyleneamino]thiourea; 1-(2-ethylphenyl)-3-[[3-[4-(trifluoromethoxy)phenyl]-5,6-dihydro-4H-benzo[g][2,1]benzoxazol-7-ylidene]methylimino]thiourea; 1-[2-chloro-5-(trifluoromethyl)phenyl]-3-[(E)-[3-[4-(trifluoromethoxy)phenyl]-4,5-dihydrobenzo[g][2,1]benzoxazol-7-yl]methyleneamino]thiourea; 1-(2-ethylphenyl)-3-[[3-[4-(trifluoromethoxy)phenyl]-5,8-dihydro-4H-benzo[e]indazol-7-ylidene]methylimino]thiourea; 1-(2,4,6-trichlorophenyl)-3-[(E)-[3-[4-(trifluoromethoxy)phenyl]-4,5-dihydrobenzo[e]indazol-7-yl]methyleneamino]thiourea; 1-(5-chloro-2-methyl-phenyl)-3-[(E)-[3-[4-(trifluoromethoxy)phenyl]benzo[e]benzimidazol-7-yl]methyleneamino]thiourea; 3-(2-ethylphenyl)-1-[[3-[4-(trifluoromethoxy)phenyl]-9aH-benzo[e]benzimidazol-7-ylidene]methylimino]isothiourea; 3-(o-tolyl)-1-[[3-[4-(trifluoromethoxy)phenyl]-9aH-benzo[e]benzimidazol-7-ylidene]methylimino]isothiourea; 1-[[3-[4-(trifluoromethoxy)phenyl]-9aH-benzo[e]benzimidazol-7-ylidene]methylimino]-3-[2-(trifluoromethyl)phenyl]isothiourea; 1-(2-methoxy-5-methyl-phenyl)-3-[(E)-[3-[4-(trifluoromethoxy)phenyl]benzo[e]benzimidazol-7-yl]methyleneamino]thiourea; 3-(2-methoxyphenyl)-1-[[3-[4-(trifluoromethoxy)phenyl]-9aH-benzo[e]benzimidazol-7-ylidene]methylimino]isothiourea; 1-(2,4-dichlorophenyl)-3-[(E)-[3-[4-(trifluoromethoxy)phenyl]benzo[e]benzimidazol-7-yl]methyleneamino]thiourea; 1-(2,3-dimethylphenyl)-3-[(E)-[3-[4-(trifluoromethoxy)phenyl]benzo[e]benzimidazol-7-yl]methyleneamino]thiourea; 1-(2H-naphthalen-1-ylidene)-3-[[3-[4-(trifluoromethoxy)phenyl]-9aH-benzo[e]benzimidazol-7-ylidene]methylimino]thiourea; 3-(2-chlorophenyl)-1-[[3-[4-(trifluoromethoxy)phenyl]-8H-benzo[e]benzimidazol-7-ylidene]methylimino]isothiourea; 3-(2-nitrophenyl)-1-[[3-[4-(trifluoromethoxy)phenyl]-9aH-benzo[e]benzimidazol-7-ylidene]methylimino]isothiourea; 1-(2-ethylphenyl)-3-[[3-[4-(trifluoromethoxy)phenyl]-5,6-dihydro-4H-benzo[e]benzotriazol-7-ylidene]methylimino]thiourea; 1-(4-bromo-2,6-dimethyl-phenyl)-3-[(E)-[3-[4-(trifluoromethoxy)phenyl]-4,5-dihydrobenzo[e]benzotriazol-7-yl]methyleneamino]thiourea; 1-(o-tolyl)-3-[[3-[4-(trifluoromethoxy)phenyl]-5,8-dihydro-4H-benzo[e]benzotriazol-7-ylidene]methylimino]thiourea; 1-[[3-[4-(trifluoromethoxy)phenyl]-5,8-dihydro-4H-benzo[e]benzotriazol-7-ylidene]methylimino]-3-[2-(trifluoromethyl)phenyl]thiourea; 1-[2-chloro-5-(trifluoromethyl)phenyl]-3-[(E)-[3-[4-(trifluoromethoxy)phenyl]benzo[e]benzimidazol-7-yl]methyleneamino]thiourea; 1-(2,6-dichlorophenyl)-3-[(E)-[3-[4-(trifluoromethoxy)phenyl]benzo[e]benzimidazol-7-yl]methyleneamino]thiourea; 1-(4-chloro-2-methyl-phenyl)-3-[(E)-[3-[4-(trifluoromethoxy)phenyl]benzo[e]benzimidazol-7-yl]methyleneamino]thiourea; 1-(3-chloro-2-methyl-phenyl)-3-[(E)-[3-[4-(trifluoromethoxy)phenyl]benzo[e]benzimidazol-7-yl]methyleneamino]thiourea; 3-(2-fluorophenyl)-1-[[3-[4-(trifluoromethoxy)phenyl]-5H-benzo[e]benzimidazol-7-ylidene]methylimino]isothiourea; 1-(2,5-dimethylphenyl)-3-[(E)-[3-[4-(trifluoromethoxy)phenyl]benzo[e]benzimidazol-7-yl]methyleneamino]thiourea; 1-(2,5-dichlorophenyl)-3-[(E)-[3-[4-(trifluoromethoxy)phenyl]benzo[e]benzimidazol-7-yl]methyleneamino]thiourea; 1-(2-nitrophenyl)-3-[[3-[4-(trifluoromethoxy)phenyl]-5,6-dihydro-4H-benzo[e]benzotriazol-7-ylidene]methylimino]thiourea; 1-(2-isopropylphenyl)-3-[[3-[4-(trifluoromethoxy)phenyl]-3aH-benzo[e]benzimidazol-7-ylidene]methylimino]thiourea; 1-(2,6-dimethylphenyl)-3-[(E)-[3-[4-(trifluoromethoxy)phenyl]benzo[e]indazol-7-yl]methyleneamino]thiourea; 1-(2,6-dimethylphenyl)-3-[(E)-[3-[4-(trifluoromethoxy)phenyl]benzothiopheno[2,3-d]imidazol-6-yl]methyleneamino]thiourea; 1-(4-bromo-2,6-dimethyl-phenyl)-3-[(E)-[3-[4-(trifluoromethoxy)phenyl]-4,5-dihydrobenzo[e]indazol-7-yl]methyleneamino]thiourea; 1-(2,6-dichlorophenyl)-3-[(E)-[3-[4-(trifluoromethoxy)phenyl]benzo[e]indazol-7-yl]methyleneamino]thiourea; 1-(2-ethylphenyl)-3-[[3-[4-(trifluoromethoxy)phenyl]-5H-benzo[e]indazol-7-ylidene]methylimino]thiourea; (2Z)-3-(2-isopropylphenyl)-2-[(E)-[3-[4-(trifluoromethoxy)phenyl]benzo[e]benzimidazol-7-yl]methylenehydrazono]thiazolidin-4-one; 3-(2-isopropylphenyl)-2-methyl-1-[[3-[4-(trifluoromethoxy)phenyl]-3aH-benzo[e]benzimidazol-7-ylidene]methylimino]isothiourea; (E)-3-(2-isopropylphenyl)-N-[(E)[3-[4-(trifluoromethoxy)phenyl]benzo[e]benzimidazol-7-yl]methyleneamino]thiazolidin-2-imine; 1-(2,6-dimethylphenyl)-3-[(E)-[3-[4-(trifluoromethoxy)phenyl]benzo[e]benzotriazol-7-yl]methyleneamino]thiourea; (E)-3-(2-isopropylphenyl)-N-[(E)-[3-[4-(trifluoromethoxy)phenyl]benzo[e]benzimidazol-7-yl]methyleneamino]-1,3-thiazinan-2-imine; 1-(5-chloro-2-pyridyl)ethyl N-[3-[4-(trifluoromethoxy)phenyl]benzo[e]benzimidazol-7-yl]carbamate; 1-(2,6-dichlorophenyl)-3-[(E)-[3-[4-(trifluoromethoxy)phenyl]benzo[e]benzotriazol-7-yl]methyleneamino]thiourea; 1-(2,6-dimethylphenyl)-3-[1-[3-[4-(trifluoromethoxy)phenyl]-4,5-dihydrobenzo[e]benzimidazol-7-yl]vinylimino]thiourea; 1-(2,6-dichlorophenyl)-3-[1-[3-[4-(trifluoromethoxy)phenyl]-4,5-dihydrobenzo[e]benzimidazol-7-yl]vinylimino]thiourea; 1-(2-chloro-6-methyl-phenyl)-3-[(E)-[3-[4-(trifluoromethoxy)phenyl]benzo[e]benzotriazol-7-yl]methyleneamino]thiourea; 1-(2,6-diethylphenyl)-3-[(E)-[3-[4-(trifluoromethoxy)phenyl]benzo[e]benzotriazol-7-yl]methyleneamino]thiourea; 1-(2-ethyl-6-methyl-phenyl)-3-[(E)-[3-[4-(trifluoromethoxy)phenyl]benzo[e]benzotriazol-7-yl]methyleneamino]thiourea; 1-(3-methyl-2-pyridyl)-3-

[(E)-[3-[4-(trifluoromethoxy)phenyl]benzo[e]benzimidazol-7-yl]methyleneamino]thiourea; 1-(2-iodophenyl)-3-[[3-[4-(trifluoromethoxy)phenyl]-5H-benzo[e]benzimidazol-7-ylidene]methylimino]thiourea; 1-(2-methoxy-6-methyl-phenyl)-3-[(E)-[3-[4-(trifluoromethoxy)phenyl]benzo[e]benzimidazol-7-yl]methyleneamino]thiourea; 1-(2,6-dibromophenyl)-3-[(E)-[3-[4-(trifluoromethoxy)phenyl]benzo[e]benzimidazol-7-yl]methyleneamino]thiourea; 1-(2-bromophenyl)-3-[[3-[4-(trifluoromethoxy)phenyl]-5H-benzo[e]benzimidazol-7-ylidene]methylimino]thiourea; 1-(3-ethyl-2-pyridyl)-3-[(E)-[3-[4-(trifluoromethoxy)phenyl]benzo[e]benzimidazol-7-yl]methyleneamino]thiourea; 1-(3,5-dimethylisoxazol-4-yl)-3-[(E)-[3-[4-(trifluoromethoxy)phenyl]benzo[e]benzimidazol-7-yl]methyleneamino]thiourea; 1-(2,6-diethylphenyl)-3-[(E)-[3-[4-(trifluoromethoxy)phenyl]benzo[e]benzimidazol-7-yl]methyleneamino]thiourea; 1-(2,6-difluorophenyl)-3-[(E)-[3-[4-(trifluoromethoxy)phenyl]benzo[e]benzimidazol-7-yl]methyleneamino]thiourea; 1-(2,6-dimethylphenyl)-3-[(E)-[3-[4-(trifluoromethoxy)phenyl]benzo[g][1,2]benzoxazol-7-yl]methyleneamino]thiourea; 1-(3-pyridyl)-3-[(E)-[3-[4-(trifluoromethoxy)phenyl]benzo[e]benzimidazol-7-yl]methyleneamino]thiourea; 1-(2-chloro-6-methyl-phenyl)-3-[(E)-[3-[4-(trifluoromethylsulfanyl)phenyl]benzo[e]benzimidazol-7-yl]methyleneamino]thiourea; 1-(2,6-dimethylphenyl)-3-[(E)-[3-[4-(trifluoromethylsulfanyl)phenyl]benzo[e]benzimidazol-7-yl]methyleneamino]thiourea; 1-(2-ethyl-6-methyl-phenyl)-3-[(E)-[3-[4-(trifluoromethylsulfanyl)phenyl]benzo[e]benzimidazol-7-yl]methyleneamino]thiourea; 1-(2-chloro-6-methyl-phenyl)-3-[(E)-[3-[4-(trifluoromethyl)phenyl]benzo[e]benzimidazol-7-yl]methyleneamino]thiourea; 1-(2-ethyl-6-methyl-phenyl)-3-[(E)-[3-[4-(trifluoromethyl)phenyl]benzo[e]benzimidazol-7-yl]methyleneamino]thiourea; 1-(2-chloro-6-methyl-phenyl)-3-[(E)-[3-[4-(trifluoromethoxy)phenyl]benzo[e]benzimidazol-7-yl]methyleneamino]thiourea; 1-(3,5-dimethylisoxazol-4-yl)-3-[(E)-[3-[4-(trifluoromethoxy)phenyl]benzo[e]benzotriazol-7-yl]methyleneamino]thiourea; 1-(3-ethyl-2-pyridyl)-3-[(E)-[3-[4-(trifluoromethoxy)phenyl]benzo[e]benzotriazol-7-yl]methyleneamino]thiourea; 1-(2-ethyl-6-methyl-phenyl)-3-[1-[3-[4-(trifluoromethoxy)phenyl]-4,5-dihydrobenzo[e]benzimidazol-7-yl]vinylimino]thiourea; 1-(2,6-dimethylphenyl)-3-[(E)-[3-[4-(trifluoromethoxy)phenyl]-4,5-dihydrobenzo[g][2,1]benzothiazol-7-yl]methyleneamino]thiourea; 1-(2,6-dimethylphenyl)-3-[(E)-[3-[4-(trifluoromethoxy)phenyl]benzo[g][2,1]benzoxazol-7-yl]methyleneamino]thiourea; 3-(2,6-dimethylphenyl)-1-methyl-1-[(E)-[3-[4-(trifluoromethoxy)phenyl]benzo[e]benzimidazol-7-yl]methyleneamino]thiourea; 1-(2,6-dimethylphenyl)-3-[(E)-[3-[4-(trifluoromethyl)phenyl]benzo[e]benzimidazol-7-yl]methyleneamino]thiourea; 1-methyl-3-(o-tolyl)-1-[(E)-[3-[4-(trifluoromethoxy)phenyl]benzo[e]benzimidazol-7-yl]methyleneamino]thiourea; 1-(2,6-dimethylphenyl)-3-[(E)-[3-[4-(trifluoromethoxy)phenyl]benzo[g][2,1]benzothiazol-7-yl]methyleneamino]thiourea; 1-phenyl-3-[(E)-[3-[4-(trifluoromethoxy)phenyl]benzo[e]benzimidazol-7-yl]methyleneamino]urea; 3-(o-tolyl)-1-[[3-[4-(trifluoromethoxy)phenyl]-8H-benzo[e]benzimidazol-7-ylidene]methylimino]isourea; 1-(2-chloro-6-methyl-phenyl)-3-[(E)-[2-methyl-3-[4-(trifluoromethoxy)phenyl]benzo[g]indazol-7-yl]methyleneamino]thiourea; 1-(2-ethyl-6-methyl-phenyl)-3-[(E)-[2-methyl-3-[4-(trifluoromethoxy)phenyl]benzo[g]indazol-7-yl]methyleneamino]thiourea; 1-(2,6-diethylphenyl)-3-[(E)-[2-methyl-3-[4-(trifluoromethoxy)phenyl]benzo[g]indazol-7-yl]methyleneamino]thiourea; 1-(2,6-dimethylphenyl)-3-[(E)-[2-methyl-3-[4-(trifluoromethoxy)phenyl]-3,3a,4,5-tetrahydrobenzo[g]indazol-7-yl]methyleneamino]thiourea; 1-(2,6-dichlorophenyl)-3-[(E)-[2-methyl-3-[4-(trifluoromethoxy)phenyl]-3,3a,4,5-tetrahydrobenzo[g]indazol-7-yl]methyleneamino]thiourea; 1-(2,6-dimethylphenyl)-3-[(E)-[2-methyl-3-[4-(trifluoromethoxy)phenyl]benzo[g]indazol-7-yl]methyleneamino]thiourea; 1-(2-methoxy-6-methyl-phenyl)-3-[(E)-[2-methyl-3-[4-(trifluoromethoxy)phenyl]benzo[g]indazol-7-yl]methyleneamino]thiourea; 1-(2,6-dibromophenyl)-3-[(E)-[2-methyl-3-[4-(trifluoromethoxy)phenyl]benzo[g]indazol-7-yl]methyleneamino]thiourea; 1-(2,6-dichlorophenyl)-3-[(E)-[2-methyl-3-[4-(trifluoromethoxy)phenyl]benzo[g]indazol-7-yl]methyleneamino]thiourea; 3-(2-chlorophenyl)-1-[[3-[4-(trifluoromethoxy)phenyl]-8H-benzo[e]benzimidazol-7-ylidene]methylimino]isourea; 1-(3-methyl-2-pyridyl)-3-[(E)-[2-methyl-3-[4-(trifluoromethoxy)phenyl]benzo[g]indazol-7-yl]methyleneamino]thiourea; 1-(3-iodo-2-pyridyl)-3-[(E)-[2-methyl-3-[4-(trifluoromethoxy)phenyl]benzo[g]indazol-7-yl]methyleneamino]thiourea; 1-(2-methyl-6-methylsulfanyl-phenyl)-3-[(E)-[3-[4-(trifluoromethoxy)phenyl]benzo[e]benzimidazol-7-yl]methyleneamino]thiourea; 1-(2-methyl-6-methylsulfinyl-phenyl)-3-[(E)-[3-[4-(trifluoromethoxy)phenyl]benzo[e]benzimidazol-7-yl]methyleneamino]thiourea; 1-(2,6-dimethylphenyl)-3-[(E)-[3-(p-tolyl)benzo[e]benzimidazol-7-yl]methyleneamino]thiourea; 1-[(E)-[3-(4-chlorophenyl)benzo[e]benzimidazol-7-yl]methyleneamino]-3-(2,6-dimethylphenyl)thiourea; 1-(2,6-dimethylphenyl)-3-[(E)-[2-methyl-3-[4-(trifluoromethoxy)phenyl]-4,5-dihydrobenzo[g]indazol-7-yl]methyleneamino]thiourea; 1-(2,6-dimethylphenyl)-3-[(E)-[3-[6-(trifluoromethyl)-3-pyridyl]benzo[e]benzimidazol-7-yl]methyleneamino]thiourea; 1-(2,6-dimethylphenyl)-3-[(E)-[3-[5-(trifluoromethyl)-2-pyridyl]benzo[e]benzimidazol-7-yl]methyleneamino]thiourea; 1-(2,6-dimethylphenyl)-3-[(E)-[3-[4-(1,1,2,2,2-pentafluoroethyl)phenyl]benzo[e]benzimidazol-7-yl]methyleneamino]thiourea; 1-[[3-(3,5-dichlorophenyl)-9aH-benzo[e]benzimidazol-7-ylidene]methylimino]-3-(2,6-dimethylphenyl)isothiourea; 1-[[3-[3-chloro-5-(trifluoromethyl)-2-pyridyl]-3aH-benzo[e]benzimidazol-7-ylidene]methylimino]-3-(2,6-dimethylphenyl)thiourea; 1-(2,6-dimethylphenyl)-3-[[3-[2-fluoro-4-(trifluoromethyl)phenyl]-3aH-benzo[e]benzimidazol-7-ylidene]methylimino]thiourea; 1-[[3-[2-chloro-4-(trifluoromethyl)phenyl]-3aH-benzo[e]benzimidazol-7-ylidene]methylimino]-3-(2,6-dimethylphenyl)thiourea; (1Z)-1-[4-hydroxy-3-(2-isopropylphenyl)thiazol-2-ylidene]-3-[3-[4-(trifluoromethoxy)phenyl]-9aH-benzo[e]benzimidazol-7-ylidene]urea; (1Z)-1-[4-oxo-3-[2-(trifluoromethyl)phenyl]thiazolidin-2-ylidene]-3-[3-[4-(trifluoromethoxy)phenyl]-8H-benzo[e]benzimidazol-7-ylidene]urea; 3-[N-(2-isopropylphenyl)-C-sulfanyl-carbonimidoyl]-1-[3-[4-(trifluoromethoxy)phenyl]-9aH-benzo[e]benzimidazol-7-ylidene]isourea; (2Z)-3-(2,6-dimethylphenyl)-5,5-dimethyl-2-[(E)-[3-[4-(trifluoromethoxy)phenyl]benzo[e]benzimidazol-7-yl]methylenehydrazono]thiazolidin-4-one; (2Z)-3-(2,6-dimethylphenyl)-2-[(E)-[3-[4-(trifluoromethoxy)phenyl]benzo[e]benzimidazol-7-yl]methylenehydrazono]thiazolidin-4-one; (E)-3-(2,6-dimethylphenyl)-N-[(E)-[3-[4-(trifluoromethoxy)phenyl]benzo[e]benzimidazol-7-yl]methyleneamino]-1,3-thiazinan-2-imine; (2Z)-3-(2,6-dimethylphenyl)-5-methyl-2-[(E)-[3-[4-(trifluoromethoxy)phenyl]benzo[e]benzimidazol-7-yl]methylenehydrazono]thiazolidin-4-one; (E)-3-(2,6-dimethylphenyl)-N-[(E)-[3-[4-(trifluoromethoxy)phenyl]benzo[e]benzimidazol-7-yl]methyleneamino]thiazolidin-2-imine; 1-(2-pyridyl)ethyl N-[3-[4-(trifluoromethoxy)phenyl]benzo[e]benzimidazol-7-yl]carbamate; 1-(2-methoxyphenyl)ethyl N-[3-[4-(trifluoromethoxy)phenyl]-9aH-benzo[e]benzimidazol-7-ylidene]carbamate; 1-(2,4-difluorophenyl)ethyl N-[3-[4-(trifluoromethoxy)phenyl]benzo[e]benzimidazol-7-yl]carbamate; o-tolyl N-[3-[4-(trifluoromethoxy)phenyl]-9aH-benzo[e]benzimidazol-7-ylidene]carbamate; 1-(2-isopropylphenyl)-3-[[2-methyl-3-[4-(trifluoromethoxy)phenyl]-4,9a-dihydrochromeno[4,3-c]pyrazol-7-ylidene]methylimino]thiourea; (2Z)-3-(2,6-dimethylphenyl)-2-[(E)-[2-methyl-3-[4-(trifluoromethoxy)phenyl]-4H-chromeno[4,3-c]pyrazol-7-yl]methylenehydrazono]thiazolidin-4-one; 1-(2,6-dimethylphenyl)-3-[(E)-[2-methyl-3-[4-(trifluoromethoxy)phenyl]benzo[e]benzimidazol-7-yl]methyleneamino]thiourea; 3-(2-isopropylphenyl)-1-[[2-methyl-3-[4-(trifluoromethoxy)phenyl]-5H-benzo[e]benzimidazol-7-ylidene]methylimino]isothiourea; (2Z)-3-(2,6-dimethylphenyl)-2-[(E)-[2-methyl-3-[4-(trifluoromethoxy)phenyl]benzo[e]benzimidazol-7-yl]methylenehydrazono]thiazolidin-4-one; 1-(2,6-dimethylphenyl)-3-[(E)-[2-methyl-3-[4-(trifluoromethoxy)phenyl]-4H-chromeno[4,3-c]pyrazol-7-yl]methyleneamino]thiourea the tautomers and the agriculturally acceptable salt thereof.

21. The compound of the formula (INT):

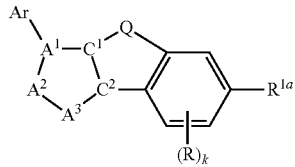

where $R^{1a}$ is C(=O)$R^{x3a}$, CN, N($R^{X1a}$)H, halogen and where $R^{x1a}$ is selected from the group consisting of hydrogen, $C_1$-$C_6$-alkyl, $C_1$-$C_6$-haloalkyl, $C_2$-$C_6$-alkenyl, $C_2$-$C_6$-alkynyl, $C_1$-$C_6$-alkoxy-$C_1$-$C_4$-alkyl, $C_3$-$C_6$-cycloalkyl, $C_3$-$C_6$-cycloalkyl-$C_1$-$C_4$-alkyl, $C_3$-$C_6$-cycloalkoxy-$C_1$-$C_4$-alkyl, where the alkyl, cycloalkyl, cycloalkoxy and alkoxy parts of the last four mentioned radicals are unsubstituted or partially or completely halogenated, $C_1$-$C_6$-alkylen-NR$^b$R$^c$, $C_1$-$C_6$-alkylen-CN, phenyl and benzyl, where the phenyl ring in the last 2 radicals is unsubstituted or carry 1, 2, 3, 4 or 5 radicals R$^f$;

$R^{x3a}$ is selected from the group consisting of hydrogen, OH, $C_1$-$C_6$-alkyl, $C_1$-$C_6$-haloalkyl, $C_1$-$C_6$-alkoxy, $C_1$-$C_6$-haloalkoxy, $C_2$-$C_6$-alkenyl, tri-$C_1$-$C_6$-alkylsilyl, $C_2$-$C_6$-alkynyl, $C_1$-$C_6$-alkoxy-$C_1$-$C_4$-alkyl, $C_1$-$C_6$-alkoxy-$C_1$-$C_4$-alkoxy, $C_3$-$C_6$-cycloalkyl, $C_3$-$C_6$-cycloalkoxy, $C_3$-$C_6$-cycloalkoxy-$C_1$-$C_4$-alkyl, $C_3$-$C_6$-cycloalkyl-$C_1$-$C_4$-alkyl, where the alkyl, cycloalkyl, cycloalkoxy and alkoxy parts of the last 6 mentioned radicals are unsubstituted or partially or completely halogenated, $C_1$-$C_6$-alkylen-NR$^b$R$^c$, O—$C_1$-$C_6$-alkylen-NR$^b$R$^c$, $C_1$-$C_6$-alkylen-CN, phenyl, phenoxy, phenylcarbonyl, phenylthio and benzyl, where the phenyl ring in the last 5 radicals is unsubstituted or carry 1, 2, 3, 4 or 5 radicals R$^f$;

or a salt thereof.

22. An agricultural composition comprising at least one compound of claim 1, a stereoisomer thereof and/or at least one agriculturally acceptable salt thereof, and at least one inert liquid and/or solid agriculturally acceptable carrier.

23. A veterinary composition comprising at least one compound of claim 1, a stereoisomer thereof and/or at least one veterinarily acceptable salt thereof, and at least one inert liquid and/or solid veterinarily acceptable carrier.

24. A method for controlling invertebrate pests which method comprises treating the pests, their food supply, their habitat or their breeding ground or a plant, plant propagation material, soil, area, material or environment in which the pests are growing or may grow, or the materials, plants, plant propagation material, soils, surfaces or spaces to be protected from invertebrate pest attack or infestation with a pesticidally effective amount of at least one imine compound of claim 1, a stereoisomer thereof and/or at least one agriculturally acceptable salt thereof.

25. A method for protecting plants from attack or infestation by invertebrate pests, which method comprises treating the plants with a pesticidally effective amount of at least one compound of the formula I as defined in claim 1, a stereoisomer thereof and/or at least one agriculturally acceptable salt thereof.

26. A method for protecting plant propagation material and/or the plants which grow therefrom from attack or infestation by invertebrate pests, which method comprises treating the plant propagation material with a pesticidally effective amount of at least one compound of claim 1, a stereoisomer thereof and/or at least one agriculturally acceptable salt thereof.

27. A plant propagation material treated with at least one compound of claim 1, a stereoisomer thereof and/or at least one agriculturally acceptable salt thereof.

28. A method for treating or protecting an animal from infestation or infection by invertebrate pests which comprises bringing the animal in contact with a pesticidally effective amount of at least one compound of claim 1 a stereoisomer thereof and/or at least one veterinarily acceptable salt thereof.

* * * * *

UNITED STATES PATENT AND TRADEMARK OFFICE
CERTIFICATE OF CORRECTION

Page 1 of 1

PATENT NO. : 9,497,970 B2
APPLICATION NO. : 14/903887
DATED : November 22, 2016
INVENTOR(S) : Arun Narine It is certified that error appears in the above-identified patent and that said Letters Patent is hereby corrected as shown below:

In the Claims

Column 294, Line 27, Claim 24 before the word "compound" delete "imine".

Signed and Sealed this
Nineteenth Day of September, 2017

Joseph Matal
*Performing the Functions and Duties of the*
*Under Secretary of Commerce for Intellectual Property and*
*Director of the United States Patent and Trademark Office*